(12) United States Patent
Stockwell et al.

(10) Patent No.: US 12,227,500 B2
(45) Date of Patent: Feb. 18, 2025

(54) SUBSTITUTED PYRROLO[2,3-b]PYRIDINES FOR SUPPRESSING TOXIC ENDOPLASMIC RETICULUM STRESS

(71) Applicant: THE TRUSTEES OF COLUMBIA UNIVERSITY IN THE CITY OF NEW YORK, New York, NY (US)

(72) Inventors: Brent R. Stockwell, New York, NY (US); Hynek Wichterle, New York, NY (US); Pieter Bos, New York, NY (US); Arie Zask, New York, NY (US); Sebastian Thams, Stockholm (SE); Emily Rhodes Lowry, Brooklyn, NY (US)

(73) Assignee: THE TRUSTEES OF COLUMBIA UNIVERSITY IN THE CITY OF NEW YORK, New York, NY (US)

( * ) Notice: Subject to any disclaimer, the term of this patent is extended or adjusted under 35 U.S.C. 154(b) by 985 days.

(21) Appl. No.: 17/009,450

(22) Filed: Sep. 1, 2020

(65) Prior Publication Data
US 2021/0040091 A1 Feb. 11, 2021

Related U.S. Application Data

(63) Continuation of application No. PCT/US2019/020362, filed on Mar. 1, 2019.

(60) Provisional application No. 62/637,242, filed on Mar. 1, 2018.

(51) Int. Cl.
*A61K 31/437* (2006.01)
*C07D 471/04* (2006.01)

(52) U.S. Cl.
CPC .................. *C07D 471/04* (2013.01)

(58) Field of Classification Search
CPC .................. A61K 31/437; C07D 471/04
USPC .................. 514/300; 546/113
See application file for complete search history.

(56) References Cited

U.S. PATENT DOCUMENTS

| 8,846,909 | B2 * | 9/2014 | Gelbard | A61P 3/00 544/118 |
|---|---|---|---|---|
| 2006/0030583 | A1 | 2/2006 | Arnold et al. | |
| 2013/0203755 | A1 | 8/2013 | Gelbard et al. | |
| 2015/0297587 | A1 | 10/2015 | Gelbard et al. | |
| 2016/0317509 | A1 | 11/2016 | Gelbard et al. | |

OTHER PUBLICATIONS

Jordan, V. C. Nature Reviews: Drug Discovery, 2, 2003, 205.*
Dörwald, F. Zaragoza. Side Reactions in Organic Synthesis: A Guide to Successful Synthesis Design, Weinheim: Wiley-VCH Verlag Gmbh & Co. KGaA, 2005, Preface.*
Vippagunta, et al. Advanced Drug Delivery Reviews, 48, 2001, 18.*
Extended European Search Report for EP 19760529.8 dated Oct. 4, 2021.
Smith, et al. "Endoplasmic reticulum stress-induced apoptosis requires bax for commitment and Apaf-1 for execution in primary neurons," Cell Death & Differentiation, vol. 14, No. 5, May 1, 2007.
Manju, et al. "Cdc42 and Rac1 are major contributors to the saturated fatty acid-stimulated JNK pathway in hepatocytes," Journal of Hepatology, vol. 56, No. 1 2012.
Salem, et al. "Non-target Genes Regulate miRNAs-Mediated Migration Steering of Colorectal Carcinoma," Pathol Oncol Res 1-8 (2018).
Sano, et al. "ER Stress-Induced Cell Death Mechanism," Biochim. Biophys. Acta 2013, 1833 (12), 3460.
Sareen, et al. "Targeting RNA foci in iPSC-derived motor neurons from ALS patients with a C9ORF72 repeat expansion," Sci Transl Med. 2013;5(208):208ra149.
Saxena, et al. "A role for motoneuron subtype-selective ER stress in disease manifestations of FALS mice," Nat Neurosci. 2009;12(5):627-36.
Saxena, et al. "Neuroprotection through excitability and mTOR required in ALS motoneurons to delay disease and extend survival," Neuron. 2013;80(1):80-96.
Sendtner, et al. "Effect of ciliary neurotrophic factor (CNTF) on motoneuron survival," J Cell Sci Suppl. 1991;15:103-9.
Sharma, et al. "ALS-associated mutant FUS induces selective motor neuron degeneration through toxic gain of function," Nat Commun. 2016;7:10465.
Shin, et al. "Dual Leucine Zipper Kinase Is Required for Retrograde Injury Signaling and Axonal Regeneration," Neuron 74, 1015-1022 (2012).
Sivadasan, et al. "C9ORF72 interaction with cofilin modulates actin dynamics in motoneurons" Nat Neurosci. 2016;19(12):1610-8.

(Continued)

*Primary Examiner* — Douglas M Willis
(74) *Attorney, Agent, or Firm* — Bryan Cave Leighton Paisner LLP

(57) ABSTRACT

The present invention provides, inter alia, a compound having the structure:

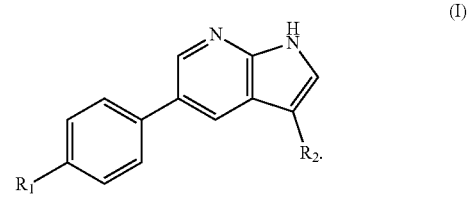

(I)

Also provided are compositions containing a pharmaceutically acceptable carrier and one or more compounds according to the present invention. Further provided are methods for treating or ameliorating the effects of a disorder in a subject, methods of suppressing the toxicity of endoplasmic reticulum (ER) stress in a subject, methods of treating or ameliorating the effects of a disease involving axon degeneration in a subject, and methods for treating or ameliorating the effects of a neurodegenerative disease.

87 Claims, 122 Drawing Sheets

Specification includes a Sequence Listing.

(56) References Cited

OTHER PUBLICATIONS

Spiller, et al. Microglia-mediated recovery from ALS-relevant motor neuron degeneration in a mouse model of TDP-43 proteinopathy. Nat Neurosci 21, 329-340 (2018).
Stein, et al. "A quantitative framework to evaluate modeling of cortical development by neural stem cells,," Neuron. 2014;83(1):69-86.
Takuma, et al. "Reduction of GluR2 RNA editing, a molecular change that increases calcium influx through AMPA receptors, selective in the spinal ventral gray of patients with amyotrophic lateral sclerosis," Ann Neurol. 1999;46(6):806-15.
Tan, et al. "Discovery of Type II Inhibitors of TGFβ-Activated Kinase 1 (TAK1) and Mitogen-Activated Protein Kinase Kinase Kinase 2 (MAP4K2)," J. Med. Chem. 2015, 58 (1), 183.
Tang, et al. An RNA interference-based screen identifies MAP4K4/NIK as a negative regulator of PPARγ, adipogenesis, and insulin-responsive hexose transport. P Natl Acad Sci USA 103, 2087-2092 (2006).
Tesz, et al. "Tumor Necrosis Factor a (TNFa) Stimulates Map4k4 Expression through TNFa Receptor 1 Signaling to c-Jun and Activating Transcription Factor 2," J Biol Chem 282, 19302-19312 (2007).
Tradewell, et al. "Calcium dysregulation, mitochondrial pathology and protein aggregation in a culture model of amyotrophic lateral sclerosis: mechanistic relationship and differential sensitivity to intervention," Neurobiol Dis. 2011;42(3):265-75.
Trias, et al. "Post-paralysis tyrosine kinase inhibition with masitinib abrogates neuroinflammation and slows disease progression in inherited amyotrophic lateral sclerosis," J Neuroinflamm 13, 177 (2016).
Tsujihata, et al. "The motor end-plate fine structure and ultrastructural localization of acetylcholine receptors in amyotrophic lateral sclerosis," Muscle Nerve. 1984;7(3):243-9.
Uppala, et al. "Chemical chaperone, TUDCA unlike PBA, mitigates protein aggregation efficiently and resists ER and non-ER stress induced HepG2 cell death," Sci Rep. 2017;7(1):3831.
Urano, et al. "Coupling of stress in the ER to activation of JNK protein kinases by transmembrane protein kinase IRE1," Science. 2000;287(5453):664-6.
Velde, et al. "Selective association of misfolded ALS-linked mutant SOD1 with the cytoplasmic face of mitochondria," Proc Natl Acad Sci U S A. 2008;105(10):4022-7.
Virbasius, et al. "Map4k4 Signaling Nodes in Metabolic and Cardiovascular Diseases," Trends Endocrinol Metabolism 27, 484-492 (2016).
Von Lewinski, et al. "Ca2+, mitochondria and selective motoneuron vulnerability: implications for ALS," Trends Neurosci. 2005;28(9):494-500.
Wainger, et al. "Intrinsic membrane hyperexcitability of amyotrophic lateral sclerosis patient-derived motor neurons," Cell Rep. 2014;7(1):1-11.
Wang, et al. "Progressive aggregation despite chaperone associations of a mutant SOD1-YFP in transgenic mice that develop ALS," Proc Natl Acad Sci U S A. 2009;106(5):1392-7.
Wichterle, et al. "Directed differentiation of embryonic stem cells into motor neurons," Cell. 2002;110(3):385-97.
Wright, et al. "The STE20 Kinase HGK Is Broadly Expressed in Human Tumor Cells and Can Modulate Cellular Transformation, Invasion, and Adhesion," Mol Cell Biol 23, 2068-2082 (2003).
Wu, et al. "MAP4K4 Activation Mediates Motor Neuron Degeneration in Amyotrophic Lateral Sclerosis," Cell Reports 26, 1143-1156.e5 (2019).
Yang, et al. "A small molecule screen in stem-cell-derived motor neurons identifies a kinase inhibitor as a candidate therapeutic for ALS," Cell Stem Cell. 2013;12(6):713-26.
Yang, et al. "Pathological Axonal Death through a MAPK Cascade that Triggers a Local Energy Deficit," Cell 160, 161-176 (2015).
Yao, et al. "A Novel Human STE20-related Protein Kinase, HGK, That Specifically Activates the c-Jun N-terminal Kinase Signaling Pathway," J Biol Chem 274, 2118-2125 (1999).
Alami, et al. "Axonal transport of TDP-43 mRNA granules is impaired by ALS-causing mutations," Neuron. 2014;81(3):536-43.
Ammirati, et al. "Discovery of anin VivoTool to Establish Proof-of-Concept for MAP4K4-Based Antidiabetic Treatment," Acs Med Chem Lett 6, 1128-1133 (2015).
Amoroso,et al. "Accelerated high-yield generation of limb-innervating motor neurons from human stem cells," J Neurosci. 2013;33(2):574-86.
Anastassiadis, et al. "Comprehensive assay of kinase catalytic activity reveals features of kinase inhibitor selectivity," Nat Biotechnol 29, 1039 (2011).
Aouadi, et al. "Orally delivered siRNA targeting macrophage Map4k4 suppresses systemic inflammation," Nature 458, 1180 (2009).
Atkin, et al. "Induction of the unfolded protein response in familial amyotrophic lateral sclerosis and association of protein-disulfide isomerase with superoxide dismutase 1," J Biol Chem. 2006;281(40):30152-65 (Withdrawn).
Atkin, et al. "Endoplasmic reticulum stress and induction of the unfolded protein response in human sporadic amyotrophic lateral sclerosis," Neurobiol Dis. 2008;30(3):400-7 (Retracted).
Azzouz, et al. "Progressive motor neuron impairment in an animal model of familial amyotrophic lateral sclerosis," Muscle Nerve. 1997;20(1):45-51.
Banerjee, et al. "Characterization of WZ4003 and HTH-01-015 as selective inhibitors of the LKB1-tumour-suppressor-activated NUAK kinases," Biochem J 457, 215-225.
Bernard-Marissal et al. "Reduced calreticulin levels link endoplasmic reticulum stress and Fas-triggered cell death in motoneurons vulnerable to ALS," J Neurosci. 2012;32(14):4901-12.
Blokhuis, et al. "Protein aggregation in amyotrophic lateral sclerosis," Acta Neuropathol. 2013, 125 (6), 777.
Boillee, et al. "Onset and progression in inherited ALS determined by motor neurons and microglia," Science. 2006;312(5778):1389-92.
Bosco, et al. "Wild-type and mutant SOD1 share an aberrant conformation and a common pathogenic pathway in ALS," Nat Neurosci. 2010;13(11):1396-403.
Bouzakri, et al. "MAP4K4 Gene Silencing in Human Skeletal Muscle Prevents Tumor Necrosis Factor-a-induced Insulin Resistance," J Biol Chem 282, 7783-7789 (200).
Carriedo, et al. "AMPA exposures induce mitochondrial Ca(2+) overload and ROS generation in spinal motor neurons in vitro," J Neurosci 2000;20(1):240-50.
Carriedo, et al. "Motor neurons are selectively vulnerable to AMPA/kainate receptor-mediated injury in vitro," J Neurosci. 1996;16(13):4069-79.
Chiu et al. "Age-dependent penetrance of disease in a transgenic mouse model of familial amyotrophic lateral sclerosis," Mol Cell Neurosci. 1995;6(4):349-62.
Chiu, et al. "A Neurodegeneration-Specific Gene-Expression Signature of Acutely Isolated Microglia from an Amyotrophic Lateral Sclerosis Mouse Model," Cell Reports 4, 385-401 (2013).
Chuang, et al. "HGK/MAP4K4 deficiency induces TRAF2 stabilization and Th17 differentiation leading to insulin resistance," Nat Commun 5, 4602 (2014).
Corradin, et al. "Inducible nitric oxide synthase activity of cloned murine microglial cells," Glia 7, 255-262 (1993).
Danai, et al. "Inducible Deletion of Protein Kinase Map4k4 in Obese Mice Improves Insulin Sensitivity in Liver and Adipose Tissues," Mol Cell Biol 35, 2356-2365 (2015).
De Stefani, et al. "VDAC1 selectively transfers apoptotic Ca2+ signals to mitochondria," Cell Death Differ. 2012;19(2):267-73.
Devlin, et al. "Human iPSC-derived motoneurons harbouring TARDBP or C9ORF72 ALS mutations are dysfunctional despite maintaining viability," Nat Commun. 2015;6:5999.
Di Giorgio, et al. "Human embryonic stem cell-derived motor neurons are sensitive to the toxic effect of glial cells carrying an ALS-causing mutation," Cell Stem Cell. 2008;3(6):637-48.
Di Giorgio, et al. "Non-cell autonomous effect of glia on motor neurons in an embryonic stem cell-based ALS model," Nat Neurosci. 2007;10(5):608-14.

(56) References Cited

OTHER PUBLICATIONS

Dimos, et al. "Induced pluripotent stem cells generated from patients with ALS can be differentiated into motor neurons," Science. 2008;321(5893):1218-21.
Donnelly, et al. "RNA toxicity from the ALS/FTD C9ORF72 expansion is mitigated by antisense intervention," Neuron. 2013;80(2):415-28.
Doutheil, et al. "Relation of neuronal endoplasmic reticulum calcium homeostasis to ribosomal aggregation and protein synthesis: implications for stress-induced suppression of protein synthesis," Brain Res. 1997;775(1-2):43-51.
Egawa, et al. "Drug screening for ALS using patient-specific induced pluripotent stem cells," Sci Transl Med. 2012;4(145):145ra04.
Flach, et al. "Protein Kinase Mitogen-activated Protein Kinase Kinase Kinase Kinase 4 (MAP4K4) Promotes Obesity-induced Hyperinsulinemia," J Biol Chem 291, 16221-16230 (2016).
Flach, et al. "Map4k4 impairs energy metabolism in endothelial cells and promotes insulin resistance in obesity," Am J Physiol-Endoc M 313, E303-E313 (2017).
Gallo, et al. "Signalling: Mixed-lineage kinase control of JNK and p38 MAPK pathways," Nat Rev Mol Cell Bio 3, 663 (2002).
Gardner, et al. "Endoplasmic reticulum stress sensing in the unfolded protein response," Cold Spring Harb Perspect Biol. 2013;5(3):a013169.
Goeger, et al. "Cyclopiazonic acid inhibition of the Ca2+-transport ATPase in rat skeletal muscle sarcoplasmic reticulum vesicles," Biochem Pharmacol. 1988;37(5):978-81.
Goodfellow, et al. "Discovery, Synthesis, and Characterization of an Orally Bioavailable, Brain Penetrant Inhibitor of Mixed Lineage Kinase 3," J Med Chem 56, 8032-8048 (2013).
Gowing, et al. "Ablation of Proliferating Microglia Does Not Affect Motor Neuron Degeneration in Amyotrophic Lateral Sclerosis Caused by Mutant Superoxide Dismutase," J Neurosci 28, 10234-10244 (2008).
Grad, et al. "Intercellular propagated misfolding of wild-type Cu/Zn superoxide dismutase occurs via exosome-dependent and -independent mechanisms," Proc Natl Acad Sci USA. 2014;111(9):3620-5.
Gros-Louis, et al. "Intracerebroventricular infusion of monoclonal antibody or its derived Fab fragment against misfolded forms of SOD1 mutant delays mortality in a mouse model of ALS," J Neurochem. 2010; 113(5): 1188-99.
Gurney, et al. "Motor neuron degeneration in mice that express a human Cu,Zn superoxide dismutase mutation," Science. 1994;264(5166):1772-5.
Haidet-Phillips, et al. "Astrocytes from familial and sporadic ALS patients are toxic to motor neurons," Nat Biotechnol. 2011;29(9):824-8.
Hall, et al. "Relationship of microglial and astrocytic activation to disease onset and progression in a transgenic model of familial ALS," Glia 23, 249-256 (1998).
Han, et al. "Lowered HGK expression inhibits cell invasion and adhesion in hepatocellular carcinoma cell line HepG2," World J Gastroentero 16, 4541-4548 (2010).
Hanson, et al. "Cyclic AMP elevation is sufficient to promote the survival of spinal motor neurons in vitro," J Neurosci. 1998;18(18):7361-71.
Henderson, et al. "GDNF: a potent survival factor for motoneurons present in peripheral nerve and muscle," Science. 1994;266(5187):1062-4.
Hetz,et al. "ER stress and the unfolded protein response in neurodegeneration," Nat Rev Neurol. 2017;13(8):477-91.
Hetz, et al. "XBP-1 deficiency in the nervous system protects against amyotrophic lateral sclerosis by increasing autophagy," Genes Dev. 2009;23(19):2294-306.
Hetz, "The unfolded protein response: controlling cell fate decisions under ER stress and beyond," Nat Rev Mol Cell Biol. 2012;13(2):89-102.
International Search Report and Written Opinion for PCT/US2019/020362 dated Jul. 1, 2019.

Hoing, et al. "Discovery of inhibitors of microglial neurotoxicity acting through multiple mechanisms using a stem-cell-based phenotypic assay," Cell Stem Cell. 2012;11(5):620-32.
Imamura, et al. "The Src/c-Abl pathway is a potential therapeutic target in amyotrophic lateral sclerosis," Sci Transl Med 9, (2017).
Islam, et al. "Mechanisms of LRRK2-dependent neurodegeneration: role of enzymatic activity and protein aggregation," Biochem Soc T 45, 163-172 (2017).
Iurlaro et al. "Cell death induced by endoplasmic reticulum stress," FEBS J. 2016;283(14):2640-52.
Jaiswal et al. "Cu/Zn superoxide dismutase typical for familial amyotrophic lateral sclerosis increases the vulnerability of mitochondria and perturbs Ca2+ homeostasis in SOD1G93A mice," Mol Pharmacol. 2009;75(3):478-89.
Jaiswal et al. "Impairment of mitochondrial calcium handling in a mtSOD1 cell culture model of motoneuron disease," BMC Neurosci. 2009;10:64.
Jayaraman, et al. "T cells deficient in inositol 1,4,5-trisphosphate receptor are resistant to apoptosis," Mol Cell Biol. 1997;17(6):3005-12.
Jeohn, et al. "The indolocarbazole Go6976 protects neurons from lipopolysaccharide/interferon-gamma-induced cytotoxicity in murine neuron/glia co-cultures," Brain Res Mol Brain Res. 2000;79(1-2):32-44.
Johnson-Kerner, et al. "Intermediate filament protein accumulation in motor neurons derived from giant axonal neuropathy iPSCs rescued by restoration of gigaxonin," Hum Mol Genet. 2015;24(5):1420-31.
Kaemmerer, et al. "Creatine-supplemented diet extends Purkinje cell survival in spinocerebellar ataxia type 1 transgenic mice but does not prevent the ataxic phenotype," Neuroscience. 2001;103(3):713-24.
Kang, et al. "Degeneration and impaired regeneration of gray matter oligodendrocytes in amyotrophic lateral sclerosis," Nat Neurosci. 2013;16(5):571-9.
Kaplan, et al. "Neuronal matrix metalloproteinase-9 is a determinant of selective neurodegeneration," Neuron. 2014;81(2):333-48.
Kase, et al. "K-252 compounds, novel and potent inhibitors of protein kinase C and cyclic nucleotide-dependent protein kinases," Biochem Biophys Res Commun. 1987;142(2):436-40.
Kawaguchi et al. "The role of the transcriptional regulator Ptf1a in converting intestinal to pancreatic progenitors," Nat Genet. 2002;32(1):128-34.
Kawamata et al. "Mitochondrial dysfunction and intracellular calcium dysregulation in ALS," Mech Ageing Dev. 2010;131(7-8):517-26.
Keene, et al. "Tauroursodeoxycholic acid, a bile acid, is neuroprotective in a transgenic animal model of Huntington's disease," Proc Natl Acad Sci U S A. 2002;99(16):10671-6.
Keene, et al. "A bile acid protects against motor and cognitive deficits and reduces striatal degeneration in the 3-nitropropionic acid model of Huntington's disease," Exp Neurol. 2001;171(2):351-60.
Kikuchi, et al. "Spinal cord endoplasmic reticulum stress associated with a microsomal accumulation of mutant superoxide dismutase-1 in an ALS model," Proc Natl Acad Sci U S A. 2006; 103(15):6025-30.
Kim, et al. "The mitochondrial calcium regulator cyclophilin D is an essential component of oestrogen-mediated neuroprotection in amyotrophic lateral sclerosis," Brain. 2012;135(Pt 9):2865-74.
Kiskinis, et al. "Pathways disrupted in human ALS motor neurons identified through genetic correction of mutant SOD1," Cell Stem Cell. 2014;14(6):781-95.
Kozutsumi, et al. "The presence of malfolded proteins in the endoplasmic reticulum signals the induction of glucose-regulated proteins," Nature. 1988;332(6163):462-4.
Larhammar, et al. "Dual leucine zipper kinase-dependent PERK activation contributes to neuronal degeneration following insult," Elife 6, e20725 (2017b).
Larhammar, et al. "The Ste20 Family Kinases MAP4K4, MINK1, and TNIK Converge to Regulate Stress-Induced JNK Signaling in Neurons," J Neurosci 37, 11074-11084 (2017a).

(56) References Cited

OTHER PUBLICATIONS

Lasagna-Reeves, et al. "Reduction of Nuak1 decreases tau and reverses phenotypes in a tauopathy mouse model," Neuron 2016, 92 (2), 407.

Lin, et al. RBM4-SRSF3-MAP4K4 splicing cascade modulates the metastatic signature of colorectal cancer cell. Biochimica Et Biophysica Acta Bba—Mol Cell Res 1865 (2018).

Liu, et al. "Direct Lineage Reprogramming Reveals Disease-Specific Phenotypes of Motor Neurons from Human ALS Patients," Cell Rep. 2016;14(1):115-28.

Lytton et al.. "Thapsigargin inhibits the sarcoplasmic or endoplasmic reticulum Ca-ATPase family of calcium pumps," J Biol Chem. 1991;266(26):17067-71.

Madisen, et al. "A robust and high-throughput Cre reporting and characterization system for the whole mouse brain," Nat Neurosci. 2010;13(1):133-40.

Maeder, et al. "Rapid "open-source" engineering of customized zinc-finger nucleases for highly efficient gene modification," Mol Cell. 2008;31(2):294-301.

Marker, et al. "The New Small-Molecule Mixed-Lineage Kinase 3 Inhibitor URMC-099 Is Neuroprotective and Anti-Inflammatory in Models of Human Immunodeficiency Virus-Associated Neurocognitive Disorders," J Neurosci 33,9998-10010 (2013).

Maselli, et al. "Neuromuscular transmission in amyotrophic lateral sclerosis," Muscle Nerve. 1993;16(11):1193-203.

Maury, et al. "Combinatorial analysis of developmental cues efficiently converts human pluripotent stem cells into multiple neuronal subtypes," Nat Biotechnol 33,89-96 (2014).

Medinas, et al. "ER stress links aging to sporadic ALS," Aging (2019), vol. 11, No. 1 pp. 5-6.

Miles, et al. "Functional properties of motoneurons derived from mouse embryonic stem cells," J Neurosci. 2004;24(36):7848-58.

Nagai, et al. "Astrocytes expressing ALS-linked mutated SOD1 release factors selectively toxic to motor neurons," Nat Neurosci. 2007;10(5):615-22.

Naujock, et al. "4-Aminopyridine Induced Activity Rescues Hypoexcitable Motor Neurons from Amyotrophic Lateral Sclerosis Patient-Derived Induced Pluripotent Stem Cells," Stem Cells. 2016;34(6):1563-75.

Ndubaku, et al. "Structure-Based Design of GNE-495, a Potent and Selective MAP4K4 Inhibitor with Efficacy in Retinal Angiogenesis," Acs Med Chem Lett 6, 913-918 (2015).

Nishitoh, et al. "ALS-linked mutant SOD1 induces ER stress- and ASK1-dependent motor neuron death by targeting Derlin-1," Genes Dev. 2008;22(11):1451-64.

Nunes, et al. "TUDCA, a bile acid, attenuates amyloid precursor protein processing and amyloid-beta deposition in APP/PS1 mice," Mol Neurobiol. 2012;45(3):440-54.

Oppenheim, et al. "Brain-derived neurotrophic factor rescues developing avian motoneurons from cell death," Nature. 1992;360(6406):755-7.

Oslowski, et al. "Measuring ER stress and the unfolded protein response using mammalian tissue culture system," Methods Enzymol. 2011;490:71-92.

Ozcan, et al. "Chemical chaperones reduce ER stress and restore glucose homeostasis in a mouse model of type 2 diabetes," Science. 2006;313(5790):1137-40.

Paliulis, et al. "Improved Synthesis of 8-Methyl-3, 8-Diazabicyclo [3.2.1] Octane," Org. Prep. Proced. Int. 2007, 39 (1), 86.

Parone, et al. "Enhancing mitochondrial calcium buffering capacity reduces aggregation of misfolded SOD1 and motor neuron cell death without extending survival in mouse models of inherited amyotrophic lateral sclerosis," J Neurosci. 2013;33(11):4657-71.

Patterson, et al. "Defining the nature of human pluripotent stem cell progeny," Cell Res. 2012;22(1):178-93.

Peters, et al. "Emerging mechanisms of molecular pathology in ALS," J Clin Invest. 2015;125(6):2548.

Pinton, et al. "Calcium and apoptosis: ER-mitochondria Ca2+ transfer in the control of apoptosis," Oncogene. 2008;27(50):6407-18.

Pulverer, et al. "Phosphorylation of c-jun mediated by MAP kinases," Nature 353, 353670a0 (1991).

Qiu, et al. "Expression and prognostic significance of MAP4K4 in lung adenocarcinoma," Pathology—Res Pract 208, 541-548 (2012).

Rothstein, et al. "Abnormal excitatory amino acid metabolism in amyotrophic lateral sclerosis," Ann Neurol. 1990;28(1):18-25.

Roux, et al. "K252a and CEP1347 are neuroprotective compounds that inhibit mixed-lineage kinase-3 and induce activation of Akt and ERK," J Biol Chem. 2002;277(51):49473-80.

Sakaki, et al. "Protein kinase Ctheta is required for autophagy in response to stress in the endoplasmic reticulum," J Biol Chem. 2008;283(22):15370-80.

\* cited by examiner 2-way ANOVA, ****p < 0.0001

| IV admin after 1 hour | Compound 1 | Compound 12k |
|---|---|---|
| Plasma concentration | <200 ng/mL | 375 ng/mL |
| Brain concentration | <200 ng/mL | 1949 ng/mL |

Healthy cell criterion

Fig. 15I

| | Compound name | Ratio G93A/WT | Description |
|---|---|---|---|
| 1 | DH 97 | 0.301 | MT2 receptor antagonist. |
| 2 | Monastrol | 0.490 | Selective inhibitor of mitotic kinesin Eg5. |
| 3 | Indirubin-3'-oxime | 0.505 | GSK-3β inhibitor. Also inhibits other protein kinases. |
| 4 | (E)-Capsaicin | 0.513 | Prototypic vanilloid receptor agonist. |
| 5 | Dobutamine hydrochloride | 0.536 | α1, β1 and β2 receptor agonist. |
| 6 | 2,3-DCPE hydrochloride | 0.574 | Selectively induces cancer cell apoptosis. |
| 7 | Fenretinide | 0.618 | Synthetic retinoid. Potent anti-cancer agent. |
| 8 | Cyclopiazonic Acid | 0.655 | Inhibitor of SERCA ATPase. |
| 9 | U 99194 maleate | 0.664 | Potent, selective D3 antagonist. |

Fig. 15K

| # | Compound name | Survival % G93A/WT | Description |
|---|---|---|---|
| 1 | Kenpaullone | 195/183 | Potent cyclin-dependent kinase inhibitor. Also inhibits GSK-3 and HGK. |
| 2 | Ro 31-8220 mesylate | 250/162 | Unselective protein kinase inhibitor (PKC >> other kinases). |
| 3 | PD 407824 | 138/154 | Chk-1 and Wee inhibitor. |

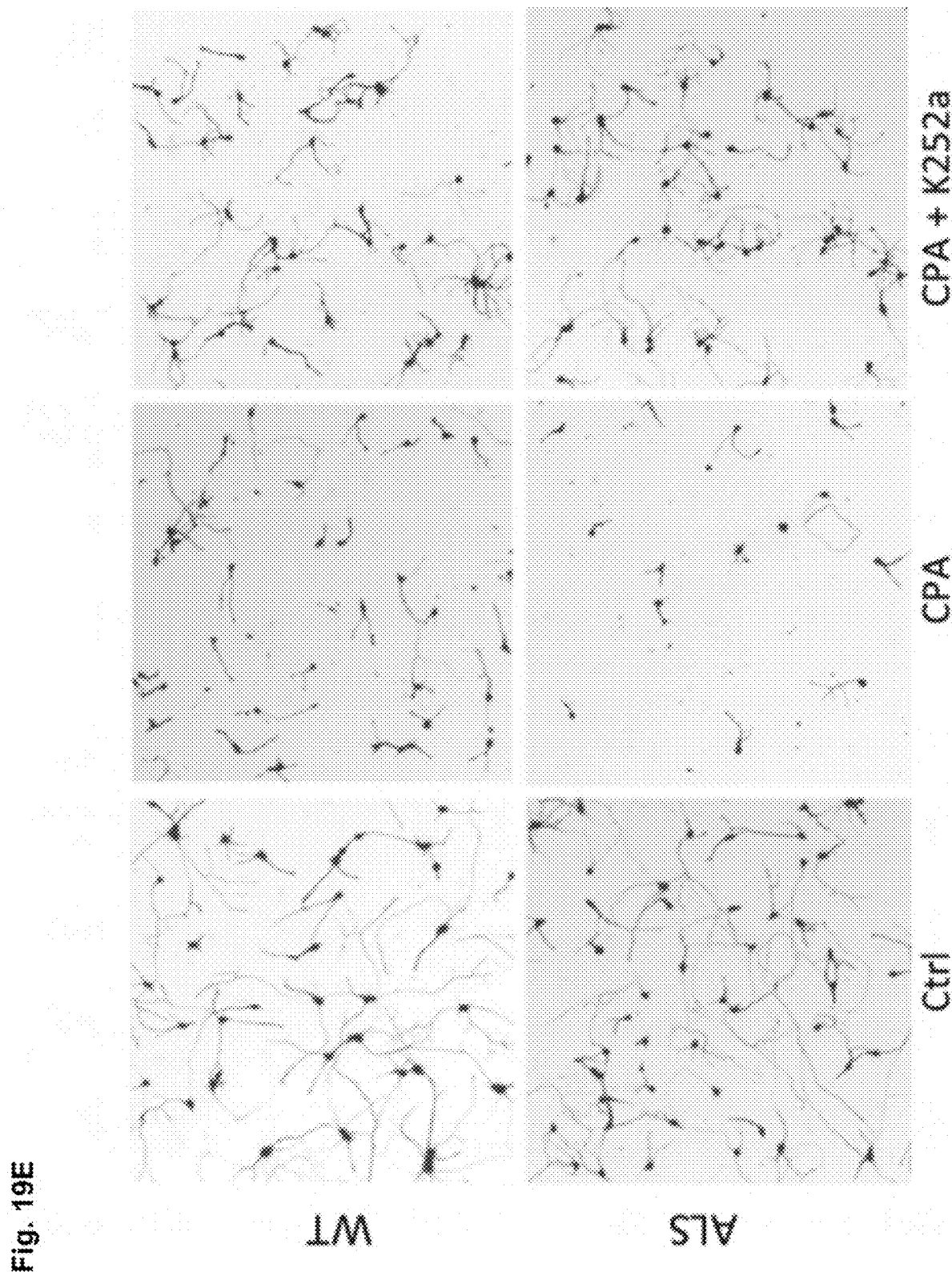

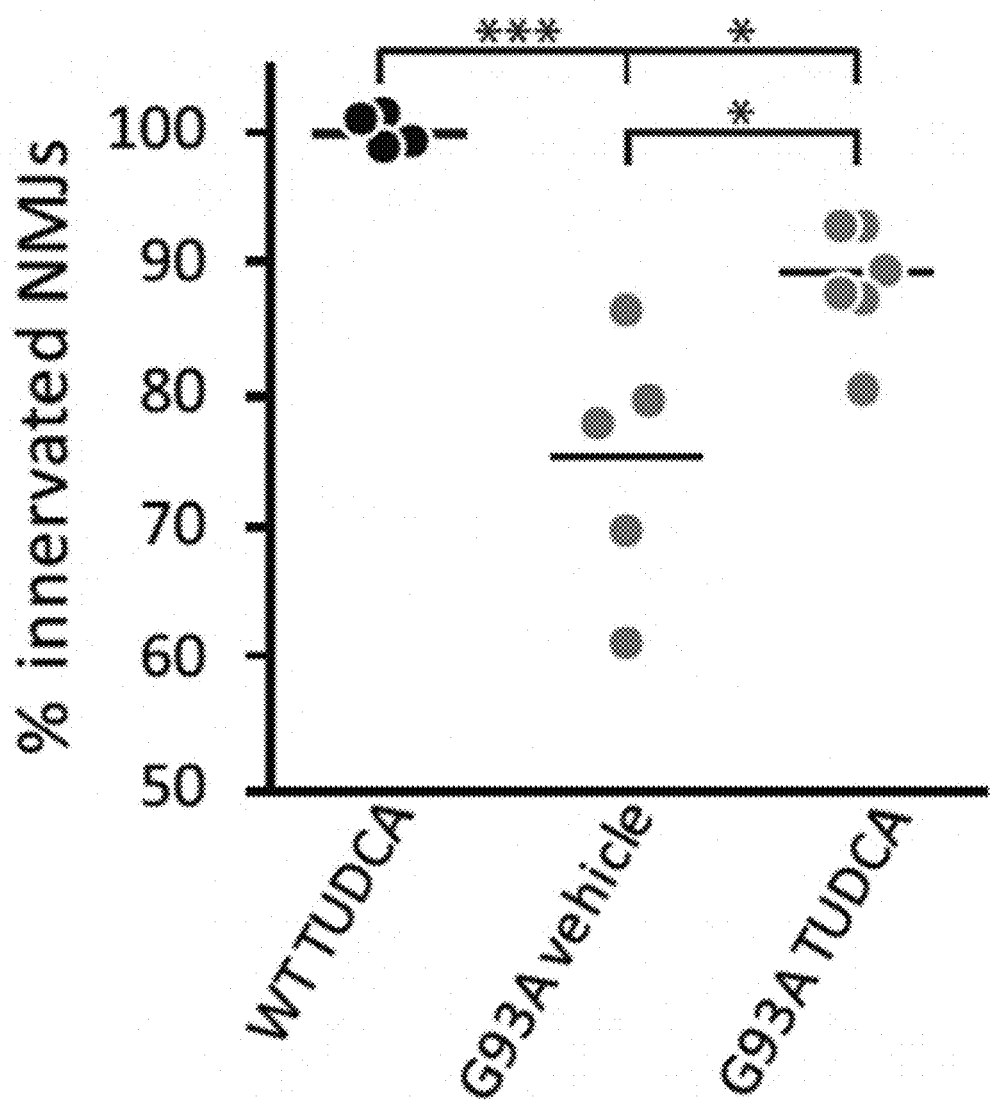

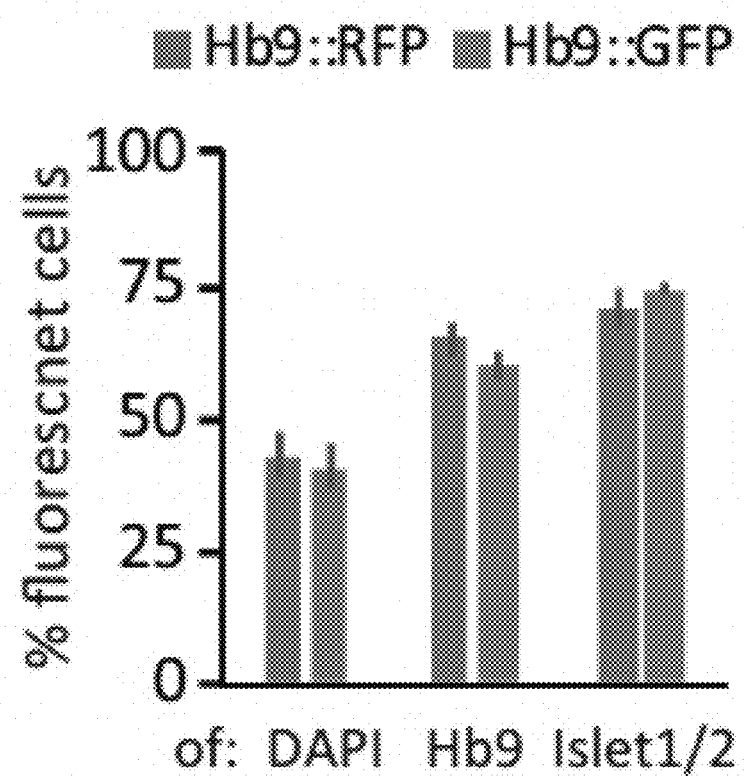

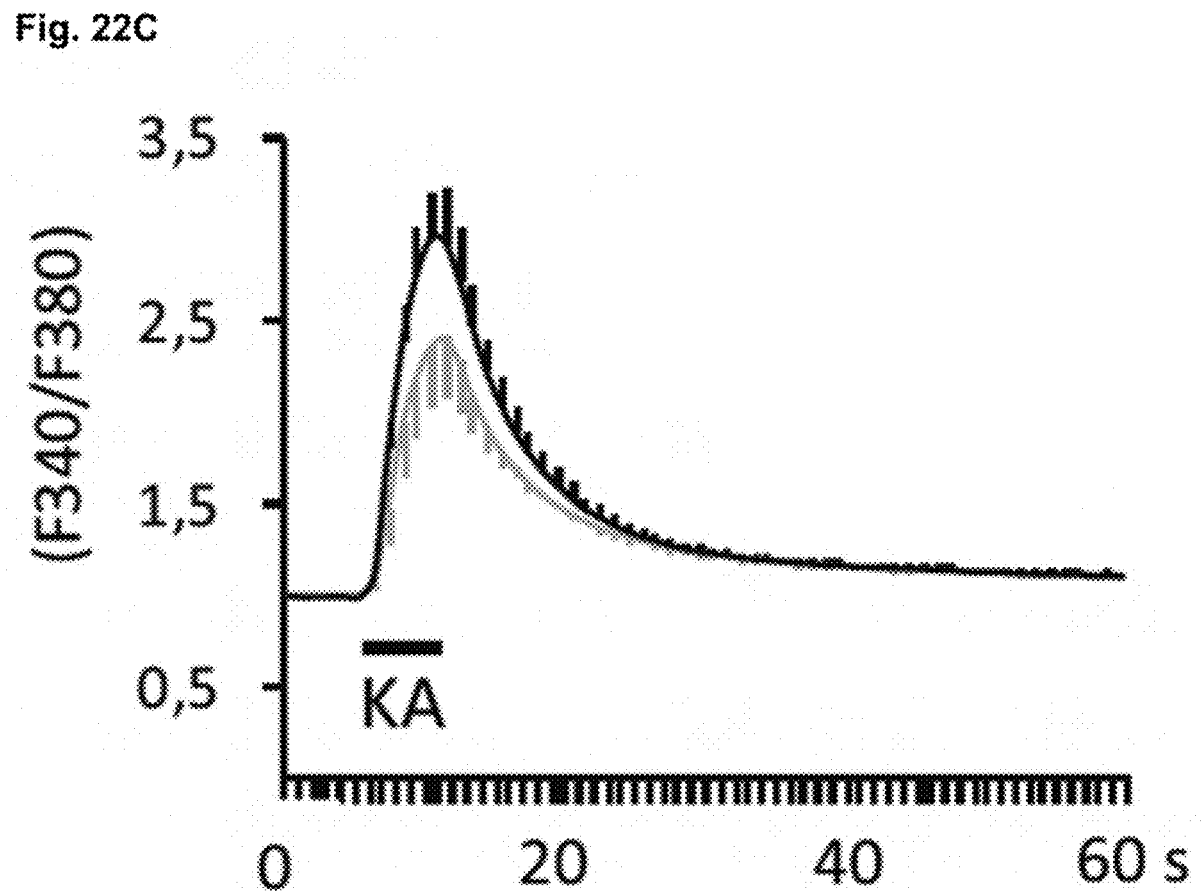

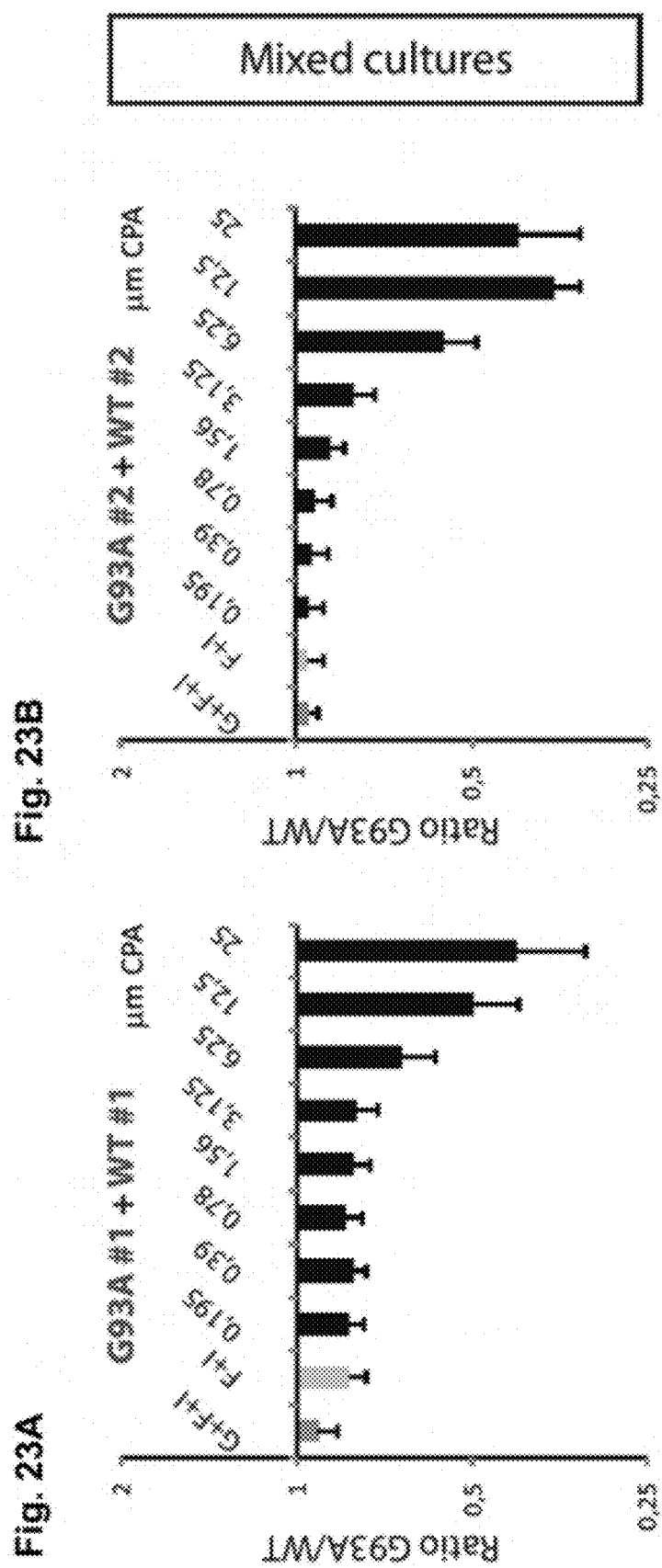

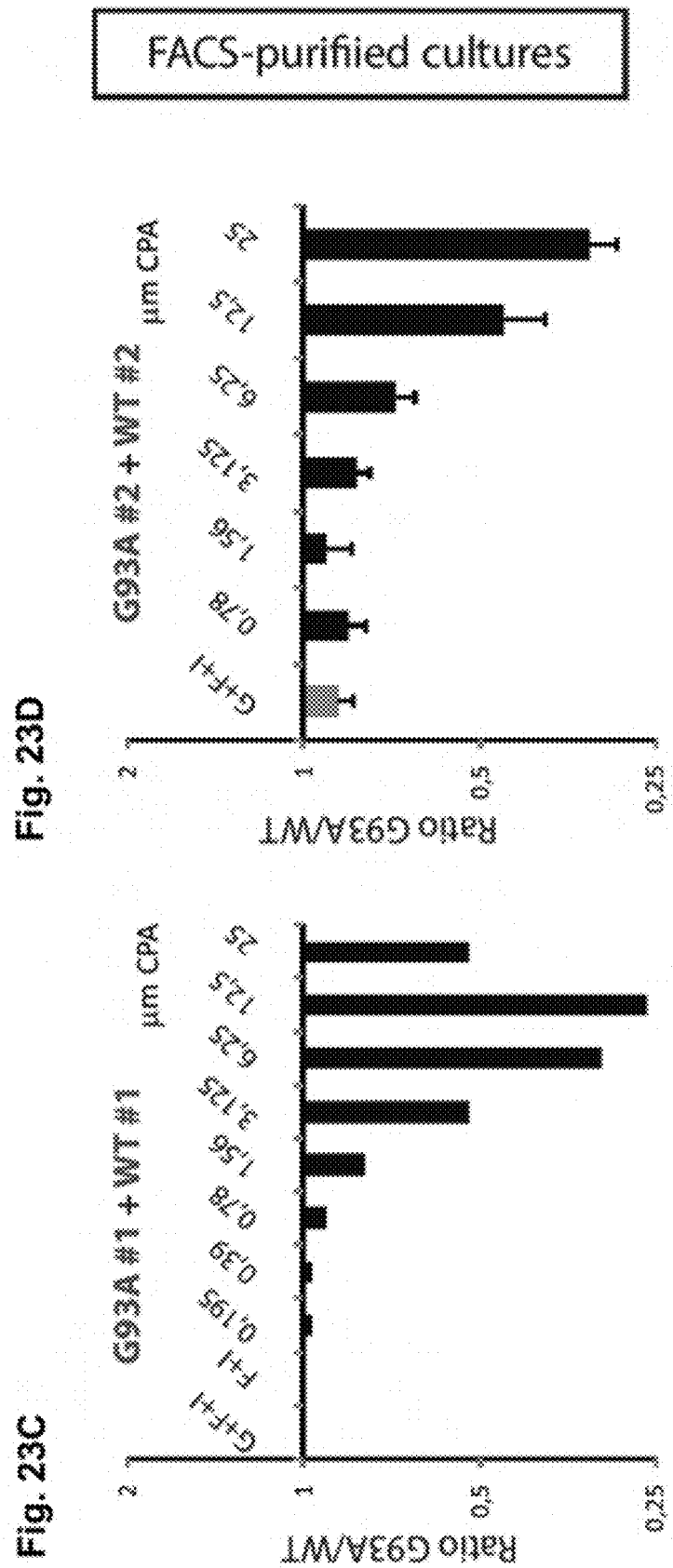

FACS: RFP

FACS: GFP

1. Mix drug with liver homogenate

2. Analyze [drug] over time by LC-MS

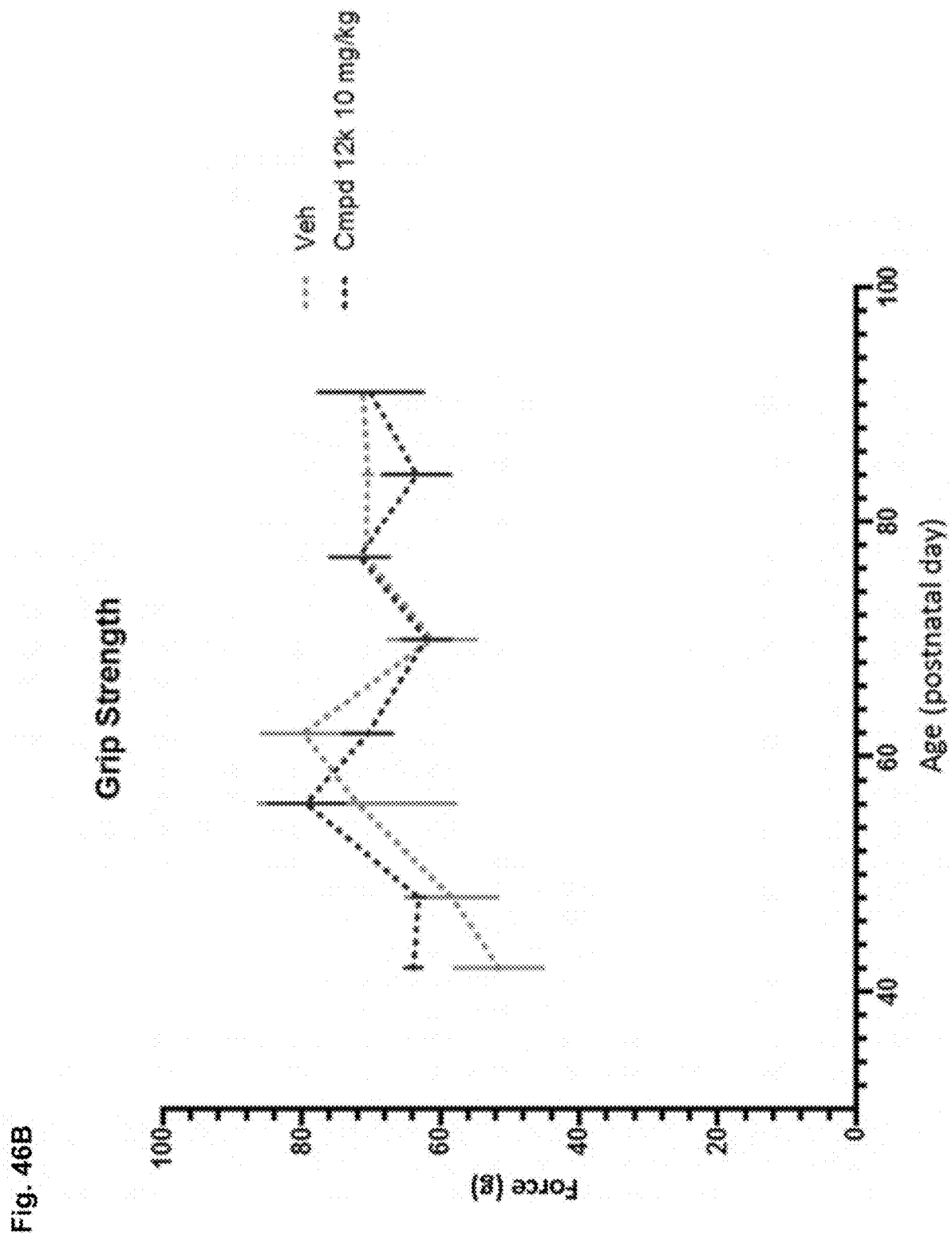

SUBSTITUTED PYRROLO[2,3-b]PYRIDINES FOR SUPPRESSING TOXIC ENDOPLASMIC RETICULUM STRESS

CROSS REFERENCE TO RELATED APPLICATIONS

The present application is a continuation of PCT international application no. PCT/US2019/020362, filed on Mar. 1, 2019, which claims benefit of U.S. Provisional Patent Application Ser. No. 62/637,242, filed on Mar. 1, 2018 which application is incorporated by reference herein in its entirety.

GOVERNMENT FUNDING

This invention was made with government support under grant no. XW81XWH-16-1-0204, awarded by DOD. The government has certain rights in the invention.

INCORPORATION BY REFERENCE OF SEQUENCE LISTING

This application contains references to amino acids and/or nucleic acid sequences that have been filed concurrently herewith as sequence listing text file "CU17020-seq.txt", file size of 1 KB, created on Sep. 1, 2020. The aforementioned sequence listing is hereby incorporated by reference in its entirety pursuant to 37 C.F.R. § 1.52(e)(5).

FIELD OF INVENTION

The present invention provides, inter alia, compounds having the structure:

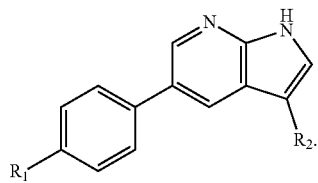

(I)

Also provided are pharmaceutical compositions containing the compounds of the present invention, as well as methods of using such compounds and compositions.

BACKGROUND OF THE INVENTION

Amyotrophic Lateral Sclerosis (ALS) is a neurodegenerative disorder that targets spinal motor neurons, the cells that control essential daily functions like moving, breathing, and eating. Like many other neurodegenerative disorders, ALS is characterized by the accumulation of misfolded proteins. Neurons engage the unfolded protein response (UPR) to re-fold or clear misfolded proteins; if these efforts are unsuccessful, the UPR gives way to endoplasmic reticulum (ER) stress pathways that commit cells to apoptotic cell death. Recent studies have implicated the UPR and ER stress in the pathogenesis of familial and sporadic ALS.

Markers of ER stress are some of the earliest pathological features that have been detected across in vitro and in vivo models of ALS, including stem cell-derived motor neurons and mice carrying ALS-linked mutations. It has been reported previously that a persistent up-regulation of ER stress markers was observed in spinal motor neurons derived from the embryonic stem (ES) cells of transgenic hSOD1$^{G93A}$ mice (see Example 12). These mice overexpress a mutant form of human SOD1 that is causally linked to ALS and their phenotype recapitulates many aspects of patient pathology, including neuromuscular denervation and progressive paralysis. ALS-causing mutations in SOD1 generally do not lead to a loss or gain of SOD1 function; instead, they promote the accumulation of misfolded SOD1 species and the formation of insoluble proteinaceous aggregates in motor neurons, which likely underlie the increase in ER stress markers in these cells. Similar aggregates have been observed across models of ALS involving multiple disease-causing mutations, including TDP-43, FUS, OPTN, and UBQLN2 (Blokhuis et al. 2013). Furthermore, it has been found that even wild-type spinal motor neurons are exceptionally sensitive to ER stress-inducing compounds like cyclopiazonic acid (CPA) (FIG. 2C) as compared to other spinal neuron sub-types. Taken together, these observations provide insight into the selective vulnerability of spinal motor neurons to ALS while other neurons are spared.

Based on the fact that motor neurons are highly susceptible to CPA, a sarco/ER calcium ATPase (SERCA) pump inhibitor that prevents $Ca^{2+}$ uptake in the ER, thereby blocking the activity of $Ca^{2+}$-dependent protein folding chaperones and rapidly inducing ER stress (FIG. 26), a library of small molecule compounds has been screened for those could reverse ER stress-induced neurodegeneration (FIG. 27).

Among the hits from this screen were over 100 biologically active small molecule, broad-spectrum kinase inhibitors, including G66976, sunitinib, K252a (FIG. 2A), and kenpaullone (see Example 12). Preliminary analysis pointed to the mitogen activated protein (MAP) kinases MLK3 and HGK as the likely functional targets of these rescue compounds. These findings were consistent with previous reports that the IRE1a branch of the ER stress pathway ultimately activates the JNK pathway, which has been associated with many neurodegenerative disease models. Previous work has also shown that CPA induces IRE1a activity and promotes the phosphorylation of c-jun, which is directly downstream of JNK (see Example 12).

Known targets have been compared for the four kinase inhibitor hit compounds as well as alsterpaullone, a structural analog of kenpaullone that was found to be more potent than kenpaullone, by mining a publicly available database (Anastassiadis et al. 2011) of the catalytic activity of 300 kinases in the presence of various kinase inhibitors at 0.5 μM and performing two-way hierarchical clustering analysis (FIG. 1).

Kinases whose activity was strongly inhibited (<15% kinase activity remaining at 1 μM inhibitor concentrations) by all 5 neuroprotective compounds included the MAP kinase HGK (MAP4K4) and the MAPK-related kinase NUAK1. NUAK1 ablation protects cortical neurons in a mouse model of tauopathy, suggesting that it might also modulate the neurotoxic effects of CPA in motor neurons (Lasagna-Reeves et al. 2016). However, it was found that the potent and selective NUAK1 inhibitor WZ4003 (IC$_{50}$ for NUAK1=20 nM) was unable to rescue CPA toxicity across a 6-point dilution series (0.1-10 μM). At concentrations of 1 μM and above, WZ4003 potentiated CPA-induced neurodegeneration and was toxic to motor neurons even in the absence of CPA (FIG. 3). Similarly, other selective NUAK 1 inhibitors, including SU6656 (10.9% activity remaining at 0.5 μM) and HTH-01-051 (IC$_{50}$=100 nM, see, Banerjee et al. 2014), not only failed to rescue CPA toxicity but further potentiated it at higher doses (FIG. 3). These results suggest that NUAK1 activity is essential to motor neuron survival in the context of ER stress and, perhaps, under basal conditions. The fact that it is a shared target of the hit rescue compounds is likely due to its structural similarity or sequence homology to the functional targets of these compounds.

Meanwhile, Yang et al. (2013) have postulated that HGK is the main functional target of kenpaullone, which they identified as a hit in a high-throughput screen for compounds that could rescue ES-derived spinal motor neurons from neurotrophic factor withdrawal-induced death. Larhammar et al (2017) later provided functional evidence that HGK, in combination with two other MAP4 kinases, TNIK and MINK1, mediates neurodegeneration following neurotrophic factor withdrawal in mouse dorsal root ganglion neurons. To further assess the role of HGK in motor neurons in the context of ER stress, the selective HGK inhibitor PF-6260933 (Ammirati et al. 2015) was tested in a 6-point dilution series (0.01 μM-5 μM) and found that it protected against CPA toxicity in a dose-dependent manner (FIG. 3). The HGK inhibitor GNE-495 was also similarly neuroprotective (FIG. 3). This finding provided preliminary support for a role of HGK in ER stress-induced neurodegeneration.

Another shared target of K252a, G66976, and alsterpaullone was the MAPK3 kinase MLK3. While kenpaullone and sunitinib only meagerly inhibited MLK3 activity (49.3% and 68.4% MLK3 activity remaining at 0.5 μM, respectively, see Anastassiadis et al, 2011), there is strong support in the literature for a role of MLK3 in many neurodegenerative contexts. It was found that a number of additional compounds that strongly (<15% activity remaining) but non-selectively inhibit MLK3 activity, including CEP1347, NU6140, Bosutinib, JAK3 inhibitor IV, and Syk inhibitor, provided dose-dependent rescue of CPA toxicity in human ES motor neurons (FIG. 3).

Based on these findings, it is hypothesized that the protective effects of the hit kinase inhibitors from the CPA survival screen were likely due to their inhibition of HGK and/or MLK3 activity. An ideal compound should: 1) strongly inhibit both HGK and MLK3, 2) completely reverse CPA-mediated neurotoxicity at low (nano- to micromolar) doses, 3) be soluble in aqueous vehicles, 4) be blood-brain barrier permeable and orally bioavailable, and 5) be amenable to further structural modification to optimize its use in vivo. However, the hit compounds from the screen did not meet these criteria. Neither G66976 nor sunitinib were able to completely rescue CPA toxicity at any of the doses tested. Meanwhile, K-252a is not a suitable lead compound due to both its broad-spectrum kinase inhibition and its recalcitrance to analog synthesis. Further dampening enthusiasm for this scaffold was the observation that a structurally related, non-specific staurosporine based kinase inhibitor, CEP-1347 (FIG. 2A), was ineffective as a neuroprotective agent in Parkinson's disease clinical trials. Kenpaullone, though highly selective, is insoluble at the concentrations we found to be effective in in vitro CPA assays and is therefore unsuitable for in vivo use Through a literature search, we identified the small molecule URMC-099 as a promising lead compound (compound 1) (FIG. 2A). Compound 1 is orally bioavailable and brain penetrant, strongly binds and inhibits both MLK3 ($IC_{50}$=14 nM) and HGK (0.54% enzyme activity remaining upon 1 μM treatment), and is amenable to analog synthesis (FIG. 28). Its ability to rescue CPA toxicity in human ALS stem cell-derived motor neurons in a 6-point dose-response assay (0.01 μM-3 μM) was tested and it was found that it completely reversed CPA-induced neurodegeneration at 1 μM, though concentrations starting at 100 nM showed protective effects (FIG. 2B).

It was then determine whether the protective effects of compound 1 following CPA treatment were mediated by HGK and MLK3. Prolonged activation of ER stress pathways leads to the activation of the JNK kinase cascade and, ultimately, apoptosis (see Sano et al., 2013). The MAP kinases JNK1-3 directly phosphorylate and activate c-jun, a transcription factor that promotes the expression of pro-apoptotic factors such as caspase 3. It has been shown previously that CPA induces the phosphorylation of c-jun in ES MNs, which are particularly vulnerable to ER stress-mediated neurodegeneration, but not in co-cultured ES-derived interneurons, which are resistant (see Example 12). It was observed that compound 1 strongly suppressed both c-jun phosphorylation and caspase 3 cleavage in CPA-treated MNs (FIG. 4), indicating that compound 1 prevents the induction of apoptosis. We then evaluated the phosphorylation state of the MAPK JNK, which is directly upstream of c-jun, and MKK4, which is directly upstream of JNK. Changes in MKK4 and JNK phosphorylation reflect the activity of upstream kinases, including HGK (a MAP4K) and/or MLK3 (a MAP3K), the putative targets of compound 1. It was observed that CPA treatment up-regulated JNK and MKK4 phosphorylation, while the addition of compound 1 strongly attenuated JNK and MKK4 phosphorylation (FIG. 4), further supporting the idea that compound 1 acts on HGK and/or MLK3 to prevent the activation of downstream apoptotic pathways.

Though these initial results were promising, compound 1 required further optimization before it could be considered a potential clinical candidate. Microsomal stability studies showed that compound 1 had a short half-life in mouse liver microsomes ($T_{1/2}$=7.8 min) and an in vivo half-life of ~2-3 h in mice. Furthermore, compound 1 is non-selective, inhibiting a number of kinases, and has a cellular potency of >100 nM, raising the possibility that more selective and potent derivatives with improved PK properties might be preferable, and obtainable.

Accordingly, there is a need for the exploration of various analogs of compound 1, as well as for compositions and methods for suppressing toxic endoplasmic reticulum (ER) stress. This invention is directed to meet these and other needs.

SUMMARY OF THE INVENTION

Without being bound to a particular theory, to aid in the design of potential analogs, the inventors docked compound 1 in a crystal structure of HGK (PDB ID: 5DI1) using Glide (FIG. 5A). From the docking pose and the binding site interaction diagram (See FIG. 5B), it was found that: 1) the 7-azaindole moiety binds to the hinge region of the kinase and is essential for activity; 2) the piperazine moiety extends into the solvent exposed region and could be modified to improve the physical properties of the molecule and enhance its stability; and 3) the sidechain could be modified to pick up additional interactions in the binding pocket and increase kinase specificity.

Accordingly, one embodiment of the present invention is a compound according to formula (I):

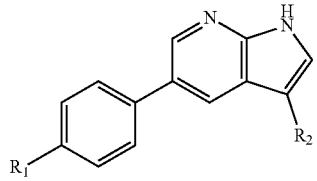
(I)

wherein:

R₁ is an alkyl-heterocycloalkyl or an alkyl-heterobicycloalkyl, wherein the heterocycloalkyl or heterobicycloalkyl is optionally substituted with one or more atoms or groups selected from alkyl, hydroxy, alcohol, or heterocycloalkyl;

R₂ is selected from phenyl, indolyl, pyridyl, dibenzofuranyl, benzodioxan, benzothiophenyl, pyrimidinyl, pyrazole, thienyl, indazole, or furanyl, any of which is optionally substituted with one or more atoms or groups selected from alkyl, alkoxy, amino, amide, cyano, ether, nitro, hydroxy, halogen, alkyl-heterocycloalkyl, sulfonyl, ketone, haloalkyl, haloalkoxy, alkylphenyl, carbamate, carboxylic acid, or urea;

or an N-oxide, crystalline form, hydrate, or a pharmaceutically acceptable salt thereof, with the proviso that the compound is not:

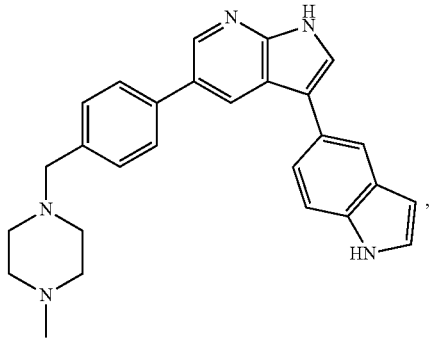
1

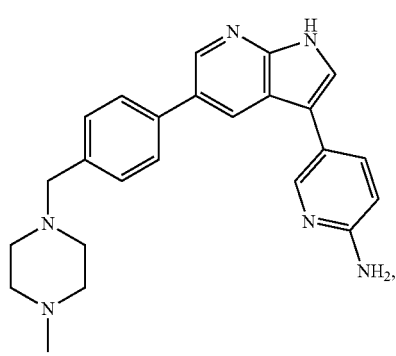
7m

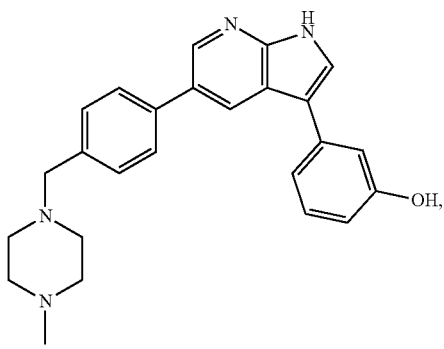
7r

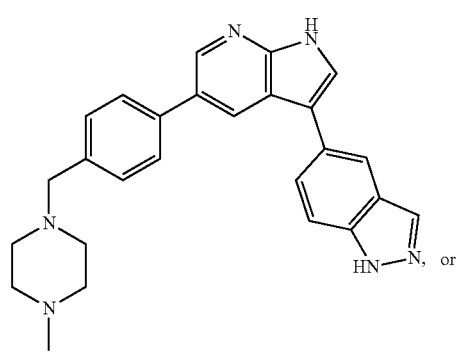
7v

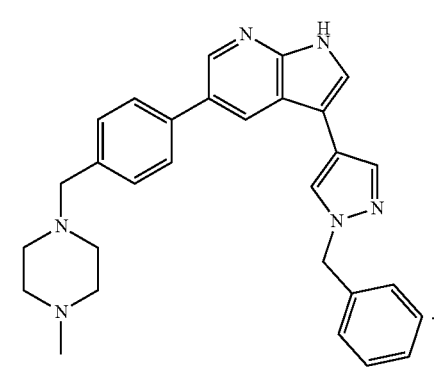
7ah

Another embodiment of the present invention is a compound having the structure of:

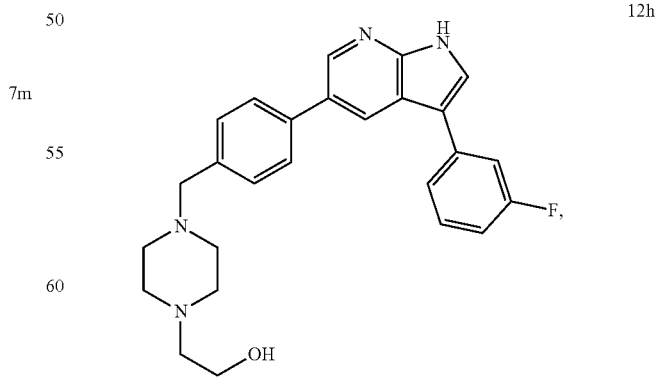
12h or an N-oxide, crystalline form, hydrate, or a pharmaceutically acceptable salt thereof.

Another embodiment of the present invention is a compound having the structure of:

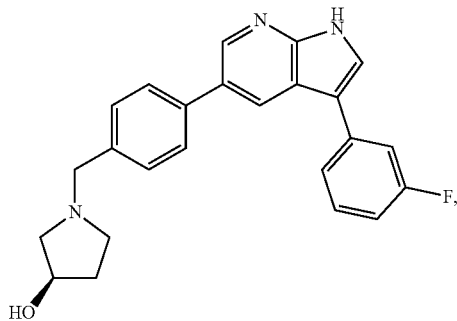

12i or an N-oxide, crystalline form, hydrate, or a pharmaceutically acceptable salt thereof.

Another embodiment of the present invention is a compound having the structure of:

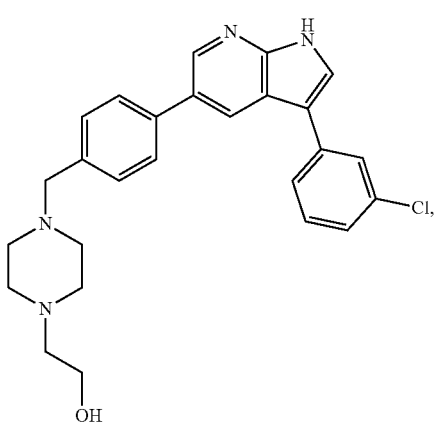

12k or an N-oxide, crystalline form, hydrate, or a pharmaceutically acceptable salt thereof.

Another embodiment of the present invention is a compound having the structure of:

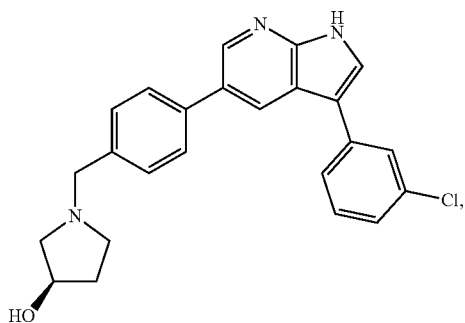

12l or an N-oxide, crystalline form, hydrate, or a pharmaceutically acceptable salt thereof.

Another embodiment of the present invention is a pharmaceutical composition. This pharmaceutical composition comprises a pharmaceutically acceptable carrier or diluent and one or more compounds according to formula (I):

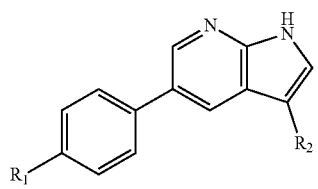

(I)

wherein:

$R_1$ is an alkyl-heterocycloalkyl or an alkyl-heterobicycloalkyl, wherein the heterocycloalkyl or heterobicycloalkyl is optionally substituted with one or more atoms or groups selected from alkyl, hydroxy, alcohol, or heterocycloalkyl;

$R_2$ is selected from phenyl, indolyl, pyridyl, dibenzofuranyl, benzodioxan, benzothiophenyl, pyrimidinyl, pyrazole, thienyl, indazole, or furanyl, any of which is optionally substituted with one or more atoms or groups selected from alkyl, alkoxy, amino, amide, cyano, ether, nitro, hydroxy, halogen, alkyl-heterocycloalkyl, sulfonyl, ketone, haloalkyl, haloalkoxy, alkylphenyl, carbamate, carboxylic acid, or urea;

or an N-oxide, crystalline form, hydrate, or a pharmaceutically acceptable salt thereof, with the proviso that the compound is not:

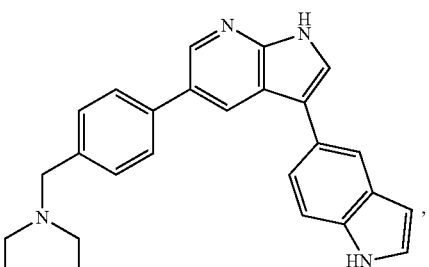

1

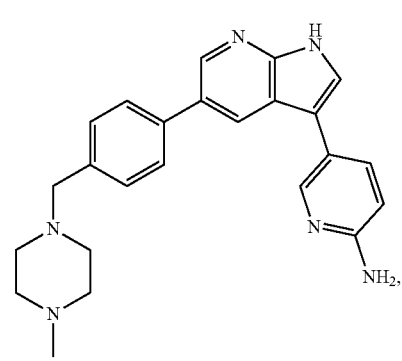

7m

-continued

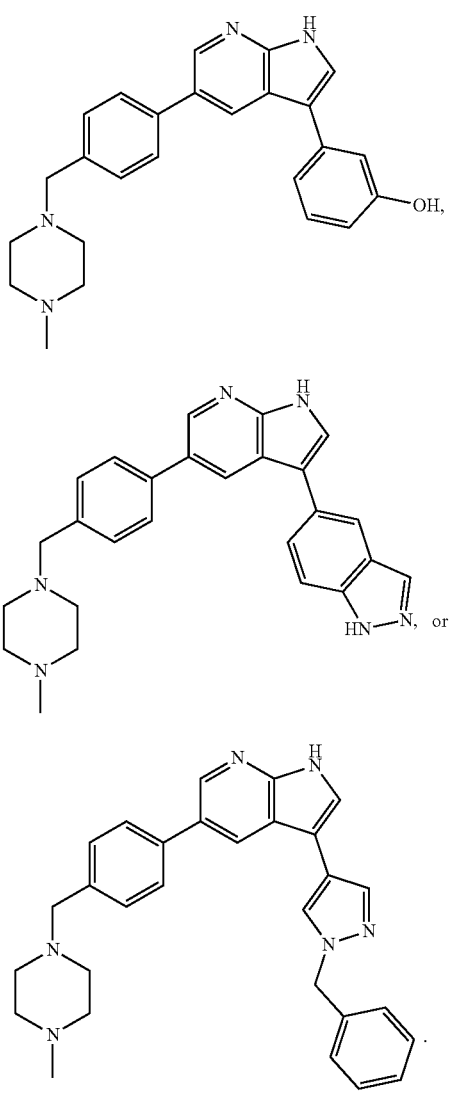

A further embodiment of the present invention is a kit. This kit comprises a compound or a pharmaceutical composition according to the present invention with instructions for the use of the compound or the pharmaceutical composition, respectively.

Another embodiment of the present invention is a method for treating or ameliorating the effects of a disorder in a subject in need thereof. This method comprises administering to the subject an effective amount of one or more compounds having the structure of formula (I):

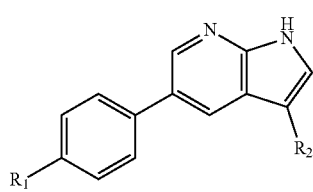

wherein:

$R_1$ is an alkyl-heterocycloalkyl or an alkyl-heterobicycloalkyl, wherein the heterocycloalkyl or heterobicycloalkyl is optionally substituted with one or more atoms or groups selected from alkyl, hydroxy, alcohol, or heterocycloalkyl;

$R_2$ is selected from phenyl, indolyl, pyridyl, dibenzofuranyl, benzodioxan, benzothiophenyl, pyrimidinyl, pyrazole, thienyl, indazole, or furanyl, any of which is optionally substituted with one or more atoms or groups selected from alkyl, alkoxy, amino, amide, cyano, ether, nitro, hydroxy, halogen, alkyl-heterocycloalkyl, sulfonyl, ketone, haloalkyl, haloalkoxy, alkylphenyl, carbamate, carboxylic acid, or urea;

or an N-oxide, crystalline form, hydrate, or a pharmaceutically acceptable salt thereof, with the proviso that the compound is not:

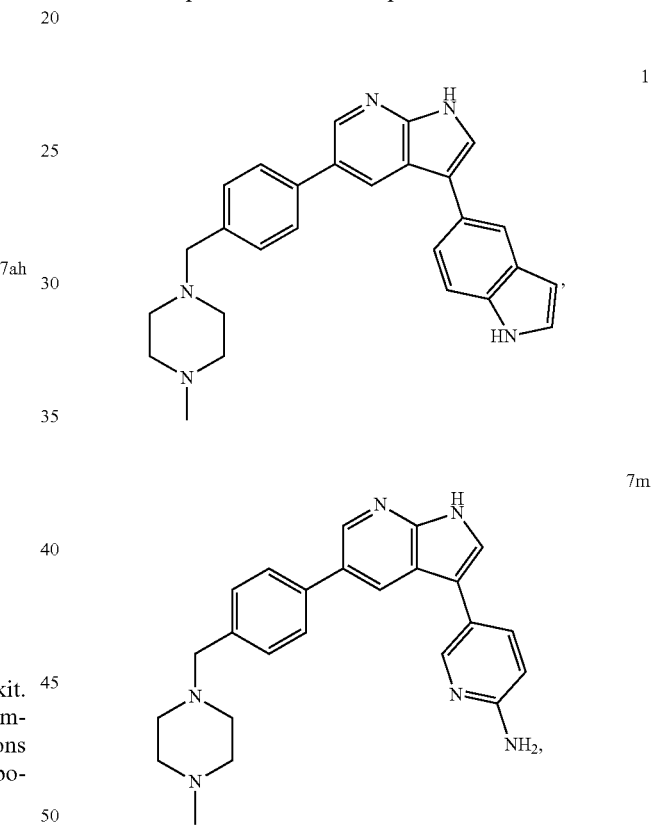

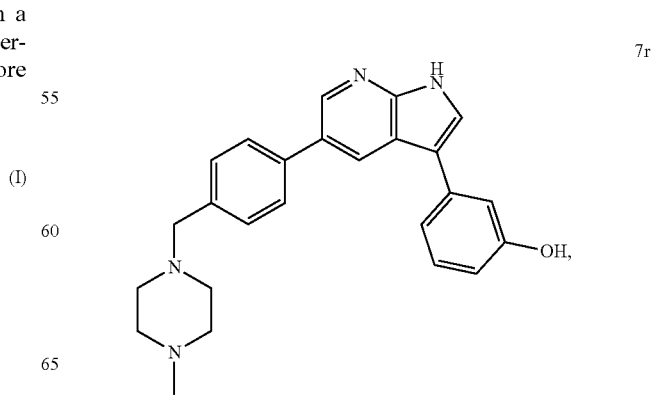

-continued

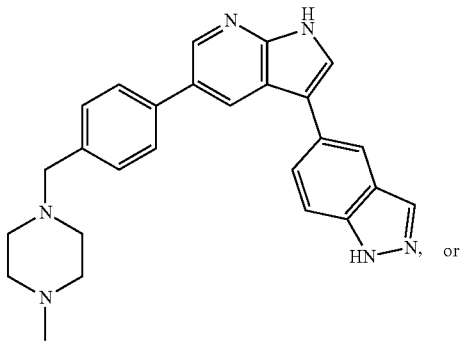
7v

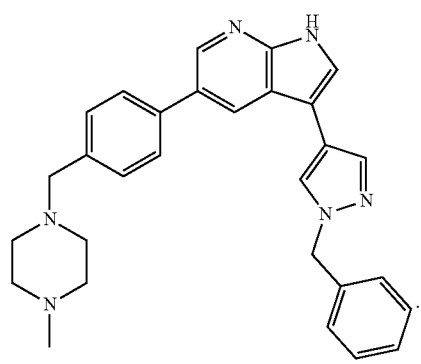
7ah

An additional embodiment of the present invention is a method for treating or ameliorating the effects of a disorder in a subject in need thereof. This method comprises administering to the subject an effective amount of a pharmaceutical composition comprising a pharmaceutically acceptable carrier or diluent and one or more compounds having the structure of formula (I):

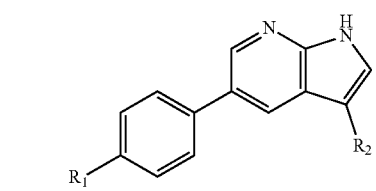
(I)

wherein:
R₁ is an alkyl-heterocycloalkyl or an alkyl-heterobicycloalkyl, wherein the heterocycloalkyl or heterobicycloalkyl is optionally substituted with one or more atoms or groups selected from alkyl, hydroxy, alcohol, or heterocycloalkyl;
R₂ is selected from phenyl, indolyl, pyridyl, dibenzofuranyl, benzodioxan, benzothiophenyl, pyrimidinyl, pyrazole, thienyl, indazole, or furanyl, any of which is optionally substituted with one or more atoms or groups selected from alkyl, alkoxy, amino, amide, cyano, ether, nitro, hydroxy, halogen, alkyl-heterocycloalkyl, sulfonyl, ketone, haloalkyl, haloalkoxy, alkylphenyl, carbamate, carboxylic acid, or urea;

or an N-oxide, crystalline form, hydrate, or a pharmaceutically acceptable salt thereof, with the proviso that the compound is not:

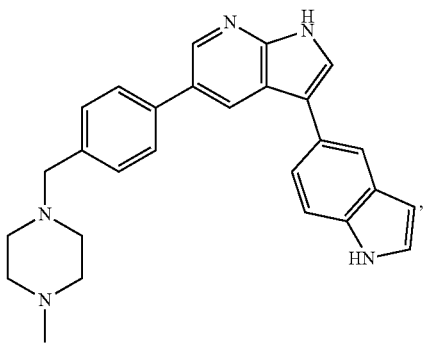
1

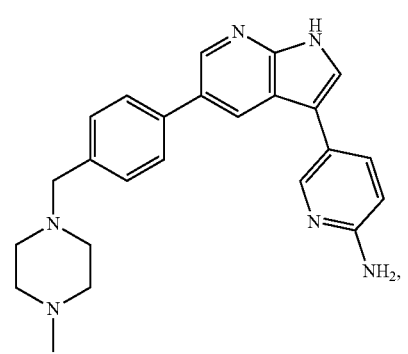
7m

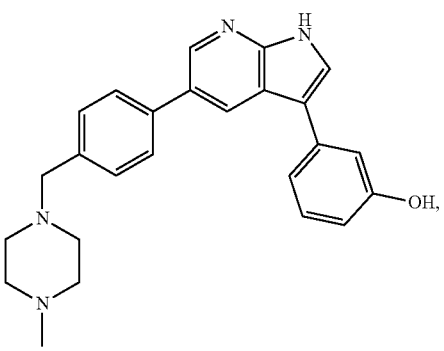
7r

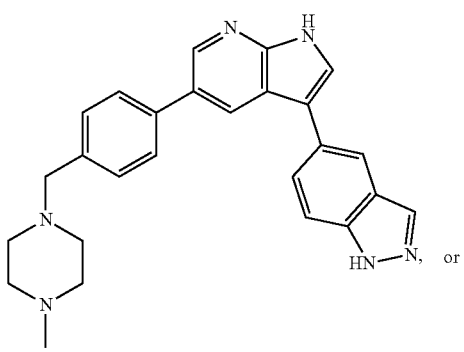
7v

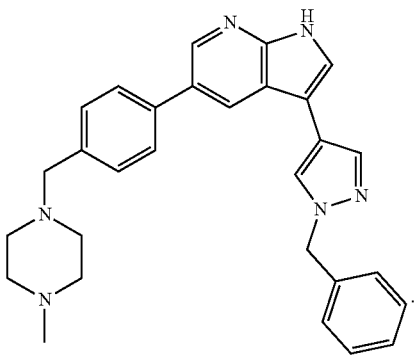

7ah

Another embodiment of the present invention is a method of suppressing the toxicity of endoplasmic reticulum (ER) stress in a subject in need thereof. This method comprises administering to the subject an effective amount of a kinase inhibitor, which comprises one or more compounds having the structure of formula (I):

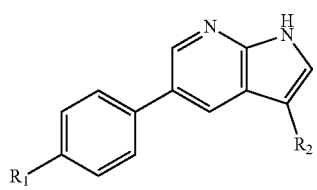

(I)

wherein:
R₁ is an alkyl-heterocycloalkyl or an alkyl-heterobicycloalkyl, wherein the heterocycloalkyl or heterobicycloalkyl is optionally substituted with one or more atoms or groups selected from alkyl, hydroxy, alcohol, or heterocycloalkyl;
R₂ is selected from phenyl, indolyl, pyridyl, dibenzofuranyl, benzodioxan, benzothiophenyl, pyrimidinyl, pyrazole, thienyl, indazole, or furanyl, any of which is optionally substituted with one or more atoms or groups selected from alkyl, alkoxy, amino, amide, cyano, ether, nitro, hydroxy, halogen, alkyl-heterocycloalkyl, sulfonyl, ketone, haloalkyl, haloalkoxy, alkylphenyl, carbamate, carboxylic acid, or urea;
or an N-oxide, crystalline form, hydrate, or a pharmaceutically acceptable salt thereof,
with the proviso that the compound is not:

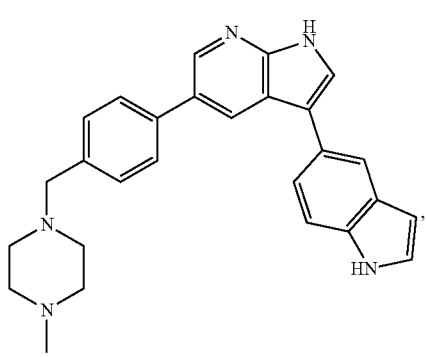

1

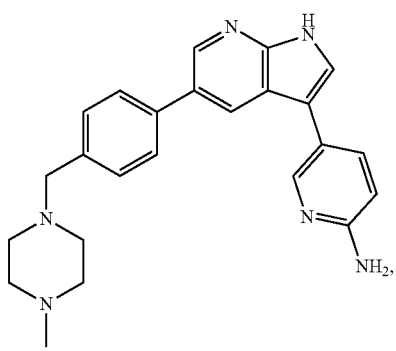

7m

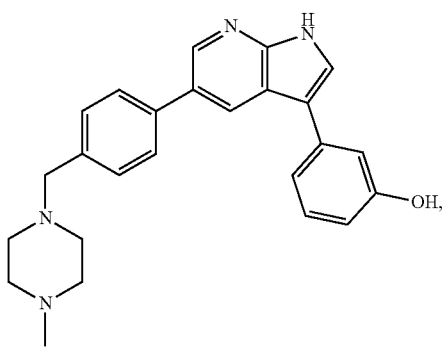

7r

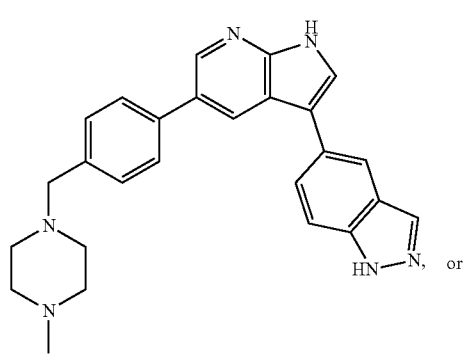

7v

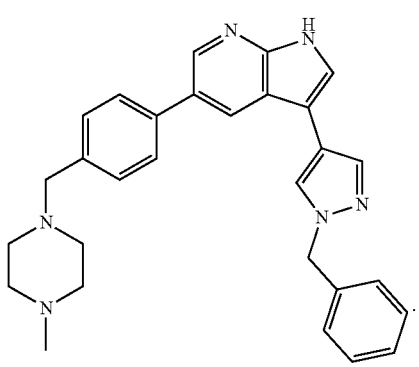

7ah

An additional embodiment of the present invention is a method of treating or ameliorating the effects of a disease involving axon degeneration in a subject in need thereof. This method comprises administering to the subject an effective amount of a kinase inhibitor, which comprises one or more compounds having the structure of formula (I):

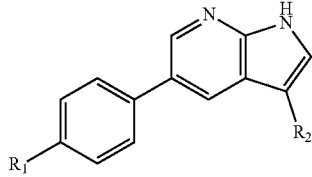

wherein:
- R₁ is an alkyl-heterocycloalkyl or an alkyl-heterobicycloalkyl, wherein the heterocycloalkyl or heterobicycloalkyl is optionally substituted with one or more atoms or groups selected from alkyl, hydroxy, alcohol, or heterocycloalkyl;
- R₂ is selected from phenyl, indolyl, pyridyl, dibenzofuranyl, benzodioxan, benzothiophenyl, pyrimidinyl, pyrazole, thienyl, indazole, or furanyl, any of which is optionally substituted with one or more atoms or groups selected from alkyl, alkoxy, amino, amide, cyano, ether, nitro, hydroxy, halogen, alkyl-heterocycloalkyl, sulfonyl, ketone, haloalkyl, haloalkoxy, alkylphenyl, carbamate, carboxylic acid, or urea;
- or an N-oxide, crystalline form, hydrate, or a pharmaceutically acceptable salt thereof, with the proviso that the compound is not:

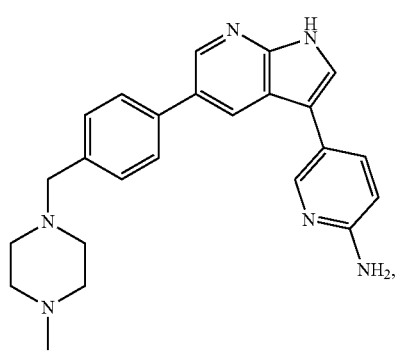

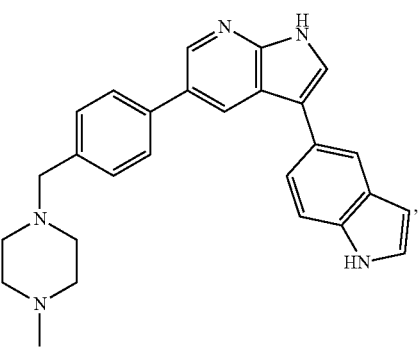

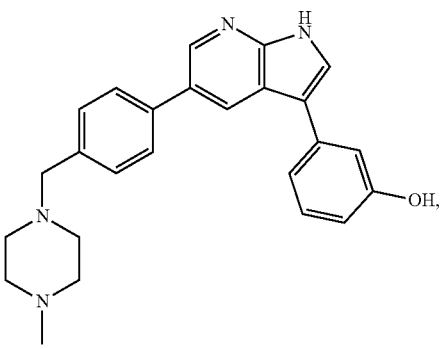

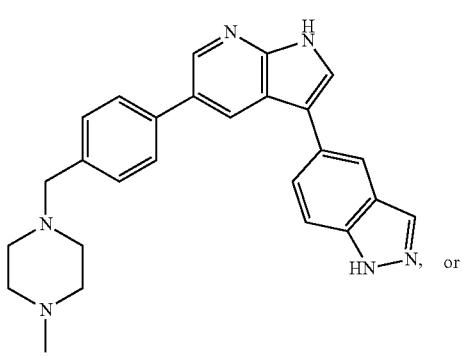

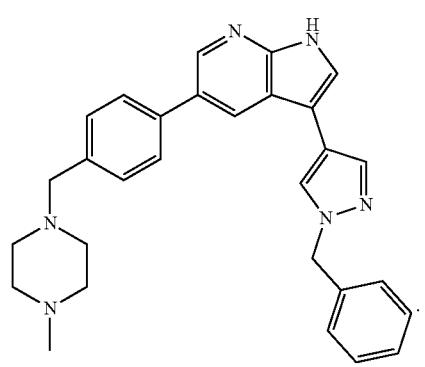

An additional embodiment of the present invention is a method for treating or ameliorating the effects of a neurodegenerative disease in a subject in need thereof. This method comprises administering to the subject an effective amount of one or more compounds having the structure of formula (I):

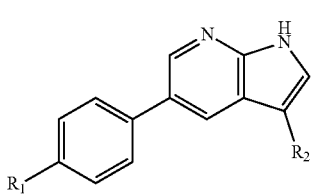

wherein:
- R₁ is an alkyl-heterocycloalkyl or an alkyl-heterobicycloalkyl, wherein the heterocycloalkyl or heterobicycloalkyl is optionally substituted with one or more atoms or groups selected from alkyl, hydroxy, alcohol, or heterocycloalkyl;

R₂ is selected from phenyl, indolyl, pyridyl, dibenzofuranyl, benzodioxan, benzothiophenyl, pyrimidinyl, pyrazole, thienyl, indazole, or furanyl, any of which is optionally substituted with one or more atoms or groups selected from alkyl, alkoxy, amino, amide, cyano, ether, nitro, hydroxy, halogen, alkyl-heterocycloalkyl, sulfonyl, ketone, haloalkyl, haloalkoxy, alkylphenyl, carbamate, carboxylic acid, or urea;

or an N-oxide, crystalline form, hydrate, or a pharmaceutically acceptable salt thereof, with the proviso that the compound is not:

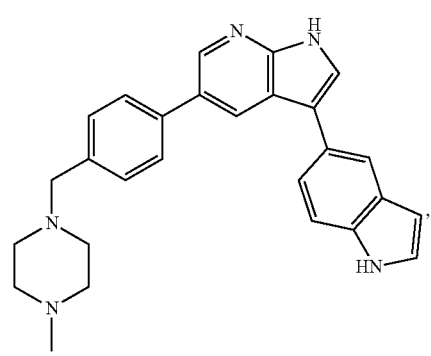

1

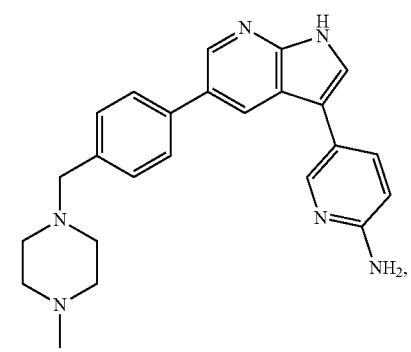

7m

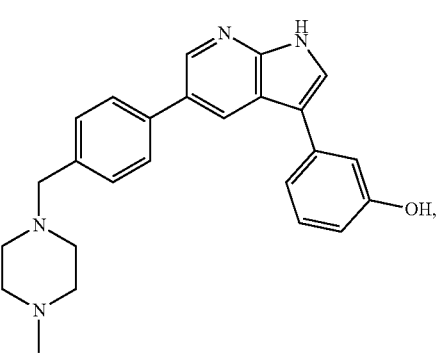

7r

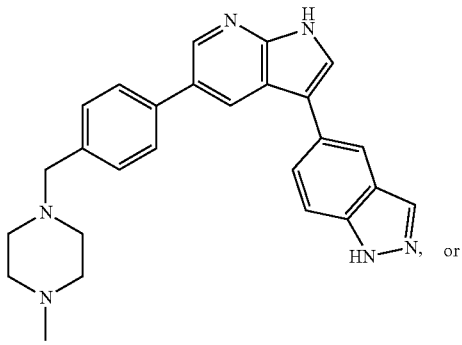

7v

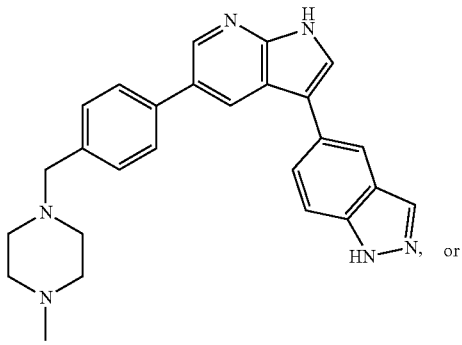

7ah

BRIEF DESCRIPTION OF THE DRAWINGS

FIG. 10C shows the results of motor neurons (MN) survival after CPA dose-response treatment in WT (in blue) and HGK knockout (in orange). Motor neurons were purified by magnetic-activated cell sorting (MACS), treated with varied doses of CPA 24 h after plating, and imaged 48 hours after that.

FIGS. 15A-15K show the derivation and characterization of new transgenic mouse ESC lines used to design a dual color motor neuron toxicity screen.

FIG. 15A shows confocal micrographs of embryoid bodies from Hb9::RFP hSOD1$^{WT}$ and Hb9::GFP hSOD1$^{G93A}$ stained for motor neuron (MN) transcription factors Hb9 and Islet1/2.

FIG. 15B shows the measurements of the overlap between fluorescent reporter protein (FP) and transcriptions factors (TF). Bars denote averages, errors bars indicate SEM.

FIG. 15C shows the schematic 96-well plate with a representative micrograph showing dual color cultures.

FIG. 15D shows a representative whole-well image of live cells, acquired with the Trophos Plate Runner$^{HD}$.

FIG. 15E shows the magnification of FIG. 15D and the result of automated image analysis using Metamorph software.

FIG. 15F shows the 'Healthy cell criterion' using the presence of a significant neurite to distinguish live cells from fluorescent debris.

FIG. 15G shows MN survival in transgenic hSOD1 WT and G93A cell lines expressing different fluorescent reporters. Survival was assessed in medium (G+F+I) and low (F+I) neurotrophic support in either mixed red-green cultures (red WT #1+green G93A #1, N=6) or separate cultures (green WT #1, green G93A #2, N=3). Bars denote average, errors bars indicate SEM, p<0.01 *p<0.001.

FIG. 15H shows the results of a small molecule screen at 48 hrs of exposure; dark blue data points denote normalized G93A/WT survival ratio for well exposed to compounds, light blue and yellow data points denote G93A/WT survival ratio for the controls. Circles denote confirmed promising lead compounds after secondary screening, which are presented in FIG. 15I.

FIG. 15I shows a list of promising lead compounds after secondary screening based on the results shown in FIG. 15H.

FIG. 15J shows the results of a small molecule screen at 48 hrs of exposure; red and green data points denote survival for Hb9::RFP-hSDO1WT (red) and Hb9::GFP-hSDO1$^{G93A}$ (green) cells exposed to compounds, light blue, yellow, blue and magenta data points denote survival for the controls. Circles denote confirmed promising lead compounds after secondary screening, which are presented in FIG. 15K.

FIG. 15K shows a list of promising lead compounds after secondary screening based on the results shown in FIG. 15J.

FIG. 16A shows a dose-response curve for cyclopiazonic acid (CPA) showing survival of Hb9::RFP hSOD1$^{WT}$ and Hb9::GFP hSOD1$^{G93A}$ MNs.

FIG. 16B shows the normalized G93A/WT survival ratio. Bars denote average, errors bars indicate SEM, **p<0.01 (N=10).

FIG. 16C shows representative images from whole-well imaging and magnification showing Hb9::RFP hSOD1WT and Hb9::GFP hSOD1$^{G93A}$ MNs in the same well exposed to CPA.

FIG. 16D shows micrographs of ctrl and CPA-exposed Hb9::GFP hSOD1$^{G93A}$ cultures stained for Tuj-1 (red).

FIG. 16E shows micrographs of ctrl and CPA-exposed mixed Hb9::GFP (green)/Ptf1α::tdTomatored) cultures.

FIG. 16F and FIG. 16G show the Survival of ctrl and CPA-exposed MNs, Tuj-1$^+$ and Ptf1α$^+$ neurons was quantified at 48 hrs (N=3 for both analyzes). Bars denote average, errors bars indicate SEM, p<0.01 *p<0.001.

FIG. 16H shows a micrograph of unpurified Hb9::GFP MN cultures stained for SERCA2 (red), Tuj-1 (magenta) and DAPI (blue).

FIG. 16I shows the CPA-induced change in cytoplasmic Ca$^{++}$ was assessed by calculating 340/380 nm ratio in Fura-2 labelled purified hSOD1$^{WT}$ and hSOD1$^{G93A}$ MN cultures (N=5 for WT, N=4 for G93A). Bars denote average, errors bars indicate SEM.

FIG. 16J shows that the slope of decrease in Fura-2 ratio (Tau) was measured in cultures exposed to kainic acid (KA) in absence or presence of CPA. Bars denote average, errors bars indicate SEM.

FIG. 17A shows a histogram showing qPCR results points for genes of particular interest at earlier time after CPA exposure. RNA was extracted from unpurified hSDO1$^{G93A}$ MNs (N=3). Bars denote average, errors bars indicate SEM.

FIG. 17B shows a histogram and an inverted gel image showing XBP1 splicing in hSDO1 G93A 967 MNs at different time points after CPA exposure (N=3). Bars denote average ratio s/u, errors bars indicate SEM.

FIG. 17C shows immunoblots of expression of ER stress-related proteins and their loading controls at different time points after CPA exposure.

FIG. 17D shows immunoblots of SOD1 expression and loading controls in lysates from CPA treated hSDO1$^{G93A}$ cells. Middle lanes shows panSOD1 expression. Lower lanes show lysates immunoprecipitated using antibodies specific for misfolded hSOD1 species (C4F6 and B8H10 clones).

FIG. 17E and FIG. 17F show a histogram and confocal micrograph of phospho-c-jun$^+$ MNs in ctrls and CPA-treated MN cultures (N=5). Bars denote average, errors bars indicate SEM, **p<0.01.

FIG. 17G shows a histogram of the differential effect of CPA exposure on Ptf1α$^+$::tdTomato interneurons (IN) and Hb9::GFP motor neurons (MN), bars denote average ratio MN/IN (N=3 technical replicates), error bars denote SEM.

FIGS. 19A-19F show the characterization of rescue compounds, including their effects on c-jun phosphorylation in mouse motor neurons and survival in human motor neurons.

FIG. 19A shows dose-response curves for the lead compounds from the rescue screen (GO6976 N=6 culture wells, K252-a N=2 independent cultures, Kenpaullone N=3 independent cultures, TUDCA N=2 independent cultures). Bars denote average, errors bars indicate SEM.

FIG. 19B and FIG. 19C show histograms and confocal micrographs of the effects of rescue compounds on phospho-c-jun expression in CPA-treated MN cultures at 2 hrs of exposure. Bars denote average, errors bars indicate SEM, ***p<0.001.

FIG. 19D shows a histogram of the effects of CPA in the absence or presence of rescue compounds in FACS-purified Hb9::GFP$^+$ human MNs differentiated from a SOD1$^{+/+}$ and an isogenic genetically modified SOD1$^{+/A4V}$ hESC line (N=9 for CPA vs. CTRL for both genotypes, N=3 for rescue compounds for both genotypes). Bars denote average, errors bars indicate SEM, *p<0.05, p<0.01, *p<0.001 (the effect of CPA was compared between SOD1$^{+/+}$ and SOD1$^{+/A4V}$ MNs, as indicated with a line; the effects of rescue compounds were compared for to CPA for each genotype).

FIG. 19E shows representative cropped whole well images of calcein$^+$ cells.

FIG. 19F is a schematic of putative signaling pathways for CPA and targets for rescue compounds. Superscript numbers denote supporting references ([1]Sakaki et al. 2008, [2]Yamada et al. 1998, [3]Roux et al. 2002, [4]Yang et al. 2013, [5]Özcan et al. 2006, [6]Uppala et al. 2017).

FIGS. 20A-20F show the characterization of TUDCA's trophic effects in vitro and effect on muscle denervation in vivo in a mouse model of ALS.

FIG. 20A and FIG. 20B show the effects of TUDCA on MN survival and neurite outgrowth, in comparison to canonical neutrophic factors (N=3 for CT-1, N=4 for the other groups). Bars denote average, errors bars indicate SEM, *p<0.05, p<0.01, *p<0.001 (compared to control).

FIG. 20C shows representative cropped whole well images of Hb9::GFP$^+$ cells.

FIG. 20D shows a schematic of the experimental design for the in vivo test of TUDCA on muscle denervation in hSOD1$^{G93A}$ mice.

FIG. 20E shows a scatter plot of NMJ innervation in the TA (N=4 for WT+TUDCA, N=6 for G93A+TUDCA, N=5 for G93A+vehicle). Data points represent individual animals, horizontal lines denote the average, *p<0.05, p<0.01, *p<0.001.

FIG. 20F shows confocal micrographs of TA NMJs (α-btx red, VAChT green) of vehicle and TUDCA treated hSOD1$^{G93A}$ mice. Circles denote denervated NMJs.

FIGS. 21A-21K show the evaluation of newly derived transgenic ES lines, biochemical analysis of normal- and misfolded SOD1 expression and pEif2α levels in differentiated cells, and titration of neurotrophic support in motor neuron cultures.

FIG. 21A shows a light microscope micrograph of typical ES colonies from newly derived reporter lines.

FIG. 21B shows sequencing results confirming the presence of wild type or mutated human SOD1.

FIG. 21C, FIG. 21D and FIG. 21E show light microscopy micrographs and histogram of reporter validation in differentiated new ES lines (two lines for each reporter were differentiated in two separate rounds, results are presented as mean value/reporter). Bars denote means and error bars SEM.

FIG. 21F and FIG. 21G show the evaluation of motor neuron survival and neurite growth in individual cultures of Hb9::GFP hSOD1$^{WT}$ or Hb9::GFP hSOD1$^{G93A}$ cells (N=3 for both genotypes). Bars denote means and error bars SEM.

FIG. 21H shows cropped images of immunoblots displaying expression of total and misfolded (C4F) SOD1 in untreated motor neuron cultures. P100 spinal cords from WT or SOD1$^{G93A}$ mice were used as controls. The dashed line indicates were the lower image was cropped.

FIG. 21I shows an immunoblot showing the specificity for the C4F6 andf B8H10 antibodies for misfolded mutant SOD1.

FIG. 21J and FIG. 21K show the histogram showing dose-response curves for motor neuron survival in cultures treated with combinations of forskolin (F, range: 100 μM-0.78125 μM), IBMX (1, range: 1 mM-7.8125 μM) and GDNF (G, range: 50 ng/mL-0.128 pg/mL), high medium support was used as control (NTFs) (N=6 cultures wells/condition). Bars denote means and error bars SEM.

FIGS. 22A-22F show additional results from the primary toxicity screen and calcium imaging experiments in CPA-treated enriched motor neuron cultures.

FIG. 22A shows the results of a small molecule screen at 48 hrs of exposure; dark blue data points denote normalized G93A/WT survival ratio for well exposed to compounds, light blue and yellow data points denote G93A/WT survival ratio for the controls. Circles denote confirmed promising lead compounds after secondary screening, which are presented in the table below.

FIG. 22B shows the results of a small molecule screen at 48 hrs of exposure; red and green data points denote survival for Hb9::RFP-hSDO1$^{WT}$ (red) and Hb9::GFP-hSDO1$^{G93A}$ (green) cells exposed to compounds, light blue, yellow, blue and magenta data points denote survival for the controls. Circles denote confirmed promising lead compounds after secondary screening, which are presented in the table below.

FIG. 22C and FIG. 22E show the Fura-2 signal ratio 340/380 in enriched motor neuron cultures subjected to a kainate pulse either prior or subsequent to CPA exposure (N=5 for WT and N=4 for G93A). Data points denote means and error bars SEM.

FIG. 22D shows representative still images from a video of kainate exposed hSOD1$^{G93A}$ motor neurons. The images show the Fura-2 signal ratio 340/380, the signal is displayed using the Image-Lookup tables function in FIJI (NIH). Arrows denote Hb9::RFP$^+$ cells.

FIG. 22F shows histograms of measurements of the peak kainate and CPA-evoked Fura-2 signal ratio 340/380 in Hb9::RFP-hSDO1$^{WT}$ (red) and Hb9::RFP-hSDO1$^{WT}$.

FIGS. 23A-23F show the evaluation of CPA toxicity in two independent pair of cell lines, in mixed and FACS-sorted motor neuron cultures.

FIG. 23A, FIG. 23B, FIG. 23C and FIG. 23D show dose response curves for survival ratios in CPA treated cultures in two different combinations of reporter cell lines. Cultures were either unpurified or purified using FACS (FIG. 23A: N=5, FIG. 23B: N=4, FIG. 23C: N=6 culture wells, FIG. 23D: N=2). Bars denote means and error bars SEM.

FIG. 23E and FIG. 23F show scatter plots of representative gates for FACS-purification of reporter lines.

FIG. 24A shows a diagram of gene targeting strategy for introduction of the SOD1A4V mutant allele into the SOD1 locus of HUES3 Hb9::GFP.

FIG. 24B shows the sequencing of the SOD1 locus.

FIG. 24C shows that the PCR-RFLP analysis for a unique PshAI restriction site confirmed correct targeting.

FIG. 24D and FIG. 24E show that the qRT-PCR and immunoblot assays for SOD1 expression in targeted stem cell lines demonstrated reduced levels of the SOD1 transcript and protein levels.

FIG. 24F shows FACS plots depicting a distinct population of differentiated cells which express the GFP reporter. Differentiated neural cells not exposed to the MN patterning molecules RA and SAG were used as negative control to gate for green fluorescence.

FIG. 24G show that Hb9::GFP$^+$ cells express the transcription factor Islet1 confirming spinal MN identity.

FIG. 24H and FIG. 24I show that cell survival assays in mixed cultures indicate a trend for reduced survival in isogenic human ES MNs expressing the SOD1$^{A4V}$ variant relative to the isogenic control. Representative images of Human Nuclei and Tuj1 staining at days 3 and 30 (P=0.09, n=4).

FIG. 24J shows a short term assessment (5 days post dissociation) of MN survival and neurite growth in FACS-purified human isogenic lines, assessed by calcein labelling in live cultures.

FIG. 24K shows a histogram of neurite growth in purified isogenic human motor neuron cultures. Cells were grown under control conditions, treated with CPA or pretreated with rescue compounds followed by CPA (N=9 for CPA vs. CTRL for both genotypes, (N=3 for rescue compounds for both genotypes). Bars denote average, errors bars indicate SEM, $*p<0.05$, $p<0.01$, $*p<0.001$ (the effect of CPA was compared between WT vs. ALS MNs, as indicated with a line; the effects of rescue compounds were compared to CPA for each genotype).

FIG. 24L shows a histogram showing a dose response survival curve for CPA toxicity in purified human $SOD1^{+/A4vES}$ MNs. Bars denote average, errors bars indicate SEM (N=3 culture wells/concentration).

FIG. 25A shows confocal micrographs of p-c-jun (blue) expression in $Hb9::GFP^+$ motor neurons (green) and Ptf1:: tdTomato interneurons (red).

FIG. 25B shows histograms depicting Fura-2 signal ratio 340/380 in motor neurons versus other neurons in the culture (N=5 for WT, N=4 for G93A). Bars denote means and error bars SEM.

FIG. 25C and FIG. 25D show a mini-screen for the rescue effect of taurine-conjugated bile acid in CPA treated Hb9:: GFP-hSDO1$^{G93A}$ motor neurons (N=3-6 culture wells/compound). Data points show mean values.

FIG. 25E and FIG. 25F show histograms depicting the rescue effects of TUDCA and canonical neurotrophic factors on survival and neurite growth in CPA treated Hb9::GFP-hSDO1$^{G93A}$ motor neurons grown in low neurotrophic support (N=3). Bars denote means and error bars SEM.

FIG. 25G shows the effect of TUDCA on survival and neurite growth in Hb9::GFP-hSDO1$^{G93A}$ motor neurons grown under high neurotrophic support (N=3). Bars denote means and error bars SEM.

FIG. 25H shows the effect of TUDCA on survival and neurite growth in CPA treated Hb9::GFP-hSDO1$^{G93A}$ motor neurons grown under high neurotrophic support (N=3). Bars denote means and error bars SEM.

FIGS. 38A-38C show that compound 12k shows enhanced MAP4K inhibition relative to compound 1.

FIG. 38A shows the global kinase inhibition profiles of compound 1, segregated by kinase families.

FIG. 38B shows the global kinase inhibition profiles of compound 12k, segregated by kinase families.

FIG. 38C shows the fold-change in inhibition of a given kinase by compound 12k compared to 1. MAP4Ks (green) are amongst the most enhanced targets of 12k.

FIG. 39 shows that compound 1 and its analogs suppress inflammatory cytokine TNFa release by microglia.

FIG. 40 shows that functional targets of compound 1 and analogs differ for inflammation vs neurodegeneration.

FIGS. 41A-41C show that HGK inhibitors are neuroprotective and act through the JNK pathway.

FIG. 41A shows the result of a two-way hierarchical clustering of the kinase targets of neuroprotective hits from previous survival screens, indicating that HGK and NUAK1 are shared targets of these compounds. MAP4 kinases are underlined.

Figure 41A:
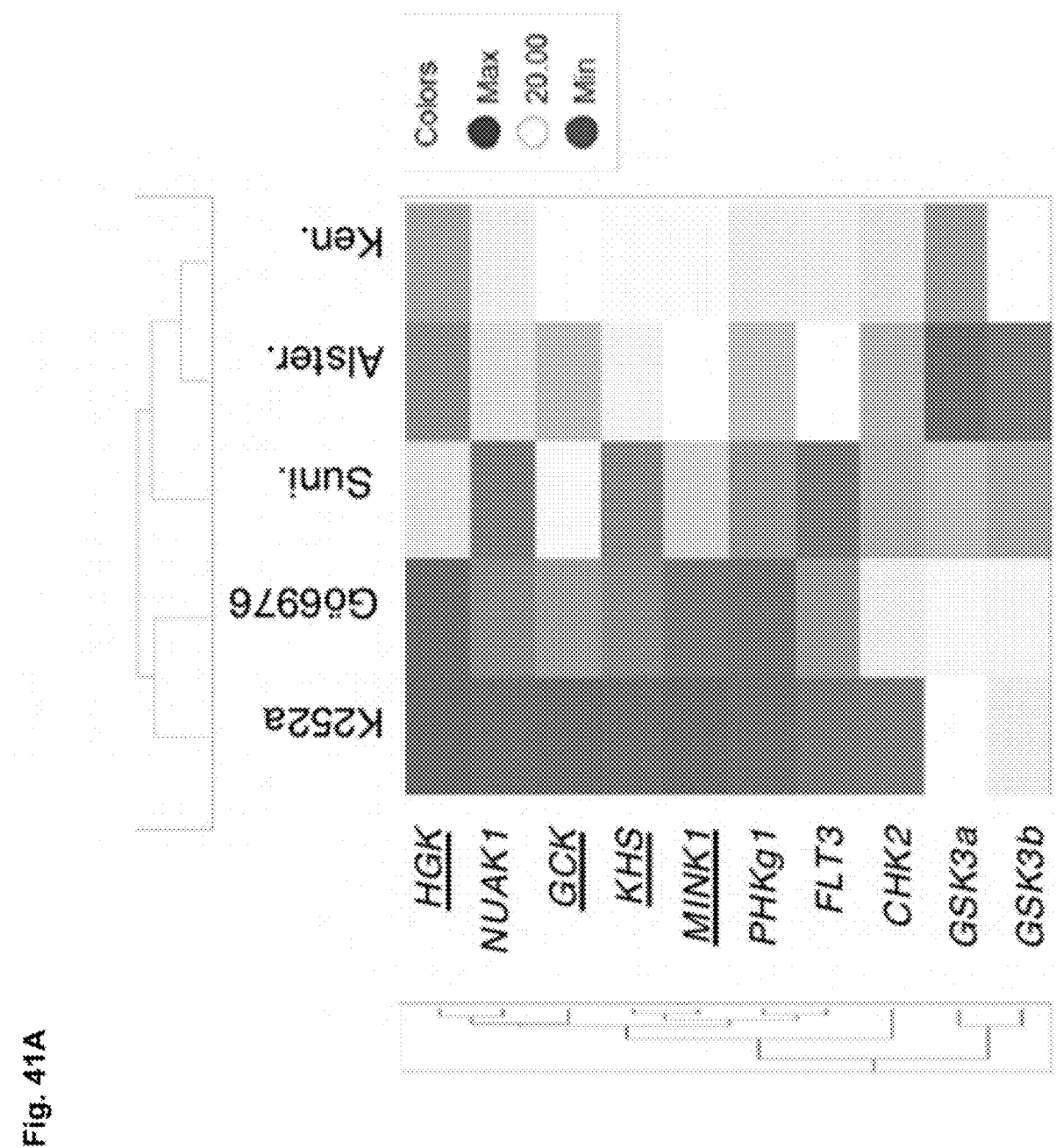
Figure 41B:
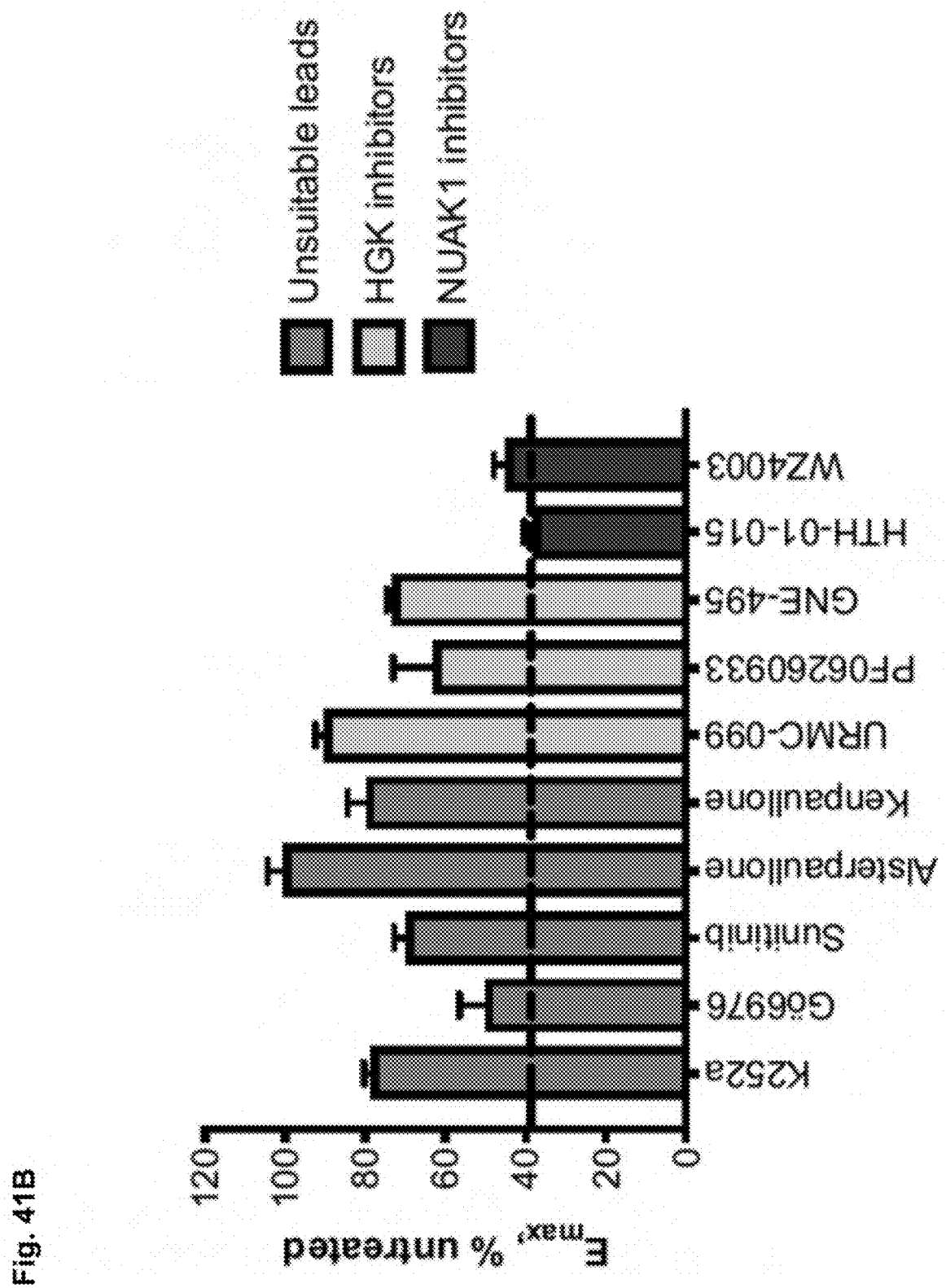

FIG. 41B shows the maximum efficacy of hits from FIG. 41A (gray) compared to more specific HGK and NUAK1 inhibitors across dilution series. Bars represent means±SEM of wild-type motor neurons treated with CPA (33 μm)+test compound normalized to vehicle controls. n=3 replicate wells from a 96-well plate. Dashed line represents average survival in cells treated with CPA alone.

Figure 41C:
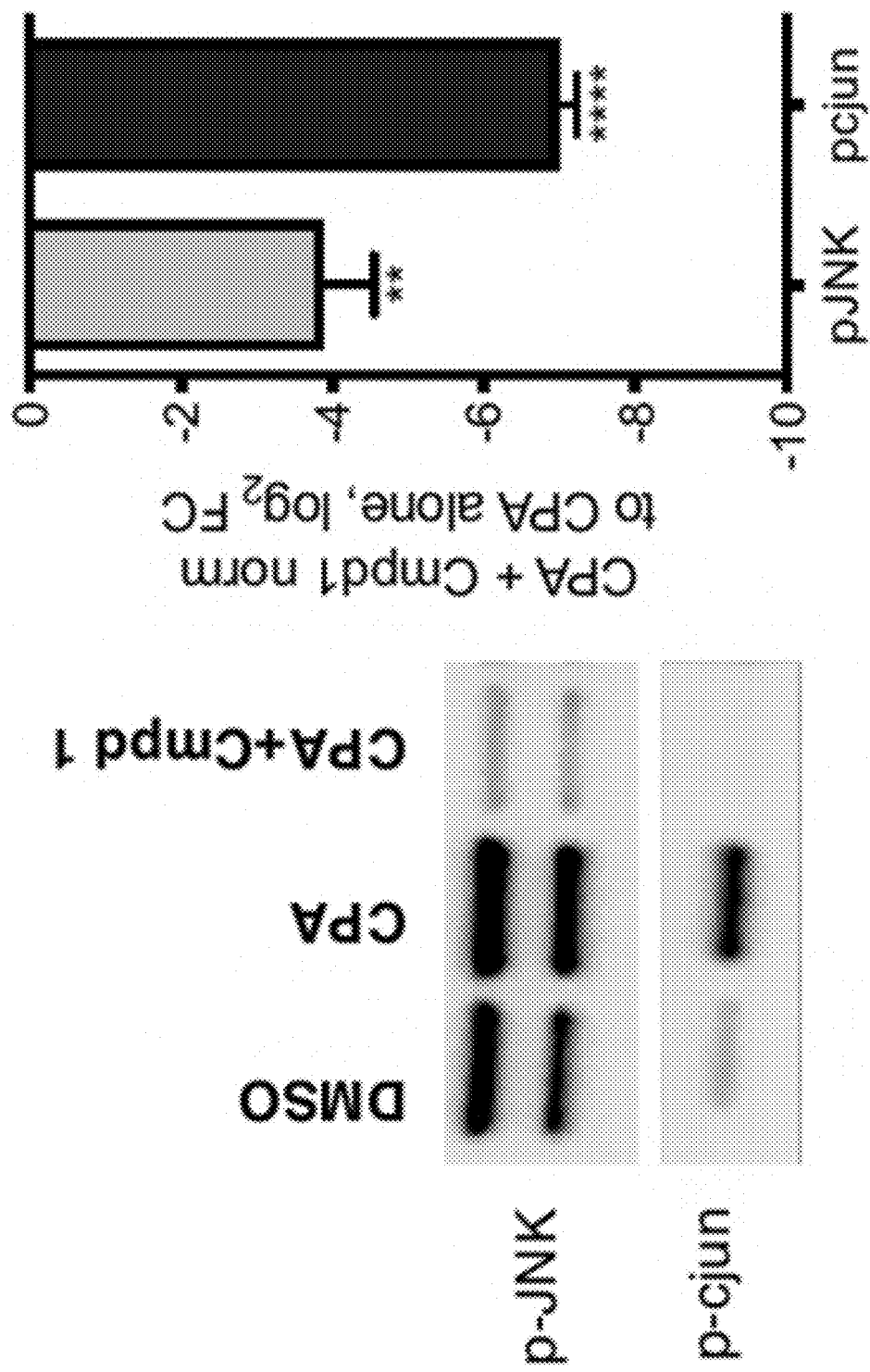

FIG. 41C shows the result of Western blots of mixed motor neuron cultures treated with vehicle, CPA, or CPA+ compound 1 (0.5 μM). Samples were harvested after 4 h of treatment. N=samples from 3 separate motor neuron differentiations treated and lysed separately. Cells from each differentiation were split into three samples, one for each treatment condition. All samples were run concurrently on the same blot. All band intensities were normalized to GAPDH to control for loading, then DMSO and CPA+ Compound 1 values were normalized to CPA values for each n. One-way ANOVAs were used to evaluate the overall effects of treatment on JNK phosphorylation (P=0.0009; F=28.33; R2=0.9042) and c-Jun phosphorylation (P<0.0001; F=101.9; R2=0.9714). Data represent mean CPA+Compound 1 values, log 2 fold-change relative to CPA alone ±SEM. Bonferroni's multiple comparison tests were used to compare CPA vs. CPA+ compound 1 conditions for phospho-JNK and phospho-c-Jun; P<0.01; *P<0.001.

Figure 42A:
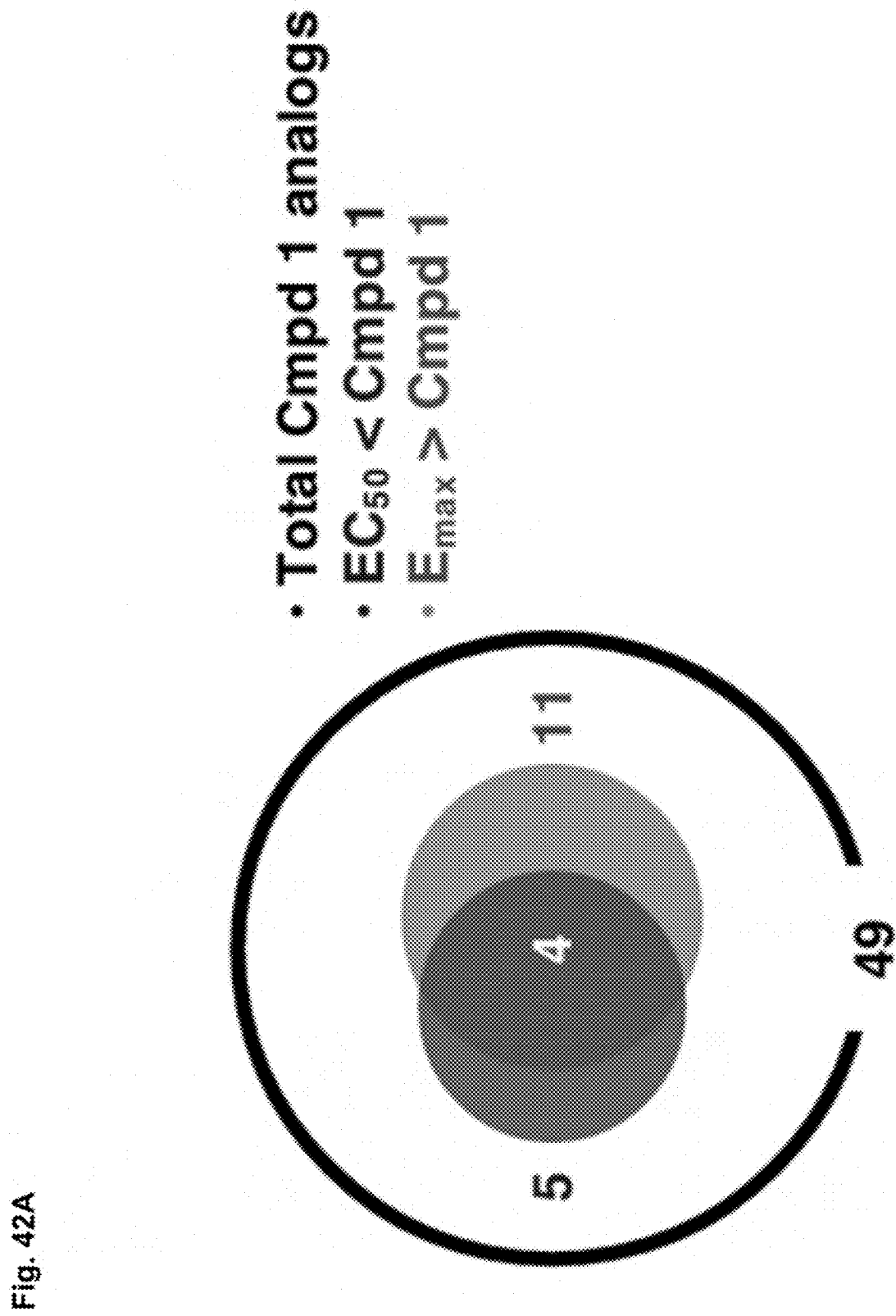
Figure 42B:
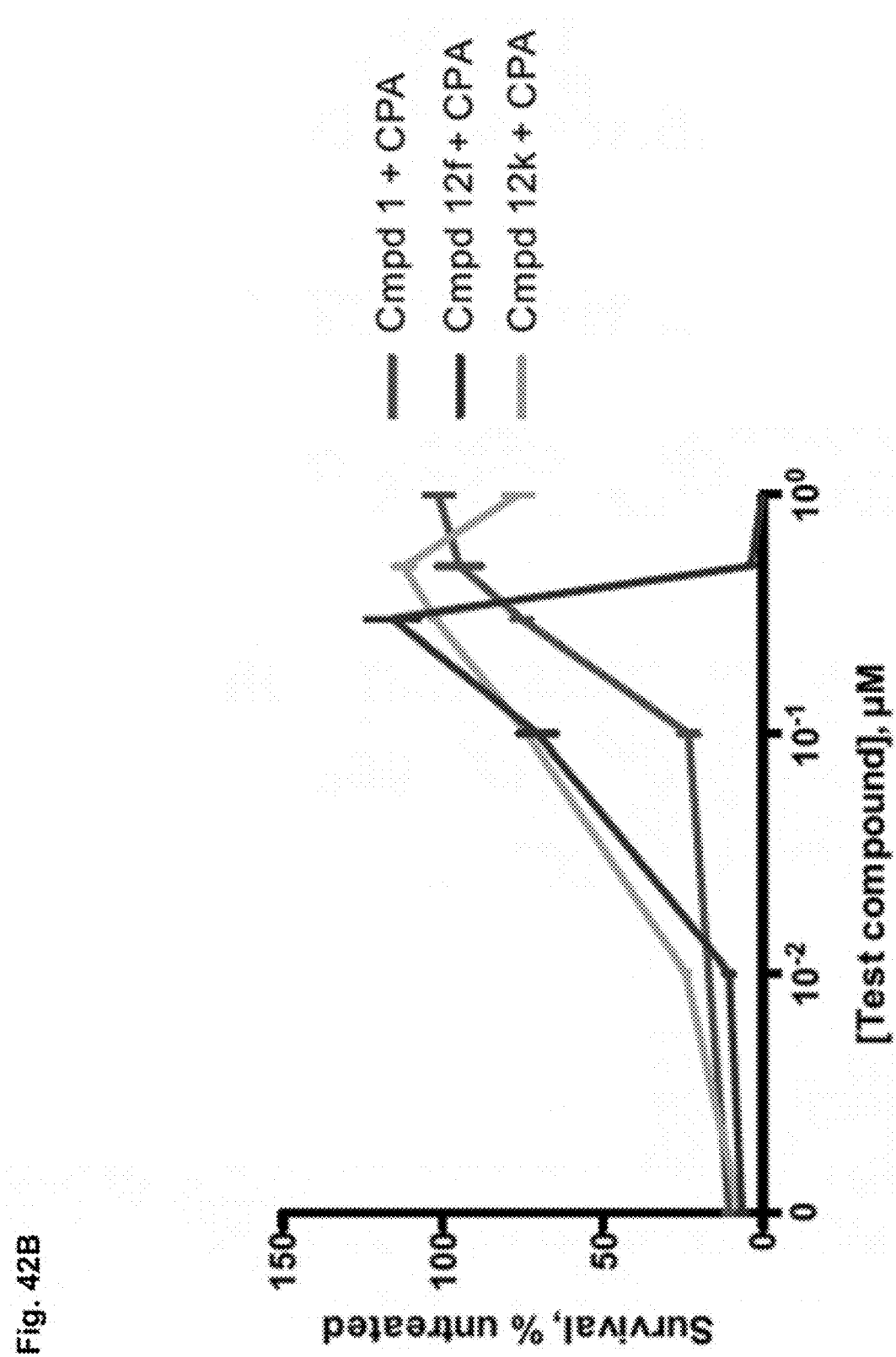
Figure 42C:
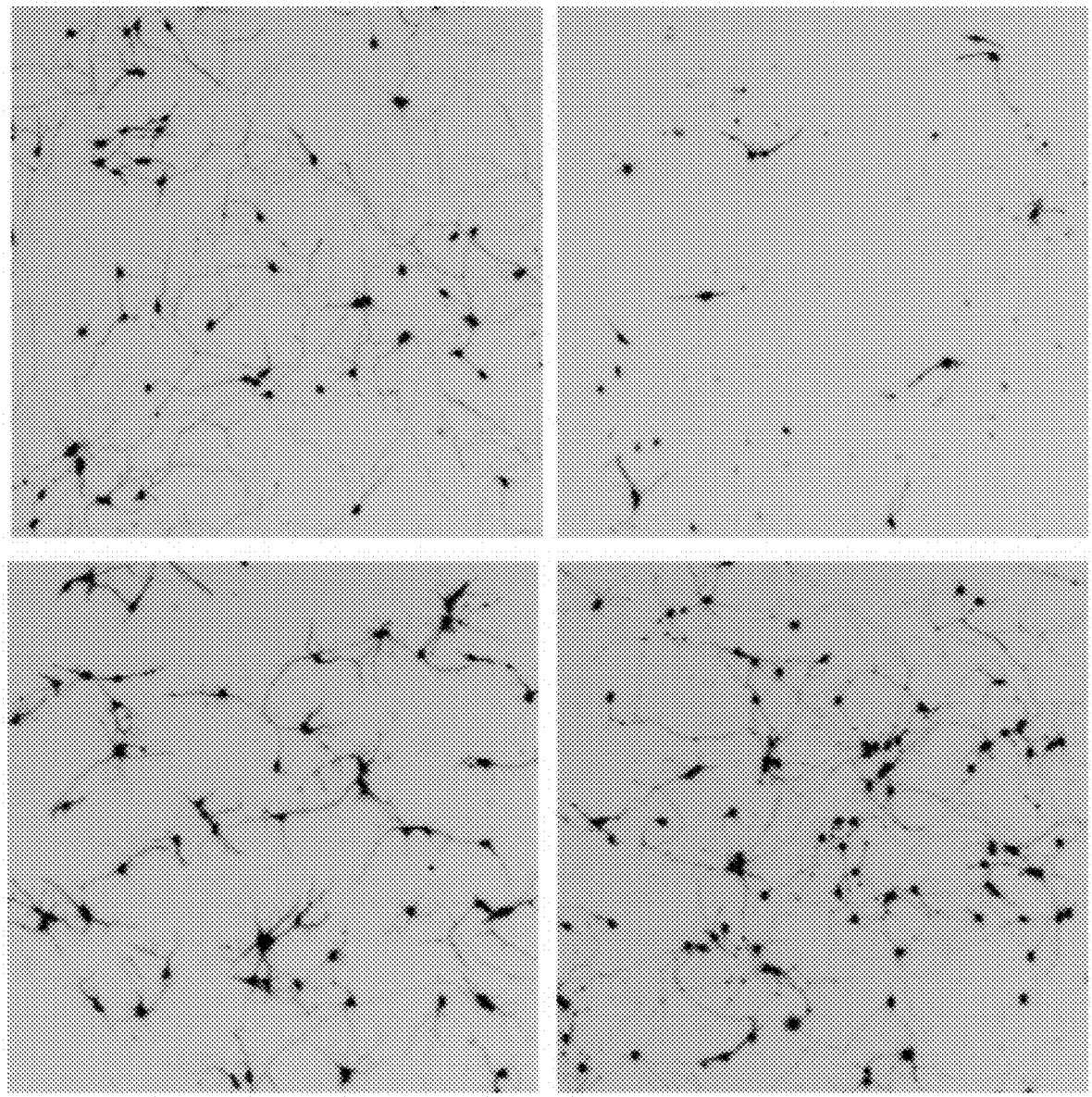

FIGS. 42A-42C show the in vitro and in vivo characterization of compound 1 analogs.

FIG. 42A provides the summary of improvements in efficacy (red) and potency (blue) amongst the 49 compound 1 analogs generated initially.

FIG. 42B shows the survival curves for SOD1$^{A4V}$ mutant ALS motor neurons treated with CPA (33 μM) and compounds 1, 12f, and 12k across dilution series (log μM). Compound 12f shows improved potency and efficacy compared to 1 but is abruptly toxic above 0.5 μM. Compound 12k shows improved potency and efficacy compared to 1, with less toxicity than 12f at higher doses. Data are means±SEM of motor neurons treated with CPA (33 μm)+ test compounds normalized to vehicle controls. n=3 replicate wells from a 96-well plate for each test compound dose.

FIG. 42C shows the representative fields from whole-well images of SOD1$^{A4V}$ motor neurons treated with vehicle (DMSO) alone (upper left); CPA (33 μm) alone (upper right); CPA+Compound 1 (0.5 μM) (lower left); or CPA+ Compound 12k (0.1 μM) (lower right).

Figure 43A:
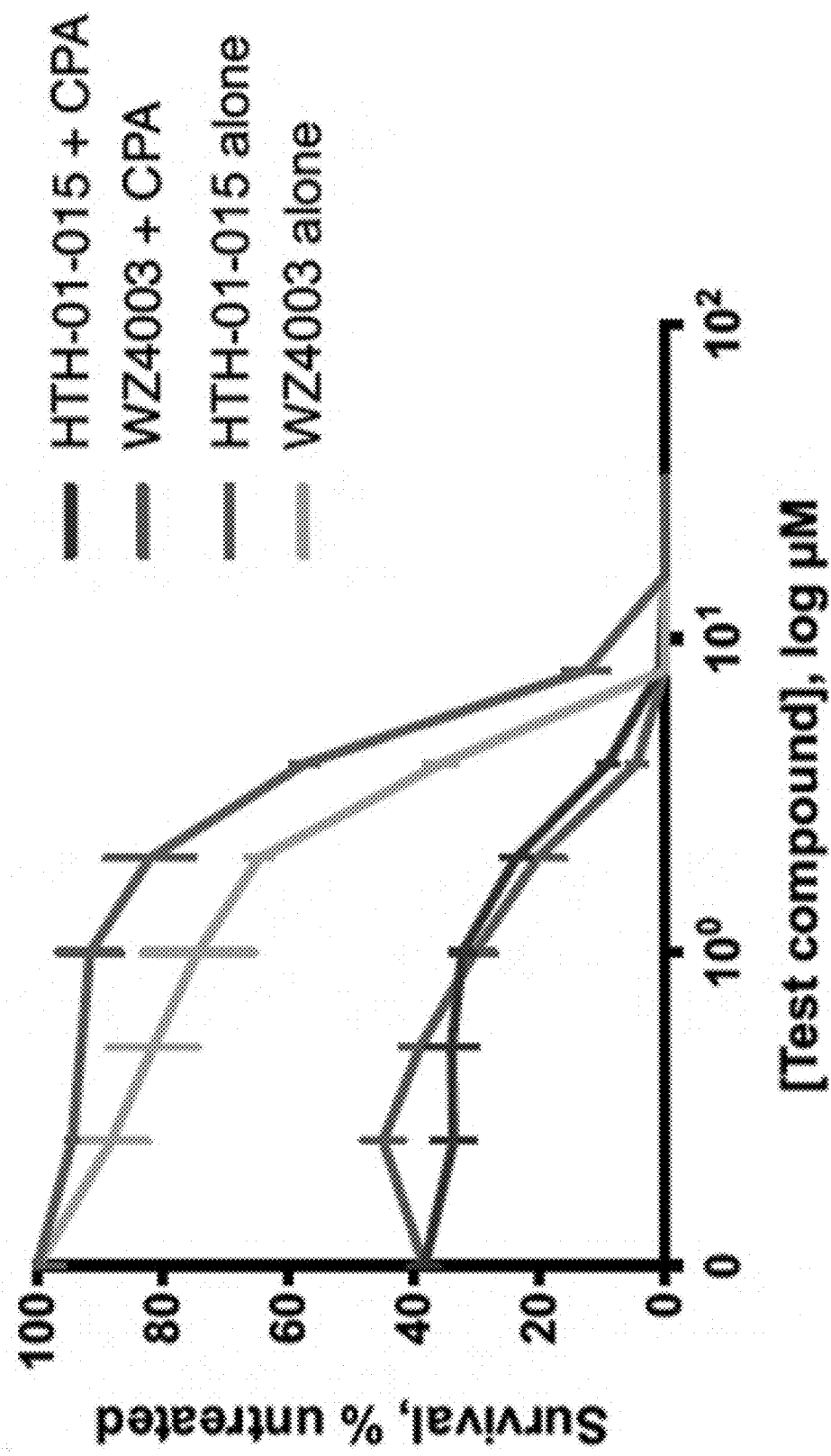
Figure 43B:
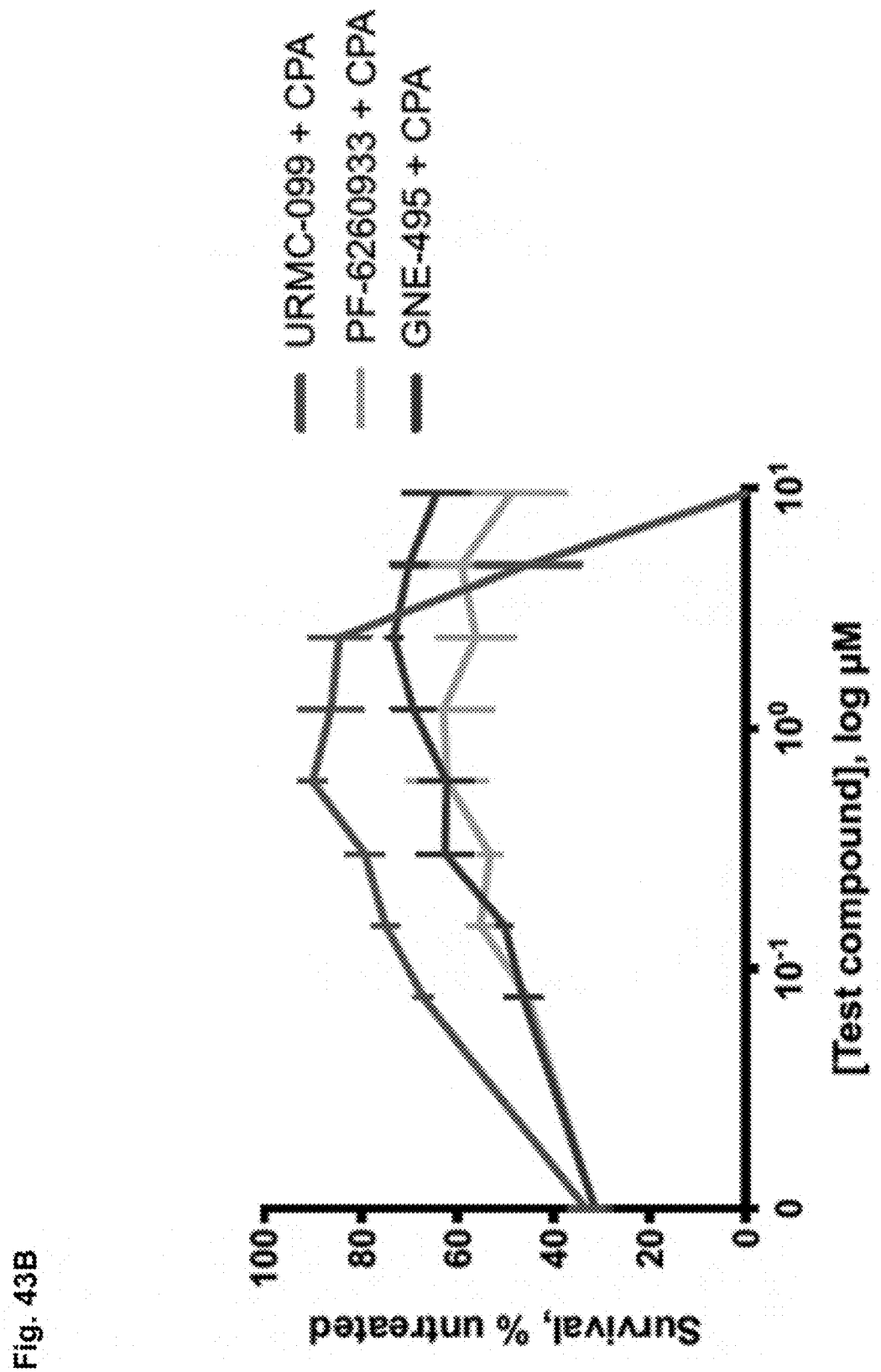

FIGS. 43A-43B show the full dose-response curves for specific NUAK1 and HGK inhibitors. Data are means of wild-type motor neurons treated with CPA+test compounds normalized to vehicle controls ±SEM. n=3 replicate wells from a 96 well plate.

FIG. 43A shows the 8-point dilution curves for NUAK1 inhibitors HTH-01-015 and WZ4003. Means without CPA are included to show inherent toxicity of compounds.

FIG. 43B shows the 8-point dilution curves for HGK inhibitors URMC-099 (compound 1), PF-6260933, and GNE-495.

Figure 44:
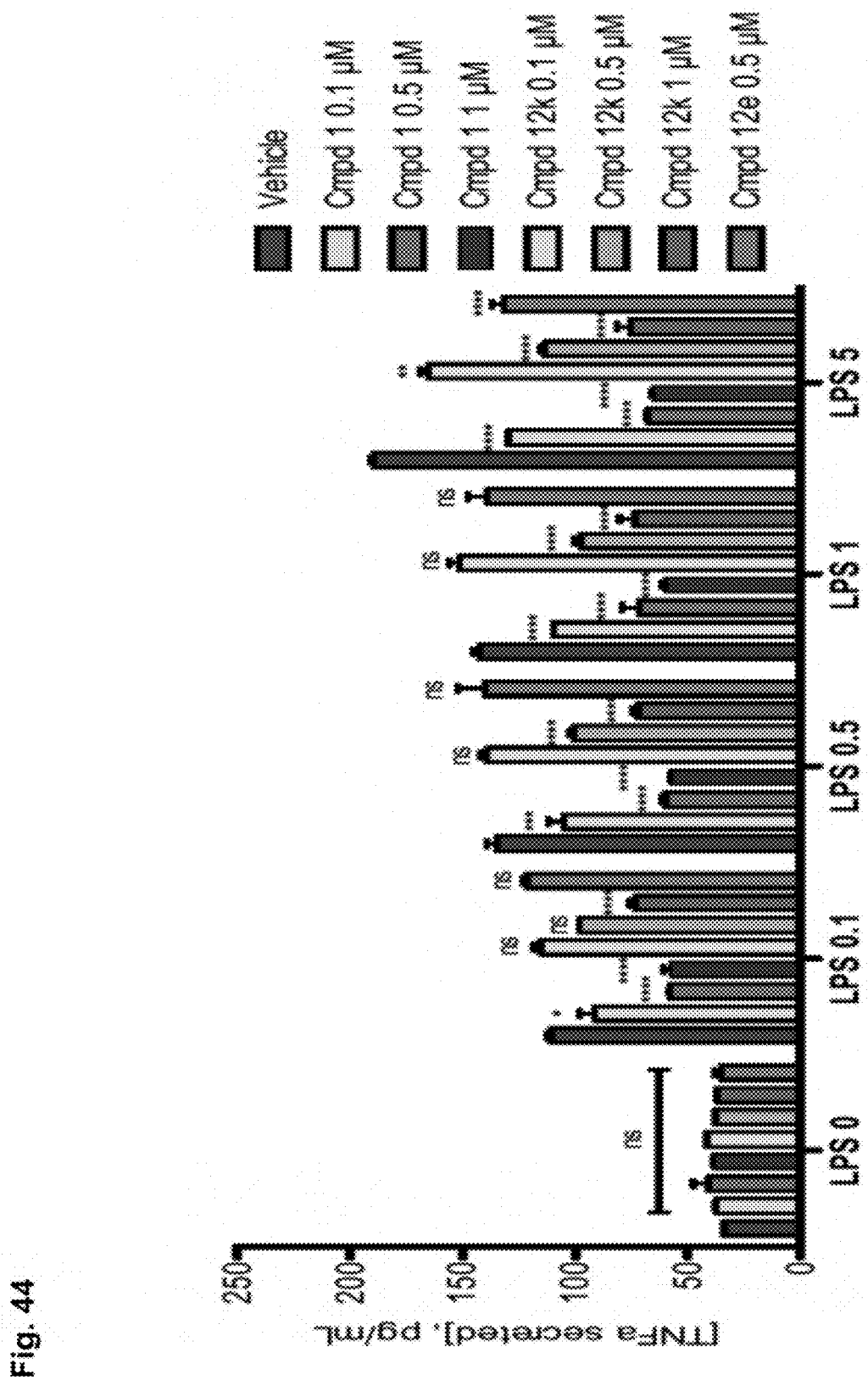

FIG. 44 shows that compound 12k maintains ability to suppress microglial cytokine release. Microglial N9 cells were treated with increasing concentrations of LPS+ compounds 1, 12k, or 12e. TNFα release was measured by quantitative ELISA from cell culture media. Compound 1 showed significant inhibition of TNFα release at 0.1 μM across all concentrations of LPS. Compound 12k was ~5× less potent than compound 1 in this assay, but still succeeded in suppressing TNFα release. Compound 12e, which strongly inhibits HGK but has little activity at MLK3, did not inhibit TNFα release at 0.5 μM except at the highest concentration of LPS, suggesting that inhibition of TNFα release may not be related to HGK inhibition but instead to the inhibition of other kinases such as MLK3. Data are mean±SEM. n=2 replicate wells of a 96-well plate. The overall effects of compound 1 analogs vs LPS concentrations were compared by Two-Way ANOVA (significant effects of compound 1 analog, LPS concentration, and interaction, all P<0.0001). The effects of individual compound 1 analogs at different LPS concentrations vs. LPS alone (vehicle, gray bars) were assessed by Bonferroni multiple comparison tests. *P<0.05, P<0.01, *P<0.001, ****P<0.0001.

Figure 45:
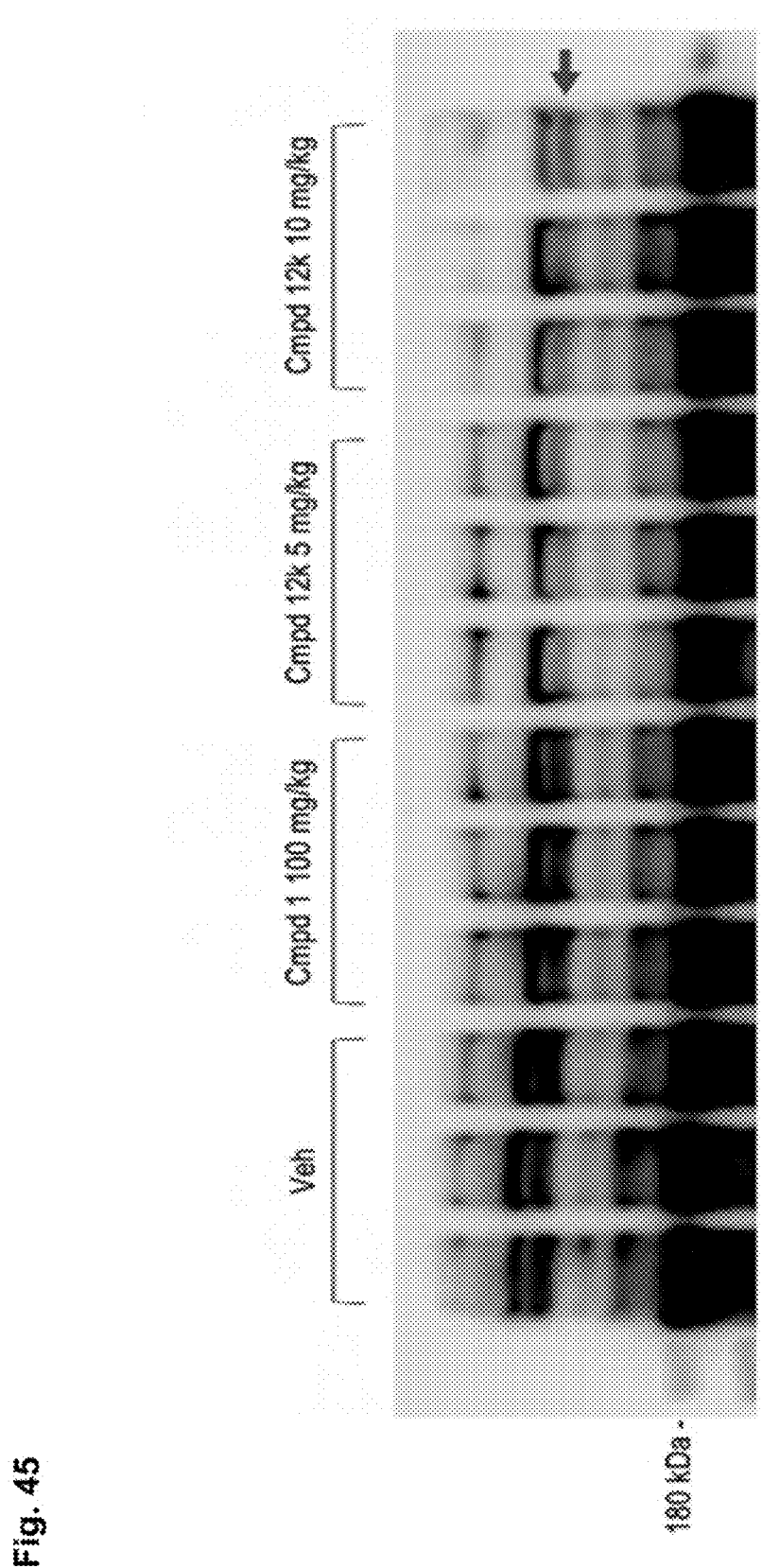

FIG. 45 shows the marker of target engagement for compound 12k.

Figure 46A:
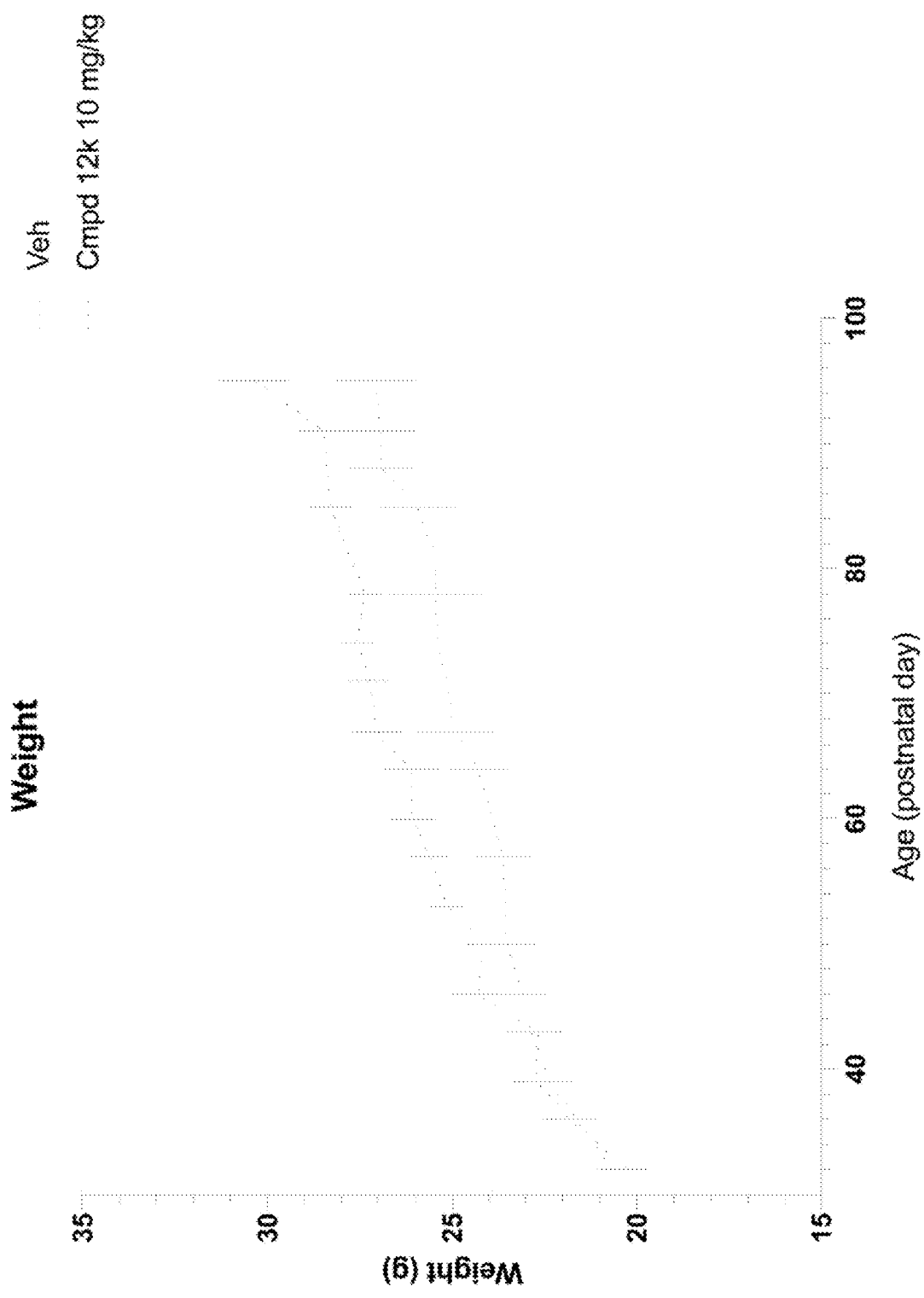

FIG. 46A shows the body weight change in mice fed with compound 12k vs. control.

FIG. 46B shows the grip strength change in mice fed with compound 12k vs. control.

DETAILED DESCRIPTION OF THE INVENTION

In the present invention, new analogs of compound 1 are provided. Certain of the analogs have improved microsomal stability and solubility while still maintaining good inhibition potency of toxic ER stress. Accordingly, one embodiment of the present invention is a compound according to formula (I):

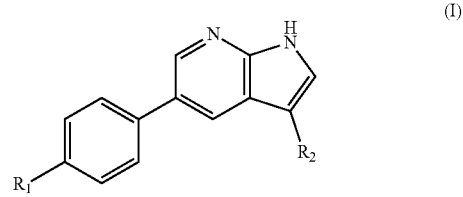

wherein:

R₁ is an alkyl-heterocycloalkyl or an alkyl-heterobicycloalkyl, wherein the heterocycloalkyl or heterobicycloalkyl is optionally substituted with one or more atoms or groups selected from alkyl, hydroxy, alcohol, or heterocycloalkyl;

R₂ is selected from phenyl, indolyl, pyridyl, dibenzofuranyl, benzodioxan, benzothiophenyl, pyrimidinyl, pyrazole, thienyl, indazole, or furanyl, any of which is optionally substituted with one or more atoms or groups selected from alkyl, alkoxy, amino, amide, cyano, ether, nitro, hydroxy, halogen, alkyl-heterocycloalkyl, sulfonyl, ketone, haloalkyl, haloalkoxy, alkylphenyl, carbamate, carboxylic acid, or urea;

or an N-oxide, crystalline form, hydrate, or a pharmaceutically acceptable salt thereof, with the proviso that the compound is not:

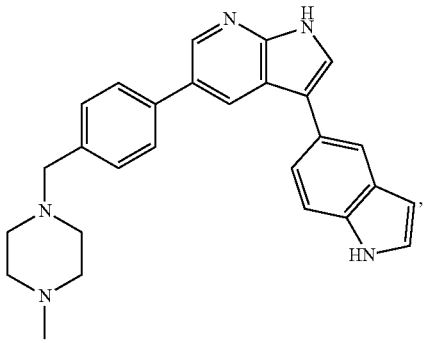
1

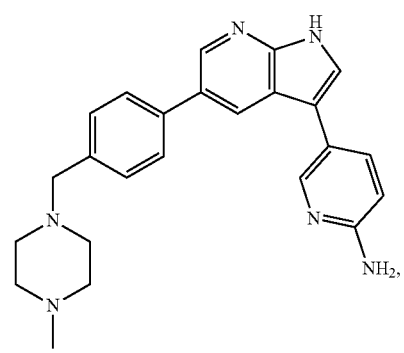
7m

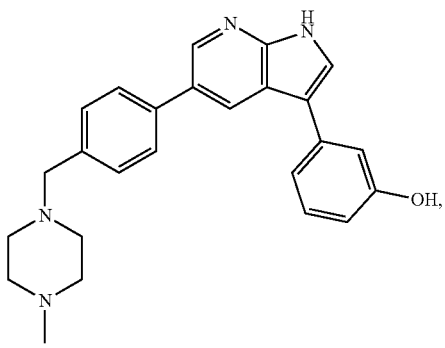
7r

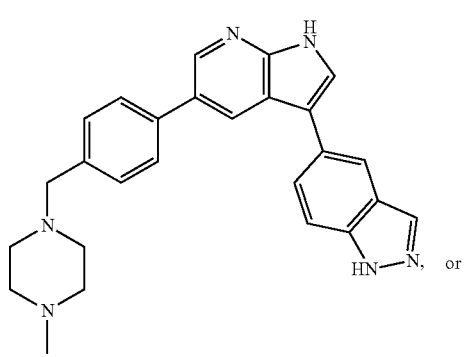
7v

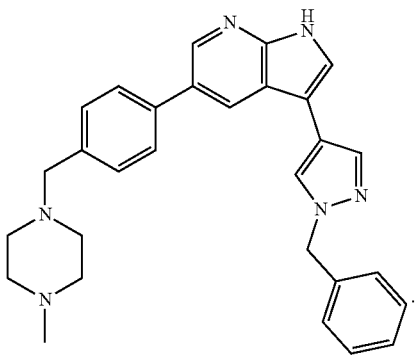
7ah

In one aspect of this embodiment, the compound has the structure of formula (II):

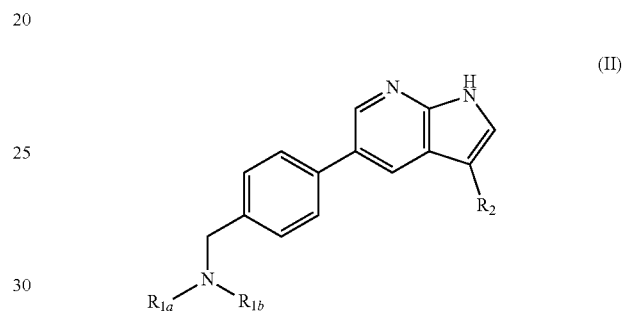
(II)

wherein:

$R_{1a}$ and $R_{1b}$ together with the nitrogen atom to which they are attached, form a $C_{5-6}$heterocycloalkyl, wherein the $C_{5-6}$heterocycloalkyl is optionally substituted with one or more atoms or groups selected from alkyl, hydroxy, alcohol, or heterocycloalkyl;

$R_2$ is selected from phenyl, indolyl, pyridyl, dibenzofuranyl, benzodioxan, benzothiophenyl, pyrimidinyl, pyrazole, thienyl, indazole, or furanyl, any of which is optionally substituted with one or more atoms or groups selected from alkyl, alkoxy, amino, amide, cyano, ether, nitro, hydroxy, halogen, alkyl-heterocycloalkyl, sulfonyl, ketone, haloalkyl, haloalkoxy, alkylphenyl, carbamate, carboxylic acid, or urea;

or an N-oxide, crystalline form, hydrate, or a pharmaceutically acceptable salt thereof, with the proviso that the compound is not:

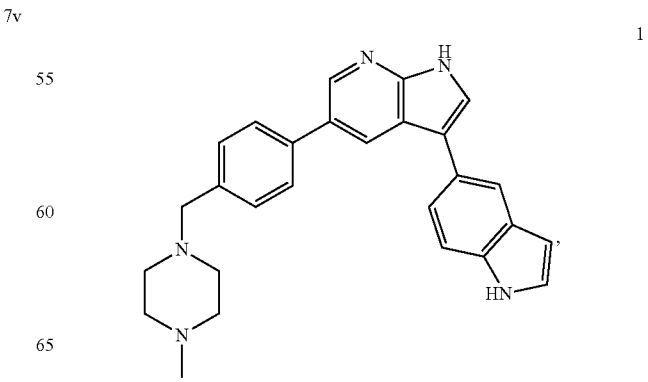
1

-continued
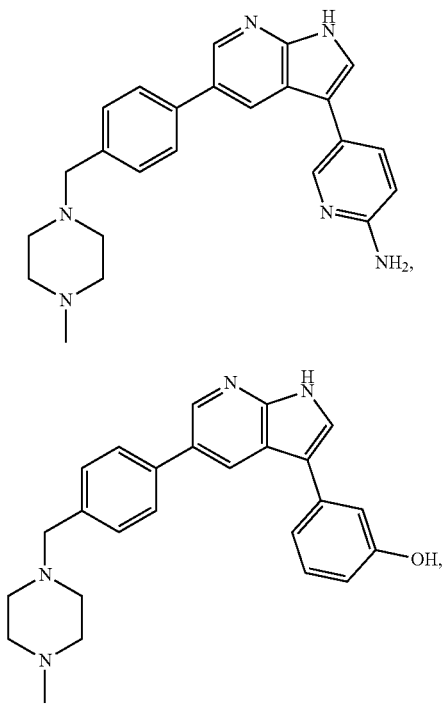
7m
7r
7v
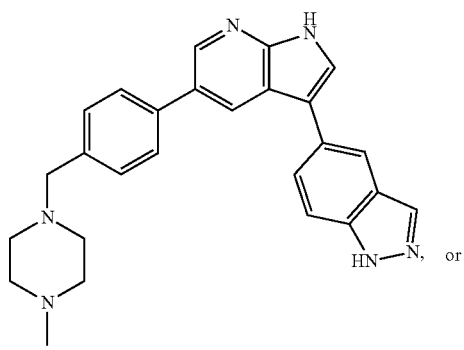
7ah
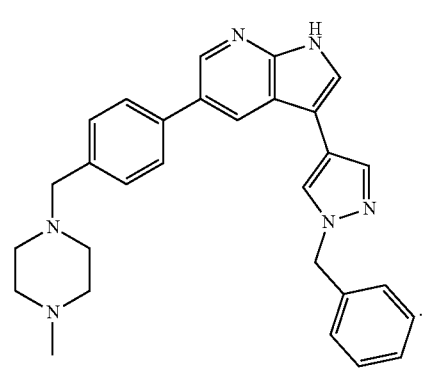
In another aspect of this embodiment, the compound is selected from the group consisting of:
7a
7b
7c
7d -continued
7e
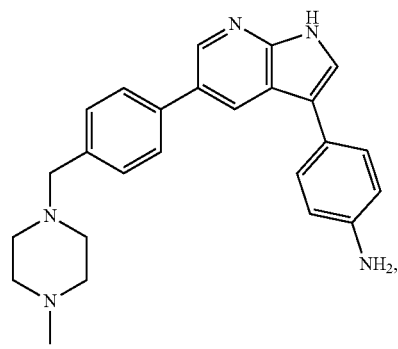
7f
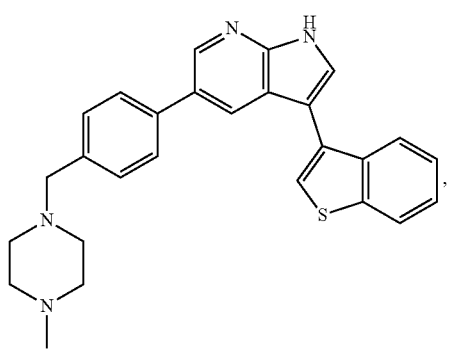
7g
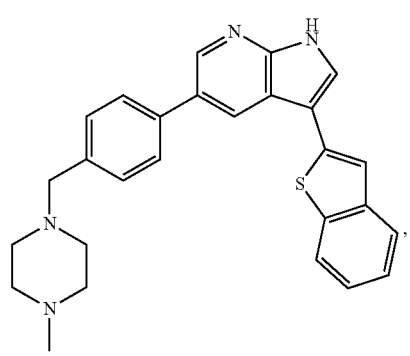
7h
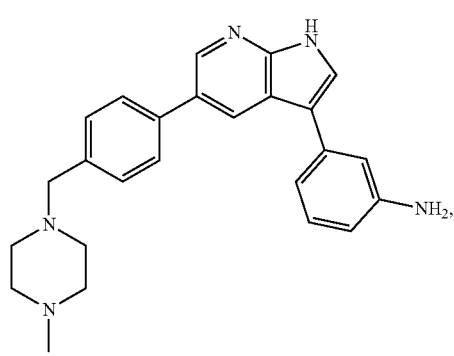
-continued
7i
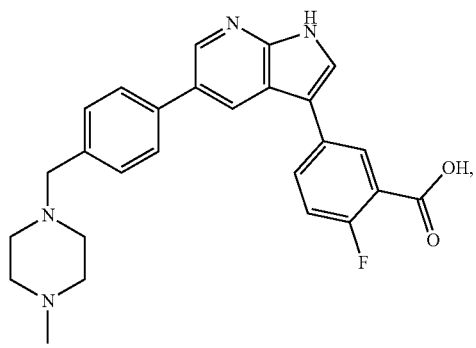
7j
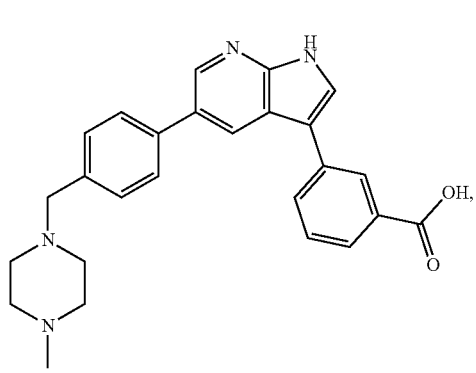
7k
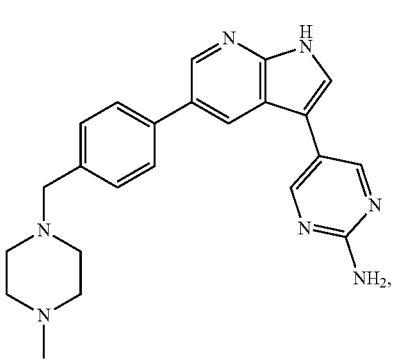
7l
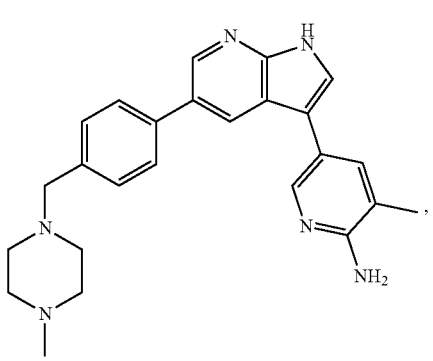

-continued
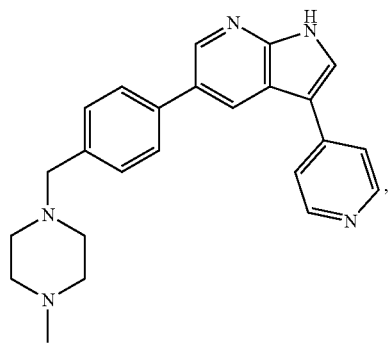
7n
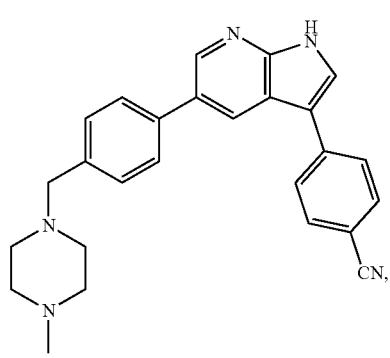
7o
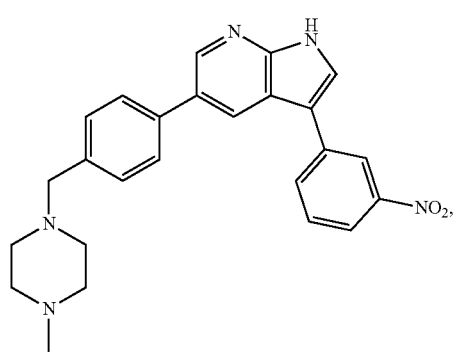
7p
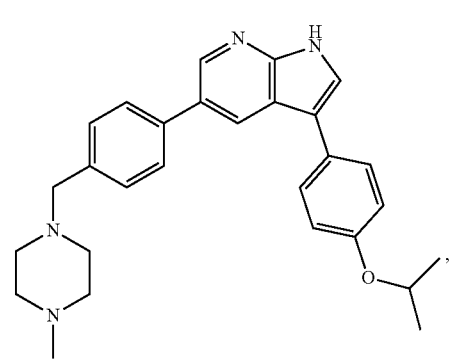
7q
-continued
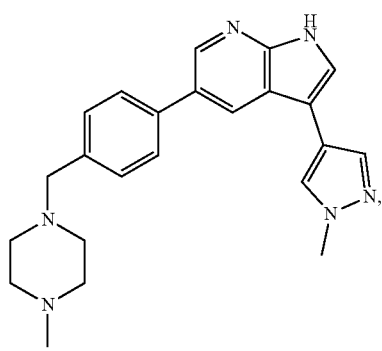
7s
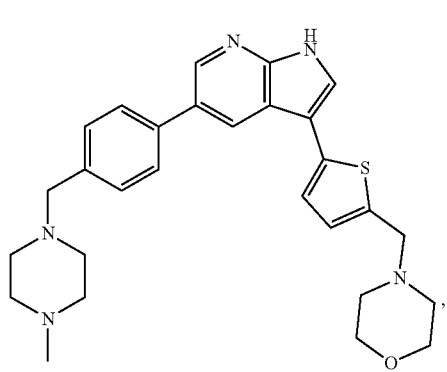
7t
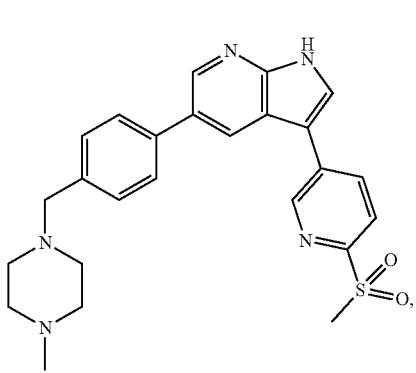
7u
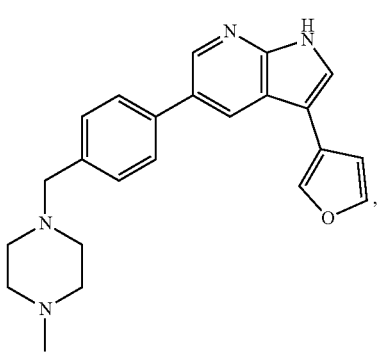
7w

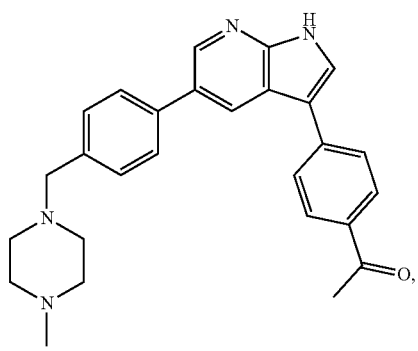
7x
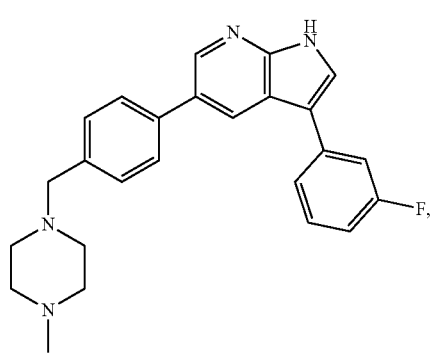
7y
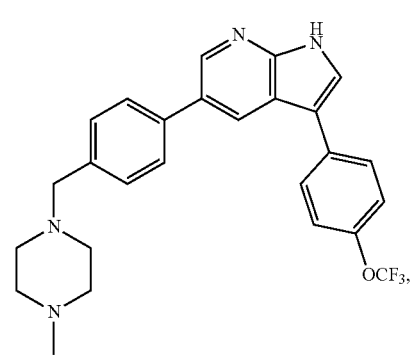
7z
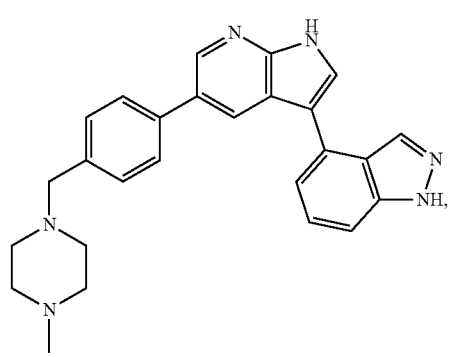
7aa
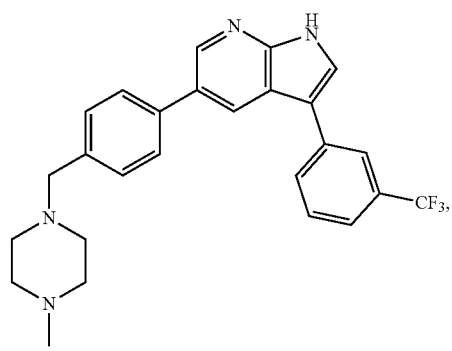
7ab
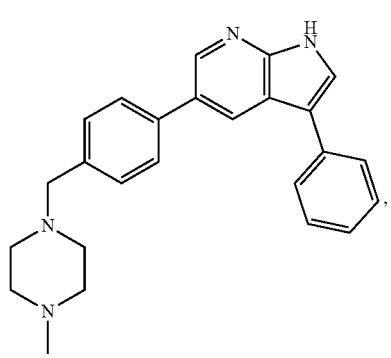
7ac
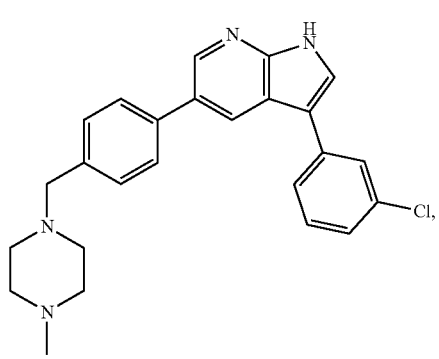
7ad
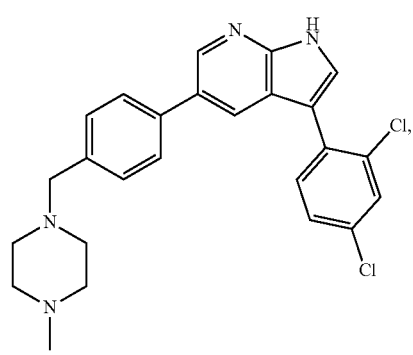
7ae

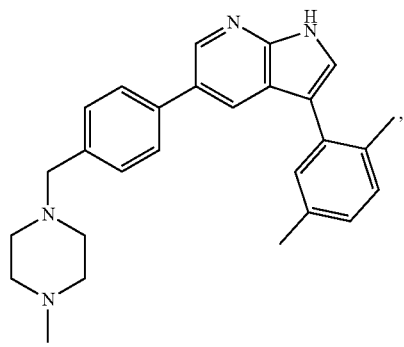 7af
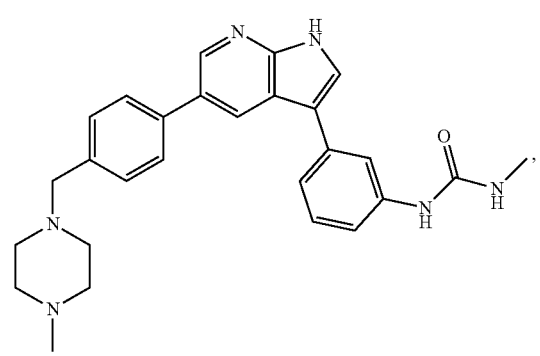 7ak
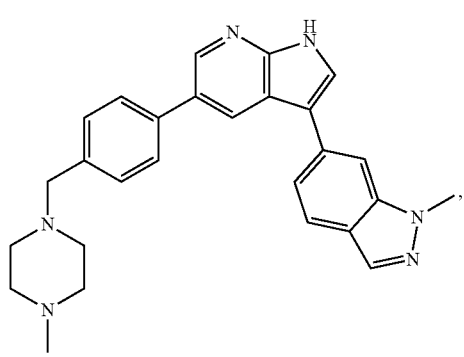 7ag
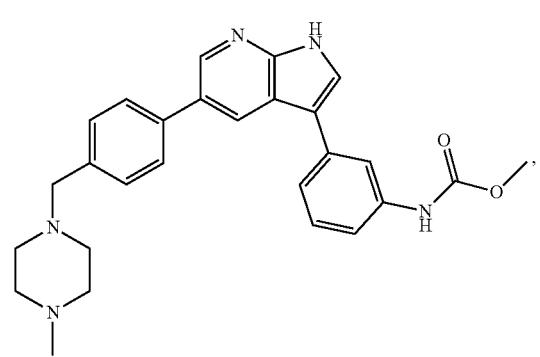 7al
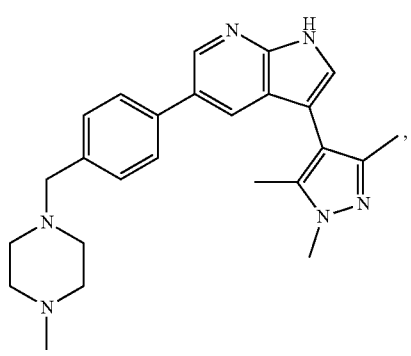 7ai
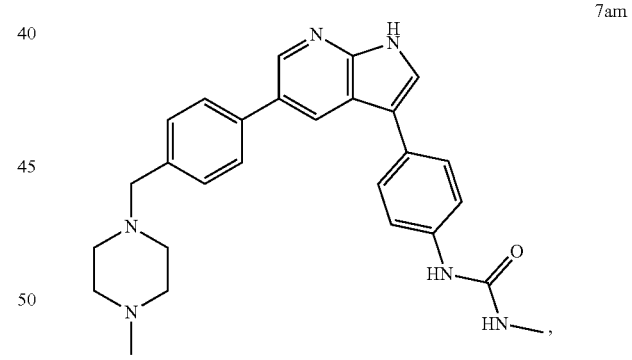 7am
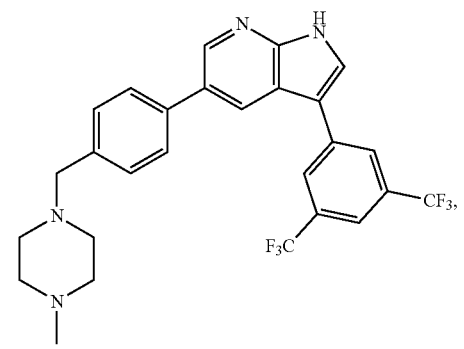 7aj
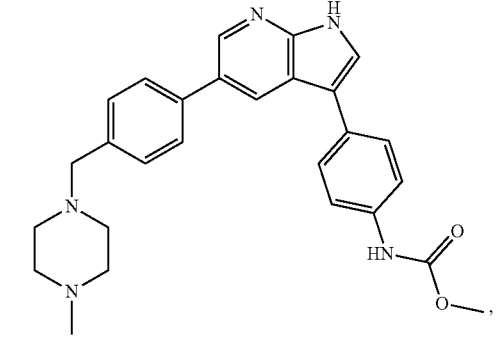 7an

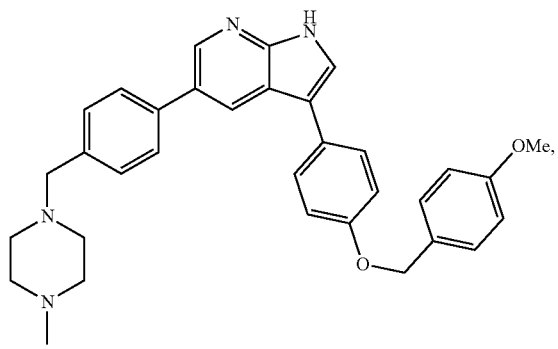
7ao
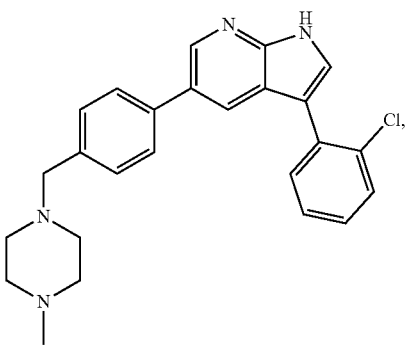
7as
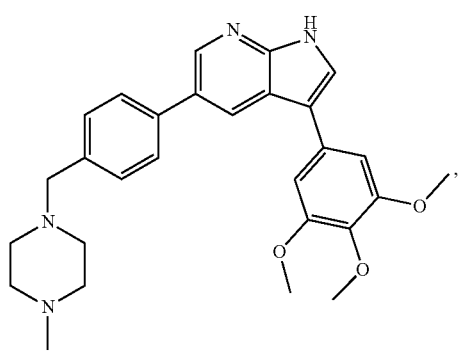
7ap
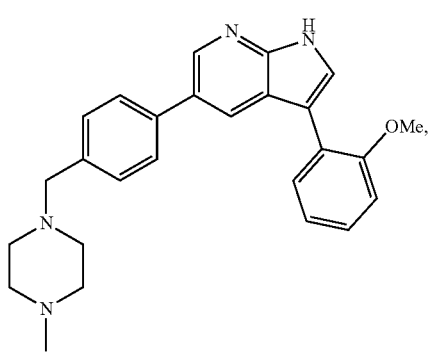
7at
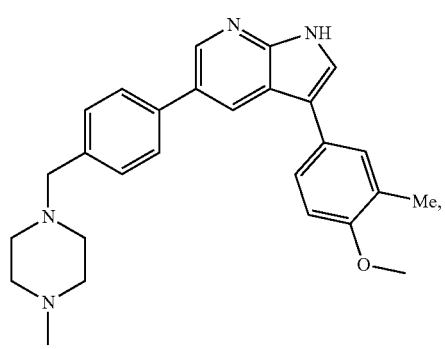
7aq
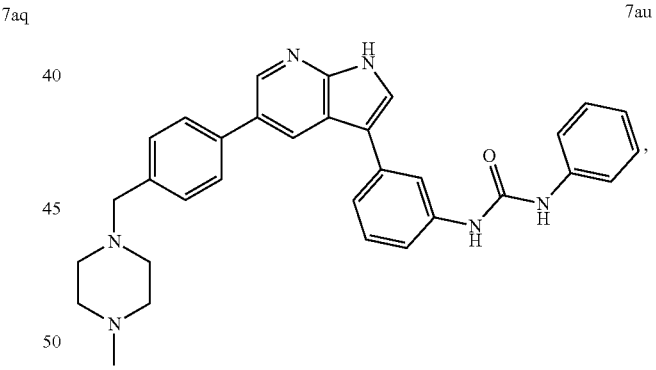
7au
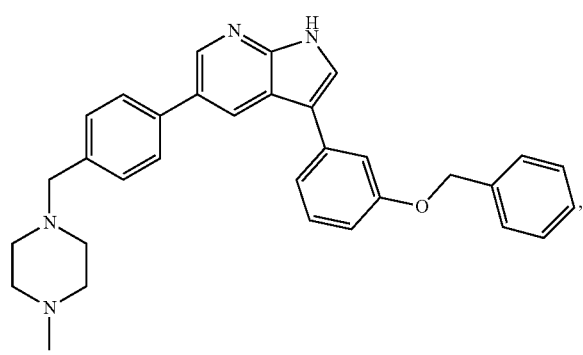
7ar
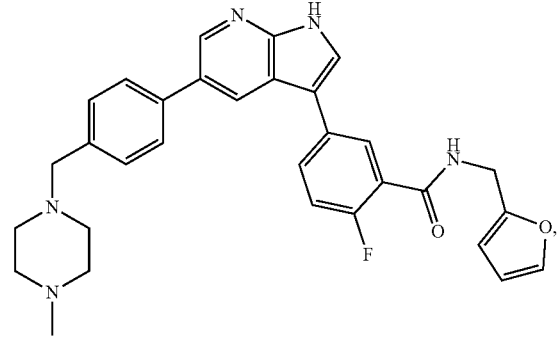
7av

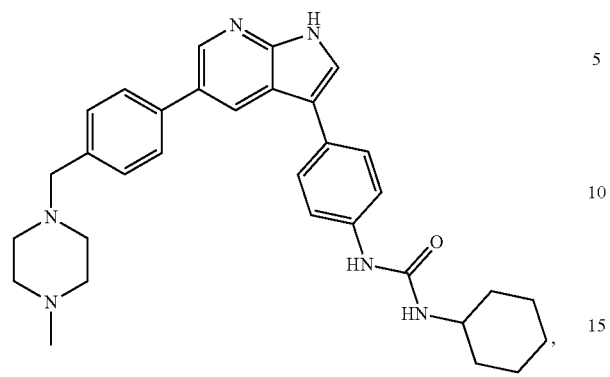
7aw
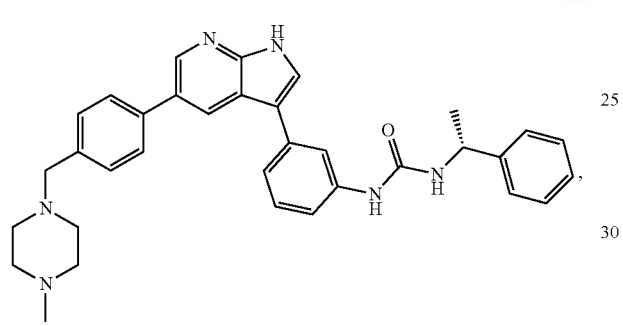
7ax
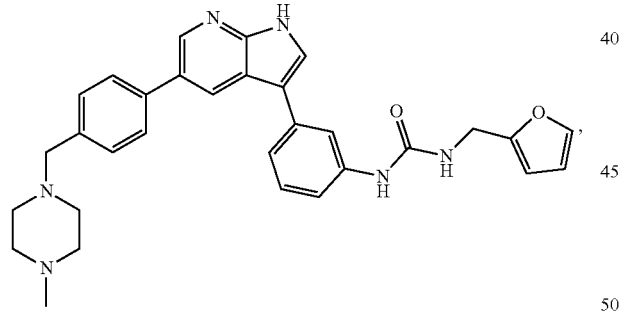
7ay
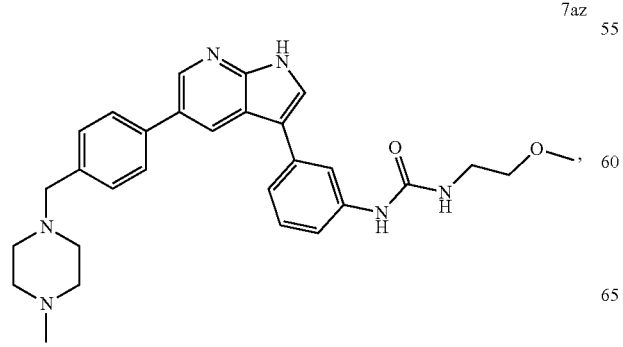
7az
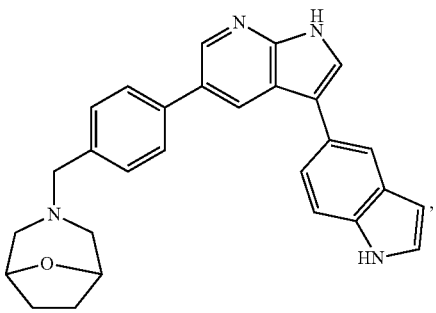
12a
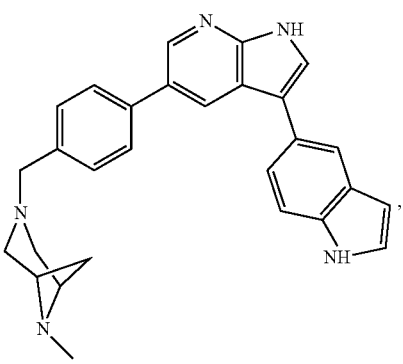
12b
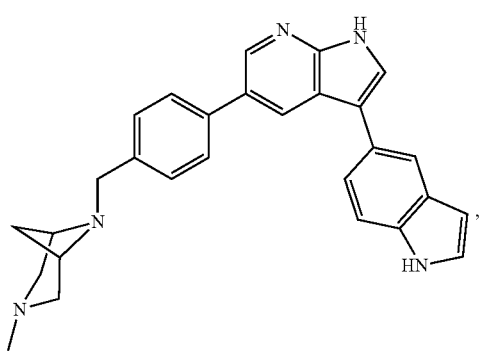
12c
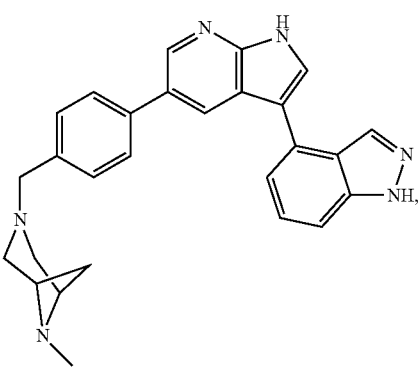
12d

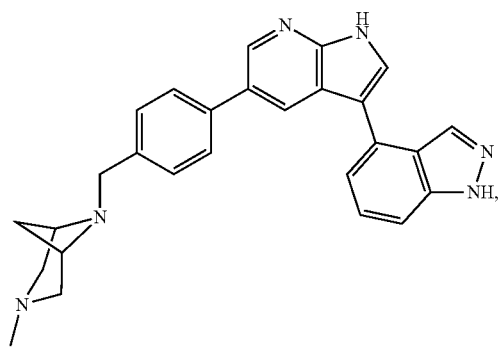
12e
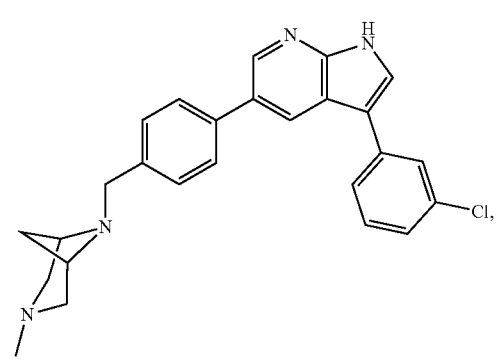
12f
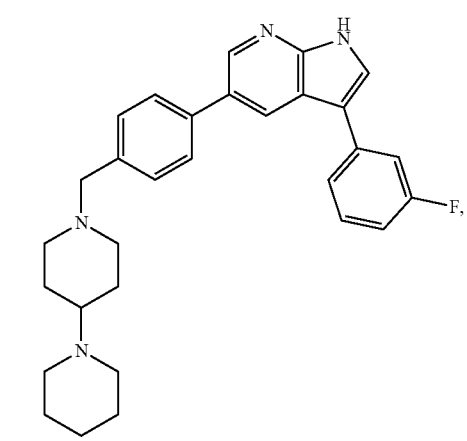
12g
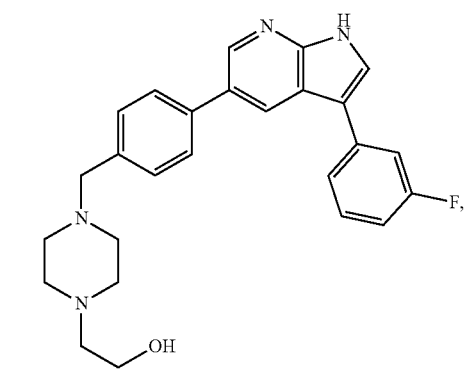
12h
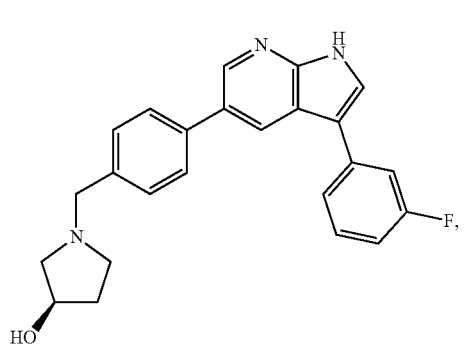
12i
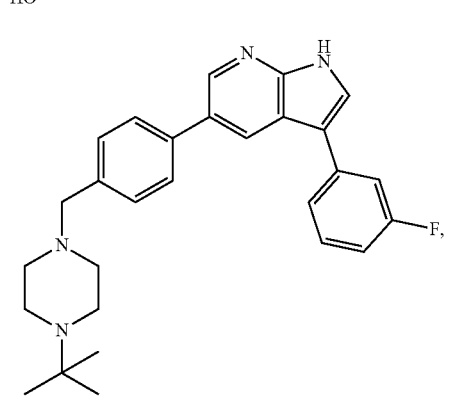
12j
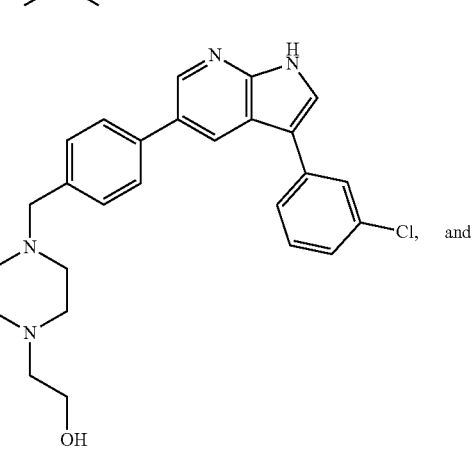
12k
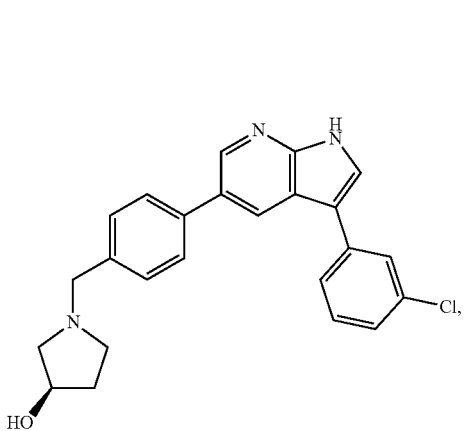
12l
and combinations thereof, or an N-oxide, crystalline form, hydrate, or a pharmaceutically acceptable salt thereof.

Preferably, the compound is selected from the group consisting of:

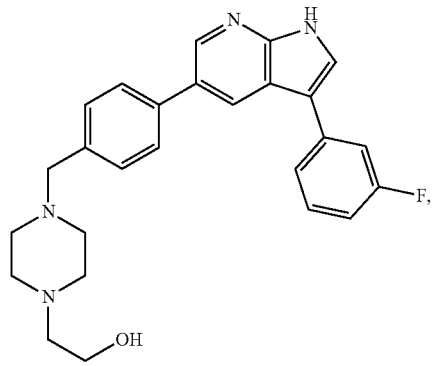

12h

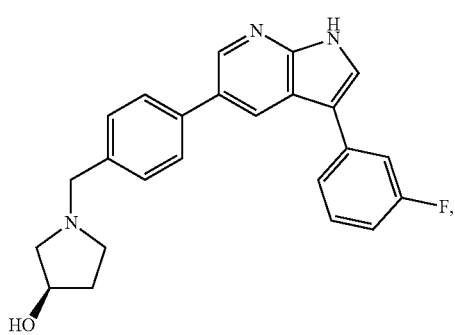

12i

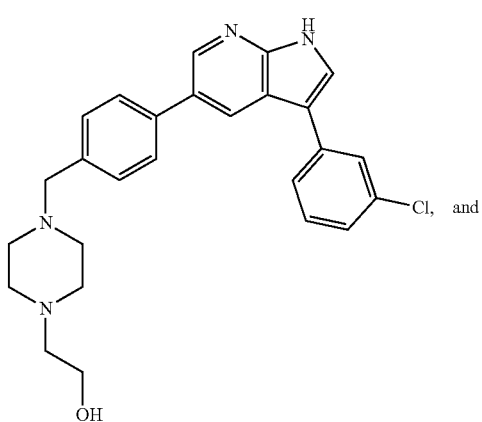

12k

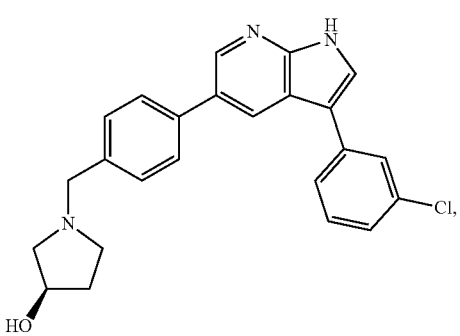

12l and combinations thereof, or an N-oxide, crystalline form, hydrate, or a pharmaceutically acceptable salt thereof.

More preferably, the compound is:

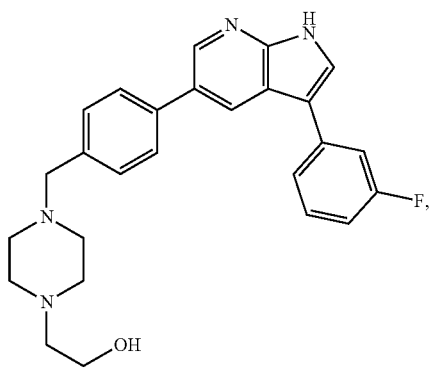

12h or an N-oxide, crystalline form, hydrate, or a pharmaceutically acceptable salt thereof.

More preferably, the compound is:

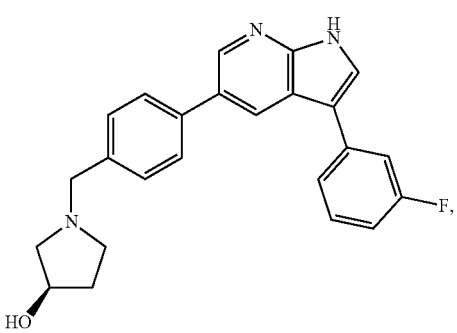

12i or an N-oxide, crystalline form, hydrate, or a pharmaceutically acceptable salt thereof.

More preferably, the compound is:

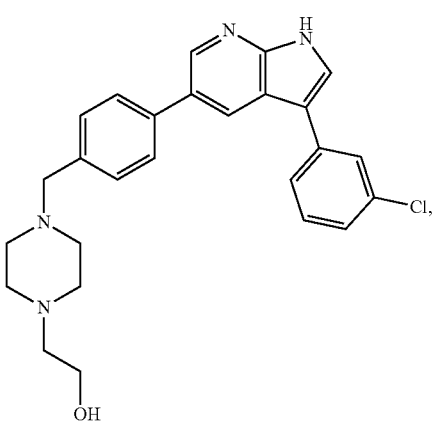

12k or an N-oxide, crystalline form, hydrate, or a pharmaceutically acceptable salt thereof.

More preferably, the compound is:

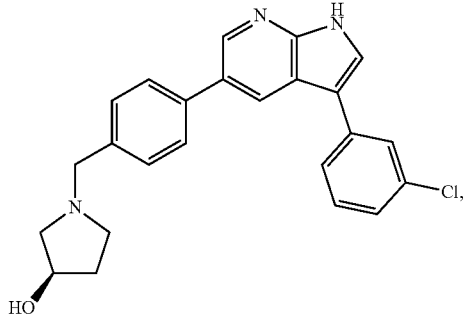

or an N-oxide, crystalline form, hydrate, or a pharmaceutically acceptable salt thereof.

Another embodiment of the present invention is a pharmaceutical composition. This pharmaceutical composition comprises a pharmaceutically acceptable carrier or diluent and one or more compounds according to formula (I):

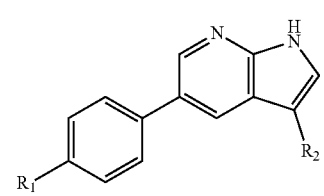

(I)

wherein:
- $R_1$ is an alkyl-heterocycloalkyl or an alkyl-heterobicycloalkyl, wherein the heterocycloalkyl or heterobicycloalkyl is optionally substituted with one or more atoms or groups selected from alkyl, hydroxy, alcohol, or heterocycloalkyl;
- $R_2$ is selected from phenyl, indolyl, pyridyl, dibenzofuranyl, benzodioxan, benzothiophenyl, pyrimidinyl, pyrazole, thienyl, indazole, or furanyl, any of which is optionally substituted with one or more atoms or groups selected from alkyl, alkoxy, amino, amide, cyano, ether, nitro, hydroxy, halogen, alkyl-heterocycloalkyl, sulfonyl, ketone, haloalkyl, haloalkoxy, alkylphenyl, carbamate, carboxylic acid, or urea;

or an N-oxide, crystalline form, hydrate, or a pharmaceutically acceptable salt thereof,
with the proviso that the compound is not:

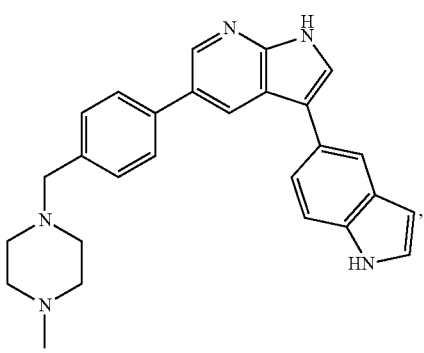

1

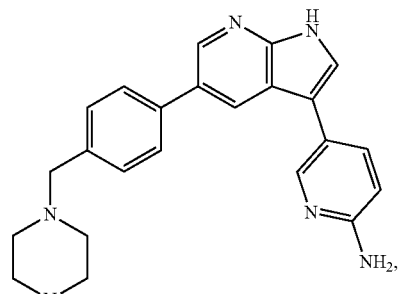

7m

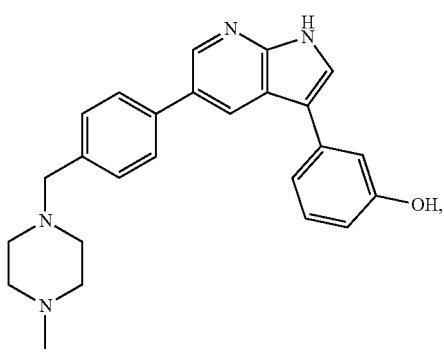

7r

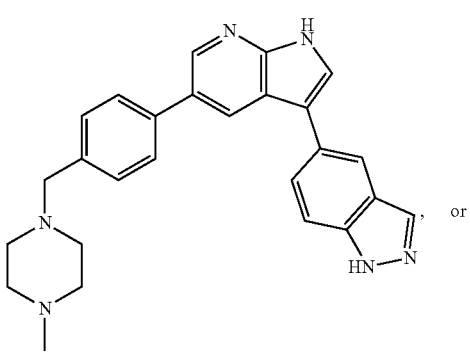

7v

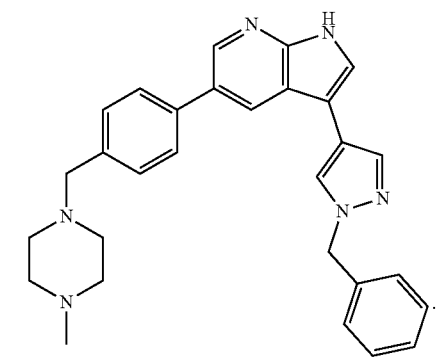

7ah

Suitable and preferred compounds that are used in the pharmaceutical compositions of the present invention are disclosed above in formulas (I)—(II), including the particular compounds also identified above.

A further embodiment of the present invention is a kit. This kit comprises a compound or a pharmaceutical composition disclosed herein with instructions for the use of the compound or the pharmaceutical composition, respectively.

The kits may also include suitable storage containers, e.g., ampules, vials, tubes, etc., for each compound of the present invention (which, e.g., may be in the form of pharmaceutical compositions) and other reagents, e.g., buffers, balanced salt solutions, etc., for use in administering the active agents to subjects. The compounds and/or pharmaceutical compositions of the invention and other reagents may be present in the kits in any convenient form, such as, e.g., in a solution or in a powder form. The kits may further include a packaging container, optionally having one or more partitions for housing the compounds and/or pharmaceutical compositions and other optional reagents.

Another embodiment of the present invention is a method for treating or ameliorating the effects of a disorder in a subject in need thereof. This method comprises administering to the subject an effective amount of one or more compounds having the structure of formula (I):

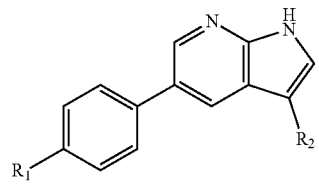

(I)

wherein:
- $R_1$ is an alkyl-heterocycloalkyl or an alkyl-heterobicycloalkyl, wherein the heterocycloalkyl or heterobicycloalkyl is optionally substituted with one or more atoms or groups selected from alkyl, hydroxy, alcohol, or heterocycloalkyl;
- $R_2$ is selected from phenyl, indolyl, pyridyl, dibenzofuranyl, benzodioxan, benzothiophenyl, pyrimidinyl, pyrazole, thienyl, indazole, or furanyl, any of which is optionally substituted with one or more atoms or groups selected from alkyl, alkoxy, amino, amide, cyano, ether, nitro, hydroxy, halogen, alkyl-heterocycloalkyl, sulfonyl, ketone, haloalkyl, haloalkoxy, alkylphenyl, carbamate, carboxylic acid, or urea;
- or an N-oxide, crystalline form, hydrate, or a pharmaceutically acceptable salt thereof, with the proviso that the compound is not:

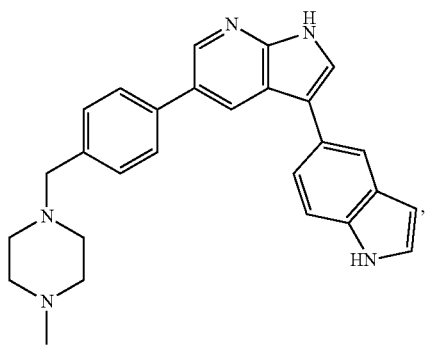

1

-continued

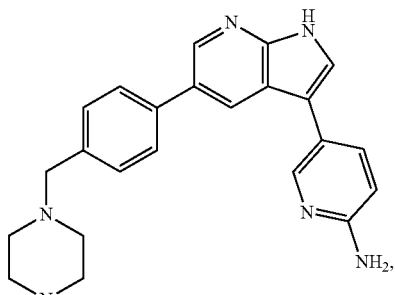

7m

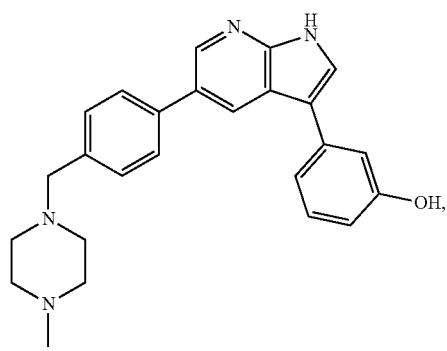

7r

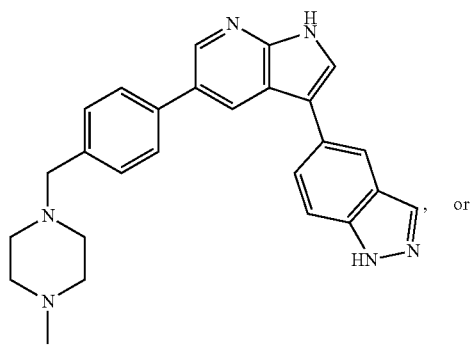

7v

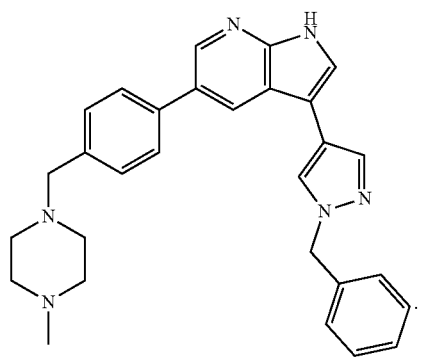

7ah

As used herein, the terms "treat," "treating," "treatment" and grammatical variations thereof mean subjecting an individual subject to a protocol, regimen, process or remedy, in which it is desired to obtain a physiologic response or outcome in that subject, e.g., a patient. In particular, the methods and compositions of the present invention may be used to slow the development of disease symptoms or delay the onset of the disease or condition, or halt the progression of disease development. However, because every treated subject may not respond to a particular treatment protocol, regimen, process or remedy, treating does not require that the desired physiologic response or outcome be achieved in each and every subject or subject population, e.g., patient population. Accordingly, a given subject or subject population, e.g., patient population, may fail to respond or respond inadequately to treatment.

As used herein, the terms "ameliorate", "ameliorating" and grammatical variations thereof mean to decrease the severity of the symptoms of a disease in a subject.

As used herein, the term "administering" means oral administration, administration as a suppository, topical contact, intravenous, intraperitoneal, intramuscular, intralesional, intranasal or subcutaneous administration, or the implantation of a slow-release device, e.g., a mini-osmotic pump, to a subject. Administration is by any route including parenteral, and transmucosal (e.g., oral, nasal, vaginal, rectal, or transdermal). Parenteral administration includes, e.g., intravenous, intramuscular, intra-arteriole, intradermal, subcutaneous, intraperitoneal, intraventricular, and intracranial. Other modes of delivery include, but are not limited to, the use of liposomal formulations, intravenous infusion, transdermal patches, and the like.

As used herein, a "subject" is a mammal, preferably, a human. In addition to humans, categories of mammals within the scope of the present invention include, for example, agricultural animals, veterinary animals, laboratory animals, etc. Some examples of agricultural animals include cows, pigs, horses, goats, etc. Some examples of veterinary animals include dogs, cats, etc. Some examples of laboratory animals include primates, rats, mice, rabbits, guinea pigs, etc.

Suitable and preferred compounds and pharmaceutical compositions for use in this method are as disclosed above in formulas (I)—(II), including the particular compounds identified above.

In certain embodiments, the disorder is a disease that involves endoplasmic reticulum (ER) stress.

In certain embodiments, the disorder is a disease characterized by aberrant kinase levels in the subject. Non-limiting examples of diseases characterized by aberrant kinase levels in the subject according to the present invention include chronic myelogenous leukemia (CML), acute myeloid leukemia (AML), acute lymphoblastic leukemia (ALL), acute promyelocytic leukemia, acute megakaryoblastic leukemia, childhood leukemias, familial chronic lymphocytic leukemia, left-right axis malformations, malignant melanoma, head and neck cancer, breast cancer, prostate cancer, lung cancer, pancreatic cancer, liver cancer, testicular cancer, gastric cancer, gastrointestinal cancer, gliomas, thyroid cancer, ovarian cancer, endometrium cancer, colon cancer, colorectal cancer, large-cell lymphomas, soft tissue sarcoma, inflammatory myofibroblastic tumors, hereditary hemorrhagic telangiectasia type 2 (Osler-Rendu-Weber syndrome 2), intestinal bleeding, arterial hypertension, arteriovenous malformations, fibrodysplasia ossificans progressiva, skeletal malformations, extra-skeletal bone formation, addiction, hypertension, myocardial infarction, acromesomelic dysplasia, ataxia, telangiectasia, Seckel syndrome, heart failure, juvenile polyposis syndrome, type A2 brachydactyly (hand malformations), acromesomelic chondrodysplasia (bone malformations), external genital abnormalities, primary pulmonary hypertension (PPH1), cardiofaciocutaneous syndrome, juvenile midline carcinomas, X-linked agammaglobulinemia, cardiac arrhythmias, somatic melanoma, familial melanoma, sarcoma, head and neck squamous cell carcinoma, epithelial tumor, cardiac hypertrophy, Rett Syndrome, X-linked infantile spasm syndrome, Li-Fraumeni syndrome, circadian disorder, mammary ductal carcinoma, mammary gland hyperplasia, cone-rod dystrophy (CORD) type 5, cone-rod dystrophy (CORD) type 6, Leber congenital amaurosis type 1 (LCA1), epilepsy, myotonia, muscle wasting, cataracts, hypogonadism, defective endocrine functions, male baldness, Down Syndrome (DS), glioblastoma, hepatocellular carcinoma, Pfeiffer syndrome, Kallmann syndrome 2, Stem cell leukemia lymphoma syndrome (SCLL), myeloproliferative disorders, Apert syndrome, Jackson-Weiss syndrome, Crouzon syndrome, Beare-Stevenson cutis gyrata syndrome, achondroplasia, hypochrondroplasia, thanatophoric dysplasia, craniosynostosis Adelaide type, San Diego skeletal displasia, Muenke syndrome, pituitary adenoma, myelodysplasia, capillary infantile hemangioma, idiopathic myelofibrosis, neuroblastoma, renal cancer, papillary carcinoma, hyper IgM syndrome, incontinentia pigmenti, hypohidrotic ectodermal dysplasia, rheumatoid arthritis, acanthosis nigricans, pineal hyperplasia, polycystic ovary syndrome, atypical migraine, diabetic hyperlipidemia, leprechaunism, bacterial-induced macrophage apoptosis, pyrogenic bacterial infections, uterine leiomyosarcoma, post-transplant lymphoproliferative disorder, myeloproliferative disease (MPD), polycythermia vera, brain tumor, gastrointestinal stromal tumor (GIST), mastocytosis, piebaldism, T cell leukemias, Williams-Beuren syndrome, Peutz-Jeghers syndrome, systemic lupus erythematosus, autosomal dominant thrombocytopenia, retinitis pigmentosa, hereditary papillary renal carcinoma, Müllerian duct syndrome type II, familial hypertrophic cardiomyopathy, myasthenia gravis, progressive deafness, polycystic kidney disease, Ewing's tumors, nonsyndromic mental retardation type 30 (MRX30), idiopathic hypereosinophilic syndrome, spina bifida, Wolcott-Rallison syndrome (WRS), liver glycogenosis, liver cirrhosis, hematopoietic malignancies, Carney complex tumors, heart contractility, diabetic nephropathy, diabetic retinopathy, diabetic vascular complications, autism, dominant spinocerebellar ataxia type 14, pain perception, osteoarthritic cartilage, bladder cancer, nasopharyngeal carcinoma, anaplastic large cell leukemia, familial medullary thyroid carcinoma (FMTC), multiple neoplasia type IIA (MEN2A), MEN2B, phaeochromocytoma, papillary thyroid carcinoma, Hischsprung disease, type 2 Oguchi disease, HPC1, blood coagulation, angina, renal oncocytoma, pulmonary adenomas, dominant brachydactyly type B, recessive Robinow syndrome (RRS), Coffin-Lowry syndrome, CNS tumors, Loeys-Dietz Syndrome, esophageal cancer, hereditary nonpolyposis colorectal cancer (HNPCC, Lynch syndrome), Marfan's syndrome type II, venous malformations, astrocytomas, hypertrophic and dilated cardiomyopathies, tibial muscular dystrophy, anhidrosis, pseudohypoaldosteronism type II, and chronic arthritis.

In one aspect of this embodiment, the disorder can include, but is not limited to: traumatic brain injury, stroke, ischemia, bipolar disorder, heart disease, atherosclerosis, type 1 diabetes, type 2 diabetes, obesity, cancer, autoimmune disease, and neurodegenerative disease.

In one aspect of this embodiment, the disorder is a neurodegenerative disease. Non-limiting examples of neurodegenerative diseases according to the present invention include Alzheimer's, Parkinson's, Amyotrophic Lateral Sclerosis (ALS), Friedreich's ataxia, Multiple sclerosis, Huntington's Disease, Transmissible spongiform encephalopathy, Charcot-Marie-Tooth disease, Dementia with Lewy bodies, Corticobasal degeneration, Progressive supranuclear palsy, Chronic Traumatic Encephalopathy (CTE), Polyglutamine diseases, Prion Disease, glaucoma, and Hereditary spastic paraparesis.

In certain embodiments, the disorder is Amyotrophic Lateral Sclerosis (ALS).

In another aspect of this embodiment, the method further comprises co-administering, together with one or more compounds or pharmaceutical compositions of the present invention, to the subject an effective amount of one or more of additional therapeutic agents such as 5-hydroxytryptophan, Activase, AFQ056 (Novartis Corp., New York, NY), Aggrastat, Albendazole, alpha-lipoic acid/L-acetyl carnitine, Alteplase, Amantadine (Symmetrel), amlodipine, Ancrod, Apomorphine (Apokyn), Arimoclomol, Arixtra, Armodafinil, Ascorbic acid, Ascriptin, Aspirin, atenolol, Avonex, baclofen (Lioresal), Banzel, Benztropine (Cogentin), Betaseron, BGG492 (Novartis Corp., New York, NY), Botulinum toxin, Bufferin, Carbatrol®, Carbidopa/levodopa immediate-release (Sinemet), Carbidopa/levodopa oral disintegrating (Parcopa), Carbidopa/levodopa/Entacapone (Stalevo), CERE-110: Adeno-Associated Virus Delivery of NGF (Ceregene, San Diego, CA), cerebrolysin, CinnoVex, citalopram, citicoline, Clobazam, Clonazepam, Clopidogrel, clozapine (Clozaril), Coenzyme Q, Creatine, dabigatran, dalteparin, Dapsone, Davunetide, Deferiprone, Depakene®, Depakote ER®, Depakote®, Desmoteplase, Diastat, Diazepam, Digoxin, Dilantin®, Dimebon, dipyridamole, divalproex (Depakote), Donepezil (Aricept), EGb 761, Eldepryl, ELND002 (Elan Pharmaceuticals, Dublin, Ireland), Enalapril, enoxaparin, Entacapone (Comtan), epoetin alfa, Eptifibatide, Erythropoietin, Escitalopram, Eslicarbazepine acetate, Esmolol, Ethosuximide, Ethyl-EPA (Miraxion™), Exenatide, Extavia, Ezogabine, Felbamate, Felbatol®, Fingolimod (Gilenya), fluoxetine (Prozac), fondaparinux, Fragmin, Frisium, Gabapentin, Gabitril®, Galantamine, Glatiramer (Copaxone), haloperidol (Haldol), Heparin, human chorionic gonadotropin (hCG), Idebenone, Inovelon®, insulin, Interferon beta 1a, Interferon beta 1b, ioflupane 123I (DATSCAN®), IPX066 (Impax Laboratories Inc., Hayward, CA), JNJ-26489112 (Johnson and Johnson, New Brunswick, NJ), Keppra®, Klonopin, Lacosamide, L-Alpha glycerylphosphorylcholine, Lamictal®, Lamotrigine, Levetiracetam, liraglutide, Lisinopril, Lithium carbonate, Lopressor, Lorazepam, losartan, Lovenox, Lu AA24493, Luminal, LY450139 (Eli Lilly, Indianapolis, Indiana), Lyrica, Masitinib, Mecobalamin, Memantine, methylprednisolone, metoprolol tartrate, Minitran, Minocycline, mirtazapine, Mitoxantrone (Novantrone), Mysoline®, Natalizumab (Tysabri), Neurontin®, Niacinamide, Nitro-Bid, Nitro-Dur, nitroglycerin, Nitrolingual, Nitromist, Nitrostat, Nitro-Time, Norepinephrine (NOR), Carbamazepine, octreotide, Onfi®, Oxcarbazepine, Oxybutinin chloride, PF-04360365 (Pfizer, New York, NY), Phenobarbital, Phenytek®, Phenytoin, piclozotan, Pioglitazone, Plavix, Potiga, Pramipexole (Mirapex), pramlintide, Prednisone, Primidone, Prinivil, probenecid, Propranolol, PRX-00023 (EPIX Pharmaceuticals Inc.), PXT3003, Quinacrine, Ramelteon, Rasagiline (Azilect), Rebif, ReciGen, remacemide, Resveratrol, Retavase, reteplase, riluzole (Rilutek), Rivastigmine (Exelon), Ropinirole (Requip), Rotigotine (Neupro), Rufinamide, Sabril, safinamide (EMD Serono, Rockland, MA), Salagen, Sarafem, Selegiline (1-deprenyl, Eldepryl), SEN0014196 (Siena Biotech, Siena, Italy), sertraline (Zoloft), Simvastatin, Sodium Nitroprussiate (NPS), sodium phenylbutyrate, Stanback Headache Powder, Tacrine (Cognex), Tamoxifen, tauroursodeoxycholic acid (TUDCA), Tegretol®, Tenecteplase, Tenormin, Tetrabenazine (Xenazine), THR-18 (Thrombotech Ltd.), Tiagabine, Tideglusib, tirofiban, tissue plasminogen activator (tPA), tizanidine (Zanaflex), TNKase, Tolcapone (Tasmar), Tolterodine, Topamax®, Topiramate, Trihexyphenidyl (formerly Artane), Trileptal®, ursodiol, Valproic Acid, valsartan, Varenicline (Pfizer), Vimpat, Vitamin E, Warfarin, Zarontin®, Zestril, Zonegran®, Zonisamide, Zydis selegiline HCL Oral disintegrating (Zelapar), and combinations thereof.

For example, to treat or ameliorate the effects of Alzheimer's disease, a subject may be administered an effective amount of one or more compounds or pharmaceutical compositions of the present invention and, e.g., one or more of the following: Donepezil (Aricept), Rivastigmine (Exelon), Galantamine (Razadyne), Tacrine (Cognex), Memantine (Namenda), Vitamin E, CERE-110: Adeno-Associated Virus Delivery of NGF (Ceregene), LY450139 (Eli Lilly), Exenatide, Varenicline (Pfizer), PF-04360365 (Pfizer), Resveratrol, and Donepezil (Eisai Korea).

To treat or ameliorate the effects of Parkinson's disease, a subject may be administered an effective amount of one or more compounds or pharmaceutical compositions of the present invention and, e.g., one or more of the following: Carbidopa/levodopa immediate-release (Sinemet), Carbidopa/levodopa oral disintegrating (Parcopa), Carbidopa/levodopa/Entacapone (Stalevo), Ropinirole (Requip), Pramipexole (Mirapex), Rotigotine (Neupro), Apomorphine (Apokyn), Selegiline (1-deprenyl, Eldepryl), Rasagiline (Azilect), Zydis selegiline HCL Oral disintegrating (Zelapar), Entacapone (Comtan), Tolcapone (Tasmar), Amantadine (Symmetrel), Trihexyphenidyl (formerly Artane), Benztropine (Cogentin), IPX066 (Impax Laboratories Inc.), Rasagiline (Teva Neuroscience, Inc.), ioflupane 123I (DATSCAN®), safinamide (EMD Serono), and Pioglitazone.

To treat or ameliorate the effects of Amyotrophic Lateral Sclerosis, a subject may be administered an effective amount of one or more compounds or pharmaceutical compositions of the present invention and, e.g., one or more of the following: riluzole (Rilutek), Lithium carbonate, Arimoclomol, Creatine, Tamoxifen, Mecobalamin, Memantine (Ebixa), and tauroursodeoxycholic acid (TUDCA).

To treat or ameliorate the effects of Friedreich's ataxia, a subject may be administered an effective amount of one or more compounds or pharmaceutical compositions of the present invention and, e.g., one or more of the following: Idebenone, Coenzyme Q, 5-hydroxytryptophan, Propranolol, Enalapril, Lisinopril, Digoxin, Erythropoietin, Lu AA24493, Deferiprone, Varenicline, IVIG, Pioglitazone, and EGb 761.

To treat or ameliorate the effects of multiple sclerosis, a subject may be administered an effective amount of one or more compounds or pharmaceutical compositions of the present invention and, e.g., one or more of the following: Avonex, Betaseron, Extavia, Rebif, Glatiramer (Copaxone), Fingolimod (Gilenya), Natalizumab (Tysabri), Mitoxantrone (Novantrone), baclofen (Lioresal), tizanidine (Zanaflex), methylprednisolone, CinnoVex, ReciGen, Masitinib, Prednisone, Interferon beta 1a, Interferon beta 1b, and ELND002 (Elan Pharmaceuticals).

To treat or ameliorate the effects of Huntington's disease, a subject may be administered an effective amount of one or more compounds or pharmaceutical compositions of the present invention and, e.g., one or more of the following: Tetrabenazine (Xenazine), haloperidol (Haldol), clozapine (Clozaril), clonazepam (Klonopin), diazepam (Valium), escitalopram (Lexapro), fluoxetine (Prozac, Sarafem), sertraline (Zoloft), valproic acid (Depakene), divalproex (Depakote), lamotrigine (Lamictal), Dimebon, AFQ056 (Novartis), Ethyl-EPA (Miraxion™), SEN0014196 (Siena Biotech), sodium phenylbutyrate, citalopram, ursodiol, minocycline, remacemide, and mirtazapine.

To treat or ameliorate the effects of transmissible spongiform encephalopathy, a subject may be administered an effective amount of one or more compounds or pharmaceutical compositions of the present invention and e.g., Quinacrine.

To treat or ameliorate the effects of Charcot-Marie-Tooth disease, a subject may be administered an effective amount of one or more compounds or pharmaceutical compositions of the present invention and, e.g., one or more of the following: ascorbic acid and PXT3003.

To treat or ameliorate the effects of dementia with Lewy bodies, a subject may be administered an effective amount of one or more compounds or pharmaceutical compositions of the present invention and, e.g., one or more of the following: Aricept, Galantamine, Memantine, Armodafinil, Donepezil, and Ramelteon.

To treat or ameliorate the effects of corticobasal degeneration, a subject may be administered an effective amount of one or more compounds or pharmaceutical compositions of the present invention and, e.g., one or more of the following: Davunetide and Coenzyme Q10.

To treat or ameliorate the effects of progressive supranuclear palsy, a subject may be administered an effective amount of one or more compounds or pharmaceutical compositions of the present invention and, e.g., one or more of the following: Tideglusib, Rasagiline, alpha-lipoic acid/L-acetyl carnitine, Riluzole, Niacinamide, and Rivastigmine.

To treat or ameliorate the effects of hereditary spastic paraparesis, a subject may be administered an effective amount of one or more compounds or pharmaceutical compositions of the present invention and, e.g., one or more of the following: Baclofen, Tizanidine, Oxybutinin chloride, Tolterodine, and Botulinum toxin.

In the present invention, one or more compounds or pharmaceutical compositions may be co-administered to a subject in need thereof together in the same composition, simultaneously in separate compositions, or as separate compositions administered at different times, as deemed most appropriate by a physician.

An additional embodiment of the present invention is a method for treating or ameliorating the effects of a disorder in a subject in need thereof. This method comprises administering to the subject an effective amount of a pharmaceutical composition comprising a pharmaceutically acceptable carrier or diluent and one or more compounds having the structure of formula (I):

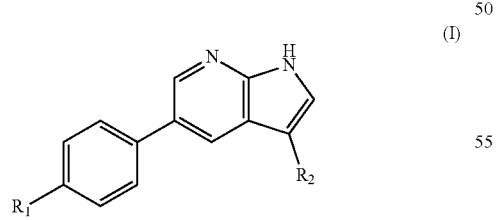

(I)

wherein:
  $R_1$ is an alkyl-heterocycloalkyl or an alkyl-heterobicycloalkyl, wherein the heterocycloalkyl or heterobicycloalkyl is optionally substituted with one or more atoms or groups selected from alkyl, hydroxy, alcohol, or heterocycloalkyl;
  $R_2$ is selected from phenyl, indolyl, pyridyl, dibenzofuranyl, benzodioxan, benzothiophenyl, pyrimidinyl, pyrazole, thienyl, indazole, or furanyl, any of which is optionally substituted with one or more atoms or groups selected from alkyl, alkoxy, amino, amide, cyano, ether, nitro, hydroxy, halogen, alkyl-heterocycloalkyl, sulfonyl, ketone, haloalkyl, haloalkoxy, alkylphenyl, carbamate, carboxylic acid, or urea;

or an N-oxide, crystalline form, hydrate, or a pharmaceutically acceptable salt thereof, with the proviso that the compound is not:

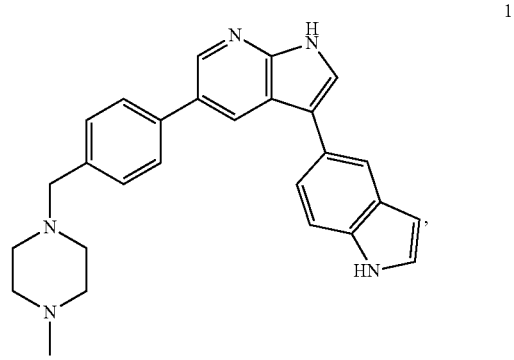

1

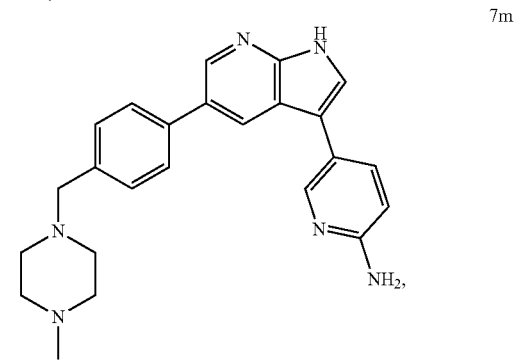

7m

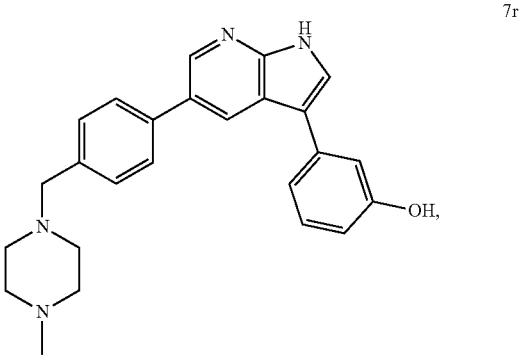

7r

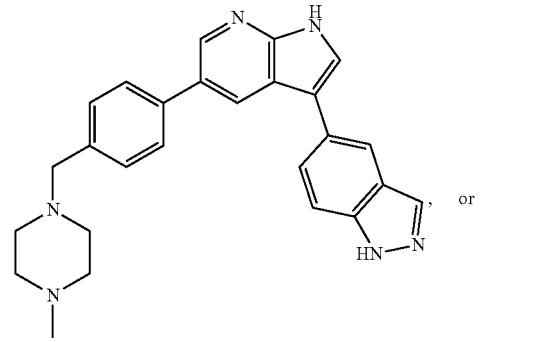

7v

, or

-continued

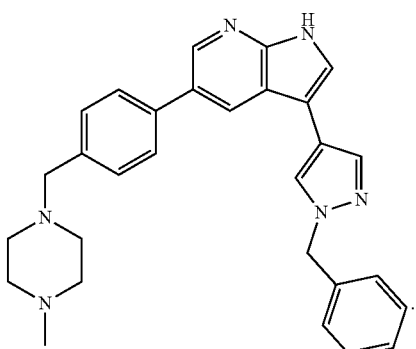
7ah

Suitable and preferred pharmaceutical compositions for use in this method are as disclosed above in formulas (I)—(II), including pharmaceutical compositions containing the particular compounds identified above. Suitable and preferred subjects who may be treated in accordance with this method are as disclosed above. In this embodiment, the methods may be used to treat disorders set forth above, including diseases that involve endoplasmic reticulum (ER) stress and diseases characterized by aberrant kinase levels in a subject.

In another aspect of this embodiment, the method further comprises co-administering to the subject an effective amount of one or more additional therapeutic agents disclosed herein.

Another embodiment of the present invention is a method of suppressing the toxicity of endoplasmic reticulum (ER) stress in a subject in need thereof. This method comprises administering to the subject an effective amount of a kinase inhibitor, which comprises one or more compounds having the structure of formula (I):

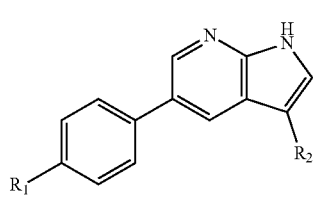
(I)

wherein:
- $R_1$ is an alkyl-heterocycloalkyl or an alkyl-heterobicycloalkyl, wherein the heterocycloalkyl or heterobicycloalkyl is optionally substituted with one or more atoms or groups selected from alkyl, hydroxy, alcohol, or heterocycloalkyl;
- $R_2$ is selected from phenyl, indolyl, pyridyl, dibenzofuranyl, benzodioxan, benzothiophenyl, pyrimidinyl, pyrazole, thienyl, indazole, or furanyl, any of which is optionally substituted with one or more atoms or groups selected from alkyl, alkoxy, amino, amide, cyano, ether, nitro, hydroxy, halogen, alkyl-heterocycloalkyl, sulfonyl, ketone, haloalkyl, haloalkoxy, alkylphenyl, carbamate, carboxylic acid, or urea;

or an N-oxide, crystalline form, hydrate, or a pharmaceutically acceptable salt thereof, with the proviso that the compound is not:

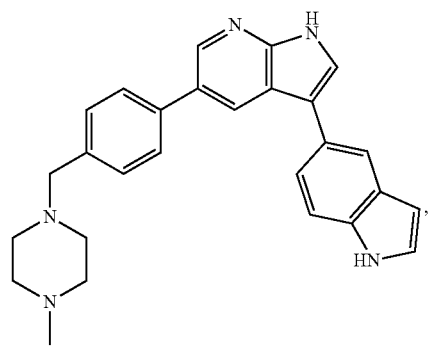
1

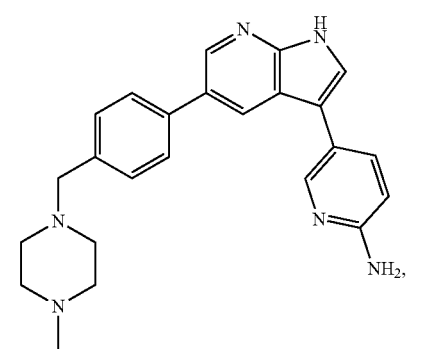
7m

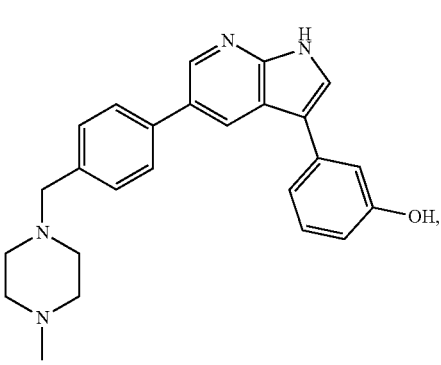
7r

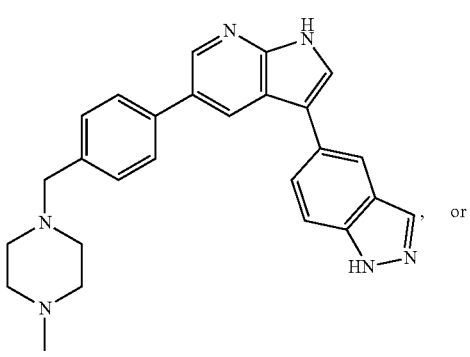
7v or

-continued

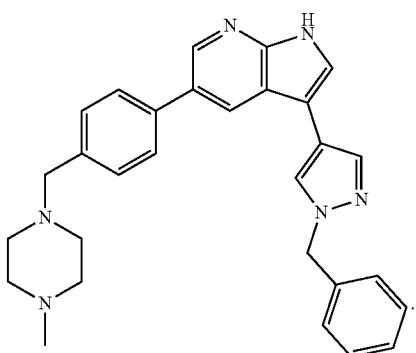

7ah

As used herein, "toxicity of endoplasmic reticulum (ER) stress" means a number of physiological and pathological conditions, as well as a variety of pharmacological agents such as cyclopiazonic acid (CPA), that are able to disturb proper ER function and thereby cause ER stress, which severely impair protein folding and therefore pose the risk of proteotoxicity. Assays for ER stress are as disclosed herein, for instance, in the Examples section.

Suitable and preferred compounds for use in this method are as disclosed above in formulas (I)—(II), including the particular compounds identified above. Suitable and preferred subjects who may be treated in accordance with this method are as disclosed above. In this embodiment, the methods may be used to treat the disorders set forth above, including neurodegenerative diseases.

In another aspect of this embodiment, the method further comprises co-administering to the subject an effective amount of one or more additional therapeutic agents disclosed herein.

As used herein, the terms "suppress", "suppressing" and grammatical variations thereof mean to change, such as decreasing or reducing the occurrence of toxic ER stress. In this embodiment, "contacting" means bringing the compound and optionally one or more additional therapeutic agents into close proximity to the cells in need of such modulation. This may be accomplished using conventional techniques of drug delivery to the subject or in the in vitro situation by, e.g., providing the compound and optionally other therapeutic agents to a culture media in which the cells are located.

In one aspect of this embodiment, the subject is a mammal. Preferably, the mammal is selected from the group consisting of humans, veterinary animals, and agricultural animals. More preferably, the mammal is a human.

An additional embodiment of the present invention is a method of treating or ameliorating the effects of a disease involving axon degeneration in a subject in need thereof. This method comprises administering to the subject an effective amount of a kinase inhibitor, which comprises one or more compounds having the structure of formula (I):

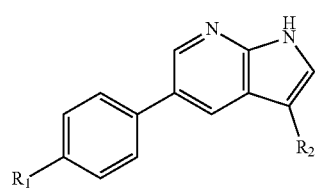

(I)

wherein:

R$_1$ is an alkyl-heterocycloalkyl or an alkyl-heterobicycloalkyl, wherein the heterocycloalkyl or heterobicycloalkyl is optionally substituted with one or more atoms or groups selected from alkyl, hydroxy, alcohol, or heterocycloalkyl;

R$_2$ is selected from phenyl, indolyl, pyridyl, dibenzofuranyl, benzodioxan, benzothiophenyl, pyrimidinyl, pyrazole, thienyl, indazole, or furanyl, any of which is optionally substituted with one or more atoms or groups selected from alkyl, alkoxy, amino, amide, cyano, ether, nitro, hydroxy, halogen, alkyl-heterocycloalkyl, sulfonyl, ketone, haloalkyl, haloalkoxy, alkylphenyl, carbamate, carboxylic acid, or urea;

or an N-oxide, crystalline form, hydrate, or a pharmaceutically acceptable salt thereof, with the proviso that the compound is not:

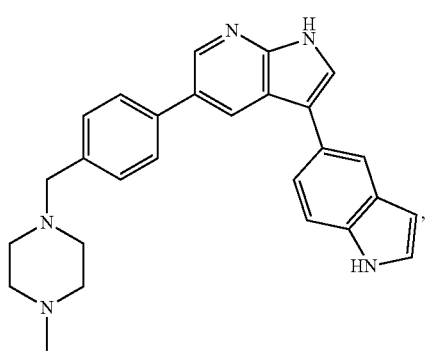

1

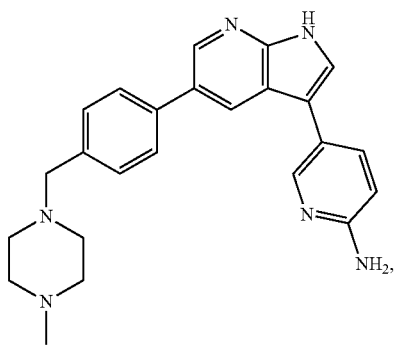

7m

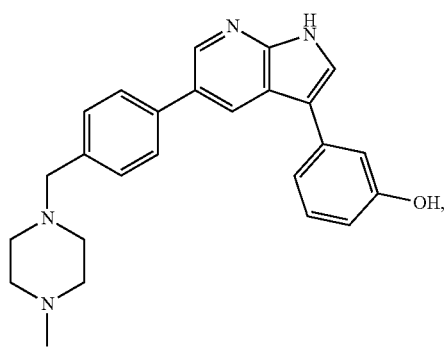

7r

-continued

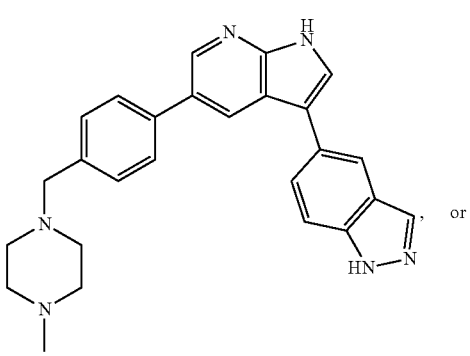
7v

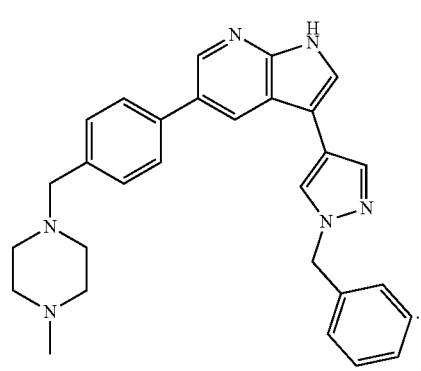
7ah

As used herein, "axon degeneration" means a characteristic event that disrupts functional connectivity of neural circuits, and is a critical feature in many neurodegenerative conditions including stroke, glaucoma, and motor neuropathies.

Suitable and preferred compounds for use in this method are as disclosed above in formulas (I)—(II), including the particular compounds identified above. Suitable and preferred subjects who may be treated in accordance with this method are as disclosed above. In this embodiment, the methods may be used to treat the disorders set forth above.

An additional embodiment of the present invention is a method for treating or ameliorating the effects of a neurodegenerative disease in a subject in need thereof. This method comprises administering to the subject an effective amount of one or more compounds having the structure of formula (I):

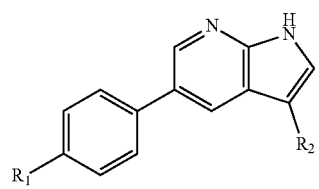
(I)

wherein:
R$_1$ is an alkyl-heterocycloalkyl or an alkyl-heterobicycloalkyl, wherein the heterocycloalkyl or heterobicycloalkyl is optionally substituted with one or more atoms or groups selected from alkyl, hydroxy, alcohol, or heterocycloalkyl;
R$_2$ is selected from phenyl, indolyl, pyridyl, dibenzofuranyl, benzodioxan, benzothiophenyl, pyrimidinyl, pyrazole, thienyl, indazole, or furanyl, any of which is optionally substituted with one or more atoms or groups selected from alkyl, alkoxy, amino, amide, cyano, ether, nitro, hydroxy, halogen, alkyl-heterocycloalkyl, sulfonyl, ketone, haloalkyl, haloalkoxy, alkylphenyl, carbamate, carboxylic acid, or urea;

or an N-oxide, crystalline form, hydrate, or a pharmaceutically acceptable salt thereof, with the proviso that the compound is not:

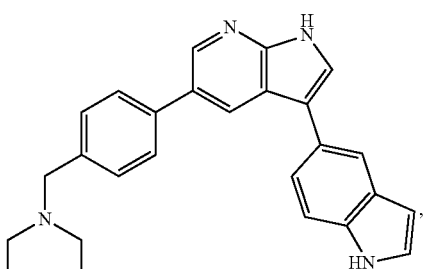
1

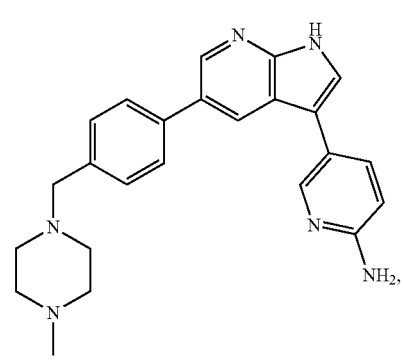
7m

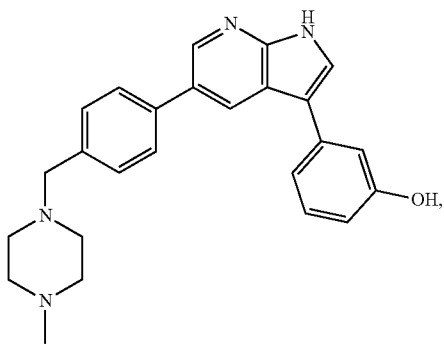
7r

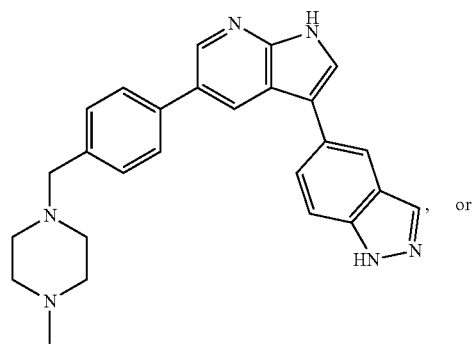
7v

-continued

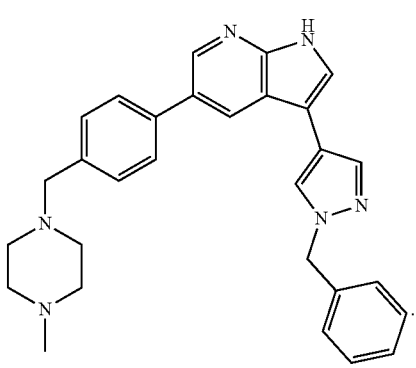

7ah

Suitable and preferred compounds for use in this method are as disclosed above in formulas (I)—(II), including the particular compounds identified above. In this embodiment, the method may be used to treat the disorders set forth above.

Suitable and preferred subjects are as disclosed herein. In this embodiment, the methods may be used to treat the neurodegenerative disorders set forth above.

In one aspect of this embodiment, the method further comprises co-administering to the subject an effective amount of one or more therapeutic agents disclosed herein.

An additional embodiment of the present invention is a compound having the structure of:

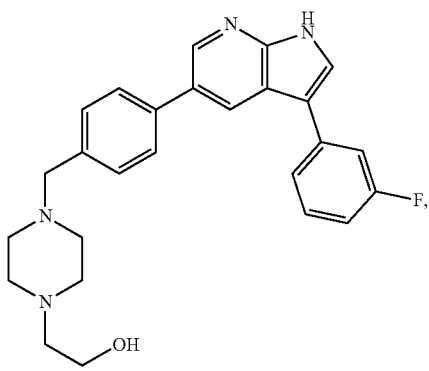

12h or an N-oxide, crystalline form, hydrate, or a pharmaceutically acceptable salt thereof.

An additional embodiment of the present invention is a compound having the structure of:

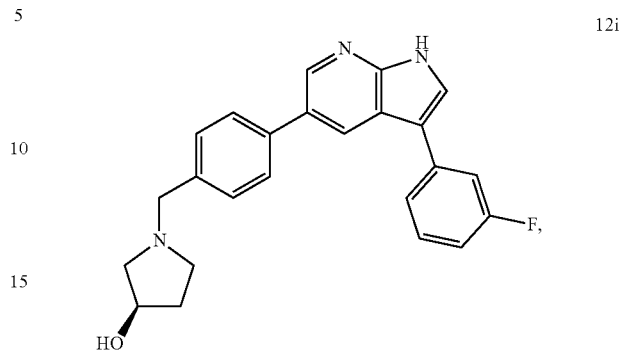

12i or an N-oxide, crystalline form, hydrate, or a pharmaceutically acceptable salt thereof.

An additional embodiment of the present invention is a compound having the structure of:

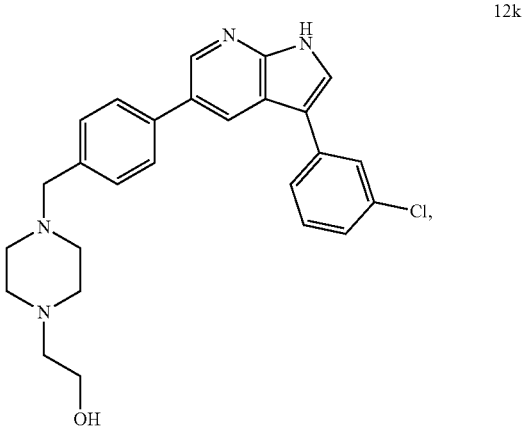 [SMILES: OCCN1CCN(Cc2ccc(-c3cnc4[nH]cc(-c5cccc(Cl)c5)c4c3)cc2)CC1]

12k or an N-oxide, crystalline form, hydrate, or a pharmaceutically acceptable salt thereof.

An additional embodiment of the present invention is a compound having the structure of:

12l or an N-oxide, crystalline form, hydrate, or a pharmaceutically acceptable salt thereof.

An additional embodiment of the present invention is a pharmaceutical composition comprising a pharmaceutically acceptable carrier or diluent and a compound having the structure of:

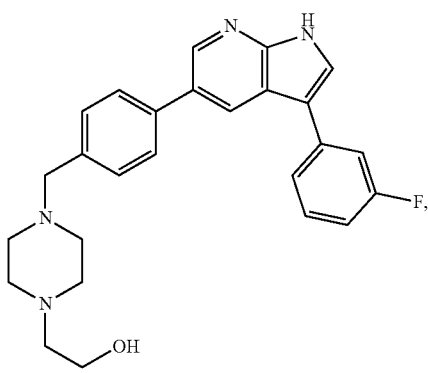

12h or an N-oxide, crystalline form, hydrate, or a pharmaceutically acceptable salt thereof.

An additional embodiment of the present invention is a pharmaceutical composition comprising a pharmaceutically acceptable carrier or diluent and a compound having the structure of:

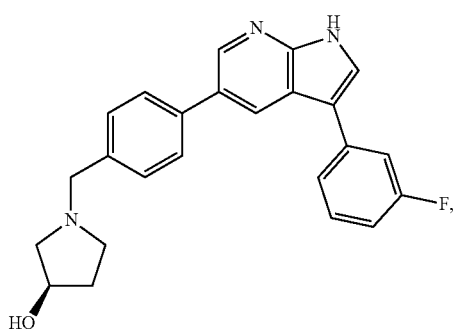

12i or an N-oxide, crystalline form, hydrate, or a pharmaceutically acceptable salt thereof.

An additional embodiment of the present invention is a pharmaceutical composition comprising a pharmaceutically acceptable carrier or diluent and a compound having the structure of:

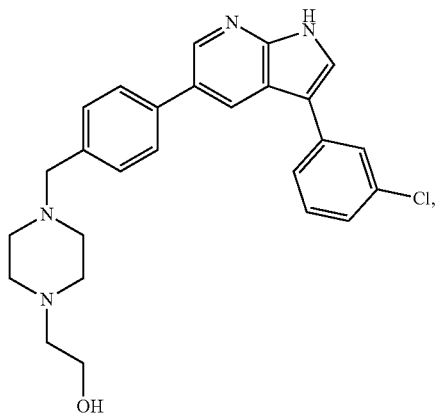

12k or an N-oxide, crystalline form, hydrate, or a pharmaceutically acceptable salt thereof.

An additional embodiment of the present invention is a pharmaceutical composition comprising a pharmaceutically acceptable carrier or diluent and a compound having the structure of:

12l or an N-oxide, crystalline form, hydrate, or a pharmaceutically acceptable salt thereof.

An additional embodiment of the present invention is a method for treating or ameliorating the effects of a disorder in a subject in need thereof. This method comprises administering to the subject an effective amount of a compound having the structure of:

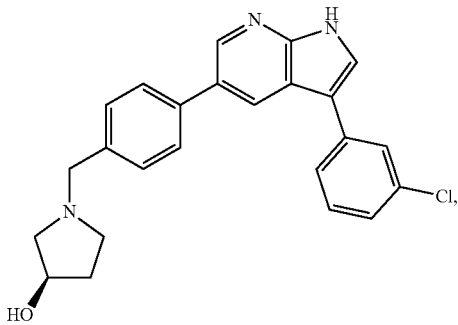

12h or an N-oxide, crystalline form, hydrate, or a pharmaceutically acceptable salt thereof.

An additional embodiment of the present invention is a method for treating or ameliorating the effects of a disorder in a subject in need thereof. This method comprises administering to the subject an effective amount of a compound having the structure of:

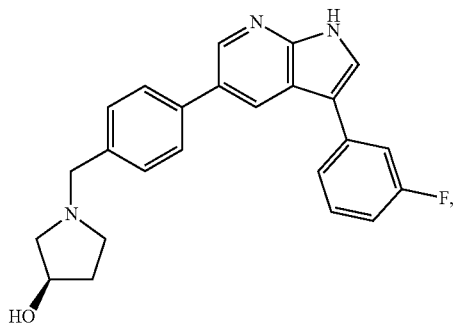

12i

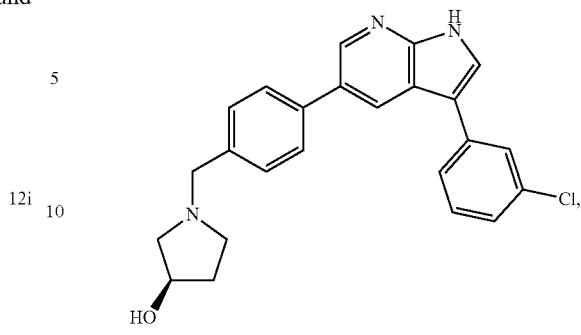

12l or an N-oxide, crystalline form, hydrate, or a pharmaceutically acceptable salt thereof.

An additional embodiment of the present invention is a method for treating or ameliorating the effects of a disorder in a subject in need thereof. This method comprises administering to the subject an effective amount of a compound having the structure of:

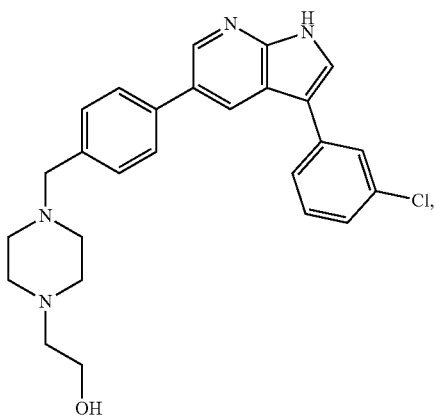

12k or an N-oxide, crystalline form, hydrate, or a pharmaceutically acceptable salt thereof.

An additional embodiment of the present invention is a method for treating or ameliorating the effects of a disorder in a subject in need thereof. This method comprises administering to the subject an effective amount of a compound having the structure of:

or an N-oxide, crystalline form, hydrate, or a pharmaceutically acceptable salt thereof.

An additional embodiment of the present invention is a method of suppressing the toxicity of endoplasmic reticulum (ER) stress in a subject in need thereof. This method comprises administering to the subject an effective amount of a kinase inhibitor, which comprises a compound having the structure of:

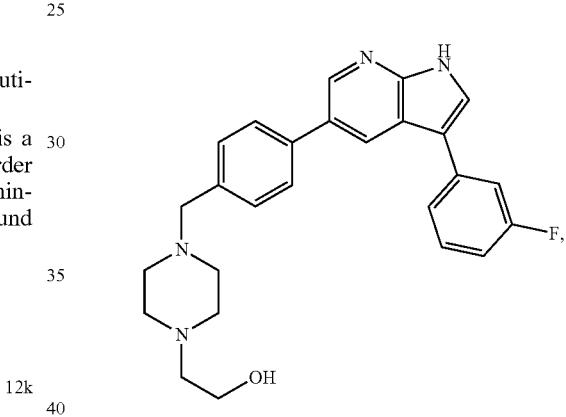

12h or an N-oxide, crystalline form, hydrate, or a pharmaceutically acceptable salt thereof.

An additional embodiment of the present invention is a method of suppressing the toxicity of endoplasmic reticulum (ER) stress in a subject in need thereof. This method comprises administering to the subject an effective amount of a kinase inhibitor, which comprises a compound having the structure of:

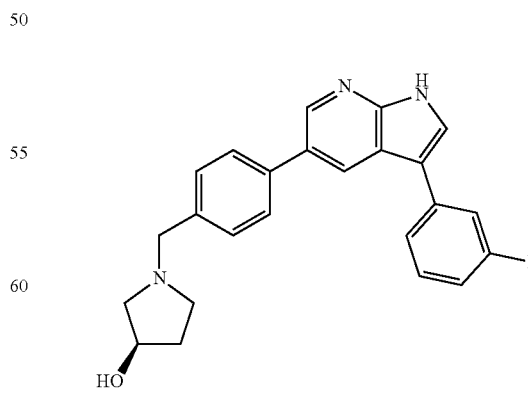

12i or an N-oxide, crystalline form, hydrate, or a pharmaceutically acceptable salt thereof.

An additional embodiment of the present invention is a method of suppressing the toxicity of endoplasmic reticulum (ER) stress in a subject in need thereof. This method comprises administering to the subject an effective amount of a kinase inhibitor, which comprises a compound having the structure of:

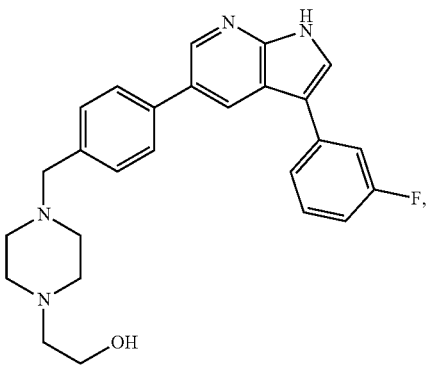

12h or an N-oxide, crystalline form, hydrate, or a pharmaceutically acceptable salt thereof.

An additional embodiment of the present invention is a method of treating or ameliorating the effects of a disease involving axon degeneration in a subject in need thereof. This method comprises administering to the subject an effective amount of a kinase inhibitor, which comprises a compound having the structure of:

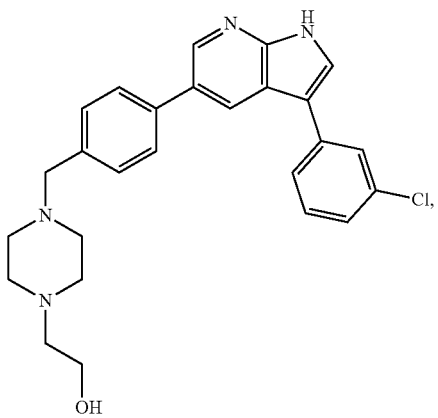

12k or an N-oxide, crystalline form, hydrate, or a pharmaceutically acceptable salt thereof.

An additional embodiment of the present invention is a method of suppressing the toxicity of endoplasmic reticulum (ER) stress in a subject in need thereof. This method comprises administering to the subject an effective amount of a kinase inhibitor, which comprises a compound having the structure of:

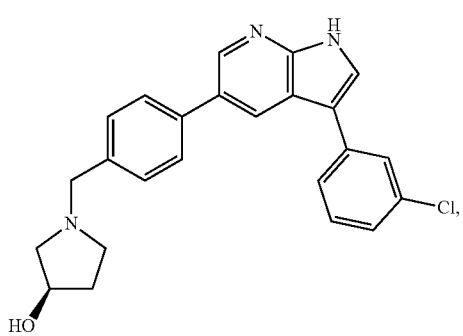

12l

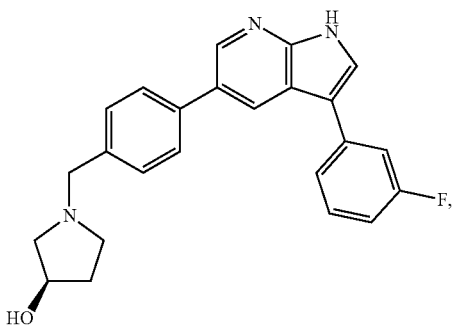

12i or an N-oxide, crystalline form, hydrate, or a pharmaceutically acceptable salt thereof.

An additional embodiment of the present invention is a method of treating or ameliorating the effects of a disease involving axon degeneration in a subject in need thereof. This method comprises administering to the subject an effective amount of a kinase inhibitor, which comprises a compound having the structure of:

or an N-oxide, crystalline form, hydrate, or a pharmaceutically acceptable salt thereof.

An additional embodiment of the present invention is a method of treating or ameliorating the effects of a disease involving axon degeneration in a subject in need thereof. This method comprises administering to the subject an effective amount of a kinase inhibitor, which comprises a compound having the structure of:

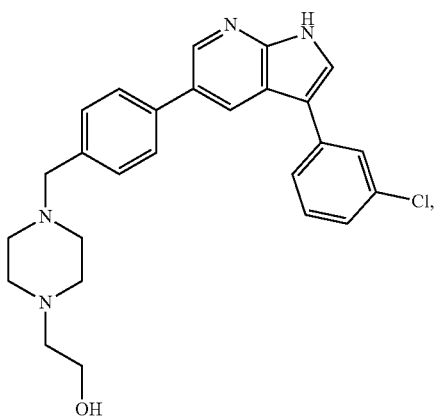

12k or an N-oxide, crystalline form, hydrate, or a pharmaceutically acceptable salt thereof.

An additional embodiment of the present invention is a method of treating or ameliorating the effects of a disease involving axon degeneration in a subject in need thereof. This method comprises administering to the subject an effective amount of a kinase inhibitor, which comprises a compound having the structure of:

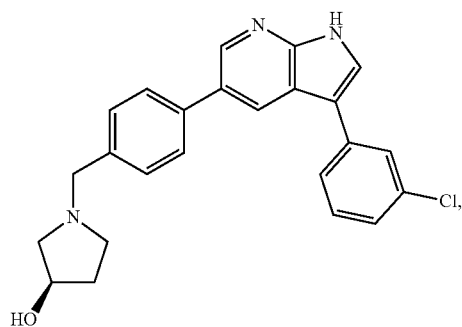

12l or an N-oxide, crystalline form, hydrate, or a pharmaceutically acceptable salt thereof.

An additional embodiment of the present invention is a method for treating or ameliorating the effects of a neurodegenerative disease in a subject in need thereof. This method comprises administering to the subject an effective amount of a compound having the structure of:

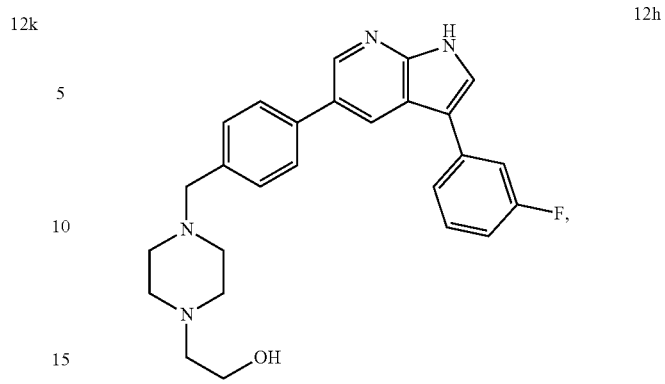

12h or an N-oxide, crystalline form, hydrate, or a pharmaceutically acceptable salt thereof.

An additional embodiment of the present invention is a method for treating or ameliorating the effects of a neurodegenerative disease in a subject in need thereof. This method comprises administering to the subject an effective amount of a compound having the structure of:

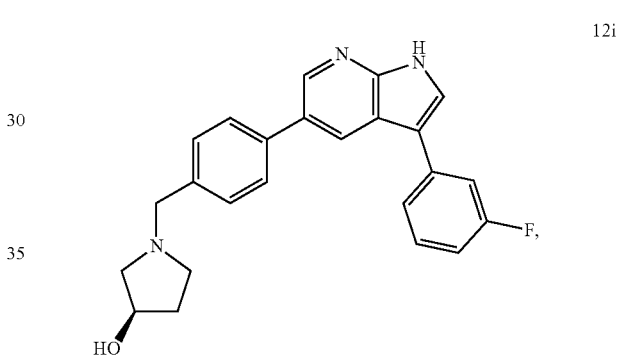

12i or an N-oxide, crystalline form, hydrate, or a pharmaceutically acceptable salt thereof.

An additional embodiment of the present invention is a method for treating or ameliorating the effects of a neurodegenerative disease in a subject in need thereof. This method comprises administering to the subject an effective amount of a compound having the structure of:

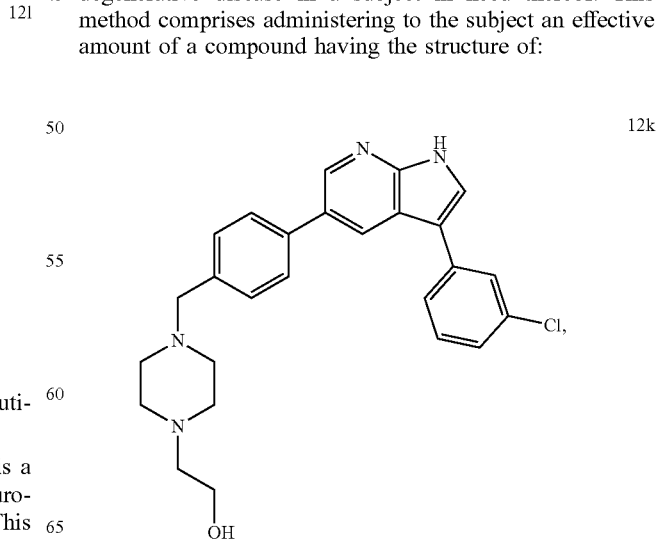

12k or an N-oxide, crystalline form, hydrate, or a pharmaceutically acceptable salt thereof.

An additional embodiment of the present invention is a method for treating or ameliorating the effects of a neurodegenerative disease in a subject in need thereof. This method comprises administering to the subject an effective amount of a compound having the structure of:

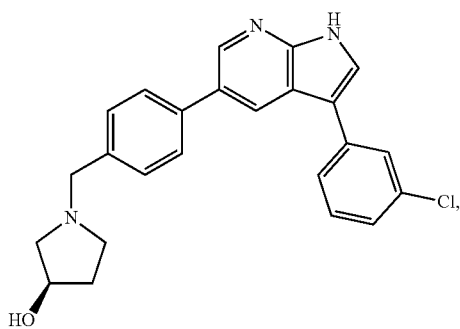

121 or an N-oxide, crystalline form, hydrate, or a pharmaceutically acceptable salt thereof.

As used herein, a "pharmaceutically acceptable salt" means a salt of the compounds of the present invention which are pharmaceutically acceptable, as defined herein, and which possess the desired pharmacological activity. Such salts include acid addition salts formed with inorganic acids such as hydrochloric acid, hydrobromic acid, sulfuric acid, nitric acid, phosphoric acid, and the like; or with organic acids such as acetic acid, propionic acid, hexanoic acid, heptanoic acid, cyclopentanepropionic acid, glycolic acid, pyruvic acid, lactic acid, malonic acid, succinic acid, malic acid, maleic acid, fumaric acid, tartaric acid, citric acid, benzoic acid, o-(4-hydroxybenzoyl)benzoic acid, cinnamic acid, mandelic acid, methanesulfonic acid, ethanesulfonic acid, 1,2-ethanedisulfonic acid, 2-hydroxyethanesulfonic acid, benzenesulfonic acid, p-chlorobenzenesulfonic acid, 2-naphthalenesulfonic acid, p-toluenesulfonic acid, camphorsulfonic acid, 4-methylbicyclo[2.2.2]oct-2-ene-1-carboxylic acid, glucoheptonic acid, 4,4'-methylenebis(3-hydroxy-2-ene-1-carboxylic acid), 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid and the like. Pharmaceutically acceptable salts also include base addition salts which may be formed when acidic protons present are capable of reacting with inorganic or organic bases. Acceptable inorganic bases include sodium hydroxide, sodium carbonate, potassium hydroxide, aluminum hydroxide and calcium hydroxide. Acceptable organic bases include ethanolamine, diethanolamine, triethanolamine, tromethamine, N-methylglucamine and the like.

In the present invention, an "effective amount" or "therapeutically effective amount" of a compound or pharmaceutical composition is an amount of such a compound or composition that is sufficient to affect beneficial or desired results as described herein when administered to a subject. Effective dosage forms, modes of administration, and dosage amounts may be determined empirically, and making such determinations is within the skill of the art. It is understood by those skilled in the art that the dosage amount will vary with the route of administration, the rate of excretion, the duration of the treatment, the identity of any other drugs being administered, the age, size, and species of the subject, and like factors well known in the arts of, e.g., medicine and veterinary medicine. In general, a suitable dose of a compound or pharmaceutical composition according to the invention will be that amount of the compound or composition, which is the lowest dose effective to produce the desired effect with no or minimal side effects. The effective dose of a compound or pharmaceutical composition according to the present invention may be administered as two, three, four, five, six or more sub-doses, administered separately at appropriate intervals throughout the day.

A suitable, non-limiting example of a dosage of a compound or pharmaceutical composition according to the present invention or a composition comprising such a compound, is from about 1 ng/kg to about 1000 mg/kg, such as from about 1 mg/kg to about 100 mg/kg, including from about 5 mg/kg to about 50 mg/kg. Other representative dosages of a compound or a pharmaceutical composition of the present invention include about 1 mg/kg, 5 mg/kg, 10 mg/kg, 15 mg/kg, 20 mg/kg, 25 mg/kg, 30 mg/kg, 35 mg/kg, 40 mg/kg, 45 mg/kg, 50 mg/kg, 60 mg/kg, 70 mg/kg, 80 mg/kg, 90 mg/kg, 100 mg/kg, 125 mg/kg, 150 mg/kg, 175 mg/kg, 200 mg/kg, 250 mg/kg, 300 mg/kg, 400 mg/kg, 500 mg/kg, 600 mg/kg, 700 mg/kg, 800 mg/kg, 900 mg/kg, or 1000 mg/kg.

A compound or pharmaceutical composition of the present invention may be administered in any desired and effective manner: for oral ingestion, or as an ointment or drop for local administration to the eyes, or for parenteral or other administration in any appropriate manner such as intraperitoneal, subcutaneous, topical, intradermal, inhalation, intrapulmonary, rectal, vaginal, sublingual, intramuscular, intravenous, intraarterial, intrathecal, or intralymphatic. Further, a compound or pharmaceutical composition of the present invention may be administered in conjunction with other treatments. A compound or pharmaceutical composition of the present invention may be encapsulated or otherwise protected against gastric or other secretions, if desired.

The pharmaceutical compositions of the invention are pharmaceutically acceptable and comprise one or more active ingredients in admixture with one or more pharmaceutically-acceptable carriers or diluents and, optionally, one or more other compounds, drugs, ingredients and/or materials. Regardless of the route of administration selected, the compounds/pharmaceutical compositions of the present invention are formulated into pharmaceutically-acceptable dosage forms by conventional methods known to those of skill in the art. See, e.g., Remington, The Science and Practice of Pharmacy (21$^{st}$ Edition, Lippincott Williams and Wilkins, Philadelphia, PA.). More generally, "pharmaceutically acceptable" means that which is useful in preparing a composition that is generally safe, non-toxic, and neither biologically nor otherwise undesirable and includes that which is acceptable for veterinary use as well as human pharmaceutical use.

Pharmaceutically acceptable carriers and diluents are well known in the art (see, e.g., Remington, The Science and Practice of Pharmacy (21$^{st}$ Edition, Lippincott Williams and Wilkins, Philadelphia, PA.) and The National Formulary (American Pharmaceutical Association, Washington, D.C.)) and include sugars (e.g., lactose, sucrose, mannitol, and sorbitol), starches, cellulose preparations, calcium phosphates (e.g., dicalcium phosphate, tricalcium phosphate and calcium hydrogen phosphate), sodium citrate, water, aqueous solutions (e.g., saline, sodium chloride injection, Ringer's injection, dextrose injection, dextrose and sodium chloride injection, lactated Ringer's injection), alcohols (e.g., ethyl alcohol, propyl alcohol, and benzyl alcohol), polyols (e.g., glycerol, propylene glycol, and polyethylene glycol), organic esters (e.g., ethyl oleate and tryglycerides), biodegradable polymers (e.g., polylactide-polyglycolide, poly(orthoesters), and poly(anhydrides)), elastomeric matrices, liposomes, microspheres, oils (e.g., corn, germ, olive, castor, sesame, cottonseed, and groundnut), cocoa butter, waxes (e.g., suppository waxes), paraffins, silicones, talc, silicylate, etc. Each pharmaceutically acceptable carrier or diluent used in a composition of the invention must be "acceptable" in the sense of being compatible with the other ingredients of the formulation and not injurious to the subject. Carriers or diluents suitable for a selected dosage form and intended route of administration are well known in the art, and acceptable carriers or diluents for a chosen dosage form and method of administration can be determined using ordinary skill in the art.

The pharmaceutical compositions of the invention may, optionally, contain additional ingredients and/or materials commonly used in such compositions. These ingredients and materials are well known in the art and include (1) fillers or extenders, such as starches, lactose, sucrose, glucose, mannitol, and silicic acid; (2) binders, such as carboxymethylcellulose, alginates, gelatin, polyvinyl pyrrolidone, hydroxypropylmethyl cellulose, sucrose and acacia; (3) humectants, such as glycerol; (4) disintegrating agents, such as agar-agar, calcium carbonate, potato or tapioca starch, alginic acid, certain silicates, sodium starch glycolate, cross-linked sodium carboxymethyl cellulose and sodium carbonate; (5) solution retarding agents, such as paraffin; (6) absorption accelerators, such as quaternary ammonium compounds; (7) wetting agents, such as cetyl alcohol and glycerol monostearate; (8) absorbents, such as kaolin and bentonite clay; (9) lubricants, such as talc, calcium stearate, magnesium stearate, solid polyethylene glycols, and sodium lauryl sulfate; (10) suspending agents, such as ethoxylated isostearyl alcohols, polyoxyethylene sorbitol and sorbitan esters, microcrystalline cellulose, aluminum metahydroxide, bentonite, agar-agar and tragacanth; (11) buffering agents; (12) excipients, such as lactose, milk sugars, polyethylene glycols, animal and vegetable fats, oils, waxes, paraffins, cocoa butter, starches, tragacanth, cellulose derivatives, polyethylene glycol, silicones, bentonites, silicic acid, talc, salicylate, zinc oxide, aluminum hydroxide, calcium silicates, and polyamide powder; (13) inert diluents, such as water or other solvents; (14) preservatives; (15) surface-active agents; (16) dispersing agents; (17) control-release or absorption-delaying agents, such as hydroxypropylmethyl cellulose, other polymer matrices, biodegradable polymers, liposomes, microspheres, aluminum monosterate, gelatin, and waxes; (18) opacifying agents; (19) adjuvants; (20) wetting agents; (21) emulsifying and suspending agents; (22), solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan; (23) propellants, such as chlorofluorohydrocarbons and volatile unsubstituted hydrocarbons, such as butane and propane; (24) antioxidants; (25) agents which render the formulation isotonic with the blood of the intended recipient, such as sugars and sodium chloride; (26) thickening agents; (27) coating materials, such as lecithin; and (28) sweetening, flavoring, coloring, perfuming and preservative agents. Each such ingredient or material must be "acceptable" in the sense of being compatible with the other ingredients of the formulation and not injurious to the subject. Ingredients and materials suitable for a selected dosage form and intended route of administration are well known in the art, and acceptable ingredients and materials for a chosen dosage form and method of administration may be determined using ordinary skill in the art.

Compounds or pharmaceutical compositions suitable for oral administration may be in the form of capsules, cachets, pills, tablets, powders, granules, a solution or a suspension in an aqueous or non-aqueous liquid, an oil-in-water or water-in-oil liquid emulsion, an elixir or syrup, a pastille, a bolus, an electuary or a paste. These formulations may be prepared by methods known in the art, e.g., by means of conventional pan-coating, mixing, granulation or lyophilization processes.

Solid dosage forms for oral administration (capsules, tablets, pills, dragees, powders, granules and the like) may be prepared, e.g., by mixing the active ingredient(s) with one or more pharmaceutically-acceptable carriers or diluents and, optionally, one or more fillers, extenders, binders, humectants, disintegrating agents, solution retarding agents, absorption accelerators, wetting agents, absorbents, lubricants, and/or coloring agents. Solid compositions of a similar type may be employed as fillers in soft and hard-filled gelatin capsules using a suitable excipient. A tablet may be made by compression or molding, optionally with one or more accessory ingredients. Compressed tablets may be prepared using a suitable binder, lubricant, inert diluent, preservative, disintegrant, surface-active or dispersing agent. Molded tablets may be made by molding in a suitable machine. The tablets, and other solid dosage forms, such as dragees, capsules, pills and granules, may optionally be scored or prepared with coatings and shells, such as enteric coatings and other coatings well known in the pharmaceutical-formulating art. They may also be formulated so as to provide slow or controlled release of the active ingredient therein. They may be sterilized by, for example, filtration through a bacteria-retaining filter. These compositions may also optionally contain opacifying agents and may be of a composition such that they release the active ingredient only, or preferentially, in a certain portion of the gastrointestinal tract, optionally, in a delayed manner. The active ingredient can also be in microencapsulated form.

Liquid dosage forms for oral administration include pharmaceutically-acceptable emulsions, microemulsions, solutions, suspensions, syrups and elixirs. The liquid dosage forms may contain suitable inert diluents commonly used in the art. Besides inert diluents, the oral compositions may also include adjuvants, such as wetting agents, emulsifying and suspending agents, sweetening, flavoring, coloring, perfuming and preservative agents. Suspensions may contain suspending agents.

Compositions for rectal or vaginal administration may be presented as a suppository, which may be prepared by mixing one or more active ingredient(s) with one or more suitable nonirritating carriers which are solid at room temperature, but liquid at body temperature and, therefore, will melt in the rectum or vaginal cavity and release the active compound. Compositions which are suitable for vaginal administration also include pessaries, tampons, creams, gels, pastes, foams or spray formulations containing such pharmaceutically-acceptable carriers as are known in the art to be appropriate.

Dosage forms for the topical or transdermal administration include powders, sprays, ointments, pastes, creams, lotions, gels, solutions, patches, drops and inhalants. The active agent(s)/compound(s) may be mixed under sterile conditions with a suitable pharmaceutically-acceptable carrier or diluent. The ointments, pastes, creams and gels may contain excipients. Powders and sprays may contain excipients and propellants.

Compositions suitable for parenteral administrations comprise one or more agent(s)/compound(s) in combination with one or more pharmaceutically-acceptable sterile isotonic aqueous or non-aqueous solutions, dispersions, suspensions or emulsions, or sterile powders which may be reconstituted into sterile injectable solutions or dispersions just prior to use, which may contain suitable antioxidants, buffers, solutes which render the formulation isotonic with the blood of the intended recipient, or suspending or thickening agents. Proper fluidity can be maintained, for example, by the use of coating materials, by the maintenance of the required particle size in the case of dispersions, and by the use of surfactants. These compositions may also contain suitable adjuvants, such as wetting agents, emulsifying agents and dispersing agents. It may also be desirable to include isotonic agents. In addition, prolonged absorption of the injectable pharmaceutical form may be brought about by the inclusion of agents which delay absorption.

In some cases, in order to prolong the effect of a drug (e.g., pharmaceutical formulation), it is desirable to slow its absorption from subcutaneous or intramuscular injection. This may be accomplished by the use of a liquid suspension of crystalline or amorphous material having poor water solubility.

The rate of absorption of the active agent/drug then depends upon its rate of dissolution which, in turn, may depend upon crystal size and crystalline form. Alternatively, delayed absorption of a parenterally-administered agent/drug may be accomplished by dissolving or suspending the active agent/drug in an oil vehicle. Injectable depot forms may be made by forming microencapsule matrices of the active ingredient in biodegradable polymers. Depending on the ratio of the active ingredient to polymer, and the nature of the particular polymer employed, the rate of active ingredient release can be controlled. Depot injectable formulations are also prepared by entrapping the drug in liposomes or microemulsions which are compatible with body tissue. The injectable materials can be sterilized for example, by filtration through a bacterial-retaining filter.

The formulations may be presented in unit-dose or multi-dose sealed containers, for example, ampules and vials, and may be stored in a lyophilized condition requiring only the addition of the sterile liquid carrier or diluent, for example water for injection, immediately prior to use. Extemporaneous injection solutions and suspensions may be prepared from sterile powders, granules and tablets of the type described above.

In the foregoing embodiments, the following definitions apply.

The term "aliphatic", as used herein, refers to a group composed of carbon and hydrogen that do not contain aromatic rings. Accordingly, aliphatic groups include alkyl, alkenyl, alkynyl, and carbocyclyl groups. Additionally, unless otherwise indicated, the term "aliphatic" is intended to include both "unsubstituted aliphatics" and "substituted aliphatics", the latter of which refers to aliphatic moieties having substituents replacing a hydrogen on one or more carbons of the aliphatic group. Such substituents can include, for example, a halogen, a deuterium, a hydroxyl, a carbonyl (such as a carboxyl, an alkoxycarbonyl, a formyl, or an acyl), a thiocarbonyl (such as a thioester, a thioacetate, or a thioformate), an alkoxyl, a phosphoryl, a phosphate, a phosphonate, a phosphinate, an amino, an amido, an amidine, an imine, a cyano, a nitro, an azido, a sulfhydryl, an alkylthio, a sulfate, a sulfonate, a sulfamoyl, a sulfonamido, a sulfonyl, a heterocyclyl, an aralkyl, an aromatic, or heteroaromatic moiety.

The term "alkyl" refers to the radical of saturated aliphatic groups that does not have a ring structure, including straight-chain alkyl groups, and branched-chain alkyl groups. In certain embodiments, a straight chain or branched chain alkyl has 6 or fewer carbon atoms in its backbone (e.g., C1-C6 for straight chains, C3-C6 for branched chains). Such substituents include all those contemplated for aliphatic groups, as discussed below, except where stability is prohibitive.

The term "alkenyl", as used herein, refers to an aliphatic group containing at least one double bond and unless otherwise indicated, is intended to include both "unsubstituted alkenyls" and "substituted alkenyls", the latter of which refers to alkenyl moieties having substituents replacing a hydrogen on one or more carbons of the alkenyl group. Such substituents include all those contemplated for aliphatic groups, as discussed below, except where stability is prohibitive. For example, substitution of alkenyl groups by one or more alkyl, carbocyclyl, aryl, heterocyclyl, or heteroaryl groups is contemplated.

Moreover, unless otherwise indicated, the term "alkyl" as used throughout the specification, examples, and claims is intended to include both "unsubstituted alkyls" and "substituted alkyls", the latter of which refers to alkyl moieties having substituents replacing a hydrogen on one or more carbons of the hydrocarbon backbone. Indeed, unless otherwise indicated, all groups recited herein are intended to include both substituted and unsubstituted options.

The term "$C_{x-y}$" when used in conjunction with a chemical moiety, such as, alkyl and cycloalkyl, is meant to include groups that contain from x to y carbons in the chain. For example, the term "$C_{x-y}$alkyl" refers to substituted or unsubstituted saturated hydrocarbon groups, including straight-chain alkyl and branched-chain alkyl groups that contain from x to y carbons in the chain, including haloalkyl groups such as trifluoromethyl and 2,2,2-trifluoroethyl, etc.

The term "aryl" as used herein includes substituted or unsubstituted single-ring aromatic groups in which each atom of the ring is carbon. Preferably the ring is a 3- to 8-membered ring, more preferably a 6-membered ring. The term "aryl" also includes polycyclic ring systems having two or more cyclic rings in which two or more carbons are common to two adjoining rings wherein at least one of the rings is aromatic, e.g., the other cyclic rings can be cycloalkyls, cycloalkenyls, cycloalkynyls, aryls, heteroaryls, and/or heterocyclyls. Aryl groups include benzene, naphthalene, phenanthrene, phenol, aniline, and the like.

The term "alkyl-aryl" refers to an alkyl group substituted with at least one aryl group.

The term "alkyl-heteroaryl" refers to an alkyl group substituted with at least one heteroaryl group.

The term "alkenyl-aryl" refers to an alkenyl group substituted with at least one aryl group.

The term "alkenyl-heteroaryl" refers to an alkenyl group substituted with at least one heteroaryl group.

The term "amino," as used herein, alone or in combination, refers to —NRR', wherein R and R' are independently chosen from hydrogen, alkyl, acyl, heteroalkyl, aryl, cycloalkyl, heteroaryl, and heterocycloalkyl, any of which may themselves be optionally substituted. Additionally, R and R' may combine to form heterocycloalkyl, either of which may be optionally substituted.

The term "amide", as used herein, alone or in combination, refers to —R$_n$E(O)$_x$NR'$_2$, wherein R and R' are independently chosen from hydrogen, alkyl, acyl, heteroalkyl, aryl, cycloalkyl, heteroaryl, and heterocycloalkyl, any of which may themselves be optionally substituted. Examples include carboxamides (n=1, E=C, x=1), phosphoramides (n=2, E=P, x=1), and sulfonamides (n=1, E=S, x=2).

The terms "benzo" and "benz," as used herein, alone or in combination, refer to the divalent radical C$_6$H$_4$= derived from benzene. Examples include benzothiophene and benzimidazole.

The term "carbamate," as used herein, alone or in combination, refers to an ester of carbamic acid (—NRC(O)O—) which may be attached to the parent molecular moiety from either the nitrogen or acid end, and which may be optionally substituted as defined herein. The term "O-carbamyl" as used herein, alone or in combination, refers to a —OC(O)NRR' group; and the term "N-carbamyl" as used herein, alone or in combination, refers to a ROC(O)NR'— group. R and R' are as defined herein, or as defined by the specifically enumerated "R" groups designated.

The term "carbonyl," as used herein, when alone includes formyl [—C(O)H] and in combination is a —C(O)— group.

The term "carboxyl" or "carboxy," as used herein, refers to —C(O)OH or the corresponding "carboxylate" anion, such as is in a carboxylic acid salt. An "O-carboxy" group refers to a RC(O)O— group, where R is as defined herein. A "C-carboxy" group refers to a —C(O)OR groups where R is as defined herein.

The term "cyano," as used herein, alone or in combination, refers to —CN.

The term "cycloalkyl," or, alternatively, "carbocycle," as used herein, alone or in combination, refers to a saturated or partially saturated monocyclic, bicyclic or tricyclic alkyl group wherein each cyclic moiety contains from 3 to 12 carbon atom ring members and which may optionally be a benzo fused ring system which is optionally substituted as defined herein. In certain embodiments, said cycloalkyl will comprise from 5 to 7 carbon atoms. Examples of such cycloalkyl groups include cyclopropyl, cyclobutyl, cyclopentyl, cyclohexyl, cycloheptyl, tetrahydronaphthyl, indanyl, octahydronaphthyl, 2,3-dihydro-1H-indenyl, adamantyl and the like. "Bicyclic" and "tricyclic" as used herein are intended to include both fused ring systems, such as decahydronaphthalene, octahydronaphthalene as well as the multicyclic (multicentered) saturated or partially unsaturated type. The latter type of isomer is exemplified in general by, bicyclo[1,1,1]pentane, camphor, adamantane, and bicyclo[3,2,1]octane.

The terms "carbocycle", "carbocyclyl", and "carbocyclic", as used herein, refer to a non-aromatic saturated or unsaturated ring in which each atom of the ring is carbon. Preferably a carbocycle ring contains from 3 to 10 atoms, more preferably from 3 to 8 atoms, including 5 to 7 atoms, such as for example, 6 atoms. The term "carbocycle" also includes bicycles, tricycles and other multicyclic ring systems, including the adamantyl ring system.

The term "heteroatom" as used herein means an atom of any element other than carbon or hydrogen. Preferred heteroatoms are nitrogen, oxygen, and sulfur; more preferably, nitrogen and oxygen.

The term "heteroalkyl," as used herein, alone or in combination, refers to a stable straight or branched chain, or cyclic hydrocarbon radical, or combinations thereof, fully saturated or containing from 1 to 3 degrees of unsaturation, consisting of the stated number of carbon atoms and from one to three heteroatoms chosen from O, N, and S, and wherein the nitrogen and sulfur atoms may optionally be oxidized and the nitrogen heteroatom may optionally be quaternized. The heteroatom(s) O, N and S may be placed at any interior position of the heteroalkyl group. Up to two heteroatoms may be consecutive, such as, for example, —CH$_2$—NH—OCH$_3$.

The term "heteroaryl" includes substituted or unsubstituted aromatic single ring structures, preferably 3- to 8-membered rings, more preferably 5- to 7-membered rings, even more preferably 5- to 6-membered rings, whose ring structures include at least one heteroatom, preferably one to four heteroatoms, more preferably one or two heteroatoms. The term "heteroaryl" also includes polycyclic ring systems having two or more cyclic rings in which two or more carbons are common to two adjoining rings wherein at least one of the rings is heteroaromatic, e.g., the other cyclic rings can be cycloalkyls, cycloalkenyls, cycloalkynyls, aryls, heteroaryls, and/or heterocyclyls. Heteroaryl groups include, for example, pyrrole, furan, thiophene, imidazole, oxazole, thiazole, pyrazole, pyridine, pyrazine, pyridazine, and pyrimidine, and the like.

The terms "heterocycloalkyl" and, interchangeably, "heterocycle," as used herein, alone or in combination, each refer to a saturated, partially unsaturated, or fully unsaturated monocyclic, bicyclic, or tricyclic heterocyclic group containing at least one heteroatom as a ring member, wherein each said heteroatom may be independently chosen from N, O, and S. Additionally, a heterocycloalkyl may contain one or two C(O), S(O), or S(O)$_2$ groups as ring members. In certain embodiments, said heterocycloalkyl will comprise from 1 to 4 heteroatoms as ring members. In further embodiments, said heterocycloalkyl will comprise from 1 to 2 heteroatoms as ring members. In certain embodiments, said heterocycloalkyl will comprise from 3 to 8 ring members in each ring. In further embodiments, said heterocycloalkyl will comprise from 3 to 7 ring members in each ring. In yet further embodiments, said heterocycloalkyl will comprise from 5 to 6 ring members in each ring. "Heterocycloalkyl" and "heterocycle" are intended to include sulfones, sulfoxides, N-oxides of tertiary nitrogen ring members, and carbocyclic fused and benzo fused ring systems; additionally, both terms also include systems where a heterocycle ring is fused to an aryl group, as defined herein, or an additional heterocycle group. Examples of heterocycle groups include aziridinyl, azetidinyl, 1,3-benzodioxolyl, dihydroisoindolyl, dihydroisoquinolinyl, dihydrocinnolinyl, dihydrobenzodioxinyl, dihydro[1,3]oxazolo[4,5-b]pyridinyl, benzothiazolyl, dihydroindolyl, dihydropyridinyl, 1,3-dioxanyl, 1,4-dioxanyl, 1,3-dioxolanyl, isoindolinyl, morpholinyl, piperazinyl, pyrrolidinyl, tetrahydropyridinyl, piperidinyl, thiomorpholinyl, and the like. The heterocycle groups may be optionally substituted unless specifically prohibited.

The term "hydroxy," as used herein, alone or in combination, refers to —OH.

The terms "halo" and "halogen" are used interchangeably herein and mean halogen and include chloro, fluoro, bromo, and iodo.

The term "haloalkoxy," as used herein, alone or in combination, refers to a haloalkyl group attached to the parent molecular moiety through an oxygen atom. Haloalkoxy includes perhaloalkoxy. The term "perhaloalkoxy" refers to an alkoxy group where all of the hydrogen atoms are replaced by halogen atoms. An example of perhaloalkoxy is perfluoromethoxy.

The term "haloalkyl," as used herein, alone or in combination, refers to an alkyl radical having the meaning as defined above wherein one or more hydrogens are replaced with a halogen. Specifically embraced are monohaloalkyl, dihaloalkyl, polyhaloalkyl, and perhaloalkyl radicals. A monohaloalkyl radical, for one example, may have an iodo, bromo, chloro or fluoro atom within the radical. Dihalo and polyhaloalkyl radicals may have two or more of the same halo atoms or a combination of different halo radicals. Examples of haloalkyl radicals include fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl and dichloropropyl. "Haloalkylene" refers to a haloalkyl group attached at two or more positions. Examples of haloalkyl radicals include fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl and dichloropropyl. "Haloalkylene" refers to a haloalkyl group attached at two or more positions. Examples include fluoromethylene (—CFH—), difluoromethylene (—CF$_2$—), chloromethylene (—CHCl—) and the like. The term "perhaloalkyl" as used herein, alone or in combination, refers to an alkyl group where all of the hydrogen atoms are replaced by halogen atoms. Examples include perfluoromethyl.

The term "alcohol" means an organic compound in which the hydroxyl functional group (—OH) is bound to a saturated carbon atom.

The term "ketone" means an organic compound with the structure RC(=O)R', wherein neither R and R' can be hydrogen atoms.

The term "ester" means an organic compound with the structure RC(=O)OR', wherein neither R and R' can be hydrogen atoms.

The term "ether," as used herein, alone or in combination, refers to an oxy group bridging two moieties linked at carbon atoms.

The term "nitro," as used herein, alone or in combination, refers to —NO$_2$.

The term "polyyne" means is an organic compound with alternating single and triple bonds; that is, a series of consecutive alkynes, (—C≡C—) n with n greater than 1.

The terms "thia" and "thio," as used herein, alone or in combination, refer to a —S— group or an ether wherein the oxygen is replaced with sulfur. The oxidized derivatives of the thio group, namely sulfinyl and sulfonyl, are included in the definition of thia and thio. The term "sulfanyl," as used herein, alone or in combination, refers to —S—. The term "sulfinyl," as used herein, alone or in combination, refers to —S(O)—. The term "sulfonyl," as used herein, alone or in combination, refers to —S(O)$_2$—.

The term "urea" or "carbamide", as used herein, alone or in combination, refers to —NHC(O)NH—.

The term "substituted" refers to moieties having substituents replacing a hydrogen on one or more carbons of the backbone. It will be understood that "substitution" or "substituted with" includes the implicit proviso that such substitution is in accordance with the permitted valence of the substituted atom and the substituent, and that the substitution results in a stable compound, e.g., which does not spontaneously undergo transformation such as by rearrangement, cyclization, elimination, etc. As used herein, the term "substituted" is contemplated to include all permissible substituents of organic compounds. In a broad aspect, the permissible substituents include acyclic and cyclic, branched and unbranched, carbocyclic and heterocyclic, aromatic and non-aromatic substituents of organic compounds. The permissible substituents can be one or more and the same or different for appropriate organic compounds. For purposes of this invention, the heteroatoms such as nitrogen may have hydrogen substituents and/or any permissible substituents of organic compounds described herein which satisfy the valences of the heteroatoms. Substituents can include any substituents described herein, for example, a halogen, a hydroxyl, a carbonyl (such as a carboxyl, an alkoxycarbonyl, a formyl, or an acyl), a thiocarbonyl (such as a thioester, a thioacetate, or a thioformate), an alkoxyl, a phosphoryl, a phosphate, a phosphonate, a phosphinate, an amino, an amido, an amidine, an imine, a cyano, a nitro, an azido, a sulfhydryl, an alkylthio, a sulfate, a sulfonate, a sulfamoyl, a sulfonamido, a sulfonyl, a heterocyclyl, an aralkyl, or an aromatic or heteroaromatic moiety. It will be understood by those skilled in the art that the moieties substituted on the hydrocarbon chain can themselves be substituted, if appropriate.

As set forth previously, unless specifically stated as "unsubstituted," references to chemical moieties herein are understood to include substituted variants. For example, reference to an "aryl" group or moiety implicitly includes both substituted and unsubstituted variants.

As used herein, the term "furanyl" means any compound or chemical group containing the following structure:

As used herein, the term "indolyl" means any compound or chemical group containing the following structure:

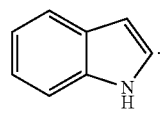

As used herein, the term "indazole" means any compound or chemical group containing the following structure:

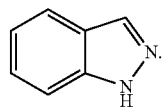

As used herein, the term "pyridyl" means any compound or chemical group containing the following structure:

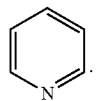

As used herein, the term "pyrimidinyl" means any compound or chemical group containing the following structure:

As used herein, the term "pyrazole" means any compound or chemical group containing the following structure:

As used herein, the term "thienyl" or "thiophene" means any compound or chemical group containing the following structure:

As used herein, the term "benzothiophenyl" means any compound or chemical group containing the following structure:

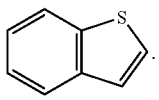

As used herein, the term "benzodioxan" means any compound or chemical group containing the following structure:

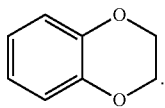

As used herein, the term "dibenzofuranyl" means any compound or chemical group containing the following structure:

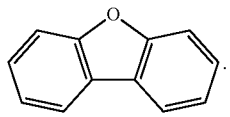

It is understood that the disclosure of a compound herein encompasses all stereoisomers of that compound. As used herein, the term "stereoisomer" refers to a compound made up of the same atoms bonded by the same bonds but having different three-dimensional structures which are not interchangeable. The three-dimensional structures are called configurations. Stereoisomers include enantiomers and diastereomers.

The terms "racemate" or "racemic mixture" refer to a mixture of equal parts of enantiomers. The term "chiral center" refers to a carbon atom to which four different groups are attached. The term "enantiomeric enrichment" as used herein refers to the increase in the amount of one enantiomer as compared to the other.

It is appreciated that to the extent compounds of the present invention have a chiral center, they may exist in and be isolated in optically active and racemic forms. Some compounds may exhibit polymorphism. It is to be understood that the present invention encompasses any racemic, optically-active, diastereomeric, polymorphic, or stereoisomeric form, or mixtures thereof, of a compound of the invention, which possess the useful properties described herein, it being well known in the art how to prepare optically active forms (for example, by resolution of the racemic form by recrystallization techniques, by synthesis from optically-active starting materials, by chiral synthesis, or by chromatographic separation using a chiral stationary phase).

Examples of methods to obtain optically active materials are known in the art, and include at least the following:
i) physical separation of crystals—a technique whereby macroscopic crystals of the individual enantiomers are manually separated. This technique can be used if crystals of the separate enantiomers exist, i.e., the material is a conglomerate, and the crystals are visually distinct;
ii) simultaneous crystallization—a technique whereby the individual enantiomers are separately crystallized from a solution of the racemate, possible only if the latter is a conglomerate in the solid state;
iii) enzymatic resolutions—a technique whereby partial or complete separation of a racemate by virtue of differing rates of reaction for the enantiomers with an enzyme;
iv) enzymatic asymmetric synthesis—a synthetic technique whereby at least one step of the synthesis uses an enzymatic reaction to obtain an enantiomerically pure or enriched synthetic precursor of the desired enantiomer;
v) chemical asymmetric synthesis—a synthetic technique whereby the desired enantiomer is synthesized from an achiral precursor under conditions that produce asymmetry (i.e., chirality) in the product, which may be achieved using chiral catalysts as disclosed in more detail herein or chiral auxiliaries;
vi) diastereomer separations—a technique whereby a racemic compound is reacted with an enantiomerically pure reagent (the chiral auxiliary) that converts the individual enantiomers to diastereomers. The resulting diastereomers are then separated by chromatography or crystallization by virtue of their now more distinct structural differences and the chiral auxiliary later removed to obtain the desired enantiomer;
vii) first- and second-order asymmetric transformations—a technique whereby diastereomers from the racemate equilibrate to yield a preponderance in solution of the diastereomer from the desired enantiomer or where preferential crystallization of the diastereomer from the desired enantiomer perturbs the equilibrium such that eventually in principle all the material is converted to the crystalline diastereomer from the desired enantiomer. The desired enantiomer is then released from the diastereomer;
viii) kinetic resolutions—this technique refers to the achievement of partial or complete resolution of a racemate (or of a further resolution of a partially resolved compound) by virtue of unequal reaction rates of the enantiomers with a chiral, non-racemic reagent or catalyst under kinetic conditions;

ix) enantiospecific synthesis from non-racemic precursors—a synthetic technique whereby the desired enantiomer is obtained from non-chiral starting materials and where the stereochemical integrity is not or is only minimally compromised over the course of the synthesis;

x) chiral liquid chromatography—a technique whereby the enantiomers of a racemate are separated in a liquid mobile phase by virtue of their differing interactions with a stationary phase. The stationary phase can be made of chiral material or the mobile phase can contain an additional chiral material to provoke the differing interactions;

xi) chiral gas chromatography—a technique whereby the racemate is volatilized and enantiomers are separated by virtue of their differing interactions in the gaseous mobile phase with a column containing a fixed non-racemic chiral adsorbent phase;

xii) extraction with chiral solvents—a technique whereby the enantiomers are separated by virtue of preferential dissolution of one enantiomer into a particular chiral solvent;

xiii) transport across chiral membranes—a technique whereby a racemate is placed in contact with a thin membrane barrier. The barrier typically separates two miscible fluids, one containing the racemate, and a driving force such as concentration or pressure differential causes preferential transport across the membrane barrier. Separation occurs as a result of the non-racemic chiral nature of the membrane which allows only one enantiomer of the racemate to pass through.

The stereoisomers may also be separated by usual techniques known to those skilled in the art including fractional crystallization of the bases or their salts or chromatographic techniques such as LC or flash chromatography. The (+) enantiomer can be separated from the (−) enantiomer using techniques and procedures well known in the art, such as that described by J. Jacques, et al., Enantiomers, Racemates, and Resolutions", John Wiley and Sons, Inc., 1981. For example, chiral chromatography with a suitable organic solvent, such as ethanol/acetonitrile and Chiralpak AD packing, 20 micron can also be utilized to effect separation of the enantiomers.

The following examples are provided to further illustrate the methods of the present invention. These examples are illustrative only and are not intended to limit the scope of the invention in any way.

EXAMPLES

The invention is further illustrated by the following examples, which are offered for illustrative purposes, and are not intended to limit the invention in any manner. Those of skill in the art will readily recognize a variety of non-critical parameters, which can be changed or modified to yield essentially the same results.

Example 1

Methods and Materials

Chemicals

Starting materials were purchased form Sigma-Aldrich, Fisher Scientific, Ark Pharm, Oakwood Chemical, Cambridge Isotope Laboratory, or AK Scientific and were used as received unless stated otherwise. All solvents were reagent grade.

Chromatography

Column chromatography was performed on a Teledyne ISCO CombiFlash® Rf+ using RediSep® Normal-phase silica flash columns. Thin layer chromatography (TLC) was performed on Silicycle SiliaPlate™ Glass TLC Plates (250 μm, 20×20 cm). Where indicated, compounds were purified by preparatory HPLC on a Phenomenex Gemini NX-C$_{18}$ column (250×21.2 mm, particle size: 5 μm, pore size: 110 Å) using a Gilson HPLC with GX-271 liquid handler.

Spectroscopy $^1$H NMR spectra were recorded at ambient temperature using 400 MHz, or 500 MHz spectrometers as indicated. Chemical shifts are reported in ppm relative to the residual solvent peaks ($^1$H NMR: DMSO-d6, δ 2.50; chloroform-d, δ 7.26; methanol-d4, δ 3.31). The following abbreviations are used to indicate multiplicity: s (singlet), d (doublet), t (triplet), q (quartet), hept (heptuplet), m (multiplet), br (broad). High resolution mass spectra (HRMS) were acquired on a time-of-flight spectrometer with atmospheric pressure chemical ionization (APCI) or electrospray ionization (ESI), as indicated, and were obtained by peak matching. All reactions were run under an atmosphere of nitrogen or argon in glassware that was flame-dried under argon unless otherwise stated. Aqueous solutions were prepared from nanopure water with a resistivity over 18 MO-cm. Unless otherwise noted, all reagents were commercially available.

Software

Molecular docking, molecular modeling, and visualizations were performed using Glide (versions 2012-2016, Schrödinger) and Schrödinger Maestro (version 2017-1). All chemical structures were drawn using ChemDraw Professional 16.0 (Perkin Elmer). All microsomal stability curves were produced using Prism 7 (GraphPad Software).

Example 2

Synthesis of Piperazine Analogs

A general route to obtain the compounds of formulas (I) to (II) follows the synthesis illustrated below. Potency-mediating groups were added in the final step instead of early-on. The preparation of each compound is also provided.

Scheme 1: General synthetic scheme for compounds 1 and 7a - 7az.

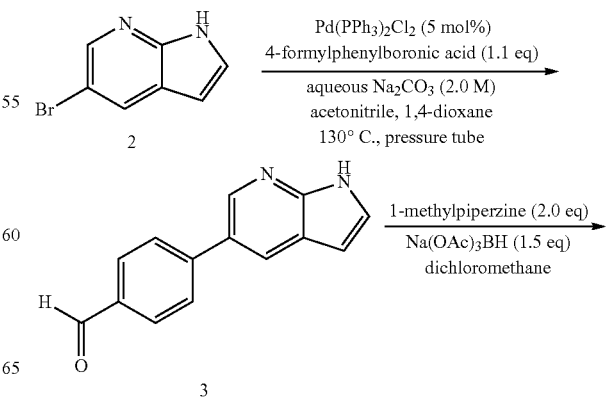

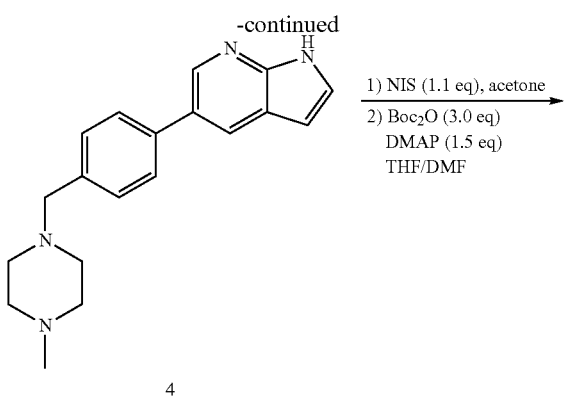

4

1) NIS (1.1 eq), acetone
2) Boc₂O (3.0 eq)
   DMAP (1.5 eq)
   THF/DMF

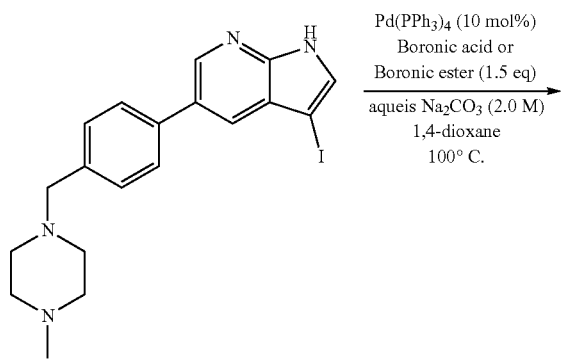

6

Pd(PPh₃)₄ (10 mol%)
Boronic acid or
Boronic ester (1.5 eq)
aqueis Na₂CO₃ (2.0 M)
1,4-dioxane
100° C.

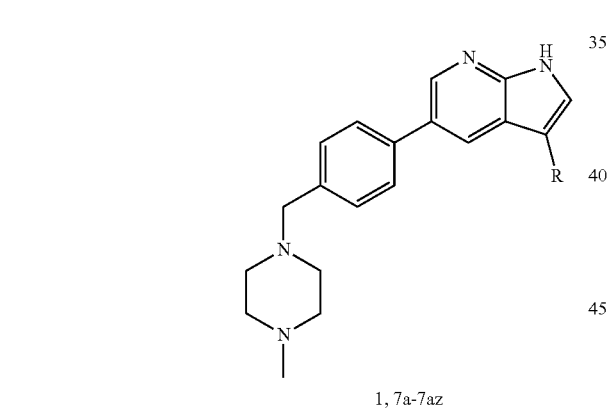

1, 7a-7az

Preparation of 4-(1H-Pyrrolo[2,3-b]pyridin-5-yl)benzaldehyde (Compound 3)

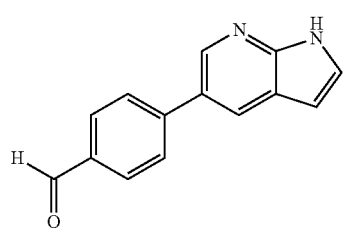 [SMILES: O=Cc1ccc(-c2cnc3[nH]ccc3c2)cc1]

5-Bromo-1H-pyrrolo[2,3-b]pyridine (2, 3.94 g, 20 mmol, 1.0 eq) and 4-formylphenylboronic acid (3.30 g, 22 mmol, 1.1 eq) were added to a pressure tube and acetonitrile (80 mL) and 1,4-dioxane (20 mL) were added. The reaction mixture was degassed and kept under argon. Pd(PPh₃)₂Cl₂ (0.70 g, 1.0 mmol, 5 mol %) was added followed by addition of aqueous Na₂CO₃ (2.0 M, 50 mL). The reaction mixture was stirred for 5 minutes, transferred to an oil bath and stirred at 130° C. overnight. After cooling to room temperature the reaction mixture was partitioned between ethyl acetate and brine, separated and the aqueous layer extracted with ethyl acetate (3×). The combined organic layers were dried with anhydrous sodium sulfate and filtered over Celite. The solvent was evaporated and the crude product purified by column chromatography (0-100% EtOAc in hexanes) to give 4-(1H-pyrrolo[2,3-b]pyridin-5-yl)benzaldehyde (3, 2.15 g, 48% yield) as a colorless solid. ¹H NMR (400 MHz, DMSO-d₆) δ 11.80 (s, 1H), 10.06 (s, 1H), 8.63 (d, J=2.2 Hz, 1H), 8.35 (d, J=2.2 Hz, 1H), 8.05-7.94 (m, 4H), 7.55 (d, J=3.5 Hz, 1H), 6.54 (d, J=3.4 Hz, 1H) ppm. HRMS (APCI⁺, m/z): calcd. for $C_{14}H_{11}N_2O$ [M+H⁺]: 223.0872, found: 223.0872.

Preparation of 5-(4-((4-Methylpiperazin-1-yl)methyl)phenyl)-1H-pyrrolo[2,3-b]pyridine (Compound 4)

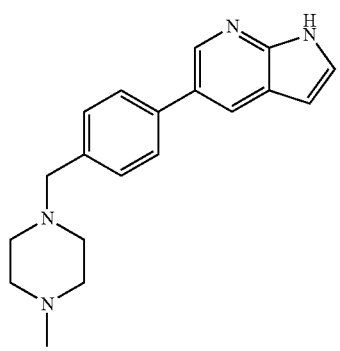 [SMILES: CN1CCN(Cc2ccc(-c3cnc4[nH]ccc4c3)cc2)CC1]

4-(1H-Pyrrolo[2,3-b]pyridin-5-yl)benzaldehyde (3, 2.15 g, 9.66 mmol, 1.0 eq) was suspended in dichloromethane (~0.1 M), and 1-methylpiperazine (1.93 g, 2.14 mL, 19.3 mmol, 2.0 eq), and Na(OAc)₃BH (3.07 g, 14.5 mmol, 1.5 eq) were added and the reaction mixture was stirred overnight at room temperature. The reaction mixture was partitioned between dichloromethane and brine, the layers separated and the aqueous layer was extracted with dichloromethane. The combined organic layer was washed with brine, dried with sodium sulfate, filtered over Celite, and the solvent evaporated to give 5-(4-((4-methylpiperazin-1-yl)methyl)phenyl)-1H-pyrrolo[2,3-b]pyridine (4, 2.2 gram, 74% yield) as a colorless solid. The product was used in the next step without further purification. ¹H NMR (400 MHz, Methanol-d₄) δ 8.43 (d, J=2.1 Hz, 1H), 8.21 (d, J=2.1 Hz, 1H), 7.64 (d, J=8.2 Hz, 2H), 7.45 (d, J=8.2 Hz, 2H), 7.42 (d, J=3.5 Hz, 1H), 6.55 (d, J=3.5 Hz, 1H), 3.64 (s, 2H), 2.71 (bs, 4H), 2.63 (bs, 4H), 2.44 (s, 3H) ppm. HRMS (APCI⁺, m/z): calcd. for $C_{19}H_{23}N_4$ [M+H⁺]: 307.1923, found: 307.1918.

Preparation of 3-Iodo-5-(4-((4-methylpiperazin-1-yl)methyl)phenyl)-1H-pyrrolo[2,3-b]pyridine (Compound 5)

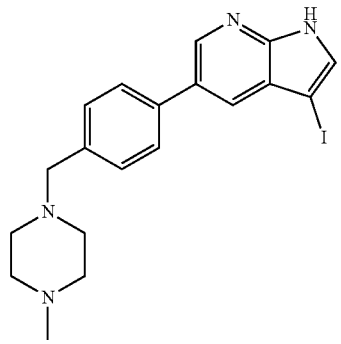 [SMILES: CN1CCN(Cc2ccc(-c3cnc4[nH]cc(I)c4c3)cc2)CC1]

5-(4-((4-Methylpiperazin-1-yl)methyl)phenyl)-1H-pyrrolo[2,3-b]pyridine (4, 2.2 g, 7.18 mmol, 1.0 eq) was suspended in acetone (0.015 M, 480 mL) and N-iodosuccinimide (1.78 g, 7.9 mmol, 1.1 eq) was added and the reaction mixture was stirred at room temperature overnight. The solvent was evaporated and the crude product was purified by column chromatography (0-10% MeOH in DCM containing 1% Et$_3$N) to give 3-iodo-5-(4-((4-methylpiperazin-1-yl)methyl)phenyl)-1H-pyrrolo[2,3-b]pyridine (5, 2.3 g, 74% yield) as a tan-colored solid. $^1$H NMR (400 MHz, Methanol-d$_4$) δ 8.46 (d, J=2.1 Hz, 1H), 7.88 (d, J=2.1 Hz, 1H), 7.64 (d, J=8.2 Hz, 2H), 7.57 (s, 1H), 7.47 (d, J=8.2 Hz, 2H), 3.71 (s, 2H), 3.35 (s, 1H), 3.21 (bs, 8H), 2.80 (s, 3H) ppm. HRMS (APCI$^+$, m/z): calcd. for C$_{19}$H$_{22}$N$_4$I [M+H$^+$]: 433.0889, found: 433.0883.

Preparation of tert-Butyl 3-iodo-5-(4-((4-methylpiperazin-1-yl)methyl)phenyl)-1H-pyrrolo[2,3-b]pyridine-1-carboxylate (Compound 6)

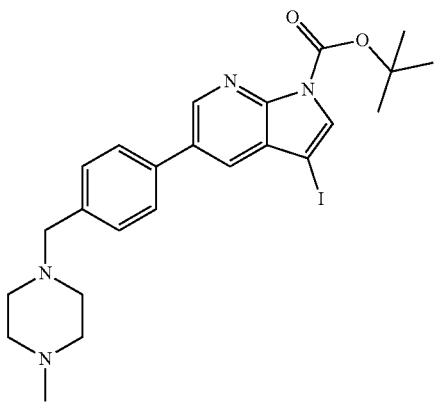 [SMILES: CN1CCN(Cc2ccc(-c3cnc4c(c3)c(I)cn4C(=O)OC(C)(C)C)cc2)CC1]

3-Iodo-5-(4-((4-methylpiperazin-1-yl)methyl)phenyl)-1H-pyrrolo[2,3-b]pyridine (5, 2.3 g, 5.32 mmol, 1.0 eq) was dissolved in a mixture of THF (250 mL) and DMF (20 mL). Boc$_2$O (3.48 g, 15.96 mmol, 3.0 eq) and DMAP (0.97 g, 7.98 mmol, 1.5 eq) were added and the mixture was stirred at room temperature overnight. Water was added and the reaction mixture was extracted with ethyl acetate (3×). The combined organic layers were washed with brine, dried with sodium sulfate, filtered and the solvent evaporated. The crude material was purified by column chromatography on silica (0-10% MeOH in DCM containing 1% Et$_3$N) to give tert-butyl 3-iodo-5-(4-((4-methylpiperazin-1-yl)methyl)phenyl)-1H-pyrrolo[2,3-b]pyridine-1-carboxylate as a tan-colored solid (6, 2.0 g, 71% yield). $^1$H NMR (400 MHz, Chloroform-d) δ 8.73 (d, J=2.1 Hz, 1H), 7.84 (d, J=2.1 Hz, 1H), 7.82 (s, 1H), 7.59 (d, J=8.2 Hz, 2H), 7.45 (d, J=8.2 Hz, 2H), 3.58 (s, 2H), 2.53 (bs, 4H), 2.47 (bs, 4H), 2.30 (s, 3H), 1.69 (s, 9H) ppm. HRMS (APCI$^+$, m/z): calcd. for C$_{24}$H$_{30}$N$_4$O$_2$I [M+H$^+$]: 533.1413, found: 533.1423.

General Procedure for the Suzuki Coupling and In Situ Deprotection

Scheme 2: General synthetic scheme for Suzuki coupling and in situ deprotection.

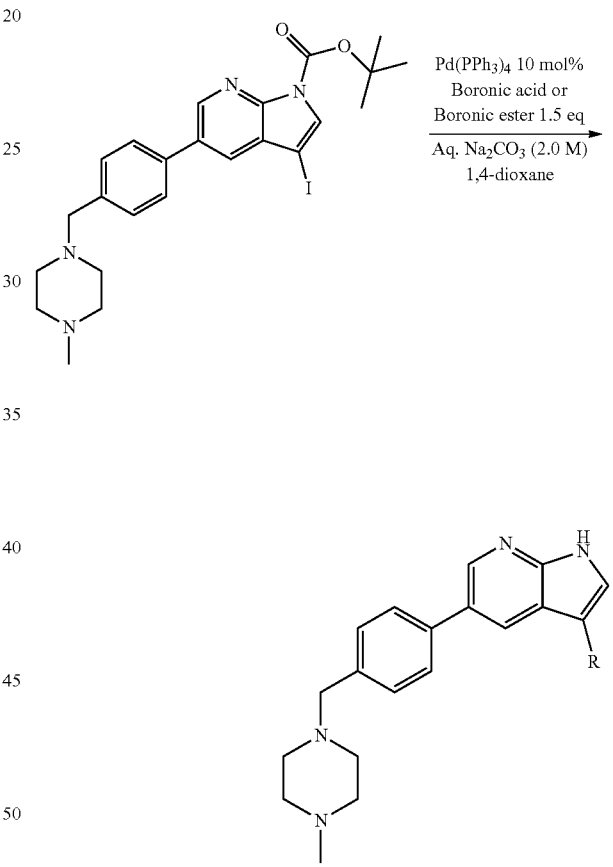

tert-butyl 3-iodo-5-(4-((4-methylpiperazin-1-yl)methyl)phenyl)-1H-pyrrolo[2,3-b]pyridine-1-carboxylate (6, 26.2 mg, 0.05 mmol, 1.0 eq) was dissolved in 1,4-dioxane (2.0 mL) in a 1 dram glass vial with Teflon lined cap. The boronic acid or boronic ester (0.075 mmol, 1.5 eq) was added, followed by addition of Tetrakis(triphenylphosphine)palladium(0) (Pd(PPh$_3$)$_4$, 5.8 mg, 5 mol %). The reaction mixture was degassed, aqueous Na$_2$CO$_3$ (2.0 M, 0.5 mL) was added, and was stirred overnight at 100° C. The reaction mixture was filtered over Celite and the Celite was washed with ethyl acetate. The solvent was evaporated and the crude product was purified by preparatory HPLC purification to give the pure material.

Preparation of 3-(1H-Indol-5-yl)-5-(4-((4-methylpiperazin-1-yl)methyl)phenyl)-1H-pyrrolo[2,3-b]pyridine (Compound 1)

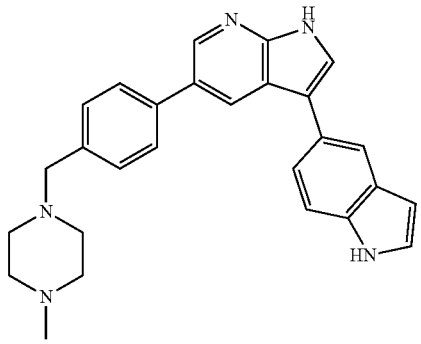 [SMILES: CN1CCN(Cc2ccc(-c3cnc4[nH]cc(-c5ccc6[nH]ccc6c5)c4c3)cc2)CC1]

Compound 1 was prepared according to the general procedure for the Suzuki coupling and in situ deprotection as described above using 5-indolylboronic acid (12.1 mg, 0.075 mmol, 1.5 eq). The crude product was purified by preparatory HPLC purification to afford 3-(1H-indol-5-yl)-5-(4-((4-methylpiperazin-1-yl)methyl)phenyl)-1H-pyrrolo[2,3-b]pyridine (1, 14.8 mg, 70% yield). $^1$H NMR (400 MHz, Methanol-$d_4$) δ 8.61 (d, J=2.0 Hz, 1H), 8.52 (d, J=2.0 Hz, 1H), 7.86 (dd, J=1.7, 0.7 Hz, 1H), 7.70 (d, J=8.2 Hz, 2H), 7.67 (s, 1H), 7.50 (m, 3H), 7.44 (dd, J=8.4, 1.7 Hz, 1H), 7.28 (d, J=3.2 Hz, 1H), 6.51 (dd, J=3.2, 0.9 Hz, 1H), 3.84 (s, 2H), 3.00-2.80 (bs, 8H), 2.87 (s, 3H) ppm. The spectroscopic data matched those reported in literature.

Preparation of 3-(1H-Indol-2-yl)-5-(4-((4-methylpiperazin-1-yl)methyl)phenyl)-1H-pyrrolo[2,3-b]pyridine (Compound 7a)

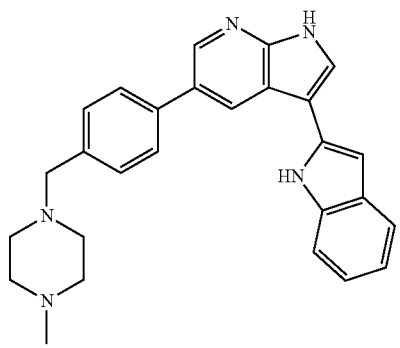 [SMILES: CN1CCN(Cc2ccc(-c3cnc4[nH]cc(-c5cc6ccccc6[nH]5)c4c3)cc2)CC1]

Compound 7a was prepared according to the general procedure for the Suzuki coupling and in situ deprotection as described above using indole-2-boronic acid pinacol ester (18.2 mg, 0.075 mmol, 1.5 eq). The crude product was purified by preparatory HPLC purification to afford 3-(1H-Indol-2-yl)-5-(4-((4-methylpiperazin-1-yl)methyl)phenyl)-1H-pyrrolo[2,3-b]pyridine (7a, 14.1 mg, 67% yield). $^1$H NMR (400 MHz, Methanol-$d_4$) δ 8.54 (d, J=2.1 Hz, 1H), 8.49 (d, J=2.1 Hz, 1H), 7.82 (s, 1H), 7.65 (d, J=8.2 Hz, 2H), 7.54 (dt, J=7.8, 1.0 Hz, 1H), 7.41 (d, J=8.1 Hz, 2H), 7.42-7.35 (m, 1H), 7.07 (ddd, J=8.0, 7.2, 1.1 Hz, 1H), 7.00 (ddd, J=8.0, 7.1, 1.1 Hz, 1H), 6.78 (d, J=1.0 Hz, 1H), 3.56 (s, 2H), 2.75-2.40 (bs, 8H), 2.34 (s, 3H) ppm. HRMS (APCI$^+$, m/z): calcd. for $C_{27}H_{28}N_5$ [M+H$^+$]: 422.2339, found: 422.2336.

Preparation of 3-(6-Ethoxypyridin-3-yl)-5-(4-((4-methylpiperazin-1-yl)methyl)phenyl)-1H-pyrrolo[2,3-b]pyridine (Compound 7b)

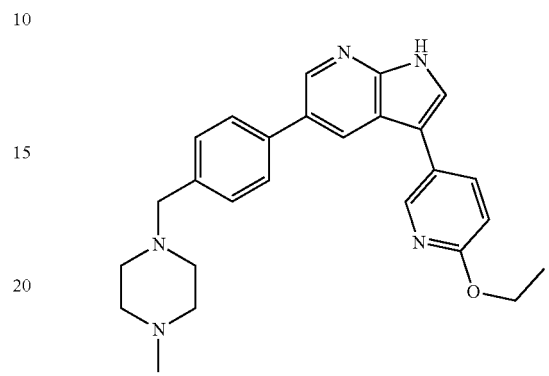

Compound 7b was prepared according to the general procedure for the Suzuki coupling and in situ deprotection as described above using 6-ethoxy-3-pyridinylboronic acid (12.5 mg, 0.075 mmol, 1.5 eq). The crude product was purified by preparatory HPLC purification to afford 3-(6-ethoxypyridin-3-yl)-5-(4-((4-methylpiperazin-1-yl)methyl)phenyl)-1H-pyrrolo[2,3-b]pyridine (7b, 16.2 mg, 76% yield). $^1$H NMR (400 MHz, Methanol-$d_4$) δ 8.48 (d, J=2.1 Hz, 1H), 8.42 (dd, J=2.6, 0.8 Hz, 1H), 8.33 (d, J=2.1 Hz, 1H), 7.99 (dd, J=8.6, 2.5 Hz, 1H), 7.66 (s, 1H), 7.63 (d, J=8.0 Hz, 2H), 7.43 (d, J=8.0 Hz, 2H), 6.88 (dd, J=8.6, 0.8 Hz, 1H), 4.34 (q, J=7.0 Hz, 2H), 2.80-2.45 (bs, 8H), 2.40 (s, 3H), 1.40 (t, J=7.1 Hz, 3H) ppm. HRMS (APCI$^+$, m/z): calcd. for $C_{26}H_{30}N_5O$ [M+H$^+$]: 428.2450, found: 428.2449.

Preparation of 3-(Dibenzo[b,d]furan-4-yl)-5-(4-((4-methylpiperazin-1-yl)methyl)phenyl)-1H-pyrrolo[2,3-b]pyridine (Compound 7c)

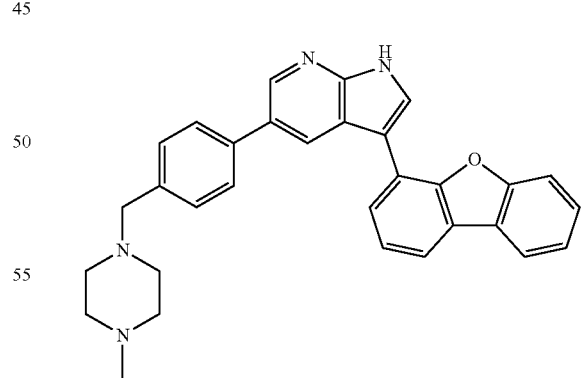

Compound 7c was prepared according to the general procedure for the Suzuki coupling and in situ deprotection as described above using 4-(dibenzofuranyl)boronic acid (15.9 mg, 0.075 mmol, 1.5 eq). The crude product was purified by preparatory HPLC purification to afford 3-(dibenzo[b,d]furan-4-yl)-5-(4-((4-methylpiperazin-1-yl)methyl)phenyl)-1H-pyrrolo[2,3-b]pyridine (7c, 12.6 mg, 58% yield). $^1$H NMR (400 MHz, Methanol-d₄) δ 8.57 (s, 2H), 8.18 (s, 1H), 8.12 (dt, J=7.7, 1.2 Hz, 1H), 8.00 (dd, J=7.7, 1.2 Hz, 1H), 7.94 (dd, J=7.6, 1.2 Hz, 1H), 7.72 (d, J=8.2 Hz, 2H), 7.70-7.65 (m, 2H), 7.57-7.48 (m, 4H), 3.69 (s, 2H), 3.05-2.75 (bs, 4H), 2.85-2.55 (bs, 4H), 2.59 (s, 3H) ppm. HRMS (APCI⁺, m/z): calcd. for $C_{31}H_{29}N_4O$ [M+H⁺]: 473.2341, found: 473.2345.

Preparation of 3-(2,3-Dihydrobenzo[b][1,4]dioxin-6-yl)-5-(4-((4-methylpiperazin-1-yl)methyl)phenyl)-1H-pyrrolo[2,3-b]pyridine (Compound 7d)

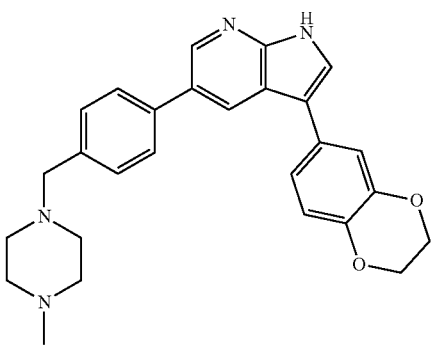 [SMILES: CN1CCN(Cc2ccc(-c3cnc4[nH]cc(-c5ccc6c(c5)OCCO6)c4c3)cc2)CC1]

Compound 7d was prepared according to the general procedure for the Suzuki coupling and in situ deprotection as described above using 1,4-benzodioxane-6-boronic acid (13.5 mg, 0.075 mmol, 1.5 eq). The crude product was purified by preparatory HPLC purification to afford 3-(2,3-dihydrobenzo[b][1,4]dioxin-6-yl)-5-(4-((4-methylpiperazin-1-yl)methyl)phenyl)-1H-pyrrolo[2,3-b]pyridine (7d, 10.2 mg, 46% yield). ¹H NMR (400 MHz, Methanol-d₄) δ 8.45 (d, J=2.1 Hz, 1H), 8.34 (d, J=2.1 Hz, 1H), 7.61 (d, J=8.2 Hz, 2H), 7.55 (s, 1H), 7.43 (d, J=8.2 Hz, 2H), 7.17-7.10 (m, 2H), 6.91 (d, J=8.8 Hz, 1H), 4.27 (s, 4H), 3.60 (s, 2H), 2.77-2.46 (bs, 8H), 2.39 (s, 3H) ppm. HRMS (APCI⁺, m/z): calcd. for $C_{27}H_{29}N_4O_2$ [M+H⁺]: 441.2291, found: 441.2287.

Preparation of 4-(5-(4-((4-Methylpiperazin-1-yl)methyl)phenyl)-1H-pyrrolo[2,3-b]pyridin-3-yl)aniline (Compound 7e)

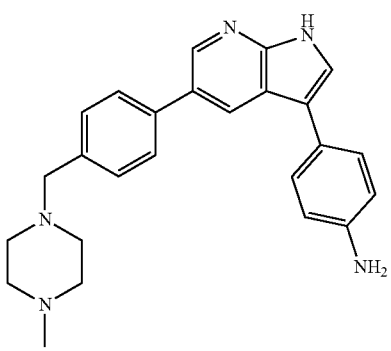 [SMILES: CN1CCN(Cc2ccc(-c3cnc4[nH]cc(-c5ccc(N)cc5)c4c3)cc2)CC1]

Compound 7e was prepared according to the general procedure for the Suzuki coupling and in situ deprotection as described above using 4-aminophenylboronic acid pinacol ester (17.0 mg, 0.075 mmol, 1.5 eq). The crude product was purified by preparatory HPLC purification to afford 4-(5-(4-((4-methylpiperazin-1-yl)methyl)phenyl)-1H-pyrrolo[2,3-b]pyridin-3-yl)aniline (7e, 14.4 mg, 73% yield). ¹H NMR (400 MHz, Methanol-d₄) δ 8.43 (d, J=2.1 Hz, 1H), 8.34 (d, J=2.1 Hz, 1H), 7.61 (d, J=8.2 Hz, 2H), 7.50 (s, 1H), 7.46-7.39 (m, 4H), 6.84 (d, J=8.5 Hz, 2H), 3.62 (s, 2H), 2.79 (bs, 4H), 2.63 (bs, 4H), 2.49 (s, 3H) ppm. HRMS (APCI⁺, m/z): calcd. for $C_{25}H_{28}N_5$ [M+H⁺]: 398.2345, found: 398.2344.

Preparation of 3-(Benzo[b]thiophen-3-yl)-5-(4-((4-methylpiperazin-1-yl)methyl)phenyl)-1H-pyrrolo[2,3-b]pyridine (Compound 7f)

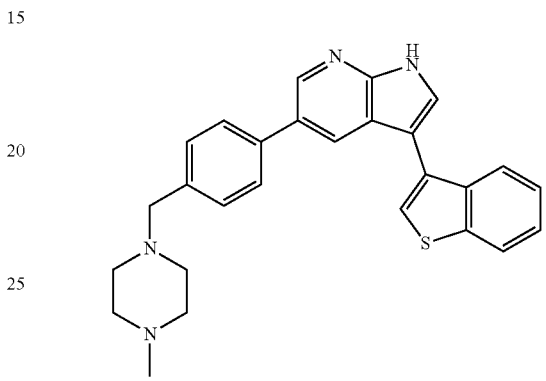

Compound 7f was prepared according to the general procedure for the Suzuki coupling and in situ deprotection as described above using benzo[b]thien-3-ylboronic acid (14.0 mg, 0.075 mmol, 1.5 eq). The crude product was purified by preparatory HPLC purification to afford 3-(benzo[b]thiophen-3-yl)-5-(4-((4-methylpiperazin-1-yl)methyl)phenyl)-1H-pyrrolo[2,3-b]pyridine (7f, 16.0 mg, 73% yield). ¹H NMR (400 MHz, Methanol-d₄) δ 8.50 (d, J=2.1 Hz, 1H), 8.17 (d, J=2.1 Hz, 1H), 7.97-7.87 (m, 2H), 7.71 (s, 1H), 7.63 (s, 1H), 7.55 (d, J=8.2 Hz, 2H), 7.44-7.33 (m, 4H), 3.55 (s, 2H), 2.71-2.45 (bs, 8H), 2.37 (s, 3H) ppm. HRMS (APCI⁺, m/z): calcd. for $C_{27}H_{27}N_4S$ [M+H⁺]: 439.1956, found: 439.1955.

Preparation of 3-(Benzo[b]thiophen-2-yl)-5-(4-((4-methylpiperazin-1-yl)methyl)phenyl)-1H-pyrrolo[2,3-b]pyridine (Compound 7g)

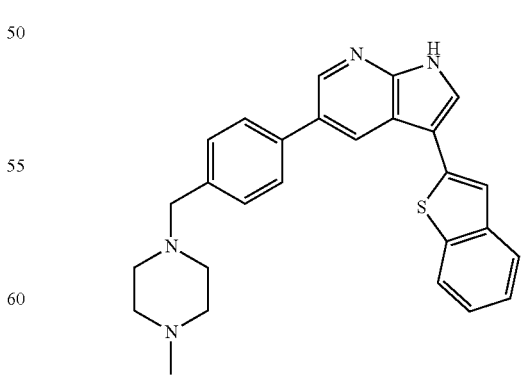

Compound 7g was prepared according to the general procedure for the Suzuki coupling and in situ deprotection as described above using benzo[b]thien-2-ylboronic acid (14.0 mg, 0.075 mmol, 1.5 eq). The crude product was purified by preparatory HPLC purification to afford 3-(benzo[b]thiophen-2-yl)-5-(4-((4-methylpiperazin-1-yl)methyl)phenyl)-1H-pyrrolo[2,3-b]pyridine (7 g, 15.9 mg, 73% yield). $^1$H NMR (400 MHz, Methanol-$d_4$) δ 8.52 (d, J=2.1 Hz, 1H), 8.50 (d, J=2.1 Hz, 1H), 7.83-7.74 (m, 3H), 7.64 (d, J=8.2 Hz, 2H), 7.57 (d, J=0.7 Hz, 1H), 7.43 (d, J=8.2 Hz, 2H), 7.32 (ddd, J=7.9, 7.2, 1.2 Hz, 1H), 7.26 (ddd, J=8.4, 7.2, 1.2 Hz, 1H), 3.59 (s, 2H), 2.72-2.48 (bs, 8H), 2.38 (s, 3H) ppm. HRMS (APCI$^+$, m/z): calcd. for $C_{27}H_{27}N_4S$ [M+H$^+$]: 439.1956, found: 439.1959.

Preparation of 3-(5-(4-((4-Methylpiperazin-1-yl)methyl)phenyl)-1H-pyrrolo[2,3-b]pyridin-3-yl)aniline (Compound 7h)

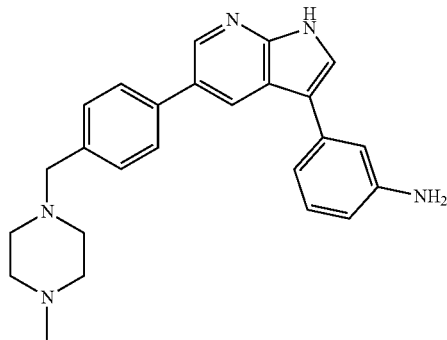

Compound 7h was prepared according to the general procedure for the Suzuki coupling and in situ deprotection as described above using 3-aminophenylboronic acid hydrochloride (13.3 mg, 0.075 mmol, 1.5 eq). The crude product was purified by preparatory HPLC purification to afford 3-(5-(4-((4-methylpiperazin-1-yl)methyl)phenyl)-1H-pyrrolo[2,3-b]pyridin-3-yl)aniline (7h, 14.9 mg, 75% yield). $^1$H NMR (400 MHz, Methanol-$d_4$) δ 8.47 (d, J=2.1 Hz, 1H), 8.45 (d, J=2.1 Hz, 1H), 7.64 (d, J=8.2 Hz, 2H), 7.61 (s, 1H), 7.44 (d, J=8.2 Hz, 2H), 7.19 (t, J=7.8 Hz, 1H), 7.11 (t, J=2.0 Hz, 1H), 7.03 (ddd, J=7.6, 1.7, 1.0 Hz, 1H), 6.68 (ddd, J=7.8, 2.3, 1.0 Hz, 1H), 3.60 (s, 2H), 2.58 (bs, 8H), 2.34 (s, 3H) ppm. HRMS (APCI$^+$, m/z): calcd. for $C_{25}H_{28}N_5$ [M+H$^+$]: 398.2345, found: 398.2337.

Preparation of 2-Fluoro-5-(5-(4-((4-methylpiperazin-1-yl)methyl)phenyl)-1H-pyrrolo[2,3-b]pyridin-3-yl)benzoic acid (Compound 7i)

Compound 7i was prepared according to the general procedure for the Suzuki coupling and in situ deprotection as described above using 3-carboxy-4-fluorophenylboronic acid (13.8 mg, 0.075 mmol, 1.5 eq). The crude product was purified by preparatory HPLC purification to afford 2-fluoro-5-(5-(4-((4-methylpiperazin-1-yl)methyl)phenyl)-1H-pyrrolo[2,3-b]pyridin-3-yl)benzoic acid (7i, 8.9 mg, 40% yield). 1H NMR (500 MHz, Methanol-$d_4$) δ 8.56 (d, J=2.0 Hz, 1H), 8.53 (d, J=2.0 Hz, 1H), 8.24 (dd, J=6.8, 2.5 Hz, 1H), 7.95 (ddd, J=8.6, 4.5, 2.5 Hz, 1H), 7.81 (s, 1H), 7.75 (d, J=8.2 Hz, 2H), 7.55 (d, J=8.2 Hz, 2H), 7.32 (dd, J=10.6, 8.6 Hz, 1H), 3.96 (s, 2H), 3.38 (bs, 4H), 3.05 (bs, 4H), 2.91 (s, 3H) ppm. HRMS (APCI$^+$, m/z): calcd. for $C_{26}H_{26}FN_4O_2$ [M+H$^+$]: 445.2040, found: 445.2035.

Preparation of 3-(5-(4-((4-Methylpiperazin-1-yl)methyl)phenyl)-1H-pyrrolo[2,3-b]pyridin-3-yl)benzoic acid (Compound 7j)

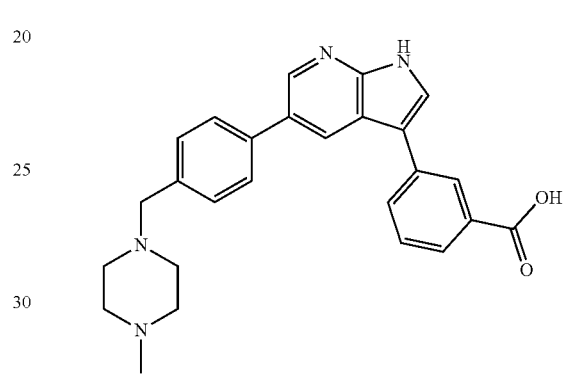

Compound 7j was prepared according to the general procedure for the Suzuki coupling and in situ deprotection as described above using 3-carboxyphenylboronic acid (12.5 mg, 0.075 mmol, 1.5 eq). The crude product was purified by preparatory HPLC purification to afford 3-(5-(4-((4-methylpiperazin-1-yl)methyl)phenyl)-1H-pyrrolo[2,3-b]pyridin-3-yl)benzoic acid (7j, 12.0 mg, 56% yield). $^1$H NMR (400 MHz, Methanol-$d_4$) δ 8.62-8.56 (m, 2H), 8.36 (s, 1H), 8.02-7.94 (m, 2H), 7.85 (s, 1H), 7.76 (d, J=8.0 Hz, 2H), 7.60 (d, J=7.8 Hz, 1H), 7.56 (d, J=8.0 Hz, 2H), 3.97 (s, 2H), 3.39 (bs, 4H), 3.05 (bs, 4H), 2.91 (s, 3H) ppm. HRMS (APCI$^+$, m/z): calcd. for $C_{26}H_{27}N_4O_2$ [M+H$^+$]: 427.2134, found: 427.2137.

Preparation of 5-(5-(4-((4-Methylpiperazin-1-yl)methyl)phenyl)-1H-pyrrolo[2,3-b]pyridin-3-yl)pyrimidin-2-amine (Compound 7k)

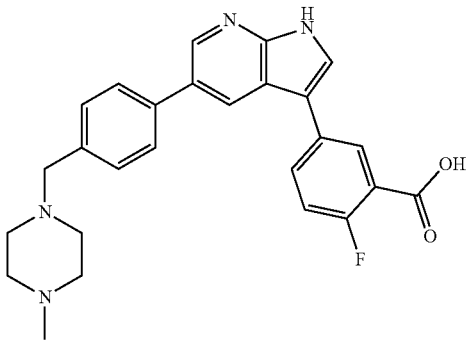 [SMILES: CN1CCN(Cc2ccc(-c3cnc4[nH]cc(-c5ccc(F)c(C(=O)O)c5)c4c3)cc2)CC1]

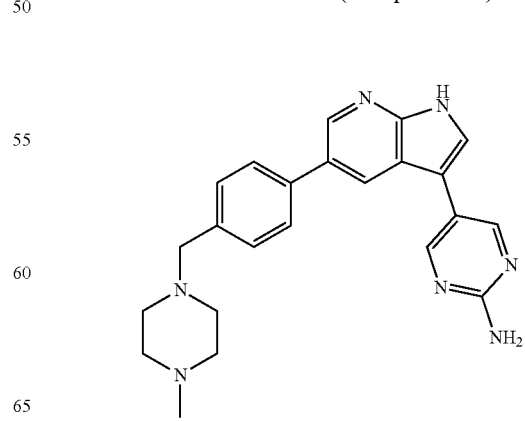

Compound 7k was prepared according to the general procedure for the Suzuki coupling and in situ deprotection as described above using 2-aminopyrimidine-5-boronic acid (11.0 mg, 0.075 mmol, 1.5 eq). The crude product was purified by preparatory HPLC purification to afford 5-(5-(4-((4-methylpiperazin-1-yl)methyl)phenyl)-1H-pyrrolo[2,3-b]pyridin-3-yl)pyrimidin-2-amine (7k, 16.4 mg, 82%). $^1$H NMR (400 MHz, Methanol-$d_4$) δ 8.87 (s, 2H), 8.58 (d, J=2.1 Hz, 1H), 8.46 (d, J=2.1 Hz, 1H), 7.87 (s, 1H), 7.76 (d, J=8.2 Hz, 2H), 7.54 (d, J=8.2 Hz, 2H), 3.93 (s, 2H), 3.37 (bs, 4H), 3.01 (bs, 4H), 2.90 (s, 3H) ppm. HRMS (APCI$^+$, m/z): calcd. for $C_{23}H_{26}N_7$ [M+H$^+$]: 400.2250, found: 400.2250.

Preparation of 3-Methyl-5-(5-(4-((4-methylpiperazin-1-yl)methyl)phenyl)-1H-pyrrolo[2,3-b]pyridin-3-yl)pyridin-2-amine (Compound 7l)

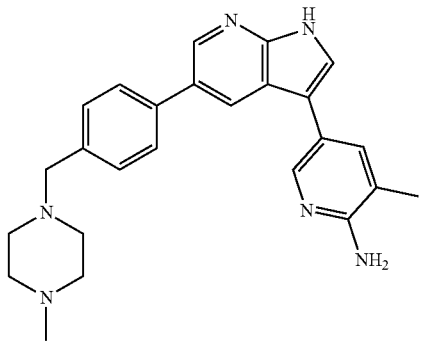 [SMILES: Cc1cc(-c2c[nH]c3ncc(-c4ccc(CN5CCN(C)CC5)cc4)cc23)cnc1N]

Compound 7l was prepared according to the general procedure for the Suzuki coupling and in situ deprotection as described above using 2-amino-3-methylpyridine-5-boronic acid pinacol ester (18.3 mg, 0.075 mmol, 1.5 eq). The crude product was purified by preparatory HPLC purification to afford 3-methyl-5-(5-(4-((4-methylpiperazin-1-yl)methyl)phenyl)-1H-pyrrolo[2,3-b]pyridin-3-yl)pyridin-2-amine (7l, 8.2 mg, 40% yield). $^1$H NMR (400 MHz, Methanol-$d_4$) δ 8.55 (s, 1H), 8.42 (d, J=2.0 Hz, 1H), 8.24 (dd, J=2.2, 1.1 Hz, 1H), 8.14-8.08 (m, 1H), 7.83 (s, 1H), 7.73 (d, J=8.2 Hz, 2H), 7.51 (d, J=8.1 Hz, 2H), 3.79 (s, 2H), 3.04-2.68 (bs, 8H), 2.87 (s, 3H), 2.37 (s, 3H) ppm. HRMS (APCI$^+$, m/z): calcd. for $C_{25}H_{29}N_6$ [M+H$^+$]: 413.2454, found: 413.2457.

Preparation of 5-(5-(4-((4-Methylpiperazin-1-yl)methyl)phenyl)-1H-pyrrolo[2,3-b]pyridin-3-yl)pyridin-2-amine (Compound 7m)

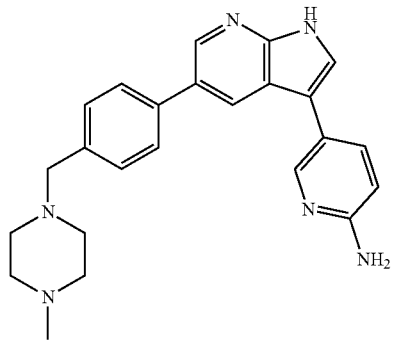 [SMILES: CN1CCN(Cc2ccc(-c3cnc4[nH]cc(-c5ccc(N)nc5)c4c3)cc2)CC1]

Compound 7m was prepared according to the general procedure for the Suzuki coupling and in situ deprotection as described above using 2-aminopyridine-5-boronic acid pinacol ester (16.5 mg, 0.075 mmol, 1.5 eq). The crude product was purified by preparatory HPLC purification to afford 5-(5-(4-((4-methylpiperazin-1-yl)methyl)phenyl)-1H-pyrrolo[2,3-b]pyridin-3-yl)pyridin-2-amine (7m, 15.2 mg, 76% yield). $^1$H NMR (400 MHz, Methanol-$d_4$) δ 8.60 (d, J=2.0 Hz, 1H), 8.52 (d, J=2.0 Hz, 1H), 8.35 (dd, J=9.3, 2.2 Hz, 1H), 8.22 (dd, J=2.2, 0.7 Hz, 1H), 7.87 (s, 1H), 7.80 (d, J=8.2 Hz, 2H), 7.59 (d, J=8.2 Hz, 2H), 7.16 (dd, J=9.2, 0.7 Hz, 1H), 4.10 (s, 2H), 3.46 (bs, 4H), 3.20 (s, 4H), 2.93 (s, 3H) ppm. HRMS (APCI$^+$, m/z): calcd. for $C_{24}H_{27}N_6$ [M+H$^+$]: 399.2297, found: 399.2307.

Preparation of 5-(4-((4-Methylpiperazin-1-yl)methyl)phenyl)-3-(pyridin-4-yl)-1H-pyrrolo[2,3-b]pyridine (Compound 7n)

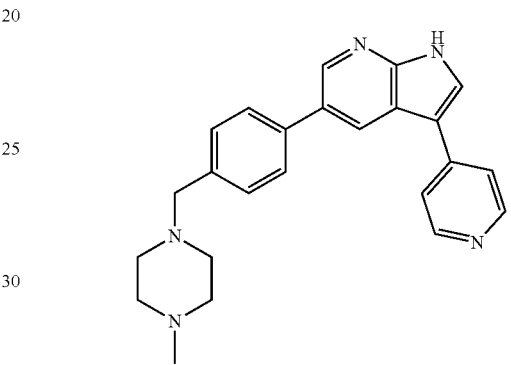

Compound 7n was prepared according to the general procedure for the Suzuki coupling and in situ deprotection as described above using 4-pyridinylboronic acid (10.3 mg, 0.075 mmol, 1.5 eq). The crude product was purified by preparatory HPLC purification to afford 5-(4-((4-methylpiperazin-1-yl)methyl)phenyl)-3-(pyridin-4-yl)-1H-pyrrolo[2,3-b]pyridine (7n, 8.7 mg, 45% yield). $^1$H NMR (400 MHz, Methanol-$d_4$) δ 8.74 (d, J=2.0 Hz, 1H), 8.68-8.64 (m, 3H), 8.57 (s, 1H), 8.43 (d, J=7.1 Hz, 2H), 7.83 (d, J=8.2 Hz, 2H), 7.60 (d, J=8.2 Hz, 2H), 4.04 (s, 2H), 3.43 (bs, 4H), 3.13 (bs, 4H), 2.92 (s, 3H) ppm. HRMS (APCI$^+$, m/z): calcd. for $C_{24}H_{26}N_5$ [M+H$^+$]: 384.2188, found: 384.2194.

Preparation of 4-(5-(4-((4-Methylpiperazin-1-yl)methyl)phenyl)-1H-pyrrolo[2,3-b]pyridin-3-yl)benzonitrile (Compound 7o)

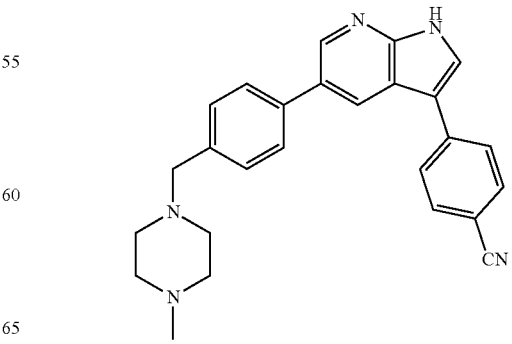

Compound 7o was prepared according to the general procedure for the Suzuki coupling and in situ deprotection as described above using 4-cyanophenylboronic acid (11.0 mg, 0.075 mmol, 1.5 eq). The crude product was purified by preparatory HPLC purification to afford 4-(5-(4-((4-methylpiperazin-1-yl)methyl)phenyl)-1H-pyrrolo[2,3-b]pyridin-3-yl)benzonitrile (7o, 14.4 mg, 71% yield). $^1$H NMR (400 MHz, Methanol-$d_4$) δ 8.56 (d, J=2.1 Hz, 1H), 8.54 (d, J=2.1 Hz, 1H), 7.97-7.91 (m, 3H), 7.83-7.77 (m, 2H), 7.75 (d, J=8.2 Hz, 2H), 7.54 (d, J=8.2 Hz, 2H), 3.89 (s, 2H), 3.35 (bs, 4H), 2.96 (bs, 4H), 2.89 (s, 3H) ppm. HRMS (APCI$^+$, m/z): calcd. for $C_{26}H_{26}N_5$ [M+H$^+$]: 408.2188, found: 408.2198.

Preparation of 5-(4-((4-Methylpiperazin-1-yl)methyl)phenyl)-3-(3-nitrophenyl)-1H-pyrrolo[2,3-b]pyridine (Compound 7p)

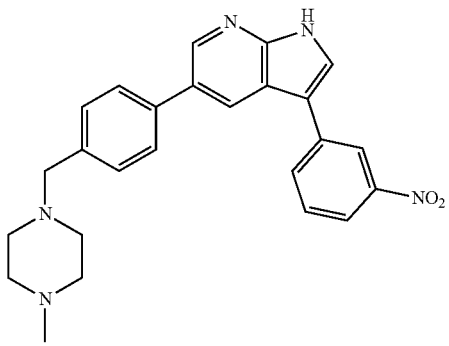 [SMILES: CN1CCN(Cc2ccc(-c3cnc4[nH]cc(-c5cccc([N+](=O)[O-])c5)c4c3)cc2)CC1]

Compound 7p was prepared according to the general procedure for the Suzuki coupling and in situ deprotection as described above using 3-nitrophenylboronic acid (12.5 mg, 0.075 mmol, 1.5 eq). The crude product was purified by preparatory HPLC purification to afford 5-(4-((4-methylpiperazin-1-yl)methyl)phenyl)-3-(3-nitrophenyl)-1H-pyrrolo[2,3-b]pyridine (7p, 15.4 mg, 72% yield). $^1$H NMR (400 MHz, Methanol-$d_4$) δ 8.59 (d, J=2.0 Hz, 1H), 8.58 (d, J=2.0 Hz, 1H), 8.54 (t, J=2.0 Hz, 1H), 8.15 (dddd, J=7.7, 4.3, 2.1, 1.0 Hz, 2H), 7.96 (s, 1H), 7.77 (d, J=8.2 Hz, 2H), 7.71 (t, J=8.0 Hz, 1H), 7.58 (d, J=8.2 Hz, 2H), 4.08 (s, 2H), 3.44 (bs, 4H), 3.17 (bs, 4H), 2.93 (s, 3H) ppm. HRMS (APCI$^+$, m/z): calcd. for $C_{25}H_{26}N_5O_2$ [M+H$^+$]: 428.2087, found: 428.2081.

Preparation of 3-(4-Isopropoxyphenyl)-5-(4-((4-methylpiperazin-1-yl)methyl)phenyl)-1H-pyrrolo[2,3-b]pyridine (Compound 7q)

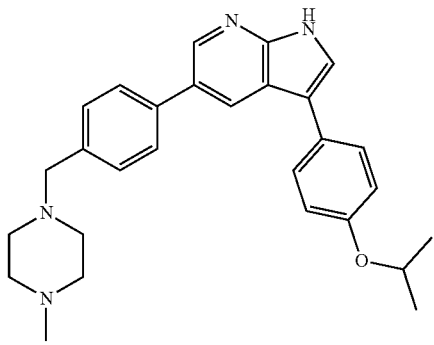 [SMILES: CC(C)Oc1ccc(-c2c[nH]c3ncc(-c4ccc(CN5CCN(C)CC5)cc4)cc23)cc1]

Compound 7q was prepared according to the general procedure for the Suzuki coupling and in situ deprotection as described above using 4-isopropoxyphenylboronic acid (13.5 mg, 0.075 mmol, 1.5 eq). The crude product was purified by preparatory HPLC purification to afford 3-(4-isopropoxyphenyl)-5-(4-((4-methylpiperazin-1-yl)methyl)phenyl)-1H-pyrrolo[2,3-b]pyridine (7q, 18.2 mg, 83% yield). $^1$H NMR (400 MHz, Methanol-$d_4$) δ 8.61 (d, J=2.0 Hz, 1H), 8.56 (d, J=2.0 Hz, 1H), 7.75 (d, J=8.2 Hz, 2H), 7.69 (s, 1H), 7.64-7.58 (m, 2H), 7.55 (d, J=8.2 Hz, 2H), 7.08-6.98 (m, 2H), 4.65 (hept, J=6.0 Hz, 1H), 3.94 (s, 2H), 3.37 (bs, 4H), 3.02 (bs, 4H), 2.90 (s, 3H), 1.35 (d, J=6.0 Hz, 6H) ppm. HRMS (APCI$^+$, m/z): calcd. for $C_{28}H_{33}N_4O$ [M+H$^+$]: 441.2654, found: 441.2646.

Preparation of 3-(5-(4-((4-Methylpiperazin-1-yl)methyl)phenyl)-1H-pyrrolo[2,3-b]pyridin-3-yl)phenol (Compound 7r)

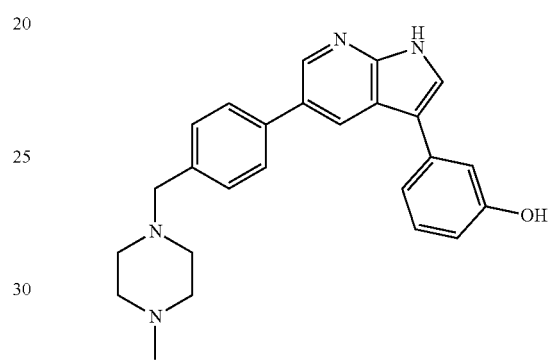

Compound 7r was prepared according to the general procedure for the Suzuki coupling and in situ deprotection as described above using 3-hydroxyphenylboronic acid (10.3 mg, 0.075 mmol, 1.5 eq). The crude product was purified by preparatory HPLC purification to afford 3-(5-(4-((4-methylpiperazin-1-yl)methyl)phenyl)-1H-pyrrolo[2,3-b]pyridin-3-yl)phenol (7r, 9.8 mg, 49% yield). H NMR (400 MHz, Methanol-$d_4$) δ 8.68 (d, J=1.9 Hz, 1H), 8.60 (s, 1H), 7.80-7.73 (m, 3H), 7.58 (d, J=8.2 Hz, 2H), 7.30 (t, J=7.8 Hz, 1H), 7.24-7.17 (m, 1H), 7.16 (t, J=2.0 Hz, 1H), 6.78 (ddd, J=8.1, 2.5, 1.0 Hz, 1H), 4.04 (s, 2H), 3.42 (bs, 4H), 3.13 (bs, 4H), 2.92 (s, 3H) ppm. HRMS (APCI$^+$, m/z): calcd. for $C_{25}H_{27}N_4O$ [M+H$^+$]: 399.2185, found: 399.2180.

Preparation of 3-(1-Methyl-1H-pyrazol-4-yl)-5-(4-((4-methylpiperazin-1-yl)methyl)phenyl)-1H-pyrrolo[2,3-b]pyridine (Compound 7s)

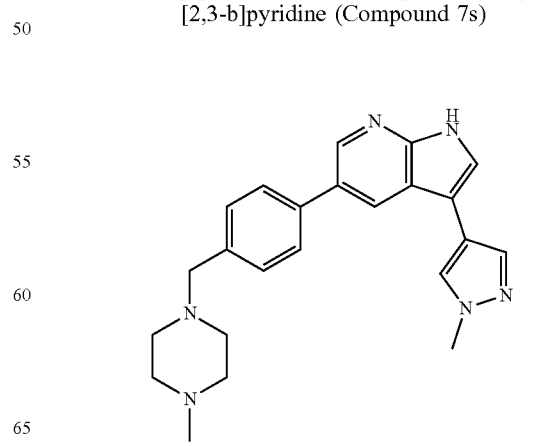

Compound 7s was prepared according to the general procedure for the Suzuki coupling and in situ deprotection as described above using 1-methylpyrazole-4-boronic acid pinacol ester (16.1 mg, 0.075 mmol, 1.5 eq). The crude product was purified by preparatory HPLC purification to afford 3-(1-methyl-1H-pyrazol-4-yl)-5-(4-((4-methylpiperazin-1-yl)methyl)phenyl)-1H-pyrrolo[2,3-b]pyridine (7s, 14.8 mg, 77% yield). $^1$H NMR (400 MHz, Methanol-$d_4$) δ 8.62 (d, J=2.0 Hz, 1H), 8.31 (d, J=2.0 Hz, 1H), 7.80 (s, 1H), 7.76 (d, J=8.2 Hz, 2H), 7.64 (d, J=2.0 Hz, 1H), 7.58 (d, J=8.2 Hz, 2H), 6.60 (d, J=2.1 Hz, 1H), 4.14 (s, 2H), 3.95 (s, 3H), 3.48 (bs, 4H), 3.25 (bs, 4H), 2.94 (s, 3H) ppm. HRMS (APCI$^+$, m/z): calcd. for $C_{23}H_{27}N_6$ [M+H$^+$]: 387.2297, found: 387.2303.

Preparation of 4-((5-(5-(4-((4-Methylpiperazin-1-yl)methyl)phenyl)-1H-pyrrolo[2,3-b]pyridin-3-yl)thiophen-2-yl)methyl)morpholine (Compound 7t)

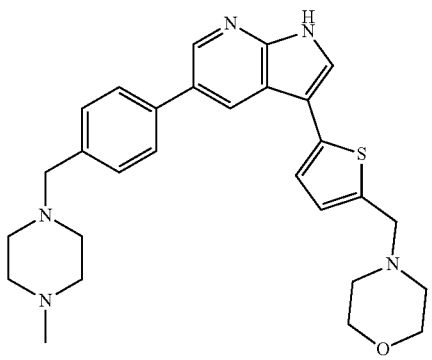 [SMILES: CN1CCN(Cc2ccc(-c3cnc4[nH]cc(-c5ccc(CN6CCOCC6)s5)c4c3)cc2)CC1]

Compound 7t was prepared according to the general procedure for the Suzuki coupling and in situ deprotection as described above using 5-(morpholinomethyl)-2-thiopheneboronic acid pinacol ester (24.4 mg, 0.075 mmol, 1.5 eq). The crude product was purified by preparatory HPLC purification to afford 4-((5-(5-(4-((4-methylpiperazin-1-yl)methyl)phenyl)-1H-pyrrolo[2,3-b]pyridin-3-yl)thiophen-2-yl)methyl)morpholine (7t, 10.0 mg, 41% yield). $^1$H NMR (400 MHz, Methanol-$d_4$) δ 8.57 (d, J=2.1 Hz, 1H), 8.52 (d, J=2.1 Hz, 1H), 7.84 (s, 1H), 7.75 (d, J=8.2 Hz, 2H), 7.57 (d, J=8.2 Hz, 2H), 7.42 (d, J=3.7 Hz, 1H), 7.37 (d, J=3.7 Hz, 1H), 4.64 (s, 2H), 4.06 (bs, 4H), 4.01 (s, 2H), 3.80 (bs, 4H), 3.41 (bs, 4H), 3.09 (bs, 4H), 2.92 (s, 3H) ppm. HRMS (APCI$^+$, m/z): calcd. for $C_{28}H_{34}N_5OS$ [M+H$^+$]: 488.2484, found: 488.2475.

Preparation of 5-(4-((4-Methylpiperazin-1-yl)methyl)phenyl)-3-(6-(methylsulfonyl)pyridin-3-yl)-1H-pyrrolo[2,3-b]pyridine (Compound 7u)

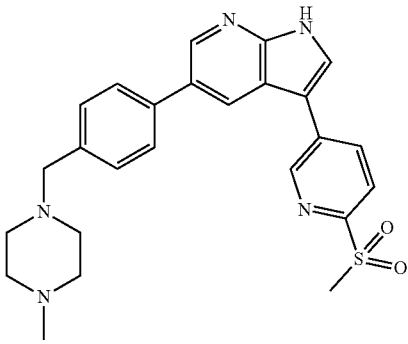 [SMILES: CN1CCN(Cc2ccc(-c3cnc4[nH]cc(-c5ccc(S(C)(=O)=O)nc5)c4c3)cc2)CC1]

Compound 7u was prepared according to the general procedure for the Suzuki coupling and in situ deprotection as described above using 6-(methylsulfonyl)pyridine-3-boronic acid (15.0 mg, 0.075 mmol, 1.5 eq). The crude product was purified by preparatory HPLC purification to afford 5-(4-((4-methylpiperazin-1-yl)methyl)phenyl)-3-(6-(methylsulfonyl)pyridin-3-yl)-1H-pyrrolo[2,3-b]pyridine (7u, 11.0 mg, 48% yield). H NMR (400 MHz, Methanol-$d_4$) δ 9.14 (dd, J=2.2, 0.8 Hz, 1H), 8.59 (q, J=2.1 Hz, 2H), 8.46 (dd, J=8.2, 2.2 Hz, 1H), 8.15 (dd, J=8.2, 0.8 Hz, 1H), 8.08 (s, 1H), 7.78 (d, J=8.2 Hz, 2H), 7.57 (d, J=8.2 Hz, 2H), 4.02 (s, 2H), 3.41 (bs, 4H), 3.27 (s, 3H), 3.11 (bs, 4H), 2.92 (s, 3H) ppm. HRMS (APCI$^+$, m/z): calcd. for $C_{25}H_{28}N_5O_2S$ [M+H$^+$]: 462.1964, found: 462.1968.

Preparation of 5-(5-(4-((4-Methylpiperazin-1-yl)methyl)phenyl)-1H-pyrrolo[2,3-b]pyridin-3-yl)-1H-indazole (Compound 7v)

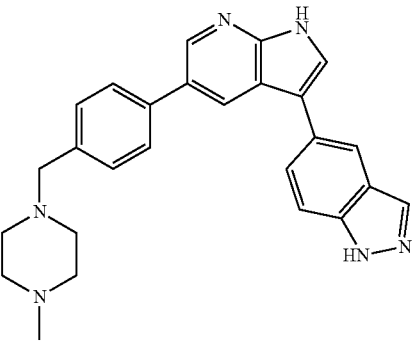 [SMILES: CN1CCN(Cc2ccc(-c3cnc4[nH]cc(-c5ccc6[nH]ncc6c5)c4c3)cc2)CC1]

Compound 7v was prepared according to the general procedure for the Suzuki coupling and in situ deprotection as described above using 1H-indazole-5-boronic acid (12.1 mg, 0.075 mmol, 1.5 eq). The crude product was purified by preparatory HPLC purification to afford 5-(5-(4-((4-methylpiperazin-1-yl)methyl)phenyl)-1H-pyrrolo[2,3-b]pyridin-3-yl)-1H-indazole (7v, 8.4 mg, 40% yield). $^1$H NMR (400 MHz, Methanol-$d_4$) δ 8.67 (d, J=1.9 Hz, 1H), 8.58 (d, J=1.9 Hz, 1H), 8.13-8.09 (m, 2H), 7.79 (s, 1H), 7.80-7.73 (m, 3H), 7.67 (dt, J=8.7, 0.9 Hz, 1H), 7.55 (d, J=8.3 Hz, 2H), 3.95 (s, 2H), 3.38 (bs, 4H), 3.03 (bs, 4H), 2.90 (s, 3H) ppm. HRMS (APCI+, m/z): calcd. for $C_{26}H_{27}N_6$ [M+H+]: 423.2297, found: 423.2298.

Preparation of 3-(Furan-3-yl)-5-(4-((4-methylpiperazin-1-yl)methyl)phenyl)-1H-pyrrolo[2,3-b]pyridine (Compound 7w)

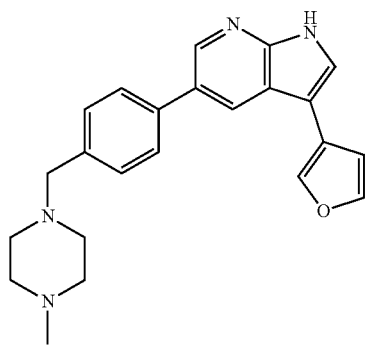 [SMILES: CN1CCN(Cc2ccc(-c3cnc4[nH]cc(-c5ccoc5)c4c3)cc2)CC1]

Compound 7w was prepared according to the general procedure for the Suzuki coupling and in situ deprotection as described above using 3-furanylboronic acid (7w, 8.4 mg, 0.075 mmol, 1.5 eq). The crude product was purified by preparatory HPLC purification to afford 3-(furan-3-yl)-5-(4-((4-methylpiperazin-1-yl)methyl)phenyl)-1H-pyrrolo[2,3-b]pyridine (12.9 mg, 69% yield). $^1$H NMR (500 MHz, Methanol-$d_4$) δ 8.58 (s, 2H), 8.08 (t, J=1.1 Hz, 1H), 7.80 (d, J=8.2 Hz, 2H), 7.76 (s, 1H), 7.62 (t, J=1.7 Hz, 1H), 7.58 (d, J=8.2 Hz, 2H), 6.87 (dd, J=1.8, 1.1 Hz, 1H), 4.00 (s, 2H), 3.41 (bs, 4H), 3.07 (bs, 4H), 2.92 (s, 3H) ppm. HRMS (APCI+, m/z): calcd. for $C_{23}H_{25}N_4O$ [M+H+]: 373.2028, found: 373.2036.

Preparation of 1-(4-(5-(4-((4-Methylpiperazin-1-yl)methyl)phenyl)-1H-pyrrolo[2,3-b]pyridin-3-yl)phenyl)ethan-1-one (Compound 7x)

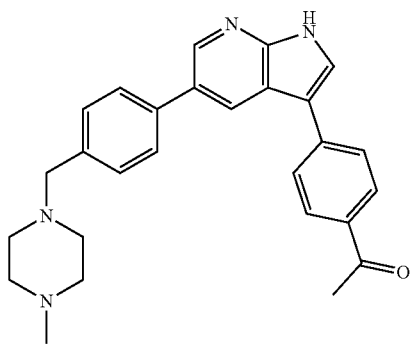 [SMILES: CC(=O)c1ccc(-c2c[nH]c3ncc(-c4ccc(CN5CCN(C)CC5)cc4)cc23)cc1]

Compound 7x was prepared according to the general procedure for the Suzuki coupling and in situ deprotection as described above using 4-acetylphenylboronic acid (12.3 mg, 0.075 mmol, 1.5 eq). The crude product was purified by preparatory HPLC purification to afford 1-(4-(5-(4-((4-methylpiperazin-1-yl)methyl)phenyl)-1H-pyrrolo[2,3-b]pyridin-3-yl)phenyl)ethan-1-one (7x, 15.1 mg, 71% yield). $^1$H NMR (500 MHz, Methanol-d4) δ 8.63 (d, J=2.0 Hz, 1H), 8.58 (d, J=2.0 Hz, 1H), 8.11 (d, J=8.4 Hz, 2H), 7.95 (s, 1H), 7.90 (d, J=8.4 Hz, 2H), 7.78 (d, J=8.2 Hz, 2H), 7.57 (d, J=8.2 Hz, 2H), 4.01 (s, 2H), 3.41 (bs, 4H), 3.09 (bs, 4H), 2.92 (s, 3H), 2.65 (s, 3H) ppm. HRMS (APCI+, m/z): calcd. for $C_{27}H_{29}N_4O$ [M+H+]: 425.2341, found: 425.2347.

Preparation of 3-(3-Fluorophenyl)-5-(4-((4-methylpiperazin-1-yl)methyl)phenyl)-1H-pyrrolo[2,3-b]pyridine (Compound 7y)

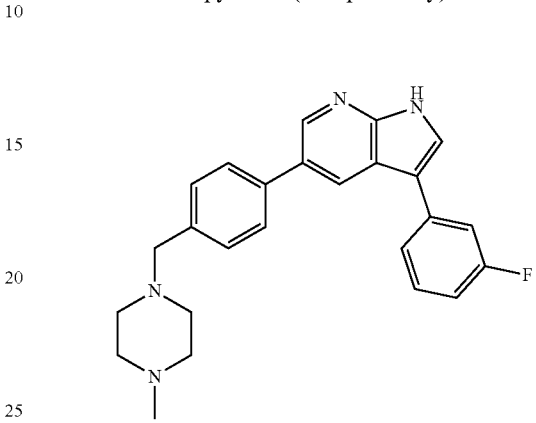

Compound 7y was prepared according to the general procedure for the Suzuki coupling and in situ deprotection as described above using 3-fluorophenylboronic acid (10.5 mg, 0.075 mmol, 1.5 eq). The crude product was purified by preparatory HPLC purification to afford 3-(3-fluorophenyl)-5-(4-((4-methylpiperazin-1-yl)methyl)phenyl)-1H-pyrrolo[2,3-b]pyridine (7y, 12.8 mg, 64% yield). $^1$H NMR (500 MHz, Methanol-$d_4$) δ 8.59 (d, J=2.0 Hz, 1H), 8.58 (d, J=2.2 Hz, 1H), 7.85 (s, 1H), 7.78 (d, J=8.2 Hz, 2H), 7.61-7.55 (m, 3H), 7.52-7.44 (m, 2H), 7.11-7.02 (m, 1H), 4.02 (s, 2H), 3.41 (bs, 4H), 3.09 (bs, 4H), 2.92 (s, 3H) ppm. HRMS (APCI+, m/z): calcd. for $C_{25}H_{26}N_4F$ [M+H+]: 401.2142, found: 401.2146.

Preparation of 5-(4-((4-Methylpiperazin-1-yl)methyl)phenyl)-3-(4-(trifluoromethoxy)phenyl)-1H-pyrrolo[2,3-b]pyridine (Compound 7z)

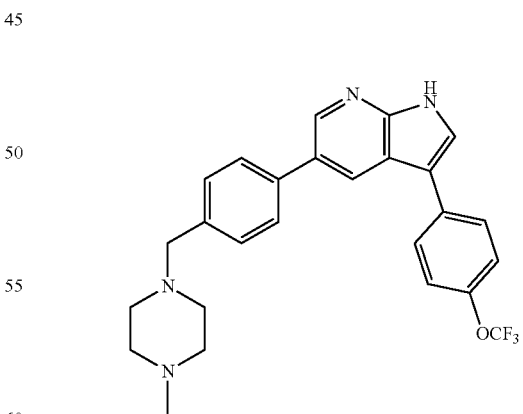

Compound 7z was prepared according to the general procedure for the Suzuki coupling and in situ deprotection as described above using 4-(trifluormethoxy)phenylboronic acid (15.4 mg, 0.075 mmol, 1.5 eq). The crude product was purified by preparatory HPLC purification to afford 5-(4-((4-methylpiperazin-1-yl)methyl)phenyl)-3-(4-(trifluoromethoxy)phenyl)-1H-pyrrolo[2,3-b]pyridine (7z, 17.4 mg, 75% yield). $^1$H NMR (500 MHz, Methanol-$d_4$) δ 8.62 (d, J=2.0 Hz, 1H), 8.59 (d, J=2.0 Hz, 1H), 7.85 (s, 1H), 7.86-7.80 (m, 2H), 7.79 (d, J=8.2 Hz, 2H), 7.58 (d, J=8.2 Hz, 2H), 7.40 (d, J=8.0 Hz, 2H), 4.05 (s, 2H), 3.43 (bs, 4H), 3.13 (bs, 4H), 2.92 (s, 3H) ppm. HRMS (APCI$^+$, m/z): calcd. for $C_{26}H_{26}F_3N_4O$ [M+H$^+$]: 467.2059, found: 467.2062.

Preparation of 4-(5-(4-((4-Methylpiperazin-1-yl)methyl)phenyl)-1H-pyrrolo[2,3-b]pyridin-3-yl)-1H-indazole (Compound 7aa)

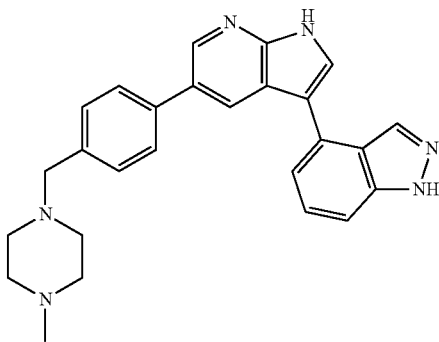 [SMILES: CN1CCN(Cc2ccc(-c3cnc4[nH]cc(-c5cccc6[nH]ncc56)c4c3)cc2)CC1]

Compound 7aa was prepared according to the general procedure for the Suzuki coupling and in situ deprotection as described above using 1H-Indazole-5-boronic acid (12.5 mg, 0.075 mmol, 1.5 eq). The crude product was purified by preparatory HPLC purification to afford 4-(5-(4-((4-methylpiperazin-1-yl)methyl)phenyl)-1H-pyrrolo[2,3-b]pyridin-3-yl)-1H-indazole (7aa, 15.6 mg, 74% yield). $^1$H NMR (400 MHz, Methanol-$d_4$) b 8.62 (d, J=2.0 Hz, 1H), 8.52 (d, J=2.0 Hz, 1H), 8.18 (s, 1H), 7.94 (s, 1H), 7.73 (d, J=8.2 Hz, 2H), 7.58-7.51 (m, 4H), 7.44 (dd, J=6.2, 1.7 Hz, 1H), 3.97 (s, 2H), 3.38 (bs, 4H), 3.05 (bs, 4H), 2.90 (s, 3H) ppm. HRMS (APCI$^+$, m/z): calcd. for $C_{26}H_{27}N_6$ [M+H$^+$]: 423.2297, found: 423.2303.

Preparation of 5-(4-((4-Methylpiperazin-1-yl)methyl)phenyl)-3-(3-(trifluoromethyl)phenyl)-1H-pyrrolo[2,3-b]pyridine (Compound 7ab)

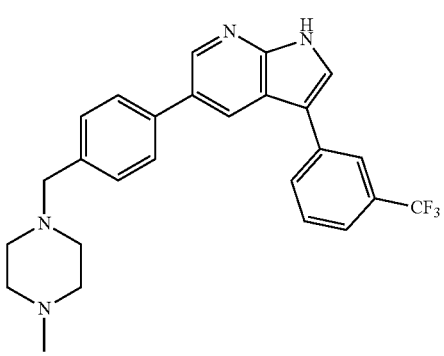 [SMILES: CN1CCN(Cc2ccc(-c3cnc4[nH]cc(-c5cccc(C(F)(F)F)c5)c4c3)cc2)CC1]

Compound 7ab was prepared according to the general procedure for the Suzuki coupling and in situ deprotection as described above using 3-(trifluoromethyl)phenylboronic acid (14.2 mg, 0.075 mmol, 1.5 eq). The crude product was purified by preparatory HPLC purification to afford 5-(4-((4-methylpiperazin-1-yl)methyl)phenyl)-3-(3-(trifluoromethyl)phenyl)-1H-pyrrolo[2,3-b]pyridine (7ab, 17.0 mg, 75% yield). $^1$H NMR (400 MHz, Methanol-$d_4$) δ 8.59 (d, J=2.0 Hz, 1H), 8.54 (d, J=2.0 Hz, 1H), 8.00 (d, J=7.8 Hz, 1H), 7.97 (s, 1H), 7.89 (s, 1H), 7.76 (d, J=8.2 Hz, 2H), 7.68 (t, J=7.7 Hz, 1H), 7.61 (d, J=8.4 Hz, 1H), 7.57 (d, J=8.2 Hz, 2H), 4.03 (s, 2H), 3.42 (bs, 4H), 3.12 (bs, 4H), 2.92 (s, 3H) ppm. HRMS (APCI$^+$, m/z): calcd. for $C_{26}H_{26}F_3N_4$ [M+H$^+$]: 451.2110, found: 451.2115.

Preparation of 5-(4-((4-Methylpiperazin-1-yl)methyl)phenyl)-3-phenyl-1H-pyrrolo[2,3-b]pyridine (Compound 7ac)

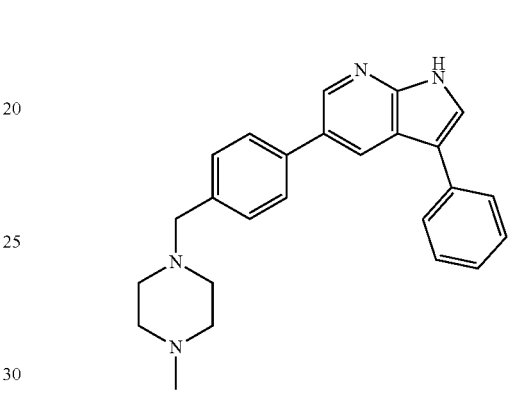

Compound 7ac was prepared according to the general procedure for the Suzuki coupling and in situ deprotection as described above using phenylboronic acid (9.6 mg, 0.075 mmol, 1.5 eq). The crude product was purified by preparatory HPLC purification to afford 5-(4-((4-methylpiperazin-1-yl)methyl)phenyl)-3-phenyl-1H-pyrrolo[2,3-b]pyridine (7ac, 16.2 mg, 85% yield). $^1$H NMR (400 MHz, Methanol-$d_4$) δ 8.69 (d, J=1.9 Hz, 1H), 8.61 (d, J=1.9 Hz, 1H), 7.82 (s, 1H), 7.78 (d, J=8.2 Hz, 2H), 7.76-7.69 (m, 2H), 7.59 (d, J=8.3 Hz, 2H), 7.53-7.44 (m, 2H), 7.39-7.29 (m, 1H), 4.08 (s, 2H), 3.45 (bs, 4H), 3.17 (bs, 4H), 2.93 (s, 3H) ppm. HRMS (APCI$^+$, m/z): calcd. for $C_{25}H_{27}N_4$ [M+H$^+$]: 383.2236, found: 383.2236.

Preparation of 3-(3-Chlorophenyl)-5-(4-((4-methylpiperazin-1-yl)methyl)phenyl)-1H-pyrrolo[2,3-b]pyridine (Compound 7ad)

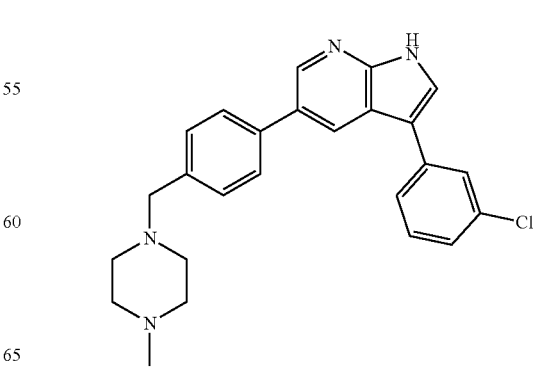

Compound 7ad was prepared according to the general procedure for the Suzuki coupling and in situ deprotection as described above using 3-chlorophenylboronic acid (11.7 mg, 0.075 mmol, 1.5 eq). The crude product was purified by preparatory HPLC purification to afford 3-(3-chlorophenyl)-5-(4-((4-methylpiperazin-1-yl)methyl)phenyl)-1H-pyrrolo[2,3-b]pyridine (7ad, 18.4 mg, 88% yield). $^1$H NMR (400 MHz, Methanol-$d_4$) δ 8.60 (d, J=1.3 Hz, 2H), 7.85 (s, 1H), 7.79 (d, J=8.2 Hz, 2H), 7.71 (t, J=1.9 Hz, 1H), 7.66 (dt, J=7.8, 1.3 Hz, 1H), 7.61 (d, J=8.2 Hz, 2H), 7.46 (t, J=7.9 Hz, 1H), 7.32 (ddd, J=8.1, 2.1, 1.0 Hz, 1H), 4.17 (s, 2H), 3.49 (bs, 4H), 3.29 (bs, 4H), 2.94 (s, 3H) ppm. HRMS (APCI$^+$, m/z): calcd. for $C_{25}H_{26}ClN_4$ [M+H$^+$]: 417.1846, found: 417.1843.

Preparation of 3-(2,4-Dichlorophenyl)-5-(4-((4-methylpiperazin-1-yl)methyl)phenyl)-1H-pyrrolo[2,3-b]pyridine (Compound 7ae)

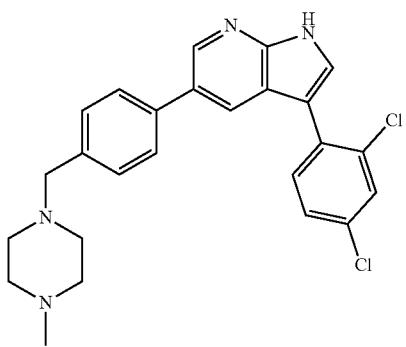 [SMILES: CN1CCN(Cc2ccc(-c3cnc4[nH]cc(-c5ccc(Cl)cc5Cl)c4c3)cc2)CC1]

Compound 7ae was prepared according to the general procedure for the Suzuki coupling and in situ deprotection as described above using 2,4-dichlorophenylboronic acid (14.3 mg, 0.075 mmol, 1.5 eq). The crude product was purified by preparatory HPLC purification to afford 3-(2,4-dichlorophenyl)-5-(4-((4-methylpiperazin-1-yl)methyl)phenyl)-1H-pyrrolo[2,3-b]pyridine (7ae, 14.9 mg, 66% yield). $^1$H NMR (400 MHz, Methanol-$d_4$) δ 8.61 (d, J=2.0 Hz, 1H), 8.32 (d, J=2.0 Hz, 1H), 7.77 (s, 1H), 7.75 (d, J=8.3 Hz, 2H), 7.64 (d, J=2.2 Hz, 1H), 7.58 (dd, J=8.3, 1.4 Hz, 3H), 7.44 (dd, J=8.3, 2.2 Hz, 1H), 4.16 (s, 2H), 3.49 (bs, 4H), 3.27 (bs, 4H), 2.94 (s, 3H) ppm. HRMS (APCI$^+$, m/z): calcd. for $C_{25}H_{25}Cl_2N_4$ [M+H$^+$]: 451.1456, found: 451.1447.

Preparation of 3-(2,5-Dimethylphenyl)-5-(4-((4-methylpiperazin-1-yl)methyl)phenyl)-1H-pyrrolo[2,3-b]pyridine (Compound 7af)

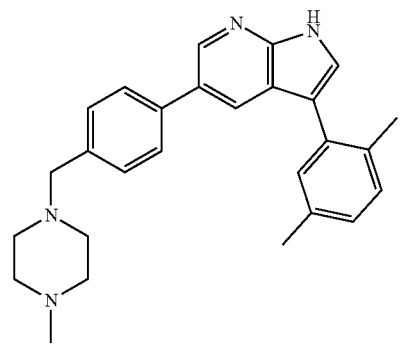 [SMILES: Cc1ccc(C)c(-c2c[nH]c3ncc(-c4ccc(CN5CCN(C)CC5)cc4)cc23)c1]

Compound 7af was prepared according to the general procedure for the Suzuki coupling and in situ deprotection as described above using 2,5-dimethylphenylboronic acid (11.2 mg, 0.075 mmol, 1.5 eq). The crude product was purified by preparatory HPLC purification to afford 3-(2,5-dimethylphenyl)-5-(4-((4-methylpiperazin-1-yl)methyl)phenyl)-1H-pyrrolo[2,3-b]pyridine (7af, 14.0 mg, 68% yield). $^1$H NMR (400 MHz, Methanol-$d_4$) δ 8.65 (d, J=1.9 Hz, 1H), 8.36 (d, J=1.9 Hz, 1H), 7.75 (d, J=8.2 Hz, 2H), 7.63 (s, 1H), 7.60 (d, J=8.2 Hz, 2H), 7.25 (d, J=7.8 Hz, 1H), 7.21 (s, 1H), 7.13 (dd, J=7.4, 1.7 Hz, 1H), 4.18 (s, 2H), 3.50 (bs, 4H), 3.30 (bs, 4H), 2.94 (s, 3H), 2.35 (s, 3H), 2.26 (s, 3H) ppm. HRMS (APCI$^+$, m/z): calcd. for $C_{27}H_{31}N_4$ [M+H$^+$]: 411.2549, found: 411.2556.

Preparation of 1-Methyl-6-(5-(4-((4-methylpiperazin-1-yl)methyl)phenyl)-1H-pyrrolo[2,3-b]pyridin-3-yl)-1H-indazole (Compound 7ag)

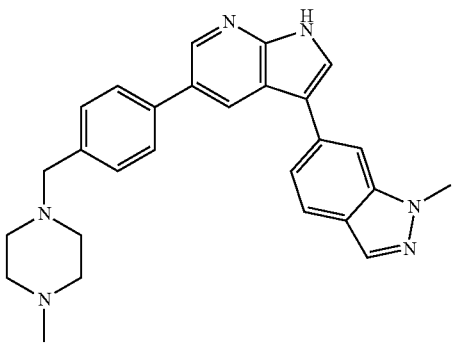 [SMILES: CN1CCN(Cc2ccc(-c3cnc4[nH]cc(-c5ccc6cnn(C)c6c5)c4c3)cc2)CC1]

Compound 7ag was prepared according to the general procedure for the Suzuki coupling and in situ deprotection as described above using 1-methyl-1H-indazole-6-boronic acid (13.2 mg, 0.075 mmol, 1.5 eq). The crude product was purified by preparatory HPLC purification to afford 1-methyl-6-(5-(4-((4-methylpiperazin-1-yl)methyl)phenyl)-1H-pyrrolo[2,3-b]pyridin-3-yl)-1H-indazole (7ag, 13.2 mg, 60% yield). $^1$H NMR (400 MHz, Methanol-$d_4$) δ 8.67 (d, J=2.0 Hz, 1H), 8.58 (d, J=2.0 Hz, 1H), 8.01 (d, J=0.9 Hz, 1H), 7.88 (s, 1H), 7.84 (dd, J=8.4, 0.9 Hz, 1H), 7.81 (d, J=1.2 Hz, 1H), 7.76 (d, J=8.2 Hz, 2H), 7.60-7.52 (m, 3H), 4.11 (s, 3H), 3.99 (s, 2H), 3.40 (bs, 4H), 3.09 (bs, 4H), 2.91 (s, 3H) ppm. HRMS (APCI$^+$, m/z): calcd. for $C_{27}H_{29}N_6$ [M+H$^+$]: 437.2454, found: 437.2449.

Preparation of 3-(1-Benzyl-1H-pyrazol-4-yl)-5-(4-((4-methylpiperazin-1-yl)methyl)phenyl)-1H-pyrrolo[2,3-b]pyridine (Compound 7ah)

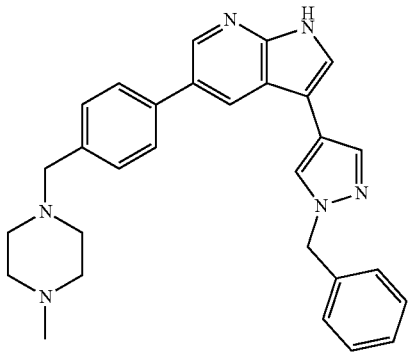 [SMILES: CN1CCN(Cc2ccc(-c3cnc4[nH]cc(-c5cnn(Cc6ccccc6)c5)c4c3)cc2)CC1]

Compound 7ah was prepared according to the general procedure for the Suzuki coupling and in situ deprotection as described above using 1-benzyl-1H-pyrazole-4-boronic acid (15.2 mg, 0.075 mmol, 1.5 eq). The crude product was purified by preparatory HPLC purification to afford 3-(1-benzyl-1H-pyrazol-4-yl)-5-(4-((4-methylpiperazin-1-yl)methyl)phenyl)-1H-pyrrolo[2,3-b]pyridine (7ah, 14.3 mg, 62% yield). $^1$H NMR (400 MHz, Methanol-$d_4$) δ 8.61 (d, J=2.0 Hz, 1H), 8.57 (d, J=2.0 Hz, 1H), 8.19 (d, J=0.8 Hz, 1H), 7.94 (d, J=0.8 Hz, 1H), 7.79 (d, J=8.2 Hz, 2H), 7.75 (s, 1H), 7.57 (d, J=8.2 Hz, 2H), 7.39-7.26 (m, 5H), 5.42 (s, 2H), 4.01 (s, 2H), 3.41 (bs, 4H), 3.09 (bs, 4H), 2.92 (s, 3H) ppm. HRMS (APCI$^+$, m/z): calcd. for $C_{29}H_{31}N_6$ [M+H$^+$]: 463.2610, found: 463.2612.

Preparation of 5-(4-((4-Methylpiperazin-1-yl)methyl)phenyl)-3-(1,3,5-trimethyl-1H-pyrazol-4-yl)-1H-pyrrolo[2,3-b]pyridine (Compound 7ai)

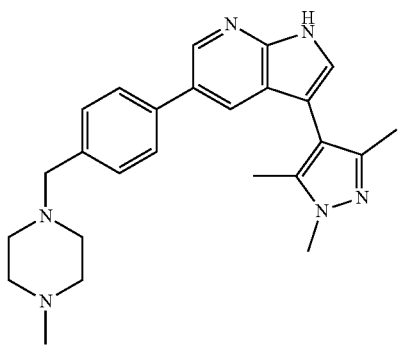 [SMILES: Cc1nn(C)c(C)c1-c1c[nH]c2ncc(-c3ccc(CN4CCN(C)CC4)cc3)cc12]

Compound 7ai was prepared according to the general procedure for the Suzuki coupling and in situ deprotection as described above using 1,3,5-trimethyl-1H-pyrazole-4-boronic acid pinacol ester (17.7 mg, 0.075 mmol, 1.5 eq). The crude product was purified by preparatory HPLC purification to afford 5-(4-((4-methylpiperazin-1-yl)methyl)phenyl)-3-(1,3,5-trimethyl-1H-pyrazol-4-yl)-1H-pyrrolo[2,3-b]pyridine (7ai, 7.6 mg, 37% yield). $^1$H NMR (400 MHz, Methanol-$d_4$) δ 8.59 (d, J=2.0 Hz, 1H), 8.16 (d, J=2.0 Hz, 1H), 7.70 (d, J=8.2 Hz, 2H), 7.56-7.50 (m, 3H), 3.93 (s, 2H), 3.88 (s, 3H), 3.37 (bs, 4H), 3.01 (bs, 4H), 2.90 (s, 3H), 2.28 (s, 3H), 2.22 (s, 3H) ppm. HRMS (APCI$^+$, m/z): calcd. for $C_{25}H_{31}N_6$ [M+H$^+$]: 415.2610, found: 415.2604.

Preparation of 3-(3,5-Bis(trifluoromethyl)phenyl)-5-(4-((4-methylpiperazin-1-yl)methyl)phenyl)-1H-pyrrolo[2,3-b]pyridine (Compound 7aj)

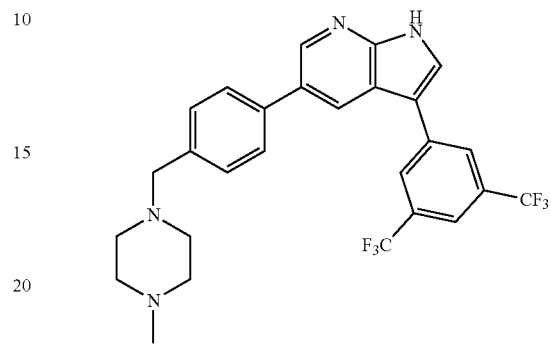

Compound 7aj was prepared according to the general procedure for the Suzuki coupling and in situ deprotection as described above using 3,5-bis(trifluoromethyl)phenylboronic acid (19.3 mg, 0.075 mmol, 1.5 eq). The crude product was purified by preparatory HPLC purification to afford 3-(3,5-bis(trifluoromethyl)phenyl)-5-(4-((4-methylpiperazin-1-yl)methyl)phenyl)-1H-pyrrolo[2,3-b]pyridine (7aj, 11.2 mg, 43% yield). $^1$H NMR (400 MHz, Methanol-$d_4$) δ 8.58 (d, J=2.0 Hz, 1H), 8.44 (d, J=2.0 Hz, 1H), 8.29-8.23 (m, 2H), 8.02 (s, 1H), 7.86 (s, 1H), 7.74 (d, J=8.2 Hz, 2H), 7.56 (d, J=8.2 Hz, 2H), 3.96 (s, 2H), 3.38 (bs, 4H), 3.04 (bs, 4H), 2.90 (s, 3H) ppm. HRMS (APCI$^+$, m/z): calcd. for $C_{27}H_{25}F_6N_4$ [M+H$^+$]: 519.1983, found: 519.1983.

Preparation of 1-Methyl-3-(3-(5-(4-((4-methylpiperazin-1-yl)methyl)phenyl)-1H-pyrrolo[2,3-b]pyridin-3-yl)phenyl)urea (Compound 7ak)

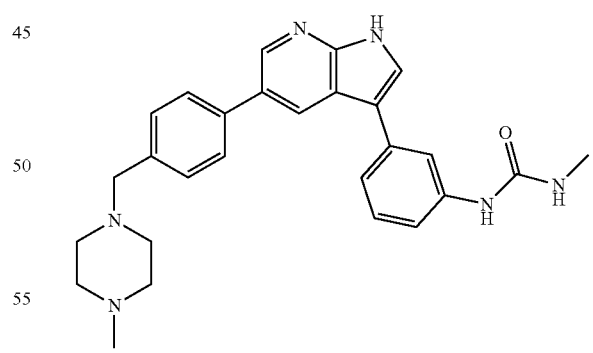

Compound 7ak was prepared according to the general procedure for the Suzuki coupling and in situ deprotection as described above using (3-(3-methylureido)phenyl)boronic acid (13a, 14.6 mg, 0.075 mmol, 1.5 eq). The crude product was purified by preparatory HPLC purification to afford 1-methyl-3-(3-(5-(4-((4-methylpiperazin-1-yl)methyl)phenyl)-1H-pyrrolo[2,3-b]pyridin-3-yl)phenyl)urea (7ak, 6.4 mg, 14% yield). $^1$H NMR (400 MHz, Methanol-$d_4$) δ 8.70 (d, J=2.0 Hz, 1H), 8.57 (d, J=2.0 Hz, 1H), 7.96 (t, J=1.8 Hz, 1H), 7.81-7.75 (m, 3H), 7.54 (d, J=8.2 Hz, 2H), 7.39-7.31 (m, 2H), 7.18 (dt, J=7.3, 2.0 Hz, 1H), 3.91 (s, 2H), 3.35 (bs, 4H), 2.98 (bs, 4H), 2.89 (s, 3H), 2.80 (s, 3H) ppm. HRMS (APCI$^+$, m/z): calcd. for $C_{27}H_{31}N_6O$ [M+H$^+$]: 455.2559, found: 455.2559.

Preparation of Methyl (3-(5-(4-((4-methylpiperazin-1-yl)methyl)phenyl)-1H-pyrrolo[2,3-b]pyridin-3-yl)phenyl)carbamate (Compound 7al)

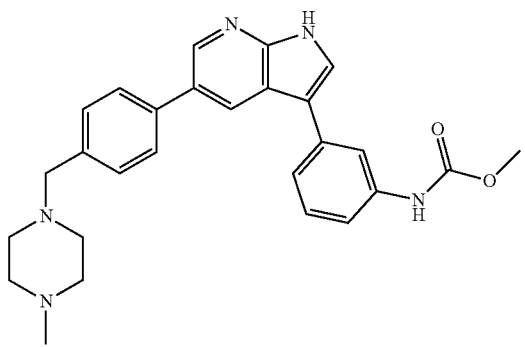 [SMILES: COC(=O)Nc1cccc(-c2c[nH]c3ncc(-c4ccc(CN5CCN(C)CC5)cc4)cc23)c1]

Compound 7al was prepared according to the general procedure for the Suzuki coupling and in situ deprotection as described above using (3-((methoxycarbonyl)amino)phenyl)boronic acid (13b, 14.6 mg, 0.075 mmol, 1.5 eq). The crude product was purified by preparatory HPLC purification to afford methyl (3-(5-(4-((4-methylpiperazin-1-yl)methyl)phenyl)-1H-pyrrolo[2,3-b]pyridin-3-yl)phenyl)carbamate (7al, 8.5 mg, 19% yield). $^1$H NMR (400 MHz, Methanol-d$_4$) δ 8.74 (d, J=2.0 Hz, 1H), 8.59 (d, J=2.0 Hz, 1H), 7.98 (s, 1H), 7.83-7.78 (m, 3H), 7.56 (d, J=8.2 Hz, 2H), 7.41-7.37 (m, 2H), 7.36-7.27 (m, 1H), 3.97 (s, 2H), 3.77 (s, 3H), 3.38 (bs, 4H), 3.04 (bs, 4H), 2.91 (s, 3H) ppm. HRMS (APCI$^+$, m/z): calcd. for $C_{27}H_{30}N_5O_2$ [M+H$^+$]: 456.2400, found: 456.2400.

Preparation of 1-Methyl-3-(4-(5-(4-((4-methylpiperazin-1-yl)methyl)phenyl)-1H-pyrrolo[2,3-b]pyridin-3-yl)phenyl)urea (Compound 7am)

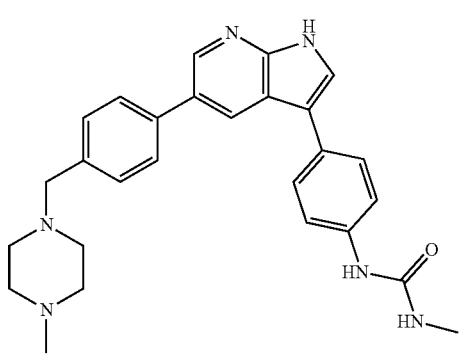 [SMILES: CNC(=O)Nc1ccc(-c2c[nH]c3ncc(-c4ccc(CN5CCN(C)CC5)cc4)cc23)cc1]

Compound 7am was prepared according to the general procedure for the Suzuki coupling and in situ deprotection as described above using (4-(3-methylureido)phenyl)boronic acid (13c, 14.6 mg, 0.075 mmol, 1.5 eq). The crude product was purified by preparatory HPLC purification to afford 1-methyl-3-(4-(5-(4-((4-methylpiperazin-1-yl)methyl)phenyl)-1H-pyrrolo[2,3-b]pyridin-3-yl)phenyl)urea (7am, 5.1 mg, 22% yield). $^1$H NMR (400 MHz, Methanol-d$_4$) δ 8.63 (d, J=2.0 Hz, 1H), 8.56 (d, J=2.0 Hz, 1H), 7.76 (s, 1H), 7.74 (d, J=4.6 Hz, 2H), 7.65-7.60 (m, 2H), 7.55 (d, J=8.1 Hz, 2H), 7.52-7.45 (m, 2H), 3.92 (s, 2H), 3.36 (bs, 4H), 2.99 (bs, 4H), 2.90 (s, 3H), 2.80 (s, 3H) ppm. HRMS (APCI$^+$, m/z): calcd. for $C_{27}H_{31}N_6O$ [M+H$^+$]: 455.2559, found: 455.2566.

Preparation of Methyl (4-(5-(4-((4-methylpiperazin-1-yl)methyl)phenyl)-1H-pyrrolo[2,3-b]pyridin-3-yl)phenyl)carbamate (Compound 7an)

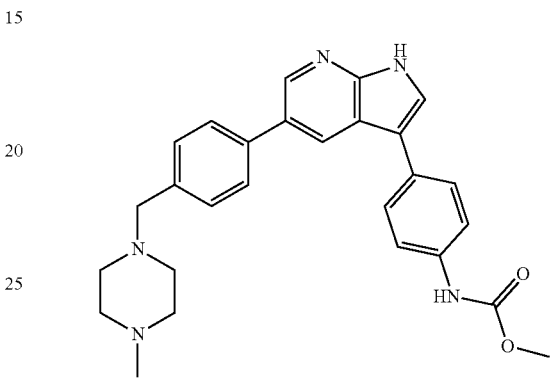

Compound 7an was prepared according to the general procedure for the Suzuki coupling and in situ deprotection as described above using (4-((methoxycarbonyl)amino)phenyl)boronic acid (13d, 14.6 mg, 0.075 mmol, 1.5 eq). The crude product was purified by preparatory HPLC purification to afford methyl (4-(5-(4-((4-methylpiperazin-1-yl)methyl)phenyl)-1H-pyrrolo[2,3-b]pyridin-3-yl)phenyl)carbamate (7an, 7.6 mg, 33% yield). $^1$H NMR (400 MHz, Methanol-d$_4$) δ 8.68 (d, J=1.9 Hz, 1H), 8.59 (d, J=2.0 Hz, 1H), 7.82-7.72 (m, 3H), 7.65 (d, J=8.7 Hz, 2H), 7.61-7.51 (m, 4H), 4.04 (s, 3H), 3.76 (s, 2H), 3.43 (bs, 4H), 3.13 (bs, 4H), 2.92 (s, 3H) ppm. HRMS (APCI$^+$, m/z): calcd. for $C_{27}H_{30}N_5O_2$ [M+H$^+$]: 456.2400, found: 456.2397.

Preparation of 3-(4-((4-Methoxybenzyl)oxy)phenyl)-5-(4-((4-methylpiperazin-1-yl)methyl)phenyl)-1H-pyrrolo[2,3-b]pyridine (Compound 7ao)

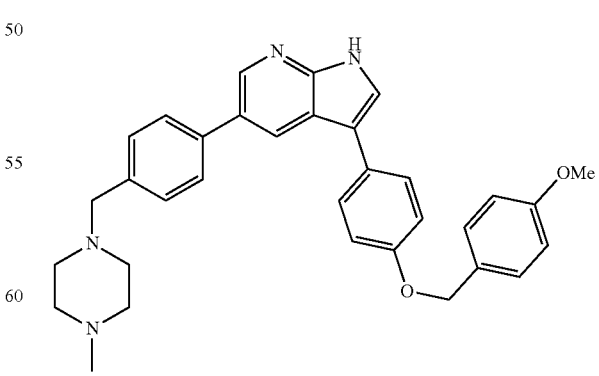

Compound 7ao was prepared according to the general procedure for the Suzuki coupling and in situ deprotection as described above using 4-(4-methoxybenzyloxy)phenylboronic acid (19.4 mg, 0.075 mmol, 1.5 eq). The crude product was purified by preparatory HPLC purification to afford 3-(4-((4-methoxybenzyl)oxy)phenyl)-5-(4-((4-methylpiperazin-1-yl)methyl)phenyl)-1H-pyrrolo[2,3-b]pyridine (7ao, 20.4 mg, 79% yield). $^1$H NMR (400 MHz, Methanol-$d_4$) δ 8.69 (dd, J=7.3, 1.9 Hz, 2H), 8.59 (d, J=1.8 Hz, 1H), 7.77 (dd, J=8.3, 1.6 Hz, 2H), 7.72 (d, J=8.2 Hz, 1H), 7.66-7.51 (m, 3H), 7.37 (dd, J=8.7, 6.9 Hz, 2H), 7.28-7.03 (m, 1H), 6.98-6.77 (m, 3H), 5.05 (s, 2H), 4.06 (s, 2H), 3.80 (s, 3H), 3.44 (bs, 4H), 3.16 (bs, 4H), 2.92 (s, 3H) ppm. HRMS (APCI$^+$, m/z): calcd. for $C_{33}H_{35}N_4O_2$ [M+H$^+$]: 519.2760, found: 519.2755.

Preparation of 5-(4-((4-Methylpiperazin-1-yl)methyl)phenyl)-3-(3,4,5-trimethoxyphenyl)-1H-pyrrolo[2,3-b]pyridine (Compound 7ap)

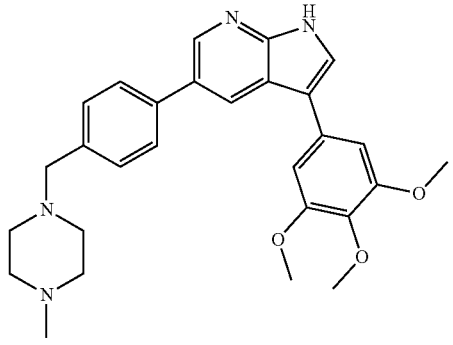 [SMILES: COc1cc(-c2c[nH]c3ncc(-c4ccc(CN5CCN(C)CC5)cc4)cc23)cc(OC)c1OC]

Compound 7ap was prepared according to the general procedure for the Suzuki coupling and in situ deprotection as described above using 3,4,5-trimethoxyphenylboronic acid (15.9 mg, 0.075 mmol, 1.5 eq). The crude product was purified by preparatory HPLC purification to afford 5-(4-((4-methylpiperazin-1-yl)methyl)phenyl)-3-(3,4,5-trimethoxyphenyl)-1H-pyrrolo[2,3-b]pyridine (7ap, 19.2 mg, 81% yield). $^1$H NMR (400 MHz, Methanol-$d_4$) δ 8.67 (d, J=1.9 Hz, 1H), 8.60 (d, J=1.9 Hz, 1H), 7.81 (s, 1H), 7.78 (d, J=8.2 Hz, 2H), 7.59 (d, J=8.2 Hz, 2H), 6.96 (s, 2H), 4.10 (s, 2H), 3.92 (s, 6H), 3.82 (s, 3H), 3.46 (bs, 4H), 3.20 (bs, 4H), 2.93 (s, 3H) ppm. HRMS (APCI$^+$, m/z): calcd. for $C_{28}H_{33}N_4O_3$ [M+H$^+$]: 473.2553, found: 473.2554.

Preparation of 3-(4-Methoxy-3-methylphenyl)-5-(4-((4-methylpiperazin-1-yl)methyl)phenyl)-1H-pyrrolo[2,3-b]pyridine (Compound 7aq)

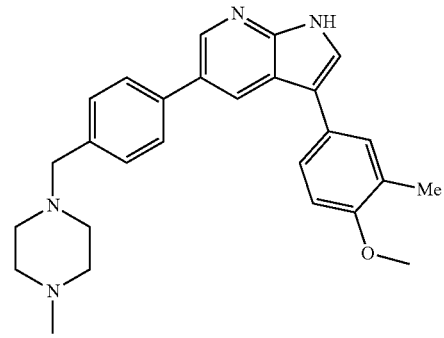 [SMILES: COc1ccc(-c2c[nH]c3ncc(-c4ccc(CN5CCN(C)CC5)cc4)cc23)cc1C]

Compound 7aq was prepared according to the general procedure for the Suzuki coupling and in situ deprotection as described above using 4-methoxy-3-methylphenylboronic acid (12.4 mg, 0.075 mmol, 1.5 eq). The crude product was purified by preparatory HPLC purification to afford 3-(4-methoxy-3-methylphenyl)-5-(4-((4-methylpiperazin-1-yl)methyl)phenyl)-1H-pyrrolo[2,3-b]pyridine (7aq, 17.2 mg, 81% yield). $^1$H NMR (400 MHz, Methanol-$d_4$) δ 8.69 (d, J=1.9 Hz, 1H), 8.59 (d, J=1.9 Hz, 1H), 7.77 (d, J=8.2 Hz, 2H), 7.72 (s, 1H), 7.59 (d, J=8.2 Hz, 2H), 7.51 (dd, J=8.4, 2.3 Hz, 1H), 7.48-7.44 (m, 1H), 7.03 (d, J=8.4 Hz, 1H), 4.03 (s, 2H), 3.88 (s, 3H), 3.43 (bs, 4H), 3.12 (bs, 4H), 2.92 (s, 3H), 2.28 (s, 3H) ppm. HRMS (APCI$^+$, m/z): calcd. for $C_{27}H_{31}N_4O$ [M+H$^+$]: 427.2498, found: 427.2501.

Preparation of 3-(3-(Benzyloxy)phenyl)-5-(4-((4-methylpiperazin-1-yl)methyl)phenyl)-1H-pyrrolo[2,3-b]pyridine (Compound 7ar)

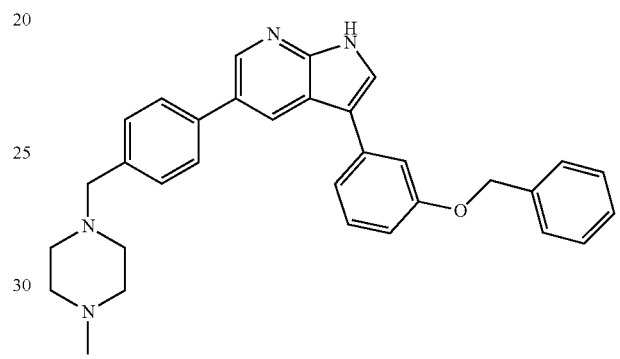

Compound 7ar was prepared according to the general procedure for the Suzuki coupling and in situ deprotection as described above using 3-(benzyloxy)phenylboronic acid (17.1 mg, 0.075 mmol, 1.5 eq). The crude product was purified by preparatory HPLC purification to afford 3-(3-(benzyloxy)phenyl)-5-(4-((4-methylpiperazin-1-yl)methyl)phenyl)-1H-pyrrolo[2,3-b]pyridine (7ar, 15.4 mg, 63% yield). $^1$H NMR (400 MHz, Methanol-$d_4$) δ 8.58 (s, 2H), 7.79 (s, 1H), 7.74 (d, J=8.2 Hz, 2H), 7.58 (d, J=8.2 Hz, 2H), 7.49-7.43 (m, 2H), 7.43-7.22 (m, 6H), 7.06-6.96 (m, 1H), 5.17 (s, 2H), 4.06 (s, 2H), 3.43 (bs, 4H), 3.15 (bs, 4H), 2.92 (s, 3H) ppm. HRMS (APCI$^+$, m/z): calcd. for $C_{32}H_{33}N_4O$ [M+H$^+$]: 489.2654, found: 489.2657.

Preparation of 3-(2-Chlorophenyl)-5-(4-((4-methylpiperazin-1-yl)methyl)phenyl)-1H-pyrrolo[2,3-b]pyridine (Compound 7as)

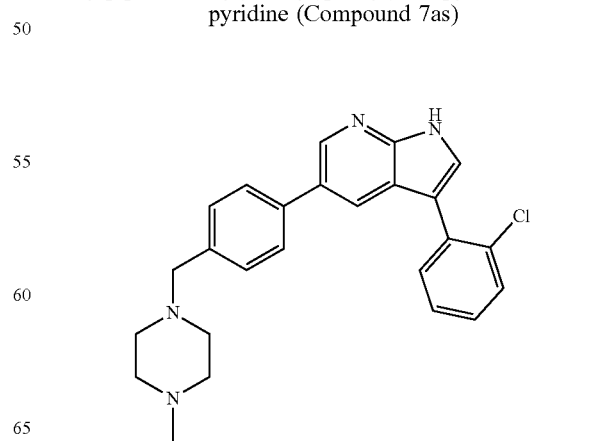

Compound 7as was prepared according to the general procedure for the Suzuki coupling and in situ deprotection as described above using 2-chlorophenylboronic acid (17.1 mg, 0.075 mmol, 1.5 eq). The crude product was purified by preparatory HPLC purification to afford 3-(2-chlorophenyl)-5-(4-((4-methylpiperazin-1-yl)methyl)phenyl)-1H-pyrrolo[2,3-b]pyridine (7as, 16.6 mg, 80% yield). $^1$H NMR (400 MHz, Methanol-$d_4$) δ 8.60 (d, J=2.0 Hz, 1H), 8.32 (d, J=2.0 Hz, 1H), 7.74 (s, 1H), 7.72 (d, J=8.2 Hz, 2H), 7.59 (ddd, J=7.7, 4.0, 1.7 Hz, 2H), 7.55 (d, J=8.2 Hz, 2H), 7.43 (td, J=7.5, 1.7 Hz, 1H), 7.38 (td, J=7.5, 2.0 Hz, 1H), 4.01 (s, 2H), 3.41 (bs, 4H), 3.10 (bs, 4H), 2.91 (s, 3H) ppm. HRMS (APCI$^+$, m/z): calcd. for $C_{25}H_{26}N_4Cl$ [M+H$^+$]: 417.1846, found: 417.1849.

Preparation of 3-(2-Methoxyphenyl)-5-(4-((4-methylpiperazin-1-yl)methyl)phenyl)-1H-pyrrolo[2,3-b]pyridine (Compound 7at)

Compound 7at was prepared according to the general procedure for the Suzuki coupling and in situ deprotection as described above using 2-methoxyphenylboronic acid (11.4 mg, 0.075 mmol, 1.5 eq). The crude product was purified by preparatory HPLC purification to afford 3-(2-methoxyphenyl)-5-(4-((4-methylpiperazin-1-yl)methyl)phenyl)-1H-pyrrolo[2,3-b]pyridine (7at, 17.1 mg, 83% yield). $^1$H NMR (400 MHz, Methanol-$d_4$) δ 8.61 (d, J=1.9 Hz, 1H), 8.58 (d, J=1.9 Hz, 1H), 7.80 (s, 1H), 7.75 (d, J=8.2 Hz, 2H), 7.61-7.54 (m, 3H), 7.38 (ddd, J=8.3, 7.4, 1.7 Hz, 1H), 7.16 (dd, J=8.3, 1.1 Hz, 1H), 7.08 (td, J=7.4, 1.1 Hz, 1H), 4.02 (s, 2H), 3.86 (s, 3H), 3.42 (s, 4H), 3.11 (s, 4H), 2.92 (s, 3H) ppm. HRMS (APCI$^+$, m/z): calcd. for $C_{26}H_{29}N_4O$ [M+H$^+$]: 413.2341, found: 413.2337.

Preparation of 1-(3-(5-(4-((4-Methylpiperazin-1-yl)methyl)phenyl)-1H-pyrrolo[2,3-b]pyridin-3-yl)phenyl)-3-phenylurea (Compound 7au)

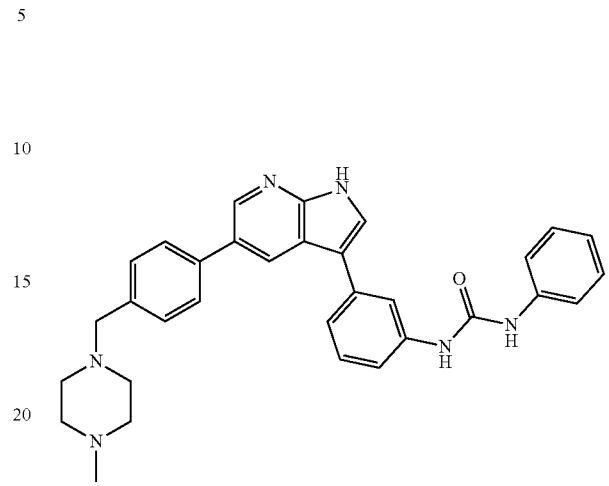

Compound 7au was prepared according to the general procedure for the Suzuki coupling and in situ deprotection as described above using (3-(3-phenylureido)phenyl)boronic acid (13e, 19.2 mg, 0.075 mmol, 1.5 eq). The crude product was purified by preparatory HPLC purification to afford 1-(3-(5-(4-((4-methylpiperazin-1-yl)methyl)phenyl)-1H-pyrrolo[2,3-b]pyridin-3-yl)phenyl)-3-phenylurea (7au, 5.4 mg, 21% yield). $^1$H NMR (400 MHz, Methanol-$d_4$) δ 8.61 (d, J=2.0 Hz, 1H), 8.51 (d, J=2.0 Hz, 1H), 8.08 (s, 1H), 7.78-7.71 (m, 3H), 7.60 (d, J=6.9 Hz, 2H), 7.49 (d, J=8.0 Hz, 2H), 7.46-7.40 (m, 1H), 7.41-7.36 (m, 2H), 7.36-7.27 (m, 2H), 7.24-7.17 (m, 1H), 3.76 (s, 2H), 3.13 (bs, 8H), 2.85 (s, 3H) ppm. HRMS (APCI$^+$, m/z): calcd. for $C_{32}H_{33}N_6O$ [M+H$^+$]: 517.2716, found: 517.2713.

Preparation of 2-Fluoro-N-(furan-2-ylmethyl)-5-(5-(4-((4-methylpiperazin-1-yl)methyl)phenyl)-1H-pyrrolo[2,3-b]pyridin-3-yl)benzamide (Compound 7av)

Scheme 3 Synthesis of compound 7av.

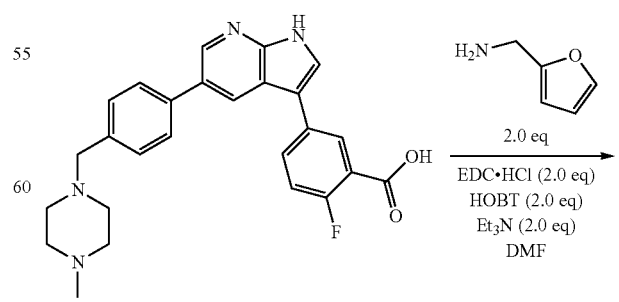

119

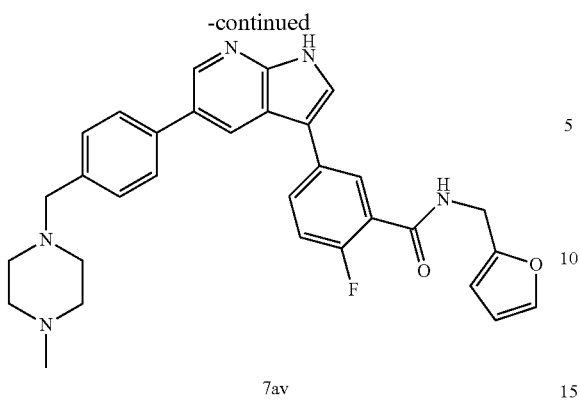

7av

120

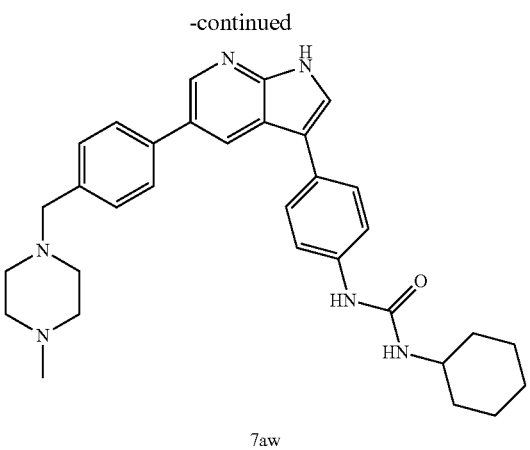

7aw

2-Fluoro-5-(5-(4-((4-methylpiperazin-1-yl)methyl)phenyl)-1H-pyrrolo[2,3-b]pyridin-3-yl)benzoic acid (7i, 3.3 mg, 7.4 μmol), EDC-HCl (2.8 mg, 14.8 μmol, 2.0 eq), and HOBT (2.0 mg, 14.8 μmol, 2.0 eq) were dissolved in DMF (1.0 mL). Furfurylamine (1.4 mg, 1.3 μL, 14.8 μmol, 2.0 eq) and Et₃N (1.5 mg, 2.0 μL, 14.8 μmol, 2.0 eq) were added and the reaction mixture was stirred at room temperature overnight. The solvent was evaporated and the crude mixture was purified by preparatory HPLC purification to afford 2-fluoro-N-(furan-2-ylmethyl)-5-(5-(4-((4-methylpiperazin-1-yl)methyl)phenyl)-1H-pyrrolo[2,3-b]pyridin-3-yl)benzamide (7av, 3.8 mg, 98% yield). $^1$H NMR (400 MHz, Methanol-d₄) δ 8.54 (d, J=2.0 Hz, 1H), 8.52 (d, J=2.0 Hz, 1H), 8.08 (dd, J=6.9, 2.4 Hz, 1H), 7.88 (ddd, J=8.6, 4.8, 2.4 Hz, 1H), 7.78 (s, 1H), 7.73 (d, J=8.2 Hz, 2H), 7.52 (d, J=8.2 Hz, 2H), 7.44 (dd, J=1.9, 0.9 Hz, 1H), 7.32 (dd, J=10.7, 8.6 Hz, 1H), 6.37 (dd, J=3.2, 1.9 Hz, 1H), 6.33 (dd, J=3.2, 0.9 Hz, 1H), 4.61 (s, 2H), 3.84 (s, 2H), 2.97-2.84 (m, 8H), 2.88 (s, 3H) ppm. HRMS (APCI⁺, m/z): calcd. for $C_{31}H_{31}FN_5O_2$ [M+H⁺]: 524.2462, found: 524.2452.

Preparation of 1-Cyclohexyl-3-(4-(5-(4-((4-methylpiperazin-1-yl)methyl)phenyl)-1H-pyrrolo[2,3-b]pyridin-3-yl)phenyl)urea (Compound 7aw)

4-(5-(4-((4-methylpiperazin-1-yl)methyl)phenyl)-1H-pyrrolo[2,3-b]pyridin-3-yl)aniline (7e, 10 mg, 0.025 mmol, 2.5 eq) was dissolved in DCM (0.5 mL) and triethylamine (10 mg, 14 μL, 0.1 mmol, 10 eq) was added. The solution was added dropwise to a solution of triphosgene (3.0 mg, 0.01 mmol, 1.0 eq) in DCM (0.5 mL) and stirred for 5 min at room temperature. The reaction mixture was added to a solution of cyclohexylamine (19.8 mg, 23 μL, 0.2 mmol, 20.0 eq) in DCM (0.5 mL) and stirred overnight. The solvent was evaporated and the crude mixture was purified by preparatory HPLC purification to afford 1-cyclohexyl-3-(4-(5-(4-((4-methylpiperazin-1-yl)methyl)phenyl)-1H-pyrrolo[2,3-b]pyridin-3-yl)phenyl)urea (7aw, 2.8 mg, 54% yield). 1H NMR (400 MHz, Methanol-d₄) δ 8.53 (m, 2H), 7.72 (d, J=8.2 Hz, 2H), 7.68 (s, 1H), 7.64-7.59 (m, 2H), 7.52 (d, J=8.2 Hz, 2H), 7.49-7.44 (m, 2H), 3.82 (s, 2H), 3.65-3.54 (m, 1H), 3.00-2.74 (bs, 8H), 2.88 (s, 3H), 2.00-1.90 (m, 2H), 1.84-1.71 (m, 2H), 1.65 (d, J=12.9 Hz, 1H), 1.48-1.34 (m, 2H), 1.36-1.16 (m, 3H) ppm. HRMS (APCI⁺, m/z): calcd. for $C_{32}H_{39}N_6O$ [M+H⁺]: 523.3185, found: 523.3182.

Preparation of (R)-1-(3-(5-(4-((4-methylpiperazin-1-yl)methyl)phenyl)-1H-pyrrolo[2,3-b]pyridin-3-yl)phenyl)-3-(1-phenylethyl)urea (Compound 7ax)

121

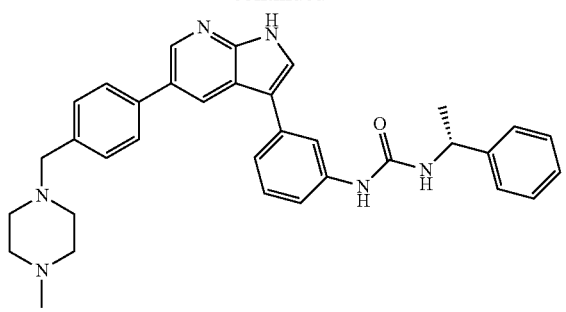

7ax 3-(5-(4-((4-Methylpiperazin-1-yl)methyl)phenyl)-1H-pyrrolo[2,3-b]pyridin-3-yl)aniline (7h, 16 mg, 0.04 mmol, 2.5 eq) was dissolved in DCM (1.0 mL) and triethylamine (16.2 mg, 22 μL, 0.16 mmol, 10 eq) was added. The solution was added dropwise to a solution of triphosgene (4.75 mg, 0.016 mmol, 1.0 eq) in DCM (1.0 mL) and stirred for 5 min at room temperature. The reaction mixture was added to a solution of (R)-(+)-α-methylbenzylamine (38.8 mg, 41 μL, 0.32 mmol, 20.0 eq) in DCM (1.0 mL) and stirred overnight. The solvent was evaporated and the crude mixture was purified by preparatory HPLC purification to afford (R)-1-(3-(5-(4-((4-methylpiperazin-1-yl)methyl)phenyl)-1H-pyrrolo[2,3-b]pyridin-3-yl)phenyl)-3-(1-phenylethyl)urea (7ax, 6.7 mg, 31% yield). H NMR (400 MHz, Methanol-$d_4$) δ 8.65 (d, J=2.0 Hz, 1H), 8.54 (d, J=2.1 Hz, 1H), 7.94 (s, 1H), 7.78-7.72 (m, 3H), 7.51 (d, J=8.0 Hz, 2H), 7.42-7.28 (m, 6H), 7.23 (t, J=7.0 Hz, 1H), 7.18-7.11 (m, 1H), 4.95 (q, J=7.0 Hz, 1H), 3.83 (s, 2H), 3.14-2.50 (bs, 8H), 2.88 (s, 3H), 1.50 (d, J=7.0 Hz, 3H) ppm. HRMS (APCI$^+$, m/z): calcd. for $C_{34}H_{37}N_6O$ [M+H$^+$]: 545.3029, found: 545.3027.

122

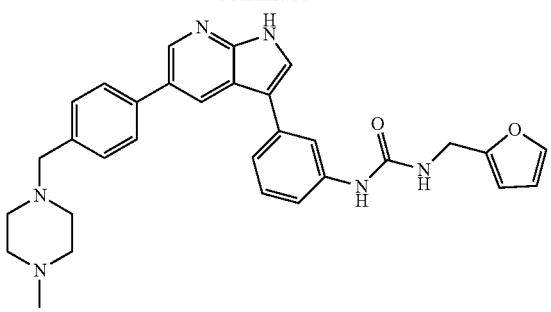

7ay 3-(5-(4-((4-Methylpiperazin-1-yl)methyl)phenyl)-1H-pyrrolo[2,3-b]pyridin-3-yl)aniline (7h, 16 mg, 0.04 mmol, 2.5 eq) was dissolved in DCM (1.0 mL) and triethylamine (16.2 mg, 22 μL, 0.16 mmol, 10 eq) was added. The solution was added dropwise to a solution of triphosgene (4.75 mg, 0.016 mmol, 1.0 eq) in DCM (1.0 mL) and stirred for 5 min at room temperature. The reaction mixture was added to a solution of furfurylamine (31.1 mg, 28.3 μL, 0.32 mmol, 20.0 eq) in DCM (1.0 mL) and stirred overnight. The solvent was evaporated and the crude mixture was purified by preparatory HPLC purification to afford 1-(furan-2-ylmethyl)-3-(3-(5-(4-((4-methylpiperazin-1-yl)methyl)phenyl)-1H-pyrrolo[2,3-b]pyridin-3-yl)phenyl)urea (7ay, 8.6 mg, 41% yield). $^1$H NMR (400 MHz, Methanol-$d_4$) δ 8.74 (d, J=2.0 Hz, 1H), 8.69-8.66 (m, 2H), 7.82-7.78 (m, 2H), 7.74 (s, 1H), 7.65 (d, J=7.9 Hz, 2H), 7.41-7.34 (m, 4H), 6.35 (dd, J=3.2, 1.9 Hz, 1H), 6.28 (dd, J=3.2, 0.8 Hz, 1H), 4.41 (s, 2H), 3.89 (s, 2H), 3.21 (bs, 4H), 3.11 (bs, 4H), 2.89 (s, 3H) ppm. HRMS (APCI$^+$, m/z): calcd. for $C_{31}H_{33}N_6O_2$ [M+H$^+$]: 521.2665, found: 521.2670.

Preparation of 1-(Furan-2-ylmethyl)-3-(3-(5-(4-((4-methylpiperazin-1-yl)methyl)phenyl)-1H-pyrrolo[2,3-b]pyridin-3-yl)phenyl)urea Preparation of 1-(2-Methoxyethyl)-3-(3-(5-(4-((4-methylpiperazin-1-yl)methyl)phenyl)-1H-pyrrolo[2,3-b]pyridin-3-yl)phenyl)urea (Compound 7az)

Scheme 6: Synthesis of compound 7ay.

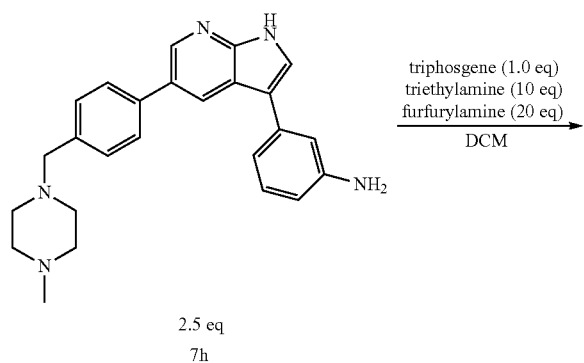

2.5 eq
7h triphosgene (1.0 eq)
triethylamine (10 eq)
furfurylamine (20 eq)
DCM
→

Scheme 7: Synthesis of compound 7az.

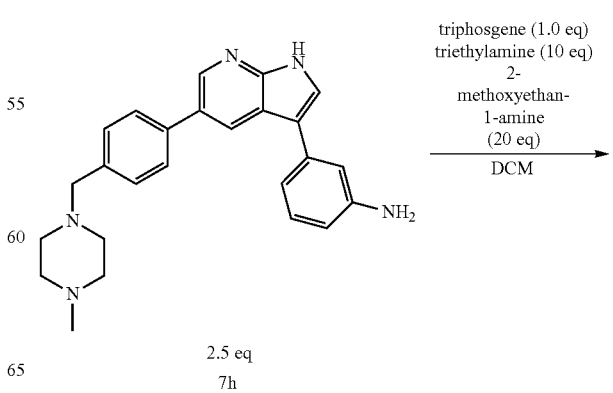

2.5 eq
7h triphosgene (1.0 eq)
triethylamine (10 eq)
2-methoxyethan-1-amine (20 eq)
DCM
→

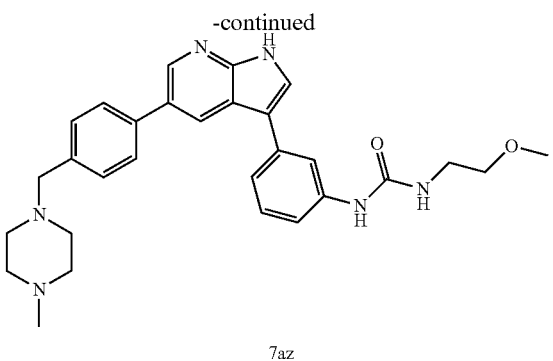

7az 3-(5-(4-((4-Methylpiperazin-1-yl)methyl)phenyl)-1H-pyrrolo[2,3-b]pyridin-3-yl)aniline (7h, 16 mg, 0.04 mmol, 2.5 eq) was dissolved in DCM (1.0 mL) and triethylamine (16.2 mg, 22 µL, 0.16 mmol, 10 eq) was added. The solution was added dropwise to a solution of triphosgene (4.75 mg, 0.016 mmol, 1.0 eq) in DCM (1.0 mL) and stirred for 5 min at room temperature. The reaction mixture was added to a solution of 2-methoxyethan-1-amine (24.0 mg, 27.8 µL, 0.32 mmol, 20.0 eq) in DCM (1.0 mL) and stirred overnight. The solvent was evaporated and the crude mixture was purified by preparatory HPLC purification to afford 1-(2-methoxyethyl)-3-(3-(5-(4-((4-methylpiperazin-1-yl)methyl)phenyl)-1H-pyrrolo[2,3-b]pyridin-3-yl)phenyl)urea (7az, 4.0 mg, 20% yield). $^1$H NMR (400 MHz, Methanol-$d_4$) δ 8.78 (d, J=2.0 Hz, 1H), 8.60 (d, J=2.0 Hz, 1H), 8.48 (d, J=2.0 Hz, 1H), 7.81 (s, 1H), 7.76 (s, 1H), 7.61-7.53 (m, 4H), 7.45-7.25 (m, 4H), 3.54 (s, 2H), 3.50 (s, 2H), 3.47 (s, 3H), 3.27-3.12 (bs, 8H), 2.87 (s, 3H) ppm. HRMS (APCI$^+$, m/z): calcd. for $C_{29}H_{35}N_6O_2$ [M+H$^+$]: 499.2821, found: 499.2827.

Example 3

Synthesis of Compounds 9a-9c

A general route to obtain compounds 9a-9c follows the synthesis illustrated below. The preparation of each compound is also provided.

Scheme 8: General synthetic scheme for compounds 9a-9c.

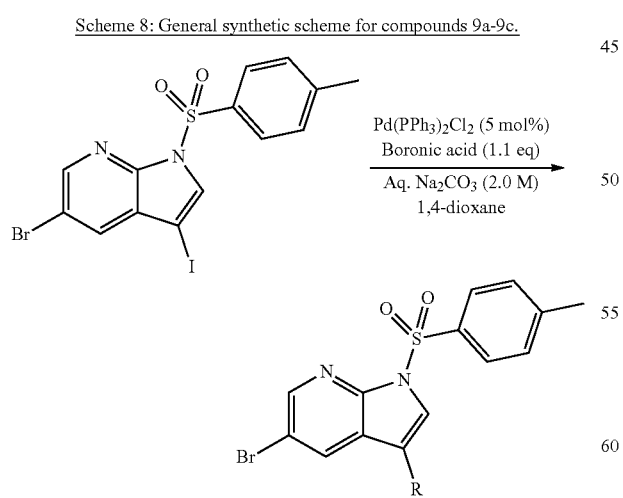

5-Bromo-3-iodo-1-tosyl-1H-pyrrolo[2,3-b]pyridine[1] (8, 1.0 g, 2.1 mmol, 1.0 eq) was dissolved in 1,4-dioxane (20 mL). The boronic acid (2.3 mmol, 1.1 eq) was added, followed by Pd(PPh$_3$)$_2$Cl$_2$ (70 mg, 0.1 mmol, 5 mol %). The reaction mixture was degassed by sonication under argon. Aqueous Na$_2$CO$_3$ was added and the reaction mixture was stirred at 45° C. until full completion (typically 8h). The reaction mixture was partitioned between EtOAc and brine, the layers separated, and the aqueous layer extracted with EtOAc (2×). The combined organic layers were dried with Na$_2$SO$_4$, filtered, and the solvent evaporated. The crude material was purified by column chromatography on silica (0-50% EtOAc in hexanes) to yield the desired product (9a-c).

Preparation of 4-(5-Bromo-1-tosyl-1H-pyrrolo[2,3-b]pyridin-3-yl)-1H-indazole (Compound 9a)

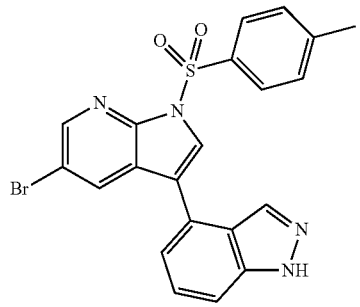 [SMILES: Cc1ccc(S(=O)(=O)n2cc(-c3cccc4[nH]ncc34)c3cc(Br)cnc32)cc1]

Following the general procedure described above, 4-(5-bromo-1-tosyl-1H-pyrrolo[2,3-b]pyridin-3-yl)-1H-indazole (9a) was isolated as a tan-colored solid (461 mg, 47% yield). 1H NMR (400 MHz, Chloroform-d) δ 10.29 (bs, 1H), 8.53 (d, J=2.2 Hz, 1H), 8.19-8.13 (m, 2H), 8.13-8.10 (m, 2H), 8.05 (s, 1H), 7.55 (d, J=8.4 Hz, 1H), 7.49 (dd, J=8.4, 6.9 Hz, 1H), 7.37-7.31 (m, 2H), 7.29 (dd, J=6.9, 1.0 Hz, 1H), 2.41 (s, 3H) ppm. HRMS (APCI$^+$, m/z): calcd. for $C_{21}H_{16}N_4O_2SBr$ [M+H$^+$]: 467.0177, found: 467.0176.

Preparation of 5-Bromo-3-(3-fluorophenyl)-1-tosyl-1H-pyrrolo[2,3-b]pyridine (Compound 9b)

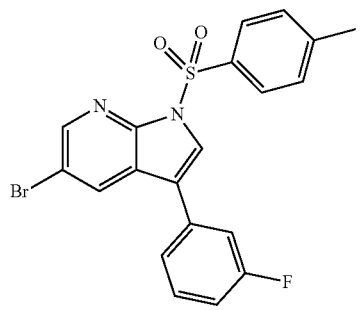 [SMILES: Cc1ccc(S(=O)(=O)n2cc(-c3cccc(F)c3)c3cc(Br)cnc32)cc1]

Following the general procedure described above, 5-bromo-3-(3-fluorophenyl)-1-tosyl-1H-pyrrolo[2,3-b]pyridine (9b) was isolated as a colorless solid (617 mg, 67% yield). 1H NMR (400 MHz, Chloroform-d) δ 8.50 (d, J=2.1 Hz, 1H), 8.19 (d, J=2.1 Hz, 1H), 8.09 (d, J=8.4 Hz, 2H), 7.90 (s, 1H), 7.44 (td, J=8.0, 5.9 Hz, 1H), 7.36-7.28 (m, 3H), 7.27-7.21 (m, 1H), 7.08 (tdd, J=8.4, 2.6, 1.0 Hz, 1H), 2.39 (s, 3H) ppm. HRMS (APCI$^+$, m/z): calcd. for $C_{20}H_{15}N_2O_2FSBr$ [M+H$^+$]: 445.0022, found: 445.0020.

Preparation of 5-Bromo-3-(3-chlorophenyl)-1-tosyl-1H-pyrrolo[2,3-b]pyridine (Compound 9c)

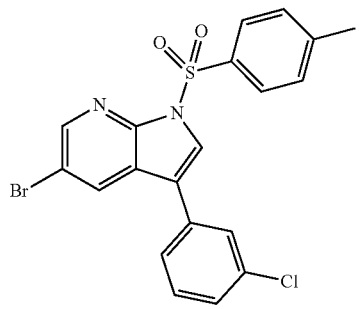 [SMILES: Cc1ccc(S(=O)(=O)n2cc(-c3cccc(Cl)c3)c3cc(Br)cnc32)cc1]

Following the general procedure described above, 5-bromo-3-(3-chlorophenyl)-1-tosyl-1H-pyrrolo[2,3-b]pyridine (9c) was isolated as a colorless solid (850 mg, 88% yield). H NMR (400 MHz, Chloroform-d) δ 8.50 (d, J=2.1 Hz, 1H), 8.18 (d, J=2.1 Hz, 1H), 8.09 (d, J=8.4 Hz, 2H), 7.89 (s, 1H), 7.56-7.50 (m, 1H), 7.46-7.40 (m, 2H), 7.40-7.34 (m, 1H), 7.31 (d, J=7.8 Hz, 2H), 2.39 (s, 3H) ppm. HRMS (APCI$^+$, m/z): calcd. for $C_{20}H_{15}N_2O_2SBrCl$ [M+H$^+$]: 460.9726, found: 460.9715.

Example 4

Synthesis of Compounds 10a-10c

A general route to obtain compounds 10a-10c follows the synthesis illustrated below. The preparation of each compound is also provided.

Scheme 9: General synthetic scheme for compounds 10a-10c.

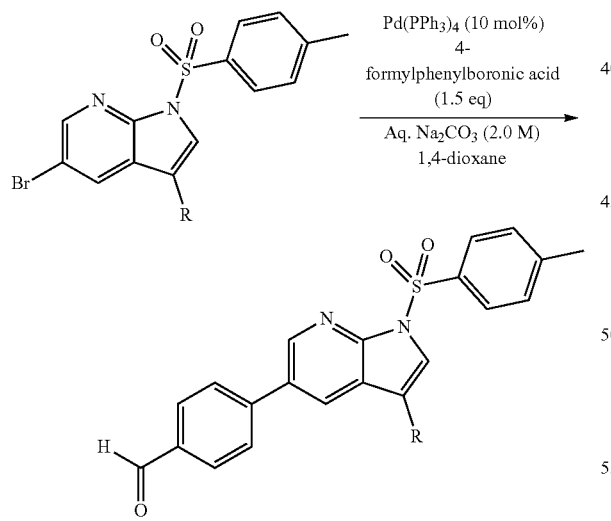

The substrate (9a-c, 1.0 mmol, 1.0 eq) was dissolved in 1,4-dioxane (40 mL) in a pressure tube, and 4-formylphenylboronic acid (225 mg, 1.5 mmol, 1.5 eq) was added. The reaction mixture was degassed by sonication under argon, and Pd(PPh$_3$)$_4$ (116 mg, 0.1 mmol, 10 mol %) was added. After addition of aqueous Na$_2$CO$_3$ (12.5 mL, 2.0 M), the reaction mixture was stirred at 100° C. overnight. The crude mixture was partitioned between EtOAc and brine, the layers separated and the aqueous layer extracted with EtOAc (3×). The combined organic layers were dried with Na$_2$SO$_4$, and filtered over Celite. The solvent was evaporated and the crude material purified by column chromatography on silica (0-100% EtOAc in hexanes) to afford the desired product (10a-c).

Preparation of 4-(3-(1H-Indazol-4-yl)-1-tosyl-1H-pyrrolo[2,3-b]pyridin-5-yl)benzaldehyde (Compound 10a)

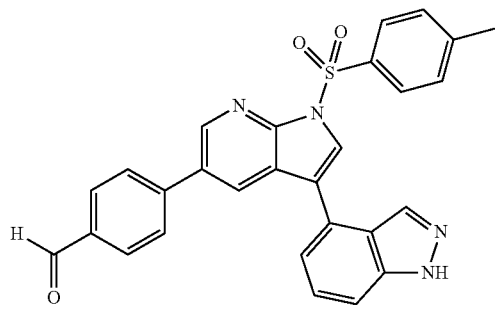 [SMILES: Cc1ccc(S(=O)(=O)n2cc(-c3cccc4[nH]ncc34)c3cc(-c4ccc(C=O)cc4)cnc32)cc1]

Following the general procedure described above, 4-(3-(1H-indazol-4-yl)-1-tosyl-1H-pyrrolo[2,3-b]pyridin-5-yl) benzaldehyde (10a) was isolated as a tan-colored solid (350 mg, 71% yield). $^1$H NMR (400 MHz, Chloroform-d) δ 10.37 (bs, 1H), 10.06 (s, 1H), 8.78 (d, J=2.2 Hz, 1H), 8.23-8.17 (m, 3H), 8.14 (d, J=1.1 Hz, 1H), 8.10 (s, 1H), 7.96 (d, J=8.3 Hz, 2H), 7.72 (d, J=8.2 Hz, 2H), 7.59-7.51 (m, 2H), 7.40-7.32 (m, 3H), 2.41 (s, 3H) ppm. HRMS (APCI$^+$, m/z): calcd. for $C_{28}H_{21}N_4O_3S$ [M+H$^+$]: 493.1334, found: 493.1329.

Preparation of 4-(3-(3-Fluorophenyl)-1-tosyl-1H-pyrrolo[2,3-b]pyridin-5-yl)benzaldehyde (Compound 10b)

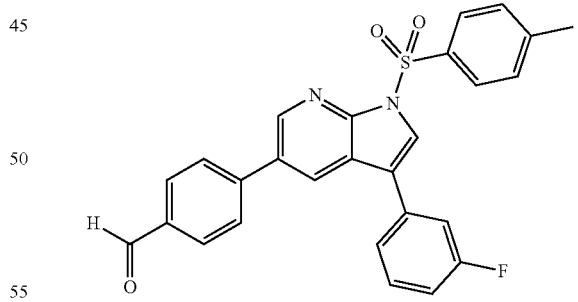

Following the general procedure described above, 4-(3-(3-fluorophenyl)-1-tosyl-1H-pyrrolo[2,3-b]pyridin-5-yl) benzaldehyde (10b) was isolated as a colorless solid (466 mg, 99% yield). $^1$H NMR (400 MHz, Chloroform-d) δ 10.08 (s, 1H), 8.74 (d, J=2.1 Hz, 1H), 8.26 (d, J=2.1 Hz, 1H), 8.16 (d, J=8.4 Hz, 2H), 7.99 (d, J=8.4 Hz, 2H), 7.96 (s, 1H), 7.74 (d, J=8.2 Hz, 2H), 7.47 (td, J=7.9, 5.8 Hz, 1H), 7.40 (dt, J=7.7, 1.3 Hz, 1H), 7.36-7.28 (m, 3H), 7.10 (tdd, J=8.4, 2.6, 1.1 Hz, 1H), 2.40 (s, 3H) ppm. HRMS (APCI$^+$, m/z): calcd. for $C_{27}H_{20}N_2O_3FS$ [M+H$^+$]: 471.1179, found: 471.1185.

Preparation of 4-(3-(3-Chlorophenyl)-1-tosyl-1H-pyrrolo[2,3-b]pyridin-5-yl)benzaldehyde (Compound 10c)

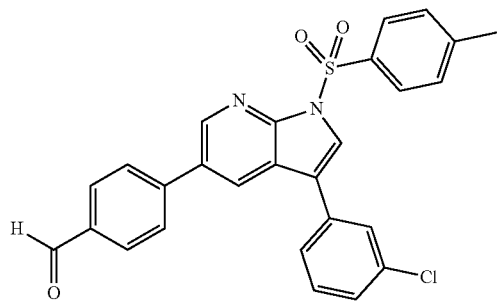 [SMILES: Cc1ccc(S(=O)(=O)n2cc(-c3cccc(Cl)c3)c3cc(-c4ccc(C=O)cc4)cnc32)cc1]

Following the general procedure described above, scaled up to 2.0 mmol starting material, 4-(3-(3-chlorophenyl)-1-tosyl-1H-pyrrolo[2,3-b]pyridin-5-yl)benzaldehyde (10c) was isolated as a colorless solid (730 mg, 87% yield). $^1$H NMR (400 MHz, Chloroform-d) δ 10.08 (s, 1H), 8.74 (d, J=2.1 Hz, 1H), 8.24 (d, J=2.1 Hz, 1H), 8.16 (d, J=8.4 Hz, 2H), 7.99 (d, J=8.2 Hz, 2H), 7.95 (s, 1H), 7.74 (d, J=8.2 Hz, 2H), 7.59 (t, J=1.8 Hz, 1H), 7.50 (dt, J=7.6, 1.5 Hz, 1H), 7.43 (t, J=7.7 Hz, 1H), 7.38 (ddd, J=7.9, 2.0, 1.3 Hz, 1H), 7.36-7.29 (m, 2H), 2.40 (s, 3H) ppm. HRMS (APCI$^+$, m/z): calcd. for $C_{27}H_{20}N_2O_3ClS$ [M+H$^+$]: 487.0883, found: 487.0878.

Example 5

Synthesis of Compounds 12a-12l

A general route to obtain compounds 12a-12l follows the synthesis illustrated below. The preparation of each compound is also provided.

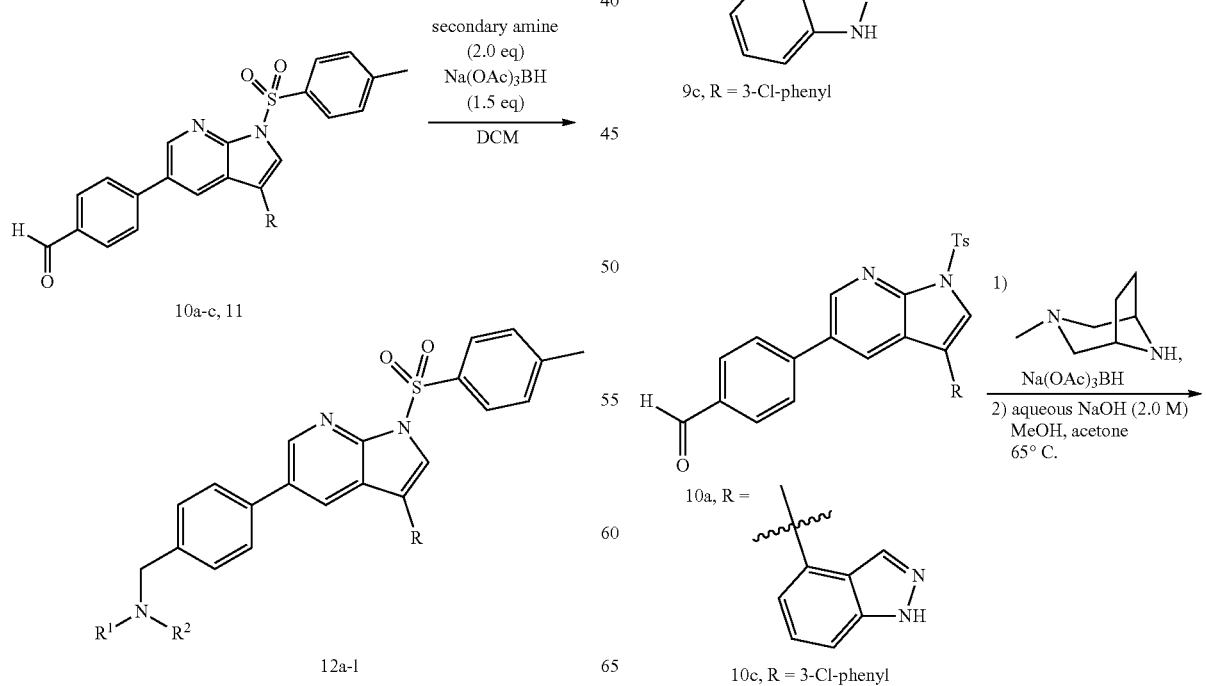

Scheme 10: General synthetic scheme for compounds 12a-12l.

A detailed synthesis of bicyclic piperazine analogs 12e and 12f are illustrated in the following scheme.

Scheme 11: Synthesis of compounds 12e and 12 f.

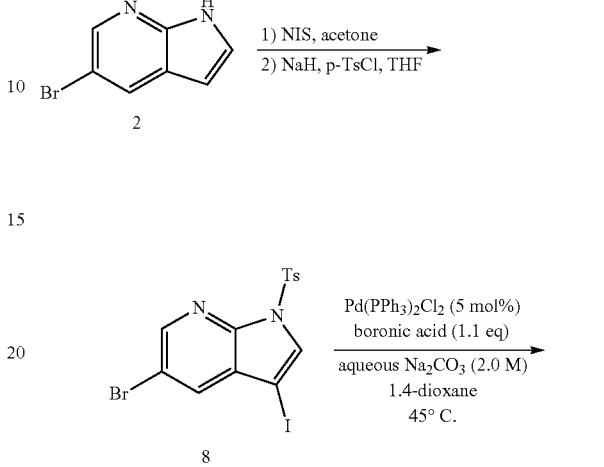

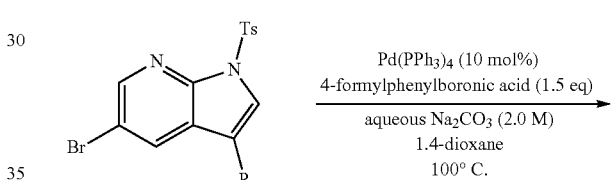

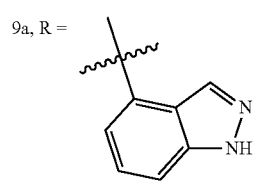

9a, R =

9c, R = 3-Cl-phenyl

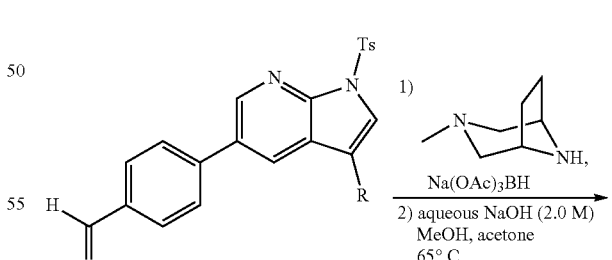

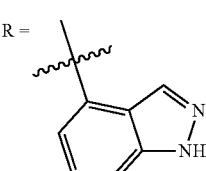

10c, R = 3-Cl-phenyl

-continued

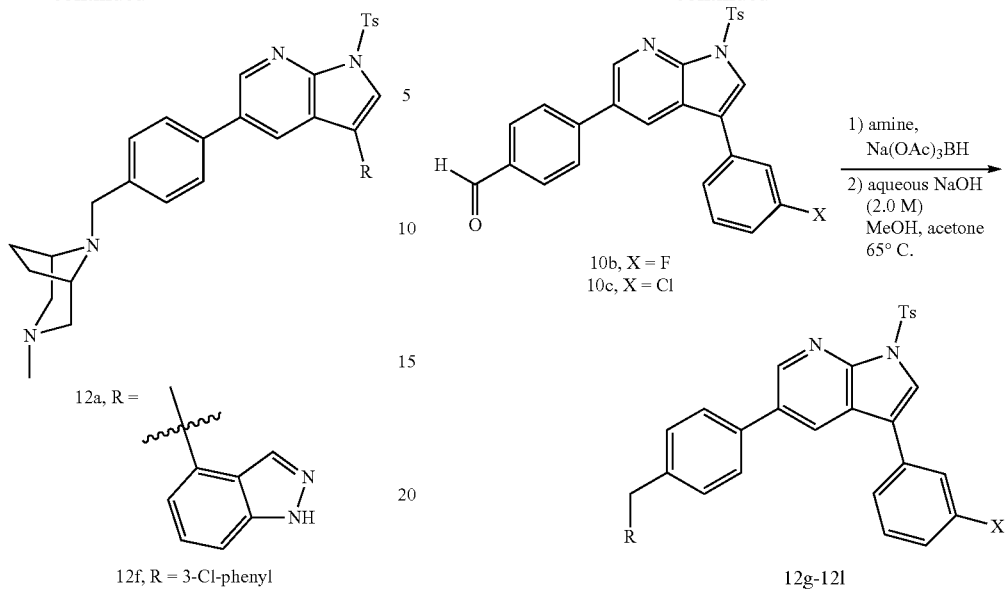

12a, R =

12f, R = 3-Cl-phenyl

The synthesis of analogs 12g-12l and their half-lives in mouse liver microsomes are shown in the scheme below.

Scheme 12: (A) Synthesis of analogs 12g - 12l; (B) Structures of analogs 12g - 12l and their half-lives in mouse liver microsomes.

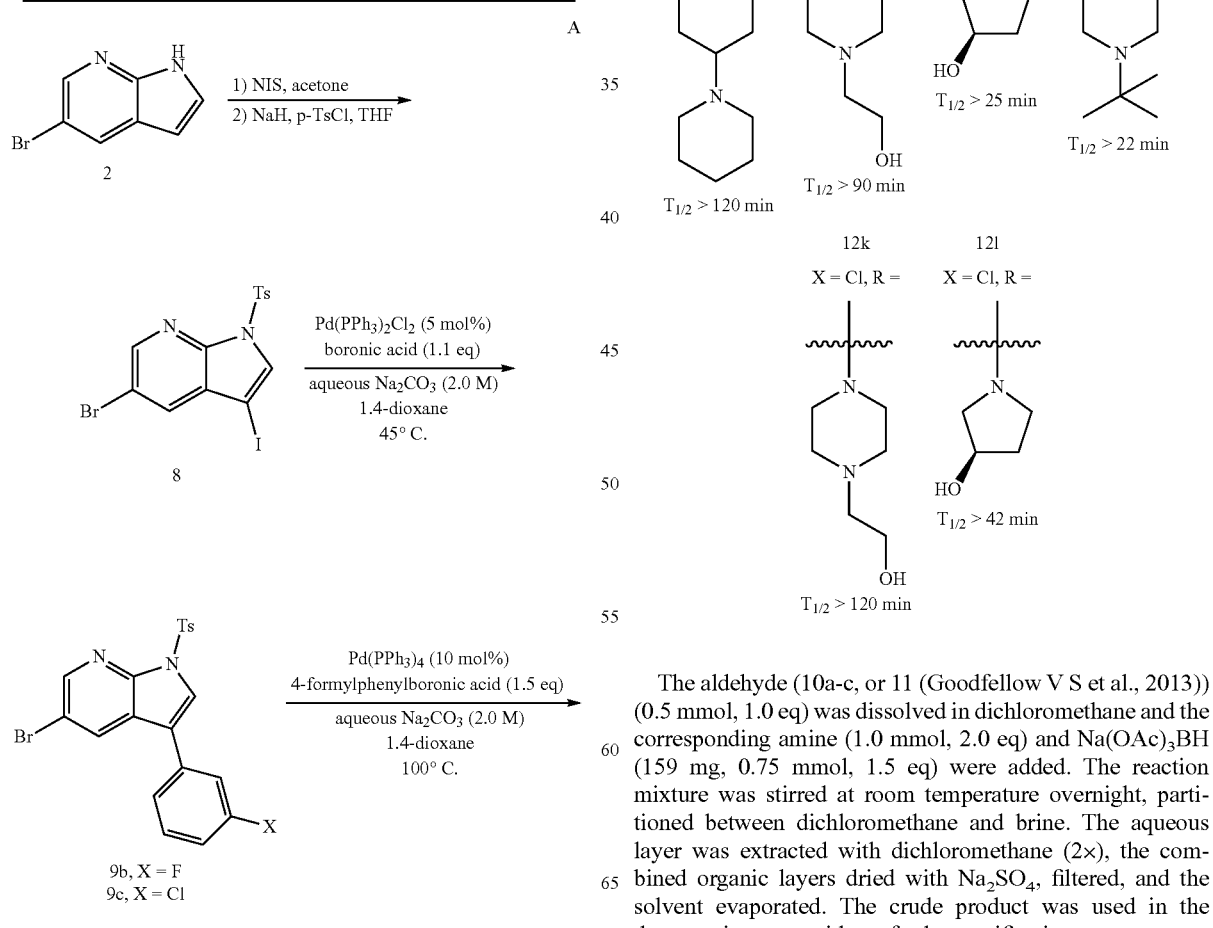

The aldehyde (10a-c, or 11 (Goodfellow V S et al., 2013)) (0.5 mmol, 1.0 eq) was dissolved in dichloromethane and the corresponding amine (1.0 mmol, 2.0 eq) and $Na(OAc)_3BH$ (159 mg, 0.75 mmol, 1.5 eq) were added. The reaction mixture was stirred at room temperature overnight, partitioned between dichloromethane and brine. The aqueous layer was extracted with dichloromethane (2×), the combined organic layers dried with $Na_2SO_4$, filtered, and the solvent evaporated. The crude product was used in the deprotection step without further purification.

The intermediate was dissolved in a mixture of acetone (20 mL), methanol (30 mL) and aqueous NaOH (2.0 M, 15 mL) and stirred at 65° C. for 3 h. The reaction mixture was partitioned between ethyl acetate and aqueous NaOH (1.0 M). The layers were separated and the aqueous layer was extracted with ethyl acetate (2×). The combined organic layers were washed with brine, dried with Na$_2$SO$_4$, filtered and the solvent evaporated. The crude material was purified by preparatory HPLC purification to afford the product (12a-1).

Preparation of 3-(4-(3-(1H-Indol-5-yl)-1H-pyrrolo [2,3-b]pyridin-5-yl)benzyl)-8-oxa-3-azabicyclo [3.2.1]octane (Compound 12a)

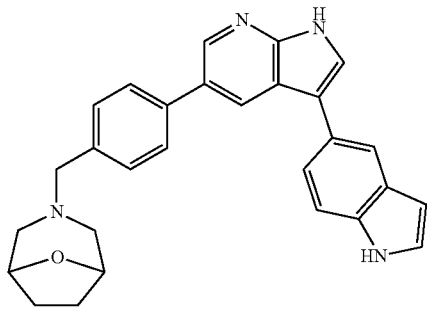 [SMILES: c1cc2cc(-c3c[nH]c4ncc(-c5ccc(CN6CC7CCC(C6)O7)cc5)cc34)ccc2[nH]1]

Following the general procedure described above, with 4-(3-(1H-Indol-5-yl)-1-tosyl-1H-pyrrolo[2,3-b]pyridin-5-yl)benzaldehyde (11, 100 mg, 0.2 mmol) and 8-oxa-3-azabicyclo[3.2.1]octane (45 mg, 0.4 mmol, 2.0 eq) as the starting materials, 3-(4-(3-(1H-indol-5-yl)-1H-pyrrolo[2,3-b]pyridin-5-yl)benzyl)-8-oxa-3-azabicyclo[3.2.1]octane (12a) was isolated as a light-brown solid (37.2 mg, 43% yield over two steps). $^1$H NMR (500 MHz, Methanol-d$_4$) δ 8.42 (d, J=2.1 Hz, 1H), 8.40 (d, J=2.1 Hz, 1H), 7.83 (d, J=1.5 Hz, 1H), 7.55 (s, 1H), 7.52 (d, J=8.1 Hz, 2H), 7.47 (d, J=8.4 Hz, 1H), 7.46-7.39 (m, 1H), 7.33 (d, J=7.9 Hz, 2H), 7.24 (d, J=3.1 Hz, 1H), 6.49 (dd, J=3.1, 0.8 Hz, 1H), 4.20 (dd, J=4.7, 2.3 Hz, 2H), 3.41 (s, 2H), 2.52 (d, J=11.5 Hz, 2H), 2.25 (dd, J=11.4, 2.1 Hz, 2H), 2.00-1.90 (m, 3H), 1.86-1.73 (m, 2H) ppm. HRMS (APCI$^+$, m/z): calcd. for C$_{32}$H$_{33}$N$_6$O [M+H$^+$]: 517.2716, found: 517.2713.

Preparation of 3-(1H-Indol-5-yl)-5-(4-((8-methyl-3, 8-diazabicyclo[3.2.1]octan-3-yl)methyl)phenyl)-1H-pyrrolo[2,3-b]pyridine (Compound 12b)

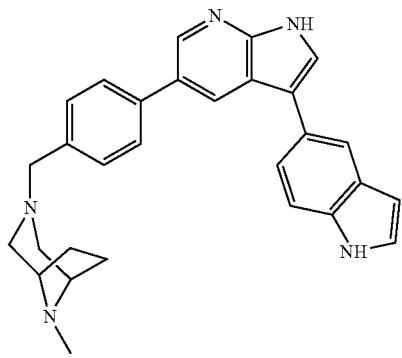 [SMILES: CN1C2CCC1CN(Cc1ccc(-c3cnc4[nH]cc(-c5ccc6[nH]ccc6c5)c4c3)cc1)C2]

Following the general procedure described above, with 4-(3-(1H-Indol-5-yl)-1-tosyl-1H-pyrrolo[2,3-b]pyridin-5-yl)benzaldehyde (11, 67.1 mg, 0.137 mmol) and 8-methyl-3,8-diazabicyclo[3.2.1]octane (16b, 55.5 mg, 0.44 mmol, 3.2 eq) as the starting materials, 3-(1H-indol-5-yl)-5-(4-((8-methyl-3,8-diazabicyclo[3.2.1]octan-3-yl)methyl)phenyl)-1H-pyrrolo[2,3-b]pyridine (12b) was isolated as a tan-colored solid (2.6 mg, 4% yield over two steps). $^1$H NMR (400 MHz, Methanol-d$_4$) δ 8.57 (d, J=2.0 Hz, 1H), 8.51 (d, J=2.0 Hz, 1H), 7.87 (dd, J=1.6, 0.7 Hz, 1H), 7.70 (d, J=8.1 Hz, 2H), 7.65 (s, 1H), 7.56-7.38 (m, 5H), 7.27 (d, J=3.2 Hz, 1H), 3.88 (s, 2H), 3.70 (s, 2H), 2.95 (d, J=12.6 Hz, 2H), 2.80 (s, 3H), 2.57 (d, J=13.0 Hz, 2H), 2.23 (s, 4H) ppm. HRMS (APCI$^+$, m/z): calcd. for C$_{29}$H$_{30}$N$_5$ [M+H$^+$]: 448.2501, found: 448.2505.

Preparation of 3-(1H-Indol-5-yl)-5-(4-((3-methyl-3, 8-diazabicyclo[3.2.1]octan-8-yl)methyl)phenyl)-1H-pyrrolo[2,3-b]pyridine (Compound 12c)

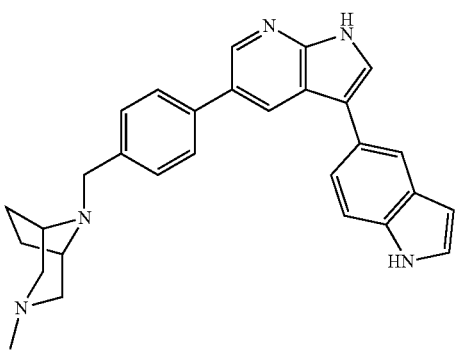 [SMILES: CN1CC2CCC(C1)N2Cc1ccc(-c2cnc3[nH]cc(-c4ccc5[nH]ccc5c4)c3c2)cc1]

Following the general procedure described above, with 4-(3-(1H-Indol-5-yl)-1-tosyl-1H-pyrrolo[2,3-b]pyridin-5-yl)benzaldehyde (11, 60.2 mg, 0.122 mmol) and 3-methyl-3,8-diazabicyclo[3.2.1]octane (16a, 36.6 mg, 0.29 mmol, 2.4 eq) as the starting materials, 3-(1H-indol-5-yl)-5-(4-((3-methyl-3,8-diazabicyclo[3.2.1]octan-8-yl)methyl)phenyl)-1H-pyrrolo[2,3-b]pyridine (12c) was isolated as a tan-colored solid (9.6 mg, 18% yield over two steps). $^1$H NMR (400 MHz, Methanol-d$_4$) δ 8.74 (d, J=2.0 Hz, 1H), 8.60 (d, J=2.0 Hz, 1H), 7.88 (dd, J=1.7, 0.8 Hz, 1H), 7.86-7.79 (m, 2H), 7.74 (s, 1H), 7.68-7.64 (m, 3H), 7.54-7.50 (m, 1H), 7.48-7.43 (m, 2H), 4.12 (s, 2H), 3.84 (bs, 4H), 3.29 (d, J=2.7 Hz, 2H), 3.10 (bs, 4H), 2.69 (s, 3H) ppm. HRMS (APCI$^+$, m/z): calcd. for C$_{29}$H$_{30}$N$_5$ [M+H$^+$]: 448.2501, found: 448.2503.

Preparation of 4-(5-(4-((8-Methyl-3,8-diazabicyclo [3.2.1]octan-3-yl)methyl)phenyl)-1H-pyrrolo[2,3-b] pyridin-3-yl)-1H-indazole (Compound 12d)

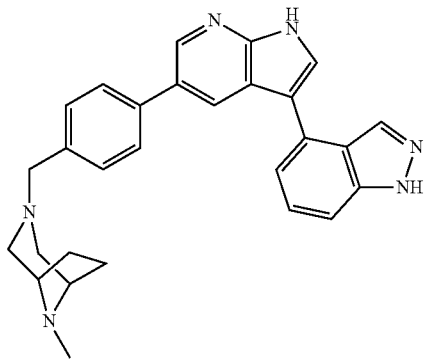 [SMILES: CN1C2CCC1CN(Cc1ccc(-c3cnc4[nH]cc(-c5cccc6[nH]ncc56)c4c3)cc1)C2]

Following the general procedure described above, with 4-(3-(1H-indazol-4-yl)-1-tosyl-1H-pyrrolo[2,3-b]pyridin-5-yl)benzaldehyde (10a, 49.2 mg, 0.1 mmol) and 8-methyl-3,8-diazabicyclo[3.2.1]octane (16b, 39.1 mg, 0.31 mmol, 3.1 eq) as the starting materials, 4-(5-(4-((8-methyl-3,8-diazabicyclo[3.2.1]octan-3-yl)methyl)phenyl)-1H-pyrrolo[2,3-b]pyridin-3-yl)-1H-indazole (12d) was isolated as a light-brown solid (11.7 mg, 26% yield over two steps). 1H NMR (400 MHz, Methanol-$d_4$) δ 8.61 (d, J=2.0 Hz, 1H), 8.55 (d, J=2.0 Hz, 1H), 8.18 (d, J=0.9 Hz, 1H), 7.95 (s, 1H), 7.67 (d, J=8.2 Hz, 2H), 7.55-7.50 (m, 2H), 7.47 (d, J=8.2 Hz, 2H), 7.43 (dd, J=6.5, 1.4 Hz, 1H), 3.88 (s, 2H), 3.70 (s, 2H), 2.94 (dd, J=13.1, 2.8 Hz, 2H), 2.80 (s, 3H), 2.67-2.62 (m, 2H), 2.27-2.19 (bs, 4H) ppm. HRMS (APCI$^+$, m/z): calcd. for $C_{28}H_{29}N_6$ [M+H$^+$]: 449.2454, found: 449.2462.

Preparation of 4-(5-(4-((3-Methyl-3,8-diazabicyclo [3.2.1]octan-8-yl)methyl)phenyl)-1H-pyrrolo[2,3-b] pyridin-3-yl)-1H-indazole (Compound 12e)

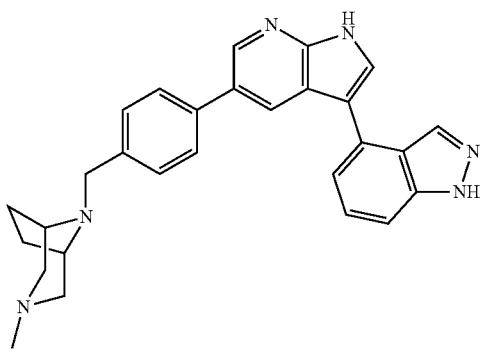 [SMILES: CN1CC2CCC(C1)N2Cc1ccc(-c2cnc3[nH]cc(-c4cccc5[nH]ncc45)c3c2)cc1]

Following the general procedure described above, with 4-(3-(1H-indazol-4-yl)-1-tosyl-1H-pyrrolo[2,3-b]pyridin-5-yl)benzaldehyde (10a, 49.2 mg, 0.1 mmol) and 3-methyl-3,8-diazabicyclo[3.2.1]octane (16a, 34.0 mg, 0.27 mmol, 2.7 eq) as the starting materials, 4-(5-(4-((3-methyl-3,8-diazabicyclo[3.2.1]octan-8-yl)methyl)phenyl)-1H-pyrrolo[2,3-b]pyridin-3-yl)-1H-indazole (12e) was isolated as a light-brown solid (12.0 mg, 27% yield over two steps). $^1$H NMR (400 MHz, Methanol-$d_4$) δ 8.60 (d, J=2.1 Hz, 1H), 8.45 (d, J=2.1 Hz, 1H), 8.18 (d, J=0.7 Hz, 1H), 7.90 (s, 1H), 7.77 (d, J=8.2 Hz, 2H), 7.62 (d, J=8.2 Hz, 2H), 7.54-7.51 (m, 2H), 7.43 (dd, J=5.6, 2.3 Hz, 1H), 4.09 (s, 2H), 3.80 (s, 2H), 3.18 (d, J=11.9 Hz, 2H), 2.94 (d, J=12.6 Hz, 2H), 2.61 (s, 3H), 2.45-2.36 (m, 2H), 2.14 (d, J=8.6 Hz, 2H) ppm. HRMS (APCI$^+$, m/z): calcd. for $C_{28}H_{29}N_6$ [M+H$^+$]: 449.2454, found: 449.2455.

Preparation of 3-(3-Chlorophenyl)-5-(4-((3-methyl-3,8-diazabicyclo[3.2.1]octan-8-yl)methyl)phenyl)-1H-pyrrolo[2,3-b]pyridine (Compound 12f)

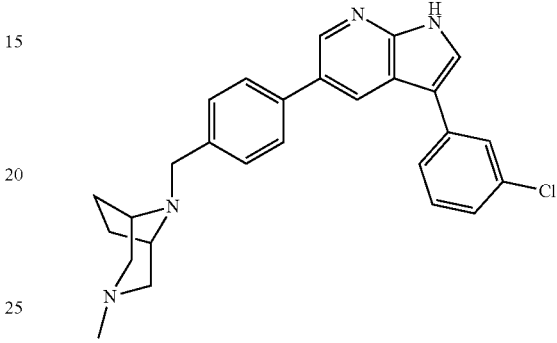

Following the general procedure described above, with 4-(3-(3-chlorophenyl)-1-tosyl-1H-pyrrolo[2,3-b]pyridin-5-yl)benzaldehyde (10c, 48.6 mg, 0.1 mmol) and 3-methyl-3,8-diazabicyclo[3.2.1]octane (16a, 25.2 mg, 0.2 mmol, 2.0 eq) as the starting materials, 3-(3-chlorophenyl)-5-(4-((3-methyl-3,8-diazabicyclo[3.2.1]octan-8-yl)methyl)phenyl)-1H-pyrrolo[2,3-b]pyridine (12f) was isolated as a pale-yellow solid (18.0 mg, 41% yield over two steps). $^1$H NMR (400 MHz, Methanol-$d_4$) δ 8.54 (d, J=2.1 Hz, 1H), 8.46 (d, J=2.1 Hz, 1H), 7.81-7.75 (m, 3H), 7.70 (t, J=1.9 Hz, 1H), 7.68-7.61 (m, 3H), 7.45 (t, J=7.9 Hz, 1H), 7.30 (ddd, J=8.0, 2.1, 1.0 Hz, 1H), 4.11 (s, 2H), 3.82 (s, 2H), 3.25-3.16 (m, 2H), 3.04-2.94 (m, 2H), 2.62 (s, 3H), 2.42 (dd, J=9.6, 4.7 Hz, 2H), 2.17 (t, J=7.3 Hz, 2H) ppm. HRMS (APCI$^+$, m/z): calcd. for $C_{27}H_{28}N_4Cl$ [M+H$^+$]: 443.2002, found: 443.2005.

Preparation of 5-(4-([1,4'-Bipiperidin]-1'-ylmethyl) phenyl)-3-(3-fluorophenyl)-1H-pyrrolo[2,3-b]pyridine (Compound 12g)

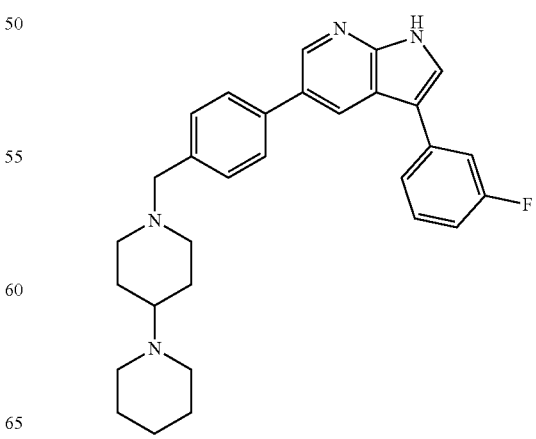

Following the general procedure described above, with 4-(3-(3-fluorophenyl)-1-tosyl-1H-pyrrolo[2,3-b]pyridin-5-yl)benzaldehyde (10b, 26.0 mg, 0.055 mmol) and 4-piperidinopiperidine (18.6 mg, 0.11 mmol, 2.0 eq) as the starting materials, 5-(4-([1,4'-bipiperidin]-1'-ylmethyl)phenyl)-3-(3-fluorophenyl)-1H-pyrrolo[2,3-b]pyridine (12g) was isolated as an off-white solid (6.2 mg, 24% yield over two steps). $^1$H NMR (400 MHz, Methanol-$d_4$) δ 8.58 (d, J=2.0 Hz, 1H), 8.56 (d, J=2.1 Hz, 1H), 7.86 (d, J=8.2 Hz, 2H), 7.82 (s, 1H), 7.66 (d, J=8.2 Hz, 2H), 7.57-7.53 (m, 1H), 7.52-7.42 (m, 2H), 7.04 (tdd, J=8.2, 2.6, 1.0 Hz, 1H), 4.43 (s, 2H), 3.72 (d, J=12.9 Hz, 2H), 3.63-3.47 (m, 4H), 3.23-3.12 (m, 4H), 3.03 (t, J=11.3 Hz, 2H), 2.41 (d, J=13.5 Hz, 2H), 2.20-2.08 (m, 3H), 2.04-1.94 (m, 2H), 1.86-1.73 (m, 2H), 1.64-1.46 (m, 1H), 1.42-1.26 (m, 2H) ppm. HRMS (APCI$^+$, m/z): calcd. for $C_{30}H_{34}N_4F$ [M+H$^+$]: 469.2768, found: 469.2771.

Preparation of 2-(4-(4-(3-(3-Fluorophenyl)-1H-pyrrolo[2,3-b]pyridin-5-yl)benzyl)piperazin-1-yl)ethan-1-ol (Compound 12h)

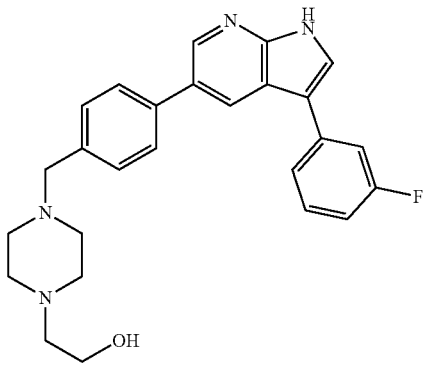 [SMILES: OCCN1CCN(Cc2ccc(-c3cnc4[nH]cc(-c5cccc(F)c5)c4c3)cc2)CC1]

Following the general procedure described above, with 4-(3-(3-fluorophenyl)-1-tosyl-1H-pyrrolo[2,3-b]pyridin-5-yl)benzaldehyde (10b, 318 mg, 0.675 mmol) and 1-(2-hydroxyethyl)piperazine (176 mg, 166 μL, 1.35 mmol, 2.0 eq) as the starting materials, 2-(4-(4-(3-(3-fluorophenyl)-1H-pyrrolo[2,3-b]pyridin-5-yl)benzyl)piperazin-1-yl)ethan-1-ol (12h) was isolated as an off-white solid (153.7 mg, 53% yield over two steps). $^1$H NMR (400 MHz, Methanol-$d_4$) δ 8.62 (d, J=2.0 Hz, 1H), 8.60 (d, J=2.0 Hz, 1H), 7.85 (s, 1H), 7.80 (d, J=8.2 Hz, 2H), 7.62 (d, J=8.2 Hz, 2H), 7.55 (dt, J=7.8, 1.3 Hz, 1H), 7.51-7.42 (m, 2H), 7.05 (dddd, J=9.0, 8.2, 2.6, 1.1 Hz, 1H), 4.22 (s, 2H), 3.95-3.85 (m, 2H), 3.58 (bs, 4H), 3.34 (bs, 6H) ppm. HRMS (APCI$^+$, m/z): calcd. for $C_{26}H_{28}N_4OF$ [M+H$^+$]: 431.2247, found: 431.2250.

Preparation of (R)-1-(4-(3-(3-Fluorophenyl)-1H-pyrrolo[2,3-b]pyridin-5-yl)benzyl)pyrrolidin-3-ol (Compound 12i)

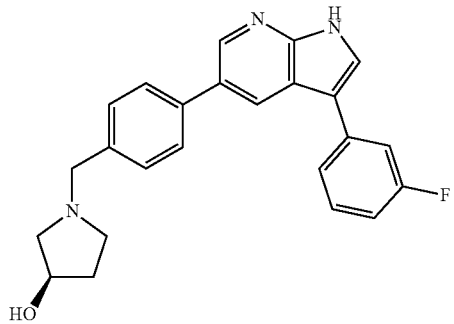 [SMILES: O[C@@H]1CCN(Cc2ccc(-c3cnc4[nH]cc(-c5cccc(F)c5)c4c3)cc2)C1]

Following the general procedure described above, with 4-(3-(3-fluorophenyl)-1-tosyl-1H-pyrrolo[2,3-b]pyridin-5-yl)benzaldehyde (10b, 318 mg, 0.675 mmol) and (R)-3-pyrrolidinol (118 mg, 109 μL, 1.35 mmol, 2.0 eq) as the starting materials, (R)-1-(4-(3-(3-fluorophenyl)-1H-pyrrolo[2,3-b]pyridin-5-yl)benzyl)pyrrolidin-3-ol (12i) was isolated as an off-white solid (113 mg, 43% yield over two steps). $^1$H NMR (400 MHz, Methanol-$d_4$) δ 8.56 (d, J=2.0 Hz, 1H), 8.53 (d, J=2.0 Hz, 1H), 7.84-7.77 (m, 3H), 7.68-7.61 (m, 2H), 7.52 (dt, J=7.8, 1.3 Hz, 1H), 7.50-7.38 (m, 2H), 7.02 (dddd, J=9.0, 8.2, 2.6, 1.1 Hz, 1H), 4.66-4.34 (m, 3H), 3.82-3.42 (m, 2H), 3.41-3.20 (m, 2H), 2.49-1.92 (m, 2H) ppm. HRMS (APCI$^+$, m/z): calcd. for $C_{24}H_{23}N_3OF$ [M+H$^+$]: 388.1825, found: 388.1824.

Preparation of 5-(4-((4-(tert-Butyl)piperazin-1-yl)methyl)phenyl)-3-(3-fluorophenyl)-1H-pyrrolo[2,3-b]pyridine (Compound 12j)

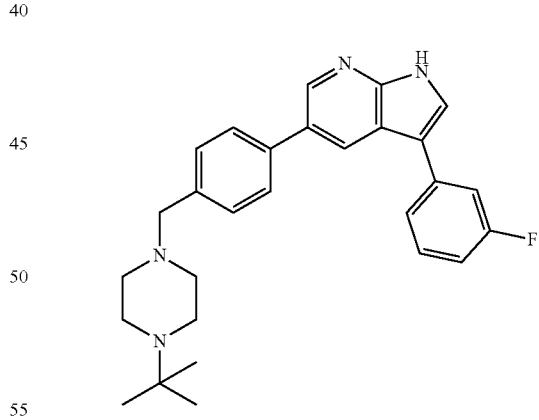

Following the general procedure described above, with 4-(3-(3-fluorophenyl)-1-tosyl-1H-pyrrolo[2,3-b]pyridin-5-yl)benzaldehyde (10b, 32.8 mg, 0.055 mmol) and 1-tert-butylpiperazine (15.7 mg, 0.11 mmol, 2.0 eq) as the starting materials, 5-(4-((4-(tert-butyl)piperazin-1-yl)methyl)phenyl)-3-(3-fluorophenyl)-1H-pyrrolo[2,3-b]pyridine (12j) was isolated as an off-white solid (9.8 mg, 40% yield over two steps). $^1$H NMR (400 MHz, Methanol-$d_4$) δ 8.63 (d, J=1.9 Hz, 1H), 8.60 (bs, 1H), 7.85 (s, 1H), 7.83-7.78 (m, 2H), 7.65-7.60 (m, 2H), 7.56 (dt, J=7.8, 1.3 Hz, 1H), 7.52-7.42 (m, 2H), 7.05 (dddd, J=9.0, 8.2, 2.6, 1.0 Hz, 1H), 4.22 (s, 2H), 3.89-3.04 (m, 8H), 1.44 (s, 9H) ppm. HRMS (APCI$^+$, m/z): calcd. for $C_{28}H_{32}N_4F$ [M+H$^+$]: 443.2611, found: 443.2610.

Preparation of 2-(4-(4-(3-(3-Chlorophenyl)-1H-pyrrolo[2,3-b]pyridin-5-yl)benzyl)piperazin-1-yl)ethan-1-ol (Compound 12k)

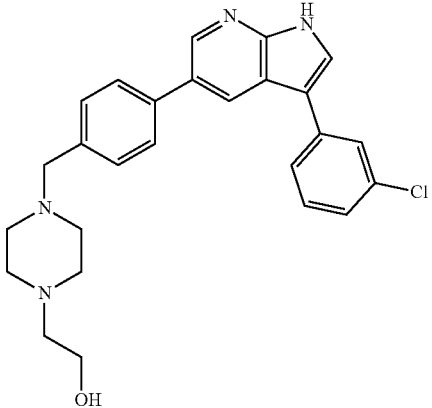 [SMILES: OCCN1CCN(Cc2ccc(-c3cnc4[nH]cc(-c5cccc(Cl)c5)c4c3)cc2)CC1]

Following the general procedure described above, with 4-(3-(3-chlorophenyl)-1-tosyl-1H-pyrrolo[2,3-b]pyridin-5-yl)benzaldehyde (10c, 418 mg, 0.86 mmol) and 1-(2-hydroxyethyl)piperazine (224 mg, 211 μL, 1.72 mmol, 2.0 eq) as the starting materials, 2-(4-(4-(3-(3-chlorophenyl)-1H-pyrrolo[2,3-b]pyridin-5-yl)benzyl)piperazin-1-yl)ethan-1-ol (12k) was isolated as an off-white solid (139.9 mg, 36% yield over two steps). 1H NMR (400 MHz, Methanol-d$_4$) δ 8.57 (d, J=2.0 Hz, 1H), 8.54 (d, J=2.0 Hz, 1H), 7.80 (s, 1H), 7.76 (d, J=8.3 Hz, 2H), 7.65 (t, J=1.9 Hz, 1H), 7.64-7.57 (m, 3H), 7.42 (t, J=7.9 Hz, 1H), 7.29 (ddd, J=8.0, 2.1, 1.0 Hz, 1H), 4.27 (s, 2H), 3.93-3.86 (m, 2H), 3.62 (s, 4H), 3.41 (s, 4H), 3.35-3.31 (m, 2H) ppm. HRMS (APCI$^+$, m/z): calcd. for $C_{26}H_{28}N_4OCl$ [M+H$^+$]: 447.1952, found: 447.1954.

Preparation of (R)-1-(4-(3-(3-Chlorophenyl)-1H-pyrrolo[2,3-b]pyridin-5-yl)benzyl)pyrrolidin-3-ol (Compound 12l)

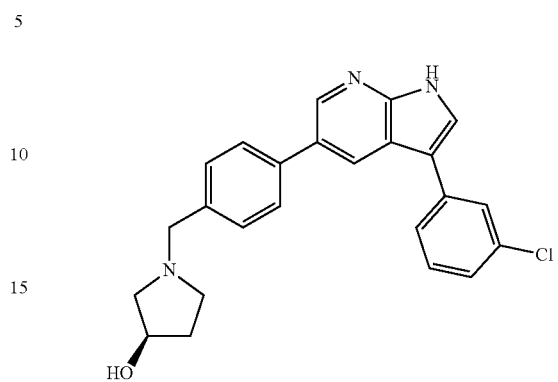

Following the general procedure described above, with 4-(3-(3-chlorophenyl)-1-tosyl-1H-pyrrolo[2,3-b]pyridin-5-yl)benzaldehyde (10c, 177 mg, 0.86 mmol) and (R)-3-pyrrolidinol (150 mg, 139 μL, 1.72 mmol, 2.0 eq) as the starting materials, (R)-1-(4-(3-(3-chlorophenyl)-1H-pyrrolo[2,3-b]pyridin-5-yl)benzyl)pyrrolidin-3-ol (12l) was isolated as an off-white solid (177 mg, 51% yield over two steps). $^1$H NMR (400 MHz, Methanol-d$_4$) δ 8.52 (d, J=2.0 Hz, 1H), 8.42 (d, J=2.0 Hz, 1H), 7.78-7.71 (m, 3H), 7.64-7.60 (m, 3H), 7.58 (ddd, J=7.7, 1.7, 1.1 Hz, 1H), 7.39 (t, J=7.9 Hz, 1H), 7.25 (ddd, J=8.0, 2.2, 1.0 Hz, 1H), 4.58 (s, 1H), 4.54-4.32 (m, 2H), 3.82-3.39 (m, 4H), 2.50-1.96 (m, 2H) ppm. HRMS (APCI$^+$, m/z): calcd. for $C_{24}H_{23}N_3OCl$ [M+H$^+$]: 404.1530, found: 404.1529.

Example 6

Synthesis of Boronic Acids 13a-13e

A general route to obtain compounds 13a-13e follows the synthesis illustrated below. The preparation of each compound is also provided.

Scheme 13: General synthetic scheme for compounds 13a - 13e.

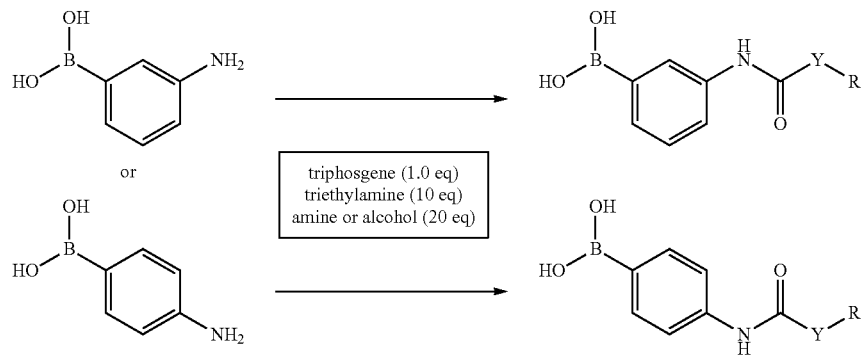

The boronic acid (3-aminophenylboronic acid or 4-aminophenylboronic acid, 87 mg, 0.5 mmol, 2.5 eq) was suspended in DCM (4 mL) and triethylamine (202 mg, 277 µL, 2.0 mmol, 10 eq) was added. The resulting solution was added dropwise to a solution triphosgene (59 mg, 0.2 mmol, 1.0 eq) in DCM (6 mL) and stirred for 5 min at room temperature. The amine (0.6 mmol, 3 eq) or alcohol (excess) was added dropwise and the mixture was stirred overnight at room temperature. The solvent was evaporated, toluene was added and the solvent was evaporated again. The crude material was analyzed by NMR and used in the next step without further purification.

Preparation of (3-(3-Methylureido)phenyl)boronic acid (Compound 13a)

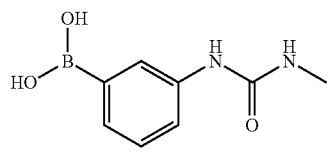

Following the general procedure described above, with 3-aminophenylboronic acid and methylamine, (3-(3-methylureido)phenyl)boronic acid (13a) was isolated as an off-white solid and used in the next step without further purification. $^1$H NMR (400 MHz, Methanol-$d_4$) δ 7.49 (bs, 1H), 7.38 (bs, 1H), 7.22 (d, J=5.3 Hz, 2H), 2.77 (s, 3H).

Preparation of (3-((Methoxycarbonyl)amino)phenyl)boronic acid (Compound 13b)

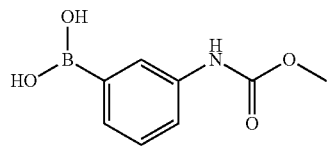

Following the general procedure described above, with 3-aminophenylboronic acid and methanol, (3-((methoxycarbonyl)amino)phenyl)boronic acid (13b) was isolated as an off-white solid and used in the next step without further purification. $^1$H NMR (400 MHz, Methanol-$d_4$) δ 7.59 (bs, 1H), 7.48 (bs, 1H), 7.26 (d, J=5.2 Hz, 2H), 3.73 (s, 3H).

Preparation of (4-(3-Methylureido)phenyl)boronic acid (Compound 13c)

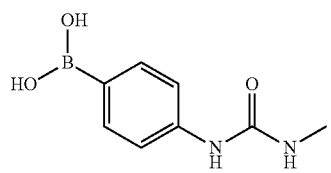

Following the general procedure described above, with 4-aminophenylboronic acid and methylamine, (4-(3-methylureido)phenyl)boronic acid (13c) was isolated as an off-white solid and used in the next step without further purification. $^1$H NMR (400 MHz, Methanol-$d_4$) δ 7.62 (d, J=8.5 Hz, 2H), 7.37 (d, J=8.5 Hz, 2H), 2.77 (s, 3H).

Preparation of (4-((Methoxycarbonyl)amino)phenyl)boronic acid (Compound 13d)

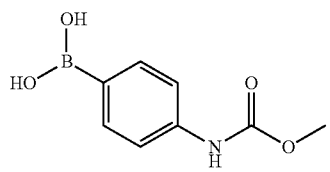

Following the general procedure described above, with 4-aminophenylboronic acid and methanol, (4-((methoxycarbonyl)amino)phenyl)boronic acid (13d) was isolated as an off-white solid and used in the next step without further purification. $^1$H NMR (400 MHz, Methanol-$d_4$) δ 7.65 (d, J=8.6 Hz, 1H), 7.43 (d, J=8.6 Hz, 2H), 3.74 (s, 3H).

Preparation of (3-(3-Phenylureido)phenyl)boronic acid (Compound 13e)

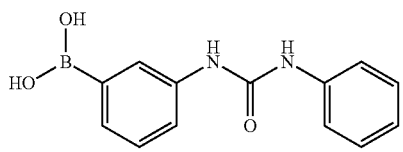 [SMILES: O=C(Nc1ccccc1)Nc1cccc(B(O)O)c1]

Following the general procedure described above, with 3-aminophenylboronic acid and aniline, (3-(3-phenylureido)phenyl)boronic acid (13e) was isolated as an off-white solid and used in the next step without further purification. $^1$H NMR (400 MHz, Methanol-$d_4$) δ 7.62 (bs, 1H), 7.51 (d, J=7.4 Hz, 1H), 7.34-7.23 (m, 2H), 7.08 (dd, J=8.5, 7.4 Hz, 2H), 6.71 (dt, J=7.7, 1.1 Hz, 2H), 6.67 (tt, J=7.4, 1.1 Hz, 1H).

Example 7

Synthesis of Bicyclic Piperazines 16a and 16b

A general route to obtain compounds 16a and 16b follows the synthesis illustrated below. The preparation of each compound is also provided.

Scheme 14: General synthetic scheme for compounds 16a and 16b.

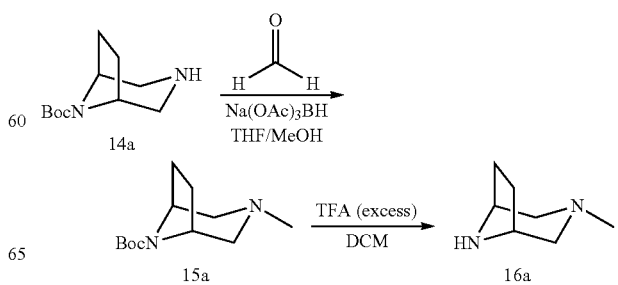

-continued

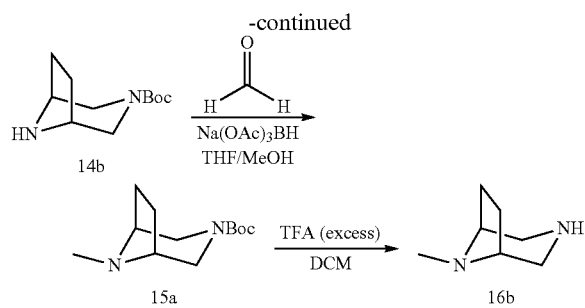

The Boc-protected bicyclic piperazine (14a-b; 250 mg, 1.18 mmol, 1.0 eq) was dissolved in a mixture of THF/MeOH (1:1). Formaldehyde (37% in $H_2O$, 287 μL, 3.53 mmol, 3.0 eq) was added, followed by addition of $Na(OAc)_3BH$ (274.5 mg, 1.30 mmol, 1.1 eq), and the reaction mixture was stirred overnight. The solvent was evaporated and the crude product purified by column chromatography on silica (0-20% MeOH in DCM). The product was visualized on the TLC plate using a $KMnO_4$ stain.

In order to remove the Boc-group, the product (15a-b) was dissolved in DCM, an excess of TFA was added, and the reaction mixture was stirred at room temperature overnight. The solvent was evaporated, toluene was added and the solvent was evaporated again. The crude products (16a-b) were used in the next step without further purification and the spectroscopic data matched those reported in literature (Paliulis O et al., 2007).

Example 8

HGK (MAP4K4) is a Prominent Biologically Relevant Target of Compound 1 and its Analogs With the analogs synthesized above, individual survival assays were performed in CPA-treated (33 μM) human embryonic stem cell derived motor neurons (HB9::GFP reporter, and SOD1 A4V mutation) that would allow for real-time feedback and optimization of the assay. Next, survival assays were performed with all the analogs at once to generate a low-variability dataset. All compounds were evaluated at concentrations ranging from 0.1-3.0 μM (five-point dilution) in three technical replicates and two biological replicates.

To evaluate the ability of the analogs to inhibit HGK phosphorylation, the analogs were submitted to a high throughput radiolabeled ATP assay from Reaction Biology Corp. at a dose of 0.025 μM or 0.1 μM in the presence of 10 μM ATP. As a control, Staurosporine was tested in a 10-dose $IC_{50}$ 4-fold serial dilution starting at 20 μM. In this way, it was able to test whether the analogs not only bound HGK, but also whether they impeded their kinase activity. It was found that ~45% of the analogs tested inhibited at least half of the HGK activity at a dose of 0.025 μM, thereby validating the computational analog design. The ability of the analogs to inhibit MLK1 and MLK3 phosphorylation was also evaluated at a dose of 0.1 μM in the presence of 10 μM ATP. Overall the inhibition of MLK1 and MKL3 was lower, but still ~40% of the analogs tested inhibited at least half of the MLK3 activity at a dose of 0.1 μM.

Next, we evaluated the correlation between the degree to which each analog suppressed enzyme activity and the degree to which it rescued CPA toxicity. Overall, a modest correlation was observed between % motor neuron survival upon CPA treatment and % MLK1 activity ($R^2$=0.40) or % MLK3 activity ($R^2$=0.52) (See FIG. 7A), suggesting that MLK1 and MLK3 are not the biologically relevant targets of compound 1 and its analogs (7a-7az) in the context of ER stress and the CPA-induced cell death pathway.

A much stronger correlation was observed between % motor neuron survival upon CPA treatment and % HGK activity ($R^2$=0.84) (See FIG. 7B), suggesting that HGK, or a member of the closely related MAP4K kinase family, could be a biologically relevant target of compound 1 and its analogs (7a-7az) in the context of CPA-induced ER stress and motor neuron degeneration.

Figure 10A:
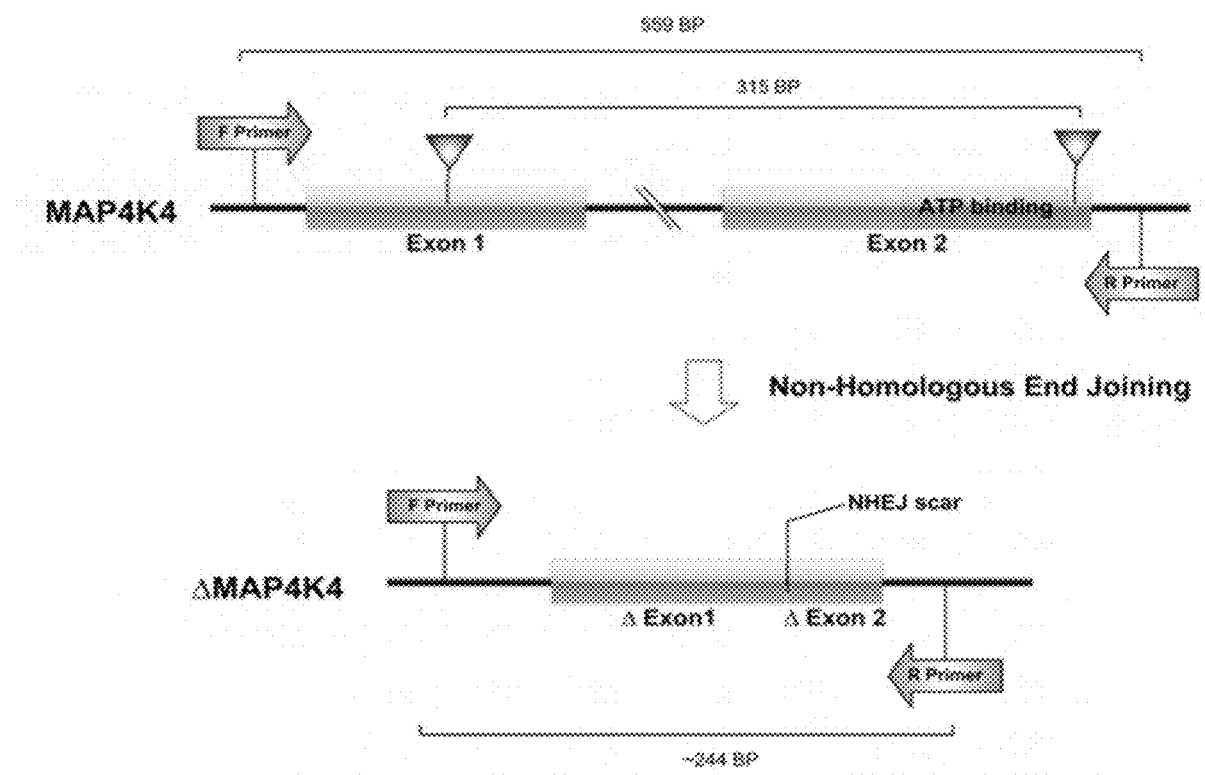
FIG. 10A shows the generation of HGK knockout by CRISPR. Two guide RNAs were designed to target the genomic region surrounding the ATP-binding domain of HGK. CRISPR-mediated excitation of this region would lead to double-stranded break repair by non-homologous end joining.
Figure 10B:
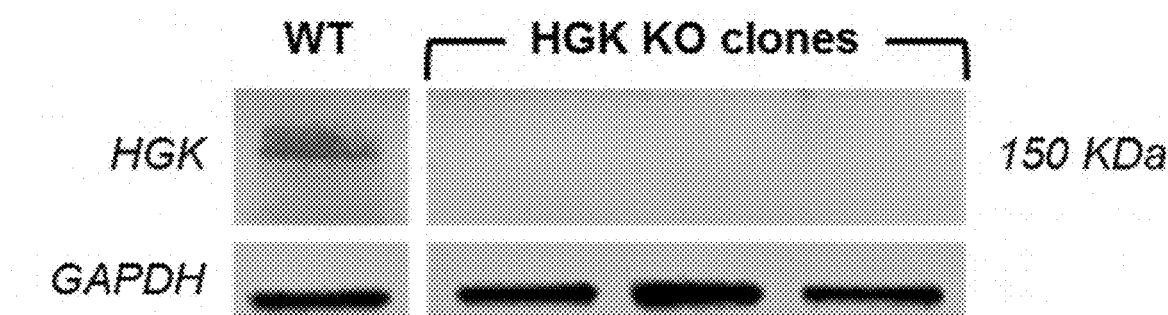
FIG. 10B shows the validation of HGK knockout clones by western blotting for HGK protein. No detectible HGK protein remained in the 3 knockout clones tested.

A CRISPR strategy was developed to completely ablate HGK expression in mouse ES cells (FIG. 10A). The ES line used contains a transgene where the cell surface marker CD14 is expressed under the control of the motor neuron-specific HB9 promotor, such that motor neurons can be purified from mixed differentiated cultures by magnetic-activated cell sorting (MACS) for downstream assays. The CRISPR strategy involves two guide RNAs targeting genomic regions up- and downstream of the ATP-binding portion of HGK that mediates its kinase activity. Double-stranded break repair is accomplished by non-homologous end-joining in this scenario, which generally results in frame shifts and complete ablation of expression. HGK ablation was confirmed in differentiated motor neurons by western blotting (FIG. 10B).

Figure 10C:
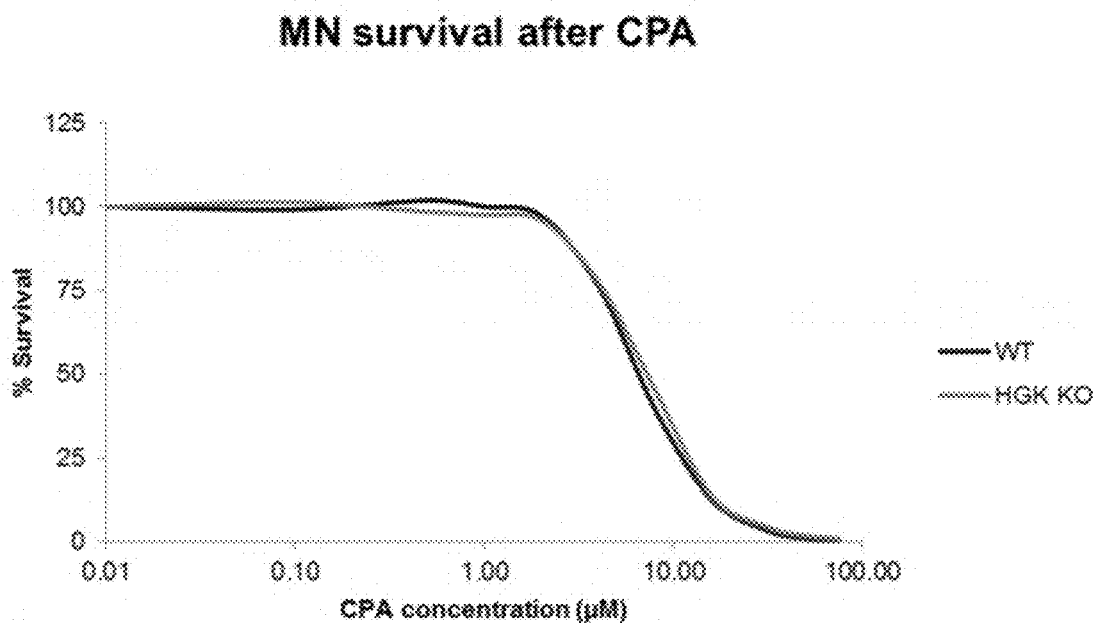

CRISPR-mediated HGK ablation did not result in neuroprotection in our typical 48h dose-response assay with increasing does of CPA (FIG. 10C). In this assay, motor neurons are MACS-purified and treated with CPA for 48h before imaging.

Figure 10D:
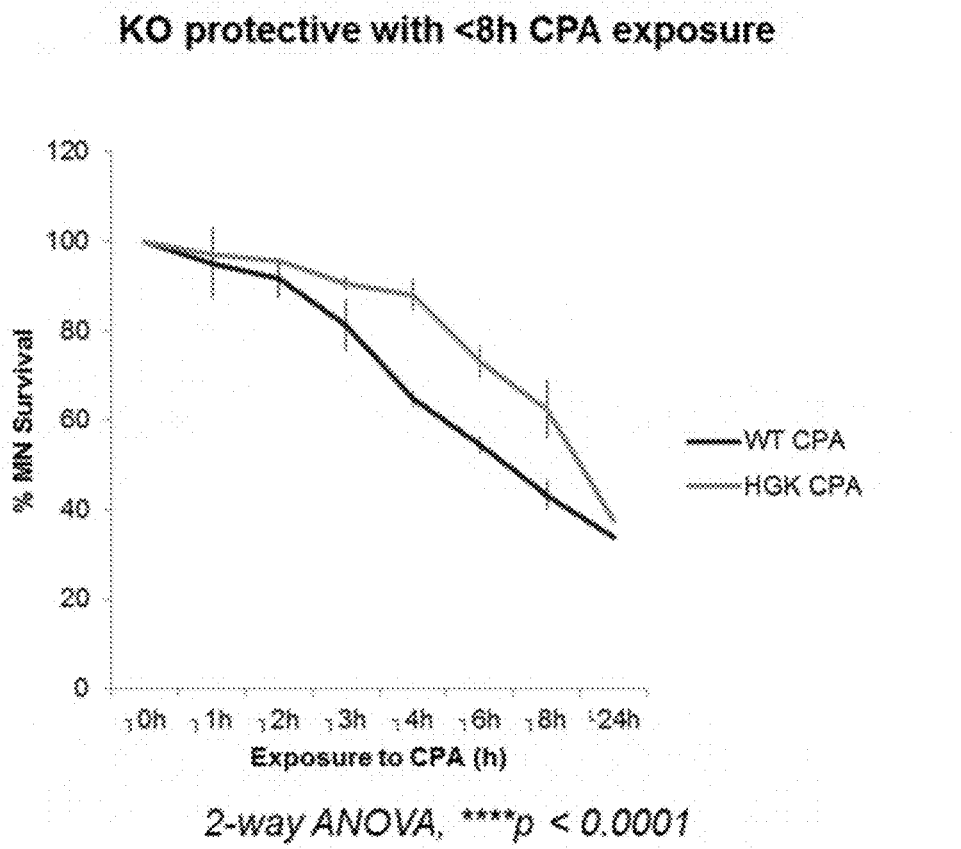
FIG. 10D shows that HGK knockout provides modest but statistically significant ($p<0.0001$, two-way ANOVA) neuroprotection early after CPA exposure (<8 h). MACS-purified motor neurons were treated with 10 μM CPA for 0-24 hours, and imaged at the 24 h hour time point. The greatest differences in survival between genotypes occurred between 3 and 8 hours of CPA exposure, but disappeared at later time points.
Figure 10E:
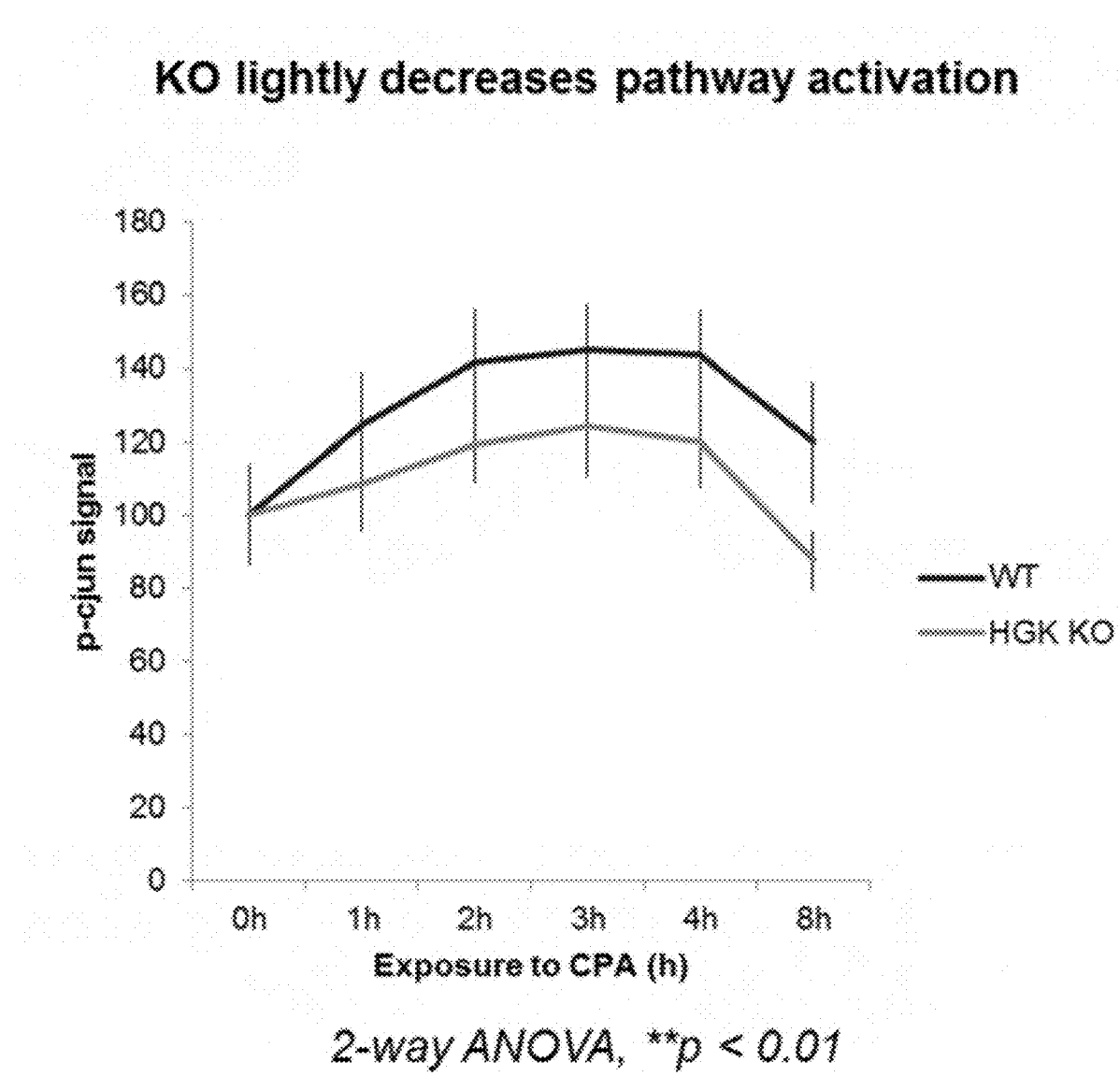
FIG. 10E shows that HGK knockout lightly decreases MAPK pathway activation ($p<0.01$, two-way ANOVA). The expression of phosphorylated (activated) c-jun, which is downstream of the putative targets of compound 1, was monitored over the course of CPA exposure (10 μM) by FRET. C-jun was modestly but significantly less activated by CPA in HGK knockout vs. wild-type motor neurons.
Figure 31A:
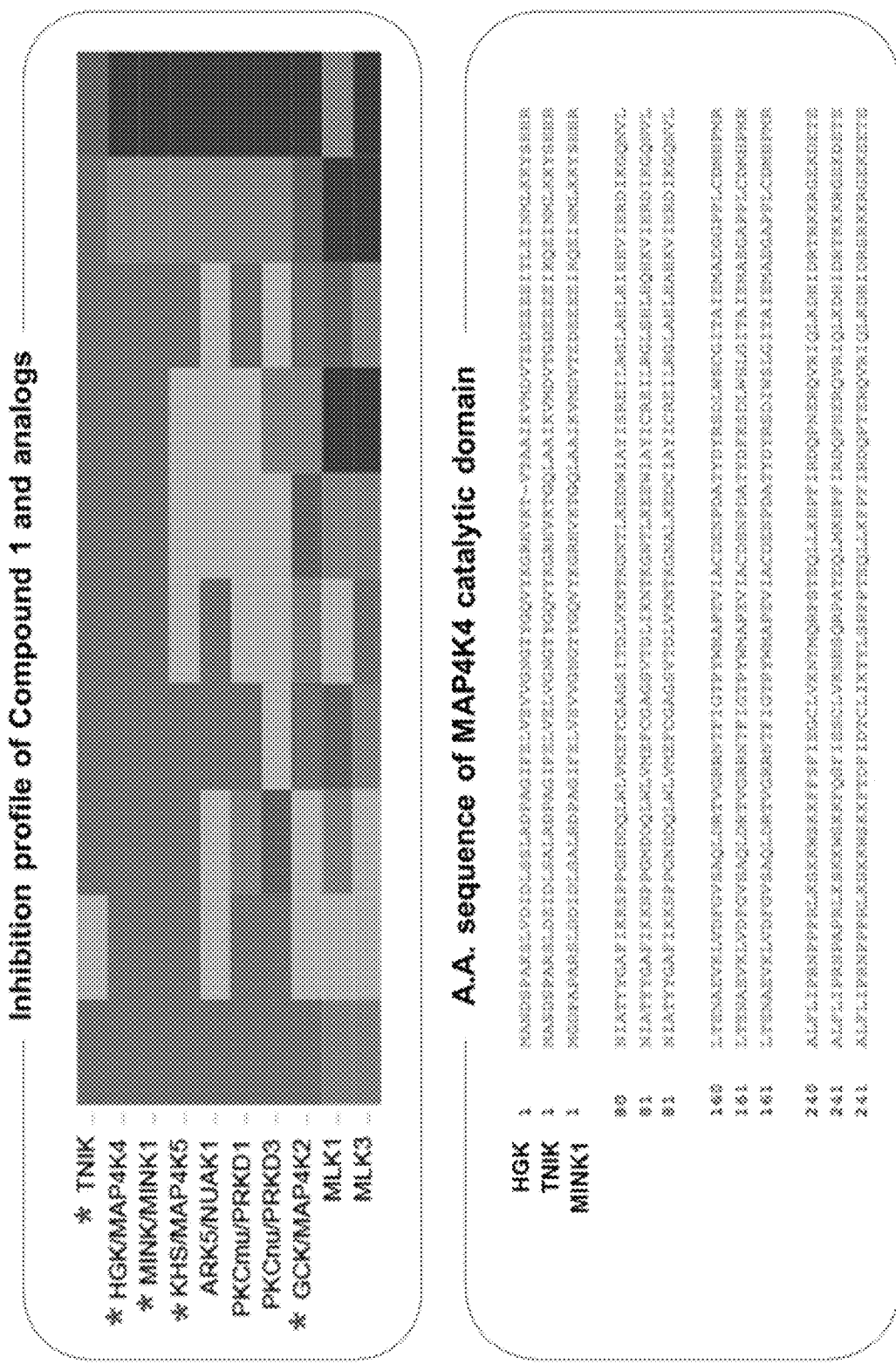
FIG. 31A shows the inhibition profile of compound 1 and analogs, indicating strong inhibition of certain MAP4K kinases including HGK, TNIK and MINK1. The amino acid sequence alignment of the MAP4K4 catalytic domain of HGK, TNIK and MINK1 is shown.

By modulating our CPA treatment paradigm such that MACS-purified WT or HGK knockout motor neurons were treated with CPA for only brief time periods (1-24h), we were able to observe that HGK ablation provides modest but highly statistically significant neuroprotection against CPA (FIG. 10D). HGK therefore plays an early role in the cell death cascades following CPA treatment; however, the fact that the effects of its ablation are undetectable at later time points suggests that there may be other redundant kinases that eventually take over in its absence. We propose that other structurally homologous MAP4K kinases such as TNIK and MINK1 may act redundantly with HGK to mediate neurodegeneration in the context of ER stress, and that compound 1 and its analogs may target all of these related MAP4Ks to promote neuronal survival (FIG. 31A).

To better understand the biologically relevant targets of compound 1 and its analogs, a second round of cell-free kinase assays was performed. In this expanded assay, we selected ten analogs ranging from moderately to very strongly protective in the CPA assay. These analogs were evaluated for their ability to inhibit a selection of 60 kinases at 0.1 μM and 0.5 μM. This list of 60 kinases was derived from known targets of compound 1 (Goodfellow et al 2013), known targets of other kinase inhibitors that showed rescue, and relevant targets from literature, known targets of other kinase inhibitors that were protective in the CPA survival assay, and relevant targets from the literature. RNAseq data were used to confirm the expression of each kinase in ES MNs (see Example 12).

Figure 8:
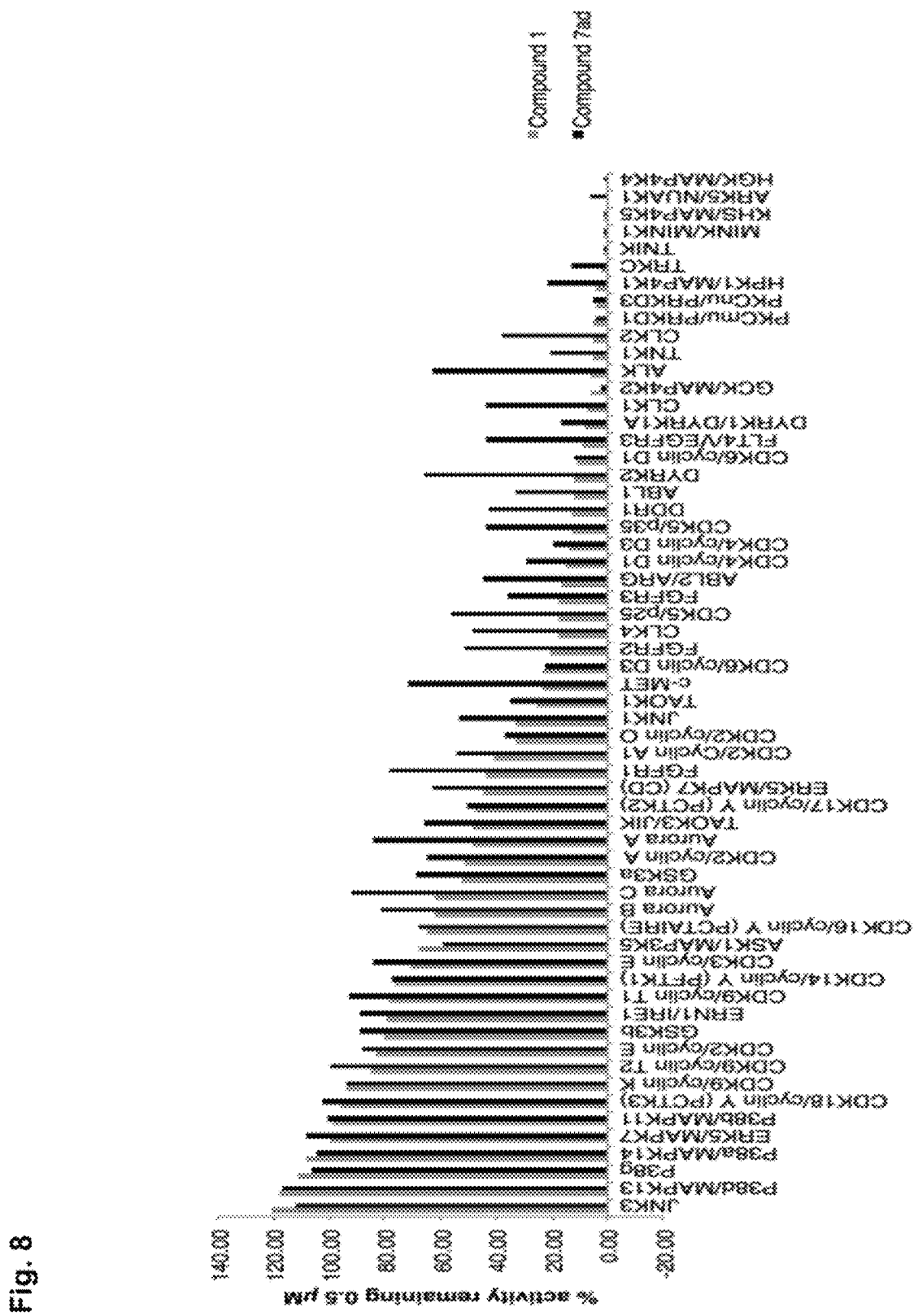
FIG. 8 shows the results of inhibition of a selection of 60 kinases by compound 1 and its analog, compound 7ad). Despite providing similar levels of protection against CPA in the motor neuron survival assay, compound 7ad inhibits the activity of fewer kinases than compound 1, thereby highlighting the putative functional targets of compound 1 and its analogs in mediating cell survival.

There was no over-arching trend towards increased target selectivity amongst the analogs relative to compound 1, indicating that the process of analog generation itself did not improve selectivity, and that neither selectivity nor promiscuity tracked with neuroprotection in the CPA survival assay. However, compound 7ad was similarly neuroprotective to compound (1) while showing increased target selectivity amongst the 60 kinases tested: at 0.5 μM, compound 1 strongly inhibited (<20% residual activity) 27 of the 60 kinases, while compound 7ad strongly inhibited 12 of the 60 kinases (FIG. 8).

Figure 1:
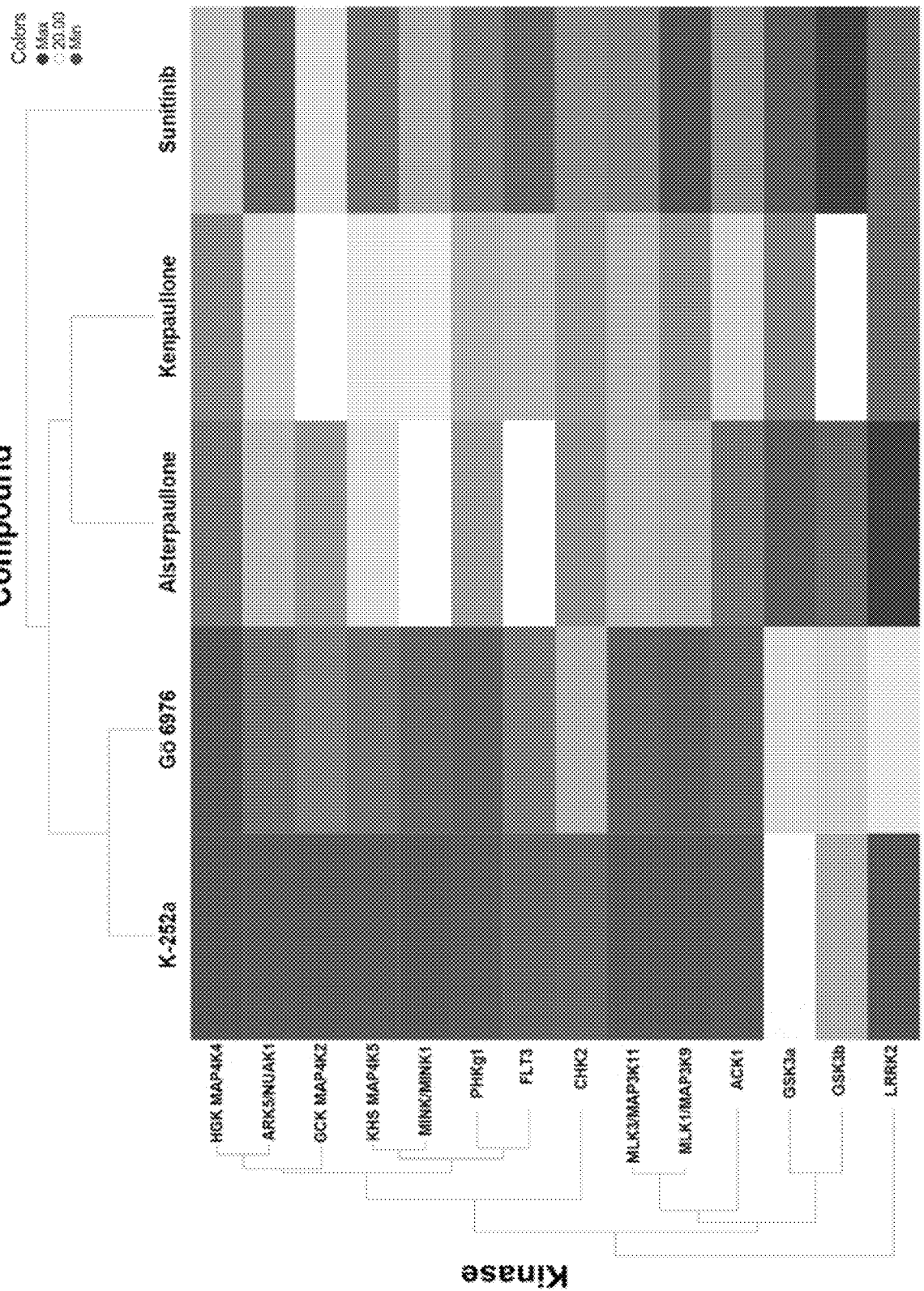
FIG. 1 shows the result of spotfire analysis of 300 kinases to rank target kinases.
Figure 2A:
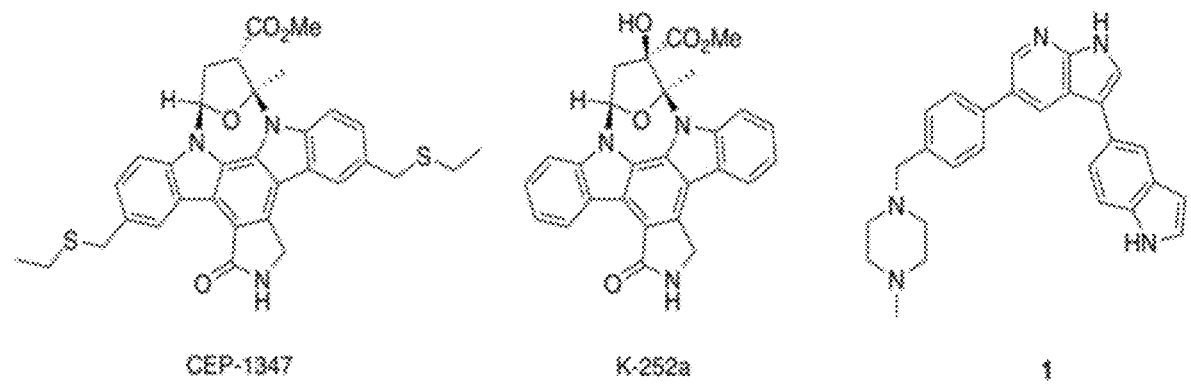
FIG. 2A shows the structures of CEP-1347, K-252a and compound 1 (URMC-099).
Figure 2B:
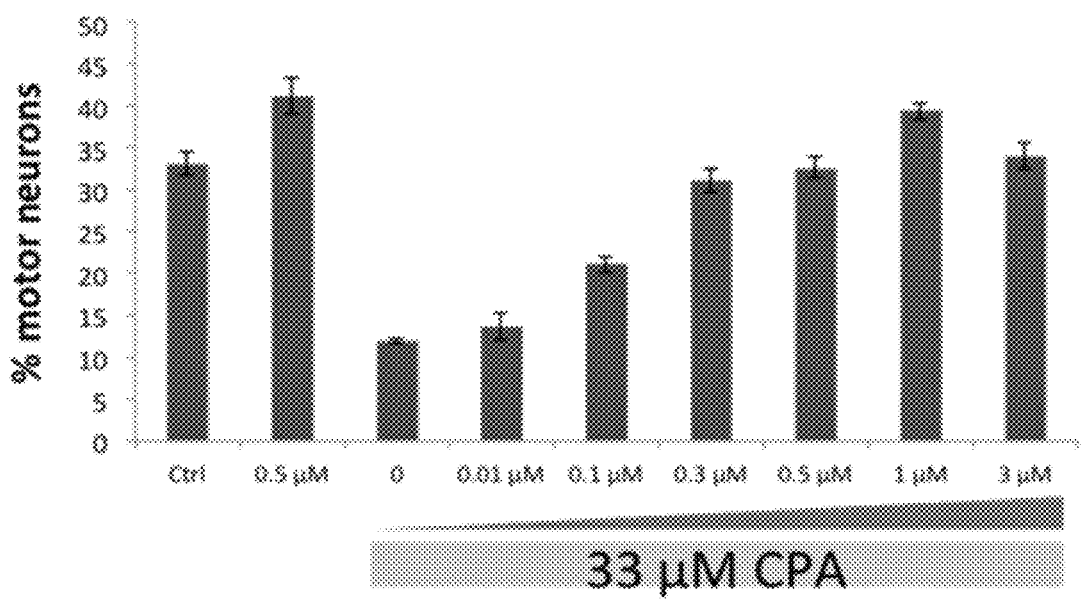
FIG. 2B shows the rescue effect of compound 1 upon ER-stress induced by treatment of human ALS iPS-MNs with 33 μM CPA.
Figure 2C:
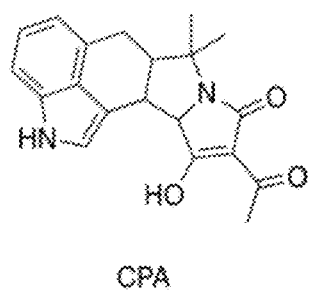
FIG. 2C shows the structure of CPA.
Figure 3:
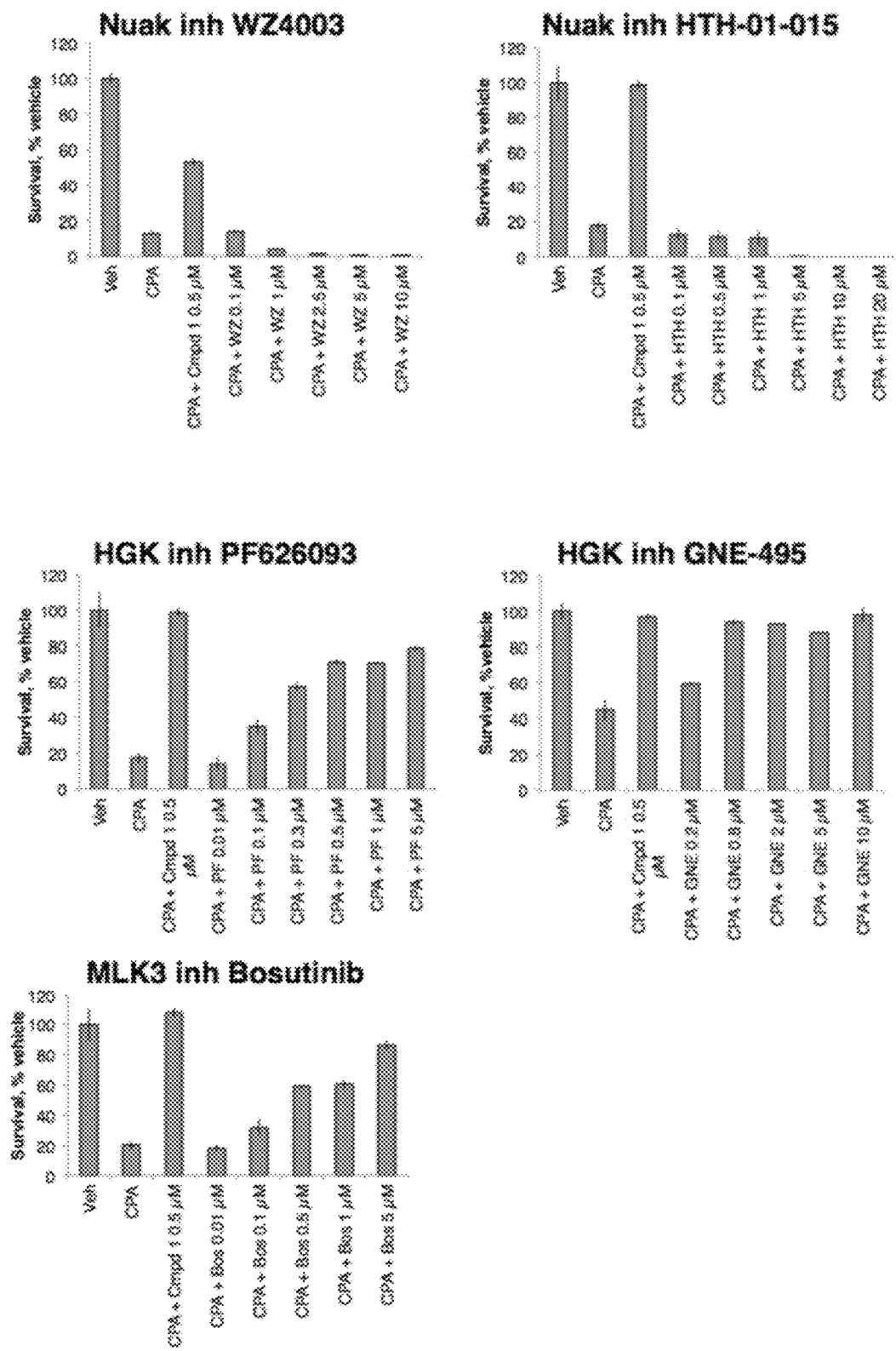
FIG. 3 shows the pharmacological inhibition of predicted targets of certain kinase inhibitors. Neither the selective NUAK1 inhibitors WZ4003 nor HTG-01-015 provided neuroprotection against CPA. Meanwhile, inhibition of HGK by the selective inhibitors PF626093 and GNE-495, and inhibition of MLK3 by the non-selective inhibitor Bosutinib were all neuroprotective. Together these results suggest that MLK3 and HGK could be targets of Compound 1, but not NUAK1.

Comparing the targets of relatively selective neuroprotective analogs with those of compound 1 highlights the targets most likely to mitigate neurodegeneration in the CPA survival assay. In addition to HGK, the selective compound 7ad most strongly inhibits closely related MAP4 kinases including TNIK, MINK1, KHS (MAP4K5), and GCK (MAP4K2) (FIG. 8). These findings are also consistent with our analyses of the shared targets of the hit compounds from our preliminary screen (FIG. 3), where HGK, MINK, KHS, and GCK were among the most highly ranked targets (TNIK activity was not assessed in the existing publicly available database; Anastassiadis et al., 2011).

Overall, we observed a modest correlation for compound 1 and its analogs between MAP4K inhibition and neuroprotection at 0.5 µM and 0.1 µM (FIG. 32), but meaningful correlations were likely obscured the fact that even moderately neuroprotective compounds still robustly inhibit MAP4Ks at these concentrations. Additionally, the high degree of structural homology between the kinase domains of the MAP4K family members makes it difficult to parse whether the inhibition of individual MAP4Ks is functionally relevant to survival in the CPA assay or is merely incidental.

Figure 9:
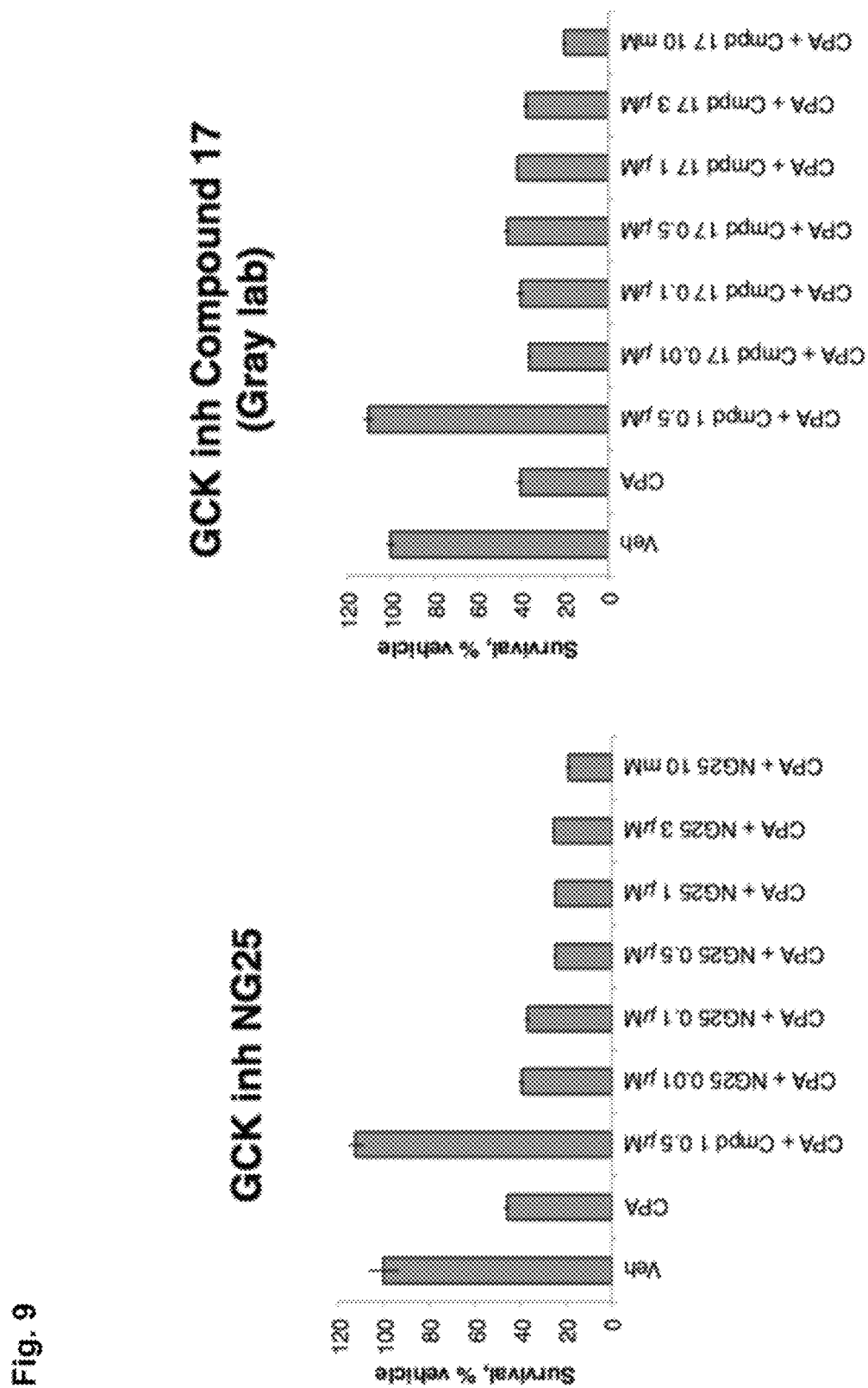
FIG. 9 shows that two GCK inhibitors, Compound 17 and NG25 (both from Tan et al, 2015), are unable to rescue motor neurons from CPA-induced ER-stress.
Figure 33:
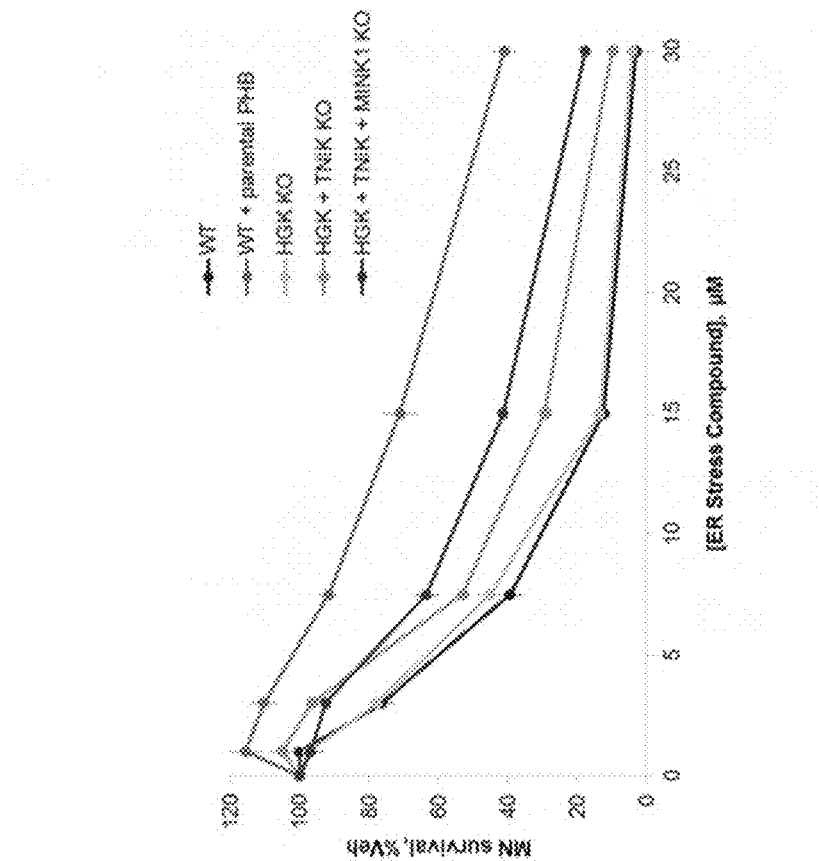
FIG. 33 shows that CRISPR knockouts of MAP4Ks are neuroprotective and have additive effects in motor neurons, indicating that they are functional targets of compound 1 and its neuroprotective analogs.
Figure 33:
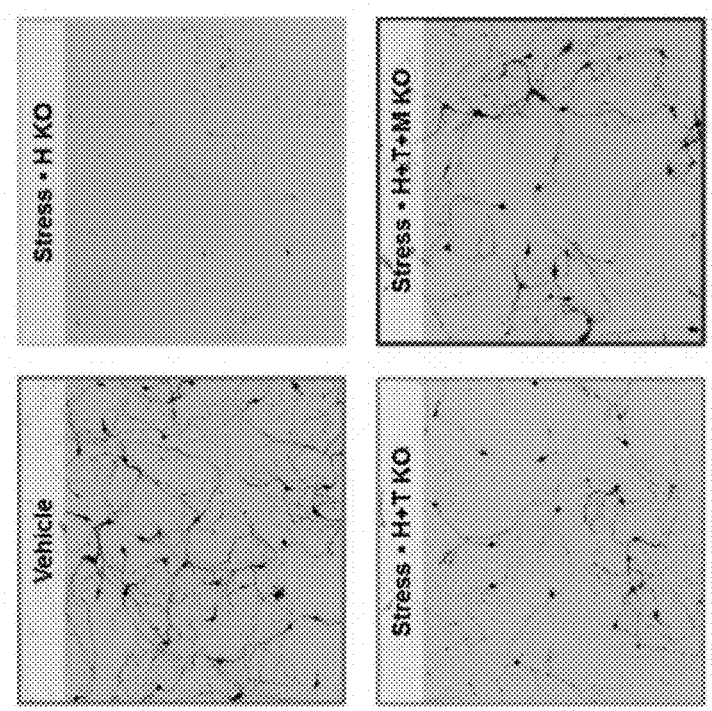

Accordingly, few compounds exist that are selective for individual MAP4Ks over the others; however, we found that GCK-selective inhibitors (compound 17 and NG-25 in Tan et al., 2015; FIG. 9) were unable to rescue MNs in the CPA survival assay, which narrows the likely functional targets of the compound 1 analogs to HGK, MINK1, TNIK, or KHS, or some combination thereof (FIG. 33).

Figure 31B:
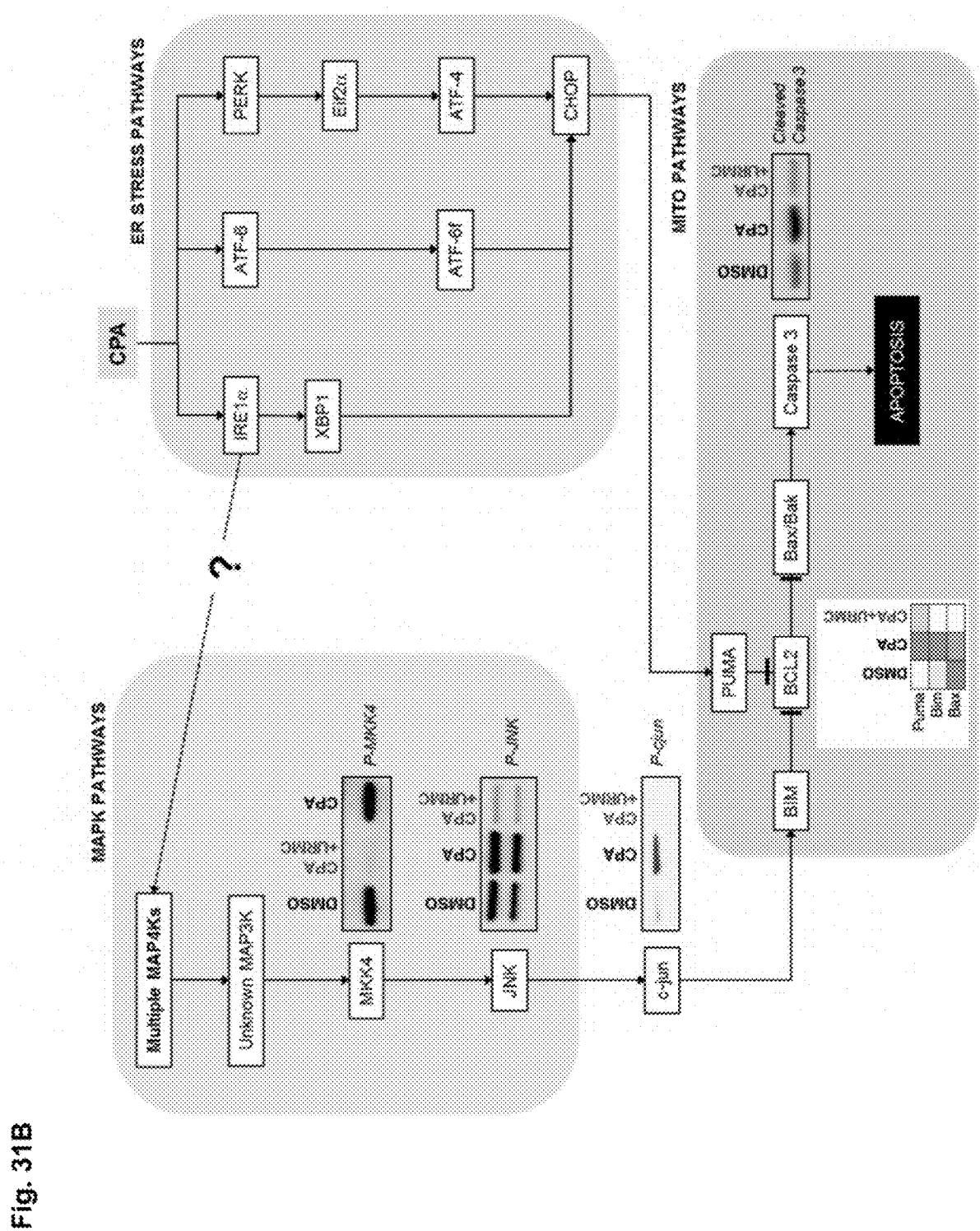
FIG. 31B is a schematic diagram of the possible mechanism of action for the neuroprotective effects of compound 1 and its analogs in CPA-treated ES MNs.
Figure 31C:
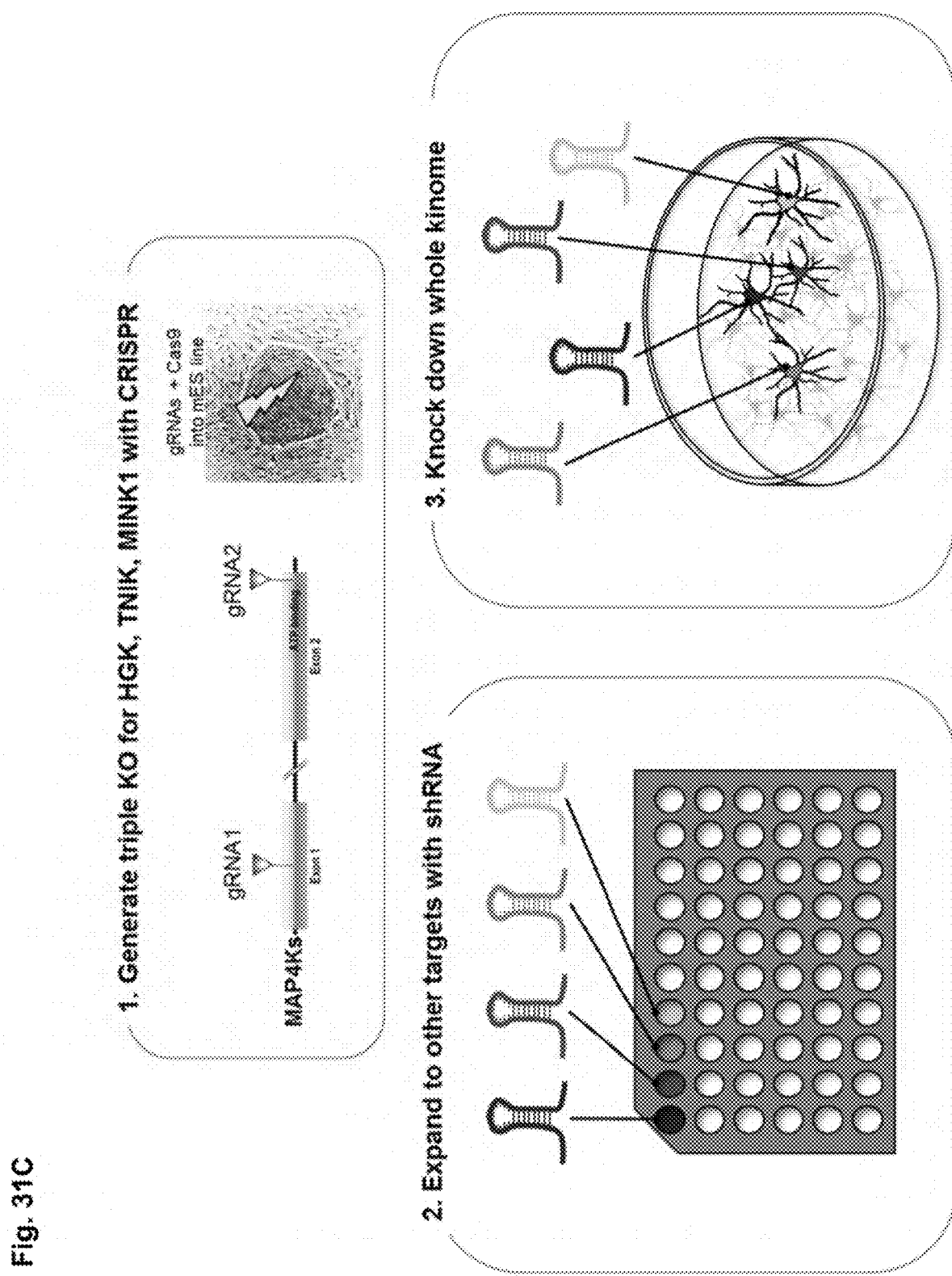
FIG. 31C is a schematic diagram showing the procedure for attenuating the expression of all three kinases (HGK, TNIK and MINK1).

Furthermore, recent work from Larhammar et al (2017) has shown that compounds inhibiting HGK, TNIK, and MINK1 are neuroprotective in primary dorsal root ganglia neurons subjected to neurotrophic factor withdrawal, and that attenuating the expression of all three kinases together—but not individually—mirrors the effects of the compounds (FIG. 31C). They argue that the roles of HGK, TNIK, and MINK1 in their neurodegeneration assay are redundant, and that the effects of inhibiting a single kinase can be overcome by the activity of the remaining kinases. It is therefore possible that the combined inhibition of multiple MAP4 kinases underlies the neuroprotective effects of compound 1 and its analogs in CPA-treated ES MNs (FIG. 31B).

Example 9

Metabolic Stability of the Analogs

Figure 29:
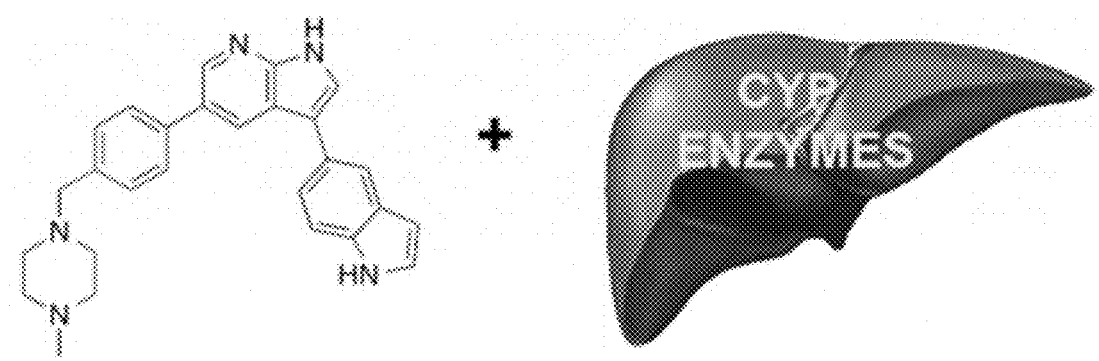
FIG. 29 shows a schematic diagram of an in vitro assay to test the metabolic stability of the analogs synthesized.
Figure 29:
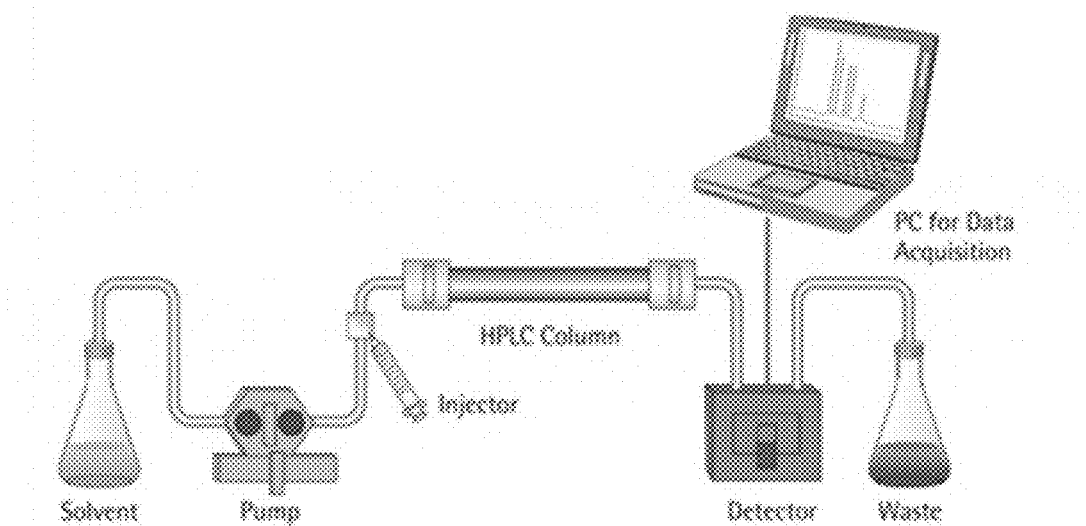

To test the metabolic stability of the analogs, an in vitro microsomal stability assay was carried out. In this assay, the analogs that showed excellent rescue properties in the ER stress assay were incubated with mouse liver microsomes in buffer containing an NADPH regenerating system. Aliquots were taken over the course of two hours and analyzed by HPLC-MS using an internal standard to assess the compound stability over time (FIG. 29).

Methods and Materials

The microsomal stability assay was performed in 96-well format (Perkin-Elmer, StorPlate-96U, PP, 96 well, round bottom). To each well was added phosphate buffer (182.2 µL, pH 7.4, 100 mM) followed by addition of NADPH regenerating system solution A (10 µL), and NADPH regenerating system solution B (2 µL) (Corning Gentest 3P NADPH regenerating system solution A (#451220) and B (#451200)). A stock solution of the compound to be analyzed (0.8 µL, 5 mM) or ethoxycoumarin (positive control, 0.8 µL, 5 mM) was added and the mixture was warmed to 37° C. for 5 minutes. The mouse microsomes (CD-1, 5 µL, thawed in a 37° C. water bath before use, 20 mg/mL, Life Technologies) were added. At selected time points (0, 15, 30, 45, 60 and 120 minutes) aliquots (15 µL) were withdrawn from the plate and quenched upon addition to cold acetonitrile (60 µL), containing an internal standard (5 µM) in a 96-well plate. The samples were centrifuged at 13,000 rpm for 10 minutes at 4° C. The supernatant (40 µL) was withdrawn and transferred to a sample vial with insert. The samples were analyzed by LC-MS.

LC-MS analysis was performed on a platform comprising a Thermo Scientific Dionex Ultimate 3000 and a Bruker amaZon SL equipped with an electrospray ionization source controlled by Bruker Hystar 3.2. Chromatographic separation was performed by injecting 5 µL of the sample onto an Agilent Eclipse Plus C18 column (2.1×50 mm, 3.5 µm) maintained at 20° C. The flow rate was maintained at 400 µL/min. The initial flow conditions were 60% solvent A (water containing 0.1% acetic acid) and 40% solvent B (methanol containing 0.1% acetic acid). Solvent B was raised to 60% over 0.25 minutes and to 70% by 6.75 minutes. Solvent B was raised to 95% by 7.00 minutes and lowered back to initial conditions (40%) by 8.00 minutes with a total run time of 9.00 minutes.

Results

Figure 11:
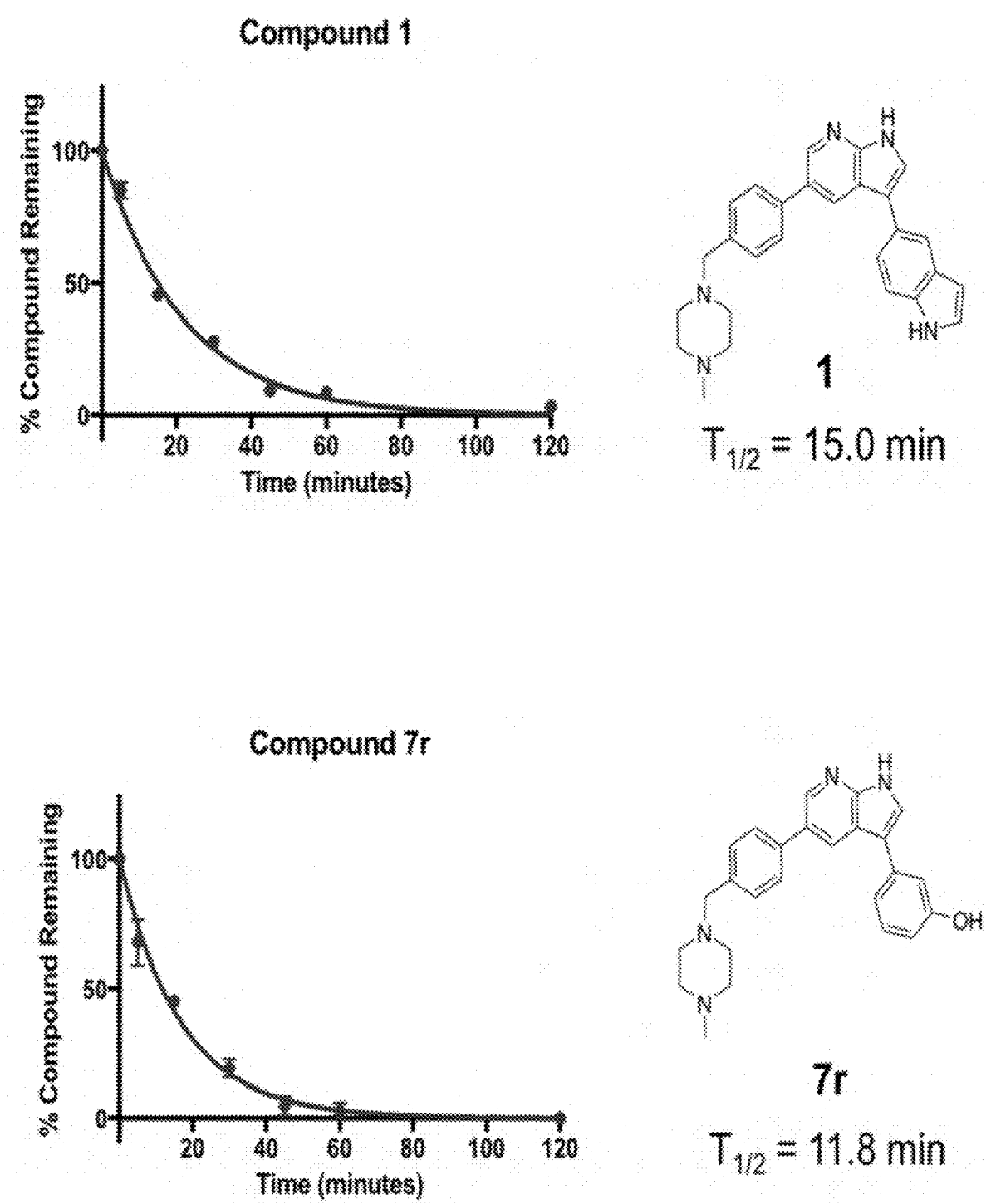
FIG. 11 shows the microsomal stability assay results of compound 1 and its analogs (7r, 7v, 7w, 7y, 7aa, 7ad, 7ah, 7al, 7as, 7at, 12e, 12f, 12g, 12 h, 12i, 12j, 12k, 12l). Their structures and half-lives in mouse liver microsomes are shown.
Figure 11:
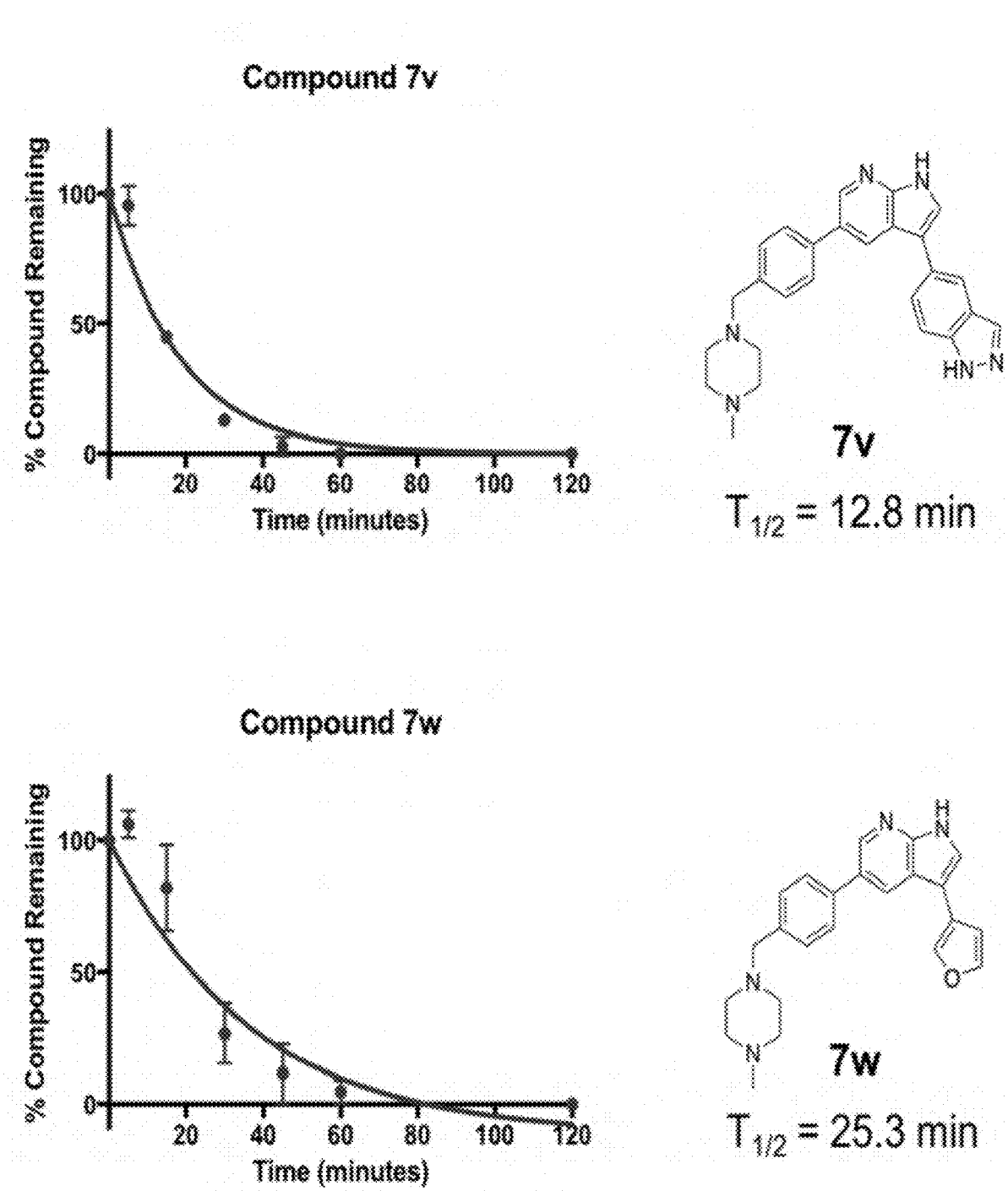
Figure 11:
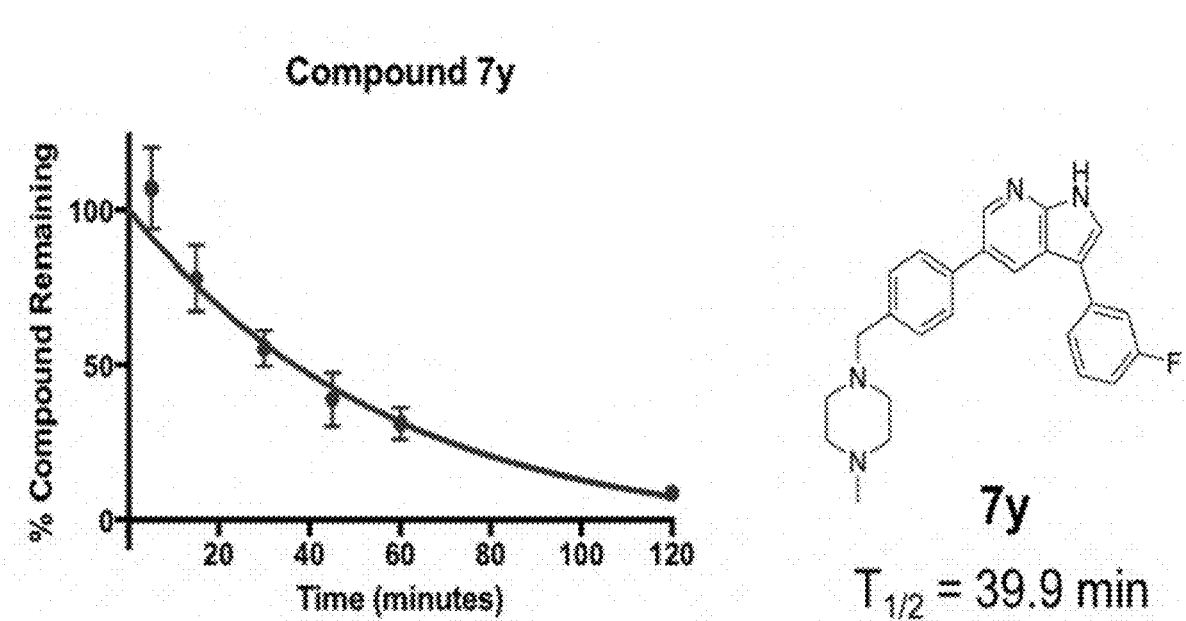
Figure 11:
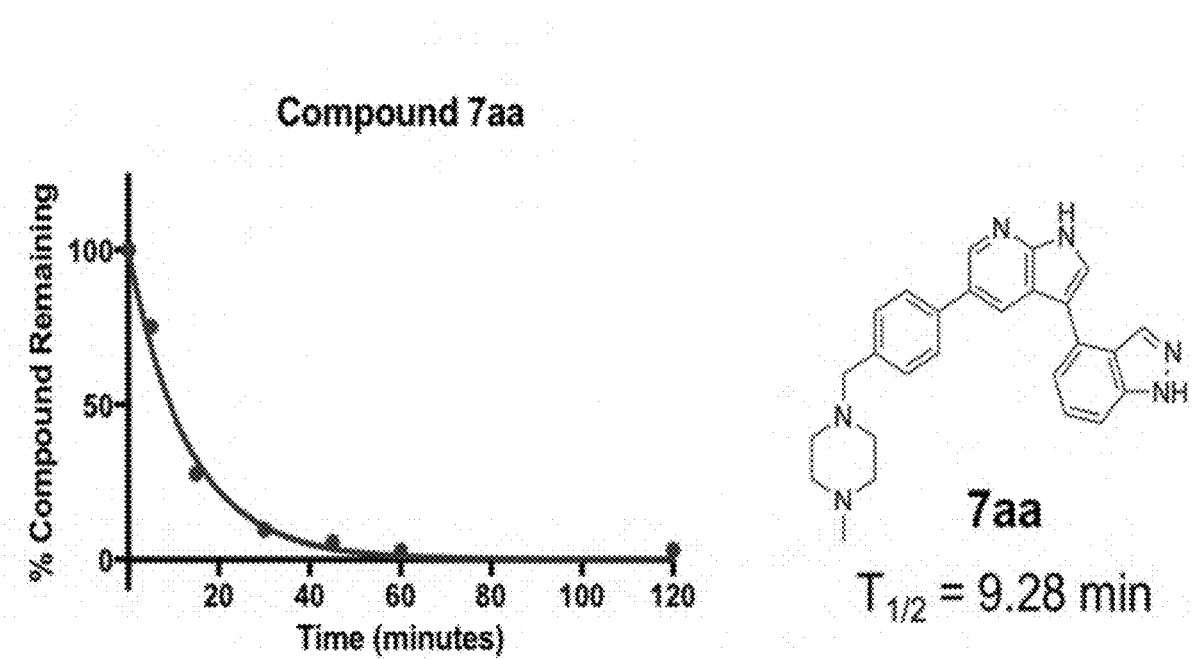
Figure 11:
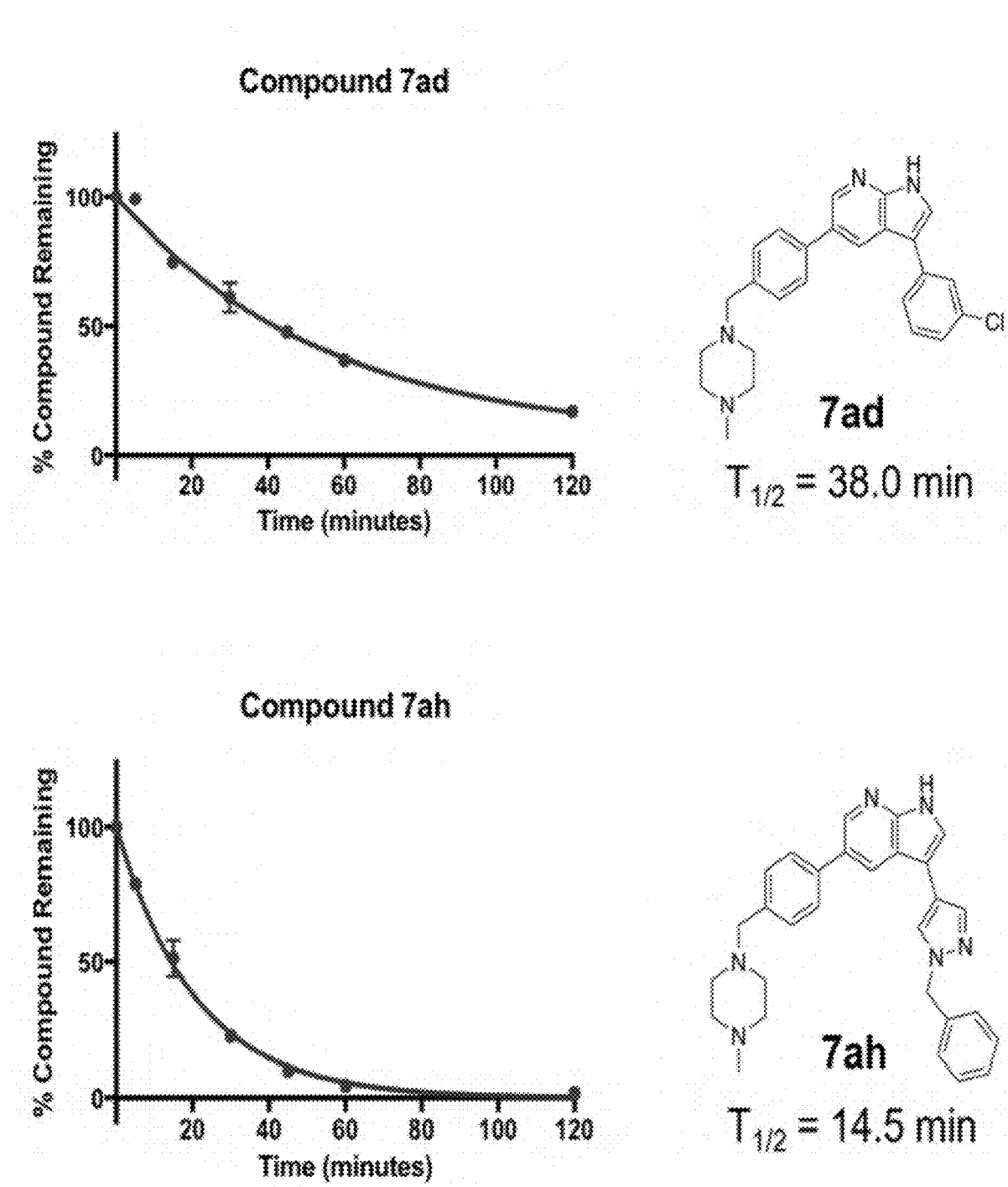
Figure 11:
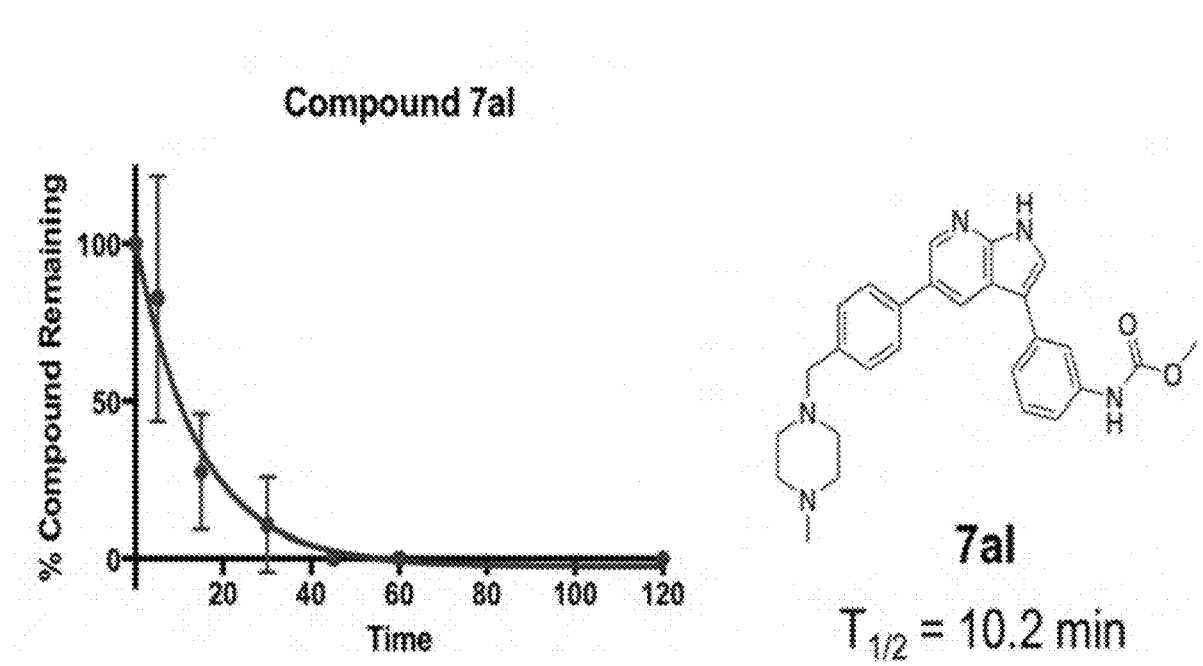
Figure 11:
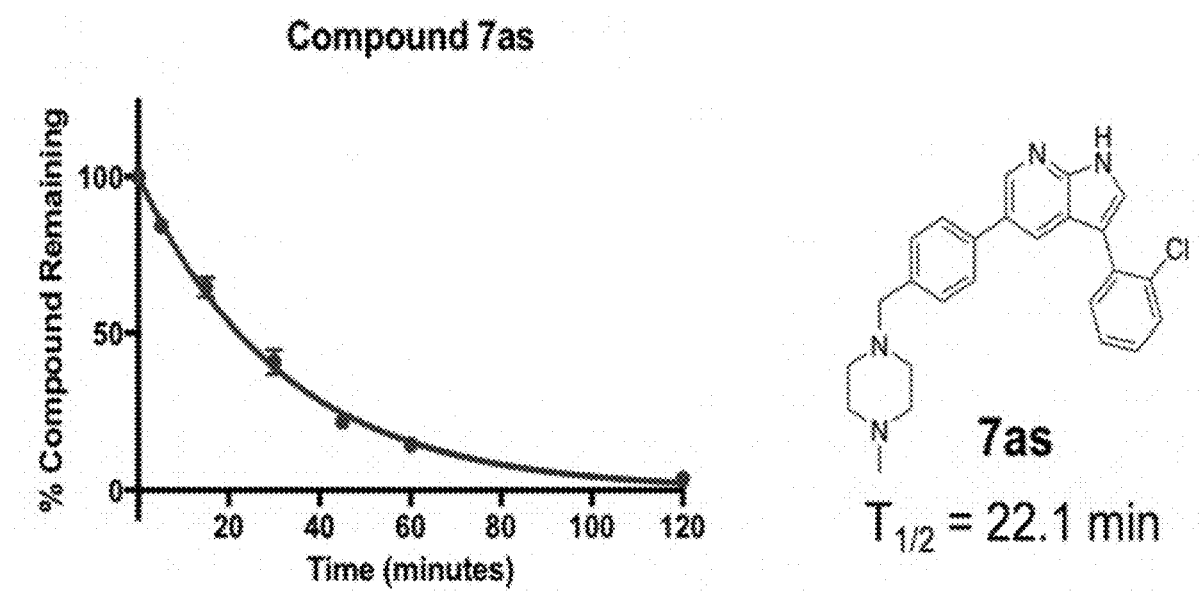
Figure 11:
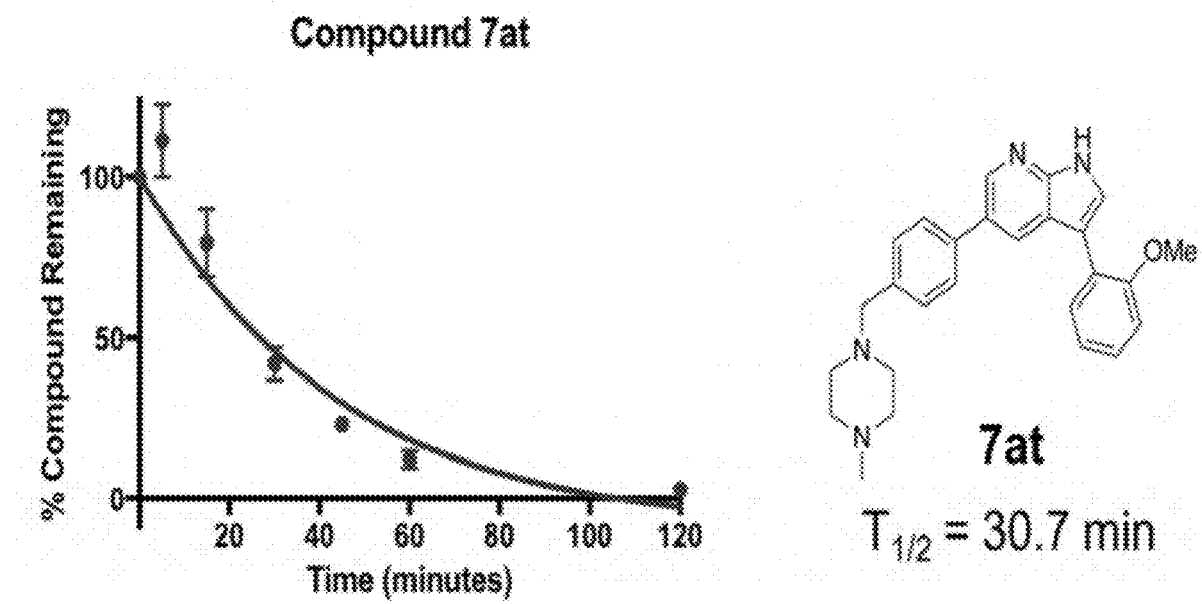
Figure 11:
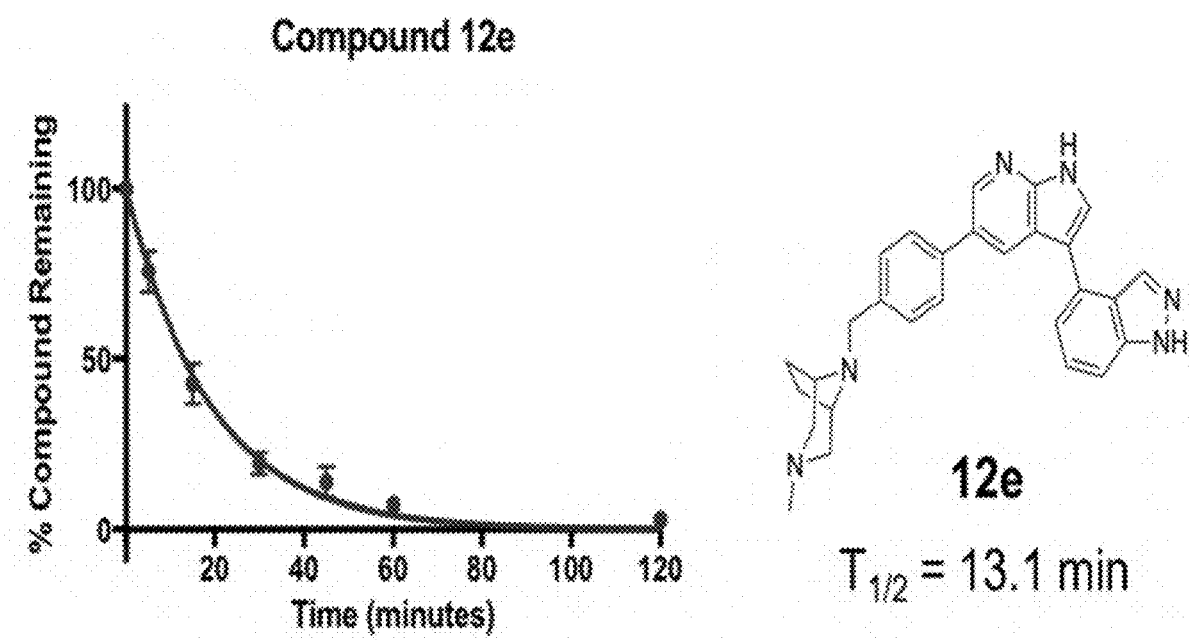
Figure 11:
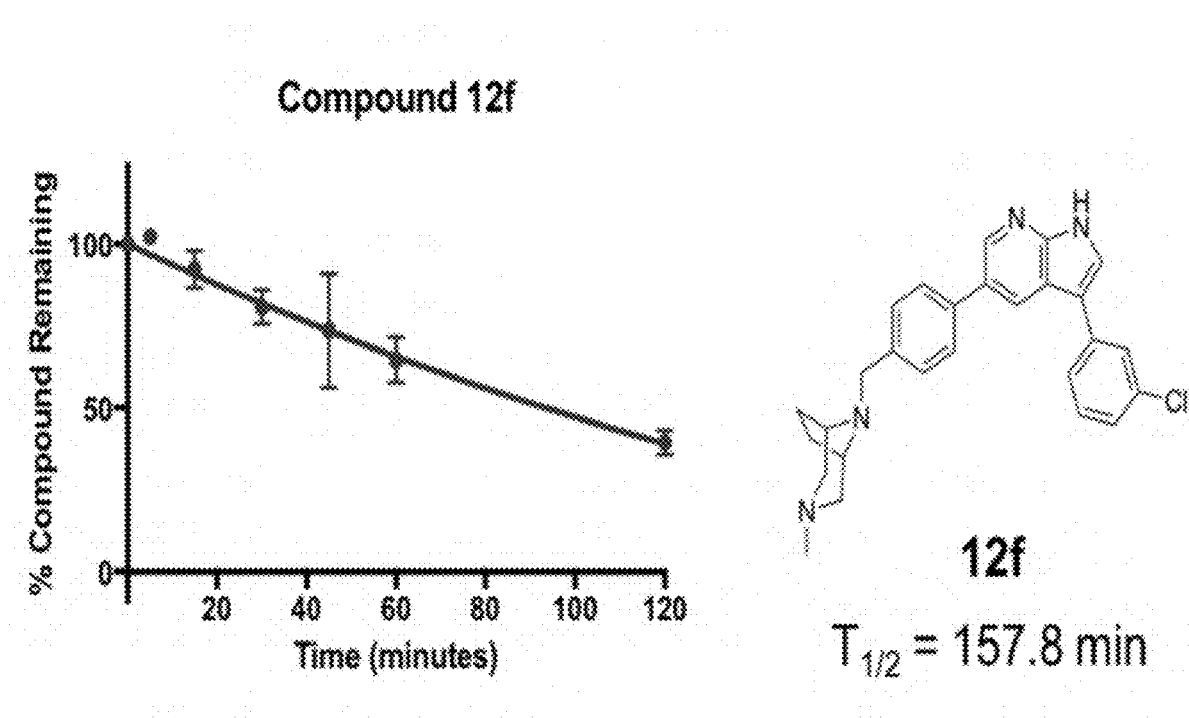
Figure 11:
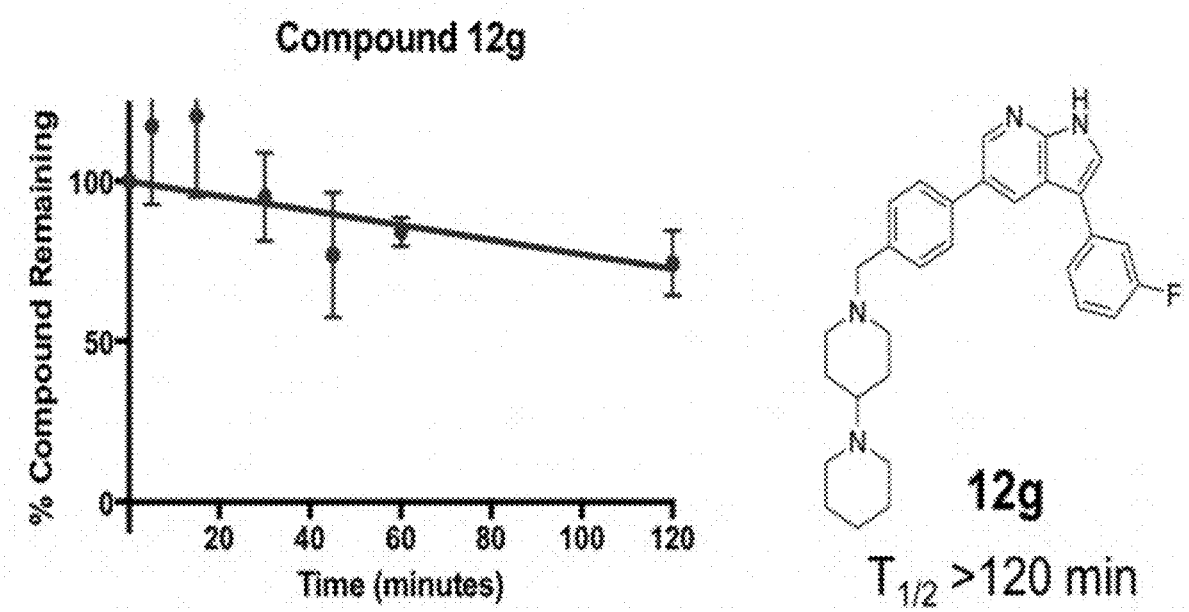
Figure 11:
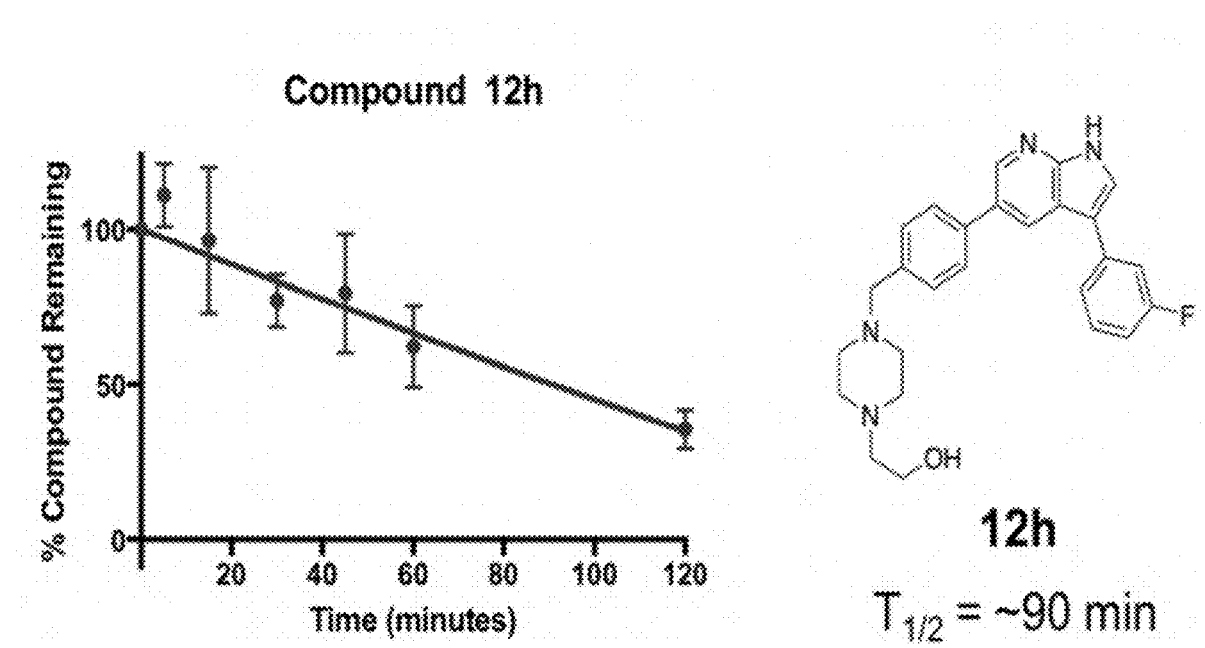
Figure 11:
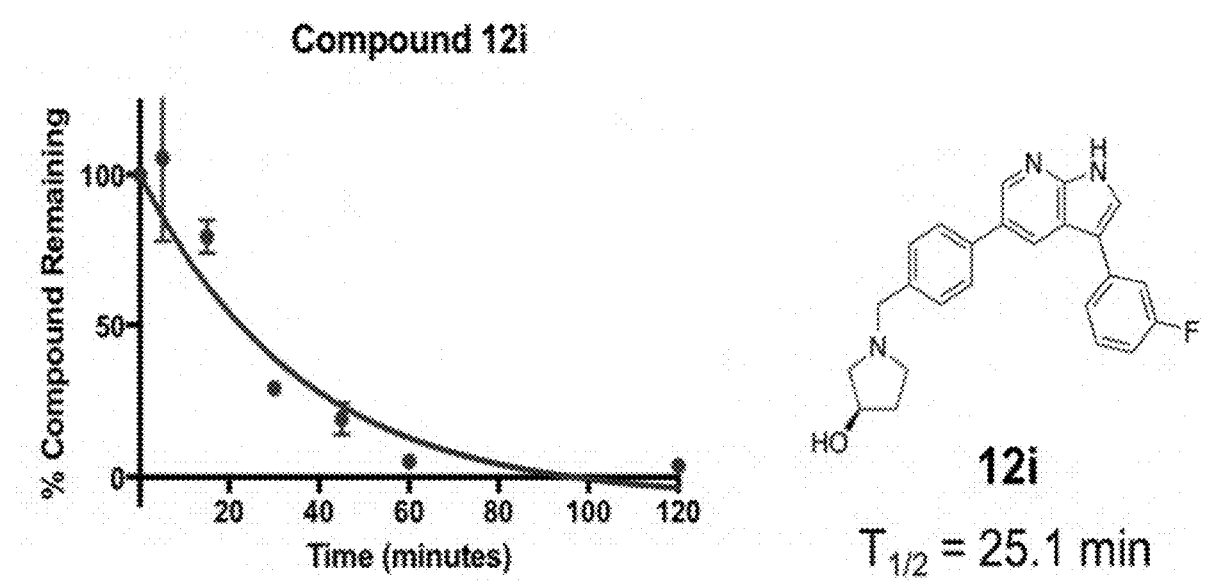
Figure 11:
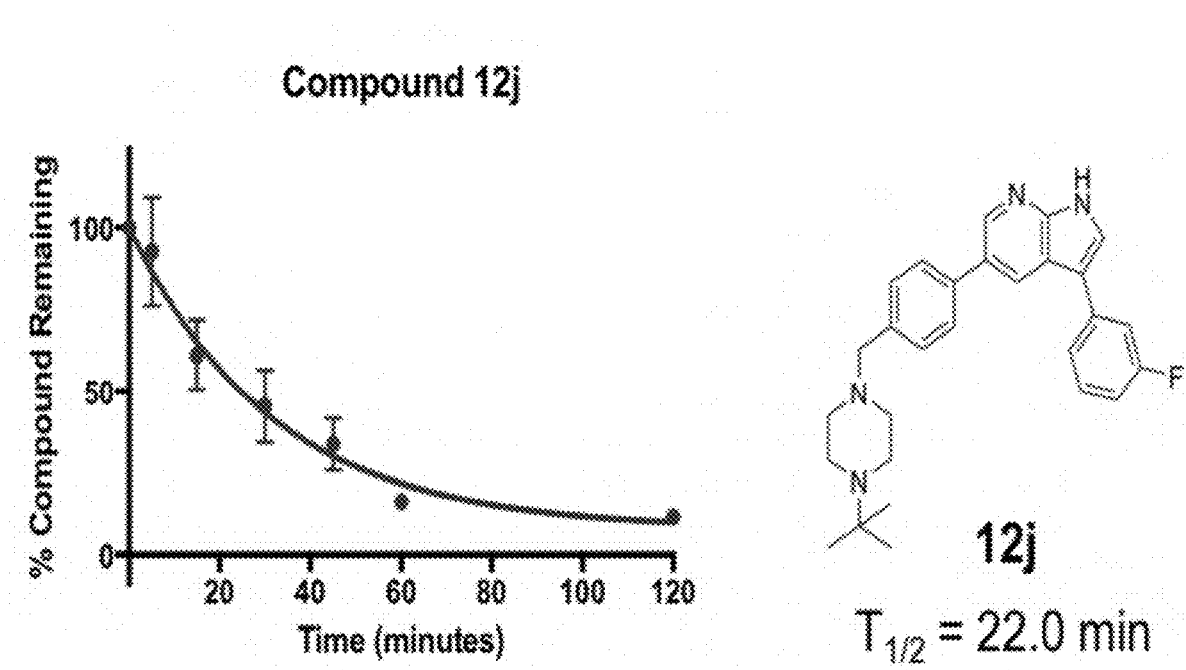
Figure 11:
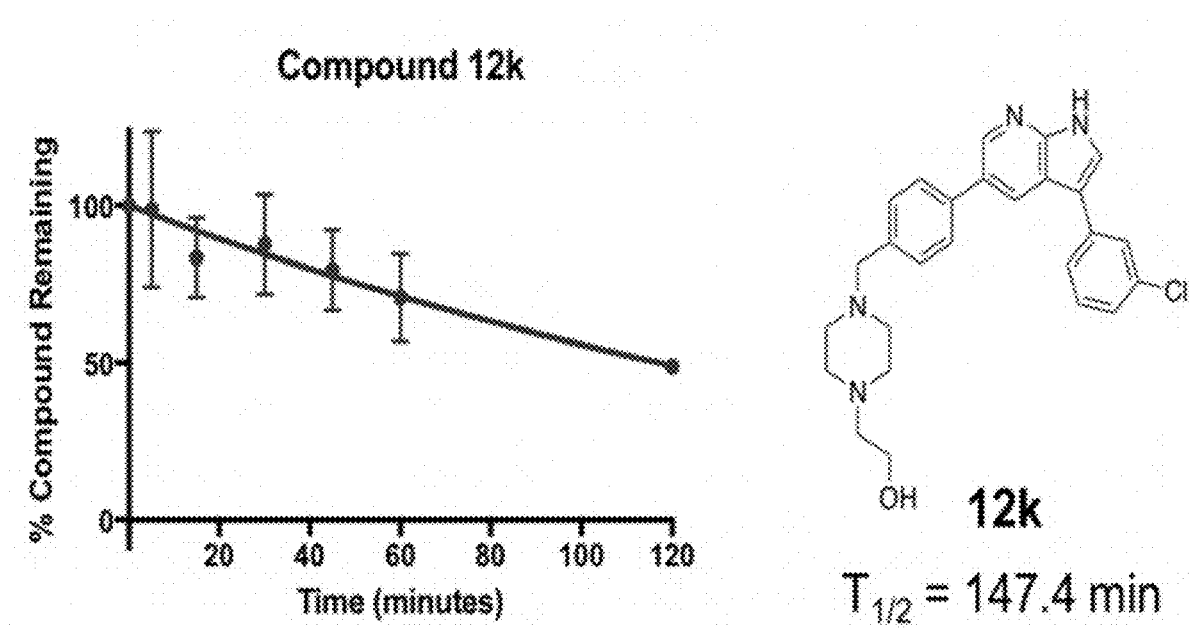
Figure 11:
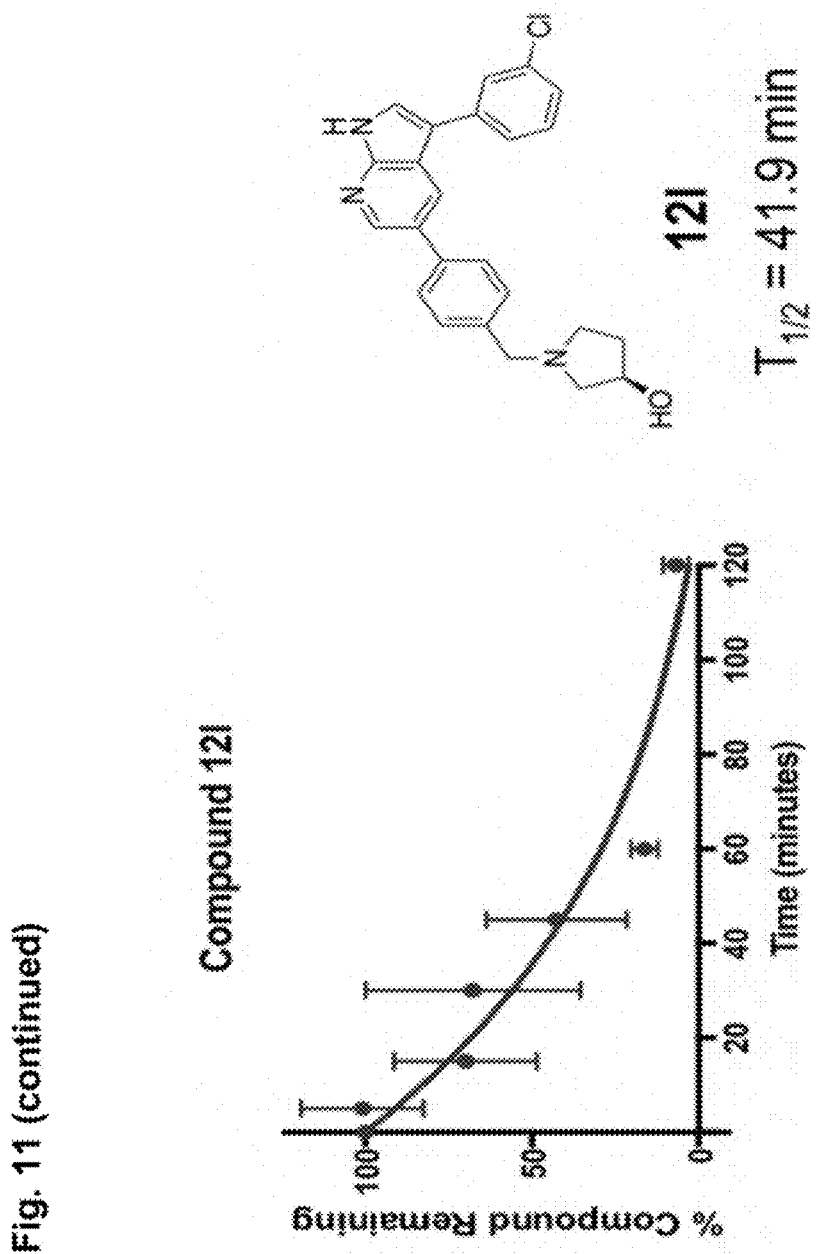

Initially, a selection of 11 analogs was analyzed for their stability in mouse liver microsomes (FIG. 11). Compounds with a half-life of less than 30 min in microsomes are generally not ideal drug candidates due to their high clearance rate. In accordance with previously published work, we found that compound 1 has a relatively short half-life in mouse liver microsomes ($T_{1/2}$=15 min). Out of the 11 analogs that were initially evaluated, only three analogs (7y, 7ad, and 7at) showed a promising half-life (>30 minutes) in the mouse liver microsomes.

Next, compound modification was carried out to improve the half-life. The computational docking experiments showed that the methylpiperazine moiety is solvent exposed. Therefore, we modified the piperazine group of the analogs with the goal to increase their metabolic stability while at the same time maintaining (or improving) their potency in the ER stress assay.

Introduction of a bicyclic methylpiperazine to one of the most potent analogs (See Scheme 11) increased the half-life from 9 minutes (compound 7aa) to 13 minutes (compound 12e). To further enhance the microsomal stability of our analogs, the same bicyclic piperazine was introduced to one of the analogs from the initial series that had a half-life>30 minutes (Scheme 11, compound 12f). In this case the half-life was increased from 38 minutes (compound 7ad) to 158 minutes (compound 12f), a significant improvement. Compound 12f was more potent in the ER stress assay and showed complete rescue at 0.3 µM, but also showed slightly higher toxicity at concentrations>0.5 µM. To reduce this increase in toxicity, while maintaining potency and microsomal stability, we synthesized another series of analogs (Scheme 12) containing the m-chlorophenyl or m-fluorophenyl substituent on the 3-position of the 7-azaindole scaffold.

Figures 13A, 13B:
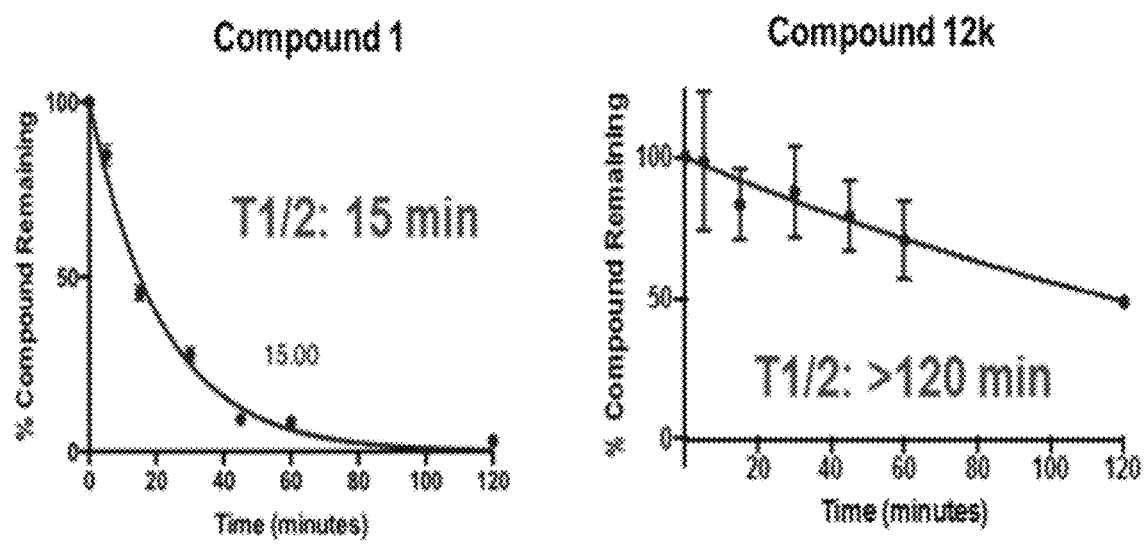
FIG. 13A shows the half-life of compounds 1 and 12k in a liver microsome stability assay. The half-life of the optimized compound 12k (>120 min) is considerably higher than that of compound 1 (15 min), indicating that 12k has much stronger metabolic stability.
FIG. 13B shows the concentration (ng/mL) of compounds 1 and 12k in plasma and brain samples of mice injected intravenously (IV) with 10 mg/kg of either compound. Drug concentrations were analyzed by LC-MS. While the levels of compound 1 1 h after injection are below the limits of detection of the LC-MS assay, 12k was still detectable. Furthermore, the amount of 12k in the brain exceeded that in the plasma, indicating that 12k is highly blood-brain-barrier penetrant.

The potency of these compounds was evaluated in the ER stress assay, and their stability was evaluated in the microsomal stability assay. Two of these compounds, 12g and 12j, either had a shorter half-life than desired or showed a decrease in potency in the ER stress assay. The remaining four compounds (12h, 12i, 12k, and 12l) strongly rescued motor neurons from CPA-induced ER stress and were able to completely negate the effects of CPA treatment at concentrations<0.3 µM. Out of these very potent analogs, 12 h and 12k were the most promising candidates for further in vivo studies because of their improved stability in mouse liver microsomes (FIG. 11; FIG. 13A).

Example 10

Figure 30:
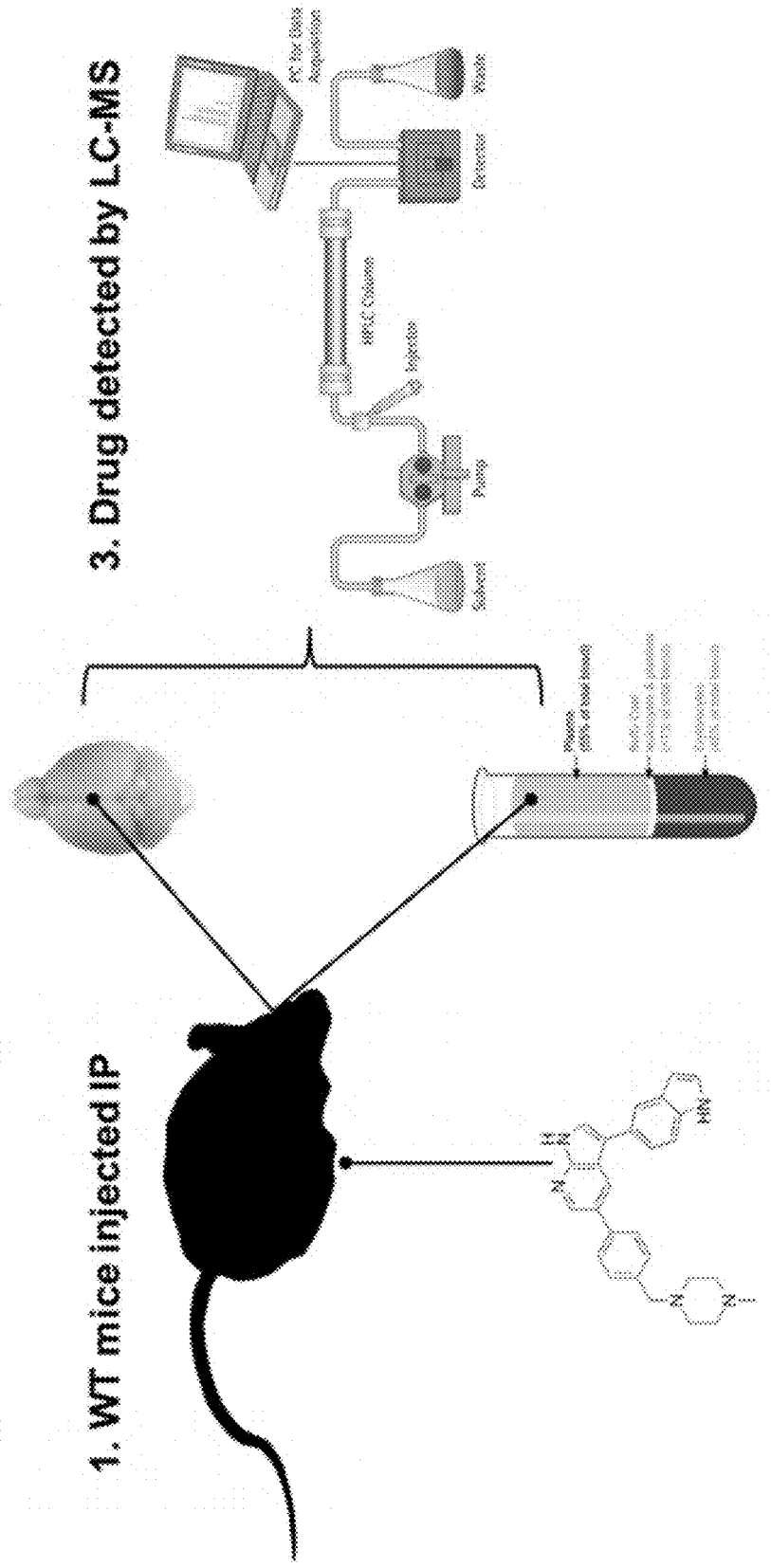
FIG. 30 shows a schematic diagram of the evaluation process for the in vivo pharmacokinetics of the analogs synthesized.

Pharmacokinetic Evaluation of Compounds
Improve the Solubility of Compound 1 and its Analogs Previous publications described a basal formulation for in vivo delivery of compound 1 that was comprised of 55% saline, 40% PEG-400, and 5% DMSO. Surprisingly, we observed that, in this formulation, compound 1 was highly insoluble in cell culture media, indicating that the formulation was not suitable for in vivo experiments. To optimize vehicle formulation we developed a 96-well format spectrophotometric assay that would allow us to rapidly screen the effects of pH and solubilizing agents at varying concentrations on the solubility of compound 1 and its analogs (FIG. 30).

Figure 12:
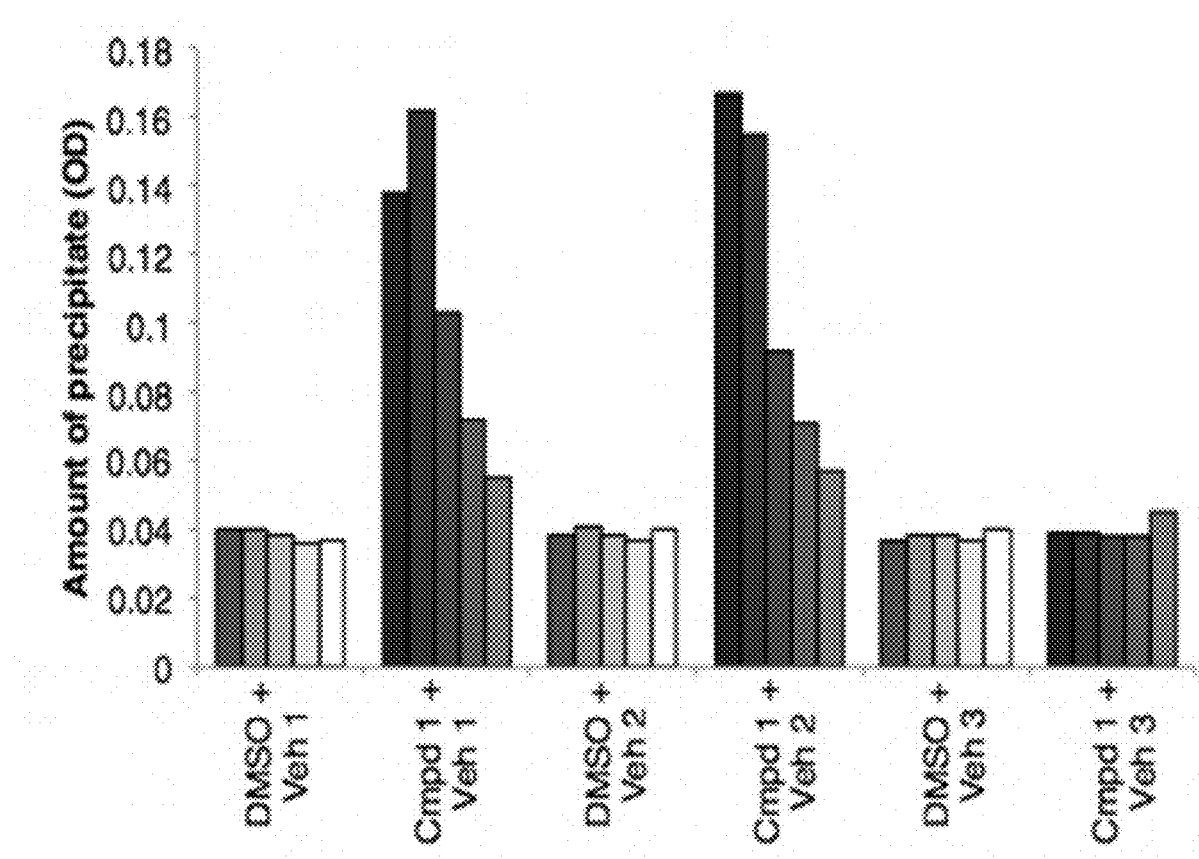
FIG. 12 shows that the addition of 2-hydroxypropyl-β-cyclodextrin can increase the solubility of compound 1 and its analogs. Compound 1 or DMSO (the diluent for compound 1 and its analogs) were mixed with different vehicle compositions at concentrations corresponding to relevant in vivo doses (2-10 mg/kg). Vehicle 1 (55% Saline, 40% PEG-400, 5% DMSO) was previously used for in vivo delivery of compound 1 (Goodfellow V S et al., 2013). These mixtures were then read on a spectrophotometer at 540 nM to assess optical density, a measure of the transparency of the mixture and an indicator of the formation of precipitates. Vehicles 1 and 2 did not form precipitates in the presence of DMSO alone, but did in the presence of compound 1. At higher concentrations, these precipitates were visible by eye. The addition of 11% 2-hydroxypropyl-β-cyclodextrin to the components of vehicle 1 was sufficient to solubilize compound 1 (vehicle 3).
Figure 12:
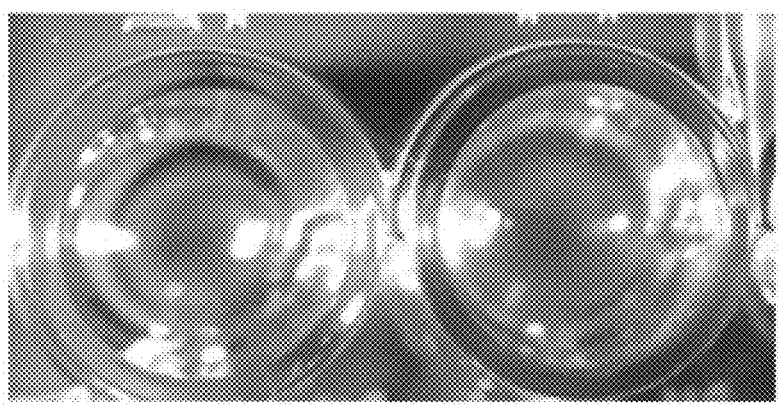

Compounds diluted in different vehicle formulations were added to clear cell culture media at ratios consistent with our in vivo dosing scheme. Plates were then read on a spectrophotometer at 540 nM, a wavelength where the compounds do not absorb light, to measure optical density and determine whether they are forming light-obstructing precipitates. We found that adding 2-hydroxypropyl-p-cyclodextrin, a cyclic sugar oligomer with a well-characterized safety profile, was sufficient to fully solubilize compound 1 and its analogs (FIG. 12).

Animal Treatment

All studies were performed on 6-week old male C57BL6/J mice that were housed in the Columbia University Medical Center facility in a 12h light/dark cycle with access to food and water ad libitum. All animal procedures were approved by the Columbia University IACUC. Compound 1 and its analogs were formulated a vehicle composed of 50% ddH2O containing 20% 2-hydroxypropyl-p-cyclodextrin (11% final concentration)+40% PEG-400+5% DMSO. Animals were weighed and injected once intraperitoneally (IP) at the indicated dose (10 or 20 mg/kg). After 30 min, animals were deeply anesthetized with 2.5% Avertin. Whole blood was collected by cardiac puncture in tubes containing 0.5M EDTA as an anticoagulant, and centrifuged for 10 min at 845 rcf at 4° to isolate plasma. Following cardiac puncture, animals were decapitated and brains were dissected and weighed. Brain samples were homogenized with a glass dounce homogenizer in 5 volumes of ddH2O. Brain and plasma samples were snap frozen in liquid nitrogen and stored at −80° C. before further processing.

Compound Concentration in Plasma

The plasma samples were transferred to Eppendorf tubes (50 µL per sample) and diluted with acetonitrile (200 µL). The samples were sonicated for 1 minute followed by centrifugation at 16,000 rpm for 10 minutes. The supernatant was transferred to another Eppendorf tube and the solvent evaporated overnight. The samples were reconstituted in a mixture of 40 µL acetonitrile and 10 µL water transferred to a sample vial with insert, and analyzed by LC-MS.

Compound Concentration in the Brain

The homogenized brain samples (250 µL) were transferred to Eppendorf tubes and diluted with acetonitrile (750 µL). The samples were sonicated for 1 minute followed by centrifugation at 16,000 rpm for 10 minutes. The supernatant (900 µL) was transferred to another Eppendorf tube and the solvent evaporated overnight. The samples were reconstituted in a mixture of 80 µL acetonitrile and 20 µL water, transferred to a sample vial with insert, and analyzed by LC-MS.

LC-MS Analysis

LC-MS analysis was performed on a platform comprising a Thermo Scientific Dionex Ultimate 3000 and a Bruker amaZon SL equipped with an electrospray ionization source controlled by Bruker Hystar 3.2. The compound concentration in each plasma sample was determined using a calibration curve. Chromatographic separation was performed by injecting 10 µL of the sample onto an Agilent Eclipse Plus C18 column (2.1×50 mm, 3.5 µm) maintained at 20° C. The flow rate was maintained at 400 µL/min. The initial flow conditions were 60% solvent A (water containing 0.1% acetic acid) and 40% solvent B (methanol containing 0.1% acetic acid). Solvent B was raised to 60% over 0.25 minutes and to 70% by 6.75 minutes. Solvent B was raised to 95% by 7.00 minutes and lowered back to initial conditions (40%) by 8.00 minutes with a total run time of 9.00 minutes.

Results

The pharmacokinetics results of selected compounds (12h, 12i, 12k, 12l) at different dosings in brain and plasma are summarized in the following tables. The comparison between compound 1 and compound 12k is further shown and discussed in at least FIG. 13B, FIGS. 34A-34B, FIGS. 35A-35C, FIG. 36, FIGS. 37A-37B and Example 13.

TABLE 1

Blood and brain concentration upon compound treatment (ip dosing, 10 mg/kg, 30 minutes)[a, b]

| compound | plasma ng/mL | brain ng/g | B/P | plasma µM | brain µM |
|---|---|---|---|---|---|
| 12h | <250[b] | <500[b] | 2.0 | <0.58[b] | <1.2[b] |
| 12i | <600[b] | 2239 | 3.7 | <1.55[b] | 5.78 |
| 12k | <375[b] | 1226 | 3.3 | <0.84[b] | 2.74 |
| 12l | <600[b] | <1000[b] | 1.7 | <1.49[b] | >2.48[b] |
| 1 | 3211 | 1010 | 0.3 | 6.00 | 1.89 |

[a]Compounds were formulated in a mixture of DMSO:PEG-500:Saline:Cyclodextrins
[b]Compound concentration below limit of quantitation

TABLE 2

Blood and brain concentration upon compound treatment (ip dosing, 20 mg/kg, 30 minutes)

| compound | plasma ng/mL | brain ng/g | B/P | plasma µM | brain µM |
|---|---|---|---|---|---|
| 12h | 505 | 1670 | 3.3 | 1.17 | 3.88 |
| 12i | 3488 | 9779 | 2.8 | 9.00 | 25.24 |
| 12k | 1289 | 5178 | 4.0 | 2.88 | 11.58 |
| 12l[c] | — | — | — | — | — |
| 1 | 3480 | 1412 | 0.4 | 6.50 | 2.64 |

[a]Compounds were formulated in a mixture of DMSO:PEG-500:Saline:Cyclodextrins
[b]Compound concentration below limit of quantitation
[c]Compound was toxic at this concentration Example 11

Bioavailability and Best Delivery Route of Compounds

Figure 4A:
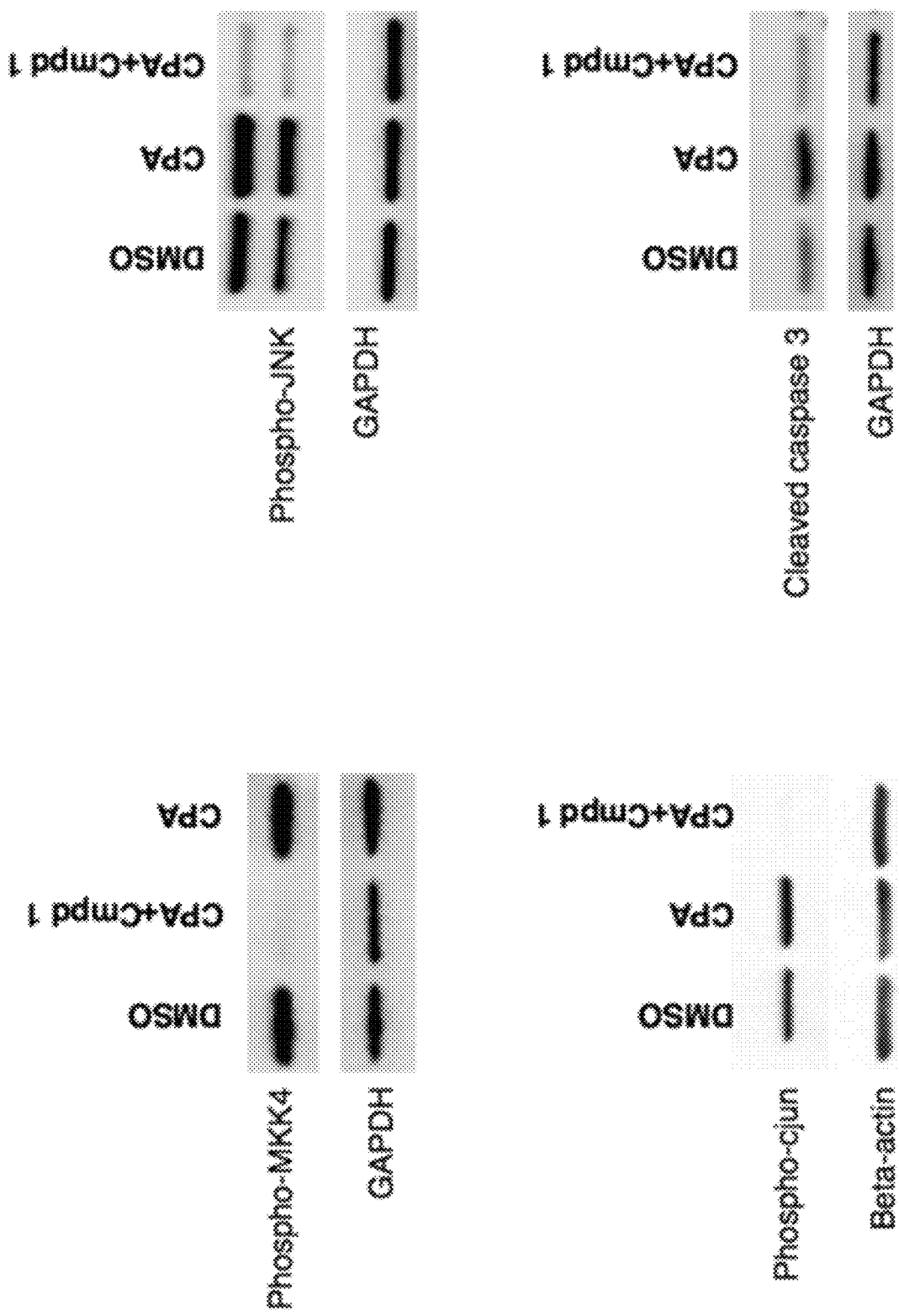
FIG. 4A shows the expression of different putative downstream targets of compound 1 in the context of ER stress. Mouse ES-derived motor neurons were treated with CPA, CPA+ compound 1, or vehicle control (DMSO) for four hours. Cells were then lysed to extract proteins. Protein extracts were analyzed by western blot for expression of the activated forms of the putative downstream targets of compound 1, including phosphorylated MKK4 (a kinase immediately downstream of the compound 1 target MLK3), phosphorylated JNK (a kinase immediately downstream of MKK4), phosphorylated c-jun (a transcription factor immediately downstream of JNK), and cleaved caspase 3 (a widely-recognized marker of apoptotic cell death). All were up-regulated by CPA, indicating that CPA causes motor neuron degeneration through JNK pathway-driven apoptosis. Meanwhile, the addition of compound 1 attenuates the activation of these pathway components, confirming that compound 1 is targeting an upstream kinase within this pathway.
Figure 4B:
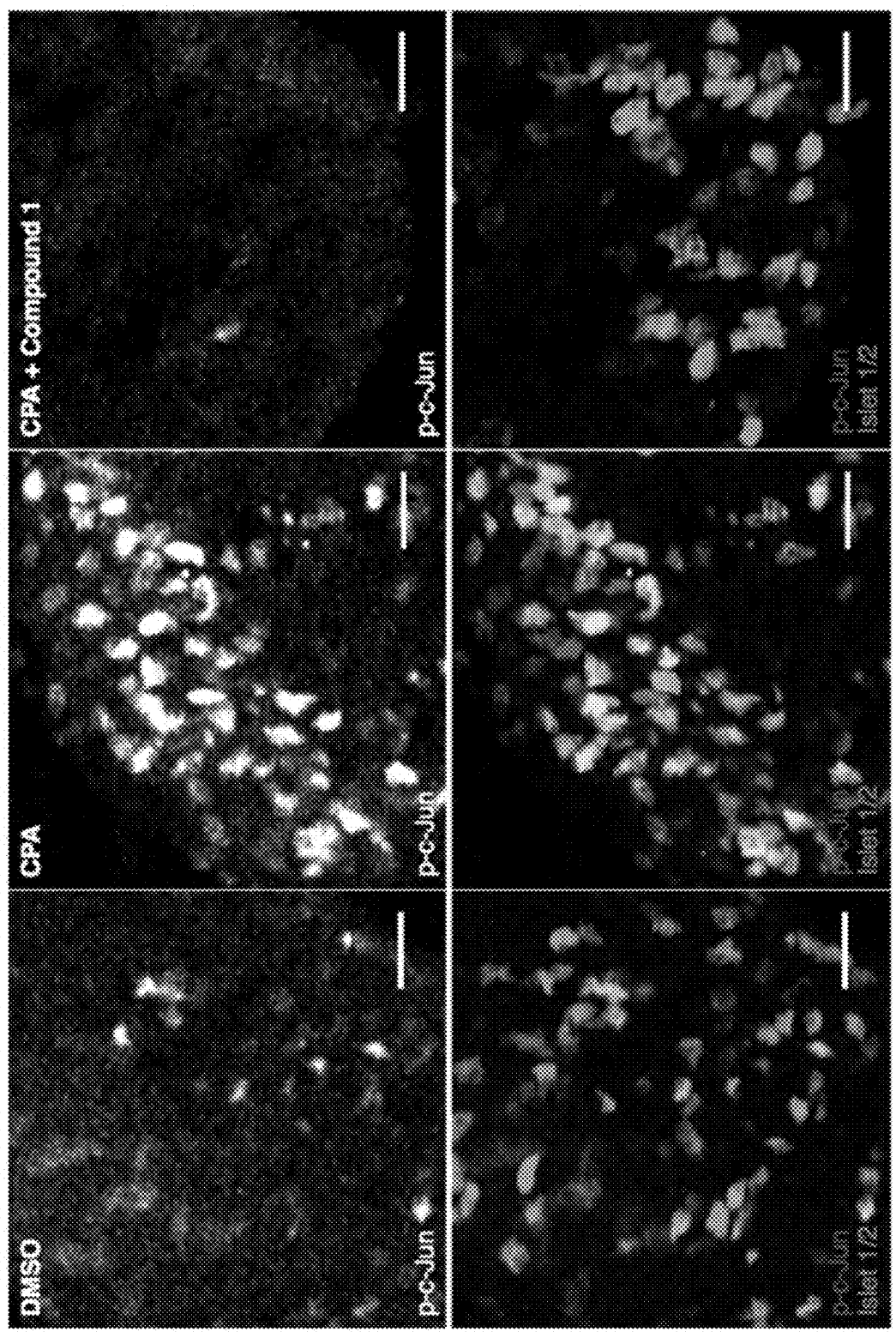
FIG. 4B shows immunostained mouse ES-derived motor neurons. ES-derived motor neurons were treated with CPA+/− compound 1 in the same manner as described in FIG. 4A to determine whether the modulation of compound 1 target activity was occurring in motor neurons or in other contaminating cell types. The resulting images indicate that CPA treatment strongly and selectively induces c-jun phosphorylation in motor neurons, while compound 1 completely attenuates it. Motor neurons are indicated by Islet 1-2 immunoreactivity.

We observed in vitro that phospho-cjun's expression is strongly up-regulated by CPA treatment and strongly attenuated by compound 1, and is a likely downstream effector of the kinase target(s) of compound 1 (FIG. 4A and FIG. 4B).

Figure 14:
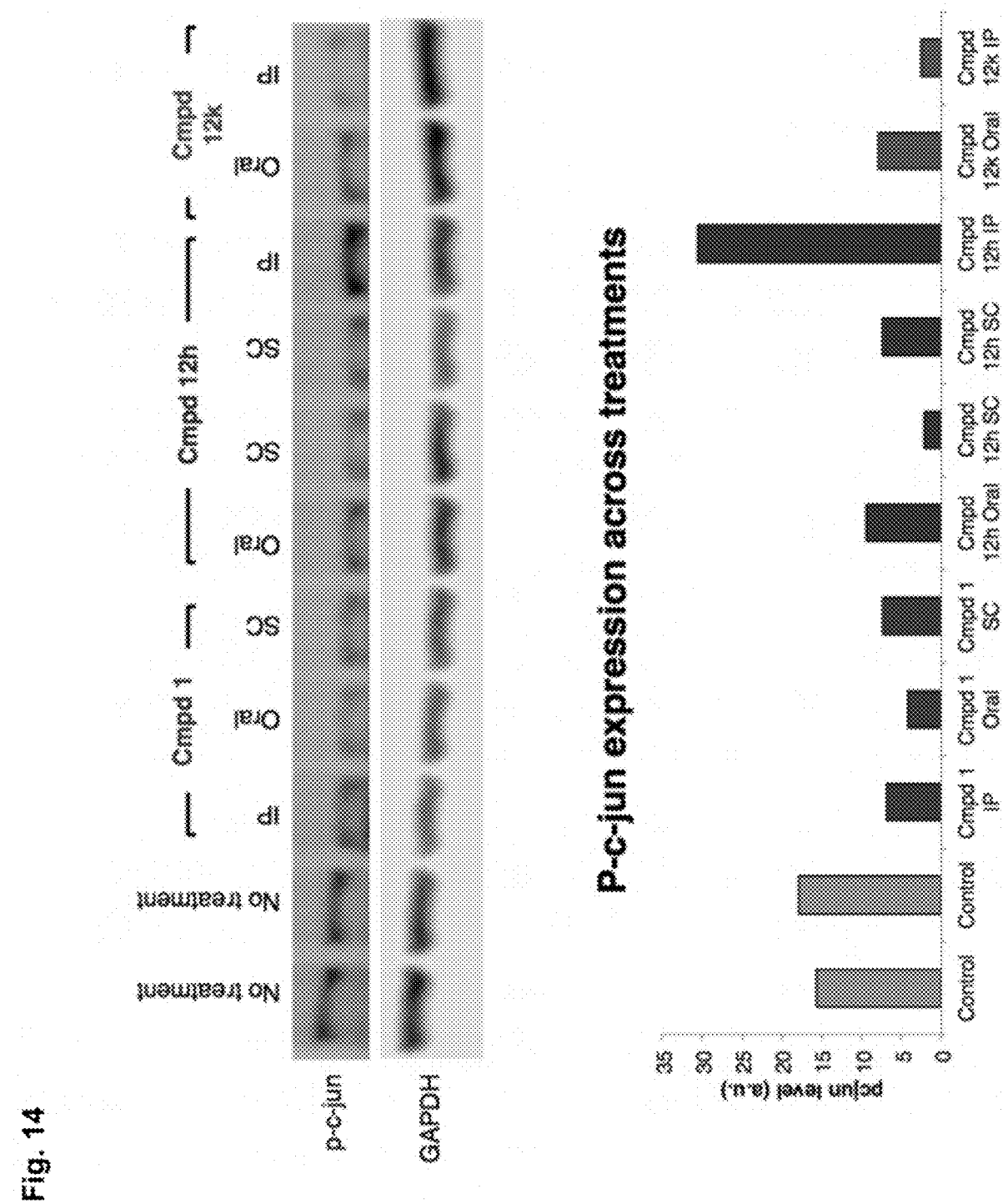
FIG. 14 shows the expression of phosphorylated (activated) c-jun in the olfactory bulbs of wild-type mice following treatment with compound 1 and its analogs 12 h and 12k. Compounds at 10 mg/kg were delivered intraperitoneally (IP), orally, or sub-cutaneously (SC). Animals were sacrificed 1 h after treatment. Their olfactory bulbs were dissected and lysed for western blot analysis. Phospho-cjun expression was normalized to the housekeeping protein GAPDH. Compared to untreated animals, phospho-cjun levels were decreased by almost all treatment conditions, indicating that compound 1 and its analogs are engaging the same targets in vivo as they are in vitro.

We therefore selected phospho-cjun as a marker of target engagement for further in vivo studies. C-jun is highly expressed throughout the murine central nervous system, especially in the olfactory bulbs. 8-week-old wildtype C57BL/6j mice (Jackson) were treated with 10 mg/kg of compound 1, 12h, or 12k delivered by oral gavage, intraperitoneal injection, or subcutaneous injection (FIG. 14). Animals were then sacrificed after 1 h, and their olfactory bulbs were sub-dissected and lysed for further western blot analysis. Samples were probed with an antibody specific to phosphorylated c-jun (at serine 63; cell signaling) and normalized to the housekeeping gene GAPDH. Nearly all drug-treated samples showed a reduction of cjun phosphorylation compared to untreated controls, indicating that the drugs engage the same targets in vivo as they do in vitro. Furthermore, the reduction of cjun phosphorylation in samples from animals treated by oral gavage indicates that both 12h and 12k are orally bioavailable.

Example 12

A Sensitive Dual Color Motor Neuron Screen Reveals ALS-Relevant Stressors and Neuroprotective Agents Amyotrophic lateral sclerosis is a neurodegenerative disease targeting neurons in the motor cortex, brainstem and spinal cord. Mutations causing ALS were discovered in dozens of diverse genes, yet the reasons for differential motor neuron susceptibility remain poorly understood. We developed a sensitive two color co-culture system to study cell-autonomous mechanisms contributing to ALS motor neuron degeneration. Screening a library of bioactive compounds identified cyclopiazonic acid (CPA), an inhibitor of a calcium pump expressed in the endoplasmic reticulum (SERCA), as a stressor to which motor neurons expressing human SOD1 carrying the ALS causing G93A mutation are highly sensitive. Importantly, motor neurons are significantly more sensitive to CPA and induction of endoplasmic reticulum (ER) stress and unfolded protein response pathways than spinal interneurons. Secondary screen identified compounds that rescue motor neurons from CPA-induced degeneration, including three kinase inhibitors and tauroursodeoxycholic acid (TUDCA), an FDA-approved bile acid derivative. Treatment of mice expressing hSOD1$^{G93A}$ with TUDCA ameliorated early muscle denervation. The neuroprotective effects of the identified compounds were validated using human motor neurons differentiated from isogenic embryonic stem cell lines carrying an SOD1$^{A4V}$ 17 mutation. Overall, our results highlight the translational potential of the developed in vitro drug discovery platform, which could serve as a valuable tool for identifying new drug targets in the treatment of neurodegenerative diseases.

Amyotrophic lateral sclerosis (ALS) is a late onset neurodegenerative disease that preferentially targets neurons in the motor cortex and motor neurons in the brainstem and spinal cord. Despite the discovery of >40 mutations causing familial ALS (Peters et al. 2015), the pathological processes leading to motor neuron degeneration, and the reasons for differential neuronal subtype susceptibility to broadly expressed mutant proteins remain poorly understood.

Effective modeling of ALS is hindered by the limited accessibility of motor neurons in patients and animal models, and by the fact that ALS is a late-onset and relatively slow-progressing disease. The development of stem cell technologies that facilitate the large scale production of spinal motor neurons carrying disease-causing mutations has circumvented the first challenge and enabled biochemical analysis and drug screening in a relevant cellular context (Amoroso et al. 2013; Dimos et al. 2008; Hoing et al. 2012; Wichterle et al. 2002; Yang et al. 2013). However, stem cell-derived motor neurons are transcriptionally and electrophysiologically immature, and most closely resemble embryonic or early postnatal motor neurons (Patterson et al. 2012; Stein et al. 2014; Miles et al. 2004). Most importantly, stem cell-derived motor neurons carrying ALS-causing mutations do not exhibit key hallmarks of motor neuron disease, such as aggregates of mutant proteins (Bosco et al. 2010; Kiskinis et al. 2014; Wang et al. 2009).

Despite their relatively immature state, several studies have reported differences in the survival, physiology, and biochemistry of cultured human and mouse stem cell-derived ALS motor neurons (Kiskinis et al. 2014; Alami et al. 2014; Devlin et al. 2015; Di Giorgio et al. 2008; Di Giorgio et al. 2007; Donnelly et al. 2013; Egawa et al. 2012; Naujock et al. 2016; Sareen et al. 2013; Sivadasan et al. 2016; Wainger et al. 2014). These phenotypes could result from a stressful in vitro environment that elicits premature or aberrant manifestations of pathological processes in cultured cells, yet the nature of these culture-related stressors remains ill-defined. Understanding which specific stressors potentiate disease-relevant motor neuron pathology would enable the development of more faithful models of ALS and, in turn, better tools to understand the onset and progression of the disease and to screen for neuroprotective drugs.

Here, we developed a highly sensitive motor neuron survival assay and used it to screen a library of bioactive compounds for stressors that sensitize motor neurons to overexpression of a human SOD1 transgene carrying a G93A mutation (hSOD1$^{G93A}$), which causes ALS-like motor neuron degeneration in transgenic mice (Gurney et al. 1994). The screen identified cyclopiazonic acid (CPA), an inhibitor of a calcium pump expressed in the endoplasmic reticulum (SERCA) (Goeger et al. 1988), as a compound to which ALS motor neurons are highly sensitive. We demonstrate that CPA rapidly induces endoplasmic reticulum (ER) stress and unfolded protein response pathways in cultured motor neurons. Accumulation of misfolded proteins is a hallmark of many neurodegenerative diseases and has been described in conjunction with the activation of ER stress in animal and stem cell based models of ALS (Kiskinis et al. 2014; Hetz et al. 2009; Saxena et al. 2009; Saxena et al. 2013), as well as in postmortem spinal cord samples from ALS patients (Hetz et al. 2009; Atkin et al. 2006; Atkin et al. 2008).

Taking advantage of this accelerated motor neuron degeneration paradigm, we performed a second screen to identify compounds that protect spinal motor neurons against CPA toxicity. We demonstrate that kenpaullone, a protein kinase inhibitor that was recently shown to protect motor neurons from neurotrophic factor withdrawal (Yang et al. 2013; Liu et al. 2016), also protects motor neurons in the CPA assay. In addition to kenpaullone, we identified several other protective compounds, including additional kinase inhibitors and a bile acid component, tauroursodeoxycholic acid (TUDCA). The rescue effects of these compounds in mouse stem cell-derived motor neurons were recapitulated in human stem cell-derived motor neurons. Furthermore, we found that TUDCA reduced neuromuscular junction denervation in transgenic hSOD1$^{G93A}$ mice at early symptomatic stages of the disease.

Taken together, these findings highlight the translational potential of the developed stem cell-based motor neuron survival assay. In identifying the ER-stress inducing compound CPA as being preferentially toxic to motor neurons, our initial stressor screen independently rediscovered a pathway that is known to contribute to ALS pathology (Kiskinis et al. 2014; Saxena et al. 2009; Saxena et al. 2013; Nishitoh et al. 2008). Additionally, the protective effects of TUDCA in hSOD1$^{G93A}$ mice serve as proof-of-principle that the compounds emerging from the in vitro screening platform can transition seamlessly into in vivo models of ALS.
Subtle Defects in the Survival and Neurite Outgrowth of Stem Cell Derived Motor Neurons Expressing hSOD1$^{G93A}$ In order to gain insight into the pathological processes contributing to the onset of motor neuron degeneration in animals expressing mutant SOD1 protein, we developed a two-color motor neuron survival assay. We reasoned that the discovery of mechanisms contributing to increased sensitivity of motor neurons to ALS-causing mutations would require a robust, sensitive, and scalable system that could distinguish between motor neuron cell-autonomous phenotypes from non-cell-autonomous phenotypes associated with more advanced stages of the disease (Di Giorgio et al. 2008; Di Giorgio et al. 2007; Boillee et al. 2006; Kang et al. 2013; Nagai et al. 2007).

Figure 15A:
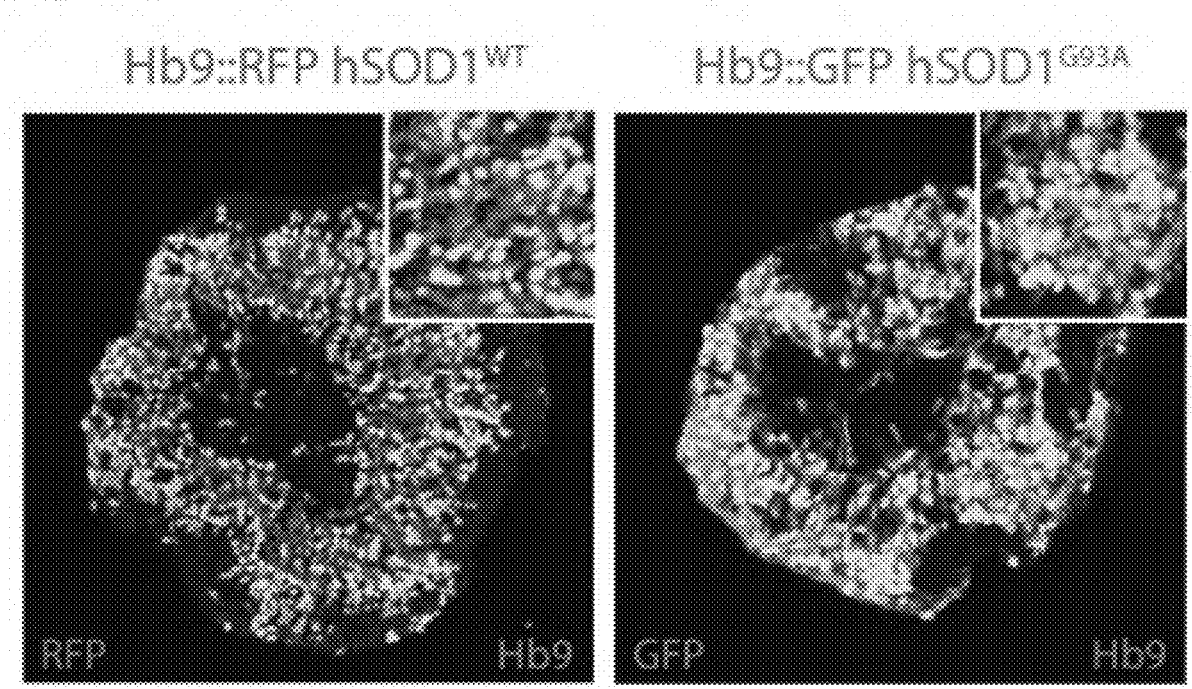
Figure 15B:
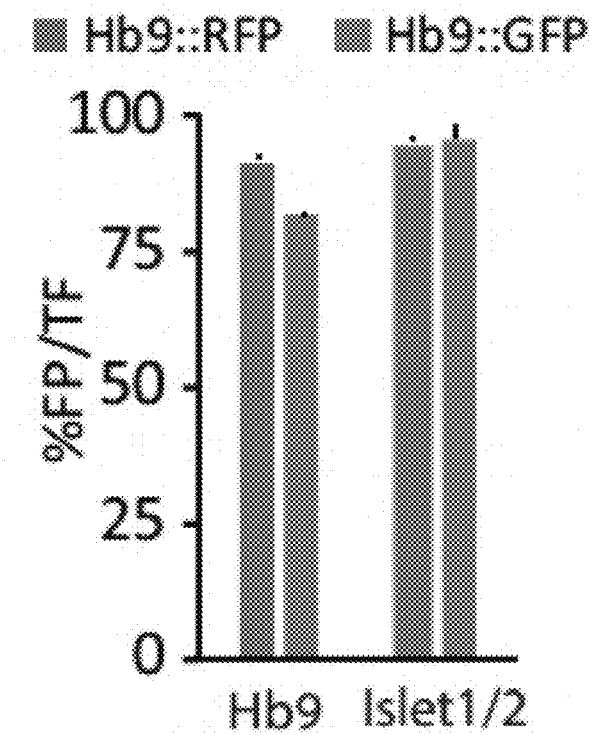
Figure 21A:
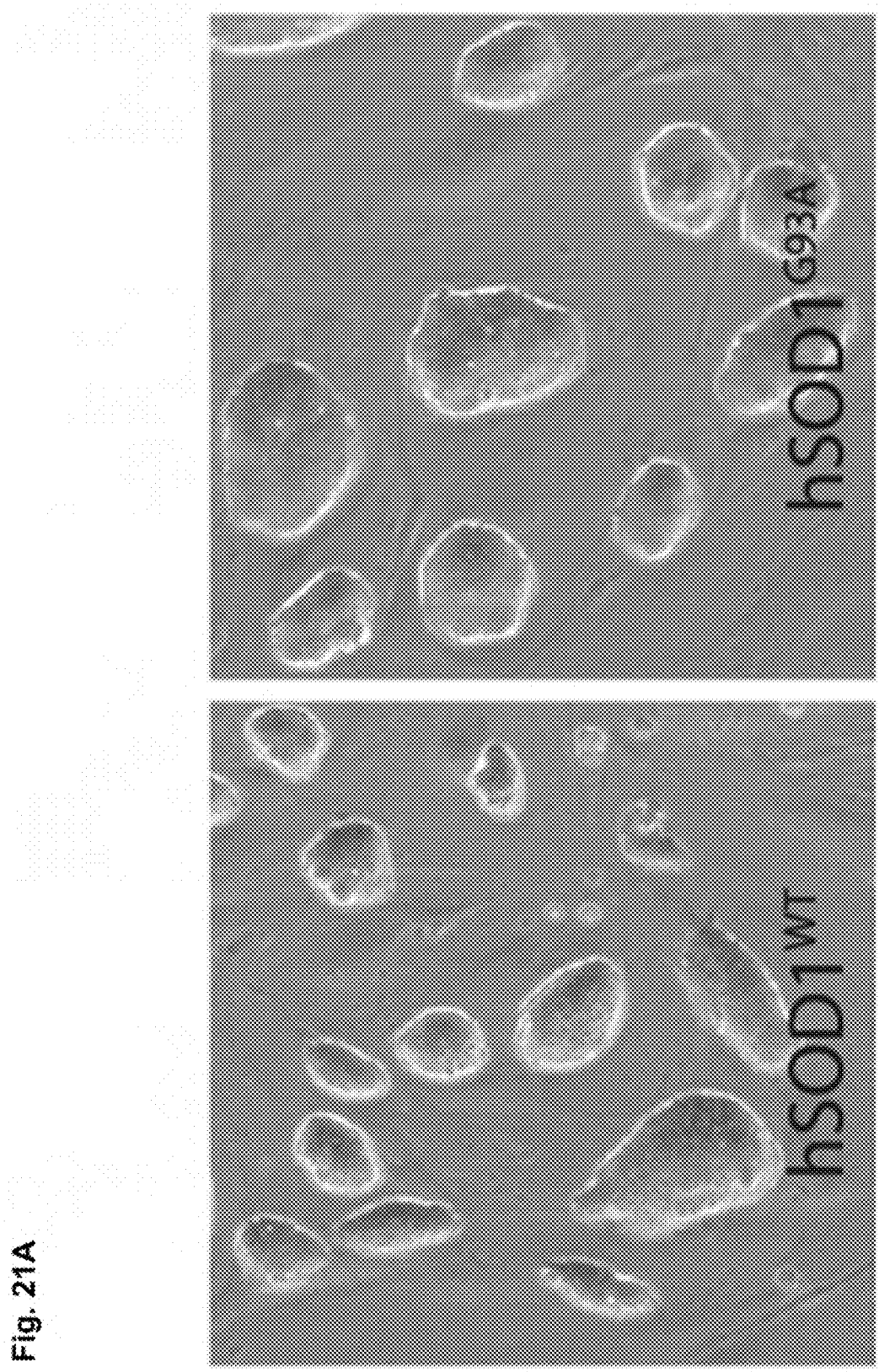
Figure 21B:
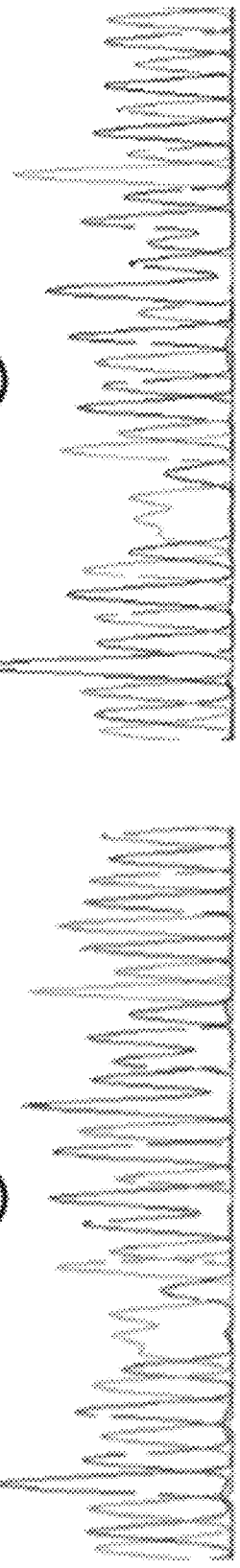
Figure 21C:
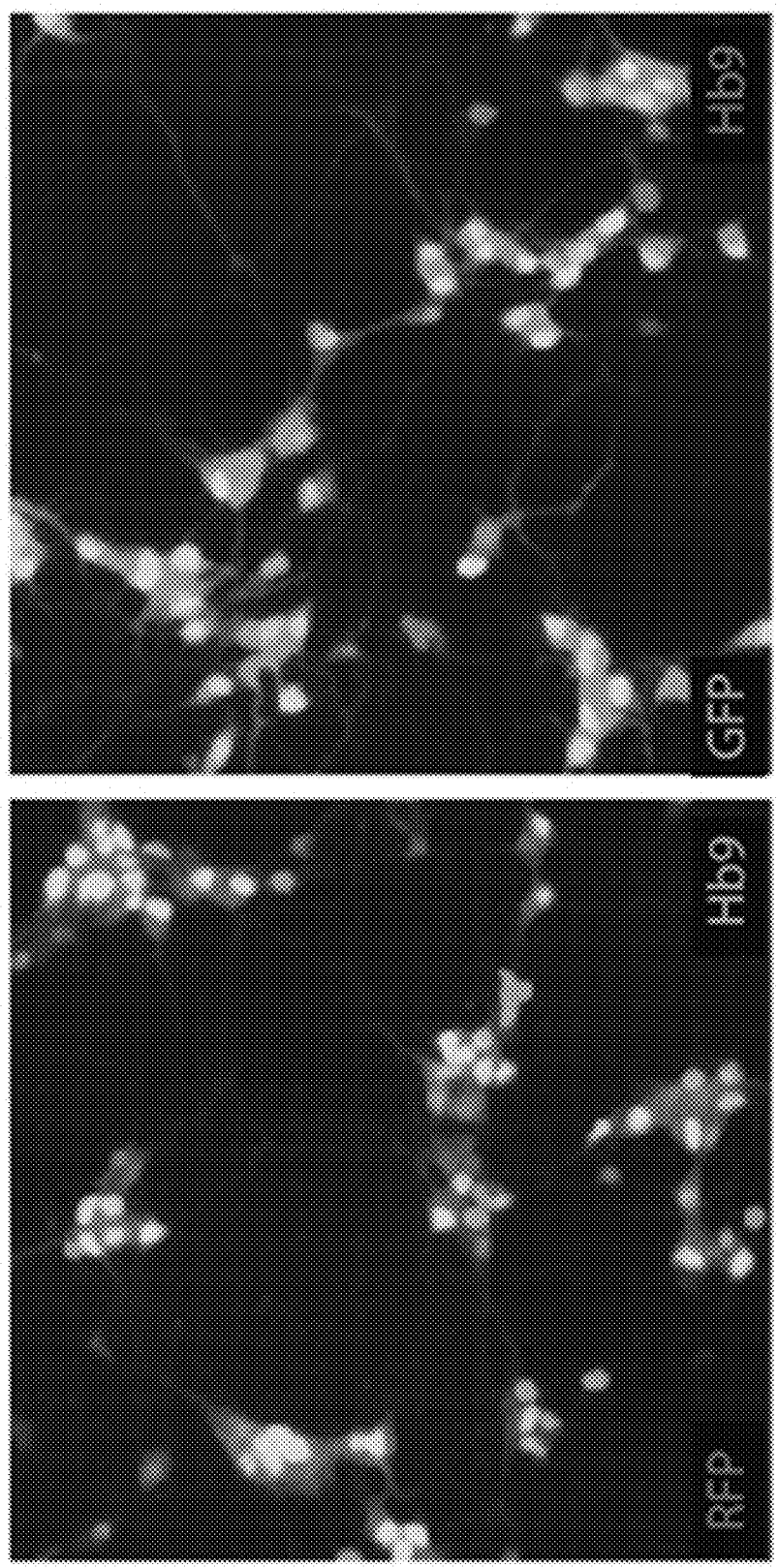
Figure 21D:
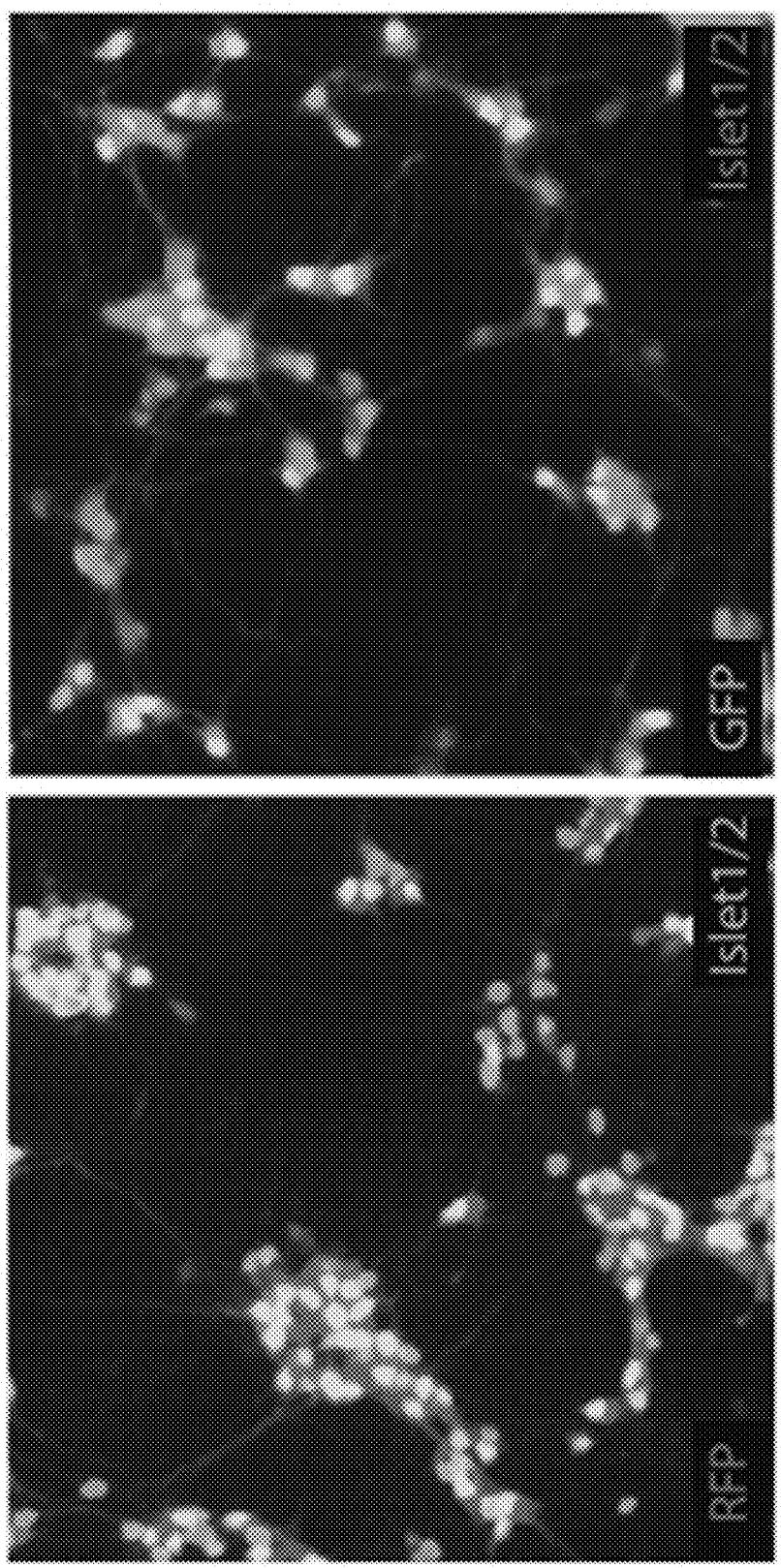

In order to distinguish between wild type (WT) and mutant motor neurons, minimize well-to-well variation and increase scalability, we generated new pluripotent embryonic stem cell (ESC) lines by crossing mice containing hSOD1$^{WT}$ (control) and hSOD1$^{G93A}$ (mutant) transgenes (Gurney et al. 1994) with mice expressing eGFP (Wichterle et al. 2002) or tagRFP under the control of a motor neuron-specific Hb9 (Mnx1) promoter (FIG. 15A; FIG. 21A and FIG. 21B). Immunostaining with antibodies against Hb9 and the motor neuron transcription factor Isl1 confirmed that the new cell lines differentiate into motor neurons with comparable efficiency (FIG. 15A and FIG. 15B, FIGS. 21C-21E). Next, we sought to determine whether the new mutant cell lines recapitulated known ALS phenotypes. Using immunohistochemistry and biochemistry (data not shown), we did not observe large SOD1 aggregates in mutant motor neurons that are typically observed in post-mortem tissue from ALS patients (Grad et al. 2014). However, immunoprecipitation with antibodies that specifically recognize conformational epitopes on misfolded human SOD1 did reveal the presence of misfolded SOD1 species (FIG. 21H), which have previously been implicated in ALS pathogenesis (Gros-Louis et al. 2010).

Figure 21F:
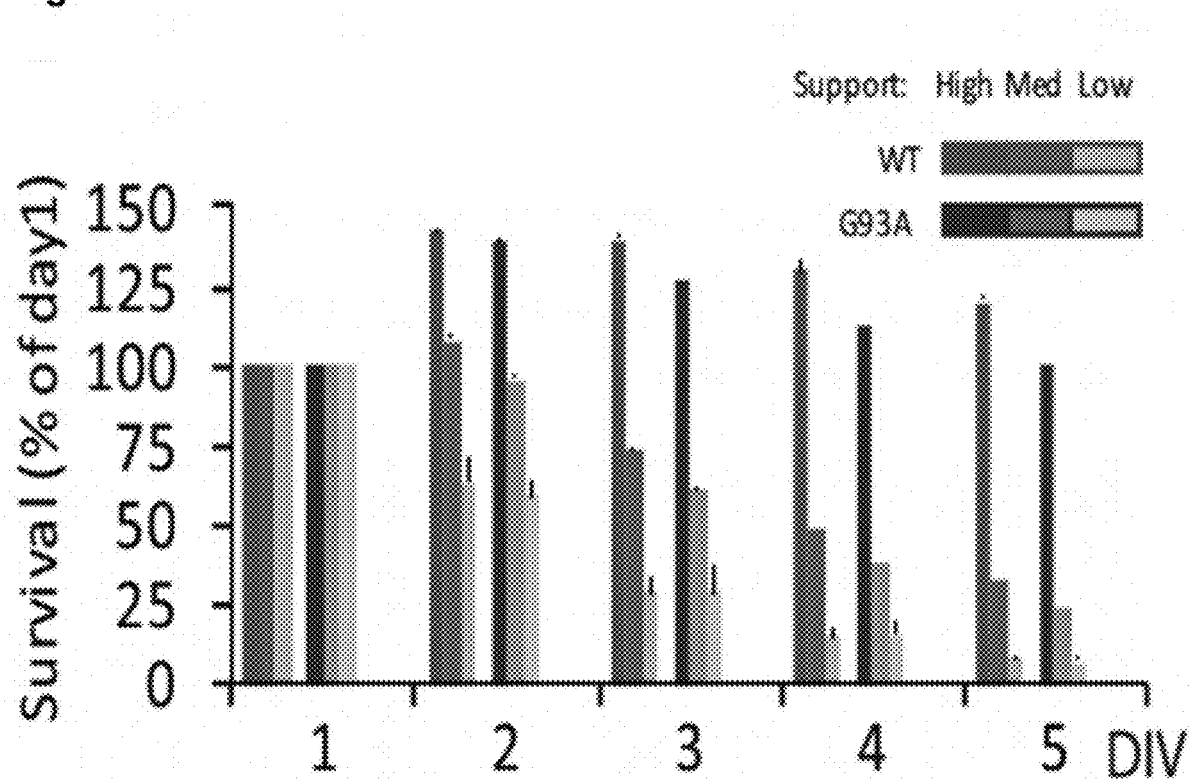
Figure 21G:
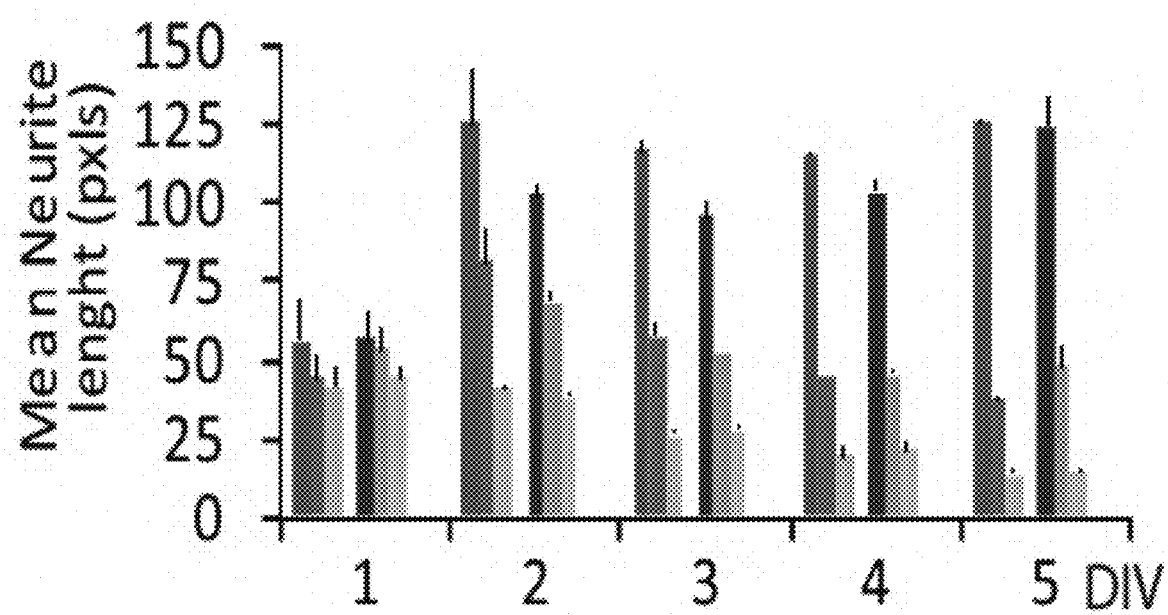
Figure 21H:
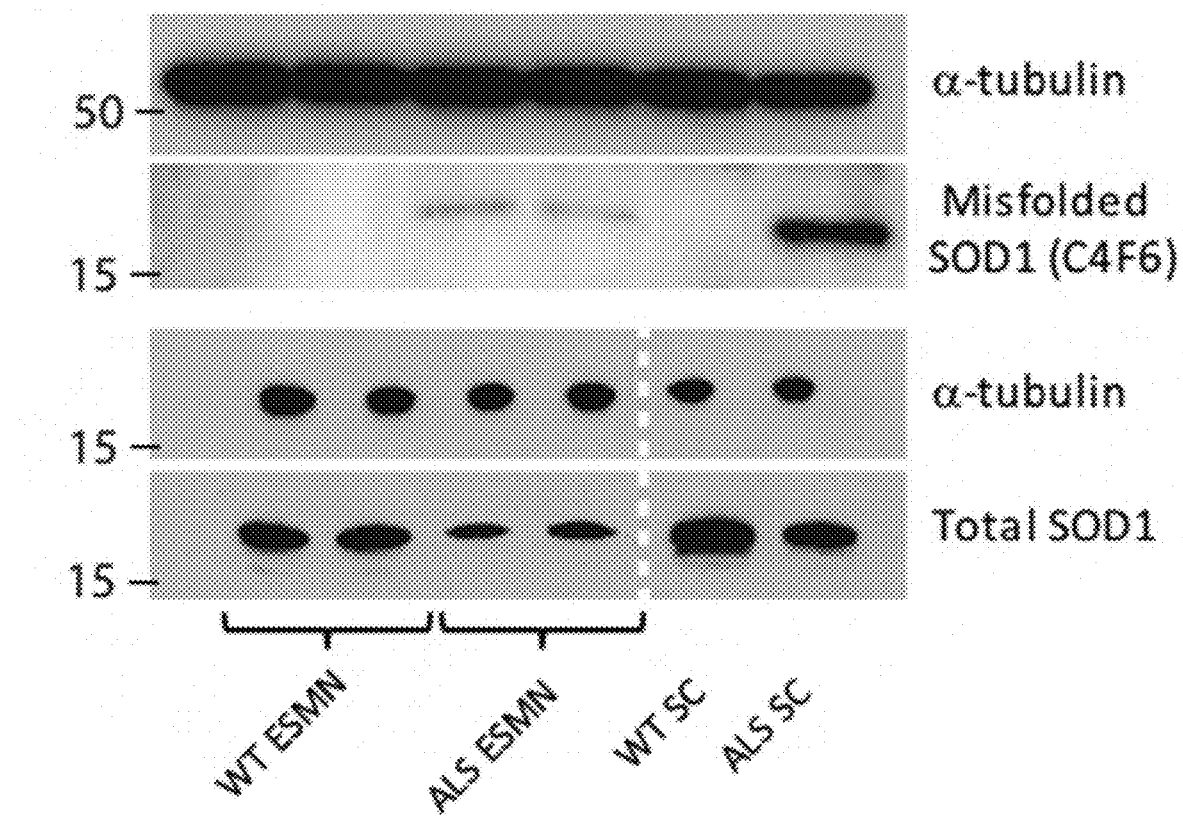
Figure 21I:
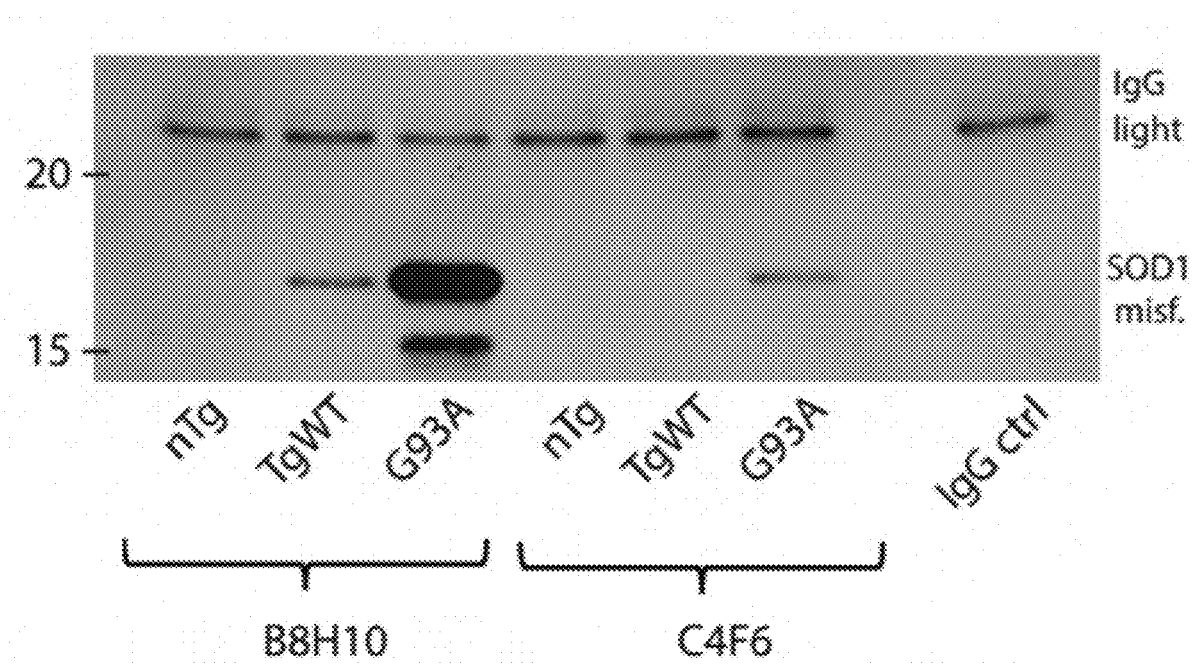
Figure 21J:
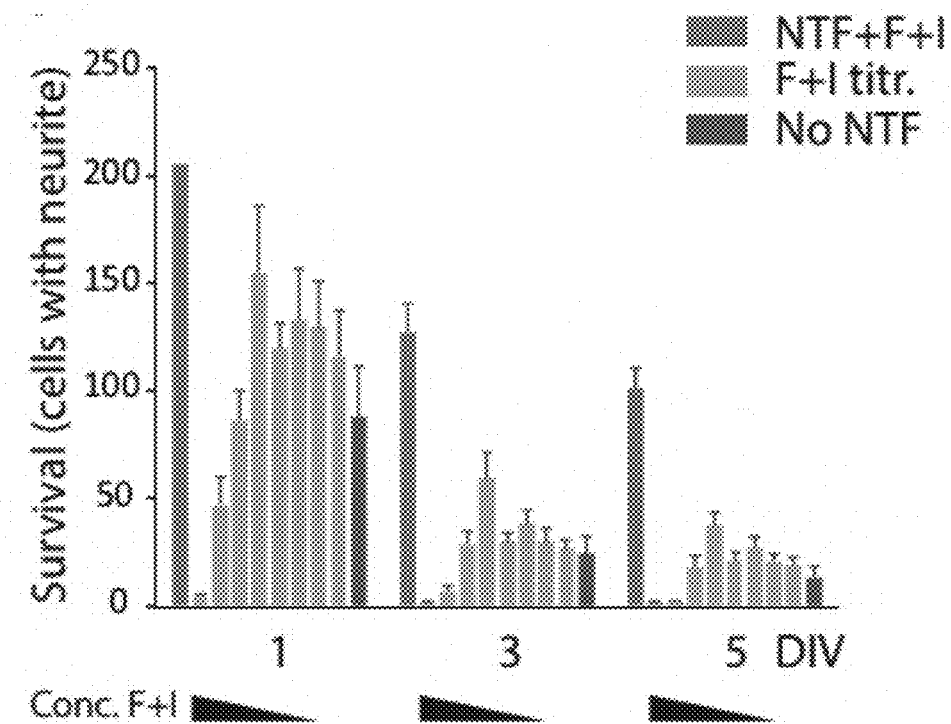
Figure 21K:
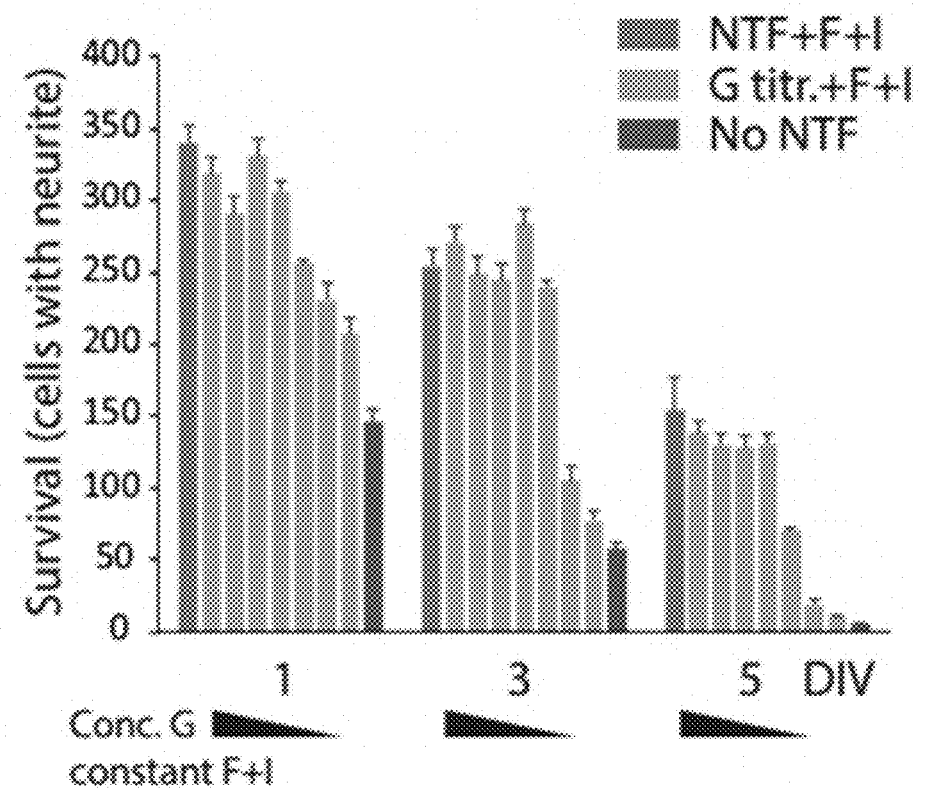

Nascent motor neurons are highly dependent on neurotrophic factors for their survival and for neurite extension (Henderson et al. 1994; Oppenheim et al. 1992; Sendtner et al. 1991). To determine whether growing motor neurons under suboptimal conditions resulted in the preferential degeneration of mutant over WT motor neurons, we cultured both genotypes in media supplemented with decreasing amounts of neurotrophic factors and assessed motor neuron survival and neurite outgrowth. The most supportive media contained neurotrophic factors with documented effects on motor neuron survival and neurite extension: glial cell-derived neurotrophic factor (GDNF), brain-derived neurotrophic factor (BDNF), ciliary neurotrophic factor (CNTF), and insulin-like growth factor-1 (IGF-1). We also assessed the effects of IBMX and forskolin, two compounds that increase levels of cyclic AMP (cAMP) and were previously shown to act synergistically with neurotrophins to support primary motor neurons survival (Hanson et al. 1998). IBMX and forskolin alone supported motor neuron survival during the first 24 hours after plating, but their effects diminished rapidly over the following 24-48 hours (FIG. 21J). Meanwhile, GDNF alone provided robust support for motor neuron survival for up to a week in culture, and its effects could be potentiated by the cAMP elevating compounds (FIG. 21K). Based on these results, we evaluated three different culture conditions: low neurotrophic support (10 µM forskolin+100 µM IBMX), medium neurotrophic support (10 µM forskolin+100 µM IBMX+0.4 ng/ml GDNF), and strong neurotrophic support (10 µM forskolin+100 µM IBMX+10 ng/ml of BDNF, CNTF, GDNF, and IGF-1) (FIG. 21F and FIG. 21G).

Figure 15C:
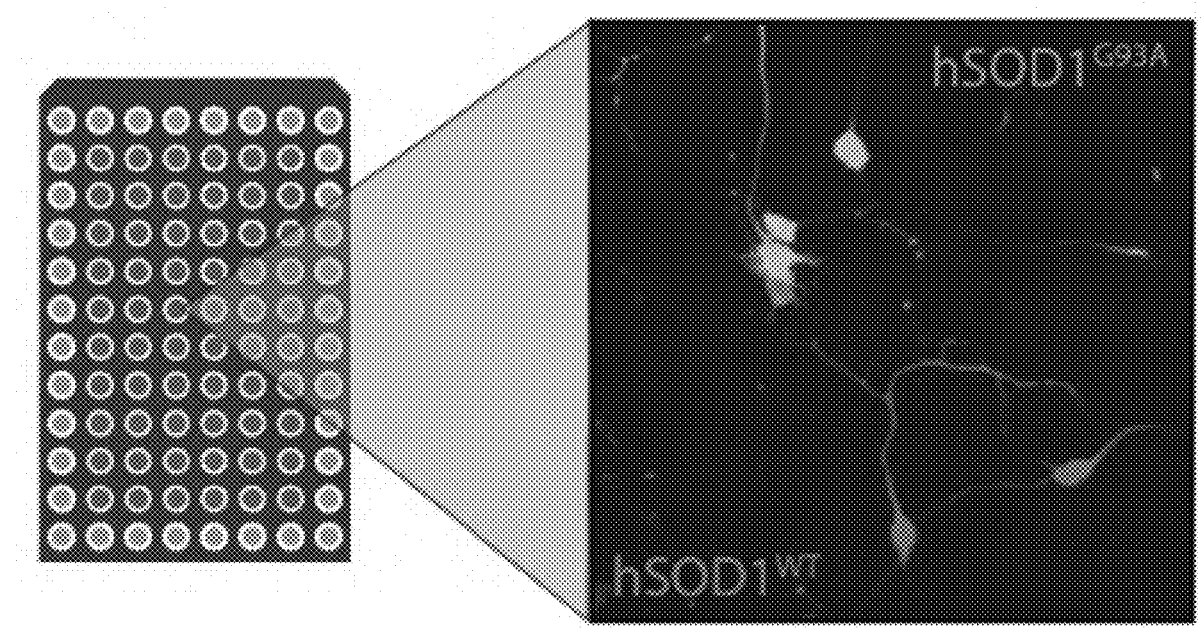
Figures 15D, 15E:
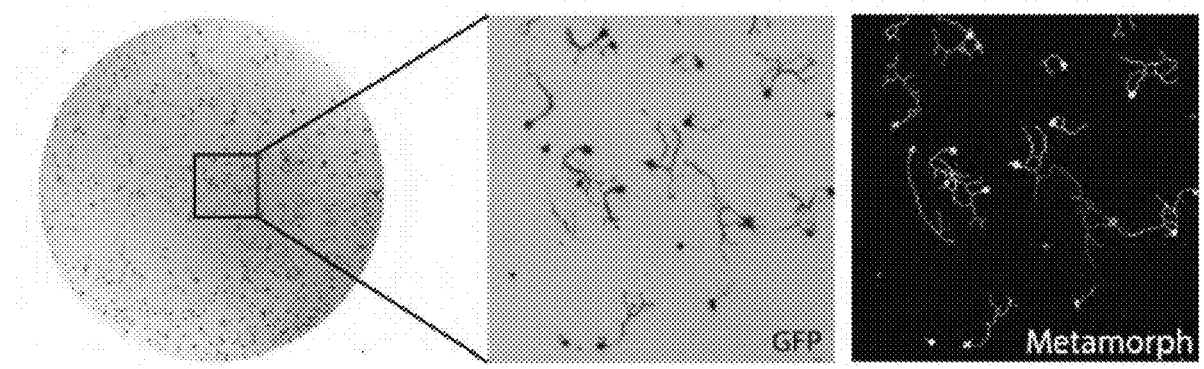
Figure 15F:
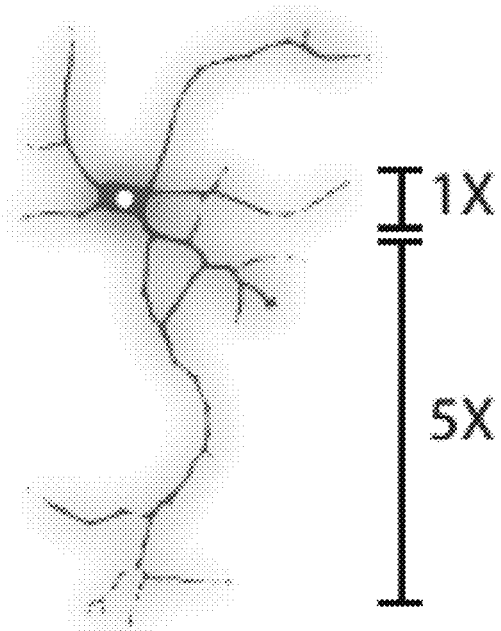
Figure 15G:
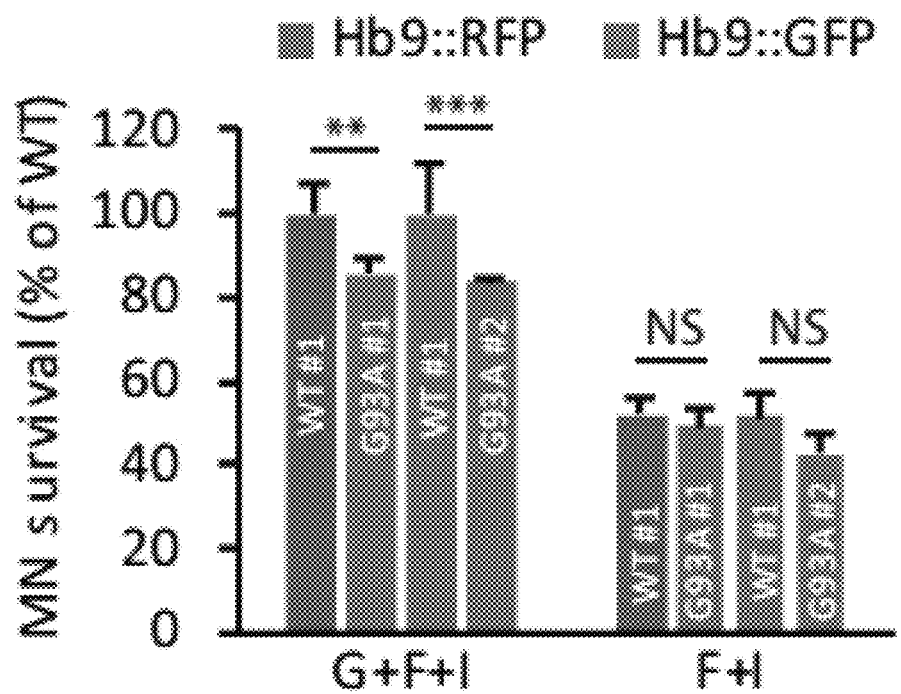

Cell survival and neurite extension were assessed by automated live imaging (Trophos Plate Runner) of fluorescent motor neurons (FIG. 15D and FIG. 15E). To distinguish between live cells and GFP-positive dead cells or fluorescent debris, we used Metamorph software (Molecular Devices) and applied a "healthy cell criterion", in which only cells with a neurite length equal to five times the average cell body diameter were included in the analysis (FIG. 15F). Quantification of the number of live motor neurons over the course of six days (FIG. 21F and FIG. 21G) revealed a modest, but consistent 15-20% reduction in survival and neurite outgrowth of mutant motor neurons compared to controls. This difference was in high and medium support, and was observed in both red-green mixed cultures or separate cultures for each genotype (FIG. 15G). Taken together, these findings indicate that withdrawal of neurotrophic factors does not potentiate survival deficit detected in ESC-derived hSOD1$^{G93A}$ expressing motor neurons.

A Dual Color Screen for Stressors Inducing Preferential Degeneration of Mutant Motor Neurons In order to identify pathways contributing to the degeneration of mutant motor neurons, we designed a stressor assay in which RFP-expressing control motor neurons were mixed with GFP-expressing mutant motor neurons in equal proportions, and cultured in 96-well plates (FIG. 15C) under medium neurotrophic support. We reasoned that analyzing motor neuron survival in mixed cultures containing also other ventral spinal neurons and glial cells from both genotypes would enable us to focus our study on cell-autonomous changes in motor neuron survival. Accordingly, the impact of any non-cell autonomous factors, such as ALS astrocyte toxicity (Kiskinis et al. 2014, Nagai et al. 2007), would be minimized as they would affect the survival of both genotypes equally.

Figure 15H:
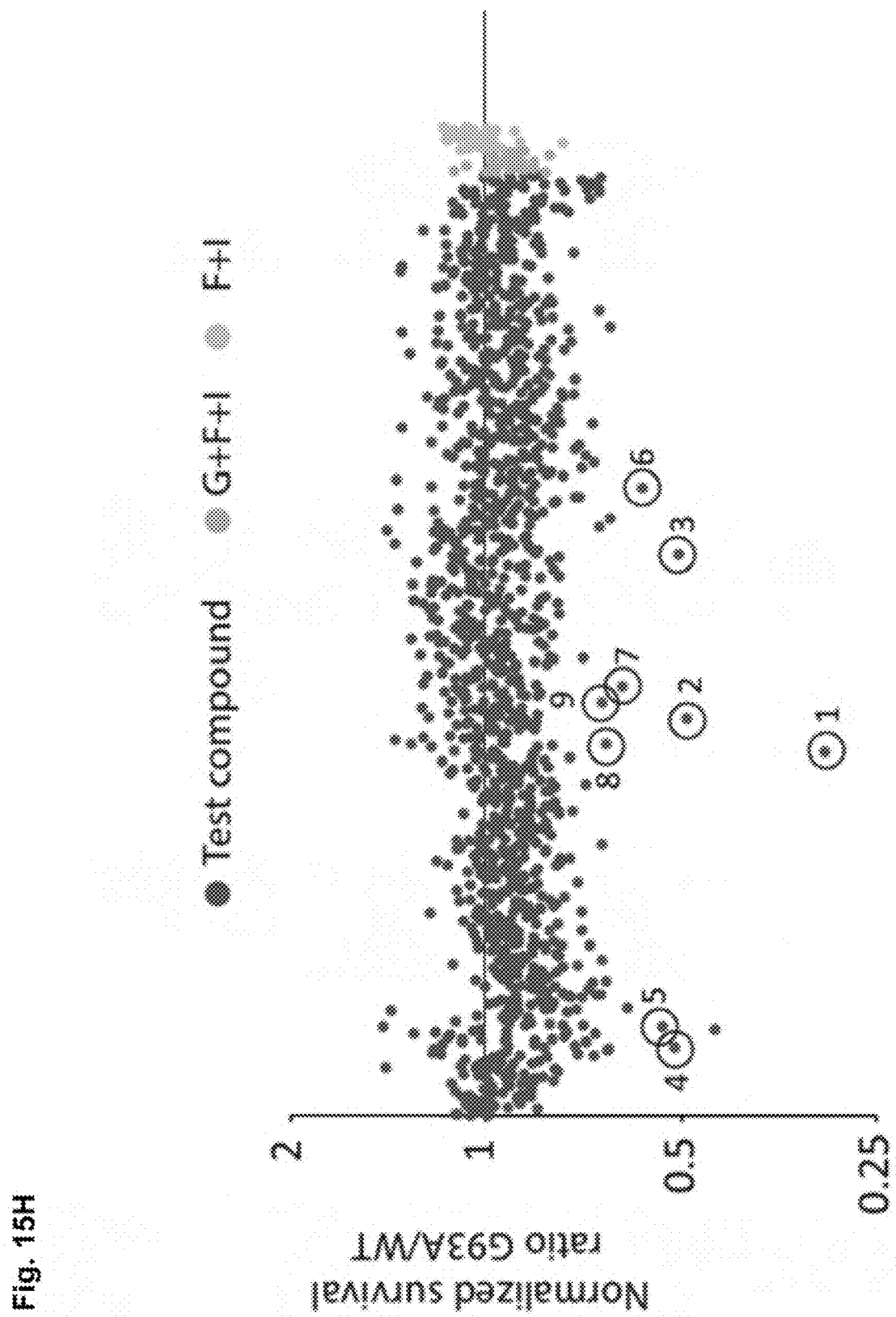
Figure 15J:
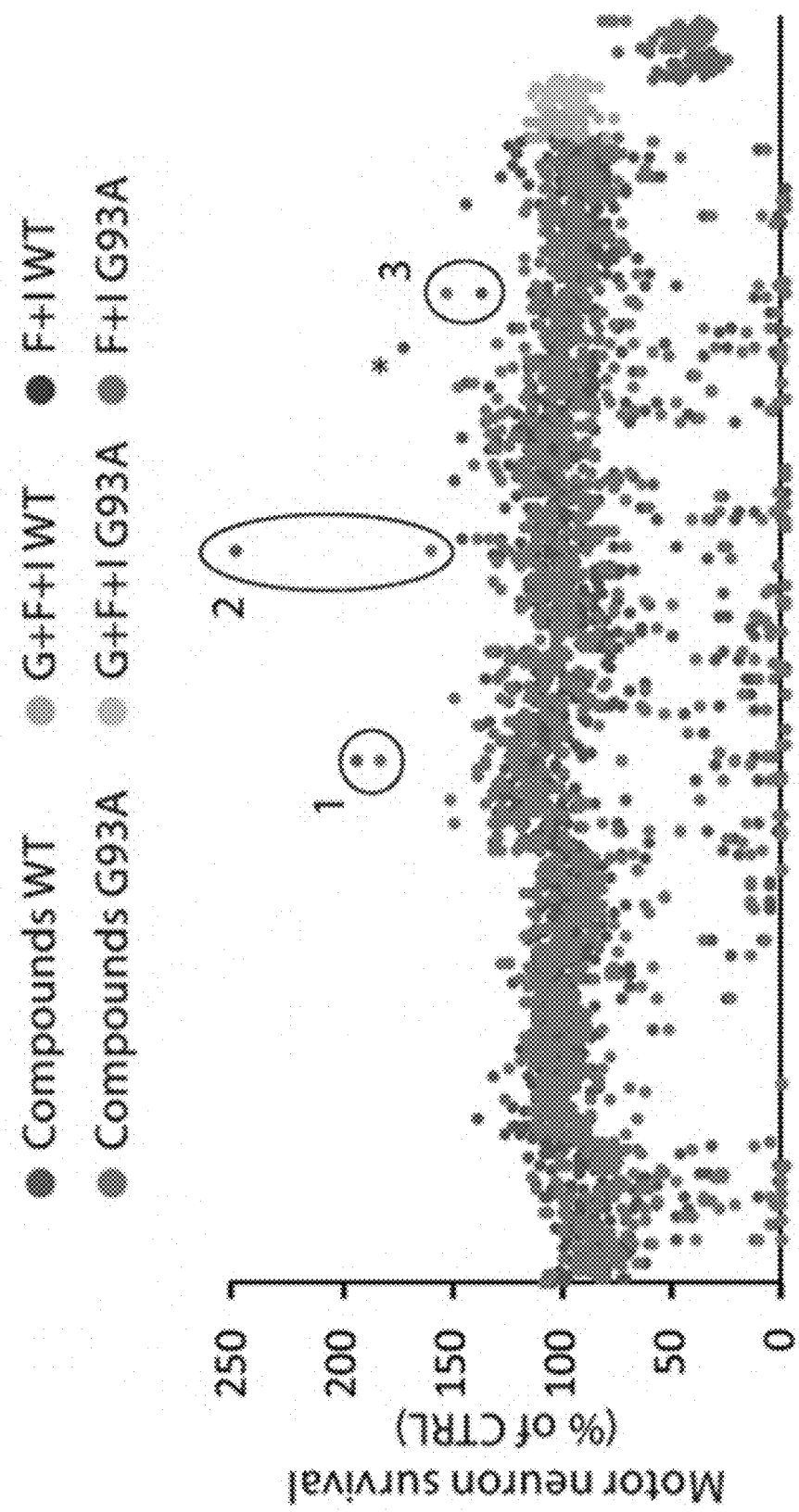
Figure 22A:
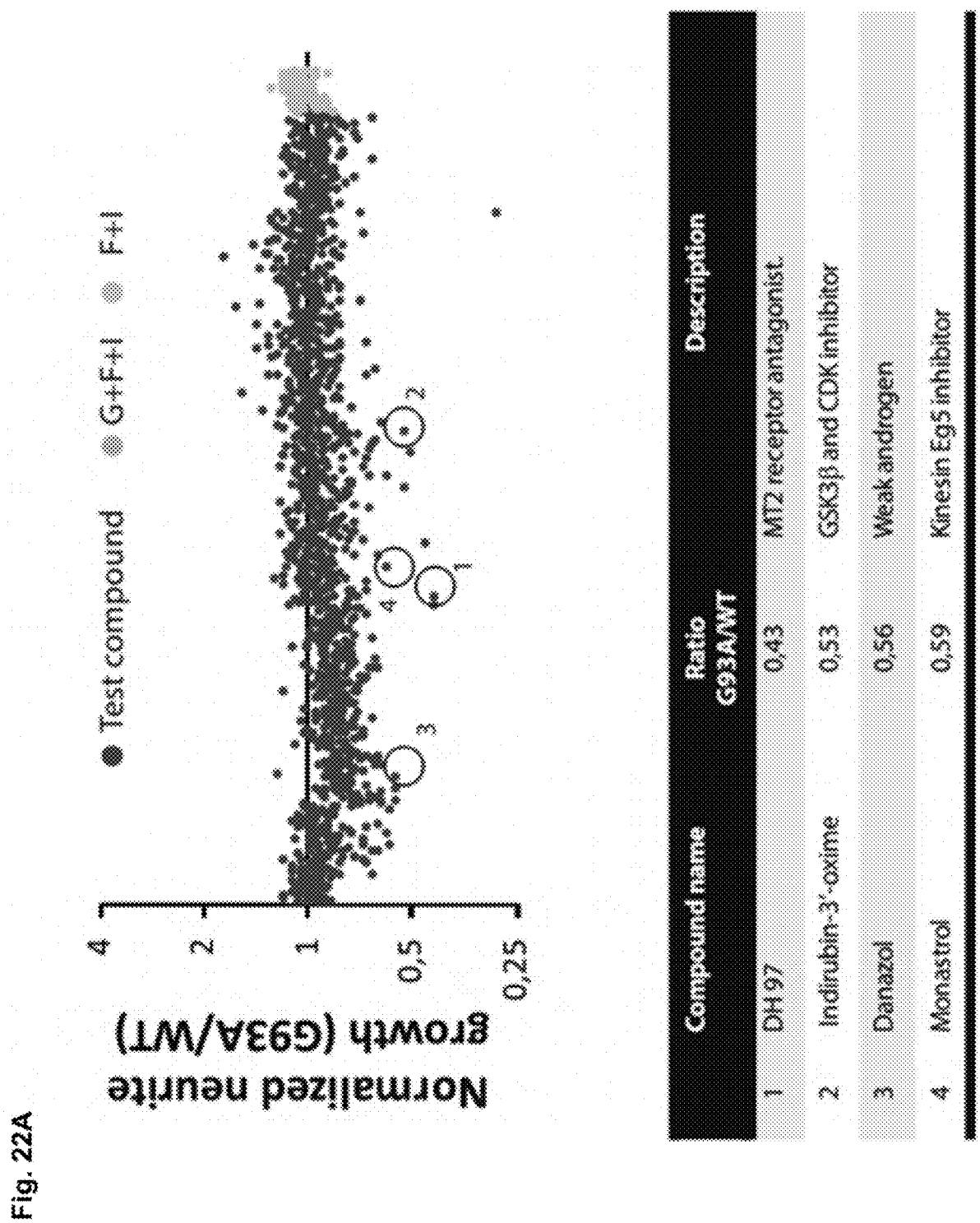
Figure 22B:
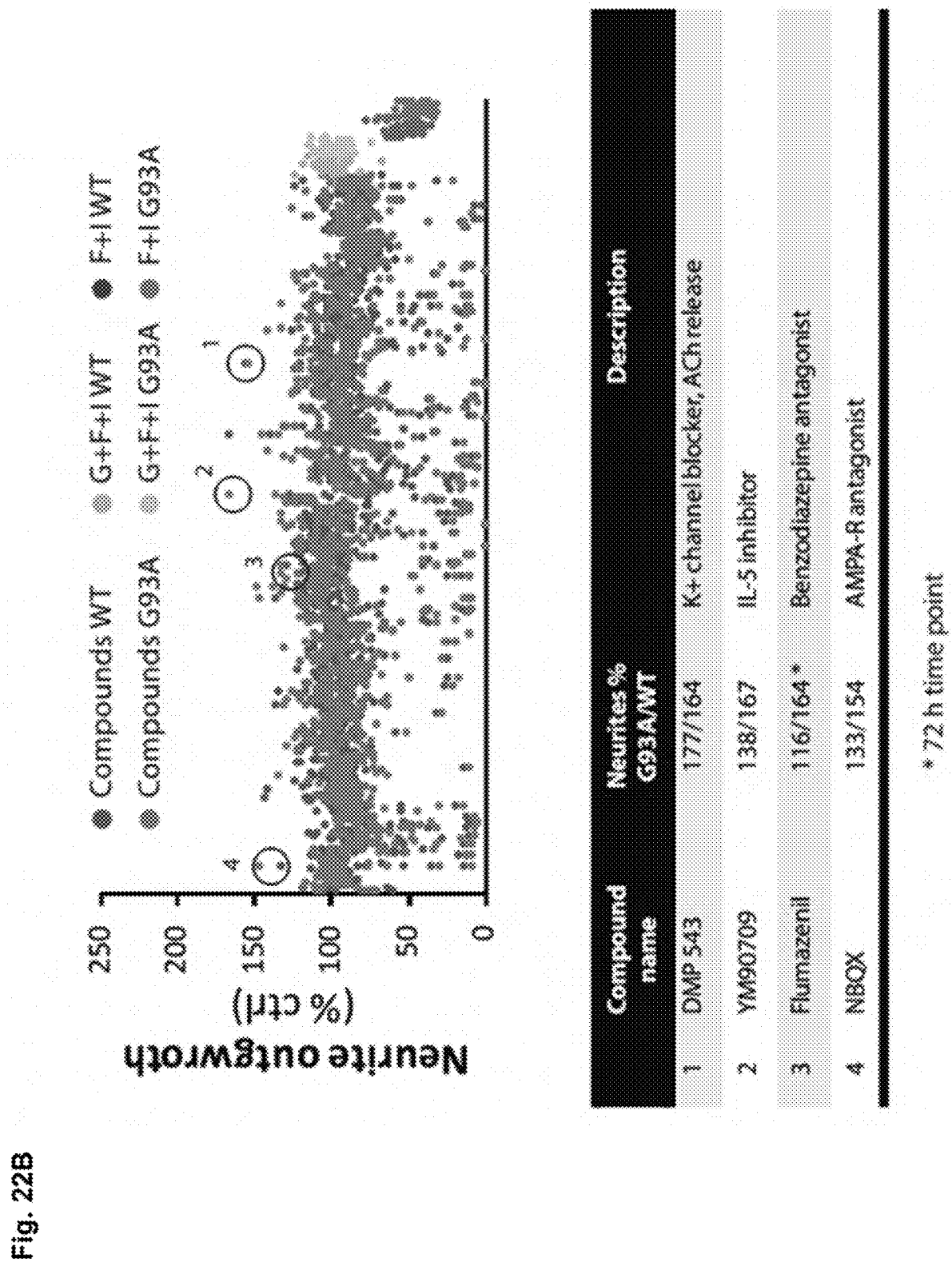

Plated motor neurons were allowed to recover and extend neurites for 24 hours before treatment with a library of 1275 biologically active small molecules (Tocris Screen Mini and Custom Collection, Tocris). Compounds were added at final concentration of 10 µM using an automated robot-assisted liquid handling platform (Tecan), and cells were analyzed by live imaging after 48 and 72 hours. We measured the following parameters: number of live fluorescent motor neurons ("motor neuron survival", FIG. 15J), mean neurite extension per cell ("overall neurite growth", FIG. 22B), GFP/RFP motor neuron ratio normalized to the GFP/RFP ratio of motor neurons in control wells ("normalized survival ratio", FIG. 15H), and GFP/RFP mean neurite growth ratio ("selective neurite growth", FIG. 22A). To identify stressors preferentially targeting mutant motor neurons, we first eliminated all compounds that were overtly toxic to both control and mutant motor neurons (average survival<25% of mutant and control cells). Among the remaining compounds, the subset that preferentially decreased the survival of mutant motor neurons and produced ratios corresponding to at least 50% survival difference, included agonists and antagonists of membrane receptors, ion pump and channel inhibitors, an anti-mitotic drug, and general pro-apoptotic agents (FIG. 15H and FIG. 15I).

One of the selective stressors that we identified was cyclopiazonic acid (CPA), a mycotoxin that reversibly blocks the sarcoendoplasmic reticulum-associated calcium ATPse (SERCA). SERCA is responsible for sequestering calcium from the cytoplasm into the endoplasmic reticulum (ER) (Goeger et al. 1988). SERCA inhibition lowers calcium concentration in the ER, leading to dysfunction of protein folding, activation of the unfolded protein response, ER stress, and apoptosis (Doutheil et al. 1997). We titrated CPA to establish the effective concentration range (6.25-12.5 µM) at which mutant motor neurons exhibit reduced survival compared to control motor neurons (FIGS. 16A-16C, FIG. 23A and FIG. 23B). For all subsequent experiments, unless stated otherwise, motor neurons were treated with 7.5 µM CPA.

To further investigate the effects of CPA, we examined whether it acts directly on motor neurons or indirectly through other cells in the culture. We found that motor neurons purified by fluorescence activated cell sorting (FACS) (FIGS. 23C-23F) were as sensitive to CPA as motor neurons in mixed cultures, indicating that CPA acts directly on motor neurons rather than on other cell types that then produce secondary toxins (Di Giorgio et al. 2008; Di Giorgio et al. 2007; Nagai et al. 2007; Haidet-Phillips et al. 2011). These findings also suggest that the other cell types present in mixed cultures do not provide protection to CPA-treated motor neurons.

Figure 16A:
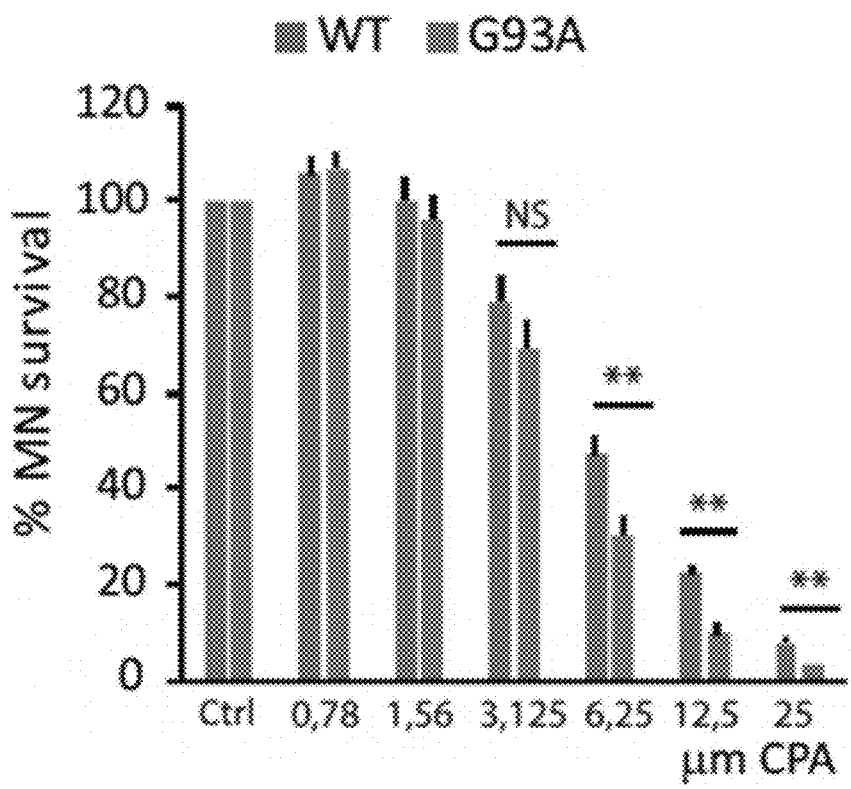
FIGS. 16A-16J show the characterization of cyclopiazonic acid and its effects on survival of motor neurons and interneurons, and the effects on calcium homeostasis.
Figure 16B:
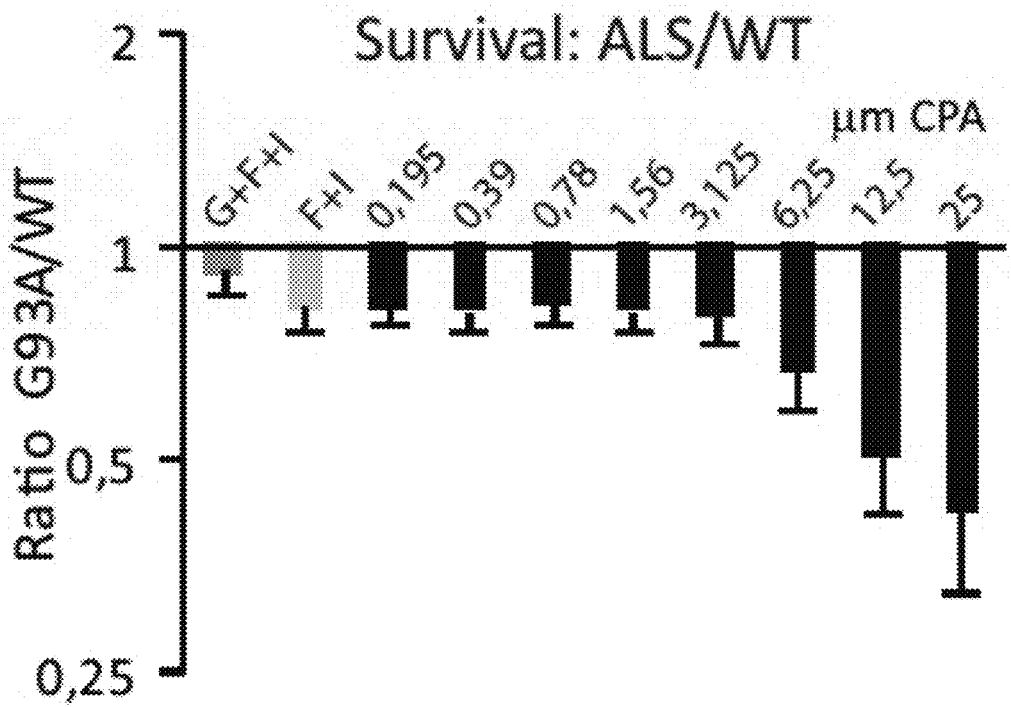
Figure 16C:
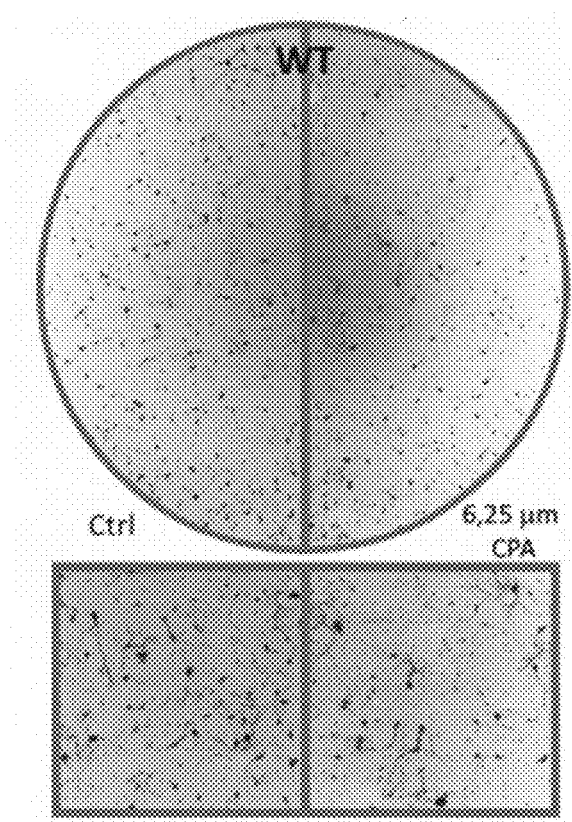
Figure 16C:
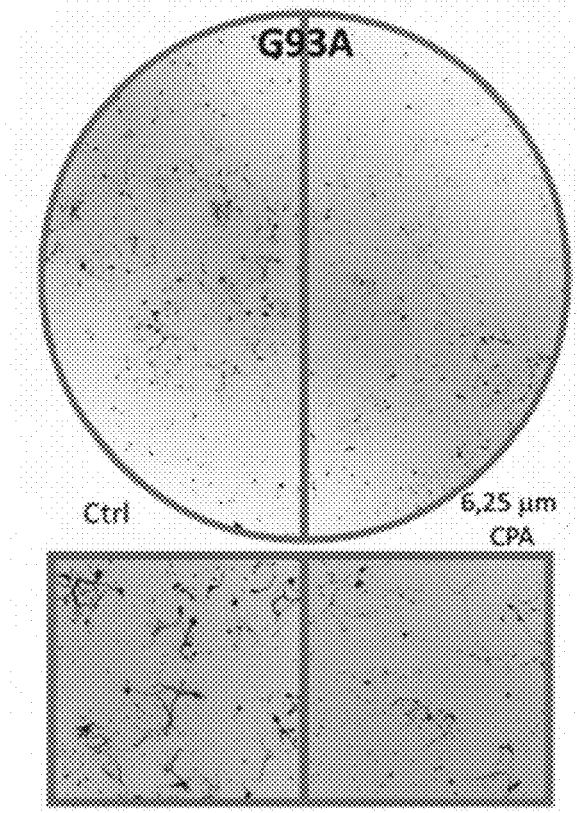
Figure 16D:
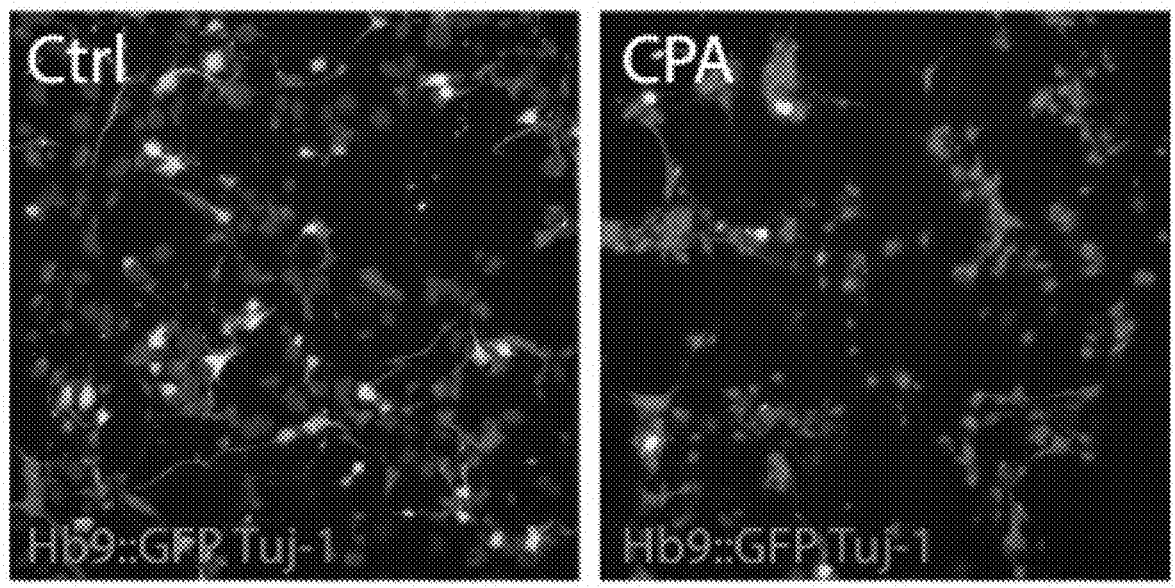
Figure 16E:
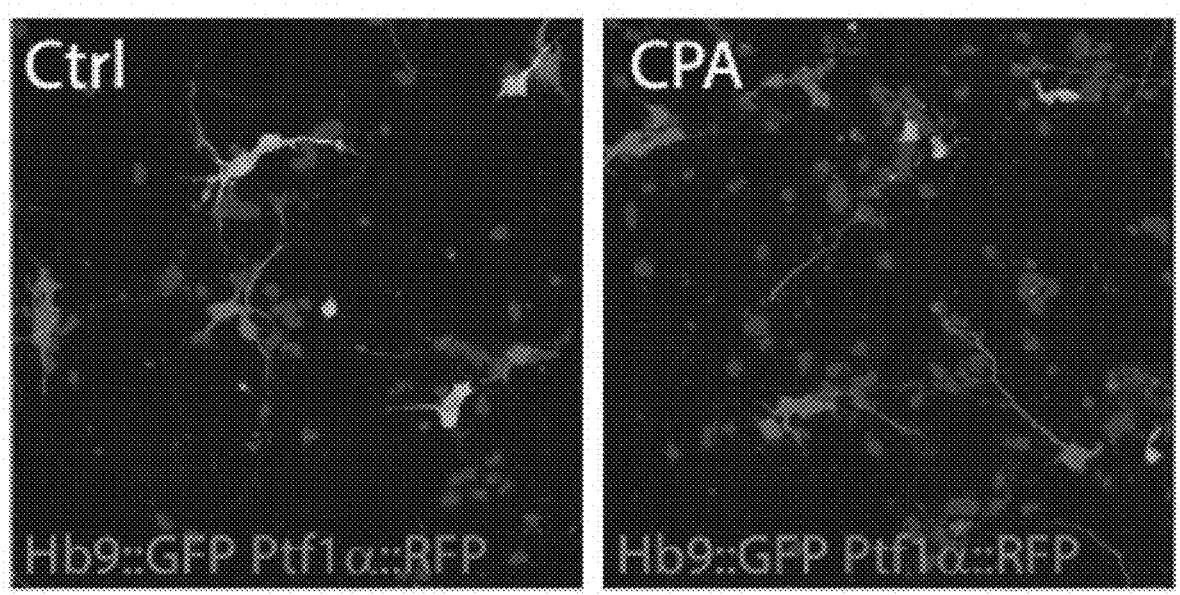
Figure 16F:
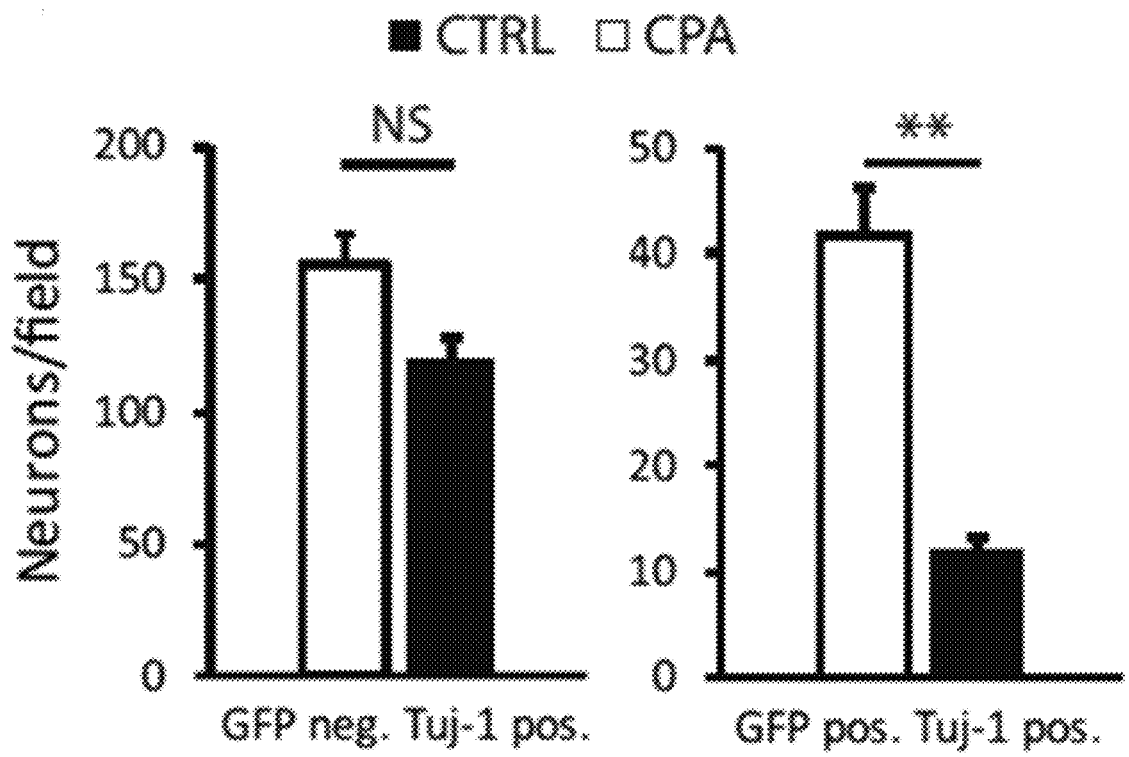

Preferential degeneration of spinal motor neurons and neurons in the motor cortex over other types of nerve cells is a hallmark of ALS. To determine whether motor neurons were more sensitive to CPA treatment than other types of neurons, we analyzed mixed cultures composed of hSOD1$^{G93A}$ expressing spinal motor neurons, interneurons, and other cell types. Immunostaining of the surviving cells revealed that the survival of motor neurons expressing GFP and the pan neuronal marker Tuj1 was reduced by ~71%, while the survival of all GFP$^-$ Tuj-1$^+$ non-motor neurons was reduced by only ~23% (FIG. 16D and FIG. 16F). This considerable difference in CPA sensitivity between the various neuronal subtypes in mixed cultures derived from hSOD1$^{G93A}$ ESC lines prompted us to ask whether the same was true for cultures derived from WT lines.

Figure 16G:
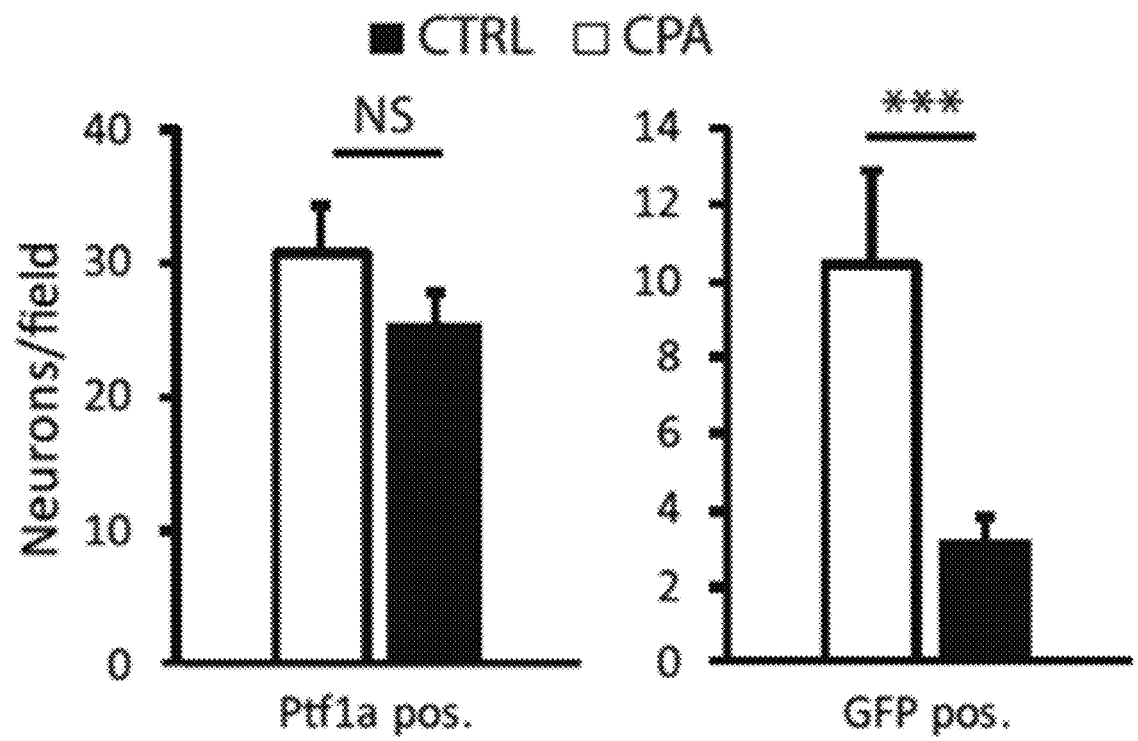

For this analysis, we generated a new ESC line that expresses tdTomato in dI4 and dIL dorsal spinal inhibitory interneurons derived from Ptf1α-expressing progenitors (Hoang et al. 2017, unpublished data). We differentiated this line under conditions that promote the specification of dorsal interneuron identity. FACS-purified tdTomato-expressing interneurons were co-cultured with FACS-purified GFP-expressing spinal motor neurons (FIG. 16E and FIG. 16G). Quantification of RFP—vs. GFP-positive neurons revealed that CPA treatment reduced dorsal spinal interneuron survival by only ~17%, compared to ~70% for co-cultured spinal motor neurons. Together these data revealed increased sensitivity of spinal motor neurons to CPA compared to other ventral or dorsal spinal neurons.

Effects of CPA on Cytosolic Calcium Level

Figure 16H:
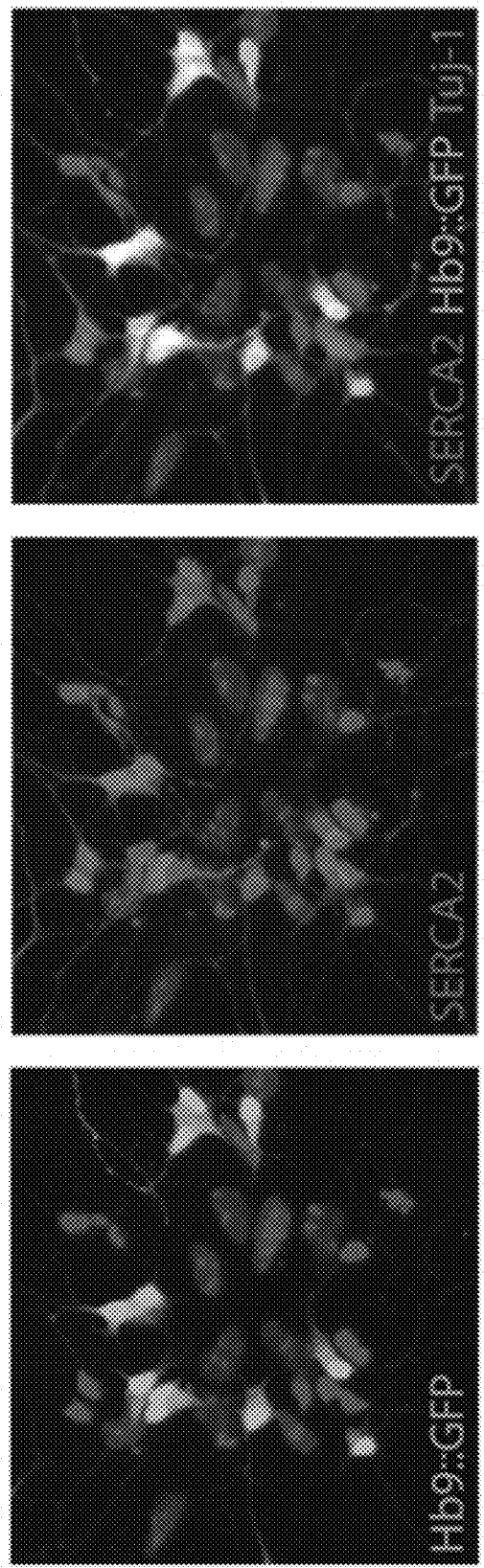
Figure 16I:
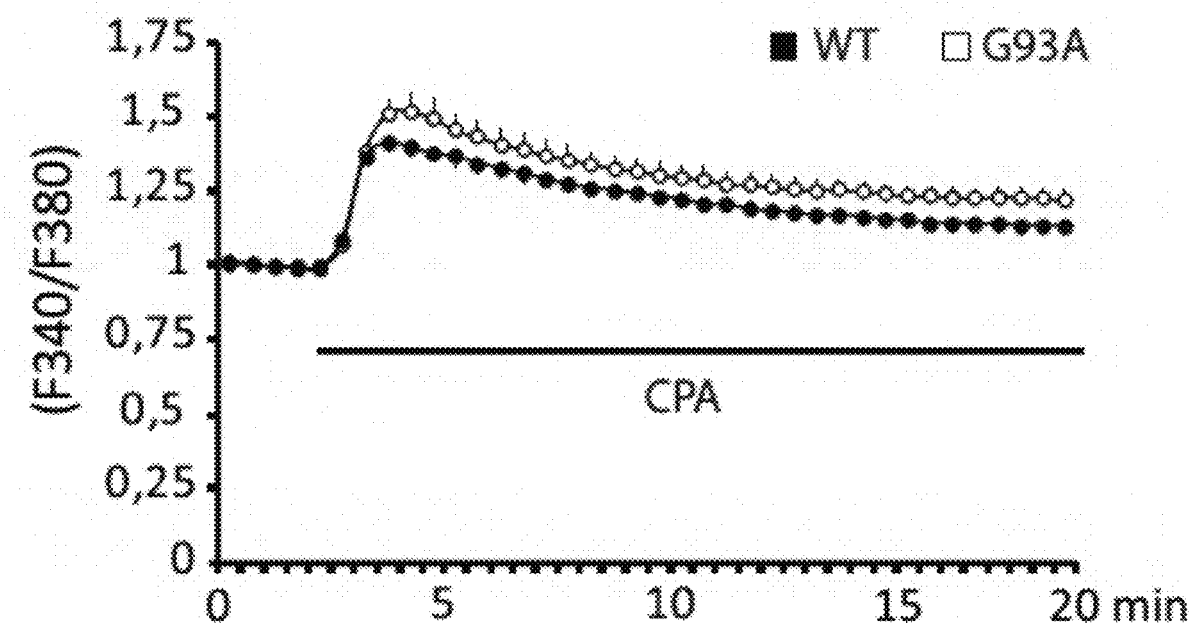
Figure 16J:
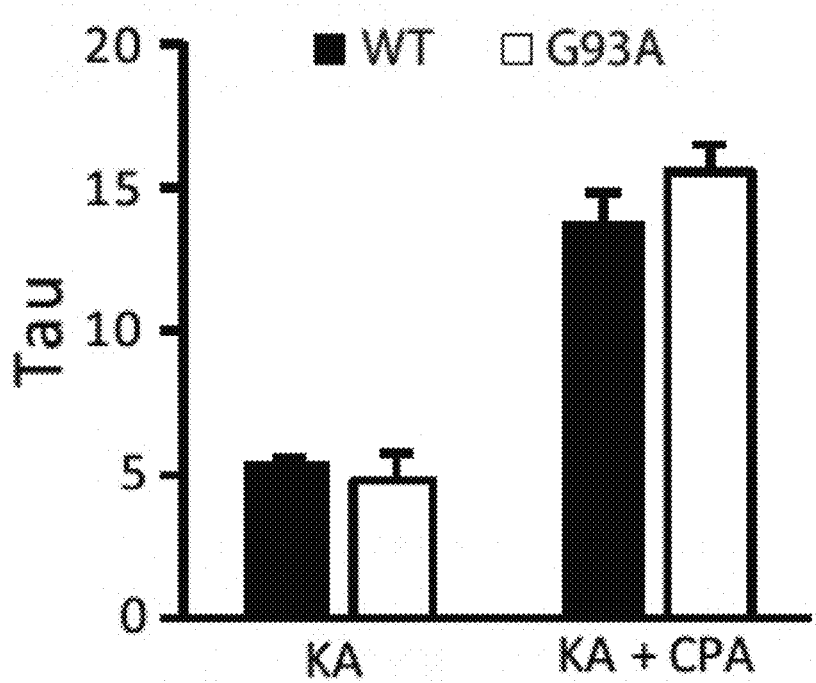
Figure 22D:
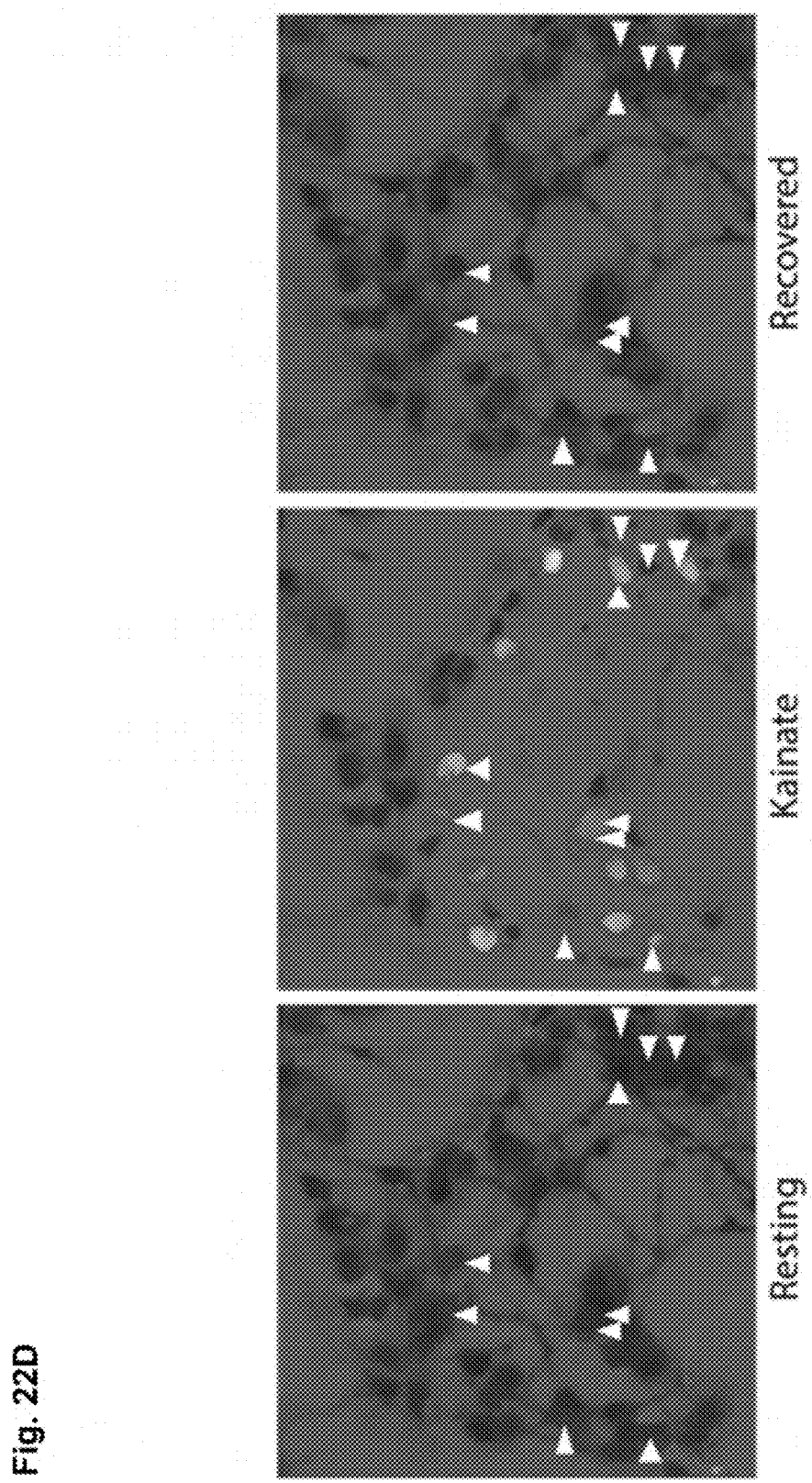
Figure 22E:
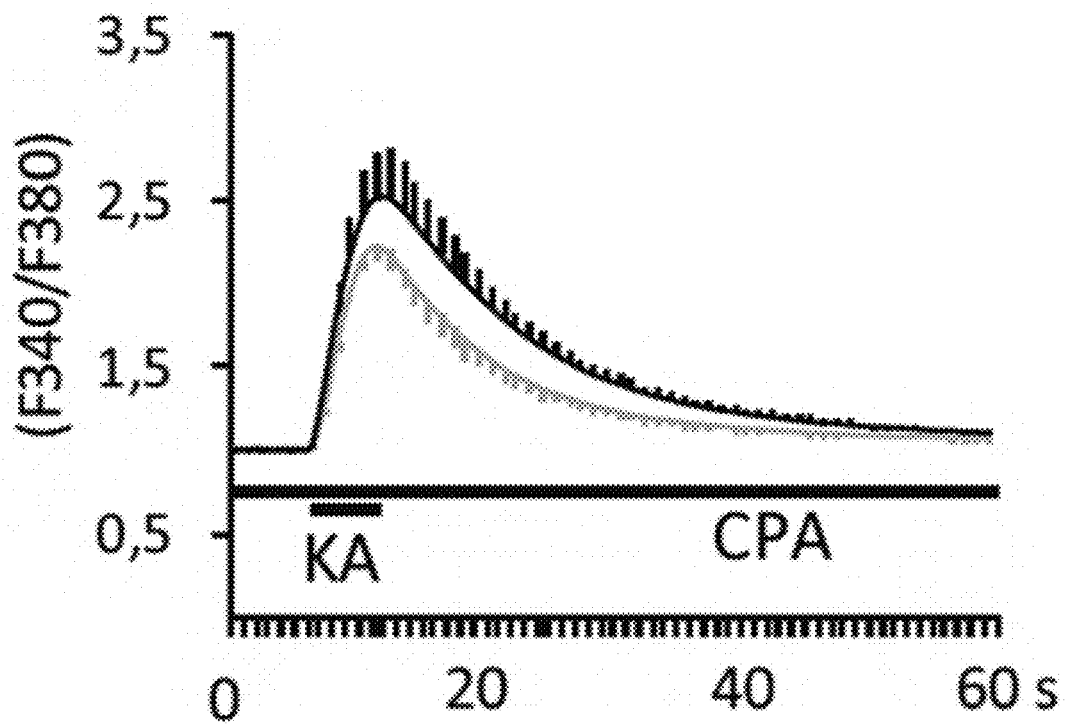
Figure 22F:
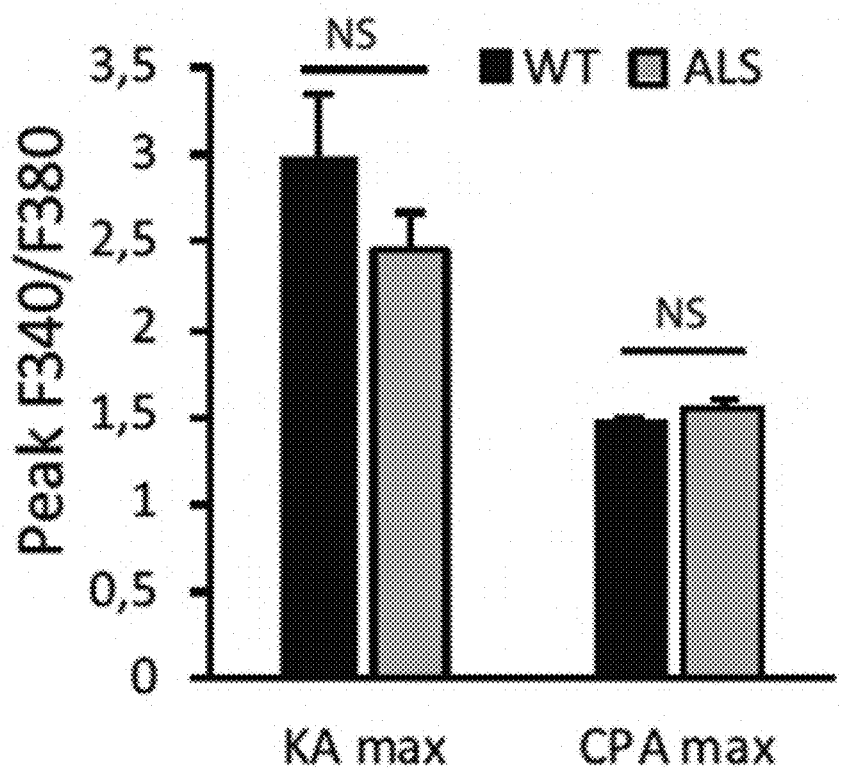
Figure 23E:
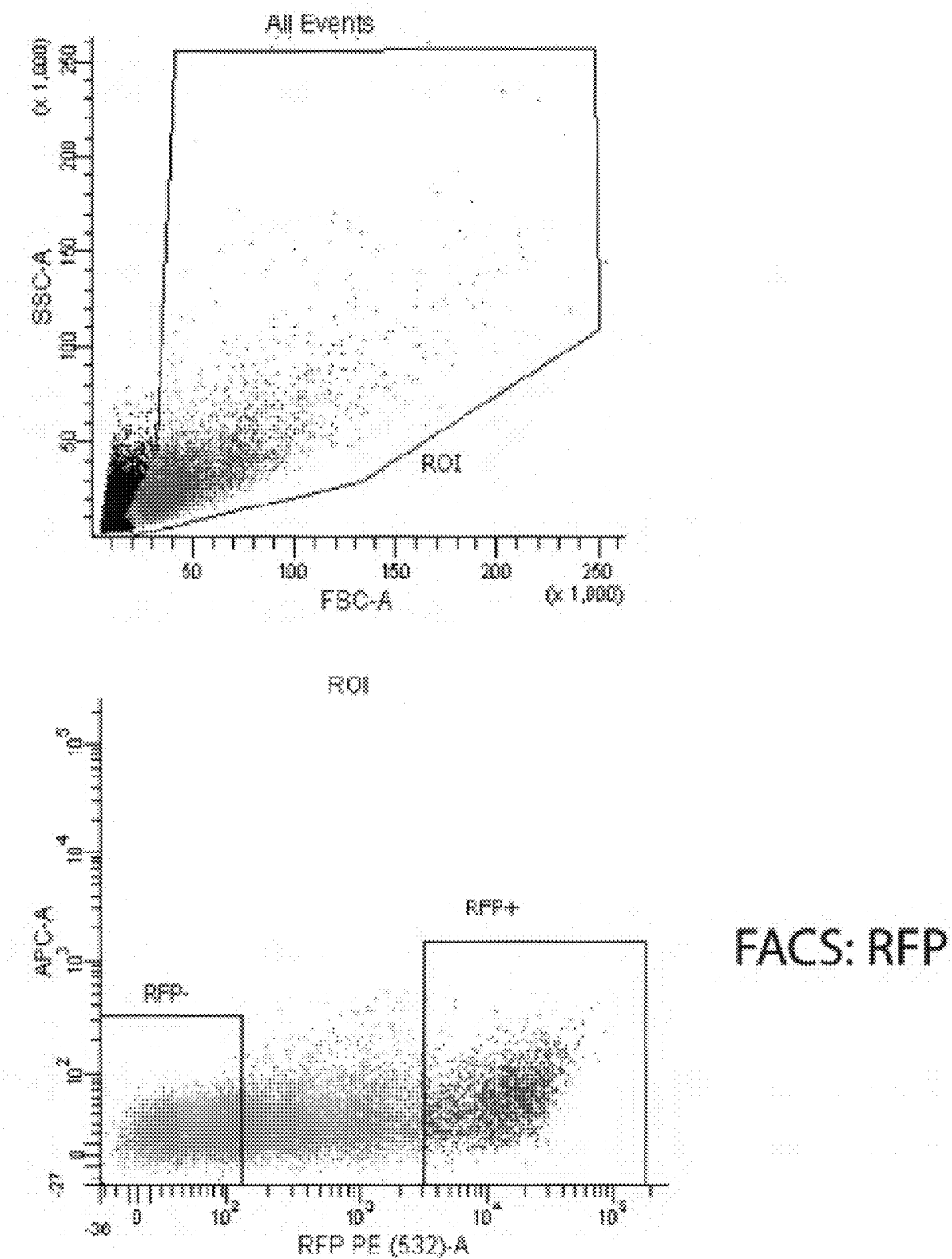
Figure 23F:
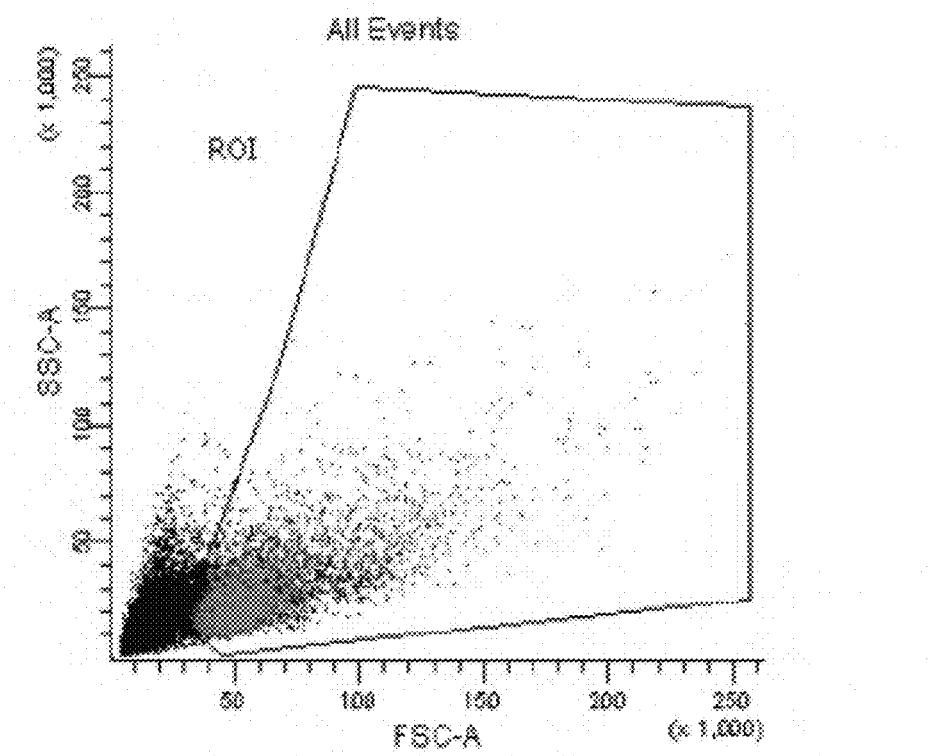
Figure 23F:
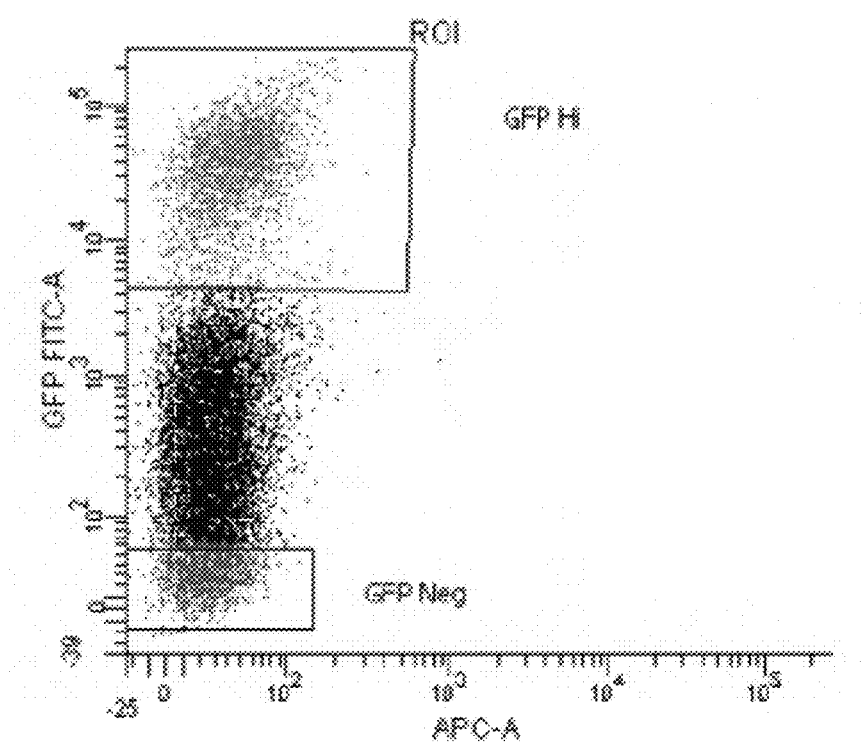

CPA is a reversible inhibitor of the SERCA pump important for sequestration of cytosolic calcium into the endoplasmic reticulum. Immunostaining revealed that cultured ESC-derived motor neurons express high levels of the SERCA2 isoform (ATP2A2) (FIG. 16H). To study the effects of CPA on calcium handling in motor neurons, we performed a series of imaging experiments in which free cytosolic calcium was visualized and measured by ratiometric analysis of the calcium indicator Fura-2. To avoid crosstalk between GFP and Fura-2 fluorescence, the experiments were performed with sorted Hb9::tagRFP-expressing motor neurons. First, we characterized overall calcium handling in control and mutant motor neurons three days after plating by measuring calcium transients elicited by the inotropic glutamate receptor agonist kainic acid (KA) (Carriedo et al. 2000; Carriedo et al. 1996). Exposure of cells to a 5 s pulse of 100 µM KA induced a rapid rise in cytosolic calcium in ESC-derived motor neurons followed by a period of sequestration in which the calcium returned to baseline levels (FIG. 22C and FIG. 22D), similar to primary motor neuron cultures (Carriedo et al. 2000). Motor neurons that failed to return to baseline within the 60 s imaging window were removed from further analysis. Following a 5-minute recovery period, cells were exposed to 7.5 µM CPA and imaged for an additional 20 min. Continuous CPA exposure induced a slow calcium transient in both genotypes (FIG. 16I), which eventually returned to a level close to baseline toward the end of the imaging sequence. The cells were allowed to recover for another 5 min, followed by a second KA pulse in presence of CPA, causing a rapid calcium transient that returned to baseline (FIG. 22E). This allowed us to examine how the cells handled a cytosolic calcium increase when calcium sequestration in the ER was blocked. CPA significantly slowed, but did not obliterate the sequestration of KA-induced calcium (FIG. 16J and FIG. 22E), indicating that motor neurons normally rely on the ER to sequester cytosolic calcium, but can use other sequestration routes upon loss of this compartment. This difference was not due to repeated stimulation with KA, since parallel experiments with multiple sequential KA pulses in the absence of CPA did not reveal any impairment in the rate of calcium-sequestration (data not shown). When comparing control and mutant motor neurons, we did not observe any difference between the genotypes in the rate (Tau) of KA-induced calcium sequestration in absence or presence of CPA (FIG. 16J), indicating that CPA affects calcium handling comparably.

Figure 18A:
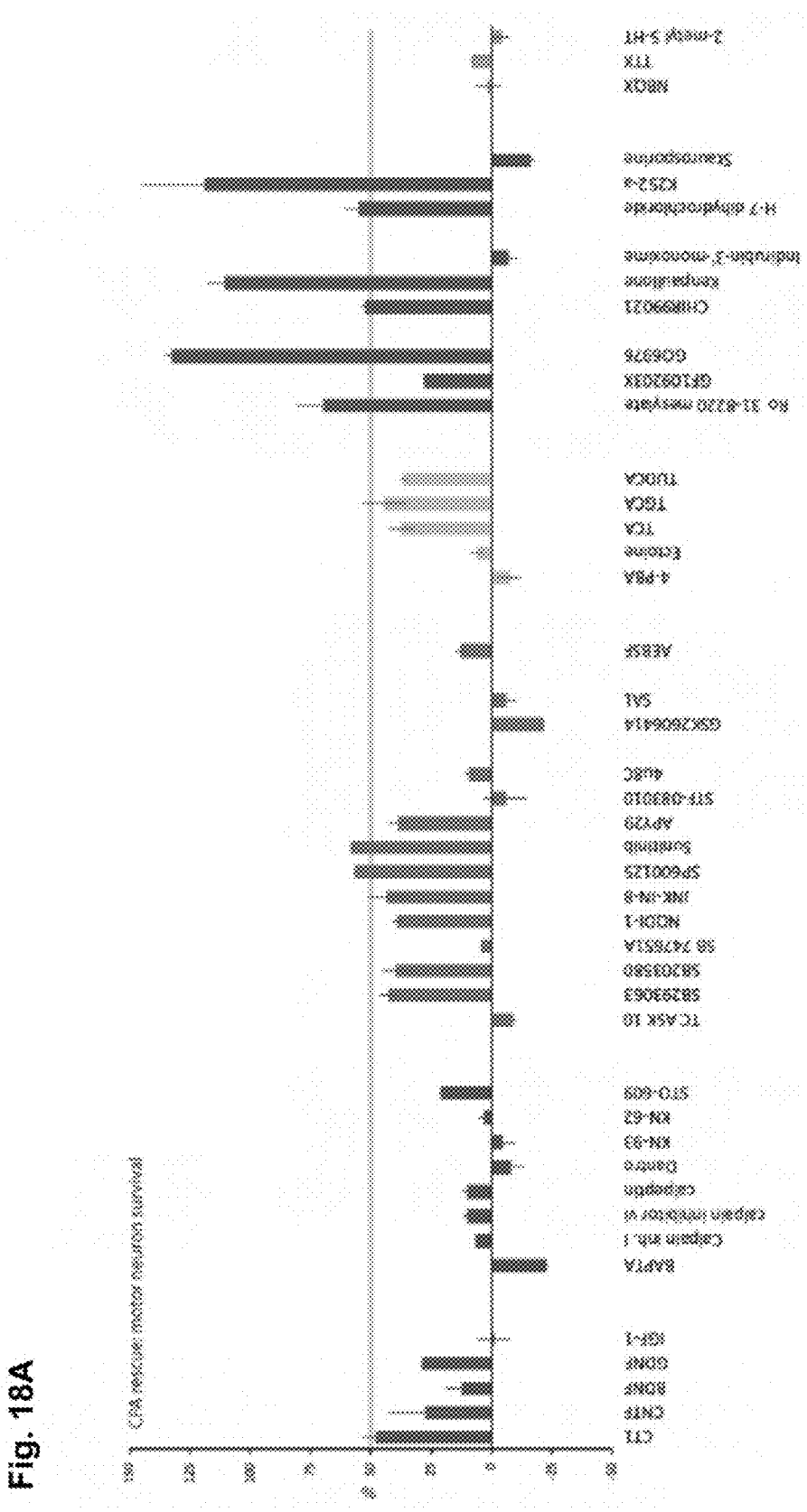
FIG. 18A and FIG. 18B show selected results from the ER stress rescue screen, in particular, the result for motor neuron survival and neurite outgrowth. Compounds are subcategorized and color-coded based on their putative mechanisms of action. Bars denote average, errors bars indicate SEM (N=3-6 culture wells/compound). The cut-off level for further analysis is indicated by a grey line.
Figure 18B:
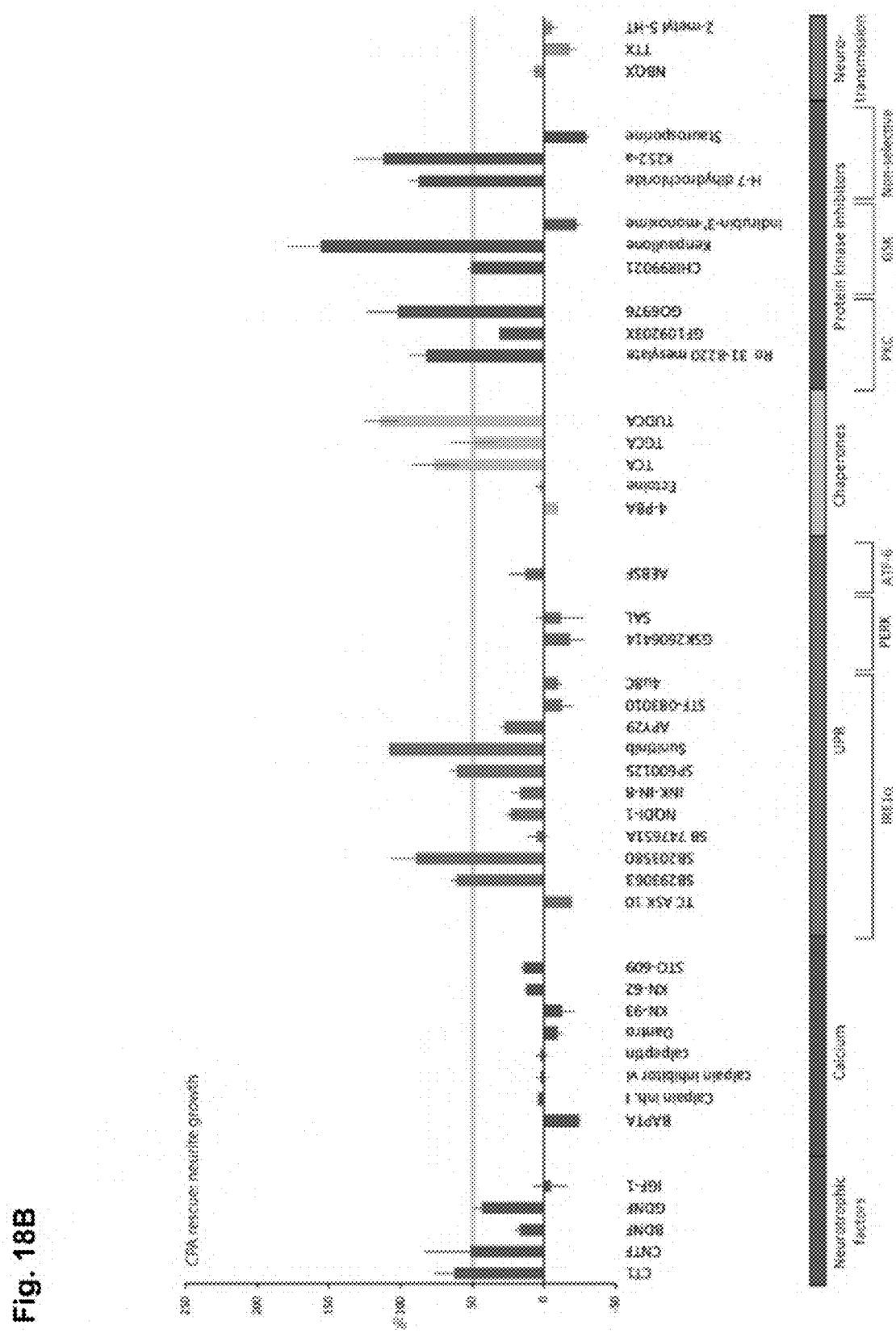
Figure 25A:
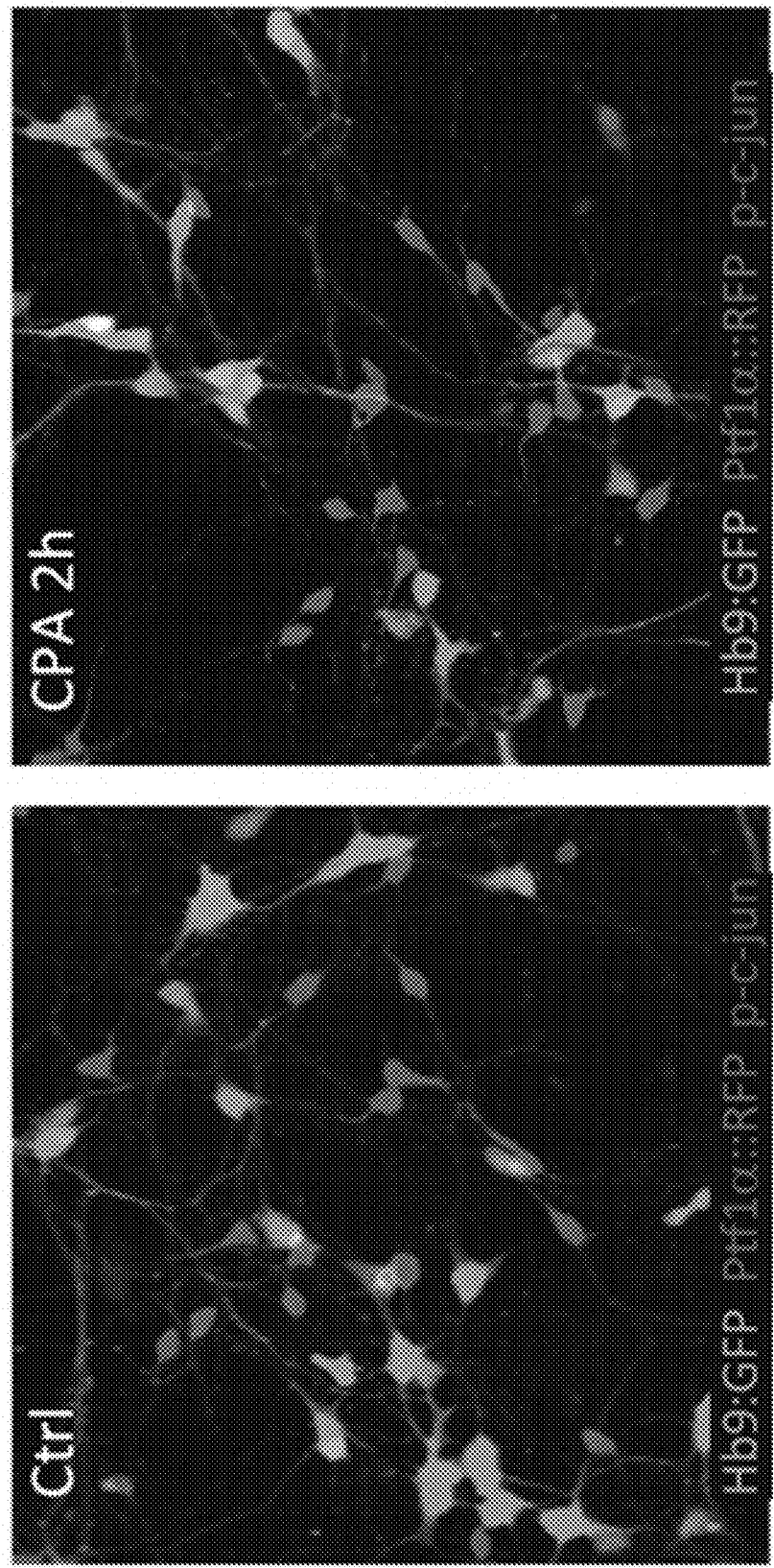
FIGS. 25A-25H show c-jun phosphorylation and calcium homeostasis in CPA treated mixed cultures with $Hb9::GFP^+$ motor neurons and $Ptf1a::dtTomato^+$ interneurons. Mini-screen for CPA rescue effect of conjugated bile acids, and survival and rescue effects of TUDCA in the presence of high and low neutrophic support.
Figure 25B:
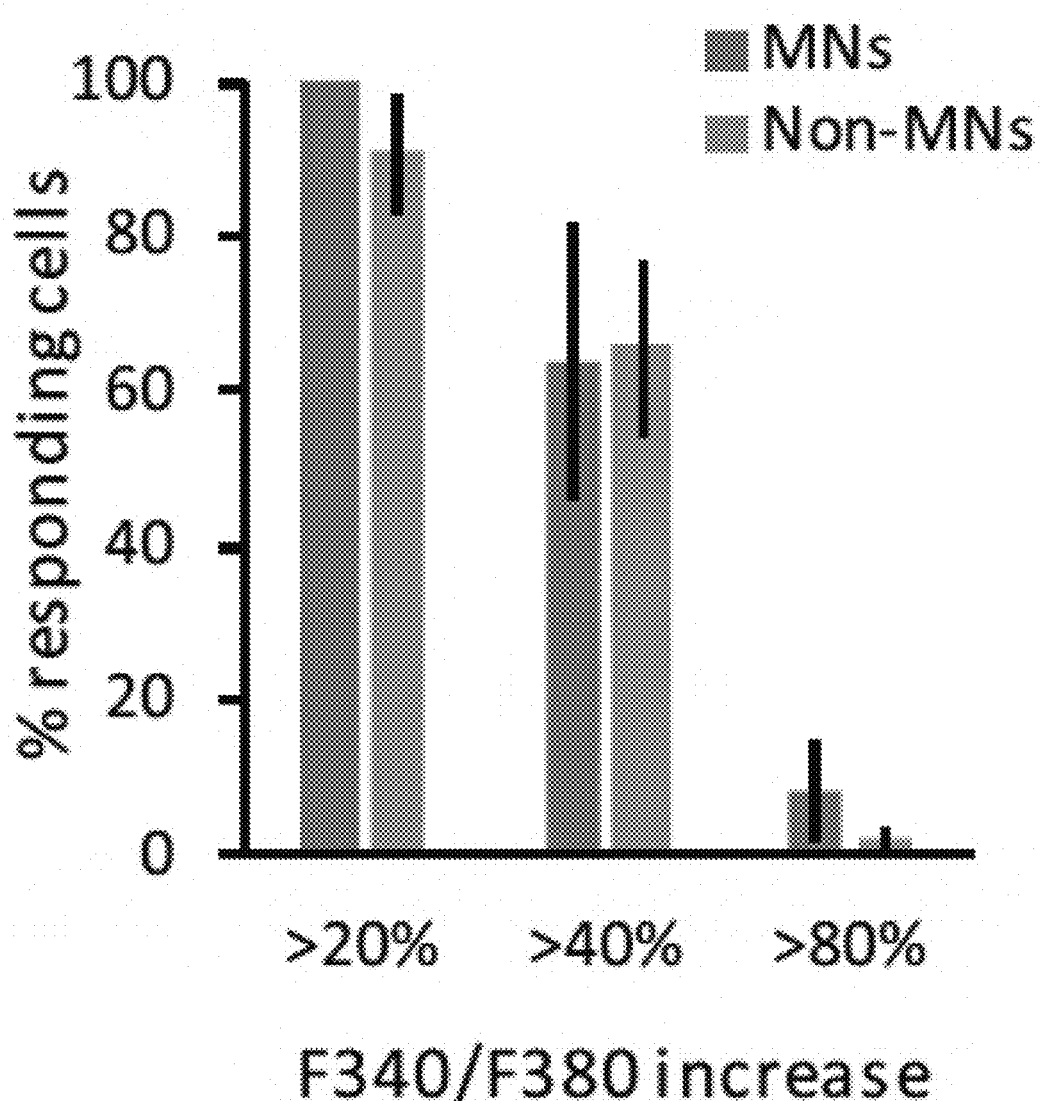

Elevated cytosolic calcium may activate multiple intracellular signaling processes, including cell death pathways (De Stefani et al. 2012; Jayaraman et al. 1997; Pinton et al. 2008), and calcium dysregulation has been implicated in many neurodegenerative conditions, including ALS (Kiskinis et al. 2014; Bernard-Marissal et al. 2012; Jaiswal et al. 2009; Jaiswal et al. 2009; Kawamata et al. 2010; Kim et al. 2012; Rothstein et al. 1990; Takuma et al. 1999; Tradewell et al. 2011; von Lewinski and Keller 2005). Improving calcium sequestration into the ER or inactivating the degenerative pathways that calcium signaling promotes could therefore potentially counteract CPA toxicity. Accordingly, we evaluated a panel of eight compounds with known effects on cytosolic calcium handling and/or signaling. These included BAPTA-am, a cell permeable calcium chelator; dantrolene, an inhibitor of the ryanodine receptors that release calcium from ER stores into the cytoplasm; three inhibitors of calpains, a family of calcium-dependent cysteine proteases; and three inhibitors of the calcium-activated kinase CaMKK/II. Notably, none of these treatments improved motor neuron survival or neurite retraction elicited by CPA exposure (FIGS. 18A-18B). These data, together with the observation that CPA-induced cytosolic calcium levels were essentially equal in vulnerable motor neurons and resistant non-motor neurons (FIG. 25B), suggested that a cytosolic calcium overload is unlikely to be the primary cause of CPA-induced motor neuron death.

Spinal Motor Neurons are Sensitive to the Activation of ER Stress Pathway

In addition to its effects on cytosolic calcium, CPA treatment has been shown to decrease calcium levels in the ER, leading to the activation of ER stress pathways (Doutheil et al. 1997). These pathways are initiated by the binding immunoglobulin protein (BiP; Heat shock protein 70, HSP70; 78 kDa glucose-regulated protein, GRP-78), an ER resident chaperone, which translocates from its binding site on ER-membrane-bound stress sensors upon detection of unfolded proteins in the ER lumen. Unbound BiP is involved in the activation of three separate signaling pathways associated with ER stress: PERK, ATF-6, and IRE1α pathways, referred to hereafter as the unfolded protein response (UPR, FIG. 19F) (Gardner et al. 2013; Hetz 2012; Lurlaro and Munoz-Pinedo 2016; Kozutsumi et al. 1988).

Figure 17A:
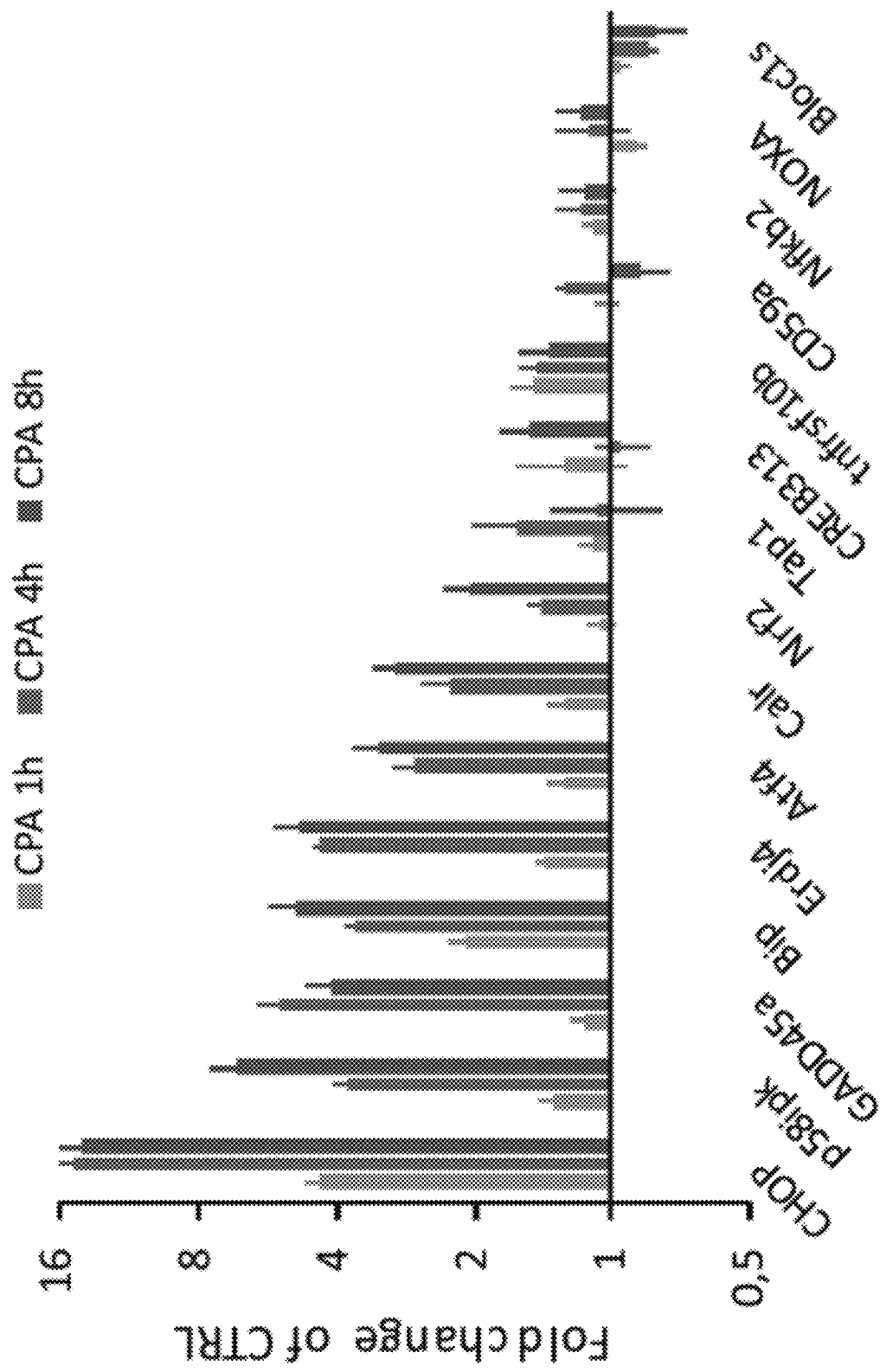
FIGS. 17A-17G show the characterization of ER stress markers in motor neuron cultures treated with cyclopiazonic acid.
Figure 19A:
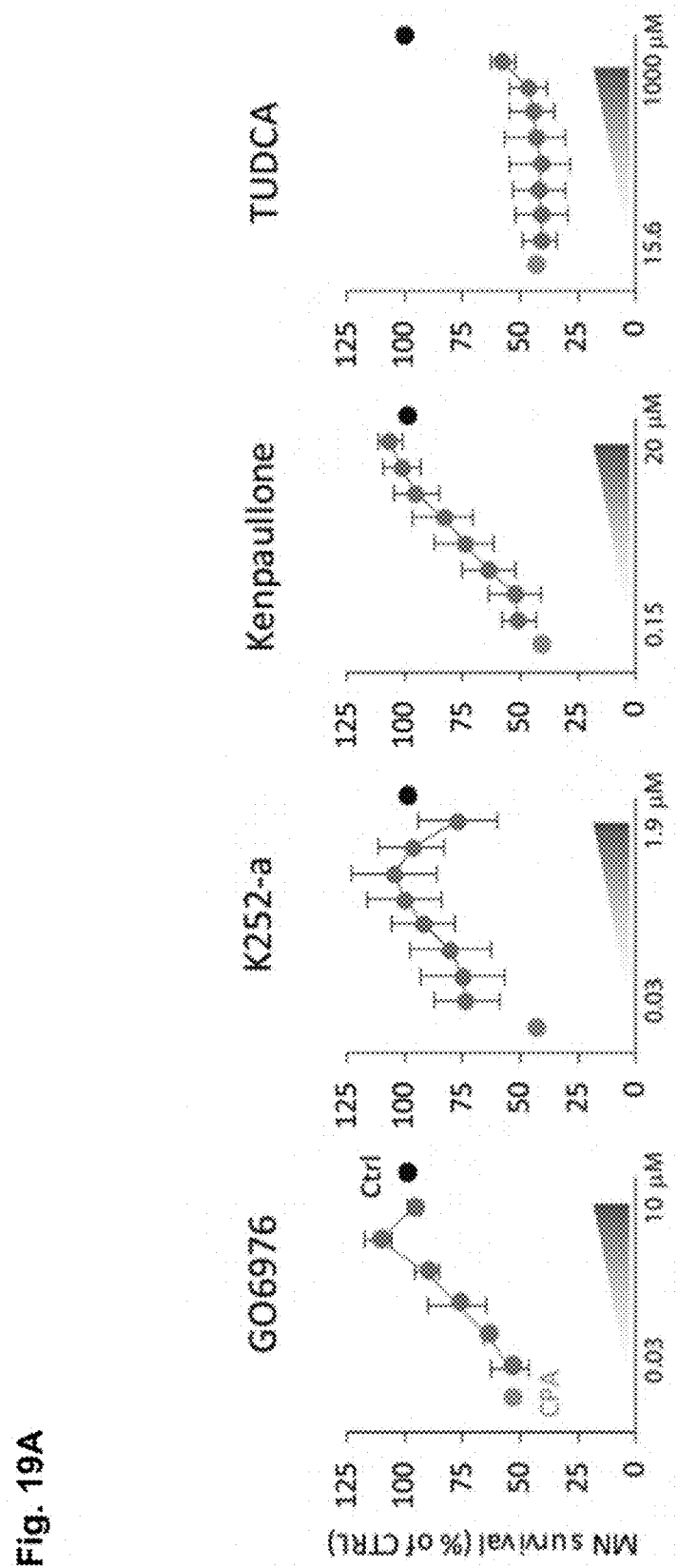
Figure 19B:
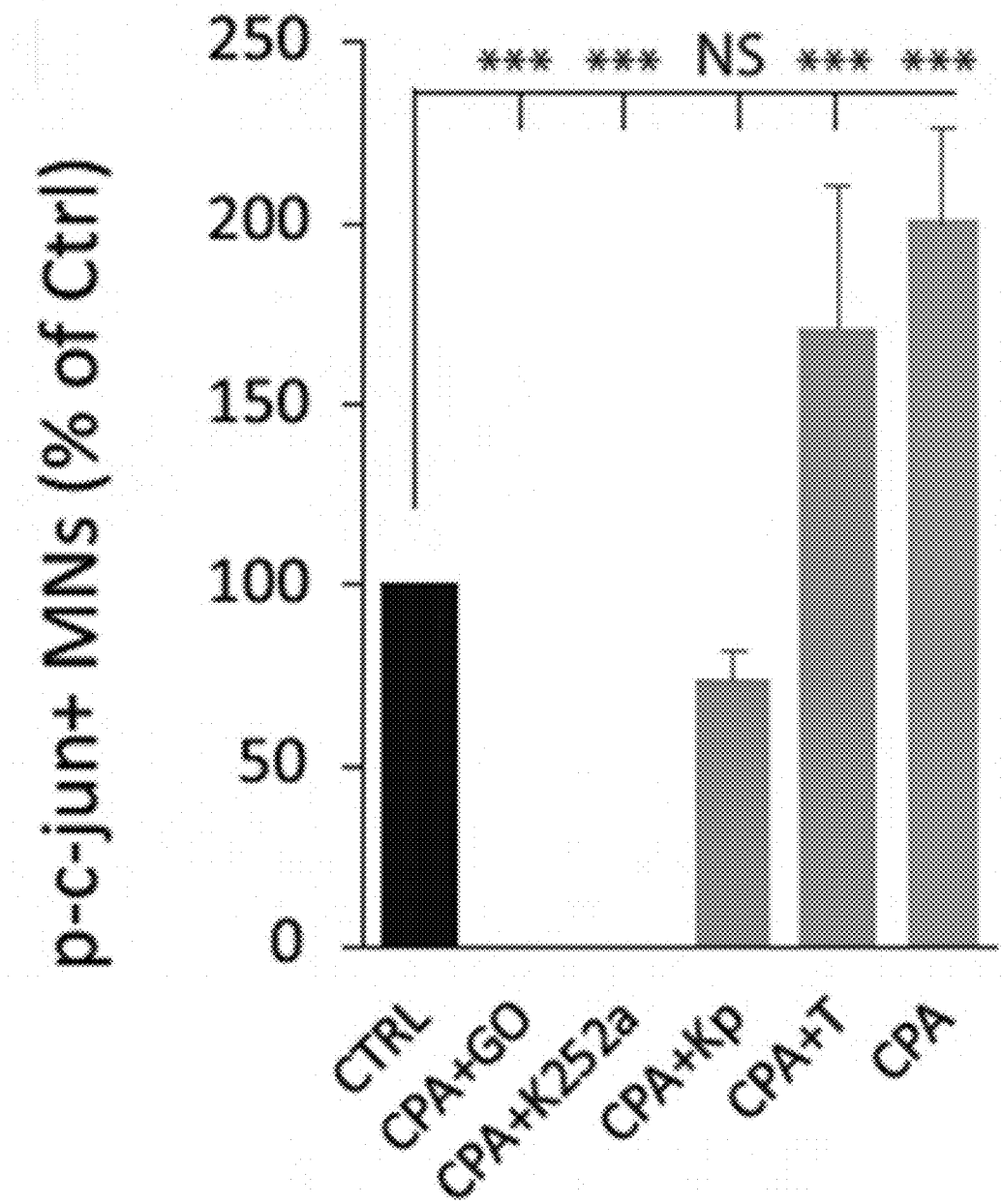
Figure 19C:
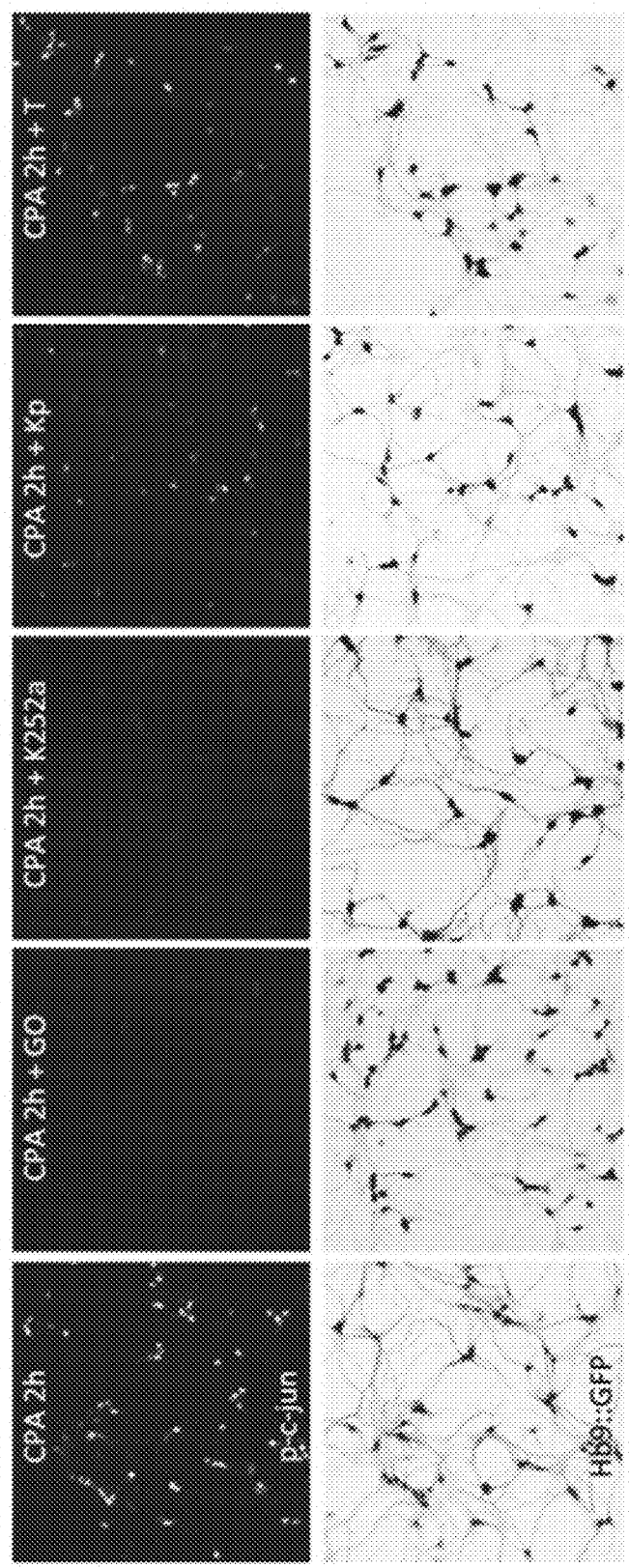
Figure 19D:
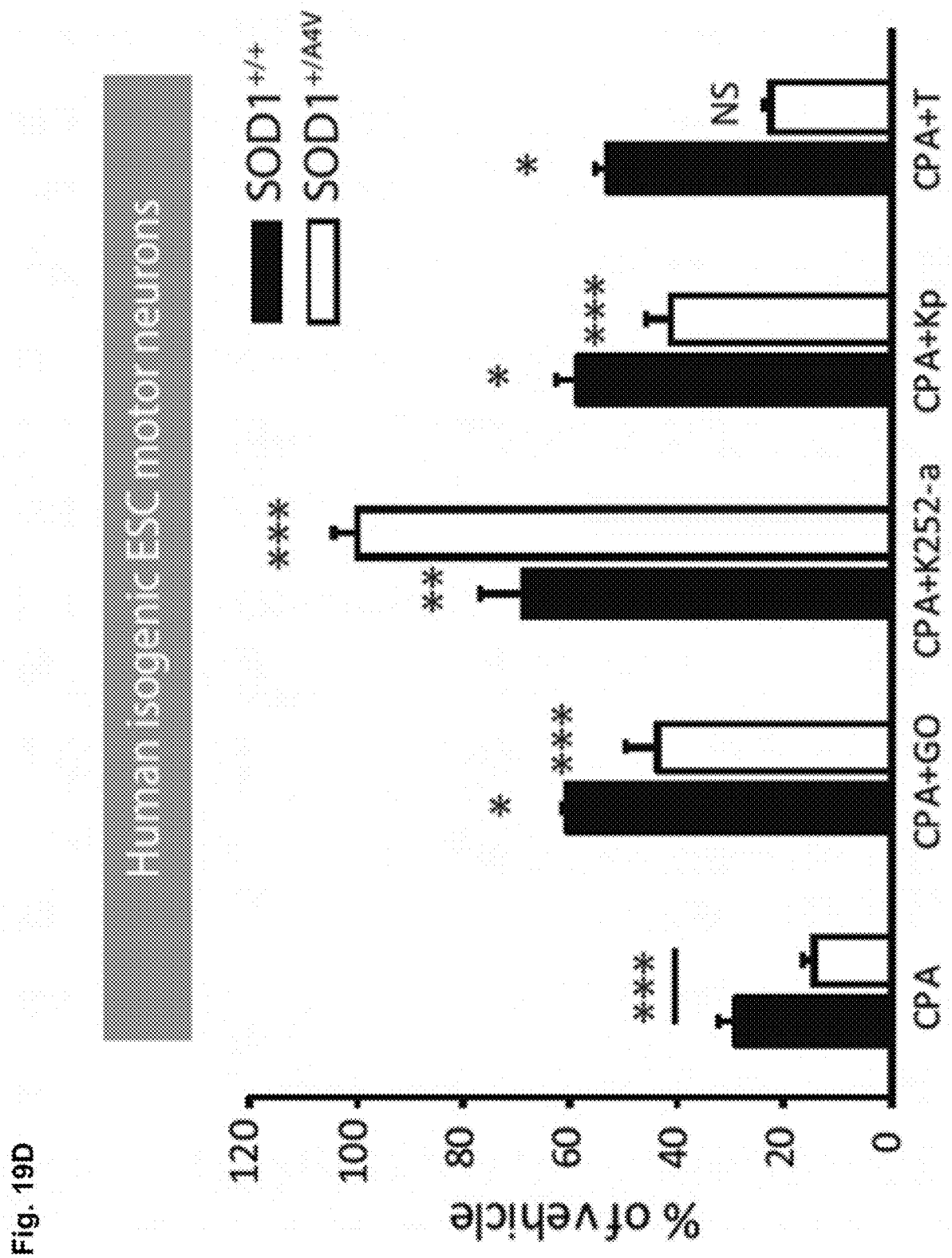
Figure 19F:
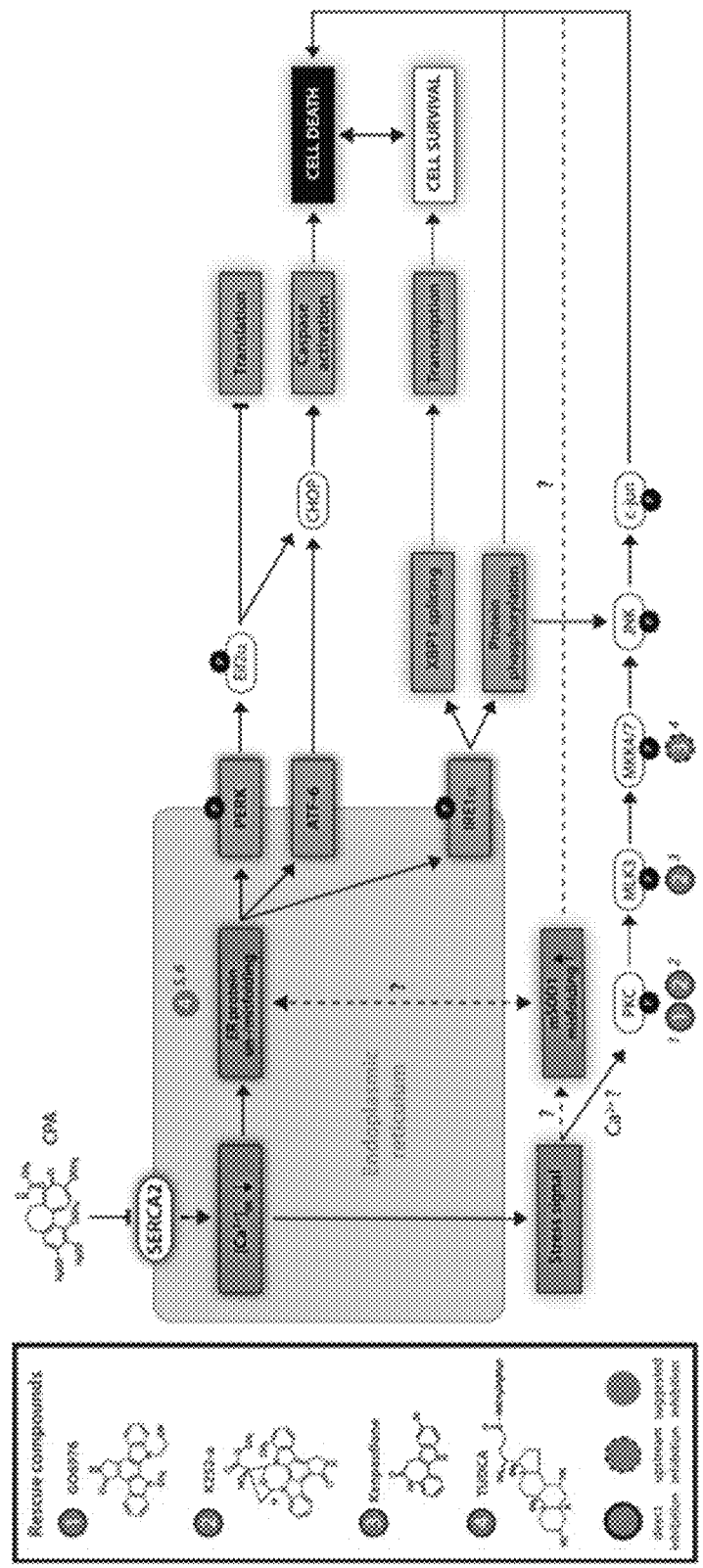

In order to assess the activation of these pathways in motor neurons exposed to CPA, we used RT-PCR to examine the expression levels of 15 stress-associated genes at three time points following CPA treatment in hSOD1$^{G93A}$ motor neurons (FIG. 17A). We observed a rapid increase in the expression of Bip and the key downstream effector Chop (Ddit3). Bip was increased 2-fold after 1 hour of CPA exposure, and continued to increase to approximately 5-fold by 8 hours. Chop was induced 4-fold at 1 hour of CPA treatment and reached 16-fold induction at 4 and 8 hours. Other genes with >2-fold induction included: p58/PK 255 (6.5 fold at 8 hours), an ER-stress-induced protein kinase; Growth arrest and DNA-damage inducible protein 45 alpha (Gadd45a; 5-fold at 4 hours), recently shown to be upregulated in the spinal cord of presymptomatic SOD1$^{G93A}$ mice (Saxena et al. 2009); Erdj4, a Bip cofactor with involvement in ER associated protein degradation (ERAD) (5-fold at 4-8 hours); Atf4, a downstream mediator of the PERK-axis of the UPR (3-fold at 8 hours); Calreticulin, an ER-associated chaperone (3-fold at 8 hours), which was linked to NO-mediated motor neuron degeneration in hSOD1$^{G93A}$ mice (Bernard-Marissal et al. 2012); and Nrf2, a PERK substrate (2 fold at 8 hours). Altogether, these expression changes pointed to strong activation of multiple axes of the unfolded protein response (UPR) in motor neurons exposed to CPA (FIG. 19F).

Figure 17B:
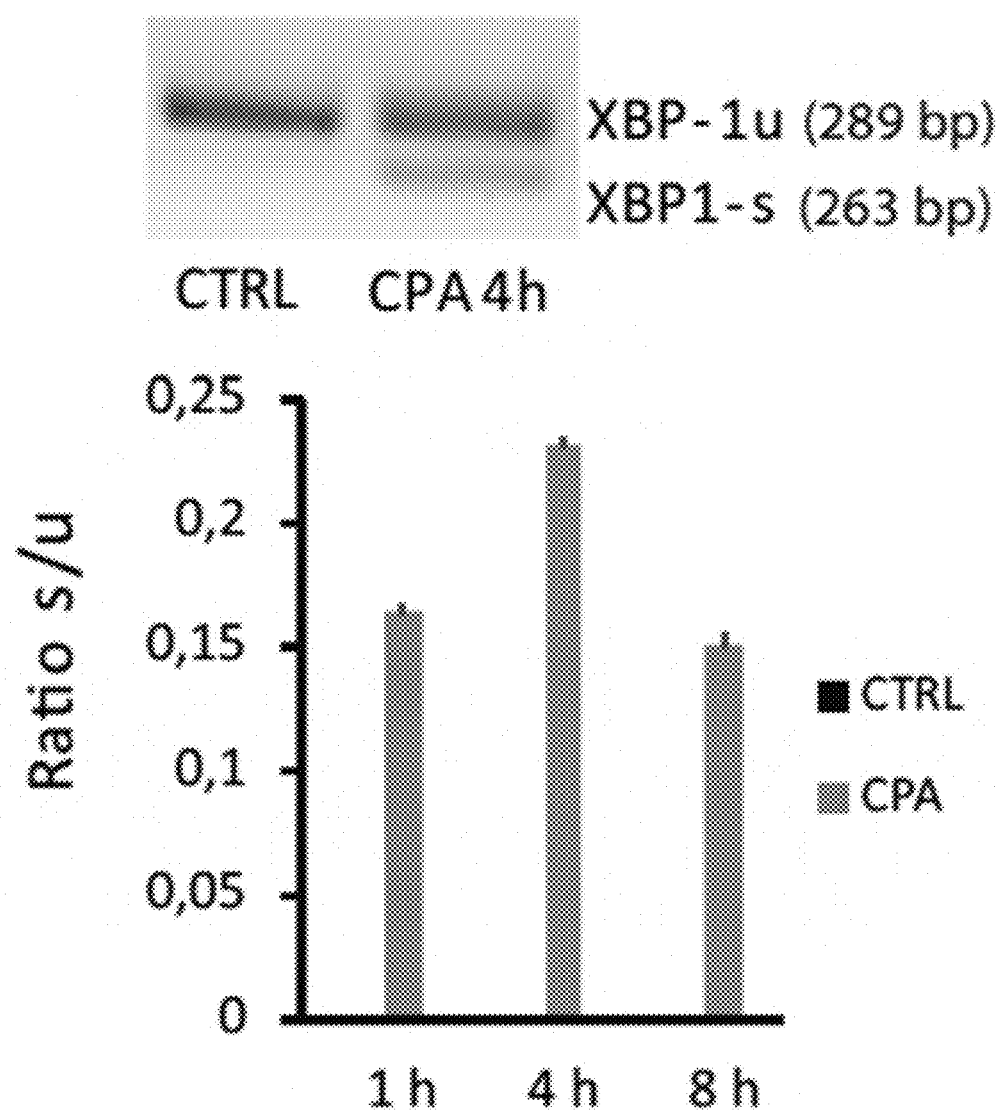
Figure 17C:
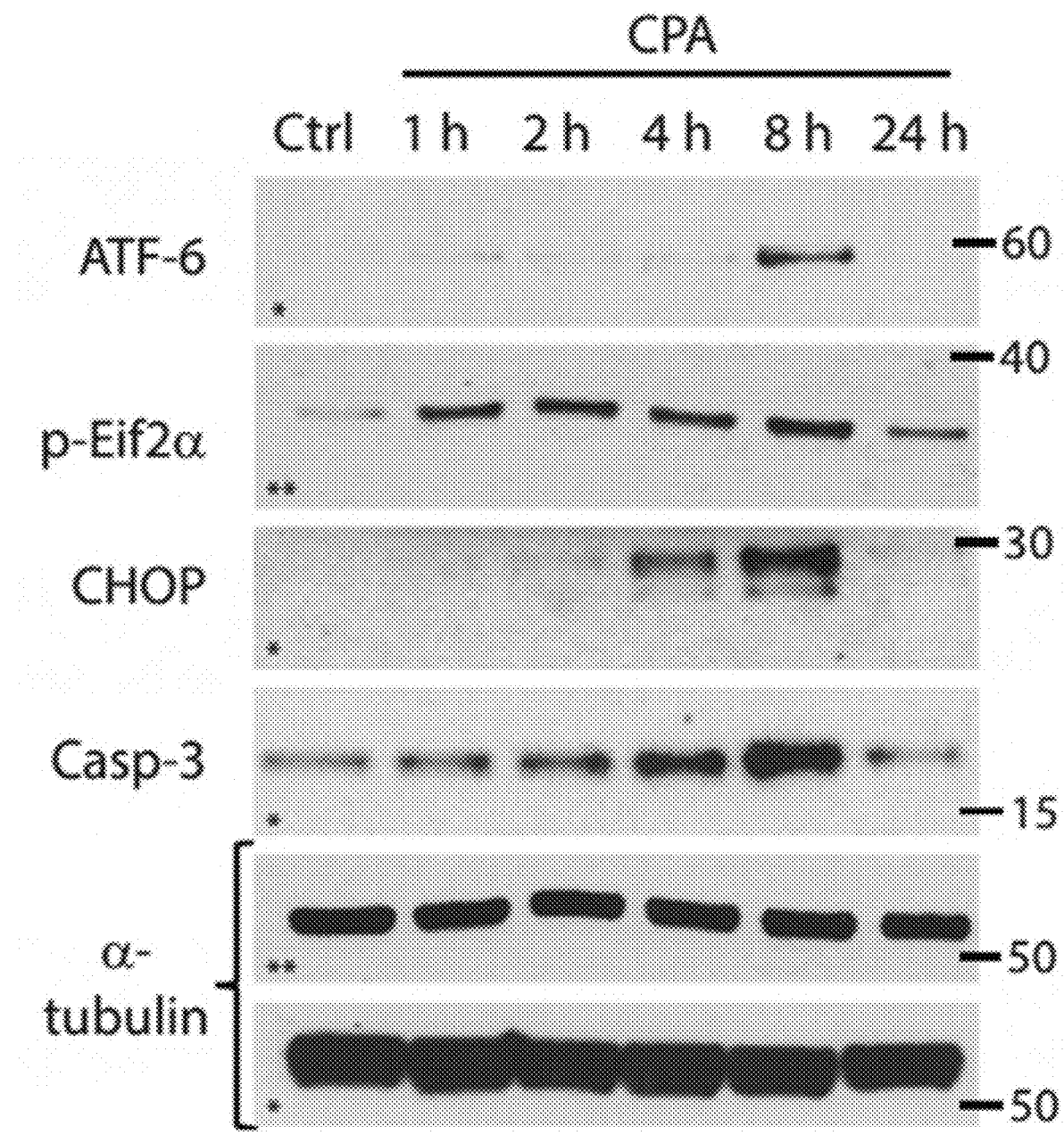
Figure 17D:
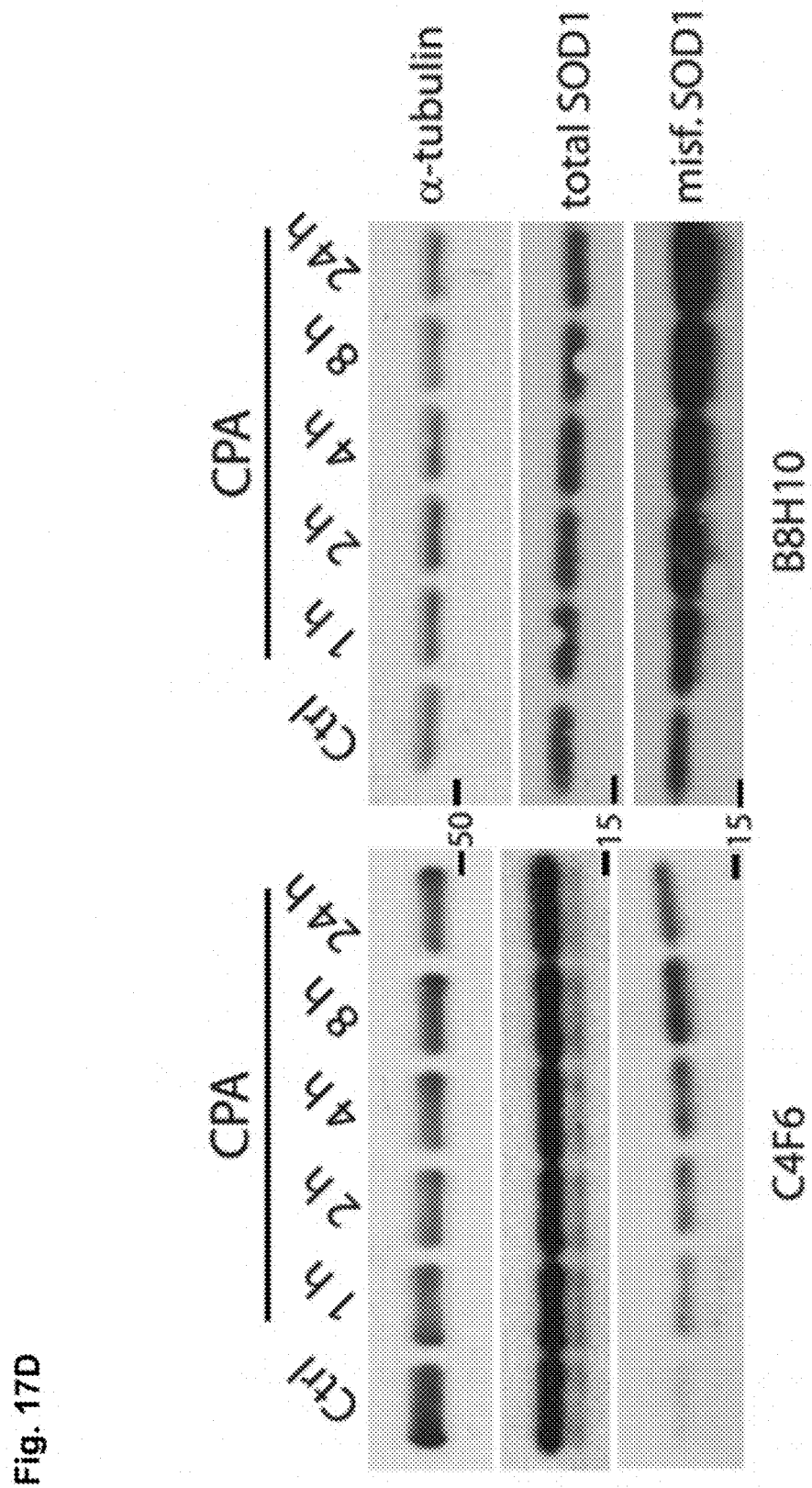
Figure 17E:
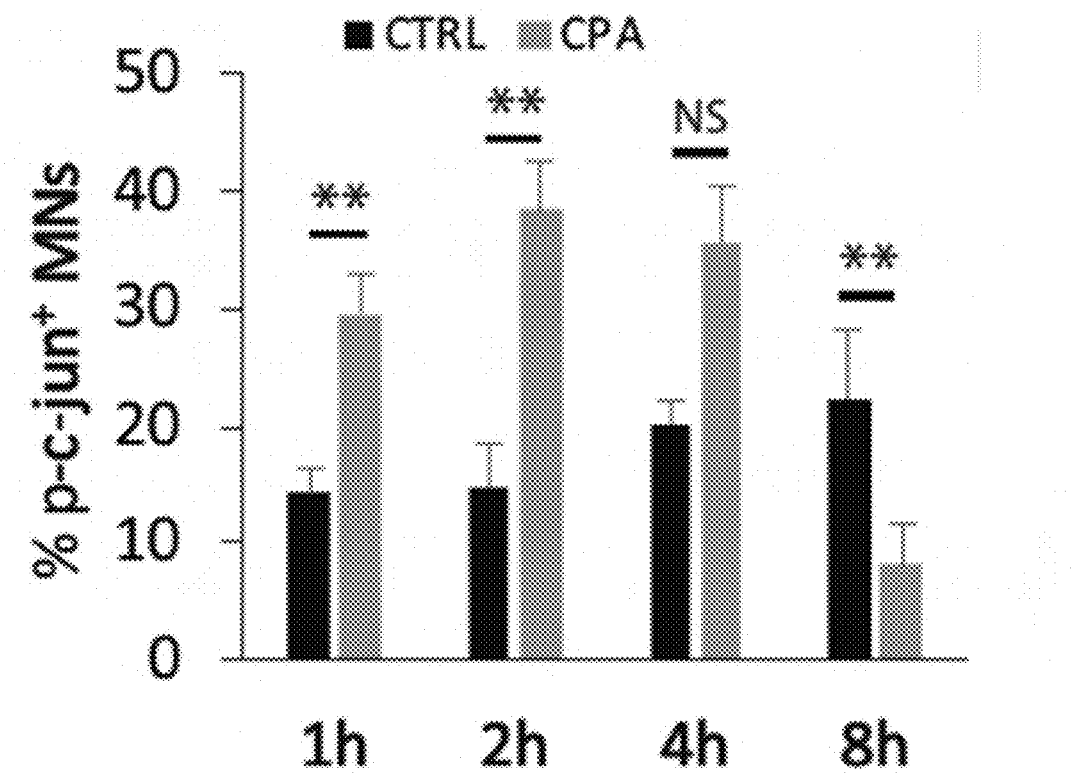
Figure 17F:
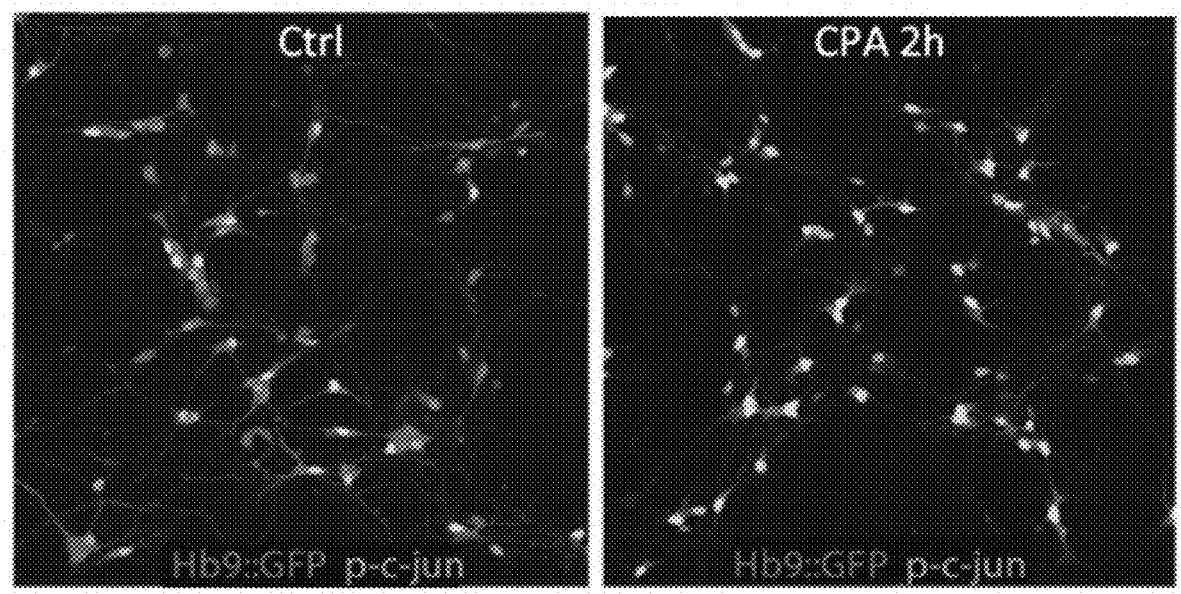
Figure 17G:
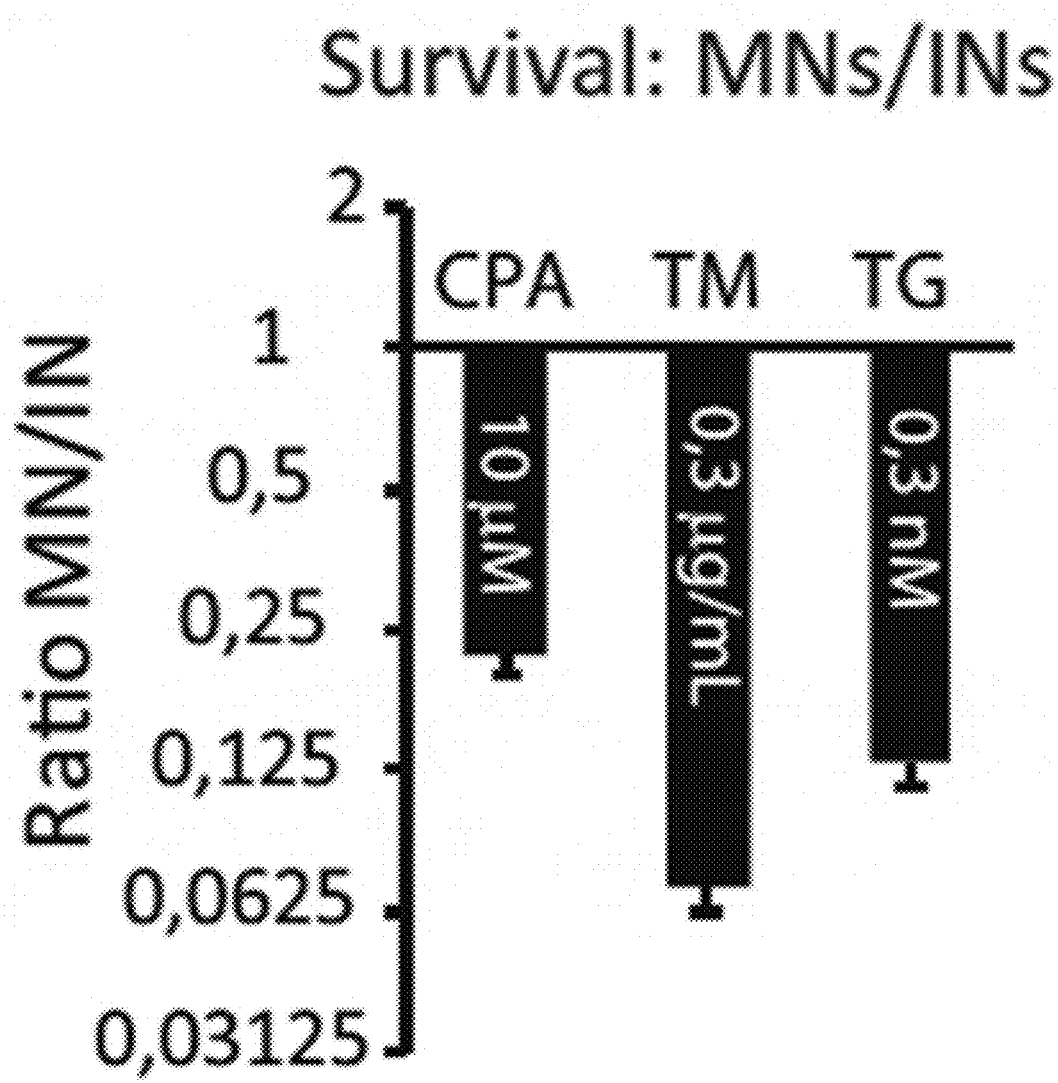

Western blot analysis of protein extracts from control and mutant motor neurons exposed for 1, 2, 4, 8 and 24 hours to CPA confirmed early activation of the PERK pathway (increase in phosphorylation of Eif2α detectable already at 1 hour of CPA exposure) and accumulation of the active cleaved form of ATF-6 detectable at 8 hours (FIG. 17C) in both genotypes. Activation of the IRE1α branch was assessed by qPCR analysis of X-box binding protein 1 (XBP1) splicing, which was already induced by 1 hour of CPA treatment and reached peak at 4 hours of exposure (FIG. 17B). We also evaluated activation of the IRE1α branch by immunocytochemical analysis of c-jun phosphorylation (Urano et al. 2000), which peaked after 2 hours of CPA treatment (FIG. 17E and FIG. 17F).

Activation of the PERK and ATF-6 branches of the UPR/ER stress pathway are associated with protective cellular responses aimed at attenuating protein synthesis and accelerating misfolded protein clearance (Hetz 2012; Lurlaro and Munoz-Pinedo 2016). We therefore sought to examine the effects of CPA treatment on the accumulation of misfolded SOD1 protein in cultured motor neurons (Bosco et al. 2010; Hetz et al. 2009; Saxena et al. 2009; Nishitoh et al. 2008; Gros-Louis et al. 2010). We treated mutant motor neurons with CPA or vehicle and immunoprecipitated misfolded SOD1 using two different conformation-specific hSOD1 antibodies. Western blot analysis revealed an unexpected CPA-dependent increase in the accumulation of misfolded SOD1, indicating that CPA treatment compromises the clearance of misfolded SOD1 protein (FIG. 17D).

To strengthen the link between the activation of ER stress and motor neuron degeneration, we extended our study to include two additional compounds that activate ER stress: thapsigargin, a drug that acts similarly to CPA by inhibiting SERCA pumps, but is irreversible (Lytton et al. 1991), and tunicamycin, a drug that triggers ER stress in a calcium-independent manner by inhibiting protein N-glycosylation in the ER (Oslowski et al. 2011). We exposed co-cultures of GFP-expressing motor neurons and tdTomato-expressing dorsal interneurons to increasing concentrations of thapsigargin and tunicamycin, and, as with CPA, we observed that spinal motor neurons are selectively sensitive to both compounds. Thus, the motor neuron-toxic effects of CPA are likely related to its activation of ER stress pathways and not to its effects on calcium levels or other off-target effects (FIG. 16G).

Compounds that Protect Motor Neurons from CPA-Induced Degeneration

Realization that motor neurons are more sensitive to the activation of UPR/ER stress pathways than other spinal neurons prompted us to setup a candidate molecule screened aimed to identify compounds that would protect motor neurons from CPA toxicity, as ER stress has been implicated in the pathogenesis of ALS as well as many other neurodegenerative conditions (Hetz and Saxena 2017). We screened a panel of >100 compounds that was compiled from in-house libraries and supplemented with compounds that emerged from a literature search (Table 3). This panel included compounds that modulate different branches of ER stress, compounds that influence calcium sequestration, compounds that act as neurotrophic factors, and compounds that have previously been shown to promote motor neuron survival. Mixed motor neuron cultures were pre-treated with rescue compounds for 45 min before exposure to 7.5 µM CPA. Survival and neurite growth were assessed after 24 and 48 hours. The screen yielded several compounds that protected more than 50% of motor neurons dying in response to CPA (FIGS. 18A-18B): the c-Jun N-terminal kinase (JNK) inhibitor SP600125; the tyrosine kinase inhibitor sunitinib; the broad kinase inhibitors Ro 31-8220 mesylate, kenpaullone, GO6976, H-7 and K252a (Sakaki et al. 2008; Kase et al. 1987; Roux et al. 2002). Compounds that rescued over 50% of neurite growth included the neurotrophic factor Cardiotrophin-1; p38 inhibitors SB293063 and SB203580; SP600125; sunitinib; the bile acids TCA, TGCA and TUDCA; and the kinase inhibitors Ro 31-8220 mesylate, GO6976, kenpaullone, H-7 and K252a (FIG. 18B). Overall, GO6976, kenpaullone, K252a and TUDCA appeared to be the most promising candidates, due to their strong survival-promoting effects at low concentrations (GO6976, kenpaullone, K252a) or strong neurite outgrowth-promoting (TUDCA), and were selected for further characterization.

Kenpaullone, a protein kinase inhibitor, recently emerged as a hit from a screen for compounds that rescued neurotrophic factor withdrawal in ESC-derived motor neurons (Yang et al. 2013). We found that it also effectively prevented motor neuron degeneration in response to CPA. We identified two additional kinase inhibitors, the staurosporine analogues GO6976 and K252a, that provided comparable rescue in motor neurons, but were active at lower concentrations than kenpaullone (0.5-2 µM compared to 5-10 µM for kenpaullone) (FIG. 19A). We also determined that TUDCA, an ambiphilic bile acid component that functions as a chemical chaperone, rescued neurite outgrowth (FIG. 25F), but only showed a moderate effect on motor neuron degeneration (FIG. 19A).

One advantage of the stem cell-derived motor neuron survival assay is that it can be easily extended to human motor neurons. To adapt the assay to human cells, we generated a new isogenic pair of ESC lines derived from a human ESC line expressing GFP under the control of the Hb9 motor neuron promoter (HUES3 HB9::GFP, (Di Giorgio et al. 2008)). The ALS-causing A4V mutation was introduced into a single allele of the SOD1 gene using zinc finger nuclease (ZFN)-based genome engineering to recapitulate human patient genotypes (FIGS. 24A-24L). The pair of cell lines was differentiated into motor neurons in parallel using previously published protocols (Amoroso et al. 2013; Maury et al. 2015) and characterized with regard to survival and neurite growth under increasing concentration of CPA. While human motor neurons were less sensitive to CPA than mouse motor neurons (FIG. 24J), we detected a significantly increased degeneration of mutant human SOD1$^{A4V}$ motor neurons exposed to 33 μM CPA (~86% loss) compared to control neurons (~71% loss), thereby recapitulating the genotype-dependent effects of CPA in mouse motor neurons (FIG. 19D and FIG. 19E).

Figure 24A:
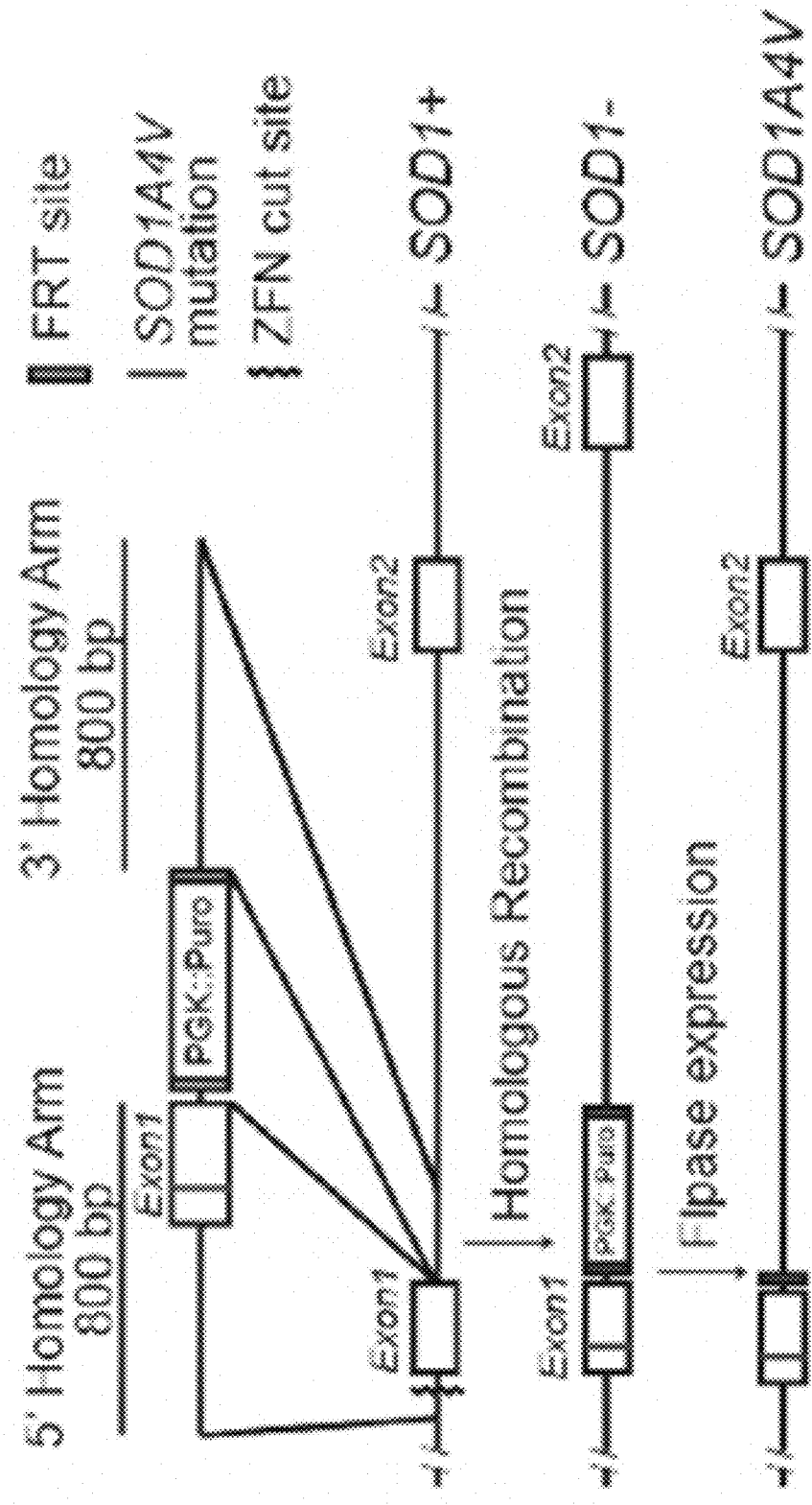
FIGS. 24A-24L show the generation of human isogenic cell lines to study aspects of ALS pathogenesis in vitro.
Figure 24B:
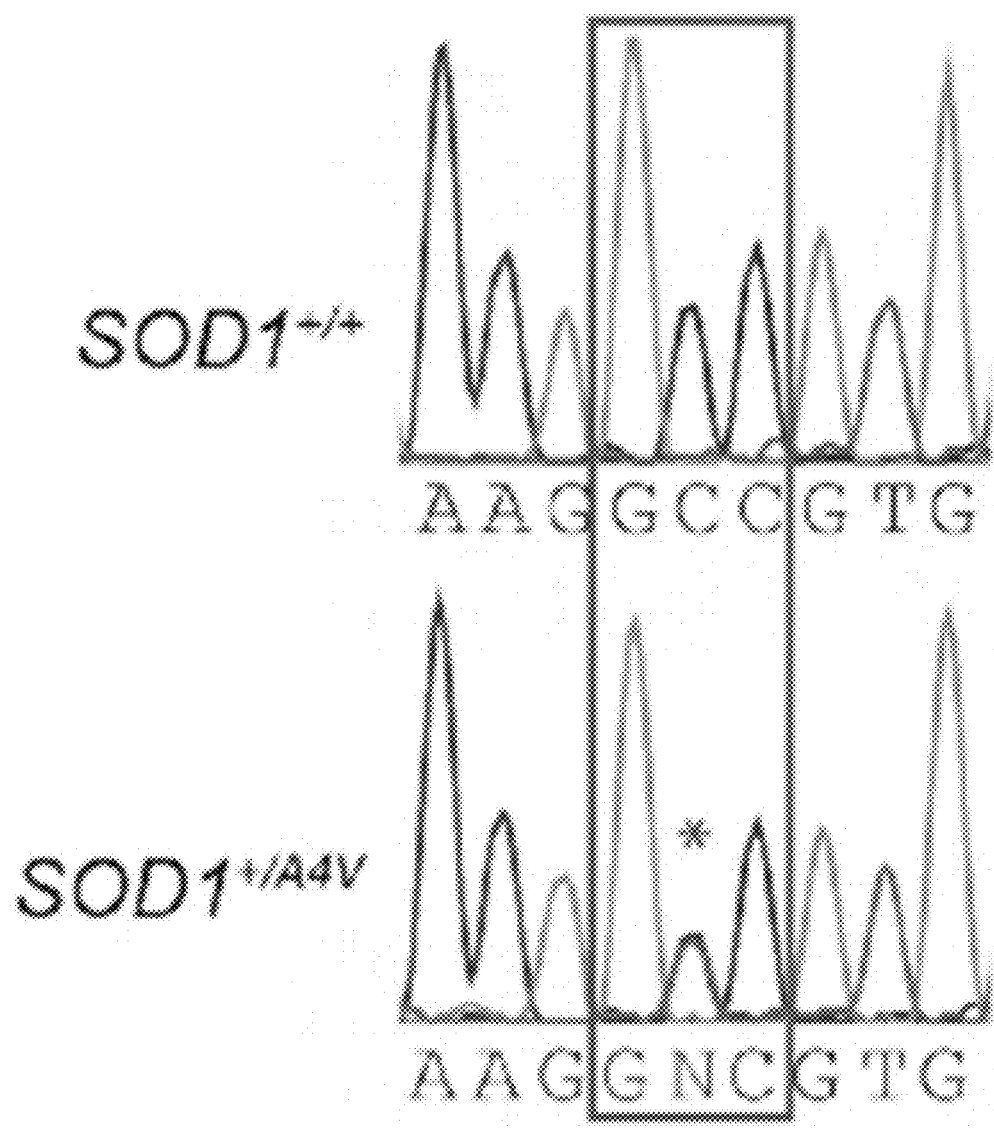
Figure 24C:
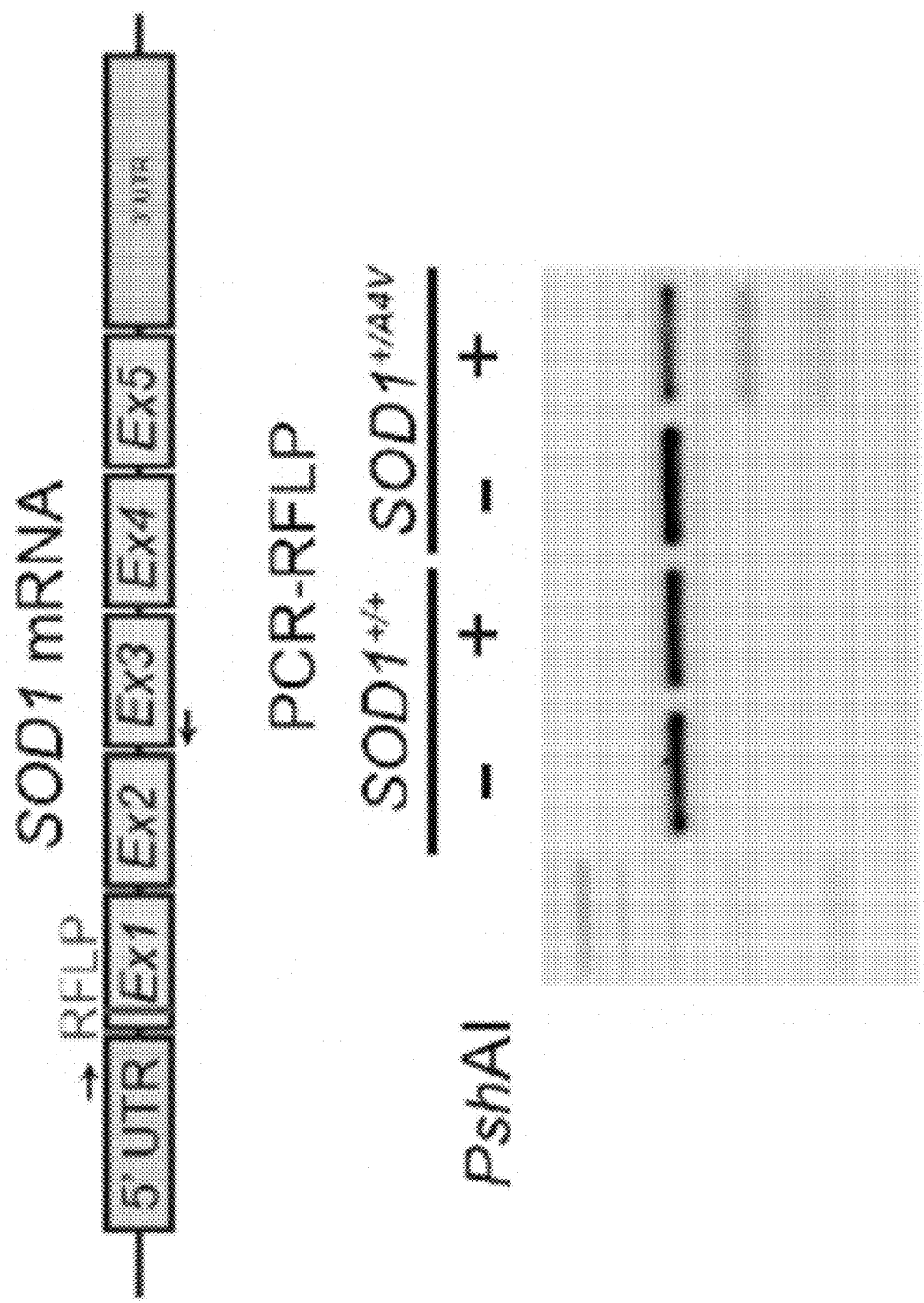
Figure 24D:
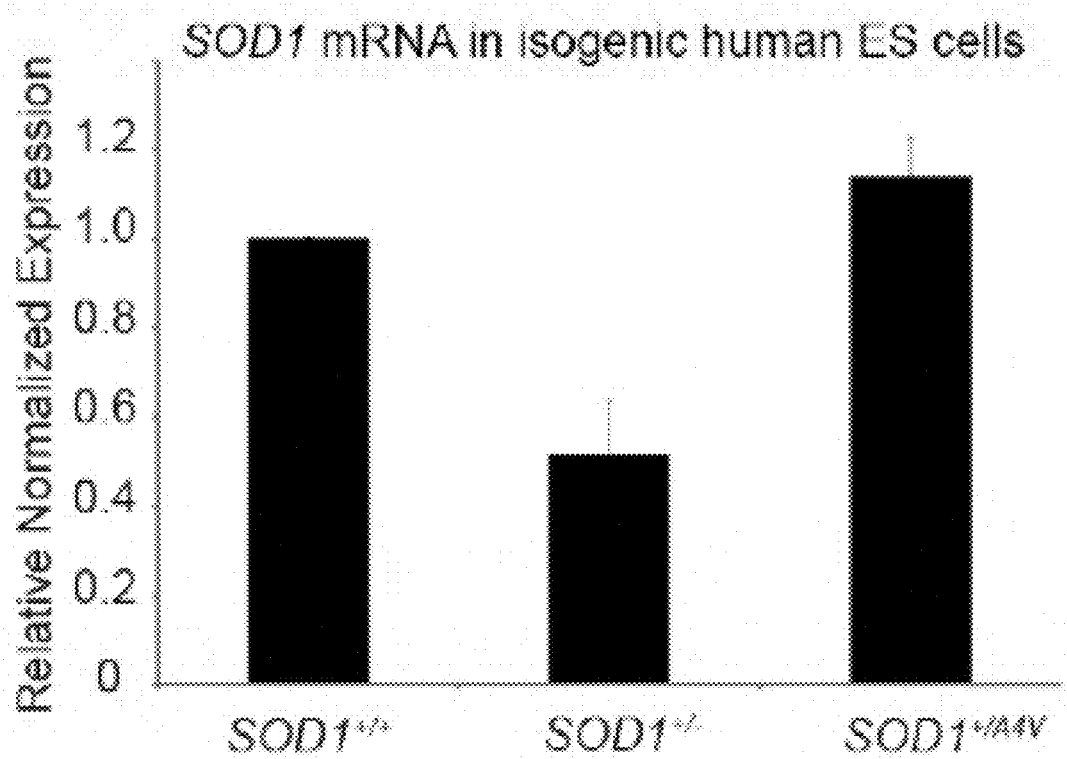
Figure 24E:
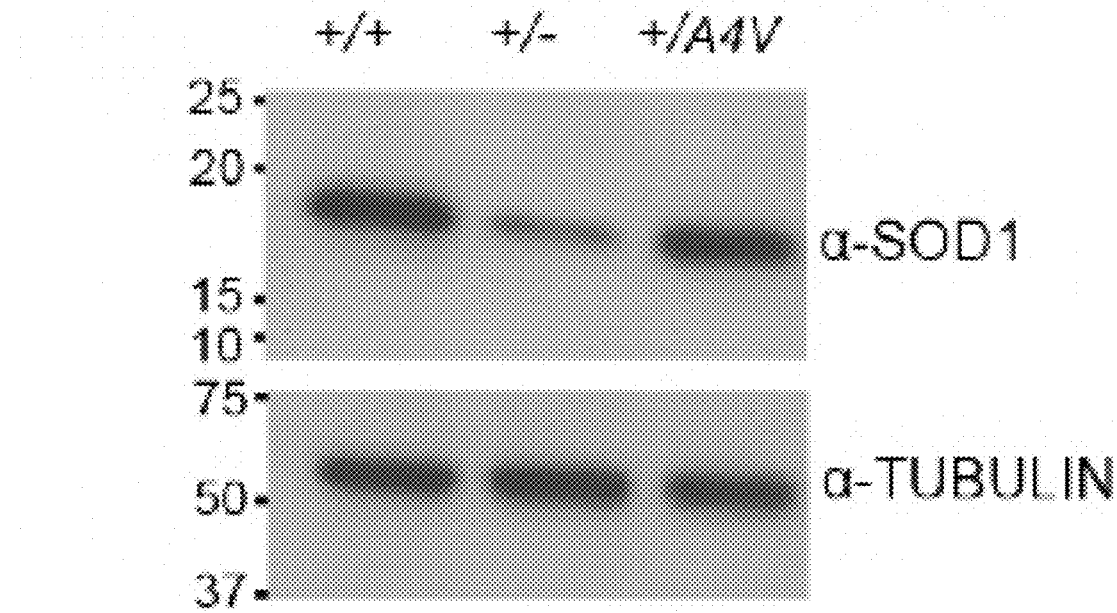
Figure 24F:
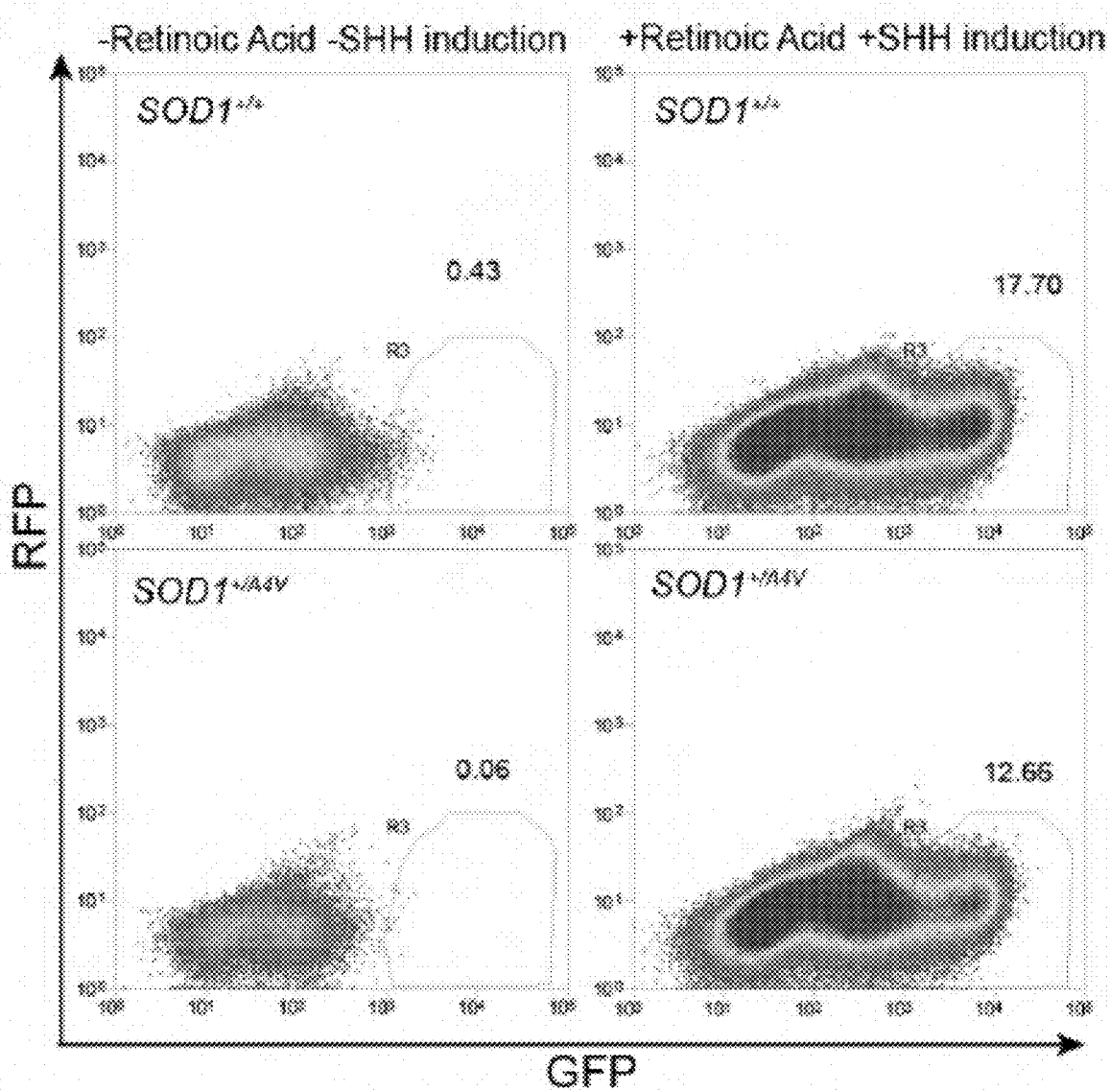
Figure 24G:
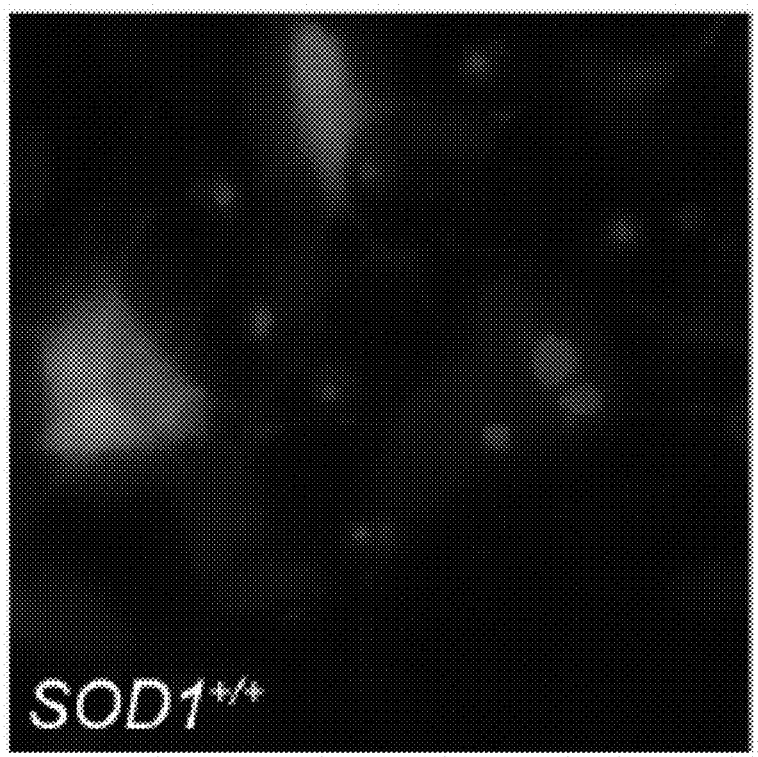
Figure 24G:
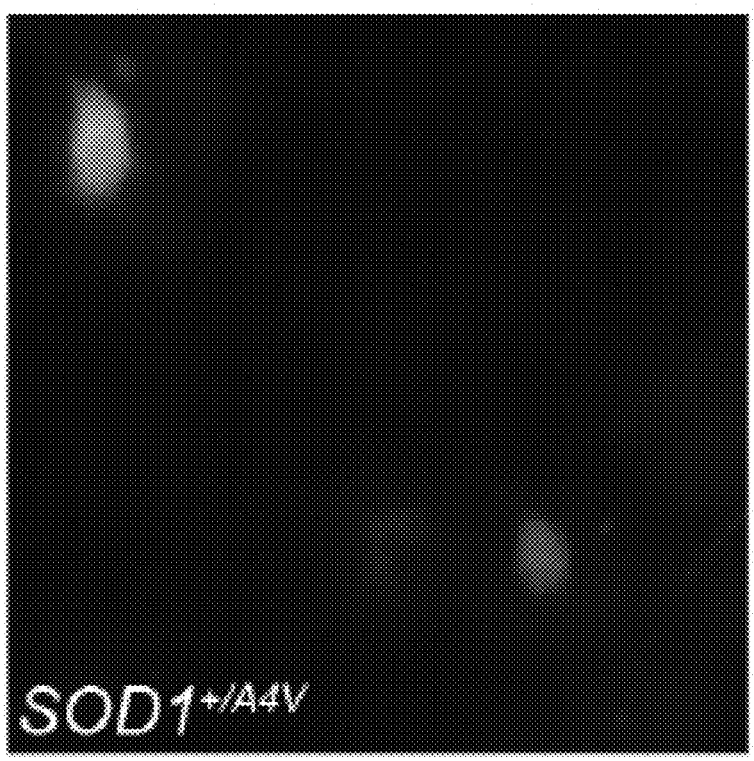
Figure 24H:
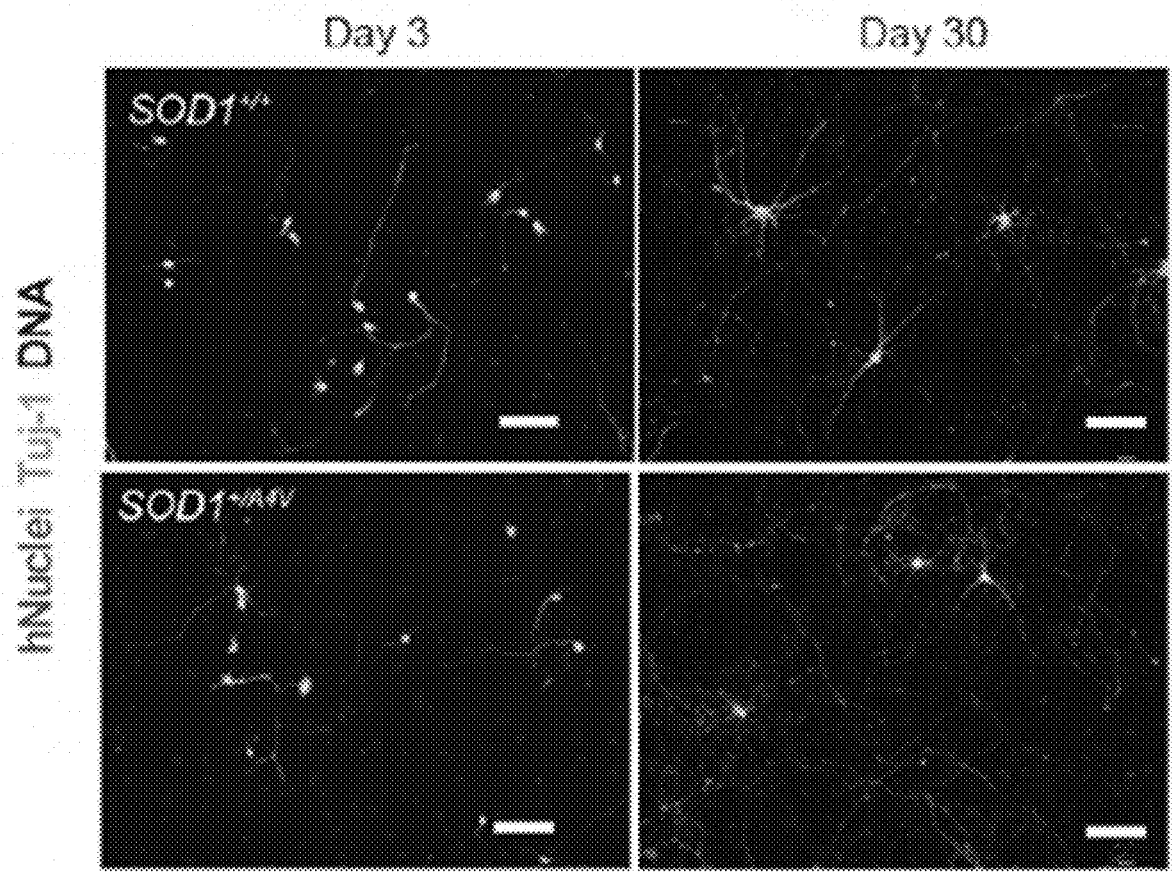
Figure 24I:
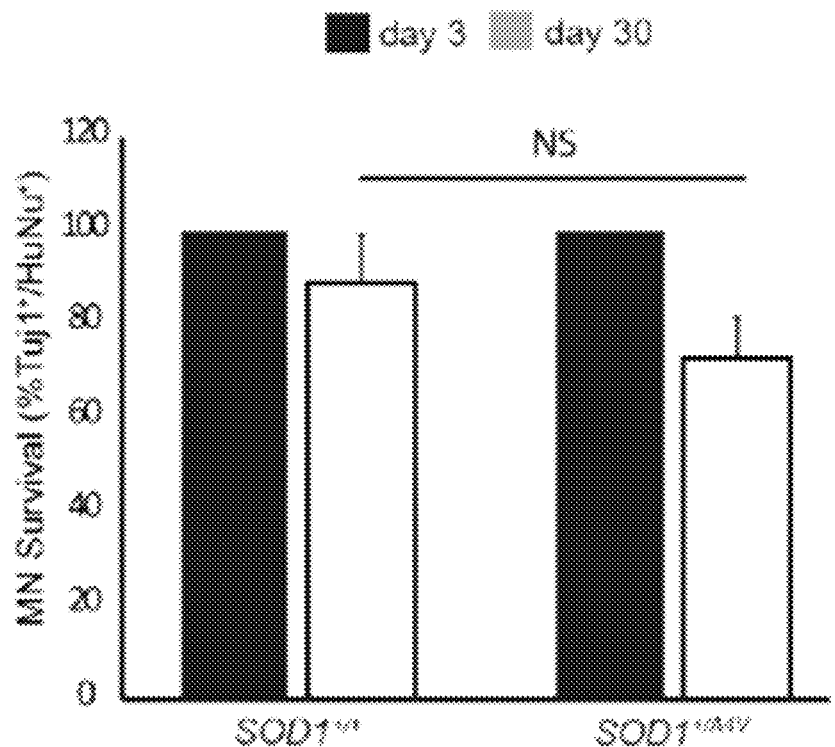
Figure 24J:
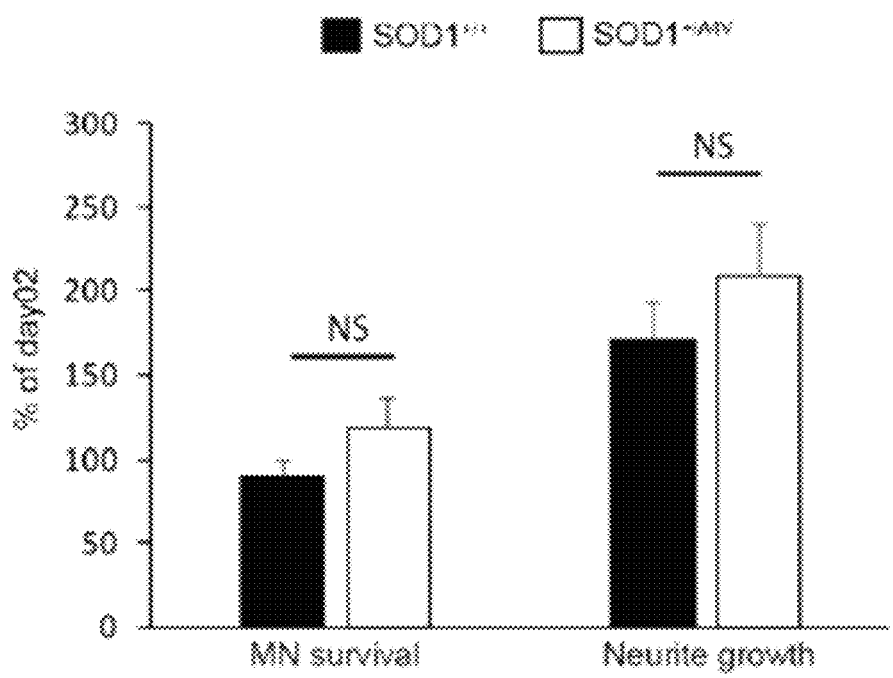
Figure 24K:
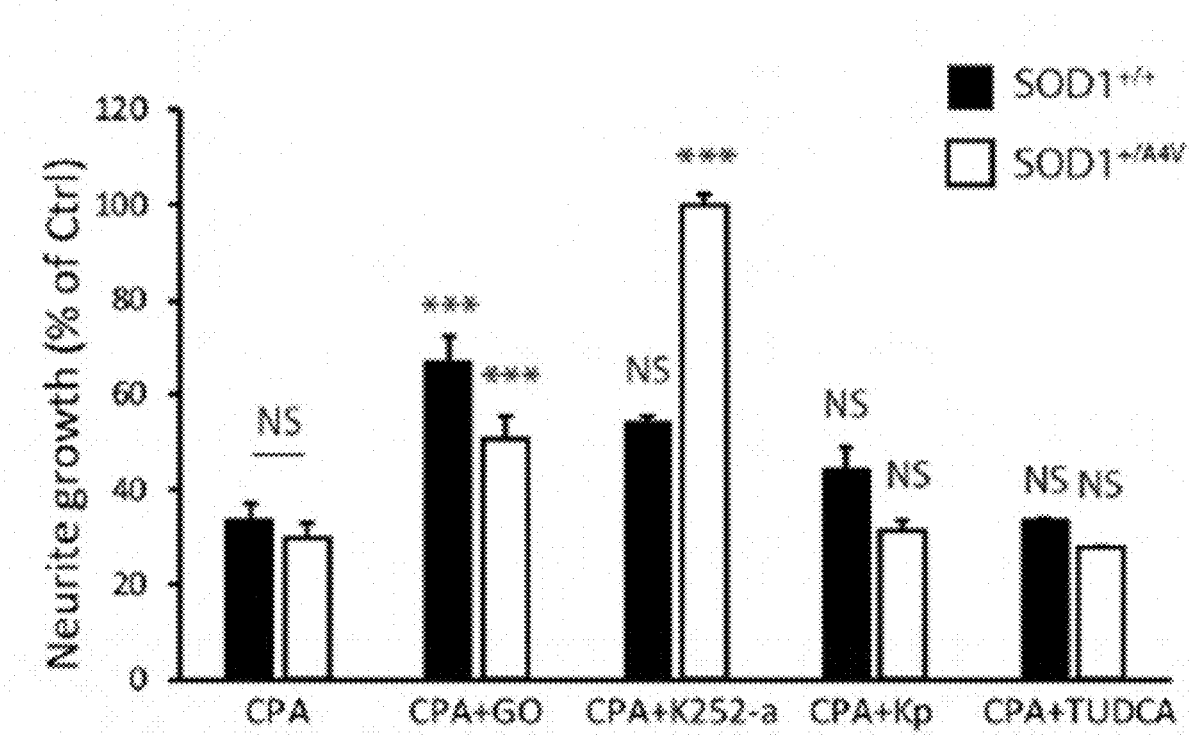
Figure 24L:
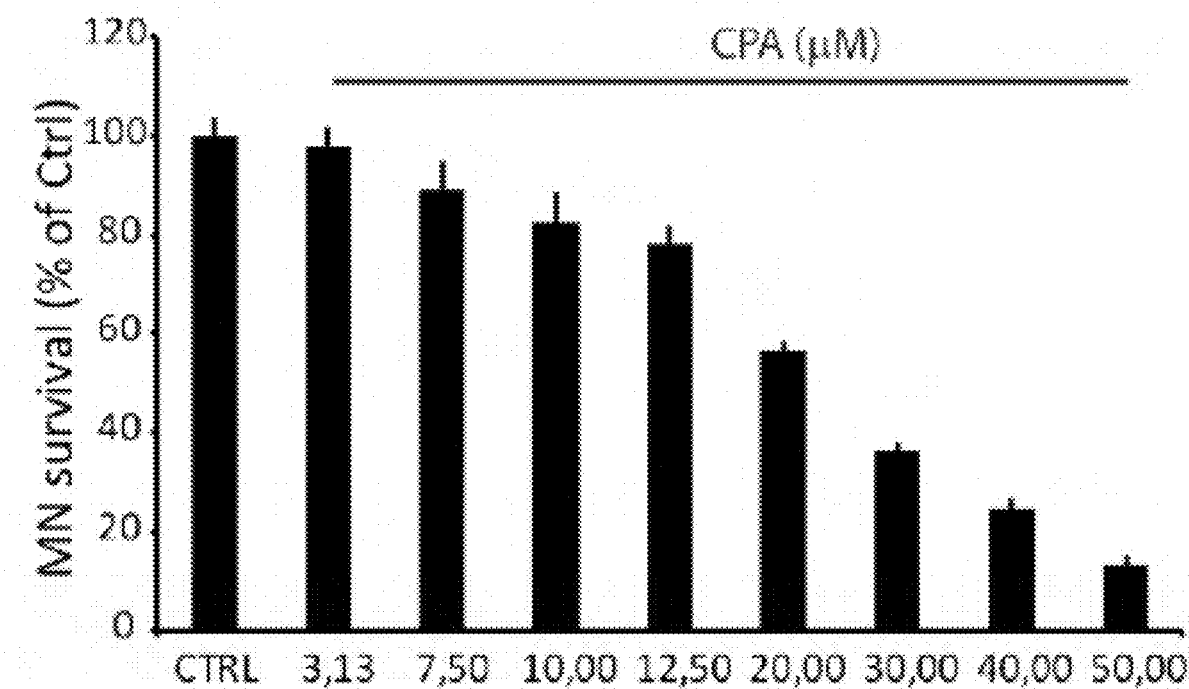

Next, we used the assay to test whether compounds protective to mouse motor neurons will be able to protect human motor neurons exposed to 33 μM CPA. Remarkably, all tested protective compounds identified in the mouse motor neuron screen were also effective in protecting human motor neurons against CPA. Pretreatment of human motor neurons with kenpaullone rescued 42% of CPA-induced cell death in WT motor neurons and 31% in SOD1$^{A4V}$ motor neurons (FIG. 19D), but had no significant effects on neurite growth (FIG. 24I). GO6976 rescued 45% of cell death in WT motor neurons and 34% in SOD1$^{A4V}$ motor neurons (FIG. 19D), and also significantly rescued the decrease in neurite outgrowth (FIG. 24K). K252a was overall the most promising compound, rescuing 56% of cell death in WT and 100% of cell death in SOD1$^{A4V}$ motor neurons (FIG. 19D and FIG. 19E), with significant effects on neurite growth for the latter group. Finally, TUDCA reduced cell death of WT and SOD1$^{A4V}$ motor neurons by 34% and 9%, respectively, with no substantial effects on neurite growth (FIG. 19D, FIG. 24K).

TABLE 3

A screen for rescue of CPA toxicity.

| CPA RESCUE SCREEN Compound | % rescue of CPA toxicity Cell death | % rescue of CPA toxicity Neurite growth | Category/ pathway |
|---|---|---|---|
| DCA | 20.50911675 | 33.79013629 | Bile acids |
| CA | 17.11925797 | 67.46744235 | Bile acids |
| HDCA | 10.18137182 | 22.25725601 | Bile acids |
| CDCA | 11.22034401 | 18.22205814 | Bile acids |
| LCA | 9.085736241 | 22.6248862 | Bile acids |
| nor-DCA | 14.57261804 | 19.56389175 | Bile acids |
| HDCA-Me ester | 7.110779149 | 18.92722876 | Bile acids |
| 6-Et-CDCA | 9.986162197 | 38.17796374 | Bile acids |
| dehydro-CA | 12.31894361 | 53.84822279 | Bile acids |
| LCA-3-sulfate disodium salt | −2.074362332 | 6.127374543 | Bile acids |
| ApoCA | 1.202390831 | −4.777710499 | Bile acids |
| TDCA | 10.95840141 | 65.83163372 | Taurine conjugated bile acids and analogues |
| TLCA | 18.97294284 | 64.49009632 | Taurine conjugated bile acids and analogues |
| TCA | 38.08527479 | 93.68497917 | Taurine conjugated bile acids and analogues |
| UDCA | 18.2051565 | 47.99114566 | Taurine conjugated bile acids and analogues |
| TCDCA | 14.28737331 | 40.5870975 | Taurine conjugated bile acids and analogues |
| GUDCA | 9.970678759 | 41.87969468 | Taurine conjugated bile acids and analogues |
| TGCA | 44.55414037 | 62.09291442 | Taurine conjugated bile acids and analogues |
| GCDCA | 2.568580788 | 4.418783172 | Taurine conjugated bile acids and analogues |
| GCA | 23.53008464 | 35.87867043 | Taurine conjugated bile acids and analogues |
| TMCA | 16.10051109 | 31.5368093 | Taurine conjugated bile acids and analogues |
| Ectoine | 5.031032977 | 4.253494542 | Chemical chaperons |
| Butylated hydroxyanisole | 1.354844525 | −0.941491828 | Chemical chaperons |
| Ferrostatin-1 | 2.79356048 | −2.344252599 | Chemical chaperons |
| AL8810 | 1.258232698 | −2.05527542 | Chemical chaperons |
| PBA | −41.56239575 | −11.70826719 | Chemical chaperons |
| AK1 | −23.86319535 | −30.83271417 | PDI inhibitors |
| AK2 | 1.337184819 | −3.257907284 | PDI inhibitors |
| AK3 | −13.69763943 | −15.12140467 | PDI inhibitors |
| AK4 | −39.65076275 | −46.47310177 | PDI inhibitors |
| AK5 | −23.68718212 | 2.312235213 | PDI inhibitors |
| AK6 | 3.063364798 | 2.312235213 | PDI inhibitors |
| AK7 | −7.303783075 | −11.93026762 | PDI inhibitors |
| AK8 | −27.88593481 | −36.62835997 | PDI inhibitors |
| AK9 | −0.382896758 | −2.05527542 | PDI inhibitors |
| AK10 | 0.714780145 | −10.31330492 | PDI inhibitors |
| AK11 | 1.17828197 | −3.620404836 | PDI inhibitors |
| AK12 | −11.97948204 | −17.65611204 | PDI inhibitors |
| AK13 | 9.871088291 | 16.26285303 | PDI inhibitors |
| AK14 | 0.788806148 | 1.478837654 | PDI inhibitors |
| AK15 | 2.542958577 | 2.436655716 | PDI inhibitors |
| H89 | −30.09836713 | −22.30613359 | PKA inhibtor |
| Ro 32-0432 | 69.45362016 | 81.40427339 | PKC pathway |
| Go 6976 | 132.071419 | 164.4046336 | PKC pathway |
| Phorbol-12-Myristate-13-Ace | 27.1651683 | 27.55476829 | PKC pathway |
| SR122782 | −10.20702158 | 18.68101413 | PKC pathway |
| H-7 dihydrochloride | 65.1027217 | 86.7200762 | PKC pathway |
| Staurosporine | 20.47359662 | 14.17999838 | PKC pathway |
| GF109203X | 27.85088299 | 30.94050956 | PKC pathway |
| Ro 31-8220 mesylate | 69.45362016 | 81.40427339 | PKC pathway |
| Calpain inh. 1 | 6.32809798 | 3.560770737 | Calcium signalling |
| calpain inh. vi | 9.877545437 | 3.897137092 | Calcium signalling |
| calpeptin | 3.098288729 | 0.67757198 | Calcium signalling |
| Dorsomorphin dihydrochloride | 6.73967196 | 27.84365219 | Calcium signalling |

TABLE 3-continued

A screen for rescue of CPA toxicity.

| CPA RESCUE SCREEN Compound | % rescue of CPA toxicity Cell death | % rescue of CPA toxicity Neurite growth | Category/ pathway |
|---|---|---|---|
| KN-93 | -4.231510218 | -9.039734584 | Calcium signalling |
| KN-62 | 3.130314662 | -4.057607419 | Calcium signalling |
| SC 79 | -12.66320348 | 24.67689953 | Calcium signalling |
| ML-7 | -16.018605 | -14.00783075 | Calcium signalling |
| BAPTA-am | -22.4076638 | -23.85843413 | Calcium signalling |
| Dantro | -7.951848422 | -9.099424947 | Calcium signalling |
| STO-609 | 20.72023166 | 14.10316415 | Calcium signalling |
| SB203580 | 42.38514236 | 60.62167911 | P38 pathway |
| SB293063 | 39.23672175 | 88.75752601 | P38 pathway |
| SB747651A | 19.57562965 | 7.742367164 | P38 pathway |
| TC ASK 10 | -1.618735713 | -2.830851895 | UPR: IRE1a pathway |
| NQDI-1 | 38.83991819 | 14.22598976 | UPR: IRE1a pathway |
| JNK-IN-8 | 43.27201114 | 16.24361567 | UPR: IRE1a pathway |
| SP600125 | 56.27881783 | 60.92493308 | UPR: IRE1a pathway |
| APY29 | 57.75930514 | 106.9694934 | UPR: IRE1a pathway |
| 4u8C | 9.303566151 | -0.004912081 | UPR: IRE1a pathway |
| STF-083010 | 9.975897399 | 3.15447713 | UPR: IRE1a pathway |
| GSK2606414 | 21.91490255 | 0.731015109 | UPR: PERK pathway |
| SAL | -5.720293345 | -11.87407306 | UPR: PERK pathway |
| AEBSF | 12.53726409 | 12.53726409 | UPR: ATF-6 pathway |
| K-252a | 118.4447322 | 112.0067487 | MLK pathway |
| Indirubin-3'-monoxime | 1.508853123 | -0.051027126 | GSK3/CDK5 pathway |
| Roscovitine | 5.759798441 | 50.80843357 | GSK3/CDK5 pathway |
| Kenpaullone | 110.5319404 | 155.2520568 | GSK3/CDK5 pathway |
| CHIR99021 | 51.87279329 | 50.56491705 | GSK3/CDK5 pathway |
| PD184352 | -24.33699154 | -16.25729121 | MEK/ERK pathway |
| BRD7386 | -0.290118349 | -4.395083851 | MEK/ERK pathway |
| TTX | 19.50429801 | 0.62468452 | Neurotransmission |
| 2-metyl 5-hydroxy tryptamin | 0.767196361 | 3.779436554 | Neurotransmission |
| Guanabenz acetate salt | -5.953047358 | -1.698662404 | Neurotransmission |
| NBQX | 1.544616023 | 5.665939173 | Neurotransmission |
| DOPA | 2.064118232 | 38.55848623 | Neurotransmission |
| PMA | -5.730983276 | 25.50379088 | Neurotransmission |
| Gambogic amide | 2.750107789 | 39.31132329 | Neurotransmission |
| CT1 | 47.45118857 | 62.31697159 | Neurotrophic factors |
| CNTF | 27.2134856 | 50.77820319 | Neurotrophic factors |
| BDNF | 12.36232474 | 16.59337082 | Neurotrophic factors |
| GDNF | 28.46762539 | 43.13787768 | Neurotrophic factors |
| IGF-1 | 4.009108083 | 0.416651788 | Neurotrophic factors |
| TRIM | 13.72176778 | 53.0837837 | NO signaling |
| CD253 (TRAIL) Antibody | -1.02268982 | 28.50003468 | TNF superfamily & apoptosis |
| Caspase-8 inhibitor II | 2.170111685 | 45.44852287 | TNF superfamily & apoptosis |
| Sorafenib | -8.33727539 | -5.065283411 | Tyrosine kinase inhibitors |
| Sunitinib | 57.75930514 | 106.9694934 | Tyrosine kinase inhibitors |
| Ehop-016 | -58.41396916 | -44.41603223 | Rac pathway |
| ZCL 278 | 3.473221912 | 13.44168678 | Rac pathway |
| Fasudil | 8.602455737 | 18.08080674 | Rho pathway |
| PF-4708671 | -11.45136888 | -16.50140601 | RSK inhibitor |
| SL0101 | 28.18089475 | 88.93617474 | RSK inhibitor |
| PD407 5 | 25.41529778 | NA | Chk1 pathway |
| NSC632839 | 3.12881176 | 10.71355041 | Isopeptidase inh. |
| Phenazine methosulfate | -43.39544535 | -18.42018807 | Miscellaneous |
| Phenethyl isothiocyanate | -29.4794646 | -5.868143127 | Miscellaneous |

A list of compounds tested for their ability to reverse CPA-induced MN toxicity and/or neurite retraction. Compounds are subdivided based on putative pathways or mechanisms of action. Rescue effects are expressed as % reversal of the CPA-effect for survival and neurite growth, for the best time point (24 or 48 hrs post CPA) and concentration tested. Values either represent the averages of replicate culture wells, or from independent experiments for compounds evaluated in follow-up experiments.

The Dietary Supplement TUDCA is Neuroprotective, Reverses CPA-Induced Neurite Retraction, and Delays ALS-Related Muscle Denervation In Vivo TUDCA is an FDA-approved dietary supplement and its effects on diverse pathological conditions have been the focus of multiple clinical trials (NCT00877604, NCT02218619, NCT00771901, NCT01829698). TUDCA is generally safe, has very few side effects, and exhibits good blood-brain-barrier penetrance when administered subcutaneously or orally (Kaemmerer et al. 2001). Because the denervation of neuromuscular junctions (NMJs) is one of the earliest phenotypes observed in mouse models of ALS (Azzouz et al. 1997; Maselli et al. 1993; Tsujihata et al. 1984; Sharma et al. 2016), we reasoned that TUDCA might promote the maintenance of motor axon terminal integrity and delay the denervation process.

Figure 25C:
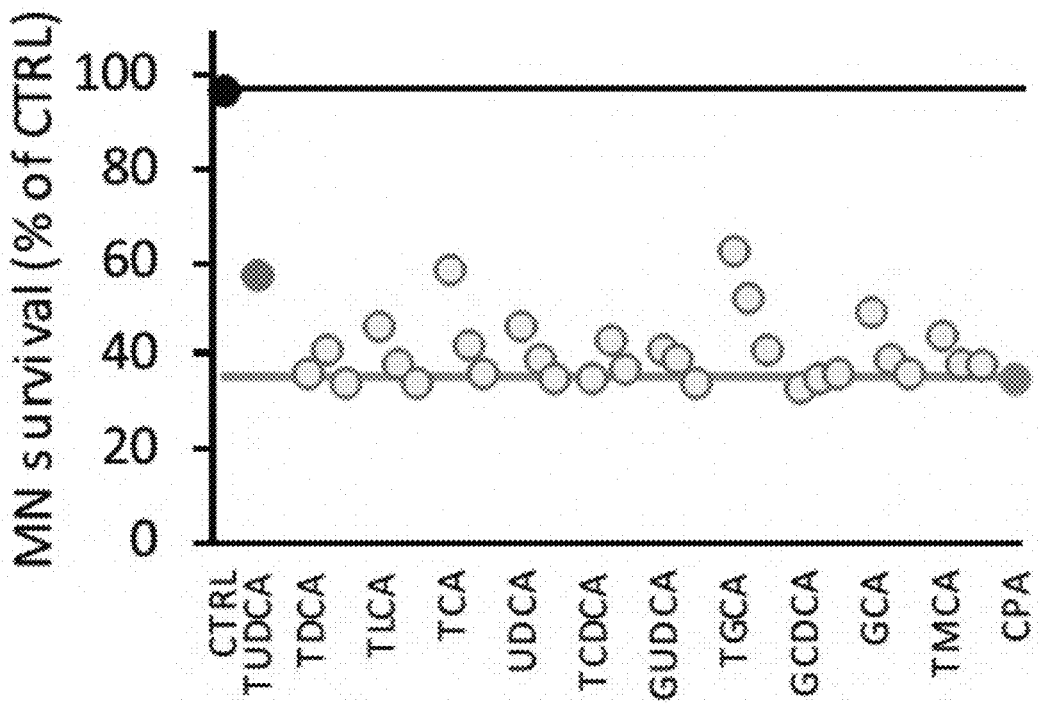
Figure 25D:
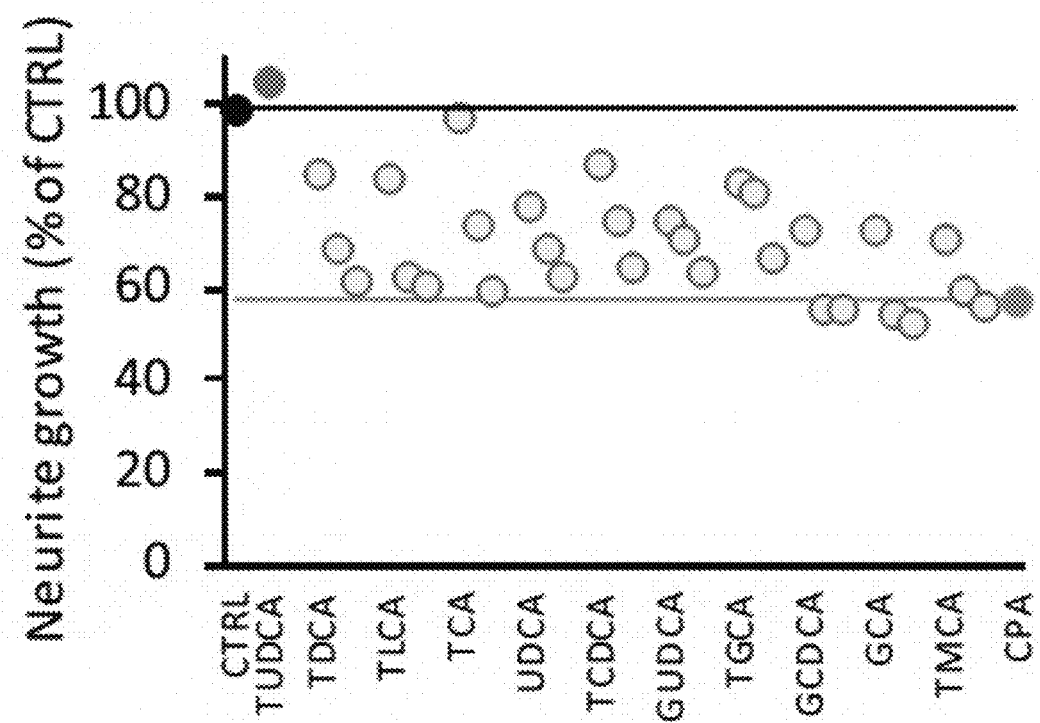
Figure 25E:
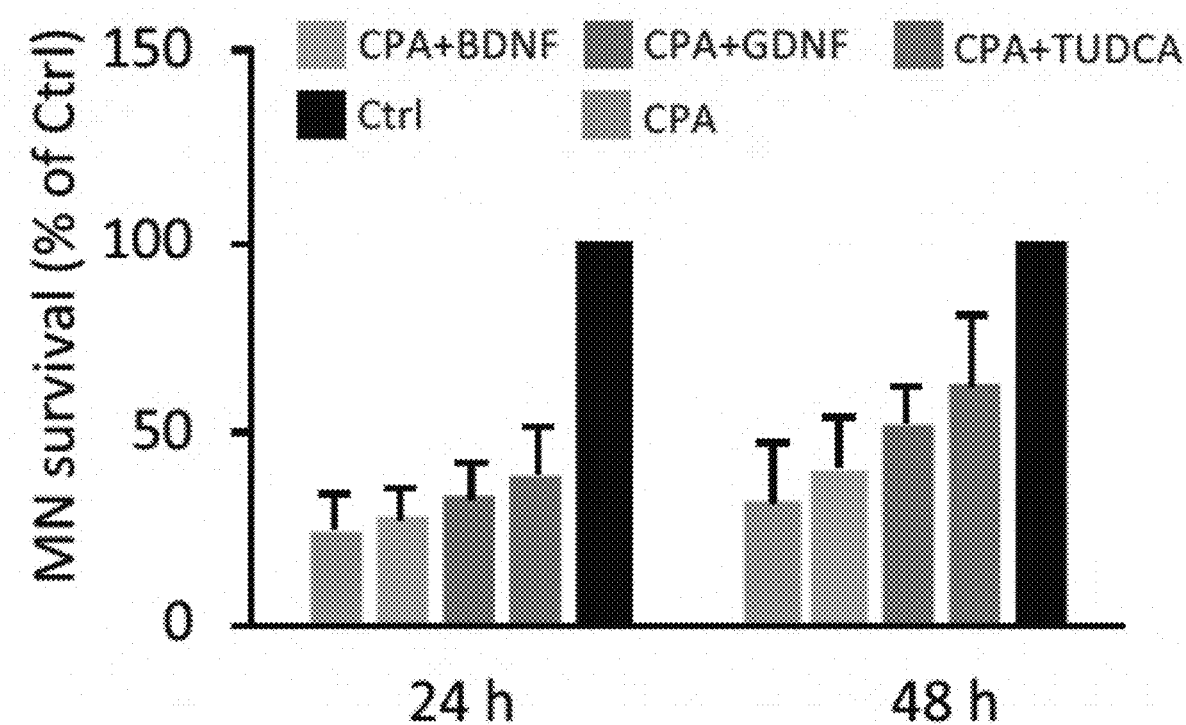
Figure 25F:
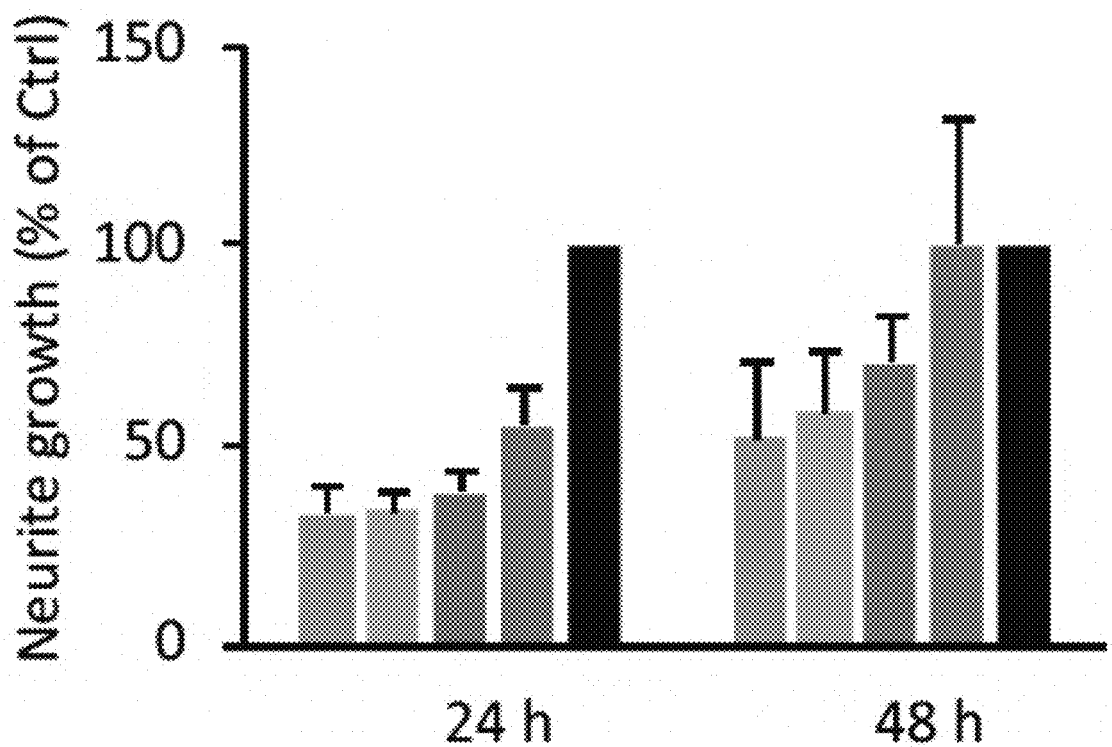
Figure 25G:
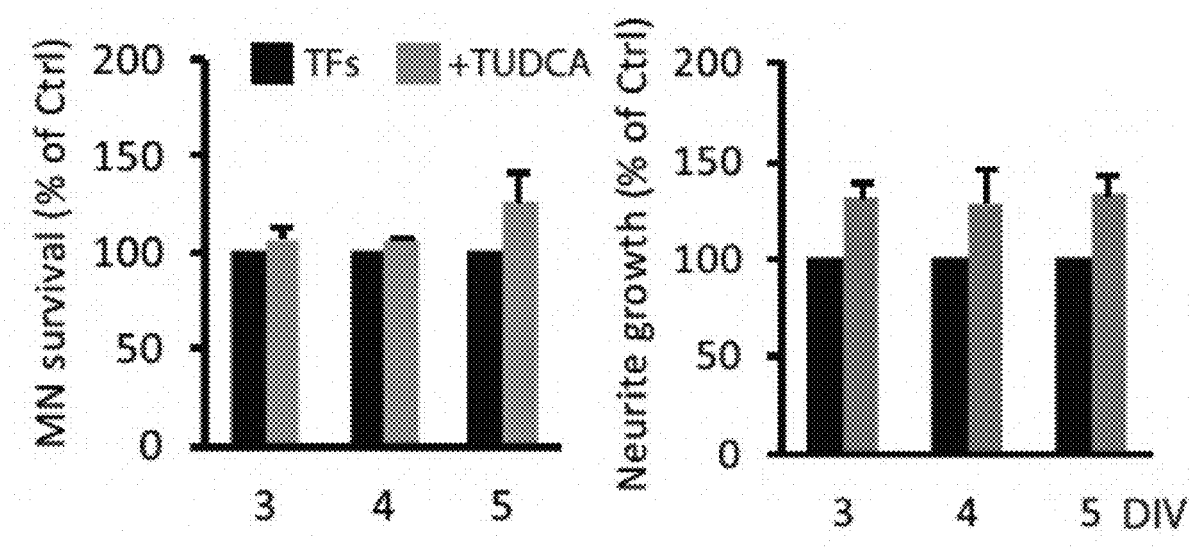
Figure 25H:
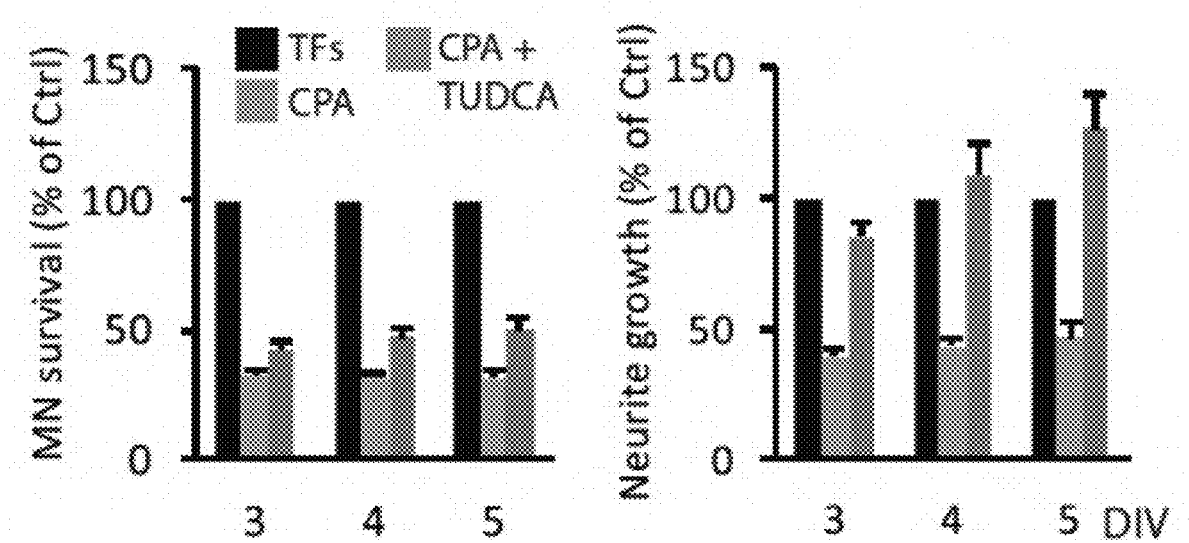
Figure 26:
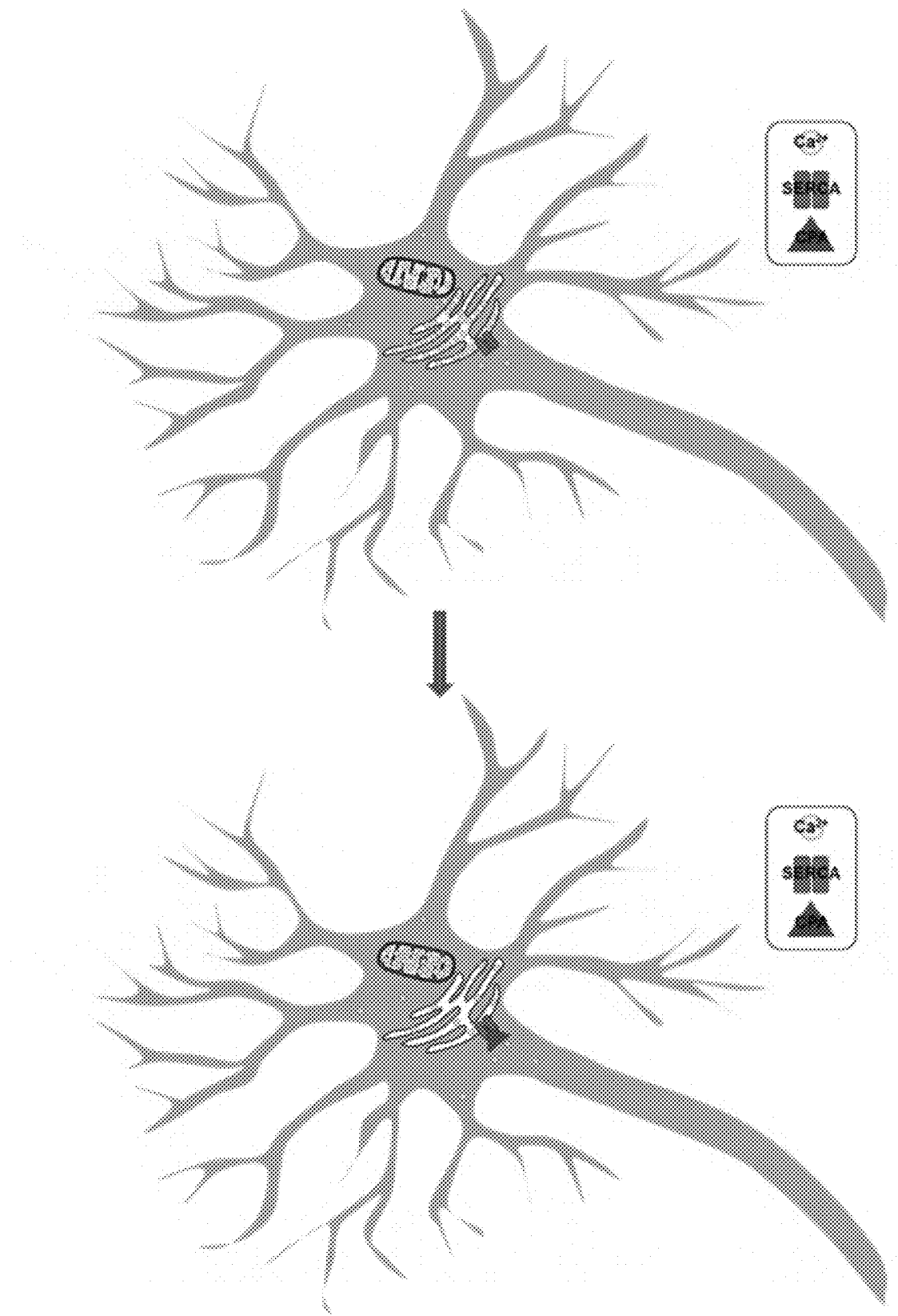
FIG. 26 shows that CPA prevents $Ca^{2+}$ uptake in the ER, thereby blocking the activity of $Ca^{2+}$-dependent protein folding chaperones and rapidly inducing ER stress.
Figure 27:
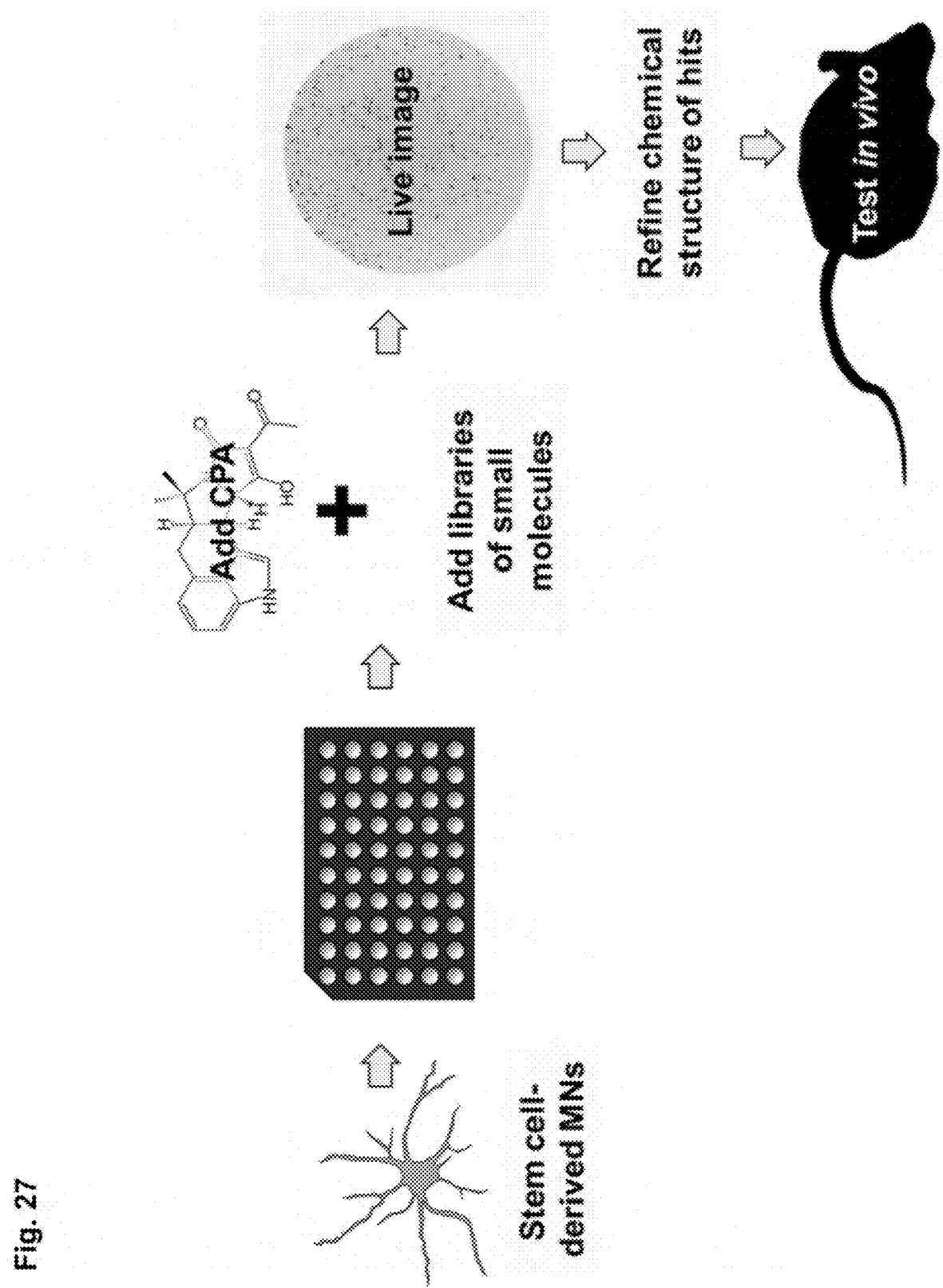
FIG. 27 shows a schematic diagram of a screen process that identifies ALS-relevant stress compounds, which also rescue CPA toxicity.
Figure 28:
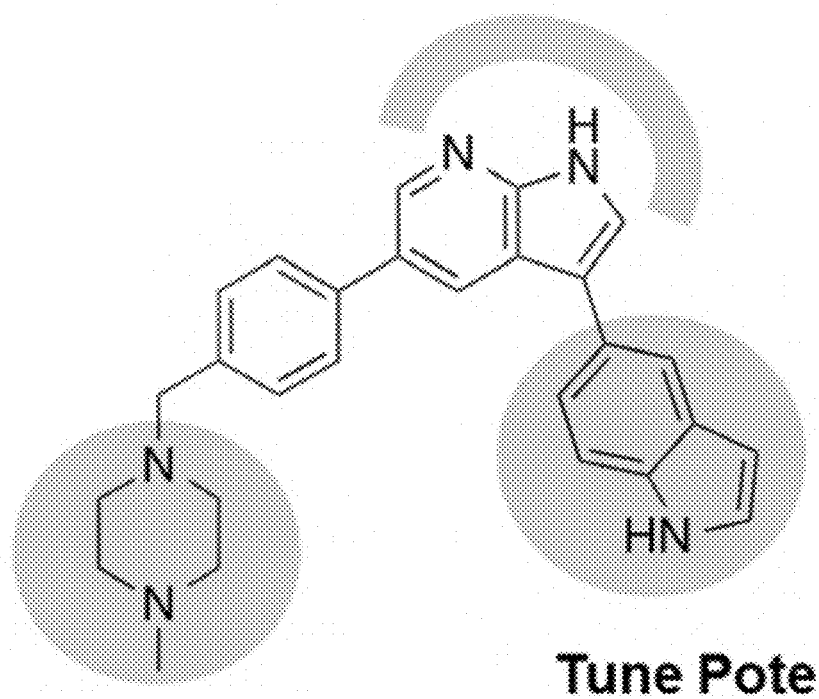
FIG. 28 shows potential modifications for synthesizing compound 1 analogs.

In order to compare the effectiveness of TUDCA to its analogs, we screened it in parallel with 10 conjugated bile acids in CPA-treated motor neurons. Taurine-glycine-conjugated cholic acid (TGCA) matched the moderate effects of TUDCA on motor neuron survival, but worked at lower concentrations; however, it had smaller effects than TUDCA on neurite extension (FIG. 25C and FIG. 25D). Taurine-conjugated cholic acid, TCA, exhibited similar effects to TUDCA on both motor neuron survival and neurite extension, but did not offer any advantages in terms of drug development. Thus, we decided to proceed with TUDCA for further in vivo experiments.

Figure 20A:
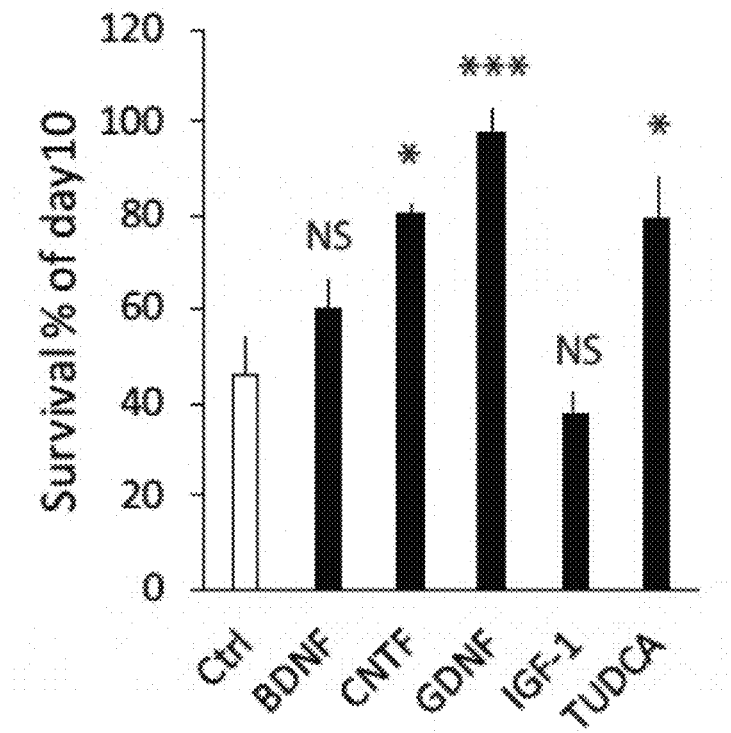
Figure 20B:
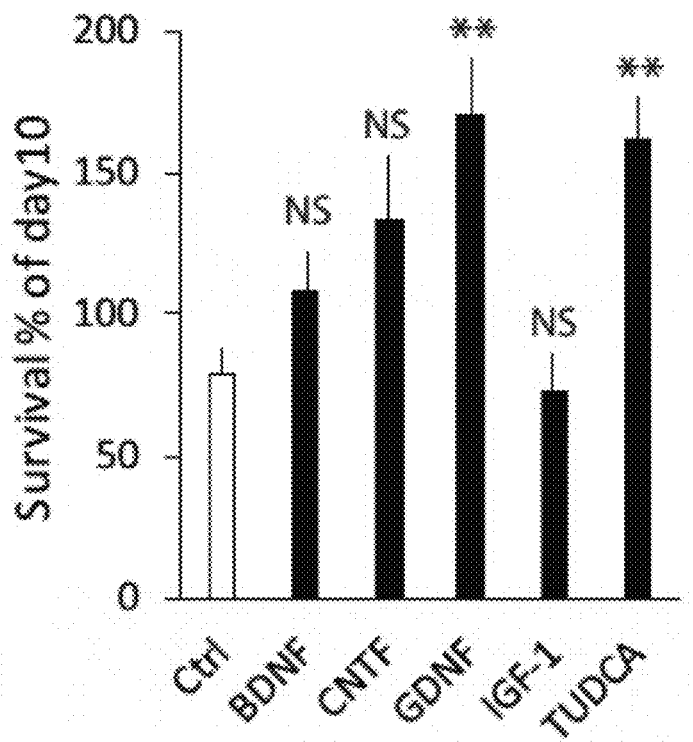
Figure 20C:
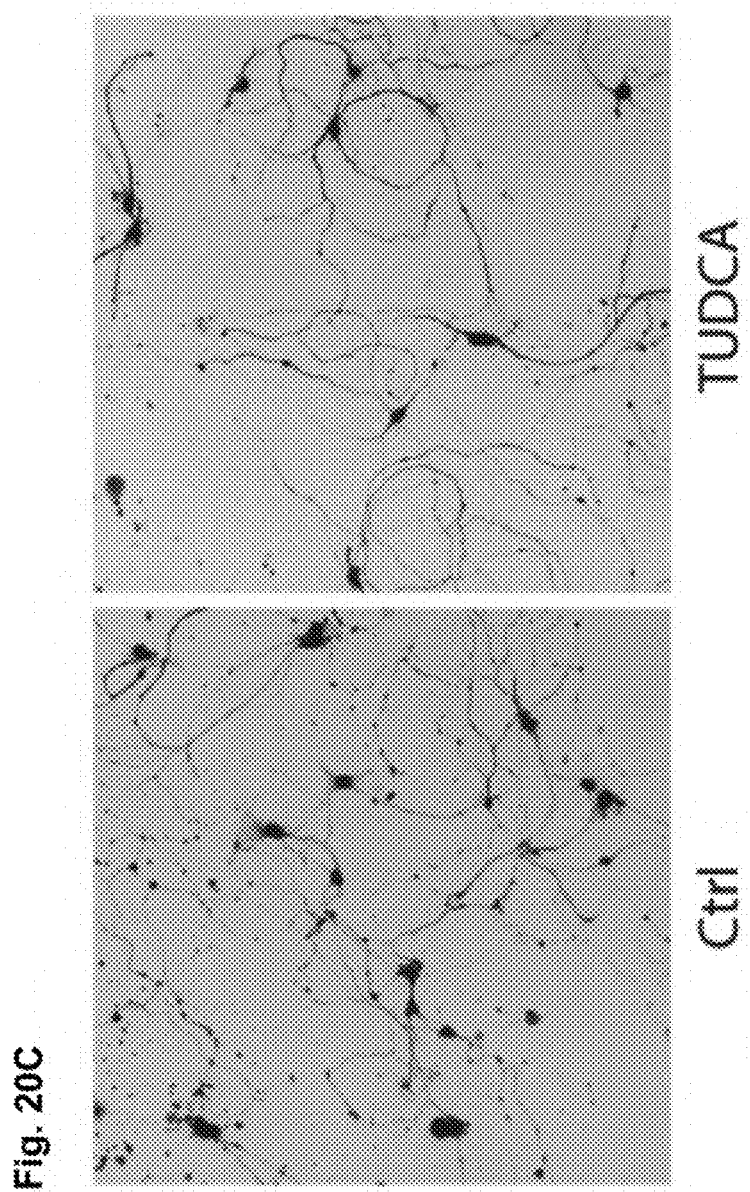
Figure 20D:
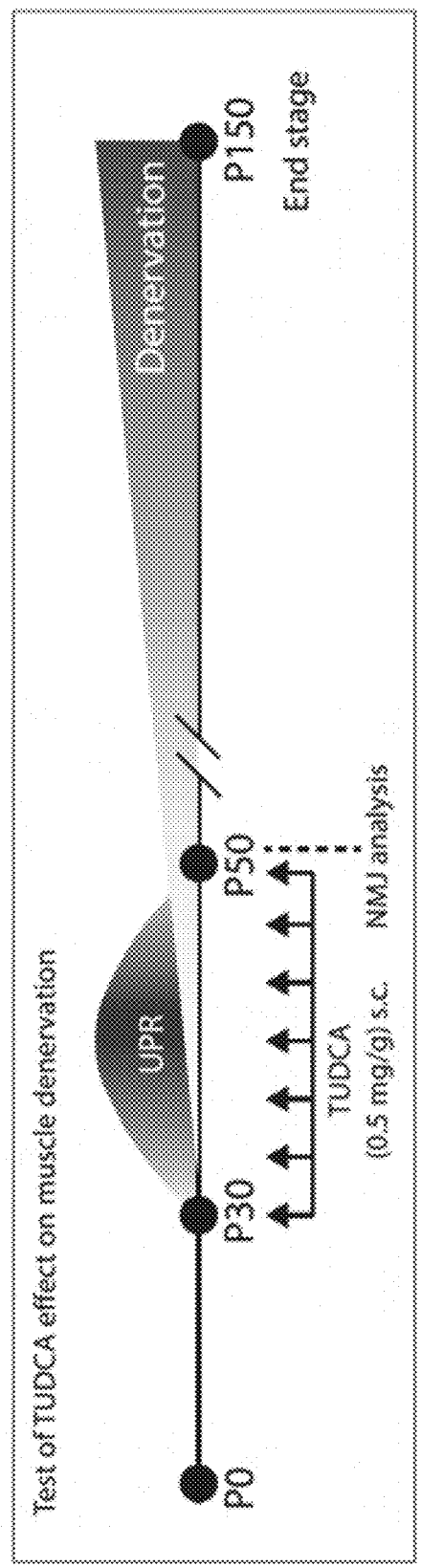
Figure 20F:
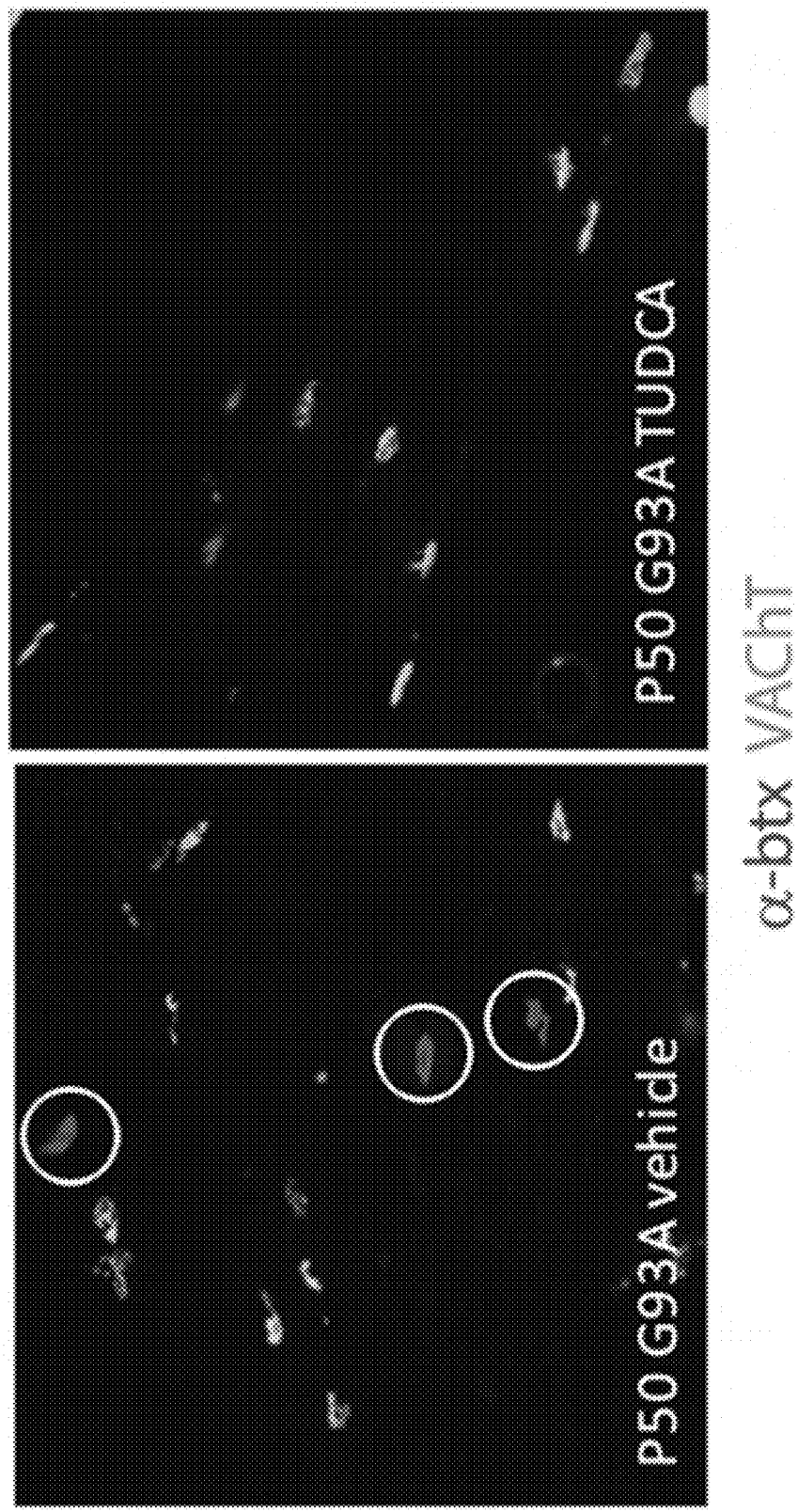

To test the ability of TUDCA to preserve motor axons in ALS models in vivo, we designed a small-scale study in which we evaluated the denervation of the fast fatigable hind limb muscle tibialis anterior (TA) (FIG. 20D). We have previously determined that TA motor neurons in B6.Cg-Tg (SOD1*G93A)1Gur/J mice undergo a period of ER stress beginning at P30, followed by muscle denervation that extends to P50 (Kaplan et al. 2014). During this period, the TA muscles display 25-40% denervation before becoming substantially atrophied at later time points. To target this window of ER-stress-related neurodegeneration, we treated hSOD1$^{G93A}$ mice with subcutaneous TUDCA injections every three days between P30 to P50. At the end of the experiment, we counted total NMJs by staining for acetylcholine receptors on the TA muscle with Alexa Fluor 488-conjugated α-bungarotoxin, and assessed their innervation by staining for motor axons with antibodies against vesicular acetylcholine transferase (VAChT) (FIG. 20F). Despite the fact that mice received only seven injections over the course of 21 days of treatment, we observed a moderate, but statistically significant increase in NMJ innervation in TUDCA-treated hSOD1$^{G93A}$ mice compared to untreated animals (FIG. 20E).

DISCUSSION

Modeling degenerative diseases in cell culture systems opens new opportunities to investigate the pathological processes associated with disease-causing mutations and to screen for novel therapeutic agents. However, adult-onset degenerative diseases where the causative mutations result in subtle changes in cellular function or mild survival or morphological phenotypes are difficult to model in the kinds of short-term culture systems that are compatible with high throughput drug screening. We reasoned that discovery of stressors that induce and accelerate phenotypic changes in motor neurons in vitro could provide insights into molecular pathways contributing to motor neuron degeneration, and could lead to the discovery of novel motor neuron-protective compounds.

ALS-causing mutations are not overtly toxic to spinal motor neurons: patients do not show any obvious motor deficits during the presymptomatic phase of the disease, which typically lasts for decades. Even in an aggressive mouse model of ALS caused by overexpression of mutant hSOD1, no motor neuron death is observed until adulthood (Chiu et al. 1995), indicating that the effects of ALS mutations are either cumulative or that they are potentiated by age- and/or environment-related stressors. To identify stressors that contribute to the degeneration of mutant motor neurons, we designed a highly sensitive, intrinsically controlled survival assay. The co-culture setup reduces effects of non-cell autonomous toxic factors, allowing us to focus on the intrinsic increased vulnerability of motor neurons expressing disease-causing mutant SOD1 protein. Using this platform, we identified CPA as a compound that is more toxic to mutant than control ESC-derived motor neurons. Perhaps even more interesting observation was that motor neurons were considerably more sensitive to CPA and other ER stress-inducing compounds than other types of spinal neurons.

CPA inhibits the SERCA pump, affecting several pathways and cellular processes previously associated with ALS (Kiskinis et al. 2014; Hetz et al. 2009; Saxena et al. 2009; Saxena et al. 2013; Nishitoh et al. 2008; Bernard-Marissal et al. 2012; Jaiswal et al. 2009; Jaiswal et al. 2009; Takuma et al. 1999; von Lewinski and Keller 2005; Kikuchi et al. 2006; Parone et al. 2013). We show that CPA treatment (Peters et al. 2015) perturbs calcium handling; (Amoroso et al. 2013) triggers ER stress and the unfolded protein response; and (Dimos et al. 2008) leads to the accumulation of mutant SOD1 in hSOD1$^{G93A}$ ESC-derived motor neurons. This last finding suggests that mutant SOD1 is normally cleared through a constitutive pathway, which is compromised upon SERCA inhibition. Misfolded forms of SOD1 have been observed in human post-mortem tissue samples as well as in several models of ALS, but the precise mechanisms through with they perpetuate motor neuron death are unclear (Gros-Louis et al. 2010; Kikuchi et al. 2006). Even though SOD1 is translated on free cytosolic ribosomes, previous studies have indicated that the mutant form can be detected inside mitochondria and the ER (Kikuchi et al. 2006; Vande Velde et al. 2008).

To parse the roles of aberrant calcium handling vs. ER stress induction in CPA-mediated neurodegeneration, we tested a series of pharmacological agents that modulate intracellular calcium levels or induce ER stress through calcium-independent routes. Based on these studies, we concluded that calcium mishandling is unlikely to be driving the acute degenerative process observed in response to CPA. We therefore focused on pathways associated with, and downstream of, the unfolded protein response and ER stress.

A screen of candidate neuroactive compounds identified several potent drugs that could reverse the harmful effects of CPA. Two classes of compounds were of particular interest: kinase inhibitors and bile acid derivatives. Kinase inhibitors exhibited a remarkable ability to protect motor neurons from CPA toxicity. One compound, kenpaullone, was previously shown to protect motor neurons from neurotrophic deprivation (Yang et al. 2013). It was also demonstrated to improve survival and reverse electrophysiological deficits in human stem cell-derived motor neurons from a patient carrying a mutation in the FUS gene (Liu et al. 2016). In addition to kenpaullone, we identified two staurosporine analogues, K252a and GO6976, that have previously been reported to increase neuronal survival in several in vitro neurodegeneration models (Roux et al. 2002; Jeohn et al. 2000). However, these inhibitors will require further optimization. Kenpaullone is insoluble in aqueous solutions at its most effective concentrations, precluding further in vivo studies without extensive efforts to reformulate its vehicle composition. K252a and GO6976 are more potent and more soluble than kenpaullone (data not shown) in our survival assays; however, these compounds are broad-spectrum inhibitors, each targeting >100 different kinases, and the identity of the targets relevant for motor neuron degeneration remain ill-defined. We are currently working to identify these targets and develop more specific analogs for further in vivo testing.

The second class of neuroprotective compounds that emerged from our screen were derivatives of mammal bile acids, which have been used extensively in traditional Tibetan and Chinese medicine. While this class of compounds protected <30% of dying motor neurons, it completely restored neurite outgrowth. In contrast to the kinase inhibitors that are not approved for human use, tauroursodeoxycholic acid (TUDCA) is a widely-available dietary supplement, and its analogue UDCA is a water-soluble FDA-approved drug for treating pruritus and liver disease. TUDCA has previously been shown to have beneficial effects in mouse models of Huntington's and Alzheimer's disease (Keene et al. 2002; Keene et al. 2001; Nunes et al. 2012). TUDCA has also been shown to reduce the expression of markers of the unfolded protein response in a mouse model of type 2 diabetes, in part by acting as a chaperone for misfolded proteins (Ozcan et al. 2006; Uppala et al. 2017). We have extended these studies by demonstrating that TUDCA preserves neuromuscular junction integrity in a mouse model of ALS, raising the possibility that TUDCA alone or in combination with other treatments might delay motor disease onset or progression.

Our findings add to mounting evidence that ER stress contributes to motor neuron cell death in ALS, and we describe a scalable stem cell-based system to probe both the cell autonomous effects of ER stress and the means by which to reverse them. This system can be easily adapted to other neurodegenerative conditions in which ER stress is a hallmark, such as Parkinson's disease, Huntington's disease, prion disease and Alzheimers disease (Hetz and Saxena 2017). Most importantly, we adapted the assay to test neuroprotective compounds directly on human motor neurons, which could accelerate the preclinical evaluation of drugs that modulate motor neuron survival by maximizing the possibility that they would be effective in human patients.

Materials and Methods

Derivation of Mouse Transgenic Embryonic Stem Cells Lines

Heterozygous Tg(Hlxb9-GFP)1Tmj or Tg(Hlxb9-tagRFP) reporter mice were crossed with mice expressing a mutated (B6.Cg-Tg(SOD1*G93A)1Gur/J) or WT form (B6SJL-Tg(SOD1)2Gur/J) of human SOD1. Blastocysts were collected at embryonic day 3.5. Mouse embryonic stem cell (ESC) lines from were derived as previously described (5). New lines were genotyped and sequenced to confirm the presence of both transgenes and the G93A point mutation.

For interneuron differentiations, mouse embryonic stem cell lines were derived from Ptf1α::cre mice (kindly provided by Dr. Kaltschmidt) crossed to Rosa-LSL-tdTomato fluorescent reporter mice (Kawaguchi et al. 2002; Madisen et al. 2010).

Generation Isogenic Human Embryonic Stem Cell Lines by Genetic Targeting

In order to extrapolate results from the mouse assays, we generated an independent set of $SOD1^{+/A4V}$ and $SOD1^{+/+}$ isogenic cell lines by introducing the A4V mutation into the wild-type SOD1 locus of the human embryonic stem cell line HUES3 Hb9::GFP (Di Giorgio et al. 2008). Using again a two-step nuclease-mediated gene targeting strategy (Maeder et al. 2008), we introduced the $SOD1^{A4V}$ mutation into the HUES3 Hb9::GFP genetic background (FIG. 24A). After corroborating the desired SOD1 gene edit (FIG. 24B and FIG. 24C), we directed the differentiation of $SOD^{+/A4V}$ and $SOD1^{+/+}$ HUES3 Hb9::GFP cells into cultures containing spinal motor neurons. GFP+ motor neurons of both genotypes could be isolated using FACS (FIG. 24D) and SOD1 transcript and protein expression in these cells was confirmed (FIG. 24F and FIG. 24G). The new lines were further validated by staining for motor neuron transcription factor Islet1 (FIG. 24E) and assessment of survival in short and long term cultures (FIG. 24H and FIG. 24I).

Mouse and Human Motor Neuron Differentiation

Motor neuron differentiation of transgenic mouse ESCs was performed as previously described (Wichterle et al. 2002). Briefly, cells were dissociated on day six of differentiation and plated on a surface coated with poly-ornithine (Sigma, 100 µg/ml) and laminin (4 µg/ml). Cells were cultured in the presence of the cAMP elevating compounds forskolin (10 µM) and IBMX (100 µM) in combination with different sets of neurotrophic factors (GDNF, BDNF, CNTF, IGF-1) as described in the text (FIG. 21G, FIG. 21K and FIG. 21L). For the majority of all experiments mouse cultures containing motor neurons, interneurons and glial progenitors were used (referred to as 'motor neuron cultures'), in a few experiments motor neurons were purified by FACS (see below).

For differentiation into dI4 interneurons, Ptf1α-tdTomato ESCs were dissociated and cultured in suspension as embryoid bodies (EBs) at density of $8.0 \times 10^5$ cells/10 cm culture-treated petri dish. On Day 2 of differentiation, EBs were collected, spun down and split 1:4 into new petri dishes and supplemented with 1 µM RA. Media was exchanged on Day 4 and 6 of differentiation. The endpoint of dI4 IN differentiation was day 8, when EBs were collected for co-culture studies.

Differentiation of human isogenic HUES3 ESC HB9::GFP reporter lines into motor neurons was performed as previously described (Maury et al. 2015). Cells were dissociated on day 16 of differentiation, FACS-sorted and plated on poly-ornithine- and laminin-coated surfaces as above. Serum-free human motor neuron plating media was supplemented with the antimitotic UFdU and the neurotrophic factors GDNF, BDNF, CNTF, and IGF1 (all at 10 ng/mL) as described (Johnson-Kerner et al. 2015).

All cell lines used were routinely tested for mycoplasma.
Flow Cytometry Assisted Cell Sorting (FACS)

Cells were sorted based on GFP or RFP-expression using a 5 laser ARIA-IIu ROU Cell Sorter (BD BioSciences) configured with a 100 µm ceramic nozzle and operating at 20 psi.

Dual Color ESC-Motor Neuron Co-Culture Assay

Dissociated fluorescent Hb9::RFP-hSOD1$^{WT}$ cells were counted by hemacytometer and mixed with an equal number of Hb9::GFP-hSOD1$^{G93A}$ motor neurons, such that 500 fluorescent cells of each genotype were plated per well. Cells were plated in coated 96-wells plates, in a medium containing FSK and IBMX (low trophic support, positive control for cell death); or FSK, IBMX and 250 pg/mL GDNF (medium trophic support, positive control for survival).

Automated Image Analysis

Whole-well images of live GFP+ cells were acquired using a Plate Runner$^{HD}$ system (Trophos). Images were analyzed using Metamorph software (Molecular Devices) to assess the number of "healthy" fluorescent cells exhibiting outgrowths>5 times the cell body diameter (assessment of overall survival) and to evaluate the mean neurite length per cell (assessment of neurite growth). These parameters were used consistently throughout the study. Because the endogenous Hb9::GFP reporters in the human lines were not bright enough to be detected on our automated imaging platform, cells were treated immediately prior to imaging with the live cell dye calcein-AM (1.33 µM) for 10 mins followed by quenching with a 10% solution of hemoglobin in PBS.

Small Molecule Screen

Approximately 1300 biologically active compounds from the Tocris Mini Screen and Custom collection were added to screening plates at a final concentration of 10 µM in singletons. The final concentration of DMSO was 0.5%. A survival ratio was calculated by dividing the number surviving GFP+ cells by the number of RFP+ cells after 48 and 72 hours of exposure to the compounds. We consistently observed that the ratio of surviving untreated G93A mutant motor neurons to untreated wild-type motor neurons was ~0.83; in order to detect compounds acting synergistically to the genotype, all data were normalized to this ratio. Compounds resulting in a G93A-to-WT survival ratio of <0.67-fold, corresponding to a 50% difference in survival, were re-tested in five-point 2-fold dilution series. All hit compounds were evaluated visually, and wells with apparent artefacts such as autofluorescence and excessive cell clumping were removed. Compounds that were generally toxic, i.e., that resulted in lower survival than the controls with low trophic support for both genotypes, were rescreened in 1:10 dilution series. Compounds recapitulating the effect of the primary screen were then tested in an independent set of cell lines, both in mixed- and FACS-purified co-cultures to confirm cell autonomous effects.

ER Stress Rescue Screen

Dissociated fluorescent Hb9::GFP-hSOD1G93A 554 cells were counted and plated in coated 96-well plates at a density of 1000 fluorescent cells/well, in a medium containing FSK, IBMX and GDNF. Cells were incubated with rescue compounds or medium+0.5% DMSO as control for 45 min. Rescue compounds were selected from the initial dual color screen or from a literature search focusing on compounds with documented effects on ER stress in other models. Cells were then exposed to 7.5 μm CPA, or medium+0.5% DMSO as control. Cells were imaged and scored as described in previous sections. Human ESC-derived HB9::GFP-SOD1$^{+/+}$ and HB9::GFP-SOD1$^{+/A4V}$ motor neurons were plated separately at 2000 cells/well in 96-well plates as described in a previous section, test compounds were added in the serum-free human motor neuron plating media supplemented with 10 ng/mL BDNF, GDNF, CNTF, and IGF1 described above. 33 μM CPA (or DMSO control) and the various rescue compounds were added concurrently.

Immunocytochemistry

Live cultures were pre-fixed with 4% PFA on ice, by adding fixative directly to the medium for 2 min, then fixed additional 15 min by replacing the well content with 4% PFA and incubating at 4ûC. Fixed cultures were blocked for 1 hr at room temperature with 0.01 M PBS containing 0.3% Triton-X and 20% donkey serum. Primary antibodies were diluted in blocking solution and incubated overnight at 4° C. Cultures were washed three times with 0.01 M PBS containing 0.3% Triton-X, prior to incubation with secondary antibodies (Alexa donkey 488/555/647) for 60 min in room temperature. The following primary antibodies were used: mouse Hb9 and mouse islet1/2 from Hybridoma Bank (1:100); Tuj-1 from Neuromics or EMD Millipore (1:500); and phospho c-jun from Cell Signalling (1:100) and SERCA2 from Pierce (2A7A1, 1:100). Slides were examined in either a Zeiss AxioObserver with a Coolsnap HQ2 camera (Photometrics), a Zeiss LSM Meta 510 or a Zeiss LSM 880 Axioobserver Z1 confocal microscope. Images were processed and sometimes cropped in Adobe Photoshop (Creative suit 6, Adobe Systems) for presentations purpose, changes were applied to the entire image, and in equal proportions to all images from the same.

Biochemistry

Day 6 EBs were lysed in TNG-T lysis buffer (36) containing protease (Complete Mini) and phosphatase (PhoStop) inhibitors for 30 min, followed by mechanical trituration with a 26G syringe. For immunoprecipitation, C4F6 and B8H10 antibodies (MediMabs) were coupled to protein-G Dynabeads and used for immunoprecipitation of misfolded hSOD1 as described by Gros-Louis et al. 2010. A control IgG antibody was used a negative control (FIG. 21I). A pan-SOD1 antibody (Novus Bio) was used for immunoblotting, 5% of the input was used as loading control. For western blotting the following antibodies were used: Caspase-3 (1:1000), CHOP (1:500), phospho-Eif2α (1:1000) (Cell Signaling Technologies), SOD1 and ATF-6 (1:200, Novus Biologicals), α-tubulin (1:50 000, AbCam). Representative gels are cropped from scanned images of the original films. Individual bands without relevance to the present study are indicated by a dashed line in the figure. Band intensity was measured using the Analyze-Gels application in Image J (NIH).

Quantitative PCR

Samples were lysed in TRIzol and frozen at −80° C. until further processing. RNA was extracted using the Qiashredder and Qiagen RNeasy Mini kits (Qiagen) according to the manufacturer's protocol. 1-2 μg total RNA was used for each reverse transcription reaction, and reactions were performed using the TaqMan RT kit (Applied Biosystems, Grand Island, NY, USA). Primer pairs were designed for target transcripts using Primer Express 3.0 (Applied Biosystems). Quantitative PCR reactions were performed using the Power SYBR Green PCR Master Mix (Applied Biosystems). Reactions were run and analyzed on a ViiA 7 (Life Technologies) qPCR instrument using absolute quantification settings.

XBP1 Splicing

PCR was performed in a 50 μL jumpstart Taq (Sigma-Aldrich, Product no. D9307) reaction containing 10 pmol of XBP-1 specific primers to detect splicing (Forward: 5'-GAATGCCCAAAAGGATATCAGACTC-3' (SEQ ID NO: 1) & Reverse: 5'-GGCCTTGTGGTTGAGAACCAG-GAG-3' (SEQ ID NO: 2)). PCR conditions were as follows: 1 cycle of 94° C. for 1 minute; 30 cycles of 94° C. for 30 seconds, 60° C. for 30 seconds, and 72° C. for 1 minute; and one cycle of 1 minute at 72° C. PCR products were run for 30 minutes on 2.5% agarose gels containing ethidium bromide. Bands were observed and quantified using the Syngene G:Box and Genesis software. Band intensity was measured using the Analyze-Gels application in Image J (NIH).

Calcium Imaging

Hb9::RFP motor neurons were dissociated on day six of differentiation and cultured on glass coverslips. On day three post-dissociation, coverslips were incubated with 5 μM Fura-2 AM, ratiometric calcium indicator dye (Life Sciences, USA) for 30 minutes at room temperature. After washing, coverslips were mounted on a Nikon Eclipse TE 3500 inverted microscope equipped with a 40×1.30 NA objective (Nikon, USA), a pco.EDGE CMOS camera (pco, Germany), a Lambda LS light source, a Lambda LS-2 filterwheel with 340 nm and 380 nm excitation filters (both Sutter, USA). Images were first acquired using bright field and a fluorescent filter to identify cells to analyze at later steps. Drug applications were carried out using a custom-built focal application system located approximately 100 μm from the field of view. A 5 s baseline for the Fura-2 signal was then acquired, followed by a 1 s pulse of 100 μM kainic acid (KA). Epifluorescent images were captured at a rate of 1 image/sec for 1 min, switching between 340 and 380 nm filters every 500 ms. Cells were allowed to recover for 2 min, and only coverslips where cells returned to baseline were analyzed further. The coverslips were then continuously exposed to 7.5 μM CPA while 1 image/30 sec was acquired for 20 min, followed by a 2 min recovery, and finally a second pulse of KA. Following acquisition, the 340/380 ratio of each pair of images was calculated on a pixel by pixel basis using FIJI software v. 1.4 (www.fiji.sc). Regions of interest were drawn manually using the morphology of the cells from a single 340 image as a template. Quantification was carried out using Igor Pro v. 6 (Wavemetrics, USA) The rate at which the evoked calcium transients returned to the baseline was calculated from the tau (time constant) of a single exponential curve fitted to the falling part of the Ca intensity trace from 80% to 20% of the peak. Only neurons that recovered to 10% of the peak ratio value were included in the analysis.

In Vivo Administration of TUDCA

P30 mice were divided into three cohorts: (1) hSOD1$^{G93A}$ mice receiving 0.5 mg/g TUDCA in 0.01 M PBS subcutaneously; (2) hSOD1$^{WT}$ mice receiving 0.5 mg/g TUDCA in 0.01 M PBS subcutaneously to evaluate the mutation-specific effects of NMJ denervation and of the drug; and (3) hSOD1$^{G93A}$ mice receiving 0.01 M PBS subcutaneously as a vehicle control. Drug was administered every three days from P30 to P51 for a total of 7 injections. At P51, mice were deeply anesthetized using ketamine/xylazine and intracardially perfused with ~15 mL room temperature phosphate-buffered saline (PBS) followed by ~30 mL of 4% PFA. Following dissection, tibialis anterior (TA) muscles were washed in PBS overnight, and then processed for cryoprotective embedding. To visualize NMJs, 30 μm longitudinal cryosections of the whole TAs were incubated with α-bungarotoxin conjugated to Alexa Fluor 488 (1:500; Invitrogen) and an antibody to vesicular acetylcholine transporter (VAChT; raised in rabbit, Covance 1:32,000) to label motor endplates and nerve terminals, respectively. Because a lack of co-localization indicated muscle denervation, % NMJ innervation was determined by dividing the total number of areas of overlap between VAChT and BTX signals (total number innervated endplates) by the number of areas containing BTX signal (total number of endplates). One TA was assessed for each animal (n=4-6), with every third section throughout the whole muscle stained and counted such that a minimum of 1000 NMJs were evaluated per animal. Images were acquired using a Nikon Eclipse TE-2000-E fluorescence microscope with a 4× or 10× objective. All animal work was performed in compliance with Columbia University IACUC protocols.

Statistics

For cell cultures, a minimum of three independent experiments were generally performed, which was considered sufficient based on previous experience with this type of assays where culture conditions and cell lines were kept constant. For in vivo experiments, a power analysis based on pilot studies was performed to estimate the number of animals required to detect the studied effects. Data sets are expressed as mean value+/−SEM throughout the paper. Statistical analyses were performed with Graph Pad Prism (v. 7, GraphPad Software Inc.) or R' ( ). If normal distribution and equal variance could be assumed, analysis of significance was performed with an unpaired two-tailed Student's t-test for pairwise comparison, or a One-way Anova with post hoc Dunnet's multiple comparison test. Otherwise, analysis was instead performed by Mann-Whitney Rank sum test or Kruskal-Wallis test with Dunn's multiple comparison post hoc test. Statistical significance is indicated by * $P<0.05$,  $P<0.01$, *$P<0.001$. Unless stated otherwise, each N represents an independent experiment or animal. In the few events where only one biological replicate was analyzed, the technical replicates were used to generate histograms, as stated in the figure legends when applicable. Statistical analyses were not performed on any of these data.

Example 13

Development of MAP4 Kinase Inhibitors as Motor Neuron-Protecting Agents

Amongst the MAP4K-inhibiting derivatives of compound 1 described herein, compound 12k stood out for its exceptional neuroprotective and pharmacokinetic profiles, especially its increased metabolic stability and high brain penetrance. Compound 12k also showed near-complete inhibition at nanomolar concentrations of several MAP4Ks. Furthermore, we showed that compound 12k retains the anti-inflammatory properties of compound 1. Compound 12k is therefore primed for future testing in animal models of neurodegenerative disease.

HGK (MAP4K4) and NUAK1 are Common Targets of Neuroprotective Kinase Inhibitors

We sought to compare the targets of the original hit compounds to inform the selection of new potential lead compounds. We mined a publicly available database (Anastassiadis et al., 2011) to compare the catalytic activity of >300 kinases in the presence of the four hits from the initial screen: G66976, sunitinib, K252a, and kenpaullone. We also added alsterpaullone to this analysis, as it is a structural analog of kenpaullone that we found to be more potent than kenpaullone in the CPA survival assay (FIG. 41B). We then performed two-way hierarchical clustering analysis to rank the shared targets of these compounds. Kinases whose activity was strongly inhibited by all five compounds (<15% kinase activity remaining at 0.5 μM inhibitor concentrations) included the MAP4K/STE20 kinase HGK (MAP4K4) and the AMPK-related kinase NUAK1 (FIG. 41A).

HGK Inhibitors, but not NUAK1 Inhibitors, are Strongly Neuroprotective

To evaluate the functional relevance of HGK and NUAK1 to ER stress-mediated neurodegeneration, we tested known HGK and NUAK1 inhibitors in the human motor neuron CPA survival assay. Compounds were tested in human stem cell-derived motor neurons derived from a healthy patient, where CPA was added at 33 μM for 72h. Under these conditions, motor neuron survival drops to ~40% of controls treated with vehicle alone.

We found that the NUAK1 inhibitors WZ4003 ($IC_{50}$ for NUAK1=20 nM (Banerjee et al., 2014)) and HTH 01-015 ($IC_{50}$ for NUAK1=100 nM (Banerjee et al., 2014)) were unable to rescue CPA toxicity across an 8-point dilution series (FIG. 41B and FIG. 43A). At concentrations above 2 μM, both WZ4003 and HTH 01-015 were toxic to motor neurons even in the absence of CPA (FIG. 43A). Taken together, these results indicated that NUAK1 inhibitors were not suitable leads in the treatment of ER stress-mediated neurodegeneration.

Meanwhile, we also tested three compounds that were previously shown to inhibit HGK activity: PF-6260933 (Ammirati et al., 2015), GNE-495 (Ndubaku et al., 2015), and URMC-099 (Goodfellow et al., 2013). PF-6260933 and GNE-495 were originally designed to inhibit HGK (both with an $IC_{50}$ of 3.7 nM; (Ammirati et al., 2015; Ndubaku et al., 2015)), while URMC-099 was originally optimized to inhibit the MAP3K kinase MLK3. Nevertheless, URMC-099 was shown to bind HGK and inhibit >99% of its activity in a cell-free assay at 1 μM (Goodfellow et al., 2013).

PF-6260933 rescued motor neuron survival following CPA treatment to 63% of vehicle controls at 1.2 μM (FIG. 41B and FIG. 43B). GNE-495 restored survival to a maximum of 73% of basal levels at 2.4 μM. Of the three compounds, URMC-099 was the most effective at rescuing motor neurons from CPA-induced neurodegeneration, restoring survival to 90% of basal levels at 0.6 μM (FIG. 41B and FIG. 43B). We therefore selected URMC-099 (compound 1) for further analysis and optimization.

Compound 1 Inhibits ER Stress-Mediated Activation of the JNK Pathway

To determine whether compound 1 was acting through the same molecular pathways as the neuroprotective kinase inhibitors that we had previously identified, we assessed its ability to inhibit the activation of the stress-related transcription factor c-Jun. We have shown that CPA treatment rapidly increases c-Jun phosphorylation at serine 63, a site known to mediate apoptotic gene transcription (Pulverer et al., 1991), and that K252A, kenpaullone, and G66976 decrease c-Jun phosphorylation at this site (see Example 12). The HGK inhibitor GNE-495 also inhibits c-Jun phosphorylation in neurons subjected to neurotrophic factor withdrawal (Larhammar et al., 2017). Here, we observed by western blotting that compound 1 decreased c-Jun phosphorylation in CPA-treated motor neurons to levels below the threshold of detection (FIG. 41C).

In stressed neurons, c-Jun is phosphorylated at serine 63 by JNK kinases (MAPK8-10) (Pulverer et al., 1991). Compound 1 has been shown to attenuate JNK phosphorylation in mouse microglia under pro-inflammatory conditions (Marker et al., 2013); similarly, the HGK inhibitor GNE-495 has been shown to attenuate JNK phosphorylation in stressed sensory neurons (Larhammar et al., 2017). To determine whether compound 1 was also acting on JNK pathways in motor neurons subjected to ER stress, we performed western blots on CPA-treated motor neuron cultures using an antibody that recognizes all three JNK kinases phosphorylated at a site known to regulate stress responses. We found that compound 1 significantly decreased JNK phosphorylation (FIG. 41C) compared to CPA treatment alone. These findings suggest that the neuroprotective activities of compound 1 are linked to its attenuation of the JNK pathway, and are in line with previous studies that have linked HGK with JNK activation (Larhammar et al., 2017; Wu et al., 2019; Yang et al., 2013).

Structure-Based Compound Design Yields Potent and Efficacious Derivatives of Compound 1

Figure 5A:
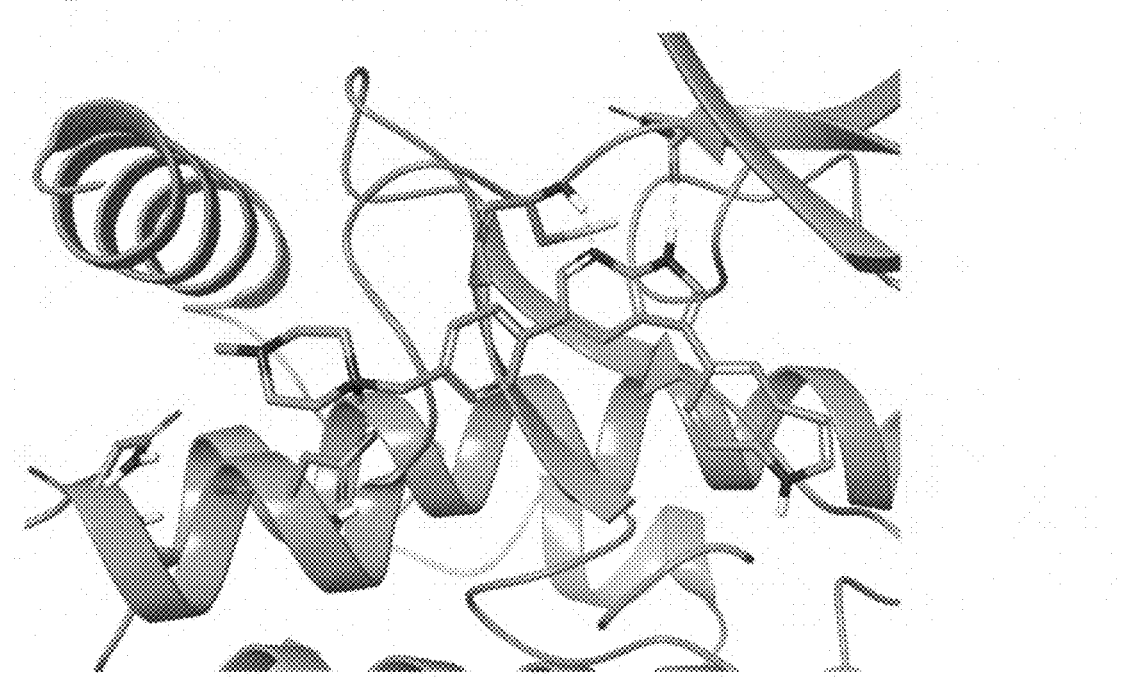
FIG. 5A shows a docking pose of Compound 1 in a HGK (MAP4K4) crystal structure (PDB ID: 5DI1).
Figure 5B:
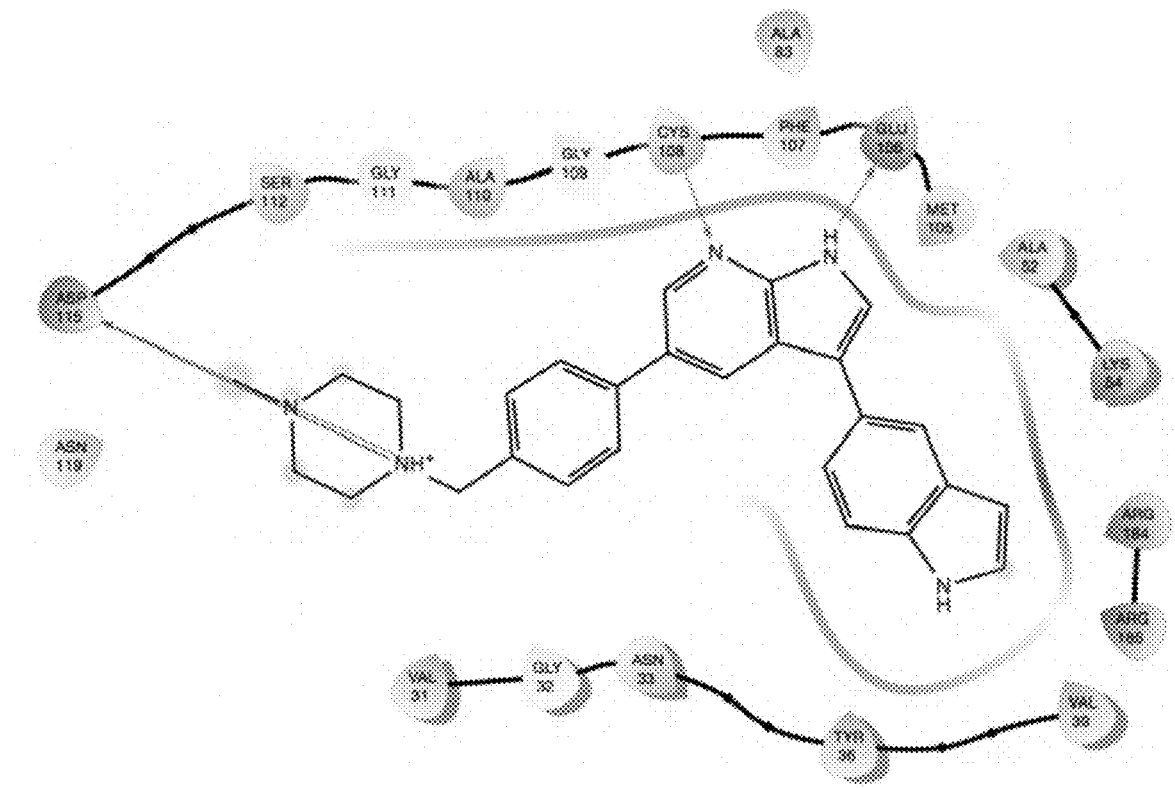
FIG. 5B shows a ligand interaction diagram of Compound 1 with HGK corresponding to the docking pose (arrows indicating hydrogen bonds).
Figure 6:
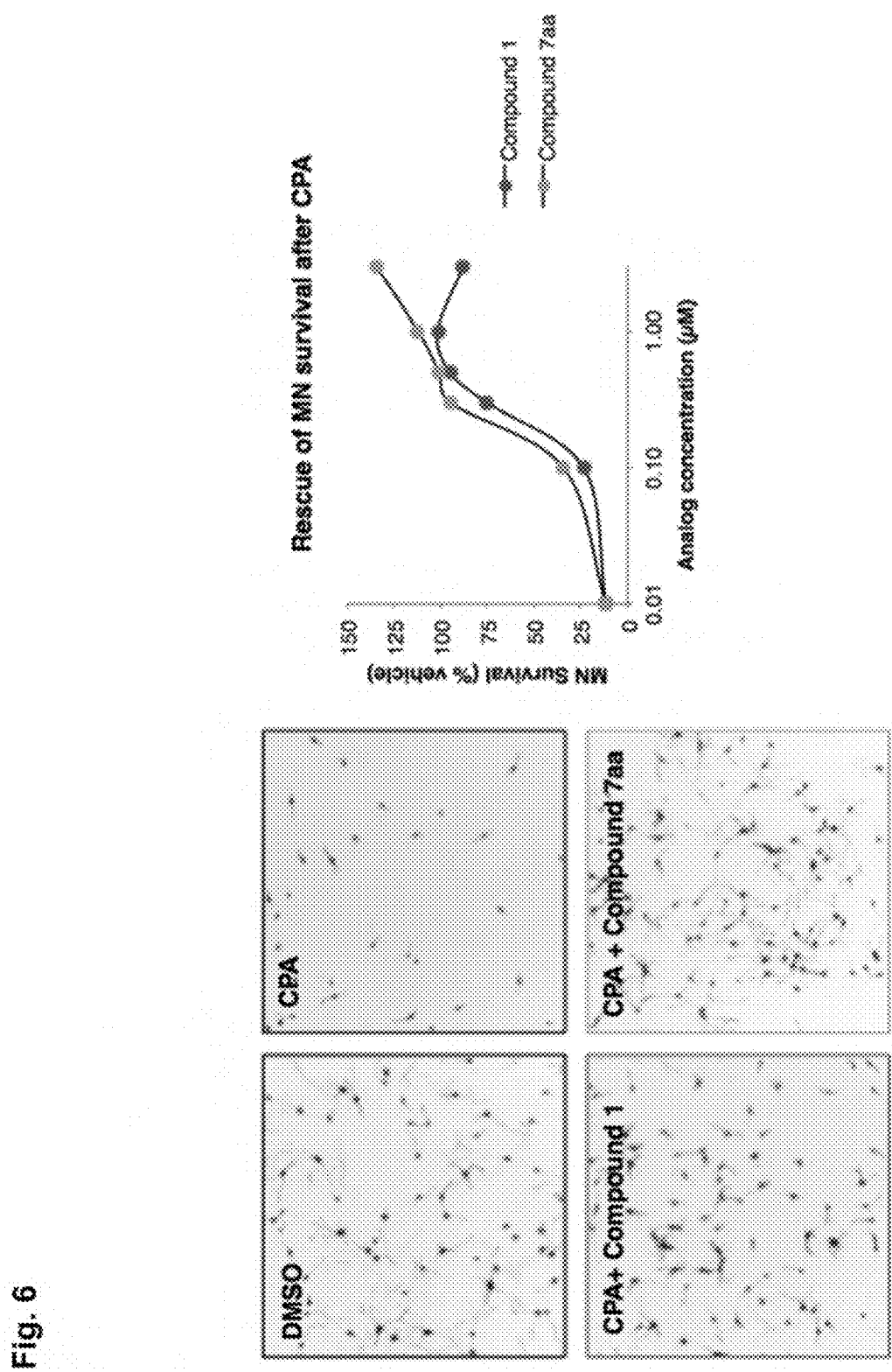
FIG. 6 shows that compound 1 analogs such as 7aa provide increased protection of motor neurons against CPA. Human embryonic stem cell-derived motor neurons were treated with 33 μM CPA and increasing concentrations of compound 1 or its analogs. The number of surviving motor neurons was normalized to vehicle-treated controls.

Considering that URMC-099 was originally optimized for MLK3 inhibition, we speculated that more potent and efficacious derivatives might be obtained by optimizing their capacity to inhibit HGK. To aid in the design of potential analogs, we docked URMC-099 (compound 1) in a crystal structure of HGK (PDB ID: 5DI1) using Glide (Schrödinger Suite) (FIG. 5A). From the docking pose and the binding site interaction diagram (FIG. 5B), it appeared that: 1) the 7-azaindole moiety binds to the hinge region of the kinase and is essential for activity; 2) the piperazine moiety extends into the solvent-exposed region and could be modified to improve the stability and the physicochemical properties of the molecule; and 3) the indole sidechain could be modified to optimize interactions in the binding pocket and increase kinase specificity.

Based on these observations, we set out to generate a series of compound 1 analogs. However, the published synthetic route was not easily scalable: the sidechain (Scheme 1, R-group) is introduced in the first step, and has to be carried through the entire synthesis, which is not efficient for the generation of multiple sidechain analogs. We therefore developed an improved synthetic route with increased flexibility (Scheme 1). In the first step, a Suzuki coupling of 5-bromo-7-azaindole (2) with 4-formylboronic acid in a pressure tube provided aldehyde 3. Reductive amination with 1-methylpiperazine at room temperature in dichloromethane yielded compound 4. In the next two steps, compound 4 was iodinated at the 3-position, followed by the introduction of a Boc-group on the azaindole. Initial attempts to forego this group led to significantly decreased yields in the subsequent Suzuki coupling. Compound 5 was used as the substrate for the final Suzuki coupling with a number of boronic acids and boronic pinacol esters. Conveniently, the Boc-group was deprotected under these reaction conditions, obviating an additional deprotection step. Compound 1 and the desired analogs, 6a-6az, were isolated in moderate to good yields (40-88%) after purification by preparatory HPLC.

Once this streamlined synthetic route was established, we evaluated the newly-designed compound 1 analogs as they were produced (~5 at a time) for their ability to rescue CPA toxicity in motor neurons, which provided us with real-time feedback on analog design. After each survival assay, the most efficacious compounds were used as scaffolds for new sets of analogs. Through this iterative optimization process we initially developed and tested 49 analogs of compound 1.

For these and all subsequent survival experiments, we used human ES motor neurons carrying the ALS-causing SOD1$^{A4V}$ mutation to maximize the translational potential of our analogs (see Example 12). Survival in these cells dropped to ~10% of untreated controls (compared to ~40% in the control human motor neuron lines used previously) after 72 h of CPA treatment (33 µM). Under these conditions, treatment with compound 1 completely rescued CPA-induced neurodegeneration (102% of untreated controls) at 1 µM (FIG. 42B). Out of the 49 analogs, 11 demonstrated greater maximum efficacy than compound 1 (FIG. 3A and Table S1), indicating that some analogs were also counteracting the basal levels of cell death that occurred across the 72 h assay independently of CPA. Furthermore, 5 analogs were more potent than compound 1 (EC$_{50}$s 0.22 mM), and 4 compounds were both more efficacious and more potent than compound 1 (FIG. 42A and Table S1). Only 2 analogs were completely ineffective (survival s CPA alone). Taken together, these results highlight the effectiveness of the iterative approach to drug design that was undertaken here.

TABLE S1

Summary of EC$_{50}$ and E$_{max}$ for compound 1 and its analog.

| Compound | EC50 (µM) | Emax (MN survival % untreated) |
|---|---|---|
| 1 | 0.2153 | 101.51 |
| 7b | 0.4964 | 52.29 |
| 7c | Ambiguous | 10.43 |
| 7d | 0.3271 | 72.94 |
| 7e | 0.2279 | 110.64 |
| 7f | 0.3375 | 68.34 |
| 7h | 0.1768 | 114.68 |
| 7i | Ambiguous | 13.35 |
| 7k | 0.3157 | 71.02 |
| 7l | 0.1769 | 106.50 |
| 7m | 0.2129 | 76.13 |
| 7aw | 0.4056 | 27.47 |
| 7n | 0.4827 | 36.29 |
| 7o | 0.7748 | 68.62 |
| 7p | 0.2928 | 130.52 |
| 7q | 0.7397 | 21.50 |
| 7s | 2.191 | 100.09 |
| 7t | 1.375 | 77.31 |
| 7u | 4.602 | 72.87 |
| 7v | 0.1429 | 127.72 |
| 7w | 1.366 | 0.42 |
| 7x | 0.3215 | 78.10 |
| 7y | 0.433 | 103.52 |
| 7z | Ambiguous | 12.83 |
| 7av | 1.046 | 53.51 |
| 7aa | 0.2084 | 134.37 |
| 7ab | 1.278 | 60.72 |
| 4 | Ambiguous | 13.73 |
| 7ac | 0.7735 | 110.34 |
| 7ad | 0.2854 | 87.66 |
| 7ae | 0.5329 | 31.99 |

TABLE S1-continued

Summary of $EC_{50}$ and $E_{max}$ for compound 1 and its analog.

| Compound | EC50 (µM) | Emax (MN survival % untreated) |
|---|---|---|
| 7af | 1.343 | 67.48 |
| 7ag | 0.418 | 88.01 |
| 7ah | 0.2343 | 67.08 |
| 7ai | 3.234 | 86.49 |
| 7ak | 0.6499 | 112.07 |
| 7al | 0.6705 | 112.92 |
| 7am | 0.9475 | 122.39 |
| 7an | 0.5341 | 100.38 |
| 7ax | 1.44 | 35.46 |
| 7ay | 0.09116 | 9.29 |
| 7az | 2.988 | 51.51 |
| 7ao | Ambiguous | 95.90 |
| 7ar | 0.5829 | 37.37 |
| 7as | 0.3286 | 80.77 |
| 7at | 0.2973 | 85.01 |
| 12b | 1.955 | 72.61 |
| 12c | 0.694 | 43.73 |
| 12d | 0.3011 | 142.76 |
| 12e | Amibiguous | 144.15 |
| 12f | 0.11 | 115.94 |
| 12g | 0.05 | 89.29 |
| 12h | 0.10 | 117.16 |
| 12i | 0.05 | 115.18 |
| 12j | 0.05 | 98.55 |
| 12k | 0.10 | 112.31 |
| 12l | 0.09 | 115.45 |

In Vitro Optimization of Metabolic Stability Leads to Compound 12k

To evaluate the metabolic stability of the strongly neuroprotective analogs, we established an in vitro assay where compounds were incubated with mouse liver microsomes in buffer containing an NADPH-regenerating system. Aliquots were taken over the course of two hours and analyzed by HPLG-MS using an internal standard to assess compound stability over time. In accordance with previously published work (Goodfellow et al., 2013), we found that compound 1 has a relatively short half-life in mouse liver microsomes ($T_{1/2}$=15 min; FIG. 13A). Compounds with a half-life of less than 30 min in microsomes are generally not ideal drug candidates due to their high clearance rate. Out of the 11 analogs that were initially evaluated, only two analogs (7y, 7ad) showed a promising half-life (>30 minutes; FIG. 11).

Next, we set out to improve the half-life of the analogs through further structural modification. Our computational docking experiments indicated that the methylpiperazine moiety is solvent-exposed, suggesting that its modifications might alter pharmacokinetic properties of compounds, while maintaining their potency in the ER stress assay.

Introduction of a bicyclic methylpiperazine to one of our most potent analogs (Scheme 11) increased the half-life from 9 minutes to 13 minutes (compound 12e; FIG. 11). To further enhance the microsomal stability of our analogs, we introduced the same bicyclic piperazine to one of the analogs from the initial series that had a half-life>30 minutes (Compound 7ad; FIG. 11). In this case we were able to considerably increase the half-life from 38 minutes to 158 minutes (compound 12f; FIG. 11).

Compound 12f was more potent than compound 1 in the motor neuron survival assay, with an $EC_{50}$ of 0.11 µM (Table S1) but was abruptly toxic at concentrations above 0.3 µM (FIG. 42B). To mitigate this increase in toxicity, while maintaining potency and microsomal stability, we synthesized another series of analogs (Scheme 12) containing the m-chlorophenyl or m-fluorophenyl substituent on the 3-position of the 7-azaindole scaffold. We evaluated the potency of these compounds in the ER stress assay, and their stability in the microsomal stability assay. Two of these compounds, 12g and 12j, either had a shorter half-life than desired or showed a decrease in potency in the ER stress assay. The remaining 4 compounds (12h, 12i, 12k, and 12l) strongly rescued motor neurons from CPA-induced ER stress and were able to completely negate the effects of CPA treatment at concentrations <0.3 µM. One of the resulting compounds, 12k, had a half-life of >120 min in the microsome assay (FIG. 13A) and rescued CPA-induced neurodegeneration with an improved $EC_{50}$ of 0.099 µM (FIG. 42B).

Compound 12k is Stable, Orally Bioavailable, and Highly Brain-Penetrant In Vivo

Based on its strong performance in the microsome assay, 12k was selected for further pharmacokinetic analysis in vivo. Compounds 1 and 12k were administered to 8 week-old wild-type B6SJLF1/J mice at 10 mg/kg through intraperitoneal (IP) injection or oral gavage (OG). Brains and plasma were collected across 4 time points over 24 h for LC-MS/MS analysis.

Figure 34A:
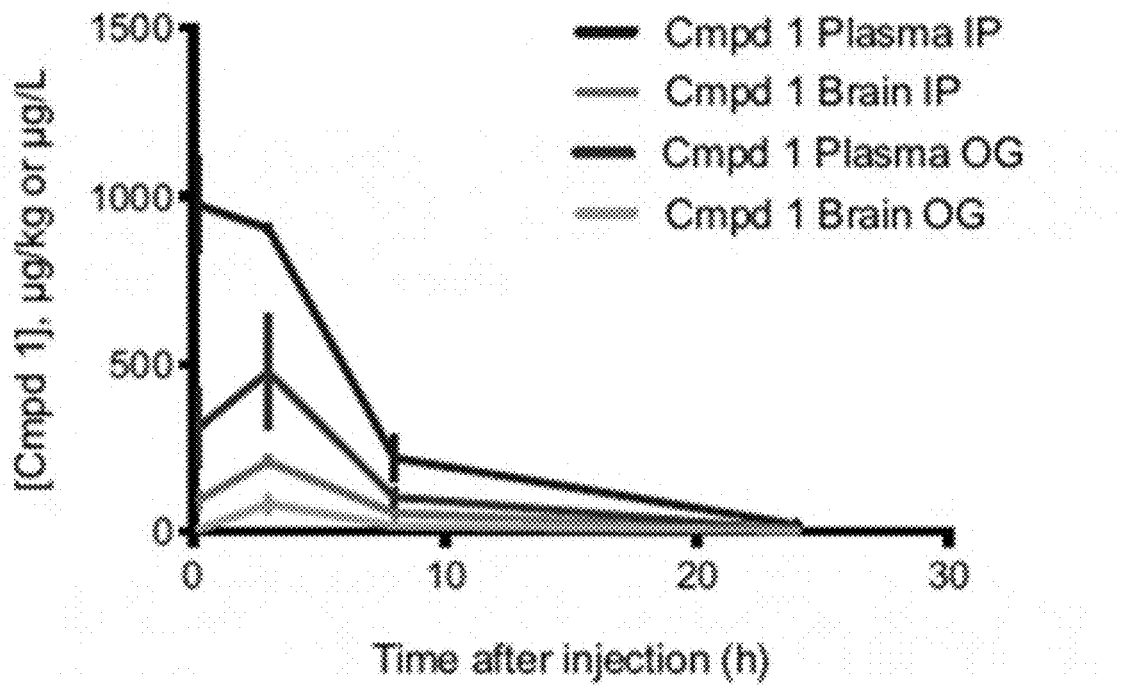
FIG. 34A shows the pharmacokinetics results of compound 1, administered once at 10 mg/kg IP or OG and assessed over time in brain and plasma.
Figure 34B:
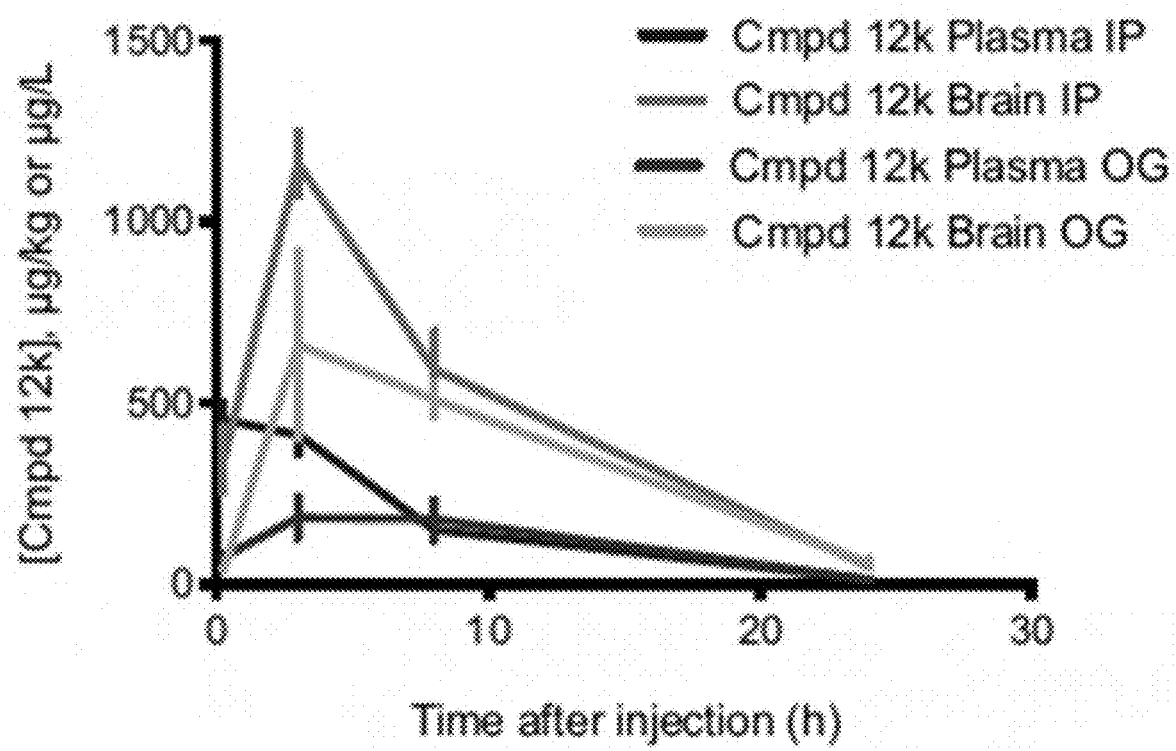
FIG. 34B shows the pharmacokinetics results of compound 12k, administered once at 10 mg/kg IP or OG and assessed over time in brain and plasma.
Figure 35A:
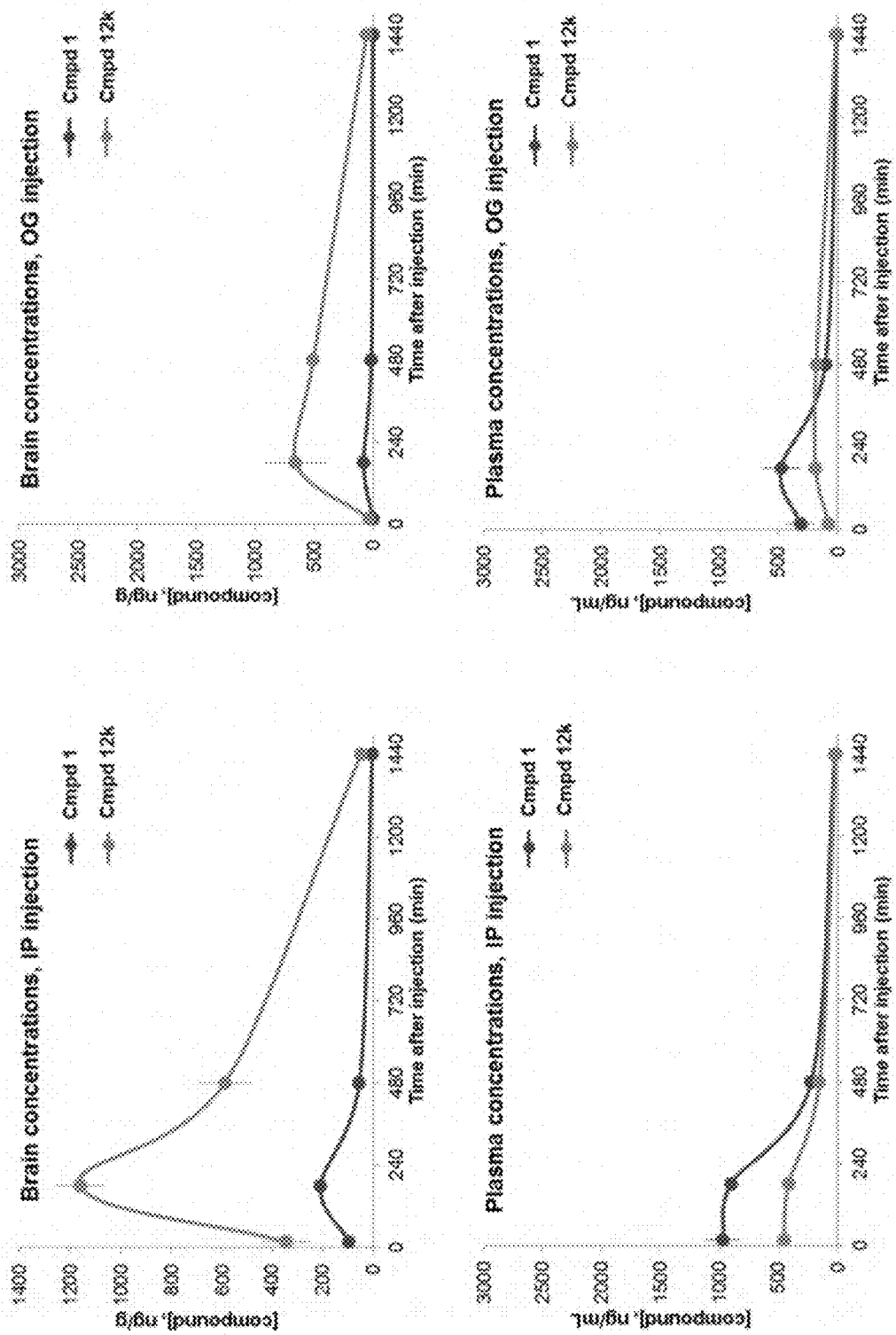
FIG. 35A shows the differences between compound 1 and compound 12k by comparing their pharmacokinetics results in the following settings: Brain vs. Plasma, concentration calculated in [ng/mL or ng/g], administered once at 10 mg/kg IP or OG and assessed over time.
Figure 35B:
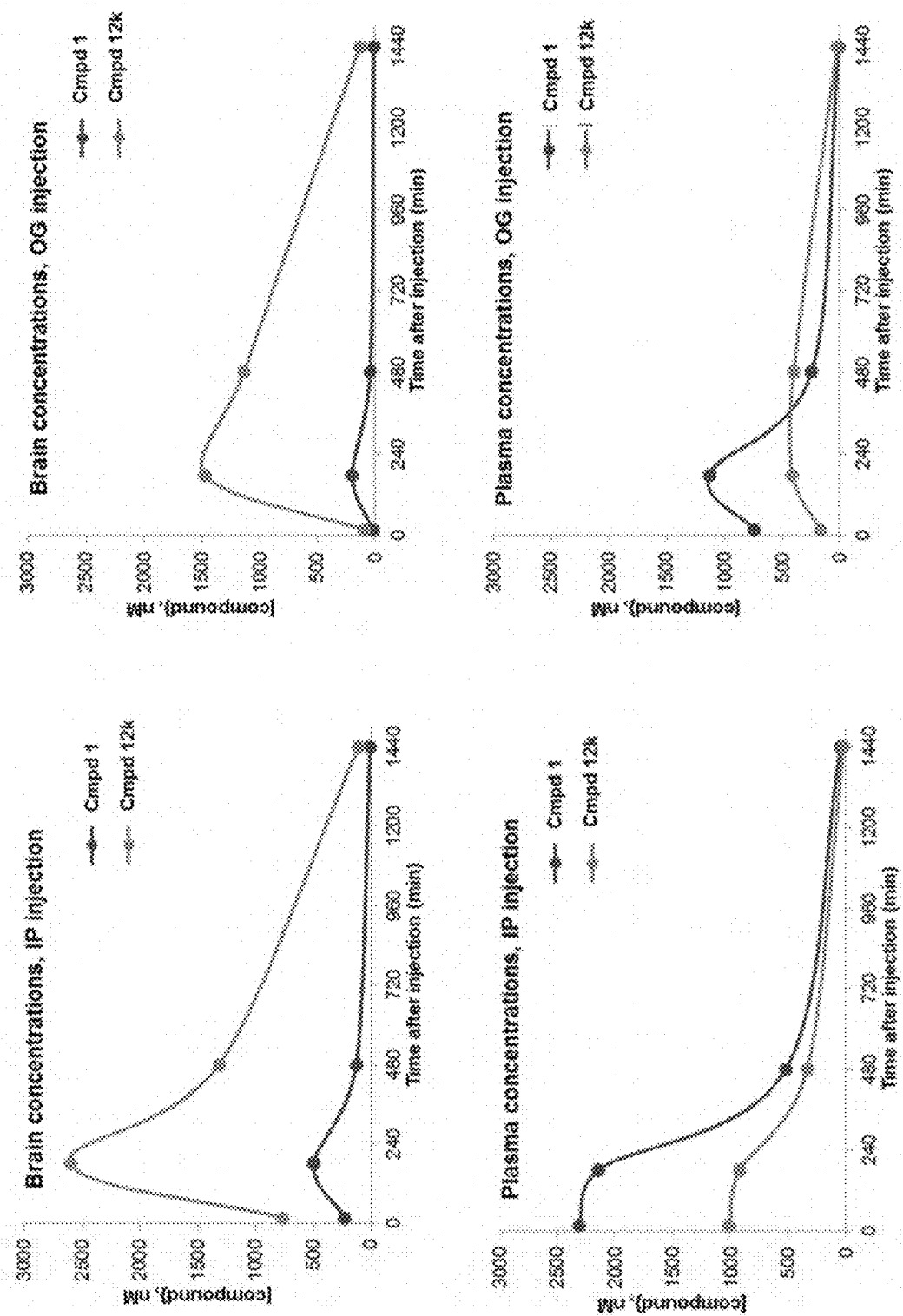
FIG. 35B shows the differences between compound 1 and compound 12k by comparing their pharmacokinetics results in the following settings: Brain vs. Plasma, concentration calculated in [nM], administered once at 10 mg/kg IP or OG and assessed over time.
Figure 35C:
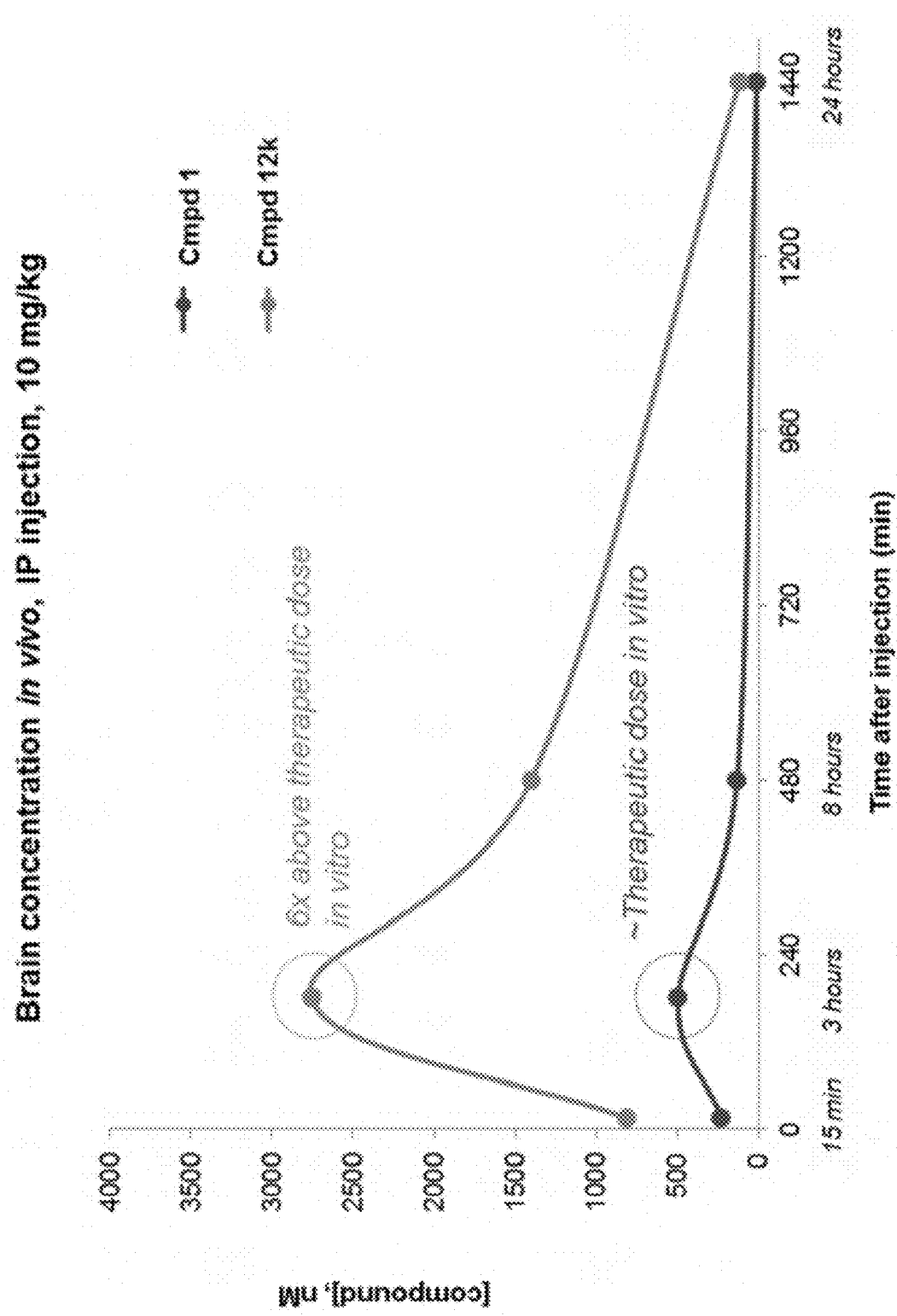
FIG. 35C shows the calculation in rough [nM], comparing to activity in vitro, with compounds administered once at 10 mg/kg IP and assessed over time.
Figure 36:
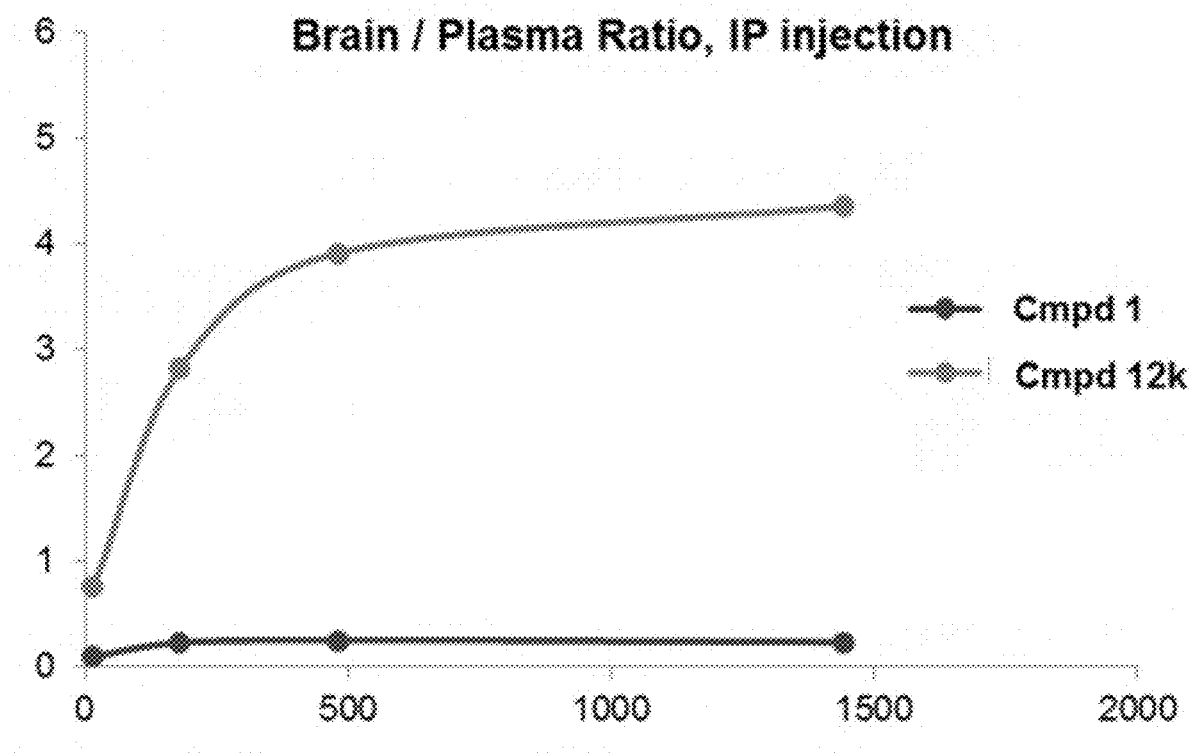
FIG. 36 shows the Brain/Plasma ratio over time, with compounds administered once at 10 mg/kg IP or OG and assessed over time.
Figure 36:
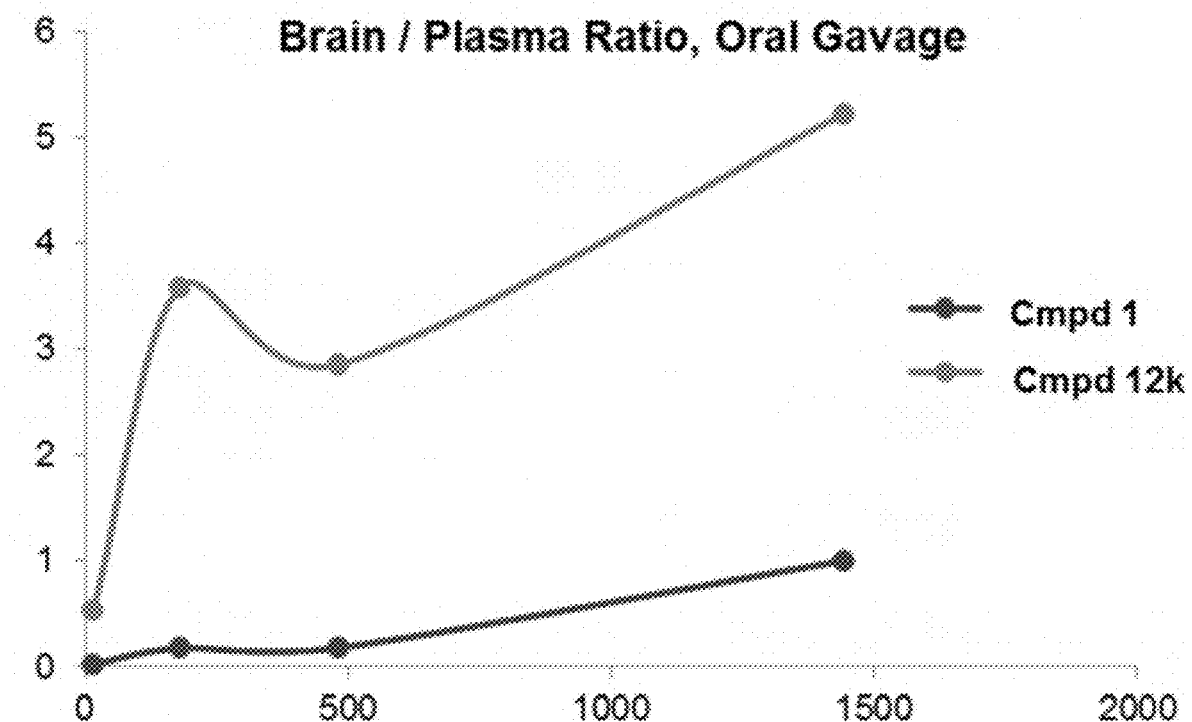
Figure 37A:
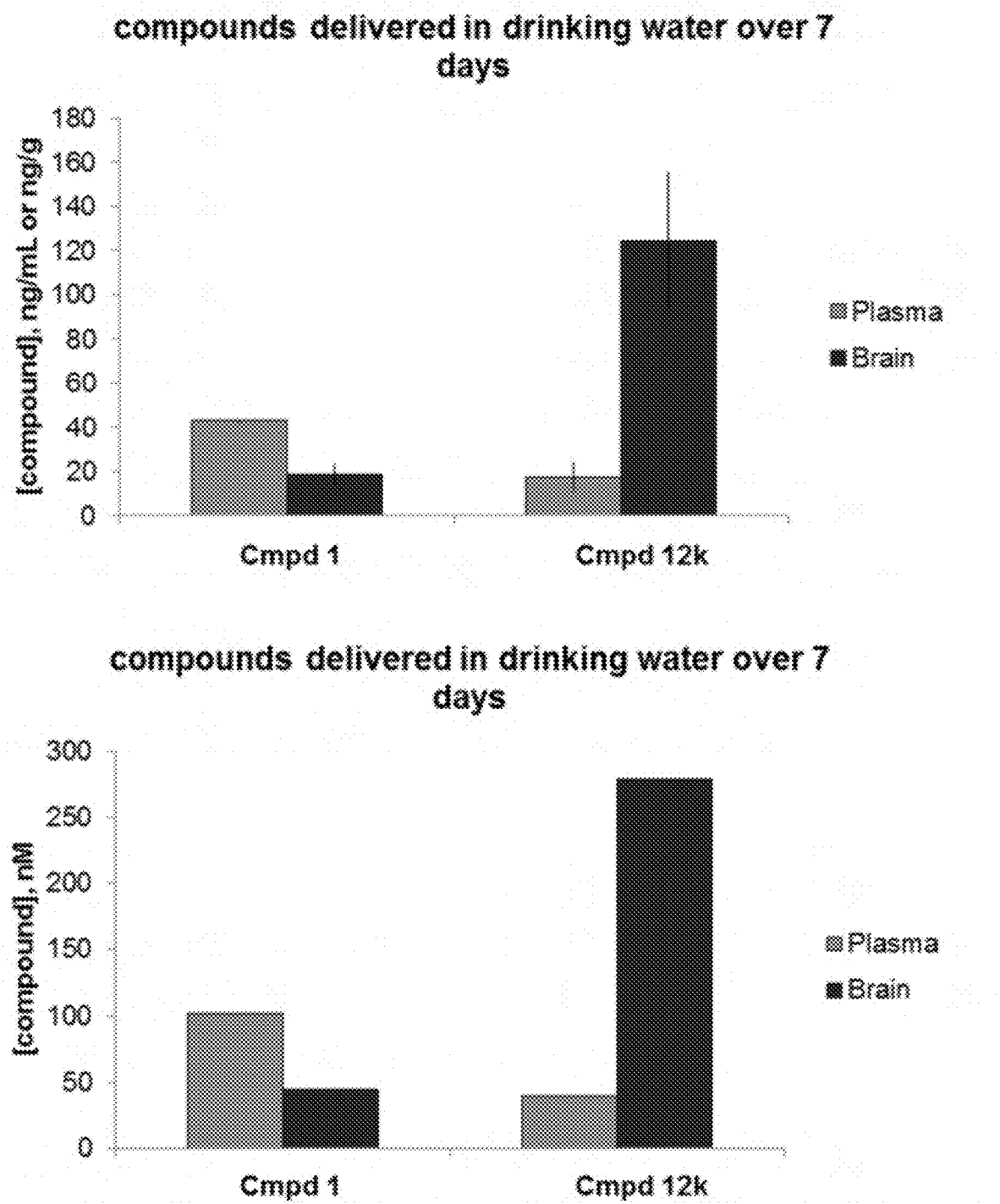
FIG. 37A shows the comparative results of compound 1 vs compound 12k, delivered per os in drinking water over 7 days and assessed at 7 day time point.
Figure 37B:
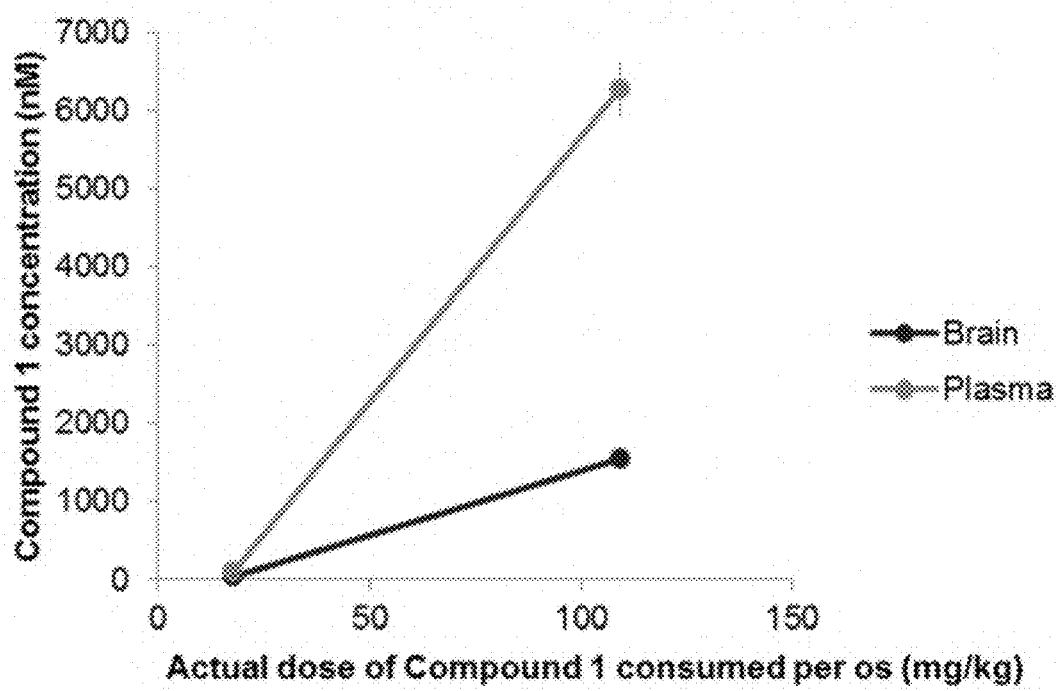
FIG. 37B shows the comparative results of compound 1 vs compound 12k, delivered per os in drinking water over 15 days and assessed at 15 day time point.
Figure 37B:
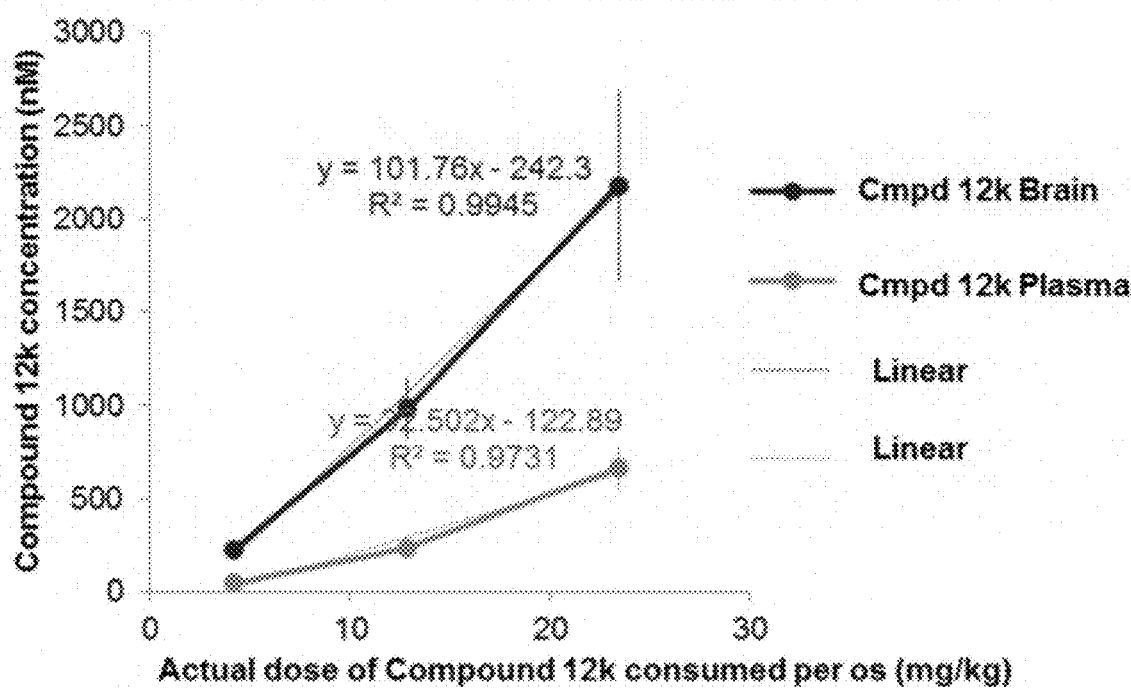

The pharmacokinetic properties of 12k were improved relative to 1 across several measures. Though the area under the curve (AUC) in plasma was reduced for 12k compared to 1, the AUC for 12k in the brain was greatly increased after both IP and OG administration, consistent with the decreased rate of clearance predicted by the in vitro microsome assay (Table 4). The concentration of 12k in the brain was increased relative to 1 across all time points and routes of administration assessed, as were brain-to-plasma ratios (FIG. 34A and FIG. 34B, and Table 4), indicating improved brain penetrance. The brain $C_{max}$ of 12k in IP-injected animals was 1162 ng/g (=2.60 µM; FIG. 34A and FIG. 34B, and Table 4), which greatly exceeds the threshold concentration required for rescue in the CPA motor neuron survival assay (FIG. 42B). Oral bioavailability (% F) based on plasma measurements in IP vs. OG-treated animals was 46% for compound 1, which is in line with the value reported by Goodfellow et al. (% F=41; (Goodfellow et al., 2013)). Meanwhile, the % F for 12k was 73%, a marked increase compared to 1. Similar results were obtained for 12k by comparing brain measurements (% F=73%). Taken together, these results indicate that 12k is well suited to future use in vivo, particularly in the study of the central nervous system.

TABLE 4

Pharmacokinetic parameters for compounds 1 vs 12k administered by IP injection or by OG.

| Parameter | Cmpd 1, IP | Cmpd 1, OG | Cmpd 12k, IP | Cmpd 12k, OG |
|---|---|---|---|---|
| Plasma AUC (µg/L · h) | 7328 | 3401 | 3899 | 2785 |
| Brain AUC (µg/L · h) | 1568 | 567.2 | 11570 | 8429 |
| Plasma mean $C_{max}$ (µg/L) | 971.69 | 476.23 | 454.03 | 184.06 |
| Brain mean $C_{max}$ (µg/kg) | 208.83 | 83.35 | 1162.23 | 658.88 |
| Brain/plasma ratio at 3 h | 0.25 | 0.18 | 3.91 | 2.58 |

HGK Inhibition, but not MLK3 Inhibition, Correlates Strongly with Motor Neuron Survival The battery of compound 1 analogs generated and tested here offered a unique opportunity to investigate whether HGK or MLK inhibition was more important for motor neuron survival, given that compound 1 was originally optimized to inhibit MLK. The neuroprotective effects of compound 1 and 53 analogs (7b-12e) were assessed concurrently in CPA-treated human ALS motor neuron cultures at 1 μM (Table S2). Meanwhile, the same analogs were analyzed in a radiolabeled ATP assay (10 μM ATP; Reaction Biology Corp.) to compare the extent to which they could inhibit the activity of HGK, MLK1, or MLK3 in a cell-free environment (Table S3 and S4). Compounds were tested at 0.1 μM for MLK1 and MLK3 inhibition and at 0.025 μM and 0.1 μM for HGK inhibition. Data from the 0.025 μM assays were selected for further analyses because many compounds completely inhibited HGK at 0.1 μM, thereby masking subtle differences in HGK inhibition between neuroprotective analogs (Table S4).

Figure 7A:
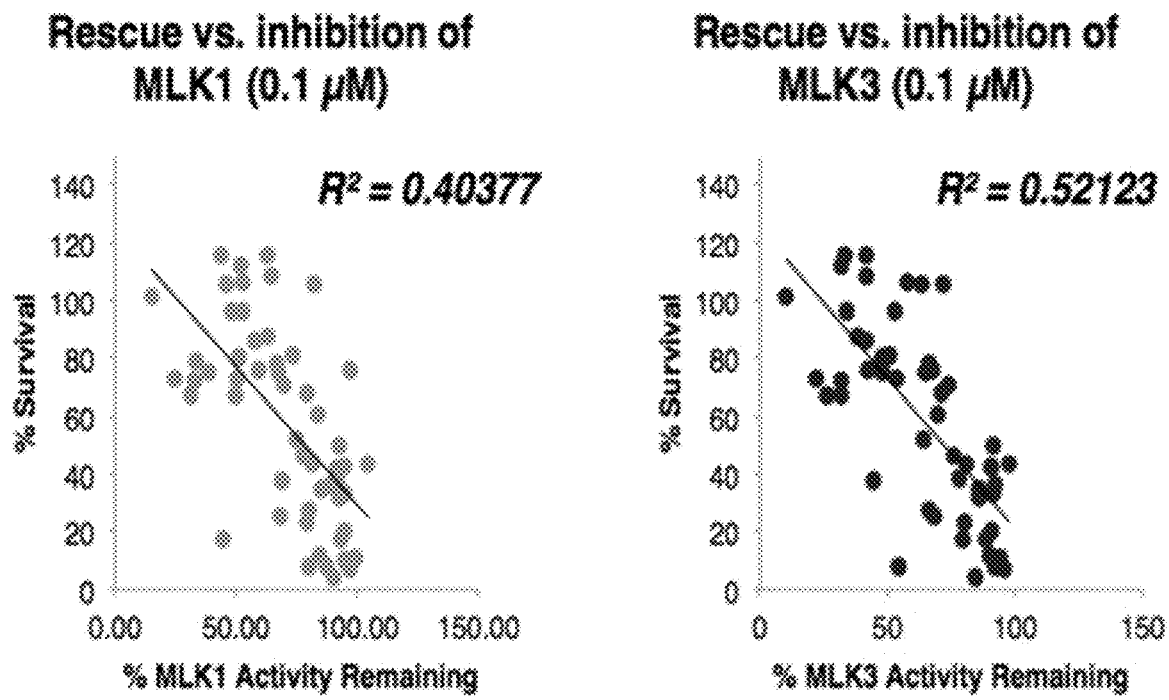
FIG. 7A shows the correlation of % motor neuron survival and % MLK1 ($R^2$=0.40) or % MLK3 ($R^2$=0.52) activity. Human embryonic stem cell-derived motor neurons were treated with 33 μM CPA and 1.0 μM of compound 1 or analogs 7a-7az. The % MN survival was based on the amount of cells showing significant outgrowth versus DMSO control. The % MLK1 or % MLK3 activity remaining is the average value of the % enzyme activity, relative to vehicle control, upon 0.1 μM compound treatment in the presence of 10 μM ATP (Reaction Biology Corp.).
Figure 7B:
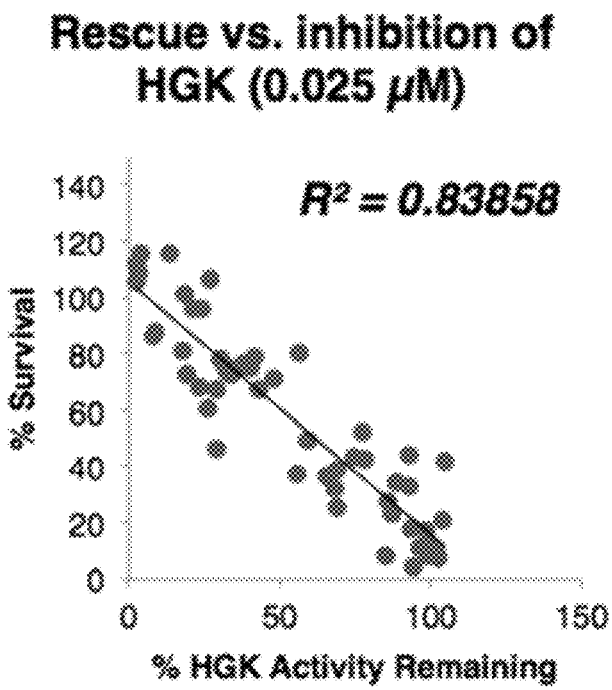
FIG. 7B shows the correlation of % motor neuron survival and % HGK ($R^2$=0.84) activity. Human embryonic stem cell-derived motor neurons were treated with 33 μM CPA and 1.0 μM of compound 1 or analogs 7a-7az. The % MN survival was based on the amount of cells showing significant outgrowth versus vehicle control. The % HGK activity remaining is the average value of the % enzyme activity, relative to DMSO control, upon 0.025 μM compound treatment in the presence of 10 μM ATP (Reaction Biology Corp.).

We then used regression analysis to compare the ability of a given analog to inhibit HGK, MLK1, or MLK3 with its ability to rescue human ALS motor neurons in the CPA survival assay. Overall, we observed a modest but significant correlation between the inhibition of MLK3 activity and neuroprotection ($R^2=0.52$; $p<0.0001$; FIG. 7A). We performed the same analysis for MLK1, a paralog of MLK3 that has also been shown to activate the JNK pathway (Gallo and Johnson, 2002), but found the correlation to be even weaker ($R^2=0.40$; $p<0.0001$; FIG. 7A). Meanwhile, we observed a robust correlation between the inhibition of HGK activity and neuroprotection ($R^2=0.84$; $p<0.0001$; FIG. 7B). These findings point to HGK as a potentially important biological target of compound 1 and its analogs.

TABLE S2

Results of SOD1$^{A4V}$ motor neuron survival across 54 analogs at 1 μM.

| Treatment | Motor Neuron Survival, % untreated |
|---|---|
| DMSO alone (vehicle control) | 100.00 |
| CPA (33 μM) alone | 11.02 |
| CPA (33 μM) + 1 (1 μM) | 101.51 |
| CPA (33 μM) + 7b (1 μM) | 52.29 |
| CPA (33 μM) + 7c (1 μM) | 7.84 |
| CPA (33 μM) + 7d (1 μM) | 72.94 |
| CPA (33 μM) + 7e (1 μM) | 96.13 |
| CPA (33 μM) + 7f (1 μM) | 68.34 |
| CPA (33 μM) + 7h (1 μM) | 105.73 |
| CPA (33 μM) + 7i (1 μM) | 7.82 |
| CPA (33 μM) + 7k (1 μM) | 71.02 |
| CPA (33 μM) + 7l (1 μM) | 106.50 |
| CPA (33 μM) + 7m (1 μM) | 76.13 |
| CPA (33 μM) + 7aw (1 μM) | 27.47 |
| CPA (33 μM) + 7n (1 μM) | 36.29 |
| CPA (33 μM) + 7o (1 μM) | 49.67 |
| CPA (33 μM) + 7p (1 μM) | 115.82 |
| CPA (33 μM) + 7q (1 μM) | 20.64 |
| CPA (33 μM) + 7s (1 μM) | 42.86 |
| CPA (33 μM) + 7t (1 μM) | 43.58 |
| CPA (33 μM) + 7u (1 μM) | 33.01 |
| CPA (33 μM) + 7v (1 μM) | 115.36 |
| CPA (33 μM) + 7w (1 μM) | 46.64 |
| CPA (33 μM) + 7x (1 μM) | 78.10 |
| CPA (33 μM) + 7y (1 μM) | 86.36 |
| CPA (33 μM) + 7z (1 μM) | 11.22 |
| CPA (33 μM) + 7av (1 μM) | 34.48 |
| CPA (33 μM) + 7aa (1 μM) | 111.80 |
| CPA (33 μM) + 7ab (1 μM) | 60.72 |
| CPA (33 μM) + 4 (1 μM) | 10.30 |
| CPA (33 μM) + 7ac (1 μM) | 75.91 |
| CPA (33 μM) + 7ad (1 μM) | 87.66 |
| CPA (33 μM) + 7ae (1 μM) | 31.99 |
| CPA (33 μM) + 7af (1 μM) | 38.62 |
| CPA (33 μM) + 7ag (1 μM) | 73.33 |
| CPA (33 μM) + 7ah (1 μM) | 67.08 |
| CPA (33 μM) + 7al (1 μM) | 42.03 |

TABLE S2-continued

Results of SOD1$^{A4V}$ motor neuron survival across 54 analogs at 1 μM.

| Treatment | Motor Neuron Survival, % untreated |
|---|---|
| CPA (33 μM) + 7ak (1 μM) | 78.52 |
| CPA (33 μM) + 7al (1 μM) | 72.32 |
| CPA (33 μM) + 7am (1 μM) | 79.98 |
| CPA (33 μM) + 7an (1 μM) | 75.00 |
| CPA (33 μM) + 7ax (1 μM) | 17.43 |
| CPA (33 μM) + 7ay (1 μM) | 4.58 |
| CPA (33 μM) + 7az (1 μM) | 22.92 |
| CPA (33 μM) + 7ao (1 μM) | 95.90 |
| CPA (33 μM) + 7ar (1 μM) | 37.37 |
| CPA (33 μM) + 7as (1 μM) | 80.77 |
| CPA (33 μM) + 7at (1 μM) | 67.48 |
| CPA (33 μM) + 12b (1 μM) | 25.17 |
| CPA (33 μM) + 12c (1 μM) | 43.73 |
| CPA (33 μM) + 12d (1 μM) | 108.63 |
| CPA (33 μM) + 12e (1 μM) | 105.85 |

TABLE S3

Inhibition profile for MLK1 and MLK3 using radioligand binding assay performed by Reaction Biology Corp for compound 1 and 60 analogs.

| | % Enzyme Activity Remaining (relative to DMSO controls) | | | |
|---|---|---|---|---|
| | MLK1/MAP3K9 | | MLK3/MAP3K11 | |
| Compound ID: | [Cmpd](μM): 0.1; Data 1 | [Cmpd](μM): 0.1; Data 2 | [Cmpd](μM): 0.1; Data 1 | [Cmpd](μM): 0.1; Data 2 |
| 1 | 16.18 | 14.18 | 10.78 | 10.22 |
| 12a | 56.17 | 46.47 | 52.18 | 46.74 |
| 7a | 74.16 | 75.13 | 63.66 | 64.82 |
| 7b | 89.16 | 87.85 | 86.71 | 86.95 |
| 7c | 88.34 | 86.78 | 90.01 | 93.44 |
| 7d | 25.65 | 23.57 | 25.04 | 18.84 |
| 7e | 51.70 | 53.98 | 51.43 | 54.29 |
| 7f | 81.08 | 76.45 | 68.84 | 73.51 |
| 7g | 55.94 | 58.53 | 45.87 | 42.66 |
| 7h | 48.82 | 43.21 | 62.91 | 63.31 |
| 7i | 80.15 | 79.43 | 57.91 | 50.75 |
| 7j | 77.72 | 77.49 | 46.91 | 44.55 |
| 7k | 68.99 | 70.84 | 71.64 | 75.32 |
| 7l | 53.17 | 52.44 | 58.50 | 57.04 |
| 7m | 96.65 | 96.29 | 67.62 | 67.85 |
| 7aw | 79.80 | 79.43 | 65.23 | 66.67 |
| 7n | 88.89 | 88.66 | 91.26 | 92.62 |
| 7o | 93.38 | 90.65 | 90.12 | 92.65 |
| 7p | 62.68 | 62.92 | 40.84 | 42.08 |
| 7q | 94.11 | 95.41 | 91.91 | 89.69 |
| 7r | 56.25 | 58.56 | 38.87 | 39.87 |
| 7s | 94.75 | 94.30 | 90.97 | 90.45 |
| 7t | 82.11 | 80.00 | 83.49 | 78.30 |
| 7u | 93.90 | 95.93 | 92.02 | 90.70 |
| 7v | 42.95 | 43.96 | 33.57 | 32.45 |
| 7w | 76.05 | 79.32 | 75.10 | 76.98 |
| 7x | 65.82 | 67.65 | 67.84 | 65.08 |
| 7y | 57.07 | 58.14 | 40.75 | 43.09 |
| 7z | 98.64 | 99.20 | 93.59 | 94.16 |
| 7av | 85.98 | 84.19 | 84.24 | 86.99 |
| 7aa | 52.85 | 51.66 | 31.88 | 31.78 |
| 7ab | 83.66 | 82.94 | 68.47 | 70.51 |
| 4 | 95.86 | 93.53 | 91.95 | 94.97 |
| 7ac | 60.84 | 57.68 | 42.00 | 43.30 |
| 7ad | 61.94 | 63.56 | 37.50 | 38.21 |
| 7ae | 92.47 | 91.82 | 84.17 | 86.93 |
| 7af | 92.61 | 90.60 | 75.32 | 81.31 |
| 7ag | 50.92 | 50.05 | 54.67 | 52.80 |
| 7ah | 51.06 | 48.17 | 32.02 | 32.11 |
| 7ai | 93.30 | 90.49 | 93.11 | 88.00 |
| 7aj | 96.41 | 92.62 | 95.75 | 93.75 |
| 7ak | 34.18 | 32.77 | 48.06 | 48.02 |
| 7al | 33.38 | 32.70 | 32.96 | 30.90 |

TABLE S3-continued

Inhibition profile for MLK1 and MLK3 using radioligand binding assay performed by Reaction Biology Corp for compound 1 and 60 analogs.

| | % Enzyme Activity Remaining (relative to DMSO controls) | | | |
|---|---|---|---|---|
| | MLK1/MAP3K9 | | MLK3/MAP3K11 | |
| Compound ID: | [Cmpd](μM): 0.1; Data 1 | [Cmpd](μM): 0.1; Data 2 | [Cmpd](μM): 0.1; Data 1 | [Cmpd](μM): 0.1; Data 2 |
| 7am | 51.04 | 51.24 | 49.77 | 46.17 |
| 7an | 68.74 | 65.38 | 65.74 | 63.06 |
| 7ax | 93.49 | 92.34 | 90.99 | 86.58 |
| 7ay | 88.50 | 91.81 | 84.43 | 83.57 |
| 7az | 79.05 | 78.45 | 79.28 | 80.78 |
| 7ao | 49.02 | 47.09 | 35.75 | 32.77 |
| 7ap | 54.18 | 52.81 | 70.05 | 68.91 |
| 7aq | 54.50 | 53.62 | 51.92 | 49.61 |
| 7ar | 70.14 | 67.99 | 44.17 | 45.09 |
| 7as | 72.65 | 73.27 | 49.99 | 51.55 |
| 7at | 31.31 | 30.59 | 24.55 | 21.30 |
| 11 | 94.99 | 95.49 | 93.68 | 88.60 |

\* Compounds were tested in single dose duplicate mode at a concentration of 0.1 μM. Reactions were carried out at 10 μM ATP.

TABLE S4

Inhibition profile for HGK using radioligand binding assay performed by Reaction Biology Corp for compound 1 and 64 analogs.

| | % Enzyme Activity (relative to DMSO controls) HGK/MAP4K4 | |
|---|---|---|
| Compound ID: | [Cmpd](μM): 0.025 Data 1 | [Cmpd](μM): 0.1 Data 1 |
| 1 | 18.53 | 5.23 |
| 12a | 72.82 | 51.50 |
| 7a | 86.06 | 58.79 |
| 7b | 77.63 | 42.84 |
| 7c | 99.28 | 81.59 |
| 7d | 19.60 | 4.25 |
| 7e | 24.03 | 7.41 |
| 7f | 23.23 | 4.89 |
| 7g | 72.29 | 39.14 |
| 7h | 98.83 | 87.39 |
| 7i | 85.32 | 54.60 |
| 7j | 63.62 | 20.58 |
| 7k | 48.27 | 16.48 |
| 7l | 27.02 | 5.45 |
| 7m | 38.39 | 10.75 |
| 7aw | 85.38 | 58.48 |
| 7n | 65.72 | 29.92 |
| 7o | 58.87 | 29.28 |
| 7p | 3.92 | 1.56 |
| 7q | 103.58 | 85.67 |
| 7r | 4.88 | 1.23 |
| 7s | 77.77 | 36.97 |
| 7t | 74.27 | 33.40 |
| 7u | 92.86 | 52.30 |
| 7v | 13.80 | 2.90 |
| 7w | 28.98 | 4.46 |
| 7x | 30.76 | 7.10 |
| 7y | 7.85 | 1.53 |
| 7z | 96.36 | 67.90 |
| 7av | 88.78 | 51.19 |
| 7aa | 2.75 | −1.36 |
| 7ab | 26.55 | 4.65 |
| 4 | 101.46 | 88.27 |
| 7ac | 31.95 | 6.69 |
| 7ad | 8.51 | 2.92 |
| 7ae | 67.88 | 42.67 |
| 7af | 68.96 | 38.69 |
| 7ag | 32.54 | 7.91 |
| 7ah | 42.79 | 3.56 |
| 7ai | 104.55 | 105.70 |

TABLE S4-continued

Inhibition profile for HGK using radioligand binding assay performed by Reaction Biology Corp for compound 1 and 64 analogs.

| | % Enzyme Activity (relative to DMSO controls) HGK/MAP4K4 | |
|---|---|---|
| Compound ID: | [Cmpd](μM): 0.025 Data 1 | [Cmpd](μM): 0.1 Data 1 |
| 7aj | 103.19 | 86.60 |
| 7ak | 41.72 | 14.21 |
| 7al | 33.76 | 6.76 |
| 7am | 56.00 | 17.72 |
| 7an | 39.94 | 10.16 |
| 7ax | 93.61 | 78.70 |
| 7ay | 93.80 | 78.99 |
| 7az | 87.12 | 64.98 |
| 7ao | 21.33 | 1.98 |
| 7ap | 35.56 | 6.76 |
| 7aq | 57.34 | 19.96 |
| 7ar | 55.55 | 27.35 |
| 7as | 17.60 | 3.61 |
| 7at | 29.31 | 4.83 |
| 11 | 101.95 | 85.55 |
| 12b | 69.05 | 34.53 |
| 12c | 92.71 | 84.15 |
| 12d | 3.17 | −0.29 |
| 12e | 2.73 | 0.99 |

\* Compounds were tested in two-dose singlicate mode at concentrations of 0.025 μM and 0.1 μM for HGK. Reactions were carried out at 10 μM ATP.

The Inhibition of Related MAP4Ks Correlates with Motor Neuron Survival

To further explore the biologically relevant targets of compound 1 and its analogs, we selected 10 analogs ranging from moderately to very strongly protective in the CPA assay and evaluated their ability to inhibit a panel of 60 human kinases at 0.1 μM in the radiolabeled ATP assay (Table 85). The kinases in the expanded panel were selected from known targets of compound 1 (Goodfellow et al., 2013), known targets of other kinase inhibitors that were protective in the CPA survival assay (see Example 12), and relevant targets from the literature. RNAseq data were used to confirm the expression of each kinase in ES motor neurons (see Example 12).

Figure 32:
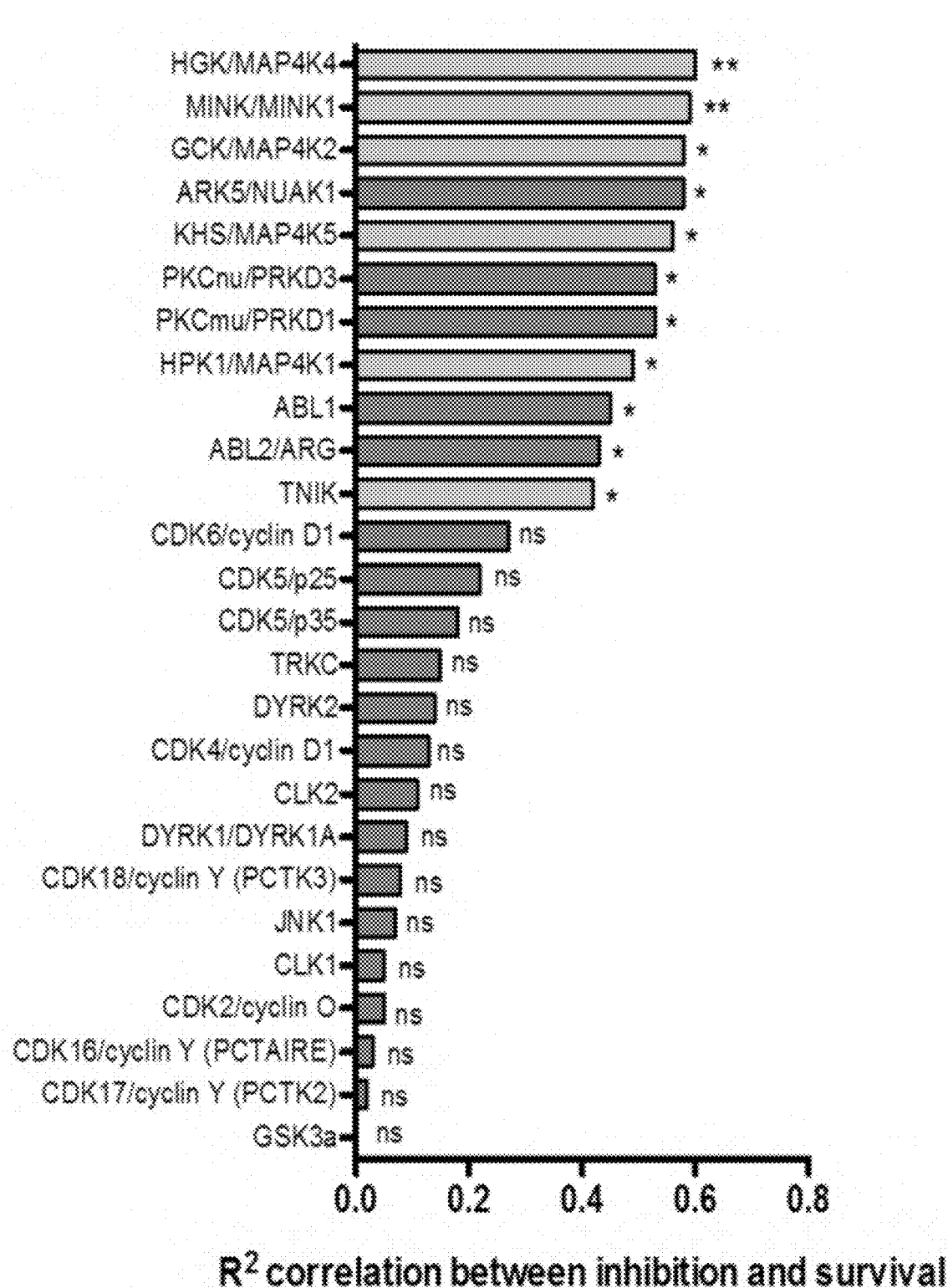
FIG. 32 shows the ranked R squared values (from Pearson's r) describing the correlation between the inhibition of a given kinase and motor neuron survival. Ten compound 1 analogs were compared for their ability to inhibit 60 different known targets of compound 1 and their ability to promote motor neuron survival following CPA treatment. MAP4Ks (highlighted in green) are amongst the most highly-ranked kinases. $**P<0.01$, $*P<0.05$.

To parse the functional targets of the analogs in the CPA assay, we performed regression analyses comparing the degree to which the inhibition of the activity of a given kinase correlated with neuroprotection in the CPA assay. Kinases whose activity was poorly inhibited by all 10 of the analogs tested (>20% activity remaining at 0.1 μM) were excluded from analysis. We found that the inhibition of HGK, TNIK, MINK1 (MAP4K6), GCK (MAP4K2), and KHS (MAP4K5) correlated strongly with neuroprotection (FIG. 32). These findings were also consistent with our analyses of the shared targets of the hit compounds from our preliminary screen (FIG. 41A), where HGK, MINK1, GCK, and KHS were all among the most highly ranked targets. (TNIK did not appear in our initial analysis of shared targets because its activity was not assessed in the existing publicly available database (Anastassiadis et al., 2011).) Because the catalytic domains of all MAP4K kinases are highly conserved, it is likely that neuroprotection is mediated by the inhibition of several MAP4K family members simultaneously (Larhammar et al., 2017).

TABLE S5

Inhibition profile for 60 known targets of compound 1 using radioligand binding assay performed by Reaction Biology Corp for compound 1 and 9 analogs.

| | % Enzyme Activity (relative to DSMO controls)* | | | | | | | | | |
|---|---|---|---|---|---|---|---|---|---|---|
| Kinase | Compound 1 | Compound 7d | d 12 from US 201 | Compound 7n | Compound 7w | Compound 7as | Compound 7ad | Compound 7ah | Compound 7ai | Compound 7at |
| ABL1 | 46.60 | 74.52 | 101.13 | 88.38 | 64.85 | 5.92 | 77.27 | 81.04 | 26.32 | 19.00 |
| ABL2/ARG | 54.86 | 72.66 | 99.47 | 91.46 | 77.64 | 0.99 | 83.70 | 95.07 | 44.40 | 21.79 |
| ALK | 25.35 | 73.84 | 104.53 | 94.12 | 89.72 | 70.50 | 108.48 | 28.78 | 76.23 | 77.84 |
| ARK5/NUAK1 | 5.96 | 20.76 | 99.69 | 39.34 | 14.83 | 4.44 | 22.38 | 0.03 | 21.60 | 22.93 |
| ASK1/MAP3K5 | 90.76 | 80.24 | 96.26 | 95.40 | 96.01 | 87.63 | 95.41 | 95.59 | 96.23 | 96.32 |
| Aurora A | 81.41 | 74.81 | 96.43 | 96.44 | 83.88 | 81.06 | 97.30 | 48.36 | 95.46 | 90.21 |
| Aurora B | 88.78 | 83.47 | 92.28 | 86.86 | 89.86 | 82.54 | 91.83 | 69.93 | 98.99 | 87.84 |
| Aurora C | 82.79 | 92.29 | 97.09 | 100.96 | 94.35 | 94.22 | 104.45 | 78.45 | 122.02 | 106.72 |
| c-MET | 55.87 | 110.07 | 98.59 | 102.18 | 96.58 | 84.12 | 86.21 | 86.63 | 77.44 | 86.84 |
| CDK14/cyclin Y (PFTK1) | 88.17 | 66.35 | 90.78 | 34.97 | 83.75 | 85.05 | 92.55 | 30.10 | 83.90 | 76.38 |
| CDK16/cyclin Y (PCTAIRE | 94.93 | 57.98 | 101.78 | 21.51 | 80.81 | 75.16 | 96.90 | 8.19 | 87.65 | 76.90 |
| CDK17/cyclin Y (PCTK2) | 66.13 | 41.07 | 68.95 | 10.65 | 61.36 | 44.09 | 70.41 | 7.55 | 69.43 | 69.65 |
| CDK18/cyclin Y (PCTK3) | 102.86 | 82.82 | 102.55 | 24.03 | 94.55 | 95.50 | 111.90 | 16.09 | 100.30 | 97.10 |
| CDK2/cyclin A | 83.69 | 34.42 | 97.34 | 66.04 | 91.12 | 69.55 | 87.36 | 44.24 | 90.90 | 56.14 |
| CDK2/cyclin A1 | 83.58 | 38.77 | 99.98 | 60.25 | 88.56 | 65.01 | 97.04 | 30.69 | 87.80 | 58.78 |
| CDK2/cyclin E | 97.91 | 89.13 | 98.52 | 54.28 | 92.40 | 88.49 | 96.23 | 48.85 | 94.76 | 80.57 |
| CDK2/cyclin O | 72.54 | 38.97 | 98.04 | 43.71 | 80.18 | 51.24 | 75.12 | 19.23 | 77.92 | 29.57 |
| CDK3/cyclin E | 89.11 | 76.70 | 98.24 | 72.29 | 93.74 | 85.48 | 95.54 | 65.20 | 95.97 | 72.68 |
| CDK4/cyclin D1 | 51.01 | 19.37 | 97.32 | 27.77 | 73.42 | 31.90 | 70.94 | 25.87 | 65.91 | 14.08 |
| CDK4/cyclin D3 | 49.06 | 26.69 | 89.90 | 36.96 | 72.23 | 39.68 | 58.10 | 25.97 | 65.37 | 24.36 |
| CDK5/p25 | 52.82 | 16.36 | 96.20 | 69.19 | 89.42 | 48.57 | 84.38 | 52.05 | 93.25 | 43.10 |
| CDK5/p35 | 52.30 | 14.16 | 91.74 | 57.46 | 82.23 | 35.98 | 83.87 | 46.33 | 87.93 | 31.92 |
| CDK6/cyclin D1 | 47.18 | 15.07 | 101.56 | 23.36 | 58.53 | 15.60 | 45.84 | 28.56 | 47.93 | 7.23 |
| CDK6/cyclin D3 | 66.13 | 52.30 | 89.97 | 51.83 | 68.39 | 36.14 | 58.84 | 33.17 | 75.99 | 46.05 |
| CDK9/cyclin K | 101.50 | 95.85 | 105.86 | 83.37 | 97.85 | 96.59 | 99.70 | 93.28 | 99.72 | 79.53 |
| CDK9/cyclin T1 | 96.63 | 85.53 | 115.70 | 47.94 | 96.13 | 82.28 | 77.99 | 57.75 | 85.84 | 46.29 |
| CDK9/cyclin T2 | 98.09 | 93.67 | 104.10 | 38.75 | 65.63 | 74.19 | 95.21 | 82.74 | 84.80 | 37.37 |
| CLK1 | 33.01 | 1.66 | 75.98 | 34.90 | 81.91 | 44.60 | 81.24 | 3.41 | 66.43 | 78.40 |
| CLK2 | 22.81 | 2.71 | 86.77 | 23.56 | 59.24 | 22.54 | 79.80 | 4.24 | 52.46 | 90.88 |
| CLK4 | 59.25 | 21.30 | 90.07 | 72.25 | 85.45 | 65.66 | 87.83 | 21.77 | 78.48 | 90.40 |
| DDR1 | 47.46 | 57.37 | 58.05 | 79.67 | 75.15 | 35.62 | 81.97 | 38.33 | 76.50 | 68.08 |
| DYRK/RK1A | 40.96 | 3.15 | 67.18 | 40.28 | 71.25 | 42.01 | 53.43 | 4.52 | 41.66 | 57.38 |
| DYRK2 | 44.02 | 8.19 | 52.53 | 63.61 | 90.42 | 18.21 | 69.70 | 59.27 | 66.48 | 96.77 |
| ERK5/MAPK7 | 108.58 | 96.79 | 106.79 | 90.59 | 108.40 | 107.05 | 109.11 | 105.29 | 100.85 | 108.28 |
| ERK5/MAPK7 (CD) | 87.52 | 87.49 | 101.20 | 98.90 | 96.35 | 51.23 | 93.90 | 52.14 | 85.96 | 92.73 |
| ERN1/IRE1 | 108.16 | 106.67 | 103.22 | 106.64 | 102.17 | 97.50 | 101.73 | 104.22 | 102.25 | 101.45 |
| FGFR1 | 82.73 | 93.18 | 106.92 | 100.25 | 93.06 | 77.89 | 98.18 | 91.41 | 97.45 | 96.40 |
| FGFR2 | 52.90 | 70.36 | 104.70 | 94.00 | 77.84 | 41.14 | 77.61 | 73.84 | 80.92 | 83.43 |
| FGFR3 | 43.48 | 73.42 | 94.99 | 85.86 | 70.72 | 42.32 | 70.13 | 76.57 | 82.04 | 82.06 |
| FLT4/VEGFR3 | 34.49 | 38.95 | 97.98 | 65.97 | 64.63 | 23.16 | 80.49 | 33.99 | 60.29 | 79.77 |
| GCK/MAP4K1 | 27.53 | 13.06 | 97.50 | 59.65 | 33.65 | 8.85 | 8.09 | 10.10 | 53.80 | 12.35 |
| GSK3a | 90.82 | 13.62 | 101.16 | 75.33 | 75.26 | 96.03 | 97.13 | 32.48 | 84.68 | 82.76 |
| GSK3b | 100.13 | 30.95 | 100.33 | 90.70 | 85.10 | 98.89 | 98.07 | 60.56 | 94.04 | 97.29 |
| HGK/MAP4K4 | 1.96 | 2.05 | 90.70 | 35.04 | 2.85 | −0.50 | 1.36 | 5.18 | 9.15 | 9.52 |
| HPK1/MAP4K1 | 23.98 | 11.32 | 105.15 | 57.71 | 62.43 | 19.47 | 62.46 | 17.79 | 67.84 | 55.59 |
| JNK1 | 75.32 | 52.20 | 106.57 | 85.48 | 76.82 | 74.62 | 88.73 | 18.63 | 77.68 | 101.63 |
| JNK3 | 122.33 | 120.34 | 115.61 | 114.58 | 112.57 | 111.33 | 106.35 | 81.80 | 106.80 | 103.80 |
| KHS/MAPK4K5 | 11.02 | 4.17 | 101.24 | 30.94 | 15.06 | 0.89 | 5.80 | 6.09 | 16.53 | 3.35 |
| MINK/MINK1 | 5.53 | 6.69 | 94.09 | 38.80 | 3.72 | 0.19 | 3.06 | 5.06 | 7.80 | 9.84 |
| P38a/MAPK14 | 107.76 | 102.06 | 109.01 | 101.03 | 109.55 | 113.01 | 104.92 | 108.75 | 98.17 | 96.25 |
| P38b/MAPK11 | 103.94 | 100.60 | 102.89 | 100.63 | 99.32 | 99.55 | 102.70 | 101.16 | 103.91 | 97.71 |
| P38d/MAPK13 | 111.82 | 98.59 | 107.10 | 104.52 | 112.43 | 113.46 | 118.87 | 108.94 | 105.77 | 103.98 |
| P38g | 99.32 | 107.75 | 112.74 | 114.14 | 115.83 | 109.10 | 107.70 | 105.58 | 106.12 | 103.08 |
| PKCmu/PRKD1 | 11.43 | 4.34 | 103.73 | 31.47 | 20.39 | 9.63 | 9.70 | 4.39 | 14.18 | 38.74 |
| PKCnu/PRKD3 | 16.14 | 6.42 | 106.53 | 42.32 | 32.82 | 18.78 | 17.47 | 7.09 | 19.16 | 50.21 |
| TAOK1 | 63.53 | 37.29 | 98.60 | 87.42 | 90.01 | 39.29 | 75.38 | 62.09 | 93.28 | 40.53 |
| TAOK3/JIK | 83.96 | 67.91 | 99.64 | 94.90 | 95.18 | 69.75 | 91.98 | 77.41 | 101.93 | 65.49 |
| TNIK | 3.00 | 12.05 | 58.89 | 6.70 | 0.45 | 0.51 | 0.68 | 0.96 | 1.35 | 2.20 |
| TNK1 | 28.81 | 44.29 | 89.62 | 87.75 | 73.19 | 33.87 | 53.55 | 37.83 | 63.63 | 38.41 |
| TRKC | 6.69 | 17.69 | 33.25 | 25.37 | 25.76 | 6.32 | 51.25 | 9.83 | 13.08 | 34.79 |

(Compounds were tested in single-dose singlicate mode at a concentration of 0.1 µM. Reactions were carried out at 10 µM ATP.)

Identification of Additional Kinase Targets of Compound 12k

Figure 38A:
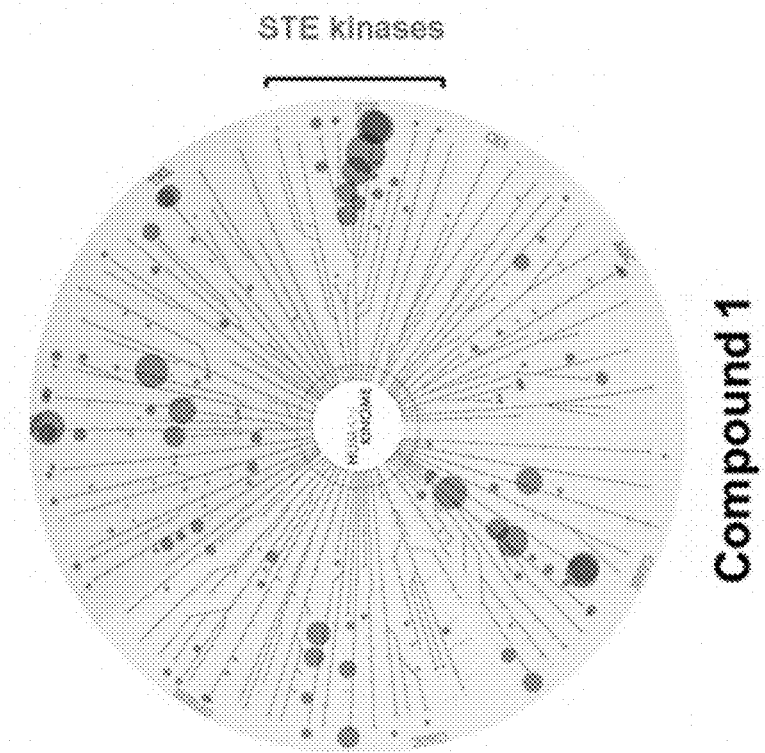
Figure 38B:
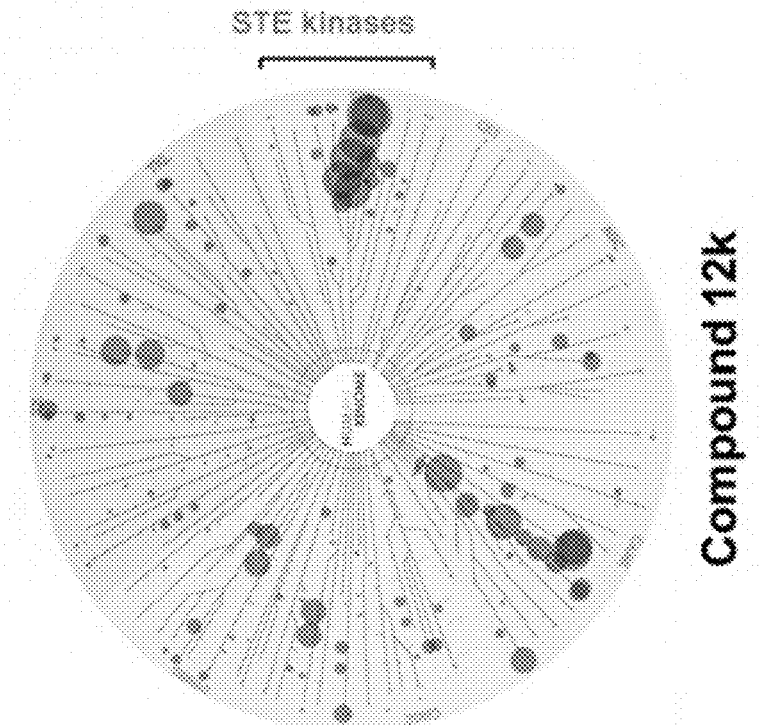
Figure 38C:
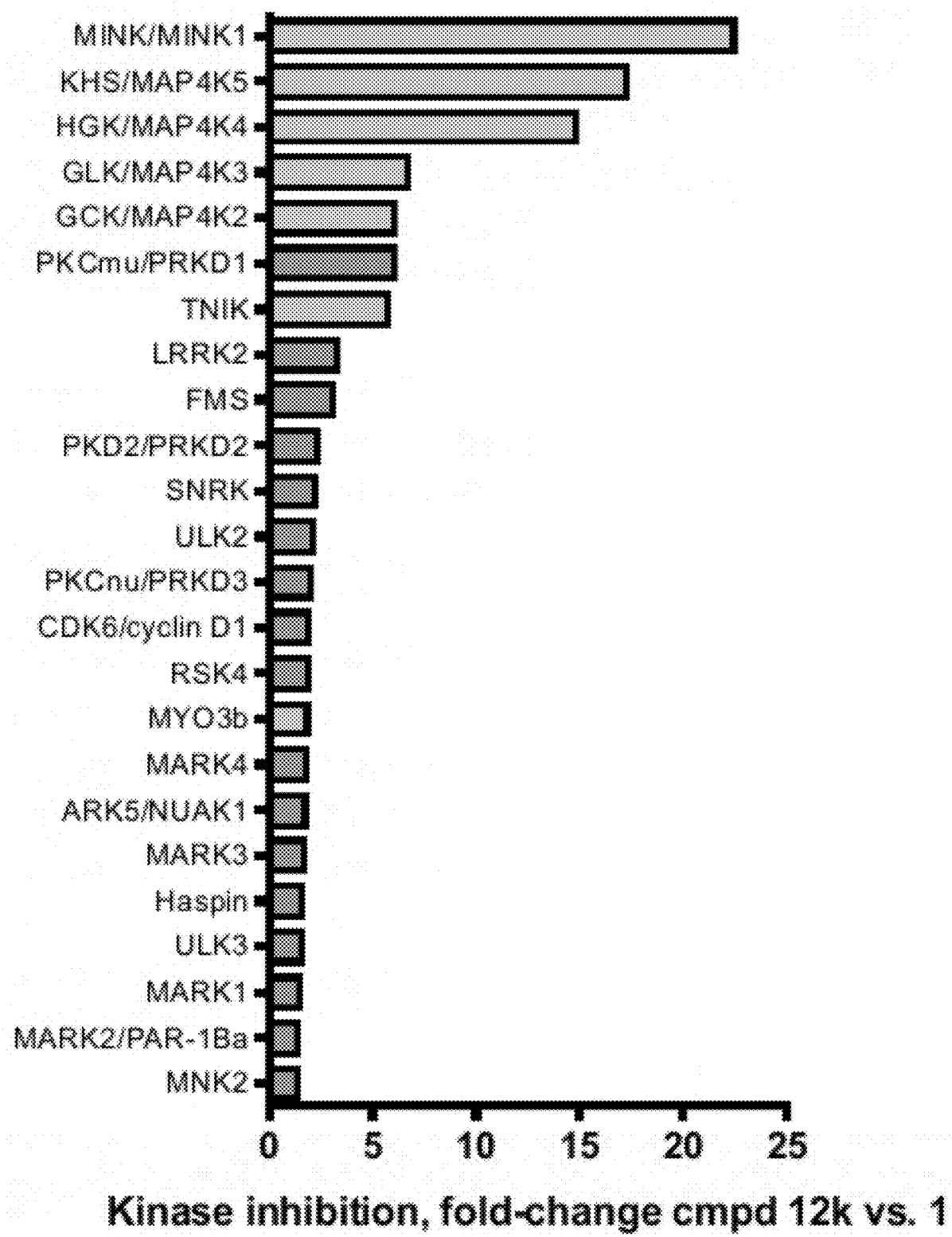
Figure 39:
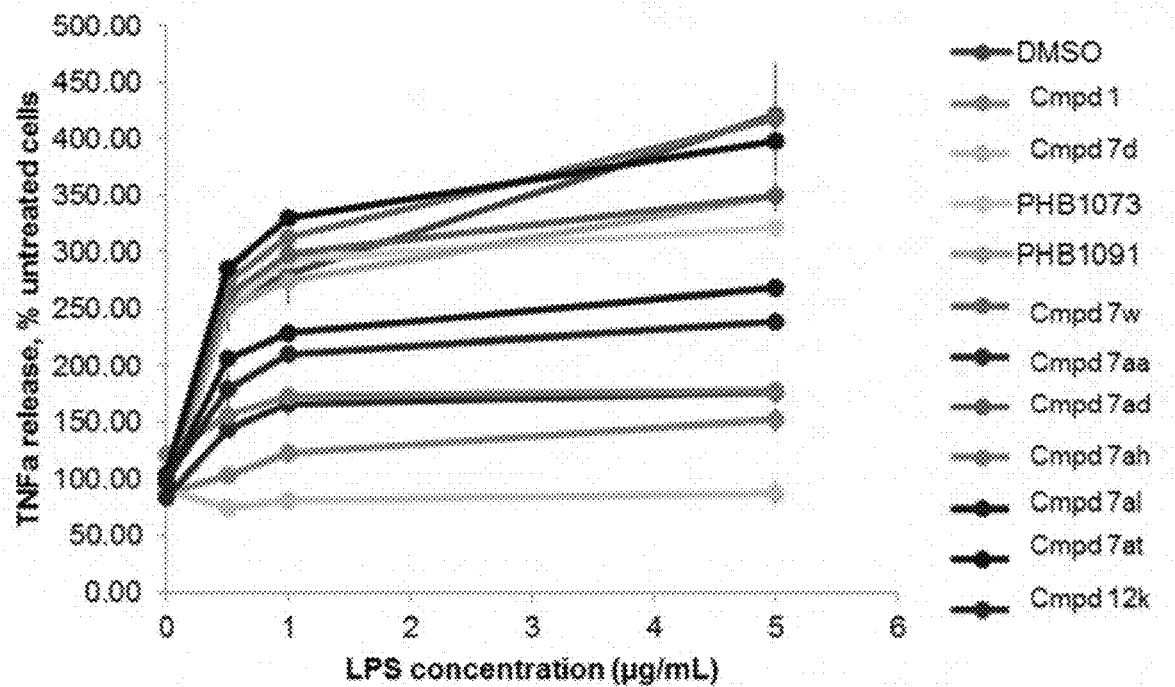
Figure 39:
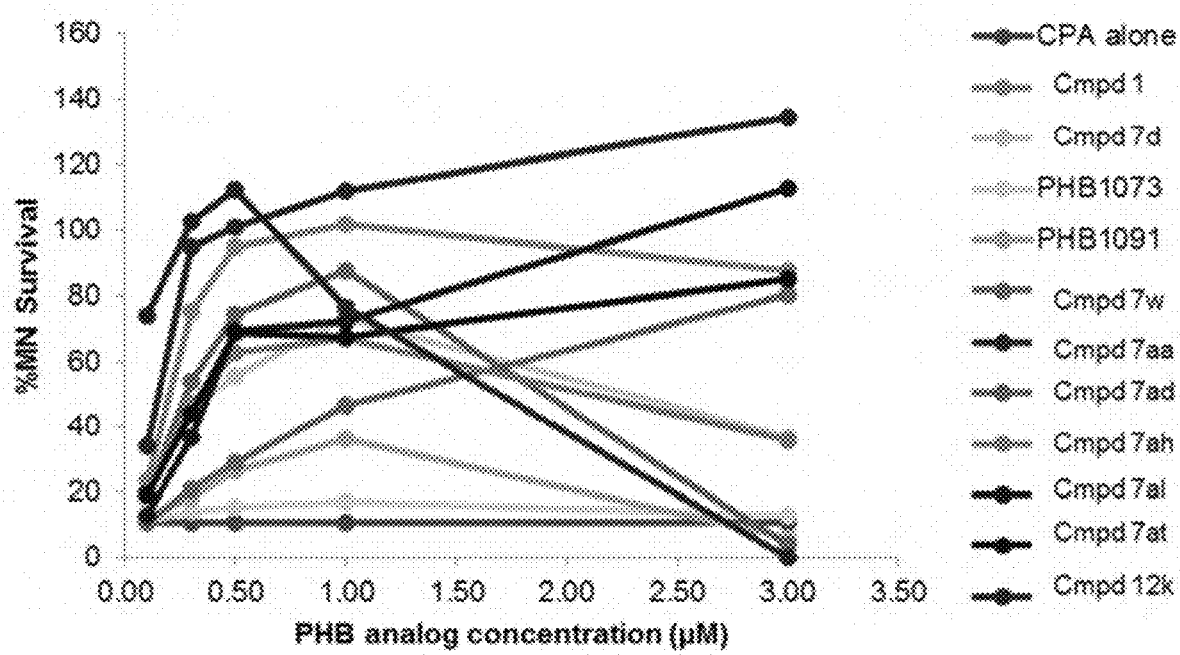
Figure 40:
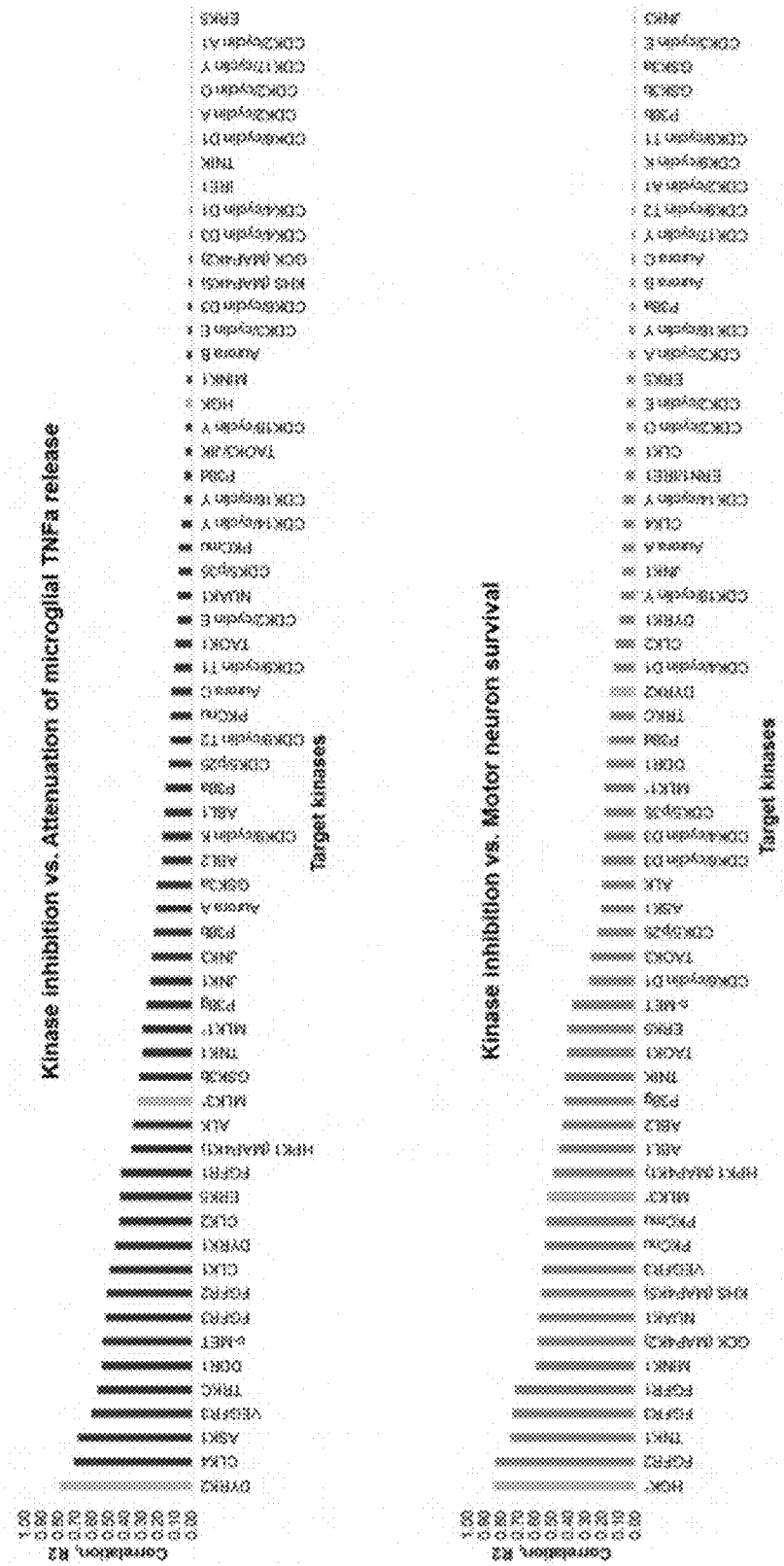

Increased potency and a favorable pharmacokinetic profile of 12k make it a strong candidate for future studies in vivo, where off-target effects will be a concern. To obtain global kinase inhibition profiles, compound 1 and 12k were tested at 0.025 µM in cell-free radiolabeled ATP assays across an expanded panel of 371 human kinases (FIG. 38A and FIG. 38B, Table S6). We found that the MAP4Ks MINK1, KHS, HGK, GLK, and GCK exhibited the highest degree of change in activity following 12k exposure relative to 1 (22.56, 17.36, 14.92, 6.84, and 6.22-fold change, respectively; FIG. 38C). However, several non-MAP4 kinases were more efficiently (>1.5-fold) inhibited by 12k vs. 1 exposure, including kinases that have previously been implicated in neurodegeneration NUAK1 (Lasagna-Reeves et al., 2016) and LRRK2 (Islam and Moore, 2017). These observations raised the possibility that additional kinase targets beyond the MAP4Ks might contribute to the enhanced potency of 12k. Further targeted analyses, such as genetic knock-down or knock-out, may be warranted to parse the role of these additional kinases in our model of neurodegeneration.

TABLE S6

Inhibition profile for 371 wild-type human kinases using radioligand binding assay performed by Reaction Biology Corp for compound 1 and 12k analogs.

| Kinase: | % Enzyme Activity (relative to DMSO controls) | |
|---|---|---|
| | Compound 1 | Compound 12k |
| ABL1 | 68.22 | 76.65 |
| ABL2/ARG | 76.81 | 75.10 |
| ACK1 | 87.33 | 93.62 |
| AKT1 | 96.98 | 100.77 |
| AKT2 | 96.68 | 102.59 |
| AKT3 | 98.44 | 97.25 |
| ALK | 73.85 | 85.28 |
| ALK1/ACVRL1 | 106.29 | 100.00 |
| ALK2/ACVR1 | 121.48 | 126.48 |
| ALK1/BMPR1A | 97.03 | 96.83 |
| ALK4/ACVR1B | 100.44 | 95.93 |
| ALK5/TGFBR1 | 97.64 | 98.49 |
| ALK6/BMPR1B | 116.42 | 125.08 |
| ARAF | 108.18 | 96.60 |
| ARK5/NUAK1 | 26.91 | 14.36 |
| ASK1/MAP3K5 | 103.48 | 95.67 |
| Aurora A | 95.17 | 104.47 |
| Aurora B | 102.70 | 82.61 |
| Aurora C | 110.48 | 97.26 |
| AXL | 35.78 | 39.84 |
| BLK | 99.50 | 101.35 |
| BMPR2 | 90.51 | 90.27 |
| BMX/ETK | 101.07 | 102.77 |
| BRAF | 104.58 | 98.00 |
| BRK | 86.39 | 95.02 |
| BRSK1 | 80.83 | 83.61 |
| BRSK2 | 97.96 | 93.52 |
| BTK | 103.13 | 99.68 |
| c-Kit | 100.02 | 89.78 |
| c-MER | 81.19 | 75.11 |
| c-MET | 87.76 | 88.23 |
| c-Src | 86.00 | 88.06 |
| CAMK1a | 100.06 | 120.85 |
| CAMK1b | 105.01 | 102.54 |
| CAMK1d | 101.48 | 96.77 |
| CAMK1g | 97.75 | 100.83 |
| CAMK2a | 101.28 | 109.93 |
| CAMK2b | 95.50 | 92.25 |
| CAMK2d | 96.99 | 81.26 |
| CAMK2g | 110.23 | 109.71 |
| CAMK4 | 95.12 | 100.26 |
| CAMKK1 | 102.73 | 101.58 |
| CAMKK2 | 97.67 | 94.89 |
| CDC7/DBF4 | 100.50 | 98.28 |
| CDK1/cyclin A | 95.09 | 79.88 |
| CDK1/cyclin B | 96.55 | 84.86 |
| CDK1/cyclin E | 98.73 | 91.11 |
| CDK14/cyclin Y (PFTK1) | 110.03 | 94.92 |
| CDK16/cyclin Y (PCTAIRE) | 129.69 | 97.29 |
| CDK17/cyclin Y (PCTK2) | 87.97 | 74.00 |
| CDK18/cyclin Y (PCTK3) | 90.26 | 77.47 |
| CDK19/cyclin C | 94.90 | 64.81 |
| CDK2/cyclin A | 90.16 | 83.06 |
| CDK2/cyclin A1 | 94.21 | 87.09 |
| CDK2/cyclin E | 96.11 | 98.32 |
| CDK2/cyclin E2 | 110.26 | 89.57 |
| CDK2/cyclin O | 101.83 | 82.53 |
| CDK3/cyclin E | 92.93 | 96.96 |
| CDK3/cyclin E2 | 92.56 | 90.18 |
| CDK4/cyclin D1 | 69.21 | 56.40 |
| CDK4/cyclin D3 | 90.86 | 67.22 |
| CDK5/p25 | 79.65 | 75.86 |
| CDK5/p35 | 81.34 | 79.18 |
| CDK6/cyclin D1 | 63.07 | 30.68 |
| CDK6/cyclin D3 | 92.25 | 68.15 |
| CDK7/cyclin H | 91.39 | 89.25 |
| CDK9/cyclin K | 79.84 | 88.45 |
| CDK9/cyclin T1 | 86.00 | 88.65 |
| CDK9/cyclin T2 | 111.54 | 99.09 |
| CHK1 | 90.04 | 74.96 |
| CHK2 | 85.18 | 93.50 |
| CK1a1 | 102.12 | 91.58 |
| CK1a1L | 94.82 | 107.06 |
| CK1d | 90.02 | 92.82 |
| CK1epsilon | 116.63 | 102.73 |
| CK1g1 | 142.73 | 115.75 |
| CK1g2 | 101.66 | 102.00 |
| CK1g3 | 92.19 | 92.37 |
| CK2a | 100.25 | 110.27 |
| CK2a2 | 84.34 | 88.96 |
| CLK1 | 58.75 | 68.57 |
| CLK2 | 48.18 | 55.82 |
| CLK3 | 95.29 | 90.97 |
| CLK4 | 94.51 | 71.93 |
| COT1/MAP3K8 | 100.79 | 87.50 |
| CSK | 87.51 | 90.77 |
| CTK/MATK | 102.08 | 96.55 |
| DAPK1 | 96.28 | 95.36 |
| DAPK2 | 118.18 | 105.47 |
| DCAMKL1 | 97.15 | 94.24 |
| DCAMKL2 | 87.14 | 87.62 |
| DDR1 | 89.92 | 86.61 |
| DDR2 | 101.64 | 100.39 |
| DLK/MAP3K12 | 90.84 | 82.81 |
| DMPK | 96.60 | 97.66 |
| DMPK2 | 76.84 | 61.26 |
| DRAK1/STK17A | 88.73 | 88.75 |
| DYRK1/DYRK1A | 52.38 | 40.71 |
| DYRK1B | 43.16 | 38.34 |
| DYRK2 | 71.74 | 85.58 |
| DYRK3 | 74.91 | 89.18 |
| DYRK4 | 110.55 | 101.40 |
| EGFR | 103.38 | 96.17 |
| EPHA1 | 74.25 | 89.39 |
| EPHA2 | 93.59 | 92.33 |
| EPHA3 | 99.83 | 98.15 |
| EPHA4 | 94.15 | 88.72 |
| EPHA5 | 94.19 | 98.75 |
| EPHA6 | 106.20 | 98.18 |
| EPHA7 | 89.46 | 91.33 |
| EPHA8 | 90.83 | 93.50 |
| EPHB1 | 82.97 | 98.35 |

TABLE S6-continued

Inhibition profile for 371 wild-type human kinases using radioligand binding assay performed by Reaction Biology Corp for compound 1 and 12k analogs.

| | % Enzyme Activity (relative to DMSO controls) | |
|---|---|---|
| Kinase: | Compound 1 | Compound 12k |
| EPHB2 | 88.59 | 98.33 |
| EPHB3 | 106.74 | 101.07 |
| EPHB4 | 91.60 | 97.52 |
| ERBB2/HER2 | 95.27 | 96.01 |
| ERBB4/HER4 | 103.62 | 97.16 |
| ERK1 | 85.99 | 92.79 |
| ERK2/MAPK1 | 104.45 | 101.46 |
| ERK5/MAPK7 | 101.56 | 113.24 |
| ERK7/MAPK15 | 108.79 | 90.40 |
| ERN1/IRE1 | 106.96 | 98.86 |
| ERN2/IRE2 | 92.33 | 64.32 |
| FAK/PTK2 | 86.28 | 88.47 |
| FER | 94.82 | 103.36 |
| FES/FPS | 68.18 | 77.90 |
| FGFR1 | 93.88 | 95.03 |
| FGFR2 | 79.92 | 89.50 |
| FGFR3 | 76.74 | 80.86 |
| FGFR4 | 97.23 | 100.15 |
| FGR | 97.17 | 84.21 |
| FLT1/VEGFR1 | 88.22 | 90.94 |
| FLT3 | 22.33 | 29.41 |
| FLT4/VEGFR3 | 81.73 | 85.75 |
| FMS | 85.44 | 26.82 |
| FRK/PTK5 | 91.13 | 98.30 |
| FYN | 92.12 | 96.35 |
| GCK/MAP4K2 | 63.63 | 10.22 |
| GLK/MAP4K3 | 49.17 | 7.18 |
| GRK1 | 106.54 | 92.01 |
| GRK2 | 94.01 | 96.28 |
| GRK3 | 105.59 | 104.38 |
| GRK4 | 105.83 | 105.53 |
| GRK5 | 98.19 | 93.26 |
| GRK6 | 91.53 | 95.20 |
| GRK7 | 101.00 | 97.09 |
| GSK3a | 84.85 | 91.56 |
| GSK3b | 99.00 | 89.62 |
| Haspin | 128.07 | 75.00 |
| HCK | 110.50 | 95.83 |
| HGK/MAP4K4 | 20.20 | 1.35 |
| HIPK1 | 105.71 | 96.03 |
| HIPK2 | 109.81 | 95.68 |
| HIPK3 | 102.82 | 112.84 |
| HIPK4 | 107.15 | 104.63 |
| HPK1/MAP4K1 | 49.57 | 47.93 |
| IGF1R | 95.40 | 95.39 |
| IKKa/CHUK | 96.81 | 101.03 |
| IKKb/IKBKE | 81.26 | 84.13 |
| IKKe/IKBKE | 82.52 | 63.83 |
| IR | 100.06 | 111.73 |
| IRAK1 | 86.15 | 73.22 |
| IRAK4 | 105.77 | 95.41 |
| IRR/INSRR | 50.15 | 89.91 |
| ITK | 101.45 | 101.66 |
| JAK1 | 103.21 | 90.54 |
| JAK2 | 90.24 | 92.95 |
| JAK3 | 90.92 | 76.15 |
| JNK1 | 98.21 | 86.76 |
| JNK2 | 99.40 | 97.02 |
| JNK3 | 89.50 | 94.38 |
| KDR/VEGFR2 | 76.18 | 84.66 |
| KHS/MAP4K5 | 31.42 | 1.81 |
| KSR1 | 98.00 | 97.29 |
| KSR2 | 102.05 | 106.00 |
| LATS1 | 83.58 | 84.39 |
| LATS2 | 83.20 | 88.10 |
| LCK | 94.18 | 98.83 |
| LCK2/ICK | 110.77 | 108.85 |
| LIMK1 | 111.81 | 102.75 |
| LIMK2 | 103.19 | 101.45 |
| LKB1 | 101.43 | 78.68 |
| LOK/STK10 | 73.25 | 59.13 |
| LRRK2 | 58.84 | 17.02 |
| LYN | 90.33 | 99.35 |
| LYN B | 81.28 | 89.48 |
| MAK | 100.68 | 87.46 |
| MAPKAPK2 | 96.87 | 99.60 |
| MAPKAPK3 | 100.68 | 96.69 |
| MAPKAPK5/PRAK | 78.50 | 84.36 |
| MARK1 | 86.25 | 52.55 |
| MARK2/PAR-1Ba | 77.97 | 51.70 |
| MARK3 | 83.23 | 46.61 |
| MARK4 | 76.00 | 40.02 |
| MEK1 | 111.26 | 92.74 |
| MEK2 | 86.72 | 93.09 |
| MEK3 | 101.17 | 99.66 |
| MEK5 | 97.64 | 85.57 |
| MEKK1 | 102.22 | 93.95 |
| MEKK2 | 101.69 | 93.30 |
| MEKK3 | 91.64 | 94.59 |
| MEKK6 | 91.56 | 94.98 |
| MELK | 48.10 | 71.00 |
| MINK/MINK1 | 22.56 | −0.71 |
| MKK4 | 105.23 | 109.64 |
| MKK6 | 115.92 | 97.87 |
| MKK7 | 99.77 | 104.70 |
| MLCK/MYLK | 93.41 | 99.06 |
| MLCK2/MYLK2 | 65.98 | 78.90 |
| MLK1/MAP3K9 | 48.20 | 73.68 |
| MLK2/MAP3K10 | 84.11 | 73.08 |
| MLK3/MAP3K11 | 56.39 | 66.99 |
| MLK4 | 99.90 | 107.91 |
| MNK1 | 94.01 | 90.68 |
| MNK2 | 97.61 | 65.21 |
| MRCKa/CDC42BPA | 105.01 | 96.10 |
| MRCKb/CDC42BPB | 100.15 | 88.97 |
| MSK1/RPS6KA5 | 101.35 | 98.44 |
| MSK2/RPS6KA4 | 114.02 | 109.78 |
| MSSK1/STK23 | 112.11 | 102.52 |
| MST1/STK4 | 80.02 | 75.86 |
| MST2/STK3 | 101.80 | 86.03 |
| MST3/STK24 | 71.21 | 78.42 |
| MST4 | 73.02 | 73.18 |
| MUSK | 100.84 | 86.71 |
| MYLK3 | 109.01 | 96.71 |
| MYLK4 | 53.57 | 37.16 |
| MYO3A | 88.61 | 79.12 |
| MYO3b | 80.76 | 40.74 |
| NEK1 | 80.09 | 76.48 |
| NEK11 | 107.00 | 100.76 |
| NEK2 | 96.25 | 91.96 |
| NEK3 | 88.35 | 91.06 |
| NEK4 | 89.81 | 87.37 |
| NEK5 | 87.14 | 92.41 |
| NEK6 | 92.69 | 95.14 |
| NEK7 | 94.90 | 101.20 |
| NEK8 | 99.09 | 97.92 |
| NEK9 | 100.85 | 95.06 |
| NIM1 | 106.01 | 105.49 |
| NLK | 101.06 | 94.34 |
| OSR1/OXSR1 | 101.58 | 97.08 |
| P38a/MAPK14 | 105.34 | 103.38 |
| P38b/MAPK11 | 87.42 | 94.23 |
| P38d/MAPK13 | 131.67 | 103.04 |
| P38g | 107.99 | 99.71 |
| p70S6K/RPS6KB1 | 93.21 | 99.29 |
| p70S6Kb/RPS6KB2 | 106.74 | 95.02 |
| PAK1 | 85.19 | 78.24 |
| PAK2 | 97.08 | 85.03 |
| PAK3 | 97.26 | 90.79 |
| PAK4 | 88.00 | 93.82 |
| PAK5 | 112.87 | 98.97 |
| PAK6 | 94.63 | 96.35 |

TABLE S6-continued

Inhibition profile for 371 wild-type human kinases using radioligand binding assay performed by Reaction Biology Corp for compound 1 and 12k analogs.

| Kinase: | % Enzyme Activity (relative to DMSO controls) | |
|---|---|---|
| | Compound 1 | Compound 12k |
| PASK | 78.05 | 90.11 |
| PBK/TOPK | 96.82 | 97.06 |
| PDGFRa | 86.89 | 87.78 |
| PDGFRb | 94.20 | 96.33 |
| PDK1/PDPK1 | 109.89 | 92.73 |
| PEAK1 | 108.87 | 100.91 |
| PHKg1 | 37.59 | 74.52 |
| PHKg2 | 85.95 | 95.18 |
| PIM1 | 93.19 | 98.54 |
| PIM2 | 105.65 | 105.84 |
| PIM3 | 92.92 | 105.80 |
| PKA | 103.85 | 94.51 |
| PKAcb | 106.33 | 92.56 |
| PKAcg | 101.96 | 99.43 |
| PKCa | 91.41 | 98.47 |
| PKCb1 | 78.28 | 86.22 |
| PKCb2 | 82.93 | 89.45 |
| PKCd | 92.30 | 102.23 |
| PKCepsilon | 110.07 | 98.63 |
| PKCeta | 102.51 | 94.61 |
| PKCg | 88.99 | 105.80 |
| PKCiota | 100.49 | 92.95 |
| PKCmu/PRKD1 | 24.37 | 3.95 |
| PKCmu/PRKD3 | 29.10 | 13.63 |
| PKCtheta | 90.75 | 94.63 |
| PKCzeta | 93.62 | 97.74 |
| PKD2/PRKD2 | 23.17 | 9.36 |
| PKG1a | 100.79 | 107.95 |
| PKG1b | 97.27 | 101.46 |
| PKG2/PRKG2 | 93.76 | 88.66 |
| PKN1/PRK1 | 94.01 | 95.03 |
| PKN2/PRK2 | 81.57 | 59.53 |
| PKN3/PRK3 | 84.73 | 93.68 |
| PLK1 | 98.56 | 100.21 |
| PLK2 | 97.24 | 101.38 |
| PLK3 | 105.80 | 103.07 |
| PLK4/SAK | 96.97 | 93.38 |
| PRKX | 95.47 | 96.07 |
| PYK2 | 84.75 | 89.24 |
| RAF1 | 103.97 | 105.30 |
| RET | 76.74 | 91.50 |
| RIPK2 | 78.51 | 92.28 |
| RIPK3 | 99.99 | 99.41 |
| RIPK4 | 98.26 | 98.00 |
| RIPK5 | 75.57 | 73.40 |
| ROCK1 | 94.66 | 79.17 |
| ROCK2 | 71.13 | 55.59 |
| RON/MST1R | 91.61 | 94.13 |
| ROS/ROS1 | 95.99 | 94.17 |
| RSK1 | 85.38 | 89.96 |
| RSK2 | 104.60 | 77.30 |
| RSK3 | 61.66 | 45.32 |
| RSK4 | 83.47 | 41.16 |
| SBK1 | 98.99 | 98.74 |
| SGK1 | 95.96 | 99.59 |
| SGK2 | 92.83 | 96.73 |
| SGK3/SGKL | 74.26 | 88.15 |
| SIK1 | 102.42 | 106.03 |
| SIK2 | 83.22 | 59.75 |
| SIK3 | 75.49 | 92.30 |
| SLK/STK2 | 93.24 | 83.49 |
| SNARK/NUAK2 | 82.78 | 59.46 |
| SNRK | 101.52 | 43.11 |
| SRMS | 104.05 | 103.16 |
| SRPK1 | 104.14 | 100.26 |
| SRPK2 | 80.35 | 93.59 |
| SSTK/TSSK6 | 120.86 | 102.12 |
| STK16 | 100.38 | 108.78 |
| STK21/CIT | 103.14 | 104.00 |
| STK22D/TSSK1 | 87.16 | 75.17 |
| STK25/YSK1 | 102.41 | 72.38 |
| STK32B/YANK2 | 97.04 | 88.55 |
| STK32C/YANK3 | 98.34 | 93.03 |
| STK33 | 72.60 | 88.57 |
| STK38/NDR1 | 88.09 | 71.88 |
| STK38/NDR2 | 87.65 | 77.84 |
| STK39/STLK3 | 90.69 | 77.30 |
| SYK | 89.64 | 93.90 |
| TAK1 | 84.58 | 77.40 |
| TAOK1 | 78.28 | 59.81 |
| TAOK2/TAO1 | 104.17 | 102.60 |
| TAOK3/JIK | 87.26 | 79.80 |
| TBK1 | 82.85 | 75.18 |
| TEC | 106.04 | 99.91 |
| TESK1 | 105.30 | 101.35 |
| TESK2 | 111.69 | 92.69 |
| TGFBR2 | 105.73 | 87.99 |
| TIE2/TEK | 95.03 | 103.41 |
| TLK1 | 102.40 | 101.74 |
| TLK2 | 93.04 | 95.18 |
| TNIK | 5.84 | −0.01 |
| TNK1 | 96.99 | 95.58 |
| TRKA | 69.20 | 75.42 |
| TRKB | 59.29 | 77.40 |
| TRKC | 19.43 | 52.23 |
| TSSK2 | 114.82 | 107.74 |
| TSSK3/STK22C | 146.02 | 128.67 |
| TTBK1 | 111.35 | 105.70 |
| TTBK2 | 101.44 | 103.40 |
| TXK | 85.33 | 87.00 |
| TYK1/LTK | 104.88 | 116.52 |
| TYK2 | 90.82 | 92.93 |
| TYRO3/SKY | 86.79 | 94.35 |
| ULK1 | 89.68 | 88.85 |
| ULK2 | 80.40 | 36.04 |
| ULK3 | 70.02 | 41.45 |
| VRK1 | 95.82 | 88.27 |
| VRK2 | 99.76 | 98.59 |
| WEE1 | 113.64 | 86.58 |
| WNK1 | 117.32 | 100.14 |
| WNK2 | 93.03 | 94.82 |
| WNK3 | 93.71 | 82.17 |
| YES/YES1 | 96.62 | 109.08 |
| VSK4/MAP3K19 | 101.08 | 107.41 |
| ZAK/MLTK | 91.30 | 77.89 |
| ZAP70 | 102.65 | 101.91 |
| ZIPK/DAPK3 | 108.44 | 99.80 |

* Compounds were tested in single-dose singlicate mode at a concentration of 0.1 μM. Reactions were carried out at 10 μM ATP.

Compound 12k Maintains the Anti-Inflammatory Properties of Compound 1, Though not Through its Activity at MAP4Ks Compound 1 was originally validated in in vitro and in vivo models of HIV-associated neuroinflammation, where it was shown to attenuate inflammatory cytokine production by microglia (Marker et al., 2013). Our aim in developing the compound 1 analogs described herein was primarily to generate potent, metabolically stable drugs that could prevent neuronal death, but given the fact that neurodegenerative disorders such as ALS are also accompanied by aggressive microgliosis (Hall et al., 1998), and that drug-mediated inhibition of microgliosis is protective in an rodent model of ALS (Trias et al., 2016), we asked whether the optimized compound could also modulate microglial cytokine release. This question was also prompted by the fact that, according to Marker et al., the anti-inflammatory effects of compound 1 are orchestrated by MLK3 in microglia (Marker et al., 2013); meanwhile, all of the analogs tested here showed diminished activity at MLK3 compared to compound 1.

To model microglial activation in vitro, we stimulated mouse N9 microglial cells with increasing concentrations of E. coli-derived lipopolysaccharides (LPS) (0.1-5 µM) to measure release of the pro-inflammatory cytokine TNFα into cell culture media. The range of LPS concentrations selected here induced dose-dependent increases in TNFα secretion (FIG. 44), but did not induce N9 cell death (data not shown). We then compared TNFα secretion in cultures co-treated with LPS and compound 1 or the optimized analog 12k, which showed increased activity at MAP4Ks (FIG. 42B), but slightly decreased activity at MLK3 (66.99% MLK3 activity remaining at 0.25 µM of 12k vs. 56.39% MLK3 activity remaining at 0.025 µM of 1; Table S6). We also tested compound 12e, which strongly inhibited HGK activity (2.73% HGK activity remaining at 0.025 µM 12e; Table S4) and was highly neuroprotective (Table S2) but had little activity at MLK3 (71.81% MLK3 activity remaining at 0.1 µM 12e compared to 10.5% for 1; Table S3).

We found that compound 1 significantly and dose-dependently decreased TNFα secretion in stimulated microglia across all concentrations of LPS, consistent with its previously reported anti-inflammatory effects (FIG. 44). Compound 12k also significantly decreased TNFα secretion, though was less potent in this assay than compound 1 (FIG. 44). Meanwhile, compound 12e did not significantly decrease TNFα levels when added at 0.5 µM except at the highest LPS concentration (FIG. 44). Taken together, these findings suggest that MAP4K inhibition does not mitigate TNFα release in this context, and that the retention of non-MAP4K targets such as MLK3 may confer anti-inflammatory activity to compound 1 analogs. Furthermore, these findings also indicate that 12e may be a valuable tool compound for dissociating the neuroprotective vs. the anti-inflammatory effects of kinase inhibition in vivo.

DISCUSSION

Our previous work in human motor neurons subjected to ER stress pointed to broad-spectrum kinase inhibitors as potent neuroprotective agents. Here we determined that the shared targets of these protective compounds included HGK, MINK1, GCK, and KHS, a group of closely related MAP4Ks. Using compound 1 as a scaffold, we developed an array of neuroprotective, pharmacologically stable compounds whose efficacy tracked with their ability to block MAP4Ks.

While our initial focus was on HGK, a kinase previously implicated in motor neuron degeneration (Wu et al., 2019; Yang et al., 2013), it is possible that multiple MAP4Ks work in concert to mediate neurodegeneration in the context of ER stress. Larhammar et al. (2017) have shown that GNE-495, a small molecule that inhibits HGK, TNIK, and MINK1, is neuroprotective in primary dorsal root ganglia neurons subjected to neurotrophic factor withdrawal. Furthermore, knockdown of all three kinases together—but not individually—recapitulated the effects of the inhibitor. They argue that the roles of related MAP4Ks in their neurodegeneration assay are redundant, and that the effects of inhibiting a single kinase can be overcome by the activity of the remaining kinases. It is therefore possible that the combined inhibition of multiple MAP4Ks underlies the robust neuroprotective effects of compound 1 and its analogs in CPA-treated motor neurons.

Meanwhile, the downstream targets of activated MAP4Ks in the context of ER stress are incompletely understood. We found that CPA treatment induces JNK and c-Jun phosphorylation, which can all be reversed by compound 1. We also found that inhibition of MLK3 and MLK1, both MAP3Ks that are strongly targeted by compound 1, correlates moderately, but significantly, with neuroprotection, suggesting that the activity of multiple MAP3K kinases may be required to engage downstream MAP2K targets. In line with this idea, Yang et al. (2013) found that the HGK inhibitor kenpaullone prevented the phosphorylation of TAK1 (MAP3K7) following neurotrophic factor withdrawal in motor neurons. Other studies have implicated DLK (MAP3K12) in axonal injuries, where it promotes both neurodegeneration (Yang et al., 2015) and axon regeneration (Shin et al., 2012). In experiments where neurotrophic factor withdrawal in sensory neurons was restricted to the axonal compartment of a Campenot chamber, the pro-apoptotic activities of DLK were shown to be mediated by MAP4Ks (Larhammar et al., 2017a). Taken together, these observations suggest that the downstream effectors of MAP4Ks may vary depending on the cell type or the insult, and, furthermore, that compound 1 and its analogs may be protective across multiple models of neurodegeneration.

At the same time, kinome-wide profiles of 1 and 12k (FIG. 38A and FIG. 38B; Table S6) make it clear that neither compound is perfectly selective for MAP kinases. It is possible that some of the non-MAPK targets of compound 1 and its analogs may enhance their neuroprotective effects. Other kinases whose inhibition correlated strongly with neuroprotection included PRKD3, ABL1, and ABL2 (Table S6). Accordingly, we have observed that kinase inhibitors targeting PKC or ABL kinases in a non-subtype-specific manner (e.g., Ro-318220 mesylate and bosutinib, respectively) are mildly protective in CPA-treated motor neurons (data not shown). Furthermore, both the addition of bosutinib and the genetic ablation of ABL1 have been shown to be neuroprotective in a human stem cell-derived motor neuron model of ALS (Imamura et al., 2017). Though it is unclear how kinases such as PRKD3 and ABL1 might be activated in the context of CPA—perhaps downstream of, or orthogonally to, the JNK pathway—the broad spectrum effects of compound 1 and its analogs may be key to their success in the in vitro motor neuron survival assay.

While our study focuses on neurodegeneration, there may also be additional considerable benefits to targeting non-MAP4 kinases and/or non-neuronal cells in vivo. A prime example is that compound 1 robustly inhibits microglial activation via MLK3, and thereby prevents synaptic loss in the context of HIV-related neuroinflammation (Marker et al., 2013). Microgliosis is a hallmark of many neurodegenerative disorders and is readily observed in murine models of ALS (Hall et al., 1998). There is some debate as to whether microglia are helpful or harmful in the context of ALS (Chiu et al., 2013; Gowing et al., 2008; Spiller et al., 2018)— perhaps both, depending on the stage of the disease—but treatment with the kinase inhibitor masitinib has been shown to attenuate microgliosis and slow disease progression in late-stage SOD1$^{G93A}$ mutant rats (Trias et al., 2016). We have found that the optimized analog 12k retains the ability to inhibit microglial cytokine release, which may be dependent on its ability to block MLK3 activity. Thus, beyond neurodegeneration, compound 12k and the other compound 1 analogs generated here that target both neuroinflammatory and neurodegenerative pathways may be particularly strong therapeutic candidates for ALS.

Finally, MAP4Ks have been implicated in multiple, diverse disorders outside of the CNS, including obesity (Danai et al., 2015), insulin resistance (Ammirati et al., 2015; Bouzakri and Zierath, 2007; Chuang et al., 2014; Flach et al., 2016; 2017; Tang et al., 2006; Tesz et al., 2007), atherosclerosis (Aouadi et al., 2009; Virbasius and Czech, 2016), hepatocellular carcinoma (Han et al., 2010), lung adenocarcinoma (Qiu et al., 2012), colorectal cancer (Lin et al., 2018; Salem et al., 2018), and general transformation and metastatic processes in many types of human tumors (Wright et al., 2003). Thus, the compounds generated here may have broad therapeutic potential across a wide swath of human diseases Materials and Methods Generation of Human and Mouse Stem Cell Lines Preliminary survival assays to identify lead compounds were performed in human motor neurons derived from a wild-type motor neuron reporter iPS cell line. This line was generated from the NCRM-1 control iPS line (RRID: CVCL-1 E71) using CRISPR-based gene targeting strategies, where iCre-IRES was inserted at the N terminus of the motor neuron-specific VAChT promoter region, and CAGGS-lox-STOP-lox-TdTomato was inserted into the AAVS1 safe harbor locus. Clones were sequenced to confirm both insertions, and the clone that was selected for further propagation was karyotyped.

Survival assays to characterized compound 1 analogs were performed in human motor neurons derived from an HB9:GFP motor neuron reporter embryonic stem cell line carrying a heterozygous $SOD1^{44V}$ point mutation as described previously (see Example 12).

Western blot experiments were carried out in ES-derived mouse motor neurons generated by Thams et al. (see Example 12) from crosses of heterozygous Tg(Hlxb9-GFP) 1Tmj motor neuron reporter mice and mice expressing wild-type human SOD1 (B6SJL-Tg(SOD1)2Gur/J).

All cell lines were routinely tested for mycoplasma.
Human Motor Neuron Differentiations Human motor neurons were differentiated from the above human ES or PS cells as previously described (Maury et al., 2014; Example 12). Stem cells were maintained on irradiated CF-1 mouse embryonic fibroblast (MEF) feeder layers (Thermo Fisher) in serum-free media (DMEM/F12, Life Technologies) supplemented with knockout serum replacement (20%, Life Technologies), Glutamax (1%, Life Technologies), non-essential amino acids (1%, Millipore), beta-mercaptoethanol (0.1%, Sigma), and human recombinant fibroblast growth factor 2 (FGF2, 20 ng/mL, Peprotech).

On day 0, stem cells were dissociated into single cells using Accutase (Thermo Fisher) and differentiated into motor neurons over the course of 16 days as embryoid bodies cultured in suspension. Differentiations were carried out in N2B27 media, which was comprised of a 1:1 mixture of Advanced DMEM/F12 and Neurobasal media (Life Technologies), Glutamax (1%), beta-mercaptoethanol (0.1%), N2 (1%, Life Technologies), B27 (2%, Life Technologies), and ascorbic acid (10 μM, Sigma). From day 0-1, differentiation medium was supplemented with FGF2 (10 ng/mL), Y-27632 dihydrochloride (10 μM, Abcam), SB 431542 hydrate (SB, 20 μM, Sigma), LDN193189 (LDN, 0.1 μM, Stemgent) and CHIR 99021 (CHIR, 3 μM, Tocris). From days 2-7, differentiation medium was supplemented with SB (20 μM), LDN (0.1 μM), CHIR (3 μM), retinoic acid (100 nM), and sonic hedgehog agonist (SAG, 500 nM; Millipore). From days 7-9, differentiation medium was supplemented with retinoic acid (100 nM), and SAG (500 nM), and brain-derived neurotrophic factor (BDNF, 10 ng/mL, Peprotech). From days 9-14, differentiation medium was supplemented with retinoic acid (100 nM), SAG (500 nM), BDNF (10 ng/mL, Peprotech), and DAPT (10 μM, Tocris). From days 14-6, differentiation medium was supplemented with retinoic acid (100 nM), SAG (500 nM), BDNF (10 ng/mL), DAPT (10 μM), and glial-derived neurotrophic factor (GDNF, 10 ng/mL; Peprotech).

On day 16 of differentiation, embryoid bodies were dissociated using 0.05% trypsin (Life Technologies) and mechanical trituration, and motor neurons were plated at 2000 cells/well in 96-well plates (Greiner) coated with poly-ornithine (100 μg/mL, Sigma) and mouse laminin (3 μg/mL, Thermo Fisher). Cultures were maintained in serum-free neurobasal media (Life Technologies) supplemented with N-2 (1%), B27 (2%), a 1:1 cocktail of uridine and flurodeoxyuridine as anti-mitotics (1 μM, Sigma), and the following recombinant human neurotrophic factors: GDNF, BDNF, ciliary neutrotrophic factor (CNTF), and insulin-like growth factor 1 (IGF-1), all at 10 ng/mL (Peprotech).
Human Motor Neuron Survival Assays 48 hours after dissociation and plating (DIV2), motor neurons were treated with simultaneously with CPA (33 μM, Tocris) and test compounds. DMSO (Sigma) was used as a vehicle control. For all test compounds, stock solutions were prepared in DMSO, and working solutions were prepared in motor neuron media. WZ4003 (Tocris) and HTH 01-015 (Selleckchem) were tested in 8-point, 2-fold dilution series from 0.25-32 μM in 3 replicate wells. PF-6260933 (Selleckchem), GNE-495 (Selleckchem), and URMC-099 (Selleckchem) were tested in 8-point, 2-fold dilution series from 0.075-9.6 μM in 3 replicate wells. Compound 1 analogs were evaluated at 0.1, 0.3, 0.5, 1, and 3 μM in 3 replicate wells. The $EC_{50}$ of compound 1 analogs were determined using Prism software (GraphPad) from experiments where compound 1 and 53 analogs were assayed simultaneously.

Motor neurons were incubated with CPA and test compounds for 72 h. Live cells were visualized using CellTrace Calcein AM (1.3 μM, Thermo Fisher) and background fluorescence was quenched with a solution of 10% brilliant black in PBS (Sigma) in PBS. Whole-well images were acquired using a Plate Runner$^{HD}$ system (Trophos). Cells were counted using Metamorph software (Molecular Devices). All cell counts are expressed as a percentage of surviving vehicle (DMSO)-treated cells.
Mouse Motor Neuron Differentiations We used mouse rather than human motor neurons for biochemistry assays because mouse motor neurons can be rapidly generated in the quantities required for protein extraction. Differentiations were carried out as described Example 12; Wichterle et al., 2002). ES cells were maintained on CF-1 MEF feeder layers, then dissociated and differentiated for 6 days using retinoic acid (1 μM) and SAG (0.5 μM). Motor neurons were maintained in media containing 2% fetal bovine serum (Life Technologies), GDNF (400 μg/mL), Forskolin (10 μM, Tocris), and IBMX (100 μM, Sigma).
Biochemical Analysis of JNK Pathway Regulation Whole mouse embryoid bodies at day 6 of differentiation were treated with CPA (10 μM) and test compounds for 4 h, then lysed and sonicated in ice-cold buffer containing HEPES (50 mM), NaCl (100 mM), Triton-X (1%), SDS (0.1%), DTT (1 mM), EDTA (1 mM), plus protease and phosphatase inhibitor cocktail tablets (Roche). Total protein content was analyzed using a BCA kit according to the manufacturer's instructions (Pierce). For each sample, 50 μg total protein were reduced with DTT (100 mM) for 10 mins at 70° C. and loaded into a NuPAGE Novex 4-12% bis-tris gel (Thermo Fisher) with LDS loading buffer (Thermo Fisher). Samples were run for 4 h at 100V at 4°, then transferred to nitrocellulose membranes using an iBlot dry transfer system (Thermo Fisher). Membranes were blocked with tris-buffered saline (TBS) containing 5% BSA (Cell Signaling Technologies), then incubated with primary antibodies in a buffer containing 5% BSA and 0.1% Tween in TBS overnight at 4°. Primary antibodies against phospho-c-Jun (serine 63; Cell Signaling Technologies #9261) were added at 1:500; primary antibodies against phospho-JNK (thr183/tyr185; Cell Signaling Technologies #4688) were added at 1:1000; primary antibodies against GAPDH (Santa Cruz Biotechnologies) were added at 1:1000 as a loading control. Following washes in TBS containing 0.1% Tween, membranes were incubated in goat anti-rabbit HRP-conjugated secondary antibody solutions (1:10,000; Santa Cruz Biotechnologies) for 1 hr. Membranes were then washed again in TBS containing 0.1% Tween, then incubated in Femto ECL (Pierce) for 5 min. Chemiluminescence was visualized using a LiCor Odyssey. Phospho-c-Jun and phospho-JNK band intensities were normalized to GAPDH.

General Experimental Details for the Synthesis of Compound 1 Analogs and Intermediates Starting materials were purchased form Sigma-Aldrich, Fisher Scientific, Ark Pharm, Oakwood Chemical, Cambridge Isotope Laboratory, or AK Scientific and were used as received unless stated otherwise. All solvents were reagent grade. Column chromatography was performed on a Teledyne ISCO CombiFlash® Rf+ using RediSep® Normal-phase silica flash columns. Thin layer chromatography (TLC) was performed on Silicycle SiliaPlate™ Glass TLC Plates (250 µm, 20×20 cm). Where indicated, compounds were purified by preparatory HPLC on a Phenomenex Gemini NX-C$_{18}$ column (250×21.2 mm, particle size: 5 µm, pore size: 110 Å) using a Gilson HPLC with GX-271 liquid handler. $^1$H NMR spectra were recorded at ambient temperature using 400 MHz, or 500 MHz spectrometers as indicated. Chemical shifts are reported in ppm relative to the residual solvent peaks ($^1$H NMR: DMSO-d6, δ 2.50; chloroform-d, δ 7.26; methanol-d4, 5 3.31). The following abbreviations are used to indicate multiplicity: s (singlet), d (doublet), t (triplet), q (quartet), hept (heptuplet), m (multiplet), br (broad). High resolution mass spectra (HRMS) were acquired on a time-of-flight spectrometer with atmospheric pressure chemical ionization (APCI) or electrospray ionization (ESI), as indicated, and were obtained by peak matching. All reactions were run under an atmosphere of nitrogen or argon in glassware that was flame-dried under argon unless otherwise stated. Aqueous solutions were prepared from nanopure water with a resistivity over 18 MΩ·cm. Unless otherwise noted, all reagents were commercially available.

In Vitro Microsomal Stability

The microsomal stability assay was performed in 96-well format (Perkin-Elmer, StorPlate-96U, PP, 96 well, round bottom). To each well was added phosphate buffer (182.2 µL, pH 7.4, 100 mM) followed by addition of NADPH regenerating system solution A (10 µL), and NADPH regenerating system solution B (2 µL) (Corning Gentest 3P NADPH regenerating system solution A (#451220) and B (#451200)). A stock solution of the compound to be analyzed (0.8 µL, 5 mM) or ethoxycoumarin (positive control, 0.8 µL, 5 mM) was added and the mixture was warmed to 37° C. for 5 minutes. The mouse microsomes (CD-1, 5 µL, thawed in a 37° C. water bath before use, 20 mg/mL, Life Technologies) were added. At selected time points (0, 15, 30, 45, 60 and 120 minutes) aliquots (15 µL) were withdrawn from the plate and quenched upon addition to cold acetonitrile (60 µL), containing an internal standard (5 µM) in a 96-well plate. The samples were centrifuged at 13,000 rpm for 10 minutes at 4° C. The supernatant (40 µL) was withdrawn and transferred to a sample vial with insert. The samples were analyzed by LC-MS.

LC-MS analysis was performed on a platform comprising a Thermo Scientific Dionex Ultimate 3000 and a Bruker amaZon SL equipped with an electrospray ionization source controlled by Bruker Hystar 3.2. Chromatographic separation was performed by injecting 5 µL of the sample onto an Agilent Eclipse Plus C18 column (2.1×50 mm, 3.5 µm) maintained at 20° C. The flow rate was maintained at 400 µL/min. The initial flow conditions were 60% solvent A (water containing 0.1% acetic acid) and 40% solvent B (methanol containing 0.1% acetic acid). Solvent B was raised to 60% over 0.25 minutes and to 70% by 6.75 minutes. Solvent B was raised to 95% by 7.00 minutes and lowered back to initial conditions (40%) by 8.00 minutes with a total run time of 9.00 minutes.

In Vivo Pharmacokinetics

Compounds 1 and 12k were dissolved in DMSO to 40 mg/mL. For in vivo administration, the DMSO stock was further diluted to 2 mg/mL in a vehicle containing 40% PEG-400 (Sigma) and 55% of a (2-hydroxypropyl)-beta-cyclodextrin solution (20% in nanopure water, Sigma). Compounds were delivered at 10 mg/kg by intraperitoneal injection or oral gavage to 8 week-old male wild-type C57Bl6J mice (Jackson). After 15 min, 3 h, 8 h or 24h, animals were anesthetized with a mixture of ketamine (100 mg/kg) and xylazine (10 mg/kg), then decapitated to collect trunk blood and dissect fresh brain tissue. Blood samples were treated with EDTA solution (50 mM final concentration) to prevent coagulation and centrifuged for 10 min at 845 rcf at 4° to separate plasma. Fresh brains were lysed in 5 volumes of ddH2O.

Plasma samples were transferred to Eppendorf tubes (50 µL per sample) and diluted with acetonitrile (200 µL). The samples were sonicated for 1 minute followed by centrifugation at 16,000 rpm for 10 minutes. The supernatant was transferred to another Eppendorf tube and the solvent evaporated overnight. The samples were reconstituted in a mixture of 40 µL acetonitrile and 10 µL water transferred to a sample vial with insert, and analyzed by LC-MS.

Homogenized brain samples (250 µL) were transferred to Eppendorf tubes and diluted with acetonitrile (750 µL). The samples were sonicated for 1 minute followed by centrifugation at 16,000 rpm for 10 minutes. The supernatant (900 µL) was transferred to another Eppendorf tube and the solvent evaporated overnight. The samples were reconstituted in a mixture of 80 µL acetonitrile and 20 µL water, transferred to a sample vial with insert, and analyzed by LC-MS.

LC-MS analysis was performed on a platform comprising a Thermo Scientific Dionex Ultimate 3000 and a Bruker amaZon SL equipped with an electrospray ionization source controlled by Bruker Hystar 3.2. The compound concentration in each plasma sample was determined using a calibration curve. Chromatographic separation was performed by injecting 10 µL of the sample onto an Agilent Eclipse Plus C18 column (2.1×50 mm, 3.5 µm) maintained at 20° C. The flow rate was maintained at 400 µL/min. The initial flow conditions were 60% solvent A (water containing 0.1% acetic acid) and 40% solvent B (methanol containing 0.1% acetic acid). Solvent B was raised to 60% over 0.25 minutes and to 70% by 6.75 minutes. Solvent B was raised to 95% by 7.00 minutes and lowered back to initial conditions (40%) by 8.00 minutes with a total run time of 9.00 minutes.

Microglia Culture, LPS Treatment, and TNFα ELISAs

Immortalized N9 mouse microglia cells (Corradin et al., 1993) were plated at 8000 cells/well in gelatin-coated (0.1%, EMD Millipore) 96-well plates. Cultures were maintained in DMEM containing FBS (10%, Life Technologies) and Glutamax (1%, Life Technologies). 24 h after plating, cells were treated with LPS from *E. coli* O111:B4 (Sigma) plus test compounds at the indicated concentrations. 24 h after the initiation of LPS treatment, 50 μL of cell culture media (25% of the final culture volume) were used to perform quantitative ELISAs for TNFα release according to the manufacturer's instructions (R&D Systems). Absorbance was assessed at 450 nM on a spectrophotometer (TECAM), and readings at 540 nM were used for wavelength correction. N9 cells remaining in the culture dishes were treated with AlamarBlue (Thermo Fisher) to assess viability. 5 μL AlamarBlue was added to each well (containing 50 μL culture media) and incubated for 4 h at 37°. Absorbance was assessed at 570 nM, and readings at 600 nM were used for wavelength correction.

Software

Spotfire (version 2017, TIBCO) was used to compare kinase targets of hit compounds from the original screen described in Example 12 and perform hierarchical clustering. Molecular docking, molecular modeling, and visualizations were performed using Glide (versions 2012-2016, Schrödinger) and Schrödinger Maestro (version 2017-1). All chemical structures were drawn using ChemDraw Professional 16.0 (Perkin Elmer). ImageStudioLite (LiCor) was used to assess western blot band intensity. Prism 5, 7, and 8 (GraphPad Software) were used to analyze motor neuron survival data and $EC_{50}$, western blot band intensity, microsomal stability data, in vivo pharmacokinetics parameters, correlations between inhibition of kinase activity and survival for compound 1 analogs, and TNFα ELISA data.

Statistical Analysis

Statistical analyses were performed with GraphPad Prism. Data are represented as means±SEM. Plots of means from motor neuron survival assays represent triplicate wells from single assays. Data were assessed for normal distribution. One-way ANOVAs were used to compare the effects of treatment on motor neurons in western blot assays. Two-way ANOVAs were used to compare the effects of LPS vs. compound 1 analog treatment on N9 microglia. One and two-way ANOVAs were supplemented with Bonferroni's multiple comparisons tests to assess interactions between conditions. Pearson's r was used as a measure of correlation between degree of kinase inhibition and degree of motor neuron rescue.

Example 14

Safety and Target Engagement in CNS for Compound 12k

To explore the target engagement in CNS for compound 12k, compounds 1 and 12k were administered continuously per os to wild-type mice (n=3 per treatment). Compound 1 was administered at 100 mg/kg; compound 12k was administered at 5 or 10 mg/kg. Fresh brain samples were harvested after 7 days of treatment. Reduced brain samples were separated by SDS-PAGE and probed with an antibody that recognizes phosphoproteins that have been phosphorylated at motifs corresponding to the targets of cyclin-dependent kinases and mitogen activated kinases. As shown in FIG. 45, compound 12k consistently decreased the intensity of a high molecular weight band (arrow) compared to vehicle or compound 1.

To assess the safety of long-term compound 12k administration, compound 12k was administered to wild-type mice continuously per os in drinking water at a concentration that corresponds to 10 mg/kg. Treatment began at P30 and continued for 60 days. Mice treated with 12k (n=3) demonstrated a mild increase in body mass compared to vehicle-treated controls (n=3), but were otherwise healthy (FIG. 46A). No differences in survival, hindlimb strength, or gross pathology were observed between treatment conditions (FIG. 46B).

DOCUMENTS CITED

Alami N H, Smith R B, Carrasco M A, Williams L A, Winborn C S, Han S S, et al. Axonal transport of TDP-43 mRNA granules is impaired by ALS-causing mutations. Neuron. 2014; 81(3):536-43.

Ammirati, M., Bagley, S. W., Bhattacharya, S. K., Buckbinder, L., Carlo, A. A., Conrad, R., Cortes, C., Dow, R. L., Dowling, M. S., E I-Kattan, A., et al. (2015). Discovery of anin VivoTool to Establish Proof-of-Concept for MAP4K4-Based Antidiabetic Treatment. Acs Med Chem Lett 6, 1128-1133.

Amoroso M W, Croft G F, Williams D J, O'Keeffe S, Carrasco M A, Davis A R, et al. Accelerated high-yield generation of limb-innervating motor neurons from human stem cells. J Neurosci. 2013; 33(2):574-86.

Anastassiadis, T., Deacon, S. W., Devarajan, K., Ma, H., and Peterson, J. R. (2011). Comprehensive assay of kinase catalytic activity reveals features of kinase inhibitor selectivity. Nat Biotechnol 29, 1039.

Aouadi, M., Tesz, G. J., Nicoloro, S. M., Wang, M., Chouinard, M., Soto, E., Ostroff, G. R., and Czech, M. P. (2009). Orally delivered siRNA targeting macrophage Map4k4 suppresses systemic inflammation. Nature 458, 1180.

Atkin J D, Farg M A, Turner B J, Tomas D, Lysaght J A, Nunan J, et al. Induction of the unfolded protein response in familial amyotrophic lateral sclerosis and association of protein-disulfide isomerase with superoxide dismutase 1. J Biol Chem. 2006; 281(40):30152-65.

Atkin J D, Farg M A, Walker A K, McLean C, Tomas D, Horne M K. Endoplasmic reticulum stress and induction of the unfolded protein response in human sporadic amyotrophic lateral sclerosis. Neurobiol Dis. 2008; 30(3): 400-7.

Azzouz M, Leclerc N, Gurney M, Warter J M, Poindron P, Borg J. Progressive motor neuron impairment in an animal model of familial amyotrophic lateral sclerosis. Muscle Nerve. 1997; 20(1):45-51.

Banerjee, S., Buhrlage, S. J., Huang, H.-T., Deng, X., Zhou, W., Wang, J., Traynor, R., Prescott, A. R., Alessi, D. R., and Gray, N. S. (2014). Characterization of WZ4003 and HTH-01-015 as selective inhibitors of the LKB1-tumour-suppressor-activated NUAK kinases. Biochem J 457, 215-225.

Bernard-Marissal N, Moumen A, Sunyach C, Pellegrino C, Dudley K, Henderson C E, et al. Reduced calreticulin levels link endoplasmic reticulum stress and Fas-triggered cell death in motoneurons vulnerable to ALS. J Neurosci. 2012; 32(14):4901-12.

Blokhuis, A. M.; Groen, E. J. N.; Koppers, M.; Van Den Berg, L. H.; Pasterkamp, R. J. *Acta Neuropathol.* 2013, 125 (6), 777.

Boillee S, Yamanaka K, Lobsiger C S, Copeland N G, Jenkins N A, Kassiotis G, et al. Onset and progression in inherited ALS determined by motor neurons and microglia. Science. 2006; 312(5778):1389-92.

Bosco D A, Morfini G, Karabacak N M, Song Y, Gros-Louis F, Pasinelli P, et al. Wild-type and mutant SOD1 share an aberrant conformation and a common pathogenic pathway in ALS. Nat Neurosci. 2010; 13(11):1396-403.

Bouzakri, K., and Zierath, J. R. (2007). MAP4K4 Gene Silencing in Human Skeletal Muscle Prevents Tumor Necrosis Factor-α-induced Insulin Resistance. J Biol Chem 282, 7783-7789.

Carriedo S G, Sensi S L, Yin H Z, Weiss J H. AMPA exposures induce mitochondrial Ca(2+) overload and ROS generation in spinal motor neurons in vitro. J Neurosci. 2000; 20(1):240-50.

Carriedo S G, Yin H Z, Weiss J H. Motor neurons are selectively vulnerable to AMPA/kainate receptor-mediated injury in vitro. J Neurosci. 1996; 16(13):4069-79.

Chiu A Y, Zhai P, Dal Canto M C, Peters T M, Kwon Y W, Prattis S M, et al. Age-dependent penetrance of disease in a transgenic mouse model of familial amyotrophic lateral sclerosis. Mol Cell Neurosci. 1995; 6(4):349-62.

Chiu, I. M., Morimoto, E., Goodarzi, H., Liao, J. T., O'Keeffe, S., Phatnani, H. P., Muratet, M., Carroll, M. C., Levy, S., Tavazoie, S., et al. (2013). A Neurodegeneration-Specific Gene-Expression Signature of Acutely Isolated Microglia from an Amyotrophic Lateral Sclerosis Mouse Model. Cell Reports 4, 385-401.

Chuang, H.-C., Sheu, W. H., Lin, Y.-T., Tsai, C.-Y., Yang, C.-Y., Cheng, Y.-J., Huang, P.-Y., Li, J.-P., Chiu, L.-L., Wang, X., et al. (2014). HGK/MAP4K4 deficiency induces TRAF2 stabilization and Th17 differentiation leading to insulin resistance. Nat Commun 5, 4602.

Corradin, S., Mausl, J., Donini, S., Quattrocchi, E., and Ricciardi-Castagnoli, P. (1993). Inducible nitric oxide synthase activity of cloned murine microglial cells. Glia 7, 255-262.

Danai, L. V., Flach, R. J., Virbasius, J. V., Menendez, L., Jung, D., Kim, J., Kim, J. K., and Czech, M. P. (2015). Inducible Deletion of Protein Kinase Map4k4 in Obese Mice Improves Insulin Sensitivity in Liver and Adipose Tissues. Mol Cell Biol 35, 2356-2365.

De Stefani D, Bononi A, Romagnoli A, Messina A, De Pinto V, Pinton P, et al. VDAC1 selectively transfers apoptotic Ca2+ signals to mitochondria. Cell Death Differ. 2012; 19(2):267-73.

Devlin A C, Burr K, Borooah S, Foster J D, Cleary E M, Geti I, et al. Human iPSC-derived motoneurons harbouring TARDBP or C9ORF72 ALS mutations are dysfunctional despite maintaining viability. Nat Commun. 2015; 6:5999.

Di Giorgio F P, Boulting G L, Bobrowicz S, Eggan K C. Human embryonic stem cell-derived motor neurons are sensitive to the toxic effect of glial cells carrying an ALS-causing mutation. Cell Stem Cell. 2008; 3(6):637-48.

Di Giorgio F P, Carrasco M A, Siao M C, Maniatis T, Eggan K. Non-cell autonomous effect of glia on motor neurons in an embryonic stem cell-based ALS model. Nat Neurosci. 2007; 10(5):608-14.

Dimos J T, Rodolfa K T, Niakan K K, Weisenthal L M, Mitsumoto H, Chung W, et al. Induced pluripotent stem cells generated from patients with ALS can be differentiated into motor neurons. Science. 2008; 321(5893):1218-21.

Donnelly C J, Zhang P W, Pham J T, Haeusler A R, Mistry N A, Vidensky S, et al. RNA toxicity from the ALS/FTD C9ORF72 expansion is mitigated by antisense intervention. Neuron. 2013; 80(2):415-28.

Doutheil J, Gissel C, Oschlies U, Hossmann K A, Paschen W. Relation of neuronal endoplasmic reticulum calcium homeostasis to ribosomal aggregation and protein synthesis: implications for stress-induced suppression of protein synthesis. Brain Res. 1997; 775(1-2):43-51.

Egawa N, Kitaoka S, Tsukita K, Naitoh M, Takahashi K, Yamamoto T, et al. Drug screening for ALS using patient-specific induced pluripotent stem cells. Sci Transl Med. 2012; 4(145):145ra04.

Flach, R. J., Danai, L. V., DiStefano, M. T., Kelly, M., Menendez, L., Jurczyk, A., Sharma, R. B., Jung, D., Kim, J., Kim, J. K., et al. (2016). Protein Kinase Mitogen-activated Protein Kinase Kinase Kinase Kinase 4 (MAP4K4) Promotes Obesity-induced Hyperinsulinemia. J Biol Chem 291, 16221-16230.

Flach, R. J., DiStefano, M. T., Danai, L. V., Senol-Cosar, O., Yawe, J. C., Kelly, M., Menendez, L., and Czech, M. P. (2017). Map4k4 impairs energy metabolism in endothelial cells and promotes insulin resistance in obesity. Am J Physiol-Endoc M 313, E303-E313.

Gallo, K. A., and Johnson, G. L. (2002). Signalling: Mixed-lineage kinase control of JNK and p38 MAPK pathways. Nat Rev Mol Cell Bio 3, 663.

Gardner B M, Pincus D, Gotthardt K, Gallagher C M, Walter P. Endoplasmic reticulum stress sensing in the unfolded protein response. Cold Spring Harb Perspect Biol. 2013; 5(3):a013169.

Goeger D E, Riley R T, Dorner J W, Cole R J. Cyclopiazonic acid inhibition of the Ca2+-transport ATPase in rat skeletal muscle sarcoplasmic reticulum vesicles. Biochem Pharmacol. 1988; 37(5):978-81.

Goodfellow, V. S., Loweth, C. J., Ravula, S. B., Wiemann, T., Nguyen, T., Xu, Y., Todd, D. E., Sheppard, D., Pollack, S., Polesskaya, O., et al. (2013). Discovery, Synthesis, and Characterization of an Orally Bioavailable, Brain Penetrant Inhibitor of Mixed Lineage Kinase 3. J Med Chem 56, 8032-8048.

Gowing, G., Philips, T., Wijmeersch, B., Audet, J.-N., Dewil, M., Bosch, L., Billiau, A. D., Robberecht, W., and Julien, J.-P. (2008). Ablation of Proliferating Microglia Does Not Affect Motor Neuron Degeneration in Amyotrophic Lateral Sclerosis Caused by Mutant Superoxide Dismutase. J Neurosci 28, 10234-10244.

Grad L I, Yerbury J J, Turner B J, Guest W C, Pokrishevsky E, O'Neill M A, et al. Intercellular propagated misfolding of wild-type Cu/Zn superoxide dismutase occurs via exosome-dependent and -independent mechanisms. Proc Natl Acad Sci USA. 2014; 111(9):3620-5.

Gros-Louis F, Soucy G, Lariviere R, Julien J P. Intracerebroventricular infusion of monoclonal antibody or its derived Fab fragment against misfolded forms of SOD1 mutant delays mortality in a mouse model of ALS. J Neurochem. 2010; 113(5):1188-99.

Gurney M E, Pu H, Chiu A Y, Dal Canto M C, Polchow C Y, Alexander D D, et al. Motor neuron degeneration in mice that express a human Cu,Zn superoxide dismutase mutation. Science. 1994; 264(5166):1772-5.

Haidet-Phillips A M, Hester M E, Miranda C J, Meyer K, Braun L, Frakes A, et al. Astrocytes from familial and sporadic ALS patients are toxic to motor neurons. Nat Biotechnol. 2011; 29(9):824-8.

Hall, E. D., Oostveen, J. A., and Gurney, M. E. (1998). Relationship of microglial and astrocytic activation to disease onset and progression in a transgenic model of familial ALS. Glia 23, 249-256.

Han, S.-X., Zhu, Q., Ma, J.-L., Zhao, J., Huang, C., Jia, X., and Zhang, D. (2010). Lowered HGK expression inhibits cell invasion and adhesion in hepatocellular carcinoma cell line HepG2. World J Gastroentero 16, 4541-4548.

Hanson M G, Jr., Shen S, Wiemelt A P, McMorris F A, Barres B A. Cyclic AMP elevation is sufficient to promote the survival of spinal motor neurons in vitro. J Neurosci. 1998; 18(18):7361-71.

Henderson C E, Phillips H S, Pollock R A, Davies A M, Lemeulle C, Armanini M, et al. GDNF: a potent survival factor for motoneurons present in peripheral nerve and muscle. Science. 1994; 266(5187):1062-4.

Hetz C, Saxena S. ER stress and the unfolded protein response in neurodegeneration. Nat Rev Neurol. 2017; 13(8):477-91.

Hetz C, Thielen P, Matus S, Nassif M, Court F, Kiffin R, et al. XBP-1 deficiency in the nervous system protects against amyotrophic lateral sclerosis by increasing autophagy. Genes Dev. 2009; 23(19):2294-306.

Hetz C. The unfolded protein response: controlling cell fate decisions under ER stress and beyond. Nat Rev Mol Cell Biol. 2012; 13(2):89-102.

Hetz, C., and Saxena, S. (2017). ER stress and the unfolded protein response in neurodegeneration. Nat Rev Neurol 13, nrneurol.2017.99.

Hoing S, Rudhard Y, Reinhardt P, Glatza M, Stehling M, Wu G, et al. Discovery of inhibitors of microglial neurotoxicity acting through multiple mechanisms using a stem-cell-based phenotypic assay. Cell Stem Cell. 2012; 11(5): 620-32.

Imamura, K., Izumi, Y., Watanabe, A., Tsukita, K., Woltjen, K., Yamamoto, T., Hotta, A., Kondo, T., Kitaoka, S., Ohta, A., et al. (2017). The Src/c-Abl pathway is a potential therapeutic target in amyotrophic lateral sclerosis. Sci Transl Med 9, eaaf3962.

Islam, M., and Moore, D. J. (2017). Mechanisms of LRRK2-dependent neurodegeneration: role of enzymatic activity and protein aggregation. Biochem Soc T 45, 163-172.

Iurlaro R, Munoz-Pinedo C. Cell death induced by endoplasmic reticulum stress. FEBS J. 2016; 283(14):2640-52.

Jaiswal M K, Keller B U. Cu/Zn superoxide dismutase typical for familial amyotrophic lateral sclerosis increases the vulnerability of mitochondria and perturbs Ca2+ homeostasis in SOD1G93A mice. Mol Pharmacol. 2009; 75(3):478-89.

Jaiswal M K, Zech W D, Goos M, Leutbecher C, Ferri A, Zippelius A, et al. Impairment of mitochondrial calcium handling in a mtSOD1 cell culture model of motoneuron disease. BMC Neurosci. 2009; 10:64.

Jayaraman T, Marks A R. T cells deficient in inositol 1,4,5-trisphosphate receptor are resistant to apoptosis. Mol Cell Biol. 1997; 17(6):3005-12.

Jeohn G H, Wilson B, Wetsel W C, Hong J S. The indolocarbazole Go6976 protects neurons from lipopolysaccharide/interferon-gamma-induced cytotoxicity in murine neuron/glia co-cultures. Brain Res Mol Brain Res. 2000; 79(1-2):32-44.

Johnson-Kerner B L, Ahmad F S, Diaz A G, Greene J P, Gray S J, Samulski R J, et al. Intermediate filament protein accumulation in motor neurons derived from giant axonal neuropathy iPSCs rescued by restoration of gigaxonin. Hum Mol Genet. 2015; 24(5):1420-31.

Kaemmerer W F, Rodrigues C M, Steer C J, Low W C. Creatine-supplemented diet extends Purkinje cell survival in spinocerebellar ataxia type 1 transgenic mice but does not prevent the ataxic phenotype. Neuroscience. 2001; 103(3):713-24.

Kang S H, Li Y, Fukaya M, Lorenzini I, Cleveland D W, Ostrow L W, et al. Degeneration and impaired regeneration of gray matter oligodendrocytes in amyotrophic lateral sclerosis. Nat Neurosci. 2013; 16(5):571-9.

Kaplan A, Spiller K J, Towne C, Kanning K C, Choe G T, Geber A, et al. Neuronal matrix metalloproteinase-9 is a determinant of selective neurodegeneration. Neuron. 2014; 81(2):333-48.

Kase H, Iwahashi K, Nakanishi S, Matsuda Y, Yamada K, Takahashi M, et al. K-252 compounds, novel and potent inhibitors of protein kinase C and cyclic nucleotide-dependent protein kinases. Biochem Biophys Res Commun. 1987; 142(2):436-40.

Kawaguchi Y, Cooper B, Gannon M, Ray M, MacDonald R J, Wright C V. The role of the transcriptional regulator Ptf1a in converting intestinal to pancreatic progenitors. Nat Genet. 2002; 32(1):128-34.

Kawamata H, Manfredi G. Mitochondrial dysfunction and intracellular calcium dysregulation in ALS. Mech Ageing Dev. 2010; 131(7-8):517-26.

Keene C D, Rodrigues C M, Eich T, Chhabra M S, Steer C J, Low W C. Tauroursodeoxycholic acid, a bile acid, is neuroprotective in a transgenic animal model of Huntington's disease. Proc Natl Acad Sci USA. 2002; 99(16): 10671-6.

Keene C D, Rodrigues C M, Eich T, Linehan-Stieers C, Abt A, Kren B T, et al. A bile acid protects against motor and cognitive deficits and reduces striatal degeneration in the 3-nitropropionic acid model of Huntington's disease. Exp Neurol. 2001; 171(2):351-60.

Kikuchi H, Almer G, Yamashita S, Guegan C, Nagai M, Xu Z, et al. Spinal cord endoplasmic reticulum stress associated with a microsomal accumulation of mutant superoxide dismutase-1 in an ALS model. Proc Natl Acad Sci USA. 2006; 103(15):6025-30.

Kim H J, Magrane J, Starkov A A, Manfredi G. The mitochondrial calcium regulator cyclophilin D is an essential component of oestrogen-mediated neuroprotection in amyotrophic lateral sclerosis. Brain. 2012; 135(Pt 9):2865-74.

Kiskinis E, Sandoe J, Williams L A, Boulting G L, Moccia R, Wainger B J, et al. Pathways disrupted in human ALS motor neurons identified through genetic correction of mutant SOD1. Cell Stem Cell. 2014; 14(6):781-95.

Kozutsumi Y, Segal M, Normington K, Gething M J, Sambrook J. The presence of malfolded proteins in the endoplasmic reticulum signals the induction of glucose-regulated proteins. Nature. 1988; 332(6163):462-4.

Larhammar, M., Huntwork-Rodriguez, S., Jiang, Z., Solanoy, H., Ghosh, A., Wang, B., Kaminker, J. S., Huang, K., Eastham-Anderson, J., Siu, M., et al. (2017b). Dual leucine zipper kinase-dependent PERK activation contributes to neuronal degeneration following insult. Elife 6, e20725.

Larhammar, M., Huntwork-Rodriguez, S., Rudhard, Y., Sengupta-Ghosh, A., and Lewcock, J. W. (2017a). The Ste20 Family Kinases MAP4K4, MINK1, and TNIK Converge to Regulate Stress-Induced JNK Signaling in Neurons. J Neurosci 37, 11074-11084.

Lasagna-Reeves, C. A.; de Haro, M.; Hao, S.; Park, J.; Rousseaux, M. W. C.; Al-Ramahi, I.; Jafar-Nejad, P.; Vilanova-Velez, L.; See, L.; De Maio, A.; Nitschke, L.; Wu, Z.; Troncoso, J. C.; Westbrook, T. F.; Tang, J.; Botas, J.; Zoghbi, H. Y. *Neuron* 2016, 92 (2), 407.

Lin, J.-C., Lee, Y.-C., Tan, T.-H., Liang, Y.-C., Chuang, H.-C., Fann, Y. C., Johnson, K. R., and Lin, Y.-J. (2018). RBM4-SRSF3-MAP4K4 splicing cascade modulates the metastatic signature of colorectal cancer cell. Biochimica Et Biophysica Acta Bba—Mol Cell Res 1865.

Liu M L, Zang T, Zhang C L. Direct Lineage Reprogramming Reveals Disease-Specific Phenotypes of Motor Neurons from Human ALS Patients. Cell Rep. 2016; 14(1):115-28.

Lytton J, Westlin M, Hanley M R. Thapsigargin inhibits the sarcoplasmic or endoplasmic reticulum Ca-ATPase family of calcium pumps. J Biol Chem. 1991; 266(26):17067-71.

Madisen L, Zwingman T A, Sunkin S M, Oh S W, Zariwala H A, Gu H, et al. A robust and high-throughput Cre reporting and characterization system for the whole mouse brain. Nat Neurosci. 2010; 13(1):133-40.

Maeder M L, Thibodeau-Beganny S, Osiak A, Wright D A, Anthony R M, Eichtinger M, et al. Rapid "open-source" engineering of customized zinc-finger nucleases for highly efficient gene modification. Mol Cell. 2008; 31(2): 294-301.

Marker, D. F., Tremblay, M.-E., Puccini, J. M., Barbieri, J., Marker, M. A., Loweth, C. J., Muly, C. E., Lu, S.-M., Goodfellow, V. S., Dewhurst, S., et al. (2013). The New Small-Molecule Mixed-Lineage Kinase 3 Inhibitor URMC-099 Is Neuroprotective and Anti-Inflammatory in Models of Human Immunodeficiency Virus-Associated Neurocognitive Disorders. J Neurosci 33, 9998-10010.

Maselli R A, Wollman R L, Leung C, Distad B, Palombi S, Richman D P, et al. Neuromuscular transmission in amyotrophic lateral sclerosis. Muscle Nerve. 1993; 16(11): 1193-203.

Maury, Y., Côme, J., Piskorowski, R. A., Salah-Mohellibi, N., Chevaleyre, V., Peschanski, M., Martinat, C., and Nedelec, S. (2014). Combinatorial analysis of developmental cues efficiently converts human pluripotent stem cells into multiple neuronal subtypes. Nat Biotechnol 33, 89-96.

Medinas, D. B., Cabral-Miranda, F., and Hetz, C. (2019). ER stress links aging to sporadic ALS. Aging 11, 5-6.

Miles G B, Yohn D C, Wichterle H, Jessell T M, Rafuse V F, Brownstone R M. Functional properties of motoneurons derived from mouse embryonic stem cells. J Neurosci. 2004; 24(36):7848-58.

Nagai M, Re D B, Nagata T, Chalazonitis A, Jessell T M, Wichterle H, et al. Astrocytes expressing ALS-linked mutated SOD1 release factors selectively toxic to motor neurons. Nat Neurosci. 2007; 10(5):615-22.

Naujock M, Stanslowsky N, Bufler S, Naumann M, Reinhardt P, Sterneckert J, et al. 4-Aminopyridine Induced Activity Rescues Hypoexcitable Motor Neurons from Amyotrophic Lateral Sclerosis Patient-Derived Induced Pluripotent Stem Cells. Stem Cells. 2016; 34(6):1563-75.

Ndubaku, C. O., Crawford, T. D., Chen, H., Boggs, J. W., Drobnick, J., Harris, S. F., Jesudason, R., McNamara, E., Nonomiya, J., Sambrone, A., et al. (2015). Structure-Based Design of GNE-495, a Potent and Selective MAP4K4 Inhibitor with Efficacy in Retinal Angiogenesis. Acs Med Chem Lett 6, 913-918.

Nishitoh H, Kadowaki H, Nagai A, Maruyama T, Yokota T, Fukutomi H, et al. ALS-linked mutant SOD1 induces ER stress- and ASK1-dependent motor neuron death by targeting Derlin-1. Genes Dev. 2008; 22(11):1451-64.

Nunes A F, Amaral J D, Lo A C, Fonseca M B, Viana R J, Callaerts-Vegh Z, et al. TUDCA, a bile acid, attenuates amyloid precursor protein processing and amyloid-beta deposition in APP/PS1 mice. Mol Neurobiol. 2012; 45(3): 440-54.

Oppenheim R W, Yin Q W, Prevette D, Yan Q. Brain-derived neurotrophic factor rescues developing avian motoneurons from cell death. Nature. 1992; 360(6406):755-7.

Oslowski C M, Urano F. Measuring ER stress and the unfolded protein response using mammalian tissue culture system. Methods Enzymol. 2011; 490:71-92.

Ozcan U, Yilmaz E, Ozcan L, Furuhashi M, Vaillancourt E, Smith R O, et al. Chemical chaperones reduce ER stress and restore glucose homeostasis in a mouse model of type 2 diabetes. Science. 2006; 313(5790):1137-40.

Paliulis, O.; Peters, D.; Miknius, L.; Šačkus, A. Org. Prep. Proced. Int. 2007, 39 (1), 86.

Parone P A, Da Cruz S, Han J S, McAlonis-Downes M, Vetto A P, Lee S K, et al. Enhancing mitochondrial calcium buffering capacity reduces aggregation of misfolded SOD1 and motor neuron cell death without extending survival in mouse models of inherited amyotrophic lateral sclerosis. J Neurosci. 2013; 33(11):4657-71.

Patterson M, Chan D N, Ha I, Case D, Cui Y, Van Handel B, et al. Defining the nature of human pluripotent stem cell progeny. Cell Res. 2012; 22(1):178-93.

Peters O M, Ghasemi M, Brown R H, Jr. Emerging mechanisms of molecular pathology in ALS. J Clin Invest. 2015; 125(6):2548.

Pinton P, Giorgi C, Siviero R, Zecchini E, Rizzuto R. Calcium and apoptosis: E R-mitochondria Ca2+ transfer in the control of apoptosis. Oncogene. 2008; 27(50):6407-18.

Pulverer, B. J., Kyriakis, J. M., Avruch, J., Nikolakaki, E., and Woodgett, J. R. (1991). Phosphorylation of c-jun mediated by MAP kinases. Nature 353, 353670a0.

Qiu, M.-H., Qian, Y.-M., Zhao, X.-L., Wang, S.-M., Feng, X.-J., Chen, X.-F., and Zhang, S.-H. (2012). Expression and prognostic significance of MAP4K4 in lung adenocarcinoma. Pathology—Res Pract 208, 541-548.

Rothstein J D, Tsai G, Kuncl R W, Clawson L, Cornblath D R, Drachman D B, et al. Abnormal excitatory amino acid metabolism in amyotrophic lateral sclerosis. Ann Neurol. 1990; 28(1):18-25.

Roux P P, Dorval G, Boudreau M, Angers-Loustau A, Morris S J, Makkerh J, et al. K252a and CEP1347 are neuroprotective compounds that inhibit mixed-lineage kinase-3 and induce activation of Akt and ERK. J Biol Chem. 2002; 277(51):49473-80.

Sakaki K, Wu J, Kaufman R J. Protein kinase Ctheta is required for autophagy in response to stress in the endoplasmic reticulum. J Biol Chem. 2008; 283(22):15370-80.

Salem, S. M., Hamed, A. R., Fayez, A. G., and Eldeen, G. (2018). Non-target Genes Regulate miRNAs-Mediated Migration Steering of Colorectal Carcinoma. Pathol Oncol Res 1-8.

Sano, R.; Reed, J. C. Biochim. Biophys. Acta 2013, 1833 (12), 3460.

Sareen D, O'Rourke J G, Meera P, Muhammad A K, Grant S, Simpkinson M, et al. Targeting RNA foci in iPSC-derived motor neurons from ALS patients with a C9ORF72 repeat expansion. Sci Transl Med. 2013; 5(208):208ra149.

Saxena S, Cabuy E, Caroni P. A role for motoneuron subtype-selective ER stress in disease manifestations of FALS mice. Nat Neurosci. 2009; 12(5):627-36.

Saxena S, Roselli F, Singh K, Leptien K, Julien J P, Gros-Louis F, et al. Neuroprotection through excitability and mTOR required in ALS motoneurons to delay disease and extend survival. Neuron. 2013; 80(1):80-96.

Sendtner M, Arakawa Y, Stockli K A, Kreutzberg G W, Thoenen H. Effect of ciliary neurotrophic factor (CNTF) on motoneuron survival. J Cell Sci Suppl. 1991; 15:103-9.

Sharma A, Lyashchenko A K, Lu L, Nasrabady S E, Elmaleh M, Mendelsohn M, et al. ALS-associated mutant FUS induces selective motor neuron degeneration through toxic gain of function. Nat Commun. 2016; 7:10465.

Shin, J., Cho, Y., Beirowski, B., Milbrandt, J., Cavalli, V., and DiAntonio, A. (2012). Dual Leucine Zipper Kinase Is Required for Retrograde Injury Signaling and Axonal Regeneration. Neuron 74, 1015-1022.

Sivadasan R, Hornburg D, Drepper C, Frank N, Jablonka S, Hansel A, et al. C9ORF72 interaction with cofilin modulates actin dynamics in motor neurons. Nat Neurosci. 2016; 19(12):1610-8.

Spiller, K. J., Restrepo, C. R., Khan, T., Dominique, M. A., Fang, T. C., Canter, R. G., Roberts, C. J., Miller, K. R., Ransohoff, R. M., Trojanowski, J. Q., et al. (2018). Microglia-mediated recovery from ALS-relevant motor neuron degeneration in a mouse model of TDP-43 proteinopathy. Nat Neurosci 21, 329-340.

Stein J L, de la Torre-Ubieta L, Tian Y, Parikshak N N, Hernandez I A, Marchetto M C, et al. A quantitative framework to evaluate modeling of cortical development by neural stem cells. Neuron. 2014; 83(1):69-86.

Takuma H, Kwak S, Yoshizawa T, Kanazawa I. Reduction of GluR2 RNA editing, a molecular change that increases calcium influx through AMPA receptors, selective in the spinal ventral gray of patients with amyotrophic lateral sclerosis. Ann Neurol. 1999; 46(6):806-15.

Tan, L.; Nomanbhoy, T.; Gurbani, D.; Patricelli, M.; Hunter, J.; Geng, J.; Herhaus, L.; Zhang, J.; Pauls, E.; Ham, Y.; Choi, H. G.; Xie, T.; Deng, X.; Buhrlage, S. J.; Sim, T.; Cohen, P.; Sapkota, G.; Westover, K. D.; Gray, N. S. J. Med. Chem. 2015, 58 (1), 183.

Tang, X., Guilherme, A., Chakladar, A., Powelka, A. M., Konda, S., Virbasius, J. V., Nicoloro, S. M., Straubhaar, J., and Czech, M. P. (2006). An RNA interference-based screen identifies MAP4K4/NIK as a negative regulator of PPARγ, adipogenesis, and insulin-responsive hexose transport. P Natl Acad Sci Usa 103, 2087-2092.

Tesz, G. J., Guilherme, A., Guntur, K. V., Hubbard, A. C., Tang, X., Chawla, A., and Czech, M. P. (2007). Tumor Necrosis Factor α (TNFα) Stimulates Map4k4 Expression through TNFα Receptor 1 Signaling to c-Jun and Activating Transcription Factor 2. J Biol Chem 282, 19302-19312.

Tradewell M L, Cooper L A, Minotti S, Durham H D. Calcium dysregulation, mitochondrial pathology and protein aggregation in a culture model of amyotrophic lateral sclerosis: mechanistic relationship and differential sensitivity to intervention. Neurobiol Dis. 2011; 42(3):265-75.

Trias, E., Ibarburu, S., Barreto-Núñez, R., Babdor, J., Maciel, T. T., Guillo, M., Gros, L., Dubreuil, P., Diaz-Amarilla, P., Cassina, P., et al. (2016). Post-paralysis tyrosine kinase inhibition with masitinib abrogates neuroinflammation and slows disease progression in inherited amyotrophic lateral sclerosis. J Neuroinflamm 13, 177.

Tsujihata M, Hazama R, Yoshimura T, Satoh A, Mori M, Nagataki S. The motor end-plate fine structure and ultrastructural localization of acetylcholine receptors in amyotrophic lateral sclerosis. Muscle Nerve. 1984; 7(3):243-9.

Uppala J K, Gani A R, Ramaiah K V A. Chemical chaperone, TUDCA unlike PBA, mitigates protein aggregation efficiently and resists E R and non-ER stress induced HepG2 cell death. Sci Rep. 2017; 7(1):3831.

Urano F, Wang X, Bertolotti A, Zhang Y, Chung P, Harding H P, et al. Coupling of stress in the E R to activation of JNK protein kinases by transmembrane protein kinase IRE1. Science. 2000; 287(5453):664-6.

Vande Velde C, Miller T M, Cashman N R, Cleveland D W. Selective association of misfolded ALS-linked mutant SOD1 with the cytoplasmic face of mitochondria. Proc Natl Acad Sci USA. 2008; 105(10):4022-7.

Virbasius, J. V., and Czech, M. P. (2016). Map4k4 Signaling Nodes in Metabolic and Cardiovascular Diseases. Trends Endocrinol Metabolism 27, 484-492.

von Lewinski F, Keller B U. Ca2+, mitochondria and selective motoneuron vulnerability: implications for ALS. Trends Neurosci. 2005; 28(9):494-500.

Wainger B J, Kiskinis E, Mellin C, Wiskow O, Han S S, Sandoe J, et al. Intrinsic membrane hyperexcitability of amyotrophic lateral sclerosis patient-derived motor neurons. Cell Rep. 2014; 7(1):1-11.

Wang J, Farr G W, Zeiss C J, Rodriguez-Gil D J, Wilson J H, Furtak K, et al. Progressive aggregation despite chaperone associations of a mutant SOD1-YFP in transgenic mice that develop ALS. Proc Natl Acad Sci USA. 2009; 106(5):1392-7.

Wichterle H, Lieberam I, Porter J A, Jessell T M. Directed differentiation of embryonic stem cells into motor neurons. Cell. 2002; 110(3):385-97.

Wright, J. H., Wang, X., Manning, G., LaMere, B. J., Le, P., Zhu, S., Khatry, D., Flanagan, P. M., Buckley, S. D., Whyte, D. B., et al. (2003). The STE20 Kinase HGK Is Broadly Expressed in Human Tumor Cells and Can Modulate Cellular Transformation, Invasion, and Adhesion. Mol Cell Biol 23, 2068-2082.

Wu, C., Watts, M. E., and Rubin, L. L. (2019). MAP4K4 Activation Mediates Motor Neuron Degeneration in Amyotrophic Lateral Sclerosis. Cell Reports 26, 1143-1156.e5.

Yang Y M, Gupta S K, Kim K J, Powers B E, Cerqueira A, Wainger B J, et al. A small molecule screen in stem-cell-derived motor neurons identifies a kinase inhibitor as a candidate therapeutic for ALS. Cell Stem Cell. 2013; 12(6):713-26.

Yang, J., Wu, Z., Renier, N., Simon, D. J., Uryu, K., Park, D. S., Greer, P. A., Tournier, C., Davis, R. J., and Tessier-Lavigne, M. (2015). Pathological Axonal Death through a MAPK Cascade that Triggers a Local Energy Deficit. Cell 160, 161-176.

Yao, Z., Zhou, G., Wang, X., Brown, A., Diener, K., Gan, H., and Tan, T.-H. (1999). A Novel Human STE20-related Protein Kinase, HGK, That Specifically Activates the c-Jun N-terminal Kinase Signaling Pathway. J Biol Chem 274, 2118-2125.

All documents cited in this application are hereby incorporated by reference as if recited in full herein.

Although illustrative embodiments of the present invention have been described herein, it should be understood that the invention is not limited to those described, and that various other changes or modifications may be made by one skilled in the art without departing from the scope or spirit of the invention.

What is claimed is:

1. A compound selected from the group consisting of:

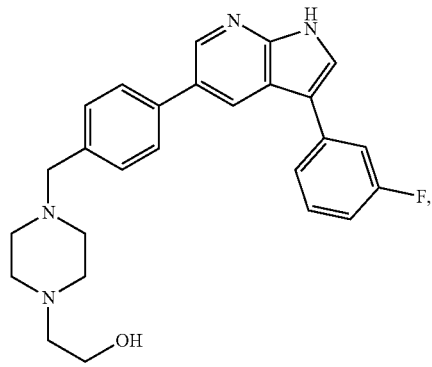
12h

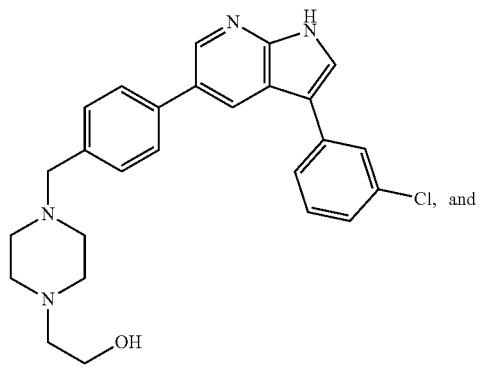
12k

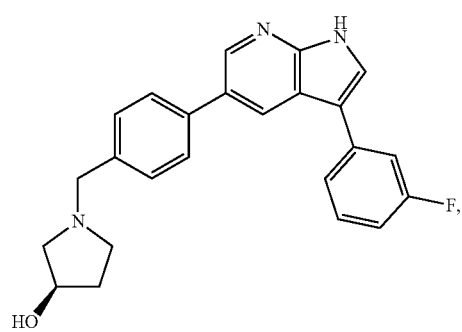
12i

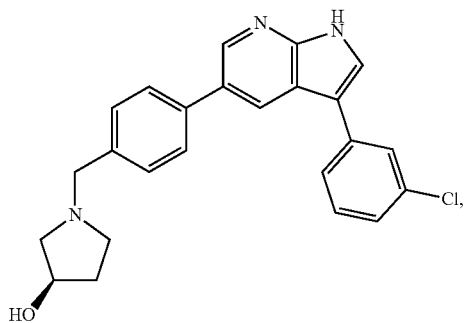
12l or a pharmaceutically acceptable salt thereof.

2. The compound according to claim 1, wherein the compound is:

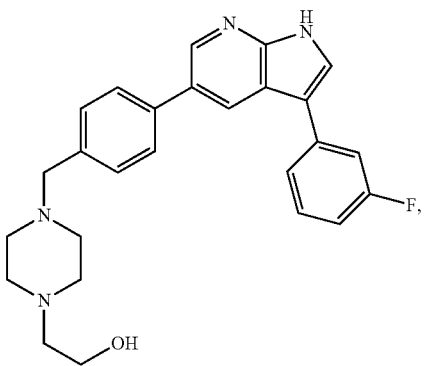

or a pharmaceutically acceptable salt thereof.

3. The compound according to claim 1, wherein the compound is:

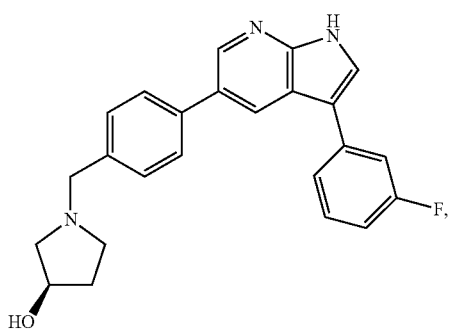

or a pharmaceutically acceptable salt thereof.

4. The compound according to claim 1, wherein the compound is:

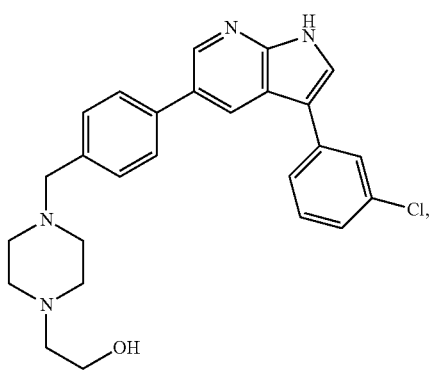

or a pharmaceutically acceptable salt thereof.

5. The compound according to claim 1, wherein the compound is:

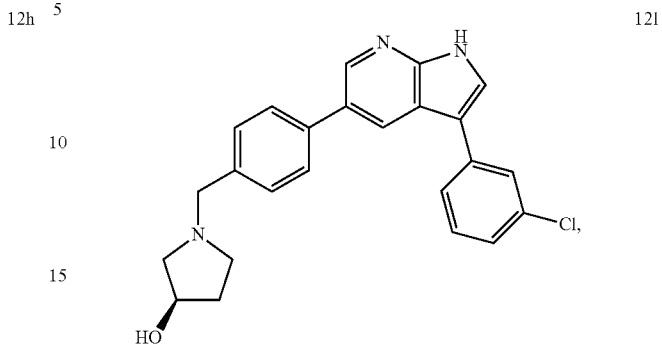

or a pharmaceutically acceptable salt thereof.

6. A kit comprising the compound according to any one of claims 1-5 together with instructions for the use of the compound.

7. A method for suppressing the toxicity of endoplasmic reticulum (ER) stress in a subject in need thereof, wherein the method comprises administering to the subject a therapeutically effective amount of a compound selected from the group consisting of:

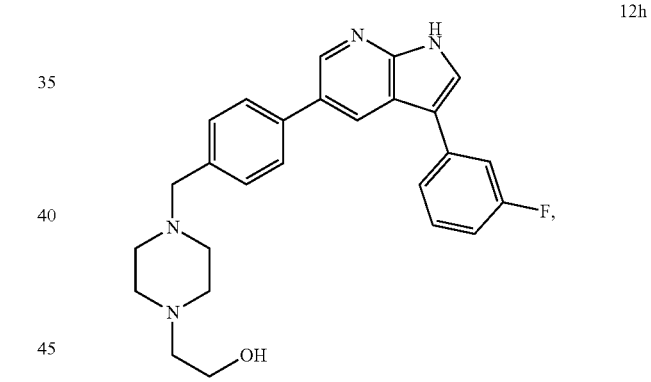

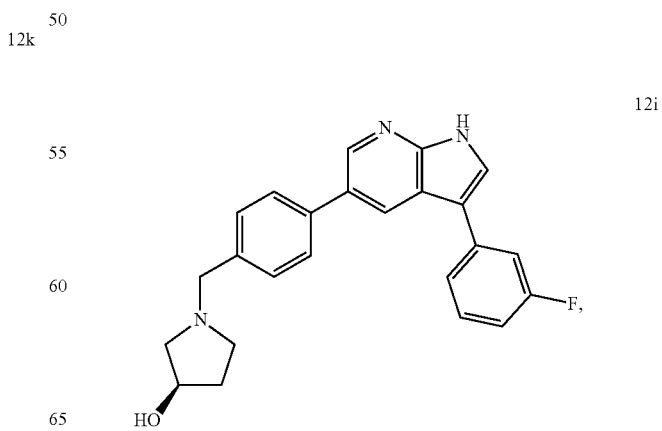

-continued

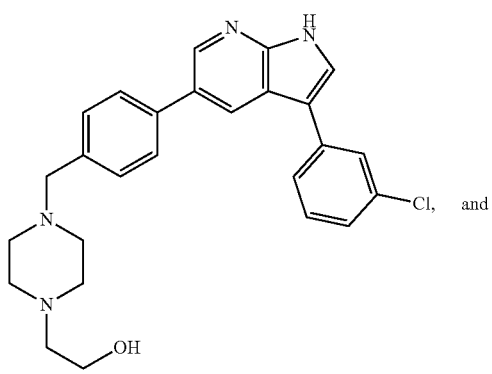

12k and

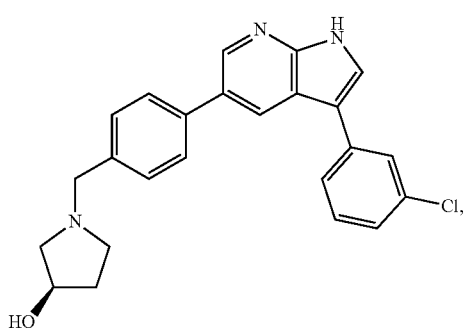

12l or a pharmaceutically acceptable salt thereof.

8. The method according to claim 7, wherein the subject has a neurodegenerative disease selected from the group consisting of Alzheimer's disease, amyotrophic lateral sclerosis (ALS), Charcot-Marie-Tooth disease, chronic traumatic encephalopathy (CTE), corticobasal degeneration, dementia with Lewy bodies, Friedreich's ataxia, glaucoma, hereditary spastic paraparesis, Huntington's disease, multiple sclerosis, Parkinson's disease, a polyglutamine disease, a prion disease, progressive supranuclear palsy, and transmissible spongiform encephalopathy.

9. The method according to claim 8, wherein the neurodegenerative disease is amyotrophic lateral sclerosis (ALS).

10. The method according to claim 7, wherein the subject is a mammal.

11. The method according to claim 10, wherein the mammal is selected from the group consisting of a human, an agricultural animal, and a veterinary animal.

12. The method according to claim 7, wherein the subject is a human.

13. The method according to claim 7, wherein the compound is:

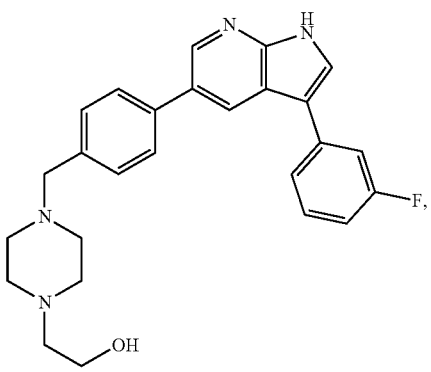

12h or a pharmaceutically acceptable salt thereof.

14. The method according to claim 7, wherein the compound is:

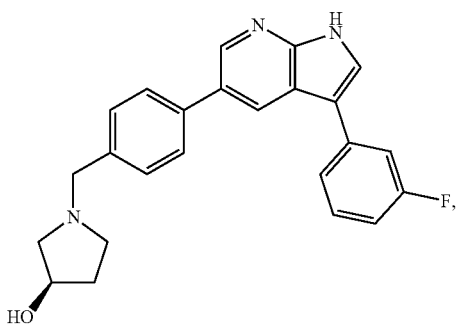

12i or a pharmaceutically acceptable salt thereof.

15. The method according to claim 7, wherein the compound is:

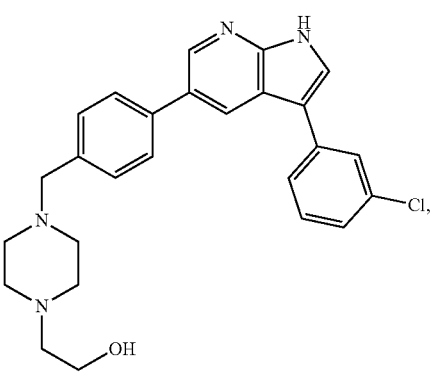

12k or a pharmaceutically acceptable salt thereof.

16. The method according to claim 7, wherein the compound is:

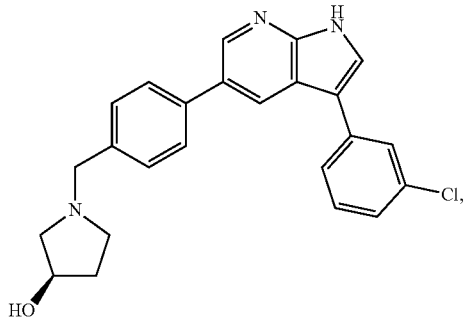

or a pharmaceutically acceptable salt thereof.

17. The method according to any one of claims 7, 13, 14, 15, or 16, wherein the method further comprises co-administering to the subject a therapeutically effective amount of one or more additional therapeutic agents selected from the group consisting of AFQO56 (Novartis), alpha-lipoic acid/L-acetyl carnitine, amantadine (Symmetrel), Apomorphine (Apokyn), Arimoclomol, armodafinil, ascorbic acid, Avonex, baclofen (Lioresal), benztropine (Cogentin), Betaseron, botulinum toxin, carbidopa/levodopa/entacapone (Stalevo), carbidopa/levodopa immediate-release (Sinemet), carbidopa/levodopa oral disintegrating (Parcopa), CERE-110: adeno-associated virus delivery of nerve growth factor (NGF) (Ceregene), CinnoVex, citalopram, clozapine (Clozaril), clonazepam (Klonopin), coenzyme Q, creatine, Davunetide, deferiprone, diazepam (Valium), Digoxin, Dimebon, divalproex (Depakote), donepezil (Aricept), EGb 761: *Ginkgo biloba* extract, ELNDOO2 (Elan Pharmaceuticals), enalapril, entacapone (Comtan), erythropoietin, escitalopram (Lexapro), ethyl-eicosapentaenoic acid (E-EPA, Miraxion™), exenatide, Extavia, fingolimod (Gilenya), fluoxetine (Prozac, Sarafem), galantamine (Razadyne), glatiramer (Copaxone), haloperidol (Haldol), 5-hydroxytryptophan, idebenone, interferon beta 1a, interferon beta 1b, intravenous immunoglobin (IVIG), ioflupane 1231 (DATSCAN®), IPXO66 (Impax Laboratories Inc.), lamotrigine (Lamictal), lisinopril, lithium carbonate, Lu AA24493, LY450139 (Eli Lilly), masitinib, mecobalamin, Memantine (Namenda), methylprednisolone, minocycline, mirtazapine, mitoxantrone (Novantrone), natalizumab (Tysabri), niacinamide, oxybutinin chloride, PF-04360365 (Pfizer), pioglitazone, pramipexole (Mirapex), prednisone, propranolol, PXT3003, quinacrine, Ramelteon, rasagiline (Azilect), Rebif, ReciGen, remacemide, resveratrol, riluzole (Rilutek), rivastigmine (Exelon), ropinirole (Requip), rotigotine (Neupro), safinamide (EMD Serono), selegiline (L-deprenyl, Eldepryl), SEN0014196 (Siena Biotech), sertraline (Zoloft), sodium phenylbutyrate, tacrine (Cognex), tamoxifen, tauroursodeoxycholic acid (TUDCA), tetrabenazine (Xenazine), Tideglusib, tizanidine (Zanaflex), tolcapone (Tasmar), tolterodine, trinexyphenidyl (formerly Artane), ursodiol, valproic acid (Depakene), varenicline (Pfizer), vitamin E, and zydis selegiline HCl oral disintegrating (Zelapar), or a combination thereof.

18. A method for ameliorating or treating the effects of a disorder in a subject in need thereof, wherein the method comprises administering to the subject a therapeutically effective amount of a compound selected from the group consisting of:

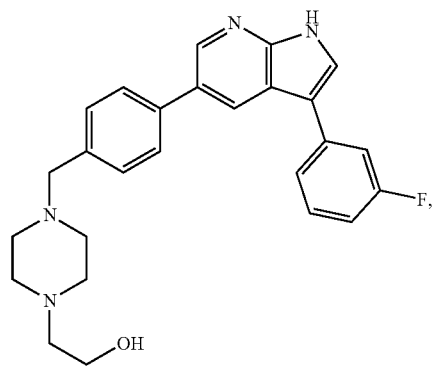

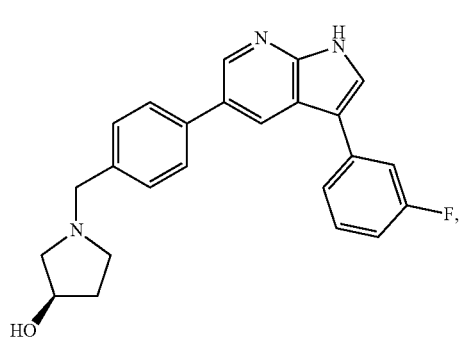

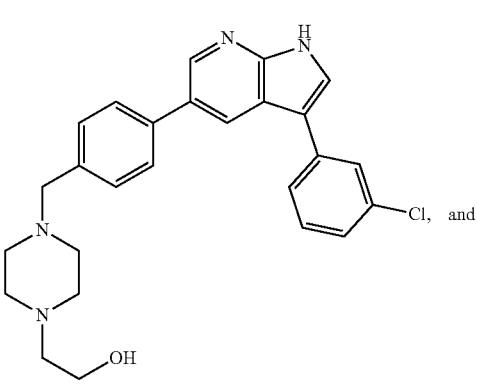

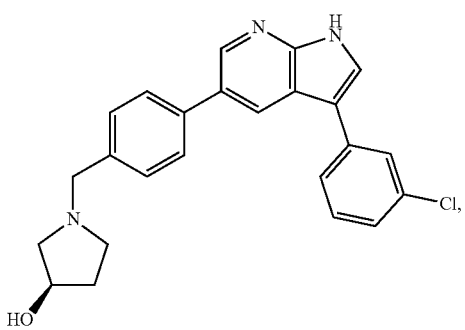

or a pharmaceutically acceptable salt thereof;
wherein the disorder is a disease characterized by aberrant kinase levels in the subject selected from the group consisting of acanthosis nigricans, achondroplasia, acromesomelic chondrodysplasia (a bone malformation), acromesomelic dysplasia, an addiction, angina, anhidrosis, Apert syndrome, arterial hypertension, an arteriovenous malformation, ataxia, atypical migraine, autism, autosomal dominant thrombocytopenia, bacterial-induced macrophage apoptosis, Beare-Stevenson cutis gyrata syndrome, bladder cancer, blood coagulation, brachydactyly type A2 (a hand malformation), breast cancer, capillary infantile hemangioma, cardiac arrhythmia, cardiac hypertrophy, cardiofaciocutaneous syndrome, Carney complex tumor, a cataract, a central nervous system (CNS) tumor, chronic arthritis, a circadian disorder, Coffin-Lowry syndrome, colon cancer, colorectal cancer, cone-rod dystrophy (CORD) type 5, cone-rod dystrophy (CORD) type 6, craniosynostosis Adelaide type, Crouzon syndrome, a defective endocrine function, diabetic hyperlipidemia, diabetic nephropathy, diabetic retinopathy, a diabetic vascular complication, dilated cardiomyopathy, dominant brachydactyly type B, dominant spinocerebellar ataxia type 14, Down syndrome (DS), endometrial cancer, epilepsy, an epithelial tumor, esophageal cancer, an external genital abnormality, extra-skeletal bone formation, familial hypertrophic cardiomyopathy, familial medullary thyroid carcinoma (FMTC), familial melanoma, fibrodysplasia ossificans progressiva, gastric cancer, gastrointestinal cancer, gastrointestinal stromal tumor (GIST), glioblastoma, a glioma, head and neck cancer, head and neck squamous cell carcinoma, heart contractility, heart failure, a hematopoietic malignancy, hepatocellular carcinoma, hereditary hemorrhagic telangiectasia type 2 (Osler-Rendu-Weber syndrome 2), hereditary nonpolyposis colorectal cancer (HNPCC, Lynch syndrome), hereditary papillary renal carcinoma, hereditary prostate cancer-1 (HPC1), Hischsprung disease, hyper-immunoglobulin M (HIgM) syndrome, hypertension, hypertrophic cardiomyopathy, hypochrondroplasia, hypogonadism, hypohidrotic ectodermal dysplasia, idiopathic hypereosinophilic syndrome, incontinentia pigmenti, an inflammatory myofibroblastic tumor, intestinal bleeding, Jackson-Weiss syndrome, a juvenile midline carcinoma, juvenile polyposis syndrome, Kallmann syndrome 2, Leber congenital amaurosis type 1 (LCA1), a left-right axis malformation, leprechaunism, Li-Fraumeni syndrome, liver cancer, liver cirrhosis, liver glycogenosis, Loeys-Dietz syndrome, lung cancer, male baldness, malignant melanoma, mammary ductal carcinoma, mammary gland hyperplasia, Marfan syndrome type 2, mastocytosis, Muenke syndrome, Müllerian duct syndrome type 2, multiple endocrine neoplasia type 2A (MEN2A), multiple endocrine neoplasia type 2B (MEN2B), muscle wasting, myasthenia gravis, myelodysplasia, a myeloproliferative disorder (MPD), myocardial infarction, myotonia, nasopharyngeal carcinoma, neuroblastoma, nonsyndromic mental retardation type 30 (MRX30), Oguchi disease type 2, osteoarthritic cartilage, ovarian cancer, pain perception, pancreatic cancer, a papillary carcinoma, Peutz-Jeghers syndrome, Pfeiffer syndrome, phaeochromocytoma, piebaldism, pineal hyperplasia, pituitary adenoma, polycystic kidney disease, polycystic ovary syndrome, a post-transplant lymphoproliferative disorder, primary pulmonary hypertension (PPH1), progressive deafness, prostate cancer, pseudohypoaldosteronism type 2, pulmonary adenoma, a pyrogenic bacterial infection, recessive Robinow syndrome (RRS), renal cancer, renal oncocytoma, retinitis pigmentosa, Rett syndrome, rheumatoid arthritis, San Diego type skeletal dysplasia, Seckel syndrome, a skeletal malformation, a sarcoma, somatic melanoma, spina bifida, systemic lupus erythematosus, telangiectasia, testicular cancer, thanatophoric dysplasia, thyroid cancer, tibial muscular dystrophy, uterine leiomyosarcoma, a venous malformation, Williams-Beuren syndrome, Wolcott-Rallison syndrome (WRS), X-linked agammaglobulinemia, and X-linked infantile spasm syndrome; or wherein the disorder is a disease that involves axon degeneration or a disease that involves endoplasmic reticulum (ER) stress, or a combination thereof, selected from the group consisting of atherosclerosis, an autoimmune disease, bipolar disorder, cancer, heart disease, ischemia, a neurodegenerative disease, obesity, stroke, traumatic brain injury, type 1 diabetes, and type 2 diabetes.

19. The method according to claim 18, wherein the central nervous system tumor is an astrocytoma or a brain tumor.

20. The method according to claim 18, wherein the hematopoietic malignancy is selected from the group consisting of acute lymphoblastic leukemia (ALL), acute megakaryoblastic leukemia, acute myeloid leukemia (AML), acute promyelocytic leukemia, anaplastic large cell leukemia, childhood leukemia, chronic myelogenous leukemia (CML), familial chronic lymphocytic leukemia, large-cell lymphoma, stem cell leukemia lymphoma syndrome (SCLL), and T-cell leukemia.

21. The method according to claim 18, wherein the myeloproliferative disorder (MPD) is selected from the group consisting of chronic myelogenous leukemia (CML), idiopathic myelofibrosis, and polycythemia vera.

22. The method according to claim 18, wherein the neurodegenerative disease is selected from the group consisting of Alzheimer's disease, amyotrophic lateral sclerosis (ALS), Charcot-Marie-Tooth disease, chronic traumatic encephalopathy (CTE), corticobasal degeneration, dementia with Lewy bodies, Friedreich's ataxia, glaucoma, hereditary spastic paraparesis, Huntington's disease, multiple sclerosis, Parkinson's disease, a polyglutamine disease, a prion disease, progressive supranuclear palsy, and transmissible spongiform encephalopathy.

23. The method according to claim 22, wherein the neurodegenerative disease is amyotrophic lateral sclerosis (ALS).

24. The method according to claim 18, wherein the papillary carcinoma is papillary thyroid carcinoma.

25. The method according to claim 18, wherein the sarcoma is Ewing's sarcoma or a soft tissue sarcoma.

26. The method according to claim 18, wherein the subject is a mammal.

27. The method according to claim 26, wherein the mammal is selected from the group consisting of a human, an agricultural animal, and a veterinary animal.

28. The method according to claim 18, wherein the subject is a human.

29. The method according to claim 18, wherein the compound is:

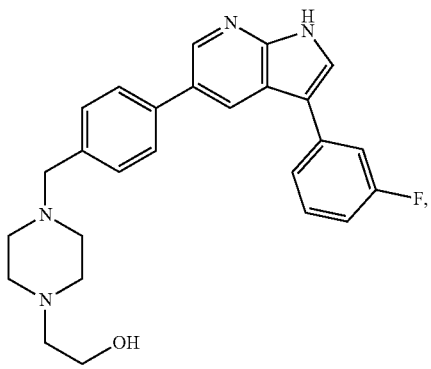

12h or a pharmaceutically acceptable salt thereof.

30. The method according to claim 18, wherein the compound is:

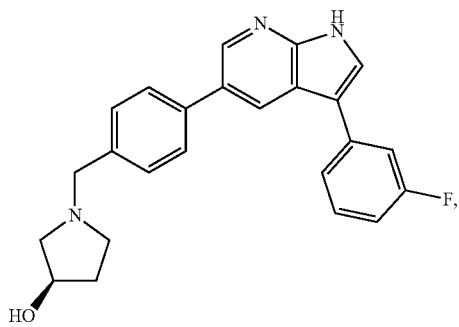

12i or a pharmaceutically acceptable salt thereof.

31. The method according to claim 18, wherein the compound is:

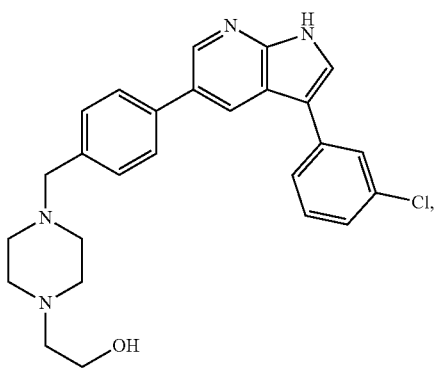

12k or a pharmaceutically acceptable salt thereof.

32. The method according to claim 18, wherein the compound is:

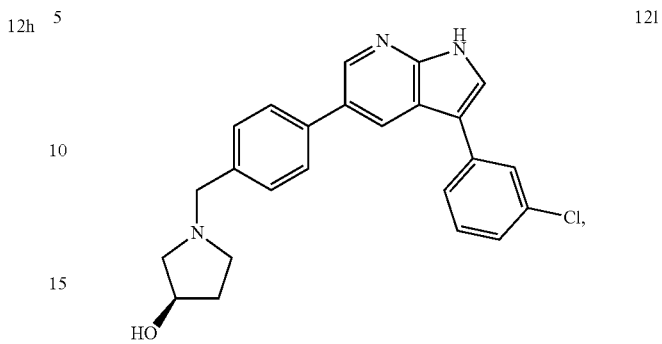

12l or a pharmaceutically acceptable salt thereof.

33. The method according to any one of claims 18, 29, 30, 31, or 32, wherein the method further comprises co-administering to the subject a therapeutically effective amount of one or more additional therapeutic agents selected from the group consisting of AFQO56 (Novartis), alpha-lipoic acid/L-acetyl carnitine, amantadine (Symmetrel), Apomorphine (Apokyn), Arimoclomol, armodafinil, ascorbic acid, Avonex, baclofen (Lioresal), benztropine (Cogentin), Betaseron, botulinum toxin, carbidopa/levodopa/entacapone (Stalevo), carbidopa/levodopa immediate-release (Sinemet), carbidopa/levodopa oral disintegrating (Parcopa), CERE-110: adeno-associated virus delivery of nerve growth factor (NGF) (Ceregene), CinnoVex, citalopram, clozapine (Clozaril), clonazepam (Klonopin), coenzyme Q, creatine, Davunetide, deferiprone, diazepam (Valium), Digoxin, Dimebon, divalproex (Depakote), donezepil (Aricept), EGb 761: *Ginkgo biloba* extract, ELNDOO2 (Elan Pharmaceuticals), enalapril, entacapone (Comtan), erythropoietin, escitalopram (Lexapro), ethyl-eicosapentaenoic acid (E-EPA, Miraxion™), exenatide, Extavia, fingolimod (Gilenya), fluoxetine (Prozac, Sarafem), galantamine (Razadyne), glatiramer (Copaxone), haloperidol (Haldol), 5-hydroxytryptophan, idebenone, interferon beta 1a, interferon beta 1b, intravenous immunoglobin (IVIG), ioflupane 1231 (DATSCAN®), IPXO66 (Impax Laboratories Inc.), lamotrigine (Lamictal), lisinopril, lithium carbonate, Lu AA24493, LY450139 (Eli Lilly), masitinib, mecobalamin, Memantine (Namenda), methylprednisolone, minocycline, mirtazapine, mitoxantrone (Novantrone), natalizumab (Tysabri), niacinamide, oxybutinin chloride, PF-04360365 (Pfizer), pioglitazone, pramipexole (Mirapex), prednisone, propranolol, PXT3003, quinacrine, Ramelteon, rasagiline (Azilect), Rebif, ReciGen, remacemide, resveratrol, riluzole (Rilutek), rivastigmine (Exelon), ropinirole (Requip), rotigotine (Neupro), safinamide (EMD Serono), selegiline (L-deprenyl, Eldepryl), SEN0014196 (Siena Biotech), sertraline (Zoloft), sodium phenylbutyrate, tacrine (Cognex), tamoxifen, tauroursodeoxycholic acid (TUDCA), tetrabenazine (Xenazine), Tideglusib, tizanidine (Zanaflex), tolcapone (Tasmar), tolterodine, trinexyphenidyl (formerly Artane), ursodiol, valproic acid (Depakene), varenicline (Pfizer), vitamin E, and zydis selegiline HCl oral disintegrating (Zelapar), or a combination thereof.

34. A pharmaceutical composition comprising a pharmaceutically acceptable carrier or diluent and a compound selected from the group consisting of:

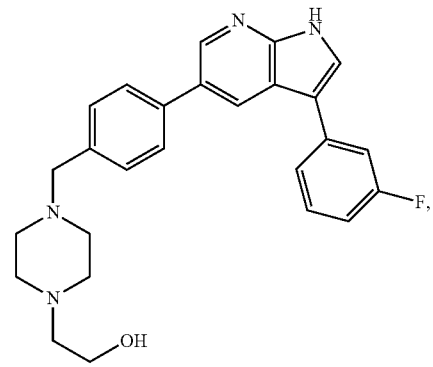
12h

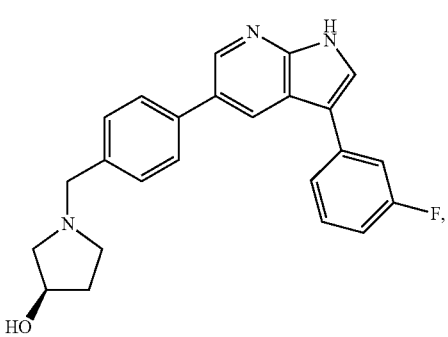
12i

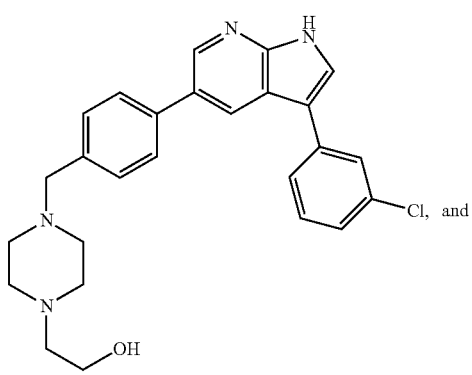
12k

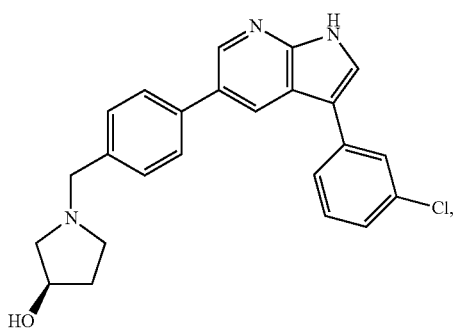
12l or a pharmaceutically acceptable salt thereof.

35. The pharmaceutical composition according to claim 34, wherein the compound is:

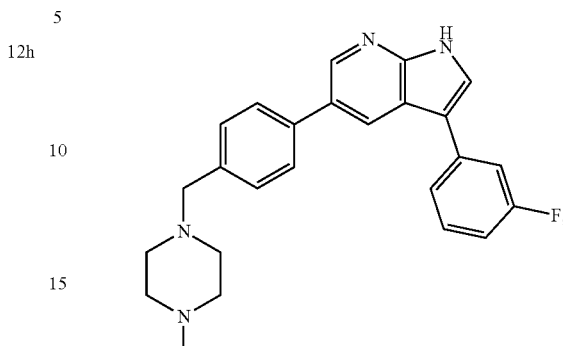
12h or a pharmaceutically acceptable salt thereof.

36. The pharmaceutical composition according to claim 34, wherein the compound is:

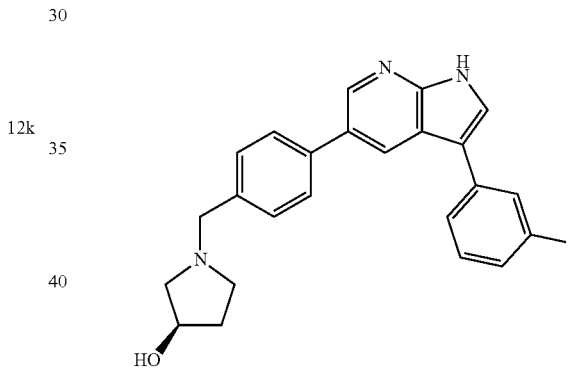
12i

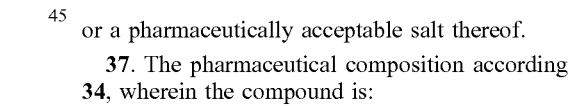

or a pharmaceutically acceptable salt thereof.

37. The pharmaceutical composition according to claim 34, wherein the compound is:

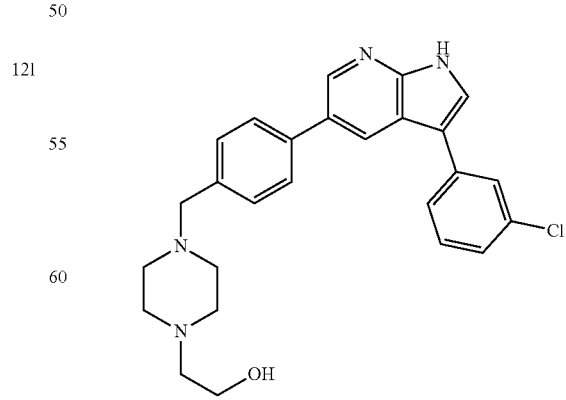
12k or a pharmaceutically acceptable salt thereof.

38. The pharmaceutical composition according to claim 34, wherein the compound is:

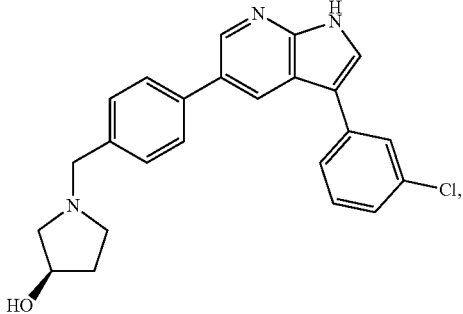

12l or a pharmaceutically acceptable salt thereof.

39. A kit comprising the pharmaceutical composition according to any one of claims 34, 35, 36, 37, or 38 together with instructions for the use of the pharmaceutical composition.

40. A method for ameliorating or treating the effects of a disorder in a subject in need thereof, wherein the method comprises administering to the subject a therapeutically effective amount of a pharmaceutical composition comprising a pharmaceutically acceptable carrier or diluent and a compound selected from the group consisting of:

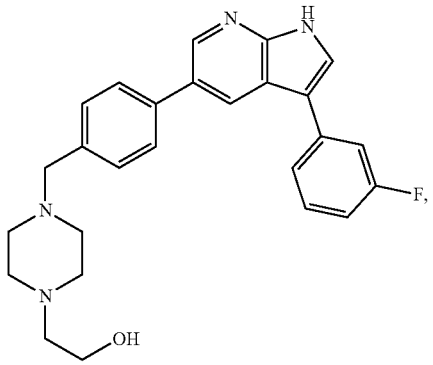

12h

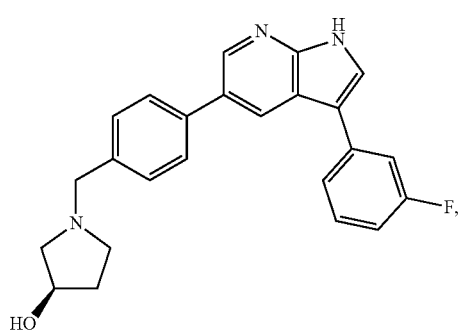

12i

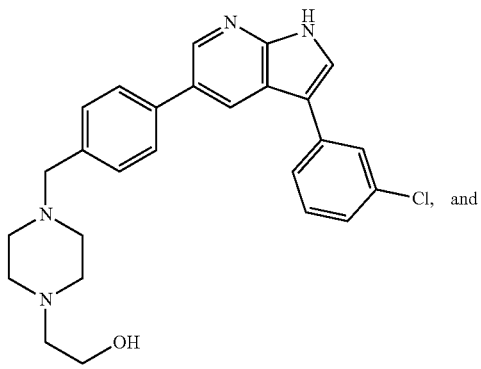

12k

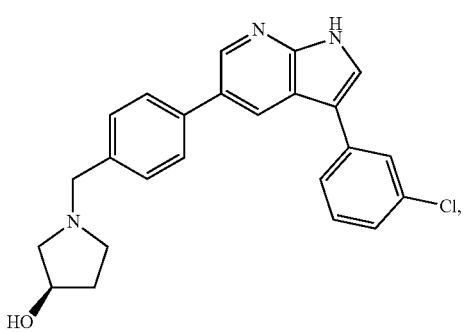

12l or a pharmaceutically acceptable salt thereof;
wherein the disorder is a disease characterized by aberrant kinase levels in the subject selected from the group consisting of acanthosis nigricans, achondroplasia, acromesomelic chondrodysplasia (a bone malformation), acromesomelic dysplasia, an addiction, angina, anhidrosis, Apert syndrome, arterial hypertension, an arteriovenous malformation, ataxia, atypical migraine, autism, autosomal dominant thrombocytopenia, bacterial-induced macrophage apoptosis, Beare-Stevenson cutis gyrata syndrome, bladder cancer, blood coagulation, brachydactyly type A2 (a hand malformation), breast cancer, capillary infantile hemangioma, cardiac arrhythmia, cardiac hypertrophy, cardiofaciocutaneous syndrome, Carney complex tumor, a cataract, a central nervous system (CNS) tumor, chronic arthritis, a circadian disorder, Coffin-Lowry syndrome, colon cancer, colorectal cancer, cone-rod dystrophy (CORD) type 5, cone-rod dystrophy (CORD) type 6, craniosynostosis Adelaide type, Crouzon syndrome, a defective endocrine function, diabetic hyperlipidemia, diabetic nephropathy, diabetic retinopathy, a diabetic vascular complication, dilated cardiomyopathy, dominant brachydactyly type B, dominant spinocerebellar ataxia type 14, Down syndrome (DS), endometrial cancer, epilepsy, an epithelial tumor, esophageal cancer, an external genital abnormality, extra-skeletal bone formation, familial hypertrophic cardiomyopathy, familial medullary thyroid carcinoma (FMTC), familial melanoma, fibrodysplasia ossificans progressiva, gastric cancer, gastrointestinal cancer, gastrointestinal stromal tumor (GIST), glioblastoma, a glioma, head and neck cancer, head and neck squamous cell carcinoma, heart contractility, heart failure, a hematopoietic malignancy, hepatocellular carcinoma, hereditary hemorrhagic telangiectasia type 2 (Osler-Rendu-Weber syndrome 2), hereditary nonpolyposis colorectal cancer (HNPCC, Lynch syndrome), hereditary papillary renal carcinoma, hereditary prostate cancer-1 (HPC1), Hischsprung disease, hyper-immunoglobulin M (HIgM) syndrome, hypertension, hypertrophic cardiomyopathy, hypochrondroplasia, hypogonadism, hypohidrotic ectodermal dysplasia, idiopathic hypereosinophilic syndrome, incontinentia pigmenti, an inflammatory myofibroblastic tumor, intestinal bleeding, Jackson-Weiss syndrome, a juvenile midline carcinoma, juvenile polyposis syndrome, Kallmann syndrome 2, Leber congenital amaurosis type 1 (LCA1), a left-right axis malformation, leprechaunism, Li-Fraumeni syndrome, liver cancer, liver cirrhosis, liver glycogenosis, Loeys-Dietz syndrome, lung cancer, male baldness, malignant melanoma, mammary ductal carcinoma, mammary gland hyperplasia, Marfan syndrome type 2, mastocytosis, Muenke syndrome, Müllerian duct syndrome type 2, multiple endocrine neoplasia type 2A (MEN2A), multiple endocrine neoplasia type 2B (MEN2B), muscle wasting, myasthenia gravis, myelodysplasia, a myeloproliferative disorder (MPD), myocardial infarction, myotonia, nasopharyngeal carcinoma, neuroblastoma, nonsyndromic mental retardation type 30 (MRX30), Oguchi disease type 2, osteoarthritic cartilage, ovarian cancer, pain perception, pancreatic cancer, a papillary carcinoma, Peutz-Jeghers syndrome, Pfeiffer syndrome, phaeochromocytoma, piebaldism, pineal hyperplasia, pituitary adenoma, polycystic kidney disease, polycystic ovary syndrome, a post-transplant lymphoproliferative disorder, primary pulmonary hypertension (PPH1), progressive deafness, prostate cancer, pseudohypoaldosteronism type 2, pulmonary adenoma, a pyrogenic bacterial infection, recessive Robinow syndrome (RRS), renal cancer, renal oncocytoma, retinitis pigmentosa, Rett syndrome, rheumatoid arthritis, San Diego type skeletal dysplasia, Seckel syndrome, a skeletal malformation, a sarcoma, somatic melanoma, spina bifida, systemic lupus erythematosus, telangiectasia, testicular cancer, thanatophoric dysplasia, thyroid cancer, tibial muscular dystrophy, uterine leiomyosarcoma, a venous malformation, Williams-Beuren syndrome, Wolcott-Rallison syndrome (WRS), X-linked agammaglobulinemia, and X-linked infantile spasm syndrome; or wherein the disorder is a disease that involves axon degeneration or a disease that involves endoplasmic reticulum (ER) stress, or a combination thereof, selected from the group consisting of atherosclerosis, an autoimmune disease, bipolar disorder, cancer, heart disease, ischemia, a neurodegenerative disease, obesity, stroke, traumatic brain injury, type 1 diabetes, and type 2 diabetes.

41. The method according to claim 40, wherein the central nervous system tumor is an astrocytoma or a brain tumor.

42. The method according to claim 40, wherein the hematopoietic malignancy is selected from the group consisting of acute lymphoblastic leukemia (ALL), acute megakaryoblastic leukemia, acute myeloid leukemia (AML), acute promyelocytic leukemia, anaplastic large cell leukemia, childhood leukemia, chronic myelogenous leukemia (CML), familial chronic lymphocytic leukemia, large-cell lymphoma, stem cell leukemia lymphoma syndrome (SCLL), and T-cell leukemia.

43. The method according to claim 40, wherein the myeloproliferative disorder (MPD) is selected from the group consisting of chronic myelogenous leukemia (CML), idiopathic myelofibrosis, and polycythemia vera.

44. The method according to claim 40, wherein the neurodegenerative disease is selected from the group consisting of Alzheimer's disease, amyotrophic lateral sclerosis (ALS), Charcot-Marie-Tooth disease, chronic traumatic encephalopathy (CTE), corticobasal degeneration, dementia with Lewy bodies, Friedreich's ataxia, glaucoma, hereditary spastic paraparesis, Huntington's disease, multiple sclerosis, Parkinson's disease, a polyglutamine disease, a prion disease, progressive supranuclear palsy, and transmissible spongiform encephalopathy.

45. The method according to claim 44, wherein the neurodegenerative disease is amyotrophic lateral sclerosis (ALS).

46. The method according to claim 40, wherein the papillary carcinoma is papillary thyroid carcinoma.

47. The method according to claim 40, wherein the sarcoma is Ewing's sarcoma or a soft tissue sarcoma.

48. The method according to claim 40, wherein the subject is a mammal.

49. The method according to claim 48, wherein the mammal is selected from the group consisting of a human, an agricultural animal, and a veterinary animal.

50. The method according to claim 40, wherein the subject is a human.

51. The method according to claim 40, wherein the compound is:

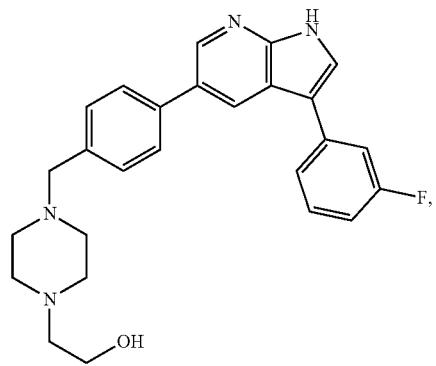

12h or a pharmaceutically acceptable salt thereof.

52. The method according to claim 40, wherein the compound is:

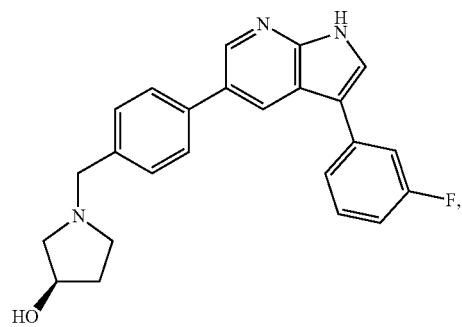

12i or a pharmaceutically acceptable salt thereof.

53. The method according to claim 40, wherein the compound is:

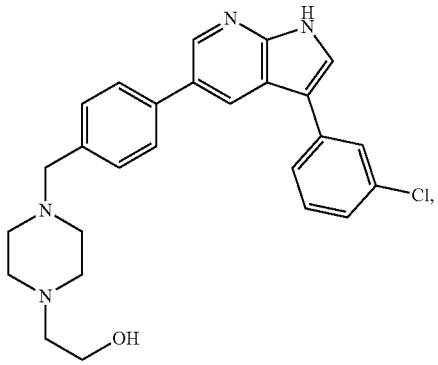

12k or a pharmaceutically acceptable salt thereof.

54. The method according to claim 40, wherein the compound is:

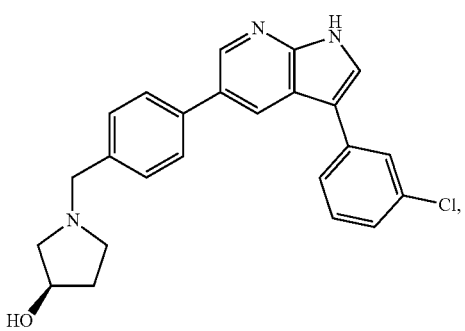

12l or a pharmaceutically acceptable salt thereof.

55. The method according to any one of claims 40, 51, 52, 53, or 54, wherein the method further comprises co-administering to the subject a therapeutically effective amount of one or more additional therapeutic agents selected from the group consisting of AFQO56 (Novartis), alpha-lipoic acid/L-acetyl carnitine, amantadine (Symmetrel), Apomorphine (Apokyn), Arimoclomol, armodafinil, ascorbic acid, Avonex, baclofen (Lioresal), benztropine (Cogentin), Betaseron, botulinum toxin, carbidopa/levodopa/entacapone (Stalevo), carbidopa/levodopa immediate-release (Sinemet), carbidopa/levodopa oral disintegrating (Parcopa), CERE-110: adeno-associated virus delivery of nerve growth factor (NGF) (Ceregene), CinnoVex, citalopram, clozapine (Clozaril), clonazepam (Klonopin), coenzyme Q, creatine, Davunetide, deferiprone, diazepam (Valium), Digoxin, Dimebon, divalproex (Depakote), donepezil (Aricept), EGb 761: *Ginkgo biloba* extract, ELNDOO2 (Elan Pharmaceuticals), enalapril, entacapone (Comtan), erythropoietin, escitalopram (Lexapro), ethyl-eicosapentaenoic acid (E-EPA, Miraxion™), exenatide, Extavia, fingolimod (Gilenya), fluoxetine (Prozac, Sarafem), galantamine (Razadyne), glatiramer (Copaxone), haloperidol (Haldol), 5-hydroxytryptophan, idebenone, interferon beta 1a, interferon beta 1b, intravenous immunoglobin (IVIG), ioflupane 1231 (DATSCAN®), IPXO66 (Impax Laboratories Inc.), lamotrigine (Lamictal), lisinopril, lithium carbonate, Lu AA24493, LY450139 (Eli Lilly), masitinib, mecobalamin, Memantine (Namenda), methylprednisolone, minocycline, mirtazapine, mitoxantrone (Novantrone), natalizumab (Tysabri), niacinamide, oxybutinin chloride, PF-04360365 (Pfizer), pioglitazone, pramipexole (Mirapex), prednisone, propranolol, PXT3003, quinacrine, Ramelteon, rasagiline (Azilect), Rebif, ReciGen, remacemide, resveratrol, riluzole (Rilutek), rivastigmine (Exelon), ropinirole (Requip), rotigotine (Neupro), safinamide (EMD Serono), selegiline (L-deprenyl, Eldepryl), SEN0014196 (Siena Biotech), sertraline (Zoloft), sodium phenylbutyrate, tacrine (Cognex), tamoxifen, tauroursodeoxycholic acid (TUDCA), tetrabenazine (Xenazine), Tideglusib, tizanidine (Zanaflex), tolcapone (Tasmar), tolterodine, trinexyphenidyl (formerly Artane), ursodiol, valproic acid (Depakene), varenicline (Pfizer), vitamin E, and zydis selegiline HCl oral disintegrating (Zelapar), or a combination thereof.

56. A compound:

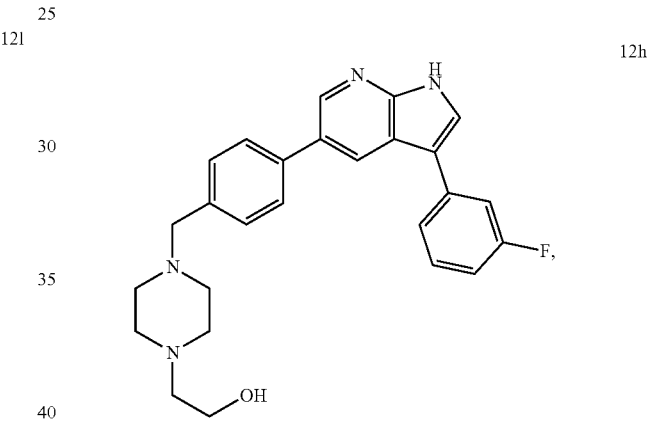

12h or a pharmaceutically acceptable salt thereof.

57. The compound according to claim 56, wherein the compound is:

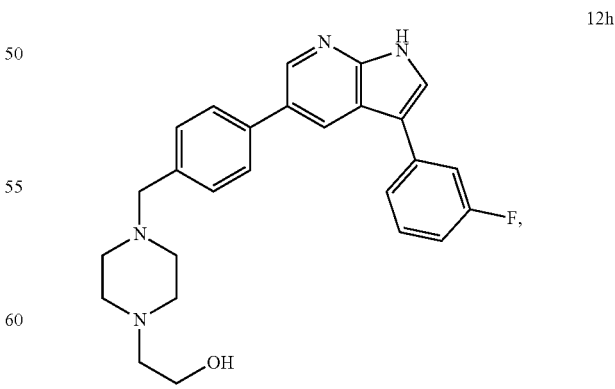

12h

58. The compound according to claim 56, or a pharmaceutically acceptable salt thereof, wherein the compound is a pharmaceutically acceptable salt of:

59. A pharmaceutical composition comprising a pharmaceutically acceptable carrier or diluent and a compound:

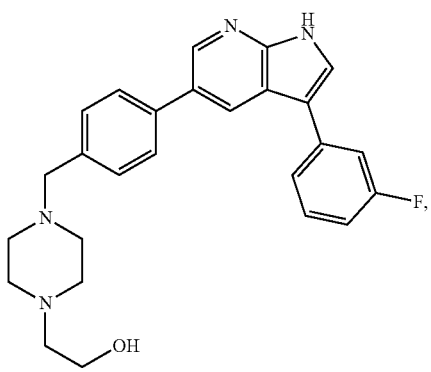

or a pharmaceutically acceptable salt thereof.

60. The pharmaceutical composition according to claim 59, wherein the compound is:

or a pharmaceutically acceptable salt thereof.

61. The pharmaceutical composition according to claim 59, wherein the compound is a pharmaceutically acceptable salt of:

62. A method for suppressing the toxicity of endoplasmic reticulum (ER) stress in a subject in need thereof, wherein the method comprises administering to the subject a therapeutically effective amount of a compound:

or a pharmaceutically acceptable salt thereof.

63. A method for ameliorating or treating the effects of a disorder in a subject in need thereof, wherein the method comprises administering to the subject a therapeutically effective amount of a compound:

or a pharmaceutically acceptable salt thereof;
wherein the disorder is a disease characterized by aberrant kinase levels in the subject selected from the group consisting of acanthosis nigricans, achondroplasia, acromesomelic chondrodysplasia (a bone malformation), acromesomelic dysplasia, an addiction, angina, anhidrosis, Apert syndrome, arterial hypertension, an arteriovenous malformation, ataxia, atypical migraine, autism, autosomal dominant thrombocytopenia, bacterial-induced macrophage apoptosis, Beare-Stevenson cutis gyrata syndrome, bladder cancer, blood coagulation, brachydactyly type A2 (a hand malformation), breast cancer, capillary infantile hemangioma, cardiac arrhythmia, cardiac hypertrophy, cardiofaciocutaneous syndrome, Carney complex tumor, a cataract, a central nervous system (CNS) tumor, chronic arthritis, a circadian disorder, Coffin-Lowry syndrome, colon cancer, colorectal cancer, cone-rod dystrophy (CORD) type 5, cone-rod dystrophy (CORD) type 6, craniosynostosis Adelaide type, Crouzon syndrome, a defective endocrine function, diabetic hyperlipidemia, diabetic nephropathy, diabetic retinopathy, a diabetic vascular complication, dilated cardiomyopathy, dominant brachydactyly type B, dominant spinocerebellar ataxia type 14, Down syndrome (DS), endometrial cancer, epilepsy, an epithelial tumor, esophageal cancer, an external genital abnormality, extra-skeletal bone formation, familial hypertrophic cardiomyopathy, familial medullary thyroid carcinoma (FMTC), familial melanoma, fibrodysplasia ossificans progressiva, gastric cancer, gastrointestinal cancer, gastrointestinal stromal tumor (GIST), glioblastoma, a glioma, head and neck cancer, head and neck squamous cell carcinoma, heart contractility, heart failure, a hematopoietic malignancy, hepatocellular carcinoma, hereditary hemorrhagic telangiectasia type 2 (Osler-Rendu-Weber syndrome 2), hereditary nonpolyposis colorectal cancer (HNPCC, Lynch syndrome), hereditary papillary renal carcinoma, hereditary prostate cancer-1 (HPC1), Hischsprung disease, hyper-immunoglobulin M (HIgM) syndrome, hypertension, hypertrophic cardiomyopathy, hypochrondroplasia, hypogonadism, hypohidrotic ectodermal dysplasia, idiopathic hypereosinophilic syndrome, incontinentia pigmenti, an inflammatory myofibroblastic tumor, intestinal bleeding, Jackson-Weiss syndrome, a juvenile midline carcinoma, juvenile polyposis syndrome, Kallmann syndrome 2, Leber congenital amaurosis type 1 (LCA1), a left-right axis malformation, leprechaunism, Li-Fraumeni syndrome, liver cancer, liver cirrhosis, liver glycogenosis, Loeys-Dietz syndrome, lung cancer, male baldness, malignant melanoma, mammary ductal carcinoma, mammary gland hyperplasia, Marfan syndrome type 2, mastocytosis, Muenke syndrome, Müllerian duct syndrome type 2, multiple endocrine neoplasia type 2A (MEN2A), multiple endocrine neoplasia type 2B (MEN2B), muscle wasting, myasthenia gravis, myelodysplasia, a myeloproliferative disorder (MPD), myocardial infarction, myotonia, nasopharyngeal carcinoma, neuroblastoma, nonsyndromic mental retardation type 30 (MRX30), Oguchi disease type 2, osteoarthritic cartilage, ovarian cancer, pain perception, pancreatic cancer, a papillary carcinoma, Peutz-Jeghers syndrome, Pfeiffer syndrome, phaeochromocytoma, piebaldism, pineal hyperplasia, pituitary adenoma, polycystic kidney disease, polycystic ovary syndrome, a post-transplant lymphoproliferative disorder, primary pulmonary hypertension (PPH1), progressive deafness, prostate cancer, pseudohypoaldosteronism type 2, pulmonary adenoma, a pyrogenic bacterial infection, recessive Robinow syndrome (RRS), renal cancer, renal oncocytoma, retinitis pigmentosa, Rett syndrome, rheumatoid arthritis, San Diego type skeletal dysplasia, Seckel syndrome, a skeletal malformation, a sarcoma, somatic melanoma, spina bifida, systemic lupus erythematosus, telangiectasia, testicular cancer, thanatophoric dysplasia, thyroid cancer, tibial muscular dystrophy, uterine leiomyosarcoma, a venous malformation, Williams-Beuren syndrome, Wolcott-Rallison syndrome (WRS), X-linked agammaglobulinemia, and X-linked infantile spasm syndrome; or wherein the disorder is a disease that involves axon degeneration or a disease that involves endoplasmic reticulum (ER) stress, or a combination thereof, selected from the group consisting of atherosclerosis, an autoimmune disease, bipolar disorder, cancer, heart disease, ischemia, a neurodegenerative disease, obesity, stroke, traumatic brain injury, type 1 diabetes, and type 2 diabetes.

64. A compound:

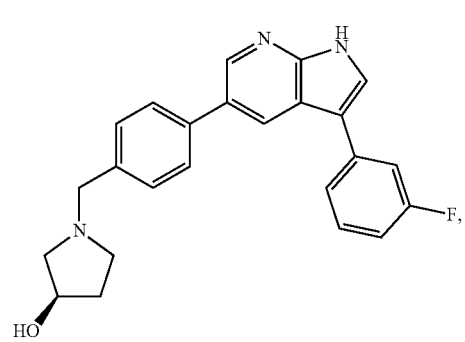

12i or a pharmaceutically acceptable salt thereof.

65. The compound according to claim 64, wherein the compound is:

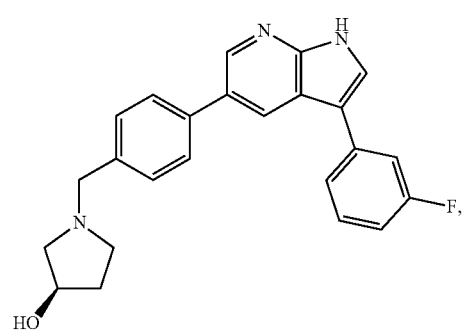

12i

66. The compound according to claim 64, or a pharmaceutically acceptable salt thereof, wherein the compound is a pharmaceutically acceptable salt of:

223

67. A pharmaceutical composition comprising a pharmaceutically acceptable carrier or diluent and a compound:

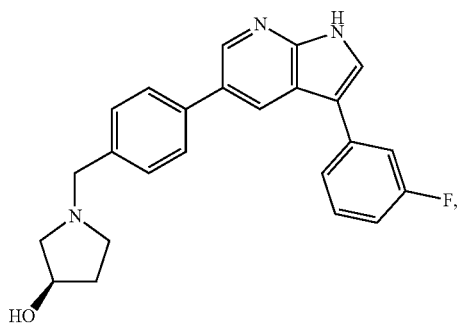

or a pharmaceutically acceptable salt thereof.

68. The pharmaceutical composition according to claim 67, wherein the compound is:

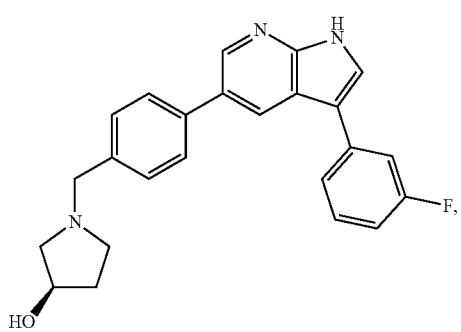

69. The pharmaceutical composition according to claim 67, wherein the compound is a pharmaceutically acceptable salt of:

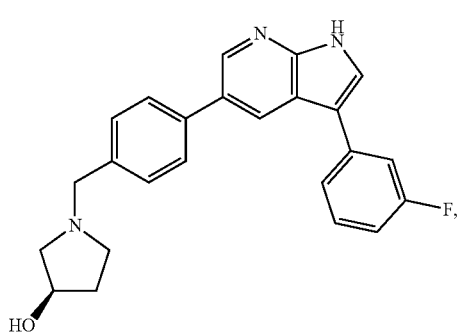

70. A method for suppressing the toxicity of endoplasmic reticulum (ER) stress in a subject in need thereof, wherein the method comprises administering to the subject a therapeutically effective amount of a compound:

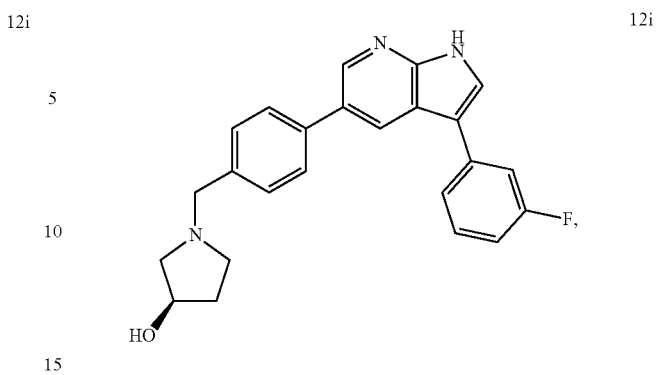

or a pharmaceutically acceptable salt thereof.

71. A method for ameliorating or treating the effects of a disorder in a subject in need thereof, wherein the method comprises administering to the subject a therapeutically effective amount of a compound:

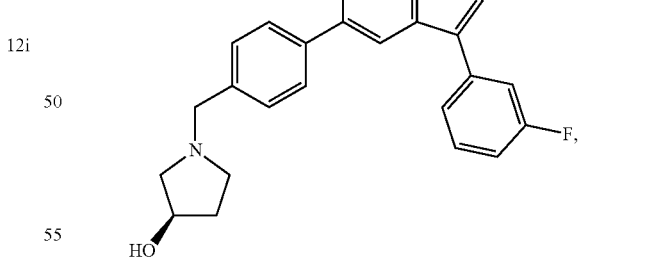

or a pharmaceutically acceptable salt thereof;
wherein the disorder is a disease characterized by aberrant kinase levels in the subject selected from the group consisting of acanthosis nigricans, achondroplasia, acromesomelic chondrodysplasia (a bone malformation), acromesomelic dysplasia, an addiction, angina, anhidrosis, Apert syndrome, arterial hypertension, an arteriovenous malformation, ataxia, atypical migraine, autism, autosomal dominant thrombocytopenia, bacterial-induced macrophage apoptosis, Beare-Stevenson cutis gyrata syndrome, bladder cancer, blood coagulation, brachydactyly type A2 (a hand malformation), breast cancer, capillary infantile hemangioma, cardiac arrhythmia, cardiac hypertrophy, cardiofaciocutaneous syndrome, Carney complex tumor, a cataract, a central nervous system (CNS) tumor, chronic arthritis, a circadian disorder, Coffin-Lowry syndrome, colon cancer, colorectal cancer, cone-rod dystrophy (CORD) type 5, cone-rod dystrophy (CORD) type 6, craniosynostosis Adelaide type, Crouzon syndrome, a defective endocrine function, diabetic hyperlipidemia, diabetic nephropathy, diabetic retinopathy, a diabetic vascular complication, dilated cardiomyopathy, dominant brachydactyly type B, dominant spinocerebellar ataxia type 14, Down syndrome (DS), endometrial cancer, epilepsy, an epithelial tumor, esophageal cancer, an external genital abnormality, extra-skeletal bone formation, familial hypertrophic cardiomyopathy, familial medullary thyroid carcinoma (FMTC), familial melanoma, fibrodysplasia ossificans progressiva, gastric cancer, gastrointestinal cancer, gastrointestinal stromal tumor (GIST), glioblastoma, a glioma, head and neck cancer, head and neck squamous cell carcinoma, heart contractility, heart failure, a hematopoietic malignancy, hepatocellular carcinoma, hereditary hemorrhagic telangiectasia type 2 (Osler-Rendu-Weber syndrome 2), hereditary nonpolyposis colorectal cancer (HNPCC, Lynch syndrome), hereditary papillary renal carcinoma, hereditary prostate cancer-1 (HPC1), Hischsprung disease, hyper-immunoglobulin M (HIgM) syndrome, hypertension, hypertrophic cardiomyopathy, hypochrondroplasia, hypogonadism, hypohidrotic ectodermal dysplasia, idiopathic hypereosinophilic syndrome, incontinentia pigmenti, an inflammatory myofibroblastic tumor, intestinal bleeding, Jackson-Weiss syndrome, a juvenile midline carcinoma, juvenile polyposis syndrome, Kallmann syndrome 2, Leber congenital amaurosis type 1 (LCA1), a left-right axis malformation, leprechaunism, Li-Fraumeni syndrome, liver cancer, liver cirrhosis, liver glycogenosis, Loeys-Dietz syndrome, lung cancer, male baldness, malignant melanoma, mammary ductal carcinoma, mammary gland hyperplasia, Marfan syndrome type 2, mastocytosis, Muenke syndrome, Müllerian duct syndrome type 2, multiple endocrine neoplasia type 2A (MEN2A), multiple endocrine neoplasia type 2B (MEN2B), muscle wasting, myasthenia gravis, myelodysplasia, a myeloproliferative disorder (MPD), myocardial infarction, myotonia, nasopharyngeal carcinoma, neuroblastoma, nonsyndromic mental retardation type 30 (MRX30), Oguchi disease type 2, osteoarthritic cartilage, ovarian cancer, pain perception, pancreatic cancer, a papillary carcinoma, Peutz-Jeghers syndrome, Pfeiffer syndrome, phaeochromocytoma, piebaldism, pineal hyperplasia, pituitary adenoma, polycystic kidney disease, polycystic ovary syndrome, a post-transplant lymphoproliferative disorder, primary pulmonary hypertension (PPH1), progressive deafness, prostate cancer, pseudohypoaldosteronism type 2, pulmonary adenoma, a pyrogenic bacterial infection, recessive Robinow syndrome (RRS), renal cancer, renal oncocytoma, retinitis pigmentosa, Rett syndrome, rheumatoid arthritis, San Diego type skeletal dysplasia, Seckel syndrome, a skeletal malformation, a sarcoma, somatic melanoma, spina bifida, systemic lupus erythematosus, telangiectasia, testicular cancer, thanatophoric dysplasia, thyroid cancer, tibial muscular dystrophy, uterine leiomyosarcoma, a venous malformation, Williams-Beuren syndrome, Wolcott-Rallison syndrome (WRS), X-linked agammaglobulinemia, and X-linked infantile spasm syndrome; or wherein the disorder is a disease that involves axon degeneration or a disease that involves endoplasmic reticulum (ER) stress, or a combination thereof, selected from the group consisting of atherosclerosis, an autoimmune disease, bipolar disorder, cancer, heart disease, ischemia, a neurodegenerative disease, obesity, stroke, traumatic brain injury, type 1 diabetes, and type 2 diabetes.

72. A compound:

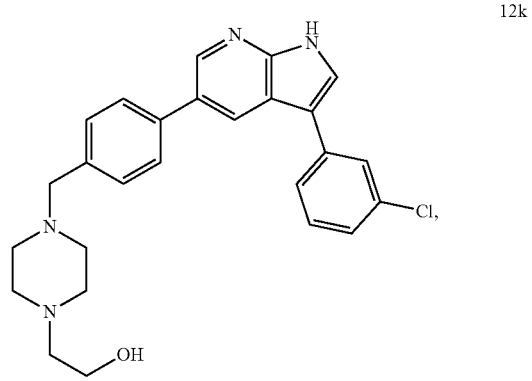

or a pharmaceutically acceptable salt thereof.

73. The compound according to claim 72, wherein the compound is:

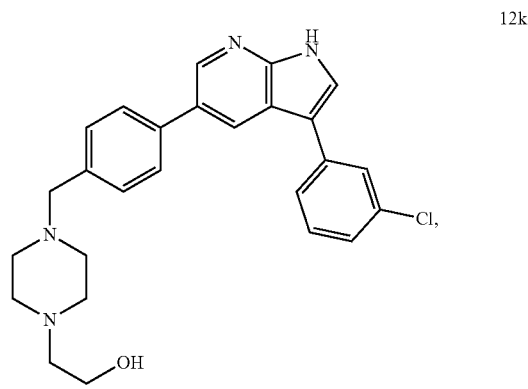 [SMILES: OCCN1CCN(Cc2ccc(-c3cnc4[nH]cc(-c5cccc(Cl)c5)c4c3)cc2)CC1]

74. The compound according to claim 72, or a pharmaceutically acceptable salt thereof, wherein the compound is a pharmaceutically acceptable salt of:

75. A pharmaceutical composition comprising a pharmaceutically acceptable carrier or diluent and a compound:

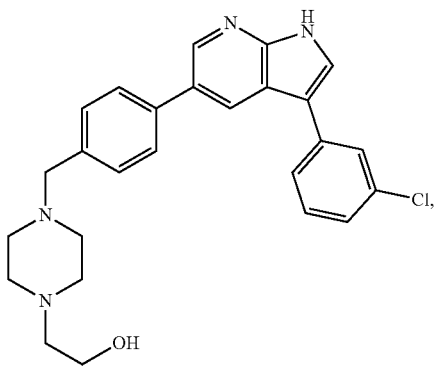

12k or a pharmaceutically acceptable salt thereof.

76. The pharmaceutical composition according to claim 75, wherein the compound is:

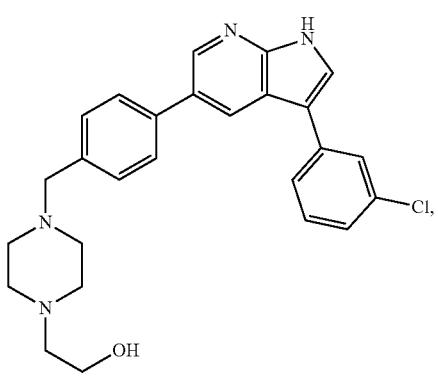

12k

77. The pharmaceutical composition according to claim 75, wherein the compound is a pharmaceutically acceptable salt of:

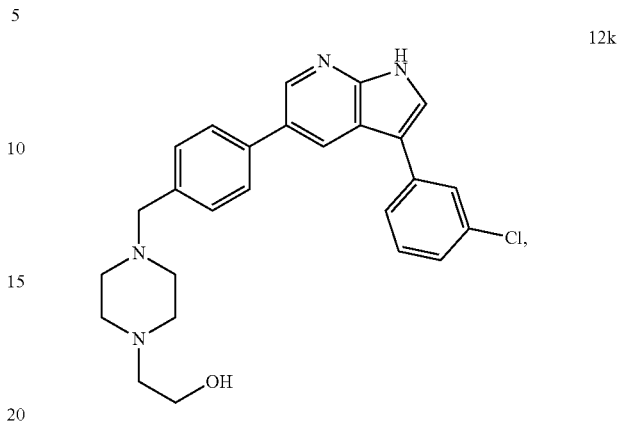

12k

78. A method for suppressing the toxicity of endoplasmic reticulum (ER) stress in a subject in need thereof, wherein the method comprises administering to the subject a therapeutically effective amount of a compound:

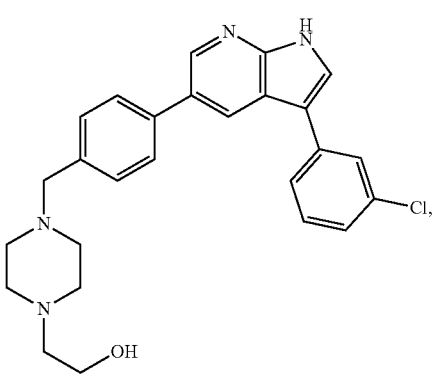

12k or a pharmaceutically acceptable salt thereof.

79. A method for ameliorating or treating the effects of a disorder in a subject in need thereof, wherein the method comprises administering to the subject a therapeutically effective amount of a compound:

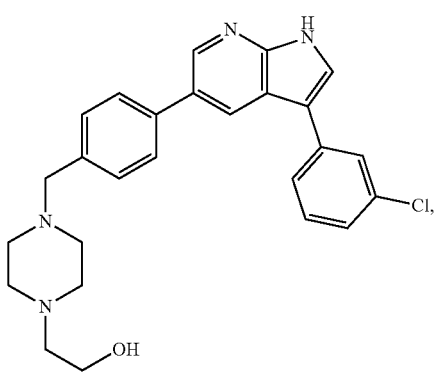

12k

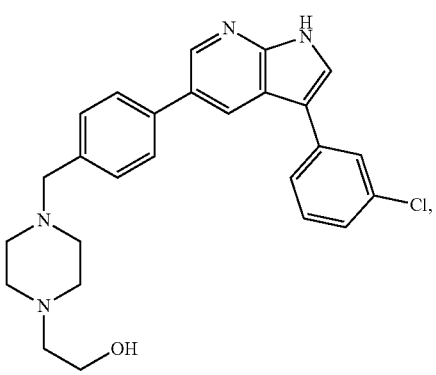

12k or a pharmaceutically acceptable salt thereof;
wherein the disorder is a disease characterized by aberrant kinase levels in the subject selected from the group consisting of acanthosis nigricans, achondroplasia, acromesomelic chondrodysplasia (a bone malformation), acromesomelic dysplasia, an addiction, angina, anhidrosis, Apert syndrome, arterial hypertension, an arteriovenous malformation, ataxia, atypical migraine, autism, autosomal dominant thrombocytopenia, bacterial-induced macrophage apoptosis, Beare-Stevenson cutis gyrata syndrome, bladder cancer, blood coagulation, brachydactyly type A2 (a hand malformation), breast cancer, capillary infantile hemangioma, cardiac arrhythmia, cardiac hypertrophy, cardiofaciocutaneous syndrome, Carney complex tumor, a cataract, a central nervous system (CNS) tumor, chronic arthritis, a circadian disorder, Coffin-Lowry syndrome, colon cancer, colorectal cancer, cone-rod dystrophy (CORD) type 5, cone-rod dystrophy (CORD) type 6, craniosynostosis Adelaide type, Crouzon syndrome, a defective endocrine function, diabetic hyperlipidemia, diabetic nephropathy, diabetic retinopathy, a diabetic vascular complication, dilated cardiomyopathy, dominant brachydactyly type B, dominant spinocerebellar ataxia type 14, Down syndrome (DS), endometrial cancer, epilepsy, an epithelial tumor, esophageal cancer, an external genital abnormality, extra-skeletal bone formation, familial hypertrophic cardiomyopathy, familial medullary thyroid carcinoma (FMTC), familial melanoma, fibrodysplasia ossificans progressiva, gastric cancer, gastrointestinal cancer, gastrointestinal stromal tumor (GIST), glioblastoma, a glioma, head and neck cancer, head and neck squamous cell carcinoma, heart contractility, heart failure, a hematopoietic malignancy, hepatocellular carcinoma, hereditary hemorrhagic telangiectasia type 2 (Osler-Rendu-Weber syndrome 2), hereditary nonpolyposis colorectal cancer (HNPCC, Lynch syndrome), hereditary papillary renal carcinoma, hereditary prostate cancer-1 (HPC1), Hischsprung disease, hyper-immunoglobulin M (HIgM) syndrome, hypertension, hypertrophic cardiomyopathy, hypochrondroplasia, hypogonadism, hypohidrotic ectodermal dysplasia, idiopathic hypereosinophilic syndrome, incontinentia pigmenti, an inflammatory myofibroblastic tumor, intestinal bleeding, Jackson-Weiss syndrome, a juvenile midline carcinoma, juvenile polyposis syndrome, Kallmann syndrome 2, Leber congenital amaurosis type 1 (LCA1), a left-right axis malformation, leprechaunism, Li-Fraumeni syndrome, liver cancer, liver cirrhosis, liver glycogenosis, Loeys-Dietz syndrome, lung cancer, male baldness, malignant melanoma, mammary ductal carcinoma, mammary gland hyperplasia, Marfan syndrome type 2, mastocytosis, Muenke syndrome, Müllerian duct syndrome type 2, multiple endocrine neoplasia type 2A (MEN2A), multiple endocrine neoplasia type 2B (MEN2B), muscle wasting, myasthenia gravis, myelodysplasia, a myeloproliferative disorder (MPD), myocardial infarction, myotonia, nasopharyngeal carcinoma, neuroblastoma, nonsyndromic mental retardation type 30 (MRX30), Oguchi disease type 2, osteoarthritic cartilage, ovarian cancer, pain perception, pancreatic cancer, a papillary carcinoma, Peutz-Jeghers syndrome, Pfeiffer syndrome, phaeochromocytoma, piebaldism, pineal hyperplasia, pituitary adenoma, polycystic kidney disease, polycystic ovary syndrome, a post-transplant lymphoproliferative disorder, primary pulmonary hypertension (PPH1), progressive deafness, prostate cancer, pseudohypoaldosteronism type 2, pulmonary adenoma, a pyrogenic bacterial infection, recessive Robinow syndrome (RRS), renal cancer, renal oncocytoma, retinitis pigmentosa, Rett syndrome, rheumatoid arthritis, San Diego type skeletal dysplasia, Seckel syndrome, a skeletal malformation, a sarcoma, somatic melanoma, spina bifida, systemic lupus erythematosus, telangiectasia, testicular cancer, thanatophoric dysplasia, thyroid cancer, tibial muscular dystrophy, uterine leiomyosarcoma, a venous malformation, Williams-Beuren syndrome, Wolcott-Rallison syndrome (WRS), X-linked agammaglobulinemia, and X-linked infantile spasm syndrome; or
wherein the disorder is a disease that involves axon degeneration or a disease that involves endoplasmic reticulum (ER) stress, or a combination thereof, selected from the group consisting of atherosclerosis, an autoimmune disease, bipolar disorder, cancer, heart disease, ischemia, a neurodegenerative disease, obesity, stroke, traumatic brain injury, type 1 diabetes, and type 2 diabetes.

80. A compound:

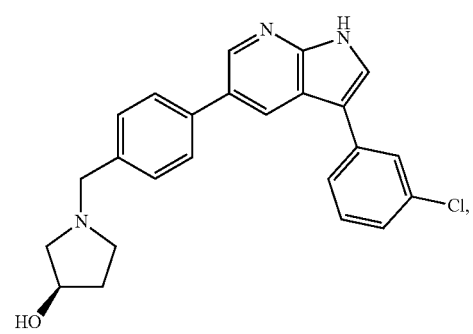

or a pharmaceutically acceptable salt thereof.

81. The compound according to claim 80, wherein the compound is:

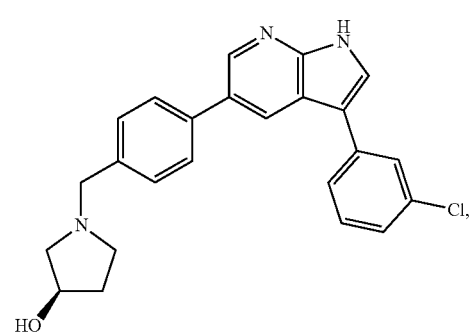

82. The compound according to claim 80, or a pharmaceutically acceptable salt thereof, wherein the compound is a pharmaceutically acceptable salt of:

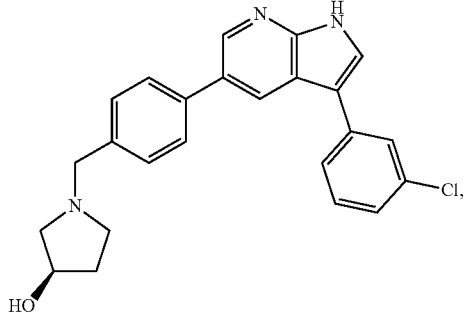

83. A pharmaceutical composition comprising a pharmaceutically acceptable carrier or diluent and a compound:

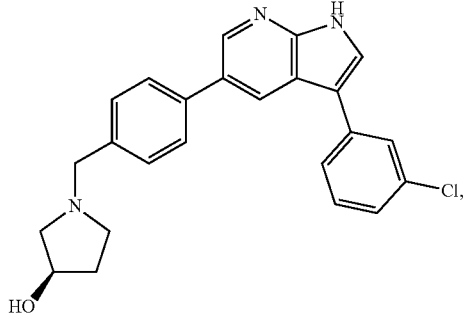

or a pharmaceutically acceptable salt thereof.

84. The pharmaceutical composition according to claim 83, wherein the compound is:

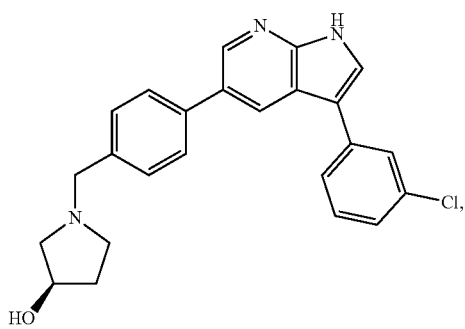

85. The pharmaceutical composition according to claim 83, wherein the compound is a pharmaceutically acceptable salt of:

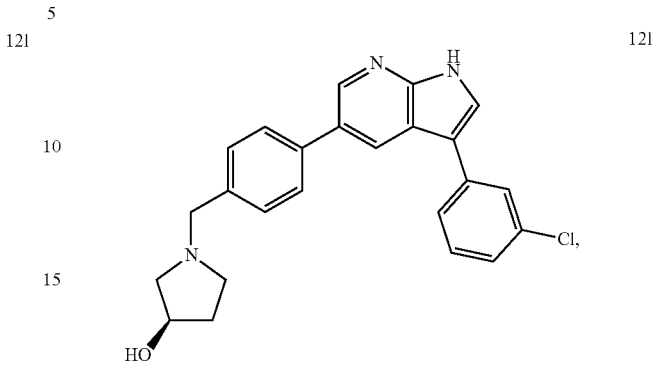

86. A method for suppressing the toxicity of endoplasmic reticulum (ER) stress in a subject in need thereof, wherein the method comprises administering to the subject a therapeutically effective amount of a compound:

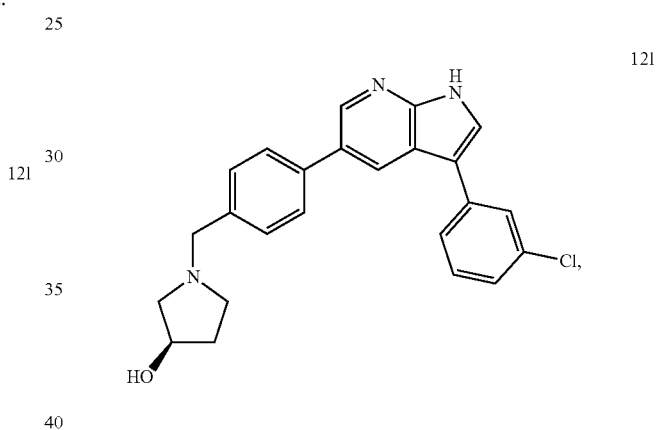

or a pharmaceutically acceptable salt thereof.

87. A method for ameliorating or treating the effects of a disorder in a subject in need thereof, wherein the method comprises administering to the subject a therapeutically effective amount of a compound:

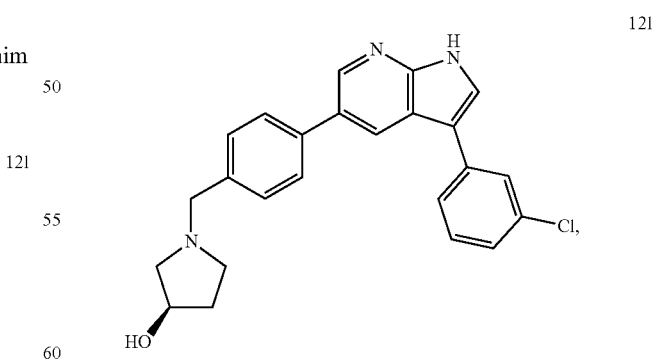

or a pharmaceutically acceptable salt thereof;
wherein the disorder is a disease characterized by aberrant kinase levels in the subject selected from the group consisting of acanthosis nigricans, achondroplasia, acromesomelic chondrodysplasia (a bone malformation), acromesomelic dysplasia, an addiction, angina, anhidrosis, Apert syndrome, arterial hypertension, an arteriovenous malformation, ataxia, atypical migraine, autism, autosomal dominant thrombocytopenia, bacterial-induced macrophage apoptosis, Beare-Stevenson cutis gyrata syndrome, bladder cancer, blood coagulation, brachydactyly type A2 (a hand malformation), breast cancer, capillary infantile hemangioma, cardiac arrhythmia, cardiac hypertrophy, cardiofaciocutaneous syndrome, Carney complex tumor, a cataract, a central nervous system (CNS) tumor, chronic arthritis, a circadian disorder, Coffin-Lowry syndrome, colon cancer, colorectal cancer, cone-rod dystrophy (CORD) type 5, cone-rod dystrophy (CORD) type 6, craniosynostosis Adelaide type, Crouzon syndrome, a defective endocrine function, diabetic hyperlipidemia, diabetic nephropathy, diabetic retinopathy, a diabetic vascular complication, dilated cardiomyopathy, dominant brachydactyly type B, dominant spinocerebellar ataxia type 14, Down syndrome (DS), endometrial cancer, epilepsy, an epithelial tumor, esophageal cancer, an external genital abnormality, extra-skeletal bone formation, familial hypertrophic cardiomyopathy, familial medullary thyroid carcinoma (FMTC), familial melanoma, fibrodysplasia ossificans progressiva, gastric cancer, gastrointestinal cancer, gastrointestinal stromal tumor (GIST), glioblastoma, a glioma, head and neck cancer, head and neck squamous cell carcinoma, heart contractility, heart failure, a hematopoietic malignancy, hepatocellular carcinoma, hereditary hemorrhagic telangiectasia type 2 (Osler-Rendu-Weber syndrome 2), hereditary nonpolyposis colorectal cancer (HNPCC, Lynch syndrome), hereditary papillary renal carcinoma, hereditary prostate cancer-1 (HPC1), Hischsprung disease, hyper-immunoglobulin M (HIgM) syndrome, hypertension, hypertrophic cardiomyopathy, hypochrondroplasia, hypogonadism, hypohidrotic ectodermal dysplasia, idiopathic hypereosinophilic syndrome, incontinentia pigmenti, an inflammatory myofibroblastic tumor, intestinal bleeding, Jackson-Weiss syndrome, a juvenile midline carcinoma, juvenile polyposis syndrome, Kallmann syndrome 2, Leber congenital amaurosis type 1 (LCA1), a left-right axis malformation, leprechaunism, Li-Fraumeni syndrome, liver cancer, liver cirrhosis, liver glycogenosis, Loeys-Dietz syndrome, lung cancer, male baldness, malignant melanoma, mammary ductal carcinoma, mammary gland hyperplasia, Marfan syndrome type 2, mastocytosis, Muenke syndrome, Müllerian duct syndrome type 2, multiple endocrine neoplasia type 2A (MEN2A), multiple endocrine neoplasia type 2B (MEN2B), muscle wasting, myasthenia gravis, myelodysplasia, a myeloproliferative disorder (MPD), myocardial infarction, myotonia, nasopharyngeal carcinoma, neuroblastoma, nonsyndromic mental retardation type 30 (MRX30), Oguchi disease type 2, osteoarthritic cartilage, ovarian cancer, pain perception, pancreatic cancer, a papillary carcinoma, Peutz-Jeghers syndrome, Pfeiffer syndrome, phaeochromocytoma, piebaldism, pineal hyperplasia, pituitary adenoma, polycystic kidney disease, polycystic ovary syndrome, a post-transplant lymphoproliferative disorder, primary pulmonary hypertension (PPH1), progressive deafness, prostate cancer, pseudohypoaldosteronism type 2, pulmonary adenoma, a pyrogenic bacterial infection, recessive Robinow syndrome (RRS), renal cancer, renal oncocytoma, retinitis pigmentosa, Rett syndrome, rheumatoid arthritis, San Diego type skeletal dysplasia, Seckel syndrome, a skeletal malformation, a sarcoma, somatic melanoma, spina bifida, systemic lupus erythematosus, telangiectasia, testicular cancer, thanatophoric dysplasia, thyroid cancer, tibial muscular dystrophy, uterine leiomyosarcoma, a venous malformation, Williams-Beuren syndrome, Wolcott-Rallison syndrome (WRS), X-linked agammaglobulinemia, and X-linked infantile spasm syndrome; or wherein the disorder is a disease that involves axon degeneration or a disease that involves endoplasmic reticulum (ER) stress, or a combination thereof, selected from the group consisting of atherosclerosis, an autoimmune disease, bipolar disorder, cancer, heart disease, ischemia, a neurodegenerative disease, obesity, stroke, traumatic brain injury, type 1 diabetes, and type 2 diabetes.

\* \* \* \* \*

SEQUENCE LISTING

<160> NUMBER OF SEQ ID NOS: 2

<210> SEQ ID NO 1
<211> LENGTH: 25
<212> TYPE: DNA
<213> ORGANISM: Artificial Sequence
<220> FEATURE:
<223> OTHER INFORMATION: PCR primer forward

<400> SEQUENCE: 1
gaatgcccaa aaggatatca gactc                          25

<210> SEQ ID NO 2
<211> LENGTH: 24
<212> TYPE: DNA
<213> ORGANISM: Artificial Sequence
<220> FEATURE:
<223> OTHER INFORMATION: PCR primer reverse

<400> SEQUENCE: 2
ggccttgtgg ttgagaacca ggag                           24